United States Patent
Che et al.

(10) Patent No.: US 8,722,692 B2
(45) Date of Patent: *May 13, 2014

(54) COMPOUNDS AND COMPOSITIONS AS SYK KINASE INHIBITORS

(76) Inventors: Jianwei Che, San Diego, CA (US); Qiang Ding, Beijing (CN); Xiaohui He, San Diego, CA (US); Hong Liu, San Diego, CA (US); Yahua Liu, San Diego, CA (US); Pierre-Yves Michellys, San Marcos, CA (US); Barun Okram, San Diego, CA (US); Xu Wu, Lexington, MA (US); Kunyong Yang, San Diego, CA (US); Xuefeng Zhu, San Diego, CA (US)

(*) Notice: Subject to any disclaimer, the term of this patent is extended or adjusted under 35 U.S.C. 154(b) by 81 days.

This patent is subject to a terminal disclaimer.

(21) Appl. No.: 13/386,645
(22) PCT Filed: Jul. 30, 2010
(86) PCT No.: PCT/US2010/043953
§ 371 (c)(1), (2), (4) Date: Apr. 6, 2012
(87) PCT Pub. No.: WO2011/014795
PCT Pub. Date: Feb. 3, 2011

(65) Prior Publication Data
US 2012/0184526 A1 Jul. 19, 2012

Related U.S. Application Data
(60) Provisional application No. 61/229,951, filed on Jul. 30, 2009.

(51) Int. Cl.
- A01N 43/90 (2006.01)
- A61K 31/519 (2006.01)
- C07D 471/00 (2006.01)
- C07D 487/00 (2006.01)

(52) U.S. Cl.
USPC ............... 514/264.11; 544/279

(58) Field of Classification Search
None
See application file for complete search history.

(56) References Cited

U.S. PATENT DOCUMENTS

| | | | |
|---|---|---|---|
| 5,654,307 A | 8/1997 | Bridges et al. | |
| 8,354,526 B2 * | 1/2013 | Ding et al. | 540/1 |
| 2007/0142402 A1 | 6/2007 | Ding et al. | |
| 2007/0219195 A1 | 9/2007 | Goldstein et al. | |

FOREIGN PATENT DOCUMENTS

| | | |
|---|---|---|
| WO | WO03057695 | 7/2003 |
| WO | WO2004041823 | 5/2004 |
| WO | WO2006112666 | 10/2006 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Cywin CL et al., Discovery and SAR of Novel [1,6]Naphthyridines as Potent Inhibitors of Spleen Tyrosine Kinase (SYK), Bioorganic & Medicinal Chemistry Letters, (2003) 1415-1418, vol. 13.
Jang M, et al., Development of Synthetic Strategies for the Construction of Pyrido[4,3-d]-pyrimidine Libraries—the Discovery of a New Class of PDE-4 Inhibitors, Eur. J. Org. Chem., (2006), 4257-4269.
Liu JL et al., Synthesis and Structure of 2-Substituted Thieno[3',2':5,6]pyrido-[4,3-d]pyrimidin-4(3H)-one Derivatives, Helvetica Chimica Acta, (2007), 999-1005, vol. 90.
Williams EJ et al., Synthesis of a 5-alkoxypyrido[4,3-d]pyrimidin-4(3H)-one derivative via a regioselective Meisenheimer N-oxide rearrangement, Tetrahedron Letters, (2004), 3737-3739, vol. 45.
Jang M et al., Regioselective cross-coupling reactions and nucleophilic aromatic substitutions on a 5,7-dichloropyrido(4,3-d)pyrimidine scaffold, Tetrahedron Letters, (2006), 8917-8920, vol. 47.
Andoux J. et al., First functionalization by metallation of the pyridine moiety of pyridopyrimidin-4(3H)-ones. Diazines. Part 36, Tetrahedron, (2004) 4107--4123, vol. 60.
Xie, H-Z et al., Pharmacore modeling study on known Spleen tyrosine kinase inhibitors together with virtual screening for identifying novel inhibitors, Bioorganic & Medicinal Chemistry Letters, (2009), 1944-1949, vol. 19.
Wong, BR et al., Targeting Syk as a treatment for allergic and autoimmune disorders, Expert Opinion, Investig. Drugs, (2004), 743-762, vol. 13.

* cited by examiner

Primary Examiner — Jeffrey H Murray
(74) Attorney, Agent, or Firm — Daniel E. Raymond; Genomics Institute of the Novartis Research Foundation

(57) ABSTRACT

Provided herein are a novel class of compounds of Formula (I),

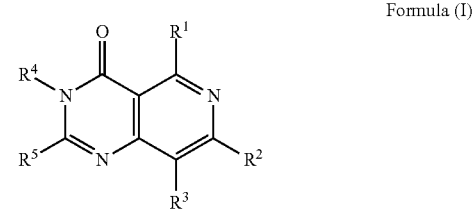

Formula (I)

pharmaceutical compositions comprising such compounds and methods of using such compounds to treat or prevent diseases or disorders associated with abnormal or deregulated Syk kinase activity.

23 Claims, No Drawings

COMPOUNDS AND COMPOSITIONS AS SYK KINASE INHIBITORS

CROSS-REFERENCE TO RELATED APPLICATIONS

This application is a 371 U.S. national phase application of international application number PCT/US2010/043953 filed 30 Jul. 2010, which application claims the benefit of priority under 35 U.S.C. §119(e) to U.S. Provisional Patent Application No. 61/229,951, filed 30 Jul. 2009. The disclosures of which are incorporated herein by reference in their entirety and for all purposes.

FIELD OF THE INVENTION

The invention relates to protein kinase inhibitors, and methods of using such compounds.

BACKGROUND OF THE INVENTION

Protein kinases (PK) are a large set of structurally related phosphoryl transferases having highly conserved structures and catalytic functions. Protein kinases are enzymatic components of the signal transduction pathways which catalyze the transfer of the terminal phosphate from ATP to the hydroxy group of tyrosine, serine and/or threonine residues of proteins, and are therefore categorized into families by the substrates they phosphorylate: Protein Tyrosine Kinases (PTK), and Protein Serine/Threonine Kinases.

Protein kinases play a critical role in the control of cell growth and differentiation and are responsible for the control of a wide variety of cellular signal transduction processes, wherein protein kinases are key mediators of cellular signals leading to the production of growth factors and cytokines. The overexpression or inappropriate expression of normal or mutant protein kinases plays a significant role in the development of many diseases and disorders including, central nervous system disorders such as Alzheimer's, inflammatory disorders such as arthritis, bone diseases such as osteoporosis, metabolic disorders such as diabetes, blood vessel proliferative disorders such as angiogenesis, autoimmune diseases such as rheumatoid arthritis, ocular diseases, cardiovascular disease, atherosclerosis, cancer, thrombosis, psoriasis, restenosis, schizophrenia, pain sensation, transplant rejection and infectious diseases such as viral, and fungal infections.

Examples of protein-tyrosine kinases include, but are not limited to, Irk, IGFR-1, Zap-70, Bmx, Btk, CHK (Csk homologous kinase), CSK (C-terminal Src Kinase), Itk-1, Src (c-Src, Lyn, Fyn, Lck, Hck, Yes, Blk, Fgr and Frk), Syk, Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-I or c-MET), PDGFR ($\alpha$ and $\beta$), Tie-1, Tie-2 (also Tek-1 or Tek), VEGFR1 (also FLT-1), VEGFR2 (also KDR), FLT-3, FLT-4, c-KIT, JAK1, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1).

Examples of protein-serine/threonine kinases include, but are not limited to, Ark, ATM (1-3), CamK (1-IV), CamKK, Chk1 and 2 (Checkpoint kinases), CK1, CK2, Erk, IKK-I (also IKK-ALPHA or CHUK), IKK-2 (also IKK-BETA), Ilk, Jnk (1-3), LimK (1 and 2), MLK3Raf (A, B, and C), CDK (1-10), PKC (including all PKC subtypes), Plk (1-3), NIK, Pak (1-3), PDK1, PKR, RhoK, RIP, RIP-2, GSK3 ($\alpha$ and $\beta$) PKA, P38, Erk (1-3), PKB (including all PKB subtypes) (also AKT-1, AKT-2, AKT-3 or AKT3-1), IRAK1, FRK, SGK, TAK1 or Tp1-2 (also COT).

SUMMARY OF THE INVENTION

Provided herein are compounds and pharmaceutical compositions thereof, which are useful as Syk kinase inhibitors.

In one aspect provided herein are compounds having the structure of Formula (I), and the pharmaceutically acceptable salts, pharmaceutically acceptable solvates (e.g. hydrates), the N-oxide derivatives, individual isomers and mixture of isomers thereof:

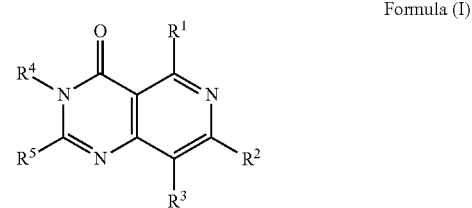

Formula (I)

wherein:

$R^1$ is —$NR^6R^7$, —$O(CR^9R^9)_nR^{11}$, —$O(CR^9R^9)_mR^{14}$, $R^{15}$, phenyl, a 5 or 6 membered heteroaryl containing 1 to 3 heteroatoms independently selected from N, O and S, or a 4-6 membered heterocycloalkyl containing 1 to 2 heteroatoms independently selected from N, O and S, or $R^1$ is selected from phenyl and a 5 or 6 membered heteroaryl containing 1 to 3 heteroatoms independently selected from N, O and S, each of which is substituted with 1 to 3 substituents independently selected from hydroxyl, hydroxyl-$C_1$-$C_6$alkyl and $R^{10}$;

or $R^1$ is a 4-6 membered heterocycloalkyl containing 1 to 2 heteroatoms independently selected from N, O and S, substituted with 1 to 3 substituents independently selected from halogen, hydroxyl, hydroxyl-$C_1$-$C_6$alkyl, —$(CR^9R^9)_nOR^9$, =N—OH, =N—$OR^9$, —$(CR^9R^9)_m$ $SR^9$, —$(CR^9R^9)_mOS(O)_2N(R^9)_2$, —$(CR^9R^9)_nS(O)_2N$ $(R^9)_2$, —$(CR^9R^9)_mN_3$, —$(CR^9R^9)_nNR^9R^9$, —$(CR^9R^9)_n$ $C(O)NR^9R^9$ and —$(CR^9R^9)_nC(O)OR^9$;

$R^2$ is selected from —$NR^9(CR^9R^9)_nR^{10}$, $R^{15}$, phenyl and a 5, 6 or 9 membered heteroaryl containing 1 to 3 heteroatoms independently selected from N, O and S;

or $R^2$ is selected from phenyl and a 5, 6, or 9 membered heteroaryl containing 1 to 3 heteroatoms independently selected from N, O and S, each of which is substituted with 1 to 3 substituents independently selected from halogen, $R^{10}$, $R^{15}$, hydroxyl-$C_1$-$C_6$alkyl —CN, —$OR^9$, —$C(O)OR^9$, —$N(R^9)_2$, —$NR^9(CR^9R^9)_nR^{10}$, —$NR^9$ $(CR^9R^9)_mR^{14}$, —$N(R^9)C(O)R^9$, —$(CR^9R^9)_mR^{10}$, —$(CR^9R^9)_mC(O)R^{10}$, —$O(CR^9R^9)_nR^{10}$, —$C(O)$ $(CR^9R^9)_mR^{14}$, —$(CR^9R^9)_nR^{14}$, —$(CR^9R^9)_mR^{14}$, —$C(R^9R^{36}R^{36})$, —$C(R^9R^9R^{14})$, —$O(CR^9R^9)_mR^{14}$, —$NR^9S(O)_2R^9$, —$S(O)_2R^9$, —$S(O)_2R^{10}$, —$S(O)_2N$ $(R^9R^{10})$, —$S(O)_2N(R^9)_2$, —$S(O)_2(CR^9R^9)_mR^{10}$, —$S(O)_2NR^9(CR^9R^9)_mR^{14}$, —$S(O)_2(CR^9R^9)_mR^{14}$, —$(CR^9R^9)_nR^{15}$, $C_1$-$C_6$alkyl and

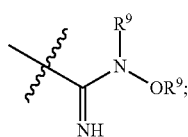

R$^4$ is H, C$_1$-C$_6$alkyl, hydroxyl-C$_1$-C$_6$alkyl, deuterated C$_1$-C$_6$alkyl or C$_1$-C$_6$haloalkyl;

R$^3$ and R$^5$ are independently selected from H or C$_1$-C$_6$alkyl;

R$^6$ is H, —(CR$^9$R$^9$)$_m$R$^{14}$, —(CR$^9$R$^9$)$_n$R$^{10}$, —(CR$^9$R$^9$)$_n$R$^{15}$, —O(CR$^9$R$^9$)$_n$R$^{10}$, —(CR$^9$R$^9$)$_n$(CR$^9$R$^{14}$)$_n$R$^{10}$, R$^{15}$; C$_1$-C$_6$ alkyl, C$_1$-C$_6$alkyl substituted with 1-4 hydroxyl groups, C$_3$-C$_8$cycloalkyl, phenyl, a 5, 6 or 9 membered heteroaryl containing 1 to 3 heteroatoms independently selected from N, O and S, or a 4-6 membered heterocycloalkyl containing 1 to 2 heteroatoms independently selected from N, O and S;

or R$^6$ is selected from phenyl, a 5, 6, or 9 membered heteroaryl containing 1 to 3 heteroatoms independently selected from N, O and S, a 4-6 membered heterocycloalkyl containing 1 to 2 heteroatoms independently selected from N, O and S, and a C$_3$-C$_8$cycloalkyl, each of which is substituted with 1 to 3 substituents independently selected from C$_1$-C$_6$alkyl, hydroxyl, hydroxyl-C$_1$-C$_6$alkyl, —CN, —OR$^9$, —C(O)OR$^9$, tetrazole, —C(O)N(R$^9$)$_2$, —S(O)$_2$R$^9$, —(CR$^9$R$^9$)$_m$R$^{14}$, —NR$^9$S(O)$_2$R$^9$, —N(R$^9$)$_2$ and —C(O)(CR$^9$R$^9$)$_m$R$^{14}$;

R$^7$ is H or C$_1$-C$_6$ alkyl;

R$^8$ is H or C$_1$-C$_6$ alkyl;

each R$^9$ is independently selected from H and C$_1$-C$_6$alkyl;

R$^{10}$ is phenyl, a C$_3$-C$_8$cycloalkyl, a 5, 6 or 9 membered heteroaryl containing 1 to 3 heteroatoms independently selected from N, O and S, or a 4-6 membered heterocycloalkyl containing 1 to 2 heteroatoms independently selected from N, O and S;

or R$^{10}$ is selected from phenyl, a C$_3$-C$_8$cycloalkyl, 5, 6 or 9 membered heteroaryl containing 1 to 3 heteroatoms independently selected from N, O and S, and a 4-8 membered heterocycloalkyl containing 1 to 2 heteroatoms independently selected from N, O and S, each of which is substituted with 1 to 3 substituents independently selected from halogen, —C$_1$-C$_6$alkyl, hydroxyl, benzyl, hydroxyl-C$_1$-C$_6$alkyl, C$_3$-C$_8$cycloalkyl, —OR$^9$, —C(O)OR$^9$, —N(R$^9$)$_2$, —C(O)(CR$^9$R$^9$)$_n$(R$^9$)$_2$, —C(O)(CR$^9$R$^9$)$_n$OR$^9$, —(CR$^9$R$^9$)$_n$R$^{14}$, —(CR$^9$R$^9$)$_m$R$^{14}$, —S(O)$_2$R$^9$, —(CR$^9$R$^9$)$_n$S(O)$_2$R$^9$ and R$^{13}$;

R$^{11}$ is C$_1$-C$_6$alkyl, C$_3$-C$_8$cycloalkyl, phenyl, a 5 or 6 membered heteroaryl containing 1 to 3 heteroatoms independently selected from N, O and S, or a 4-6 membered heterocycloalkyl containing 1 to 2 heteroatoms independently selected from N, O and S;

or R$^{11}$ is selected from C$_3$-C$_8$cycloalkyl, phenyl, a 5 or 6 membered heteroaryl containing 1 to 3 heteroatoms independently selected from N, O and S, and a 4-6 membered heterocycloalkyl containing 1 to 2 heteroatoms independently selected from N, O and S, each of which is substituted with 1 to 3 substituents independently selected from hydroxyl, —C$_1$-C$_6$alkyl, hydroxyl-C$_1$-C$_6$alkyl and —(CR$^9$R$^9$)$_n$R$^{14}$;

R$^{13}$ is halo-substituted C$_1$-C$_6$alkyl, C$_3$-C$_8$cycloalkyl, or a 4-6 membered heterocycloalkyl containing 1 to 2 heteroatoms independently selected from N, O and S;

R$^{14}$ is H, C$_1$-C$_6$alkyl, C$_1$-C$_6$haloalkyl, —OR$^9$, —N(R$^9$)$_2$, —C(O)N(R$^9$)$_2$, —C(O)R$^9$, —C(O)OR$^9$—OC(O)R$^{13}$, —CN, —S(O)$_2$R$^9$, —N(R$^9$)S(O)$_2$R$^9$, —NR$^9$C(O)(R$^9$), —N(R$^9$)C(O)(CR$^9$R$^9$)$_n$OR$^9$, —N(R$^9$)(CR$^9$R$^9$)$_m$OR$^9$, and —N(R$^9$)(CR$^9$R$^9$)$_n$R$^{10}$;

R$^{15}$ is

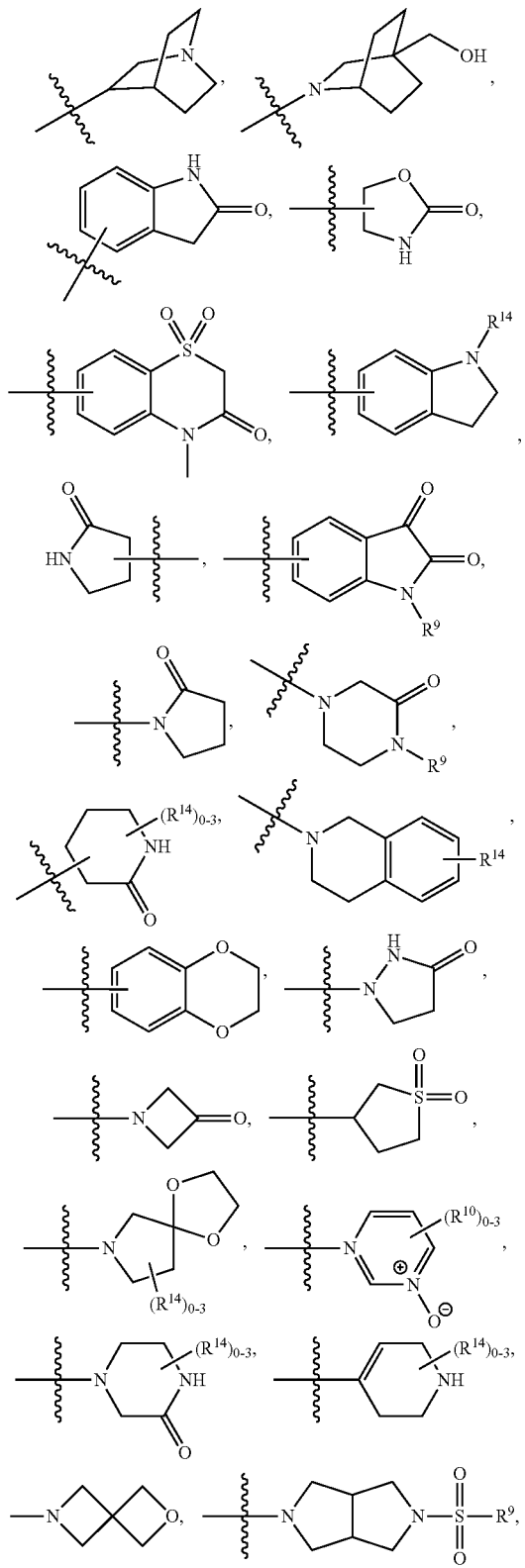

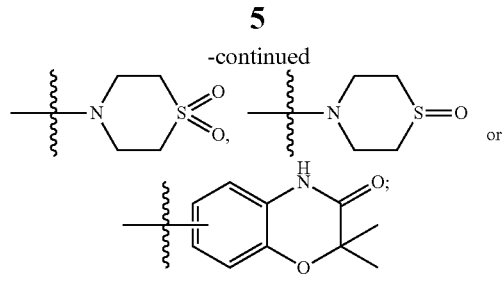

each $R^{36}$ is independently hydroxyl or $C_1$-$C_6$haloalkyl, each m is independently 1, 2, 3, 4, 5 or 6, and each n is independently 0, 1, 2, 3, 4, 5 or 6.

In certain embodiments of such compounds of Formula (I), $R^1$ is —$NR^6R^7$. In other embodiments of such compounds of Formulas (I), $R^7$ is $C_1$-$C_6$alkyl.

In certain embodiments of the aforementioned compounds of Formula (I), $R^6$ is phenyl, a 5, 6 or 9 membered heteroaryl containing 1 to 3 heteroatoms independently selected from N, O and S, a 4-6 membered heterocycloalkyl containing 1 to 2 heteroatoms independently selected from N, O and S, $C_3$-$C_8$cycloalkyl or $R^{15}$;

or $R^6$ is selected from phenyl, a 5, 6, or 9 membered heteroaryl containing 1 to 3 heteroatoms independently selected from N, O and S, a 4-6 membered heterocycloalkyl containing 1 to 2 heteroatoms independently selected from N, O and S, and a $C_3$-$C_8$cycloalkyl, each of which is substituted with 1 to 3 substituents independently selected from $C_1$-$C_6$alkyl, hydroxyl, hydroxyl-$C_1$-$C_6$alkyl, —CN, —$OR^9$, —$C(O)OR^9$, tetrazole, —$C(O)N(R^9)_2$, —$S(O)_2R^9$, —$(CR^9R^9)_mR^{14}$, —$NR^9S(O)_2R^9$, —$N(R^9)_2$ and —$C(O)(CR^9R^9)_mR^{14}$;

each m is independently 0, 1, 2, 3 or 4, and each n is independently 0, 1, 2, 3 or 4.

In certain embodiments of the aforementioned compounds of Formula (I), $R^6$ is

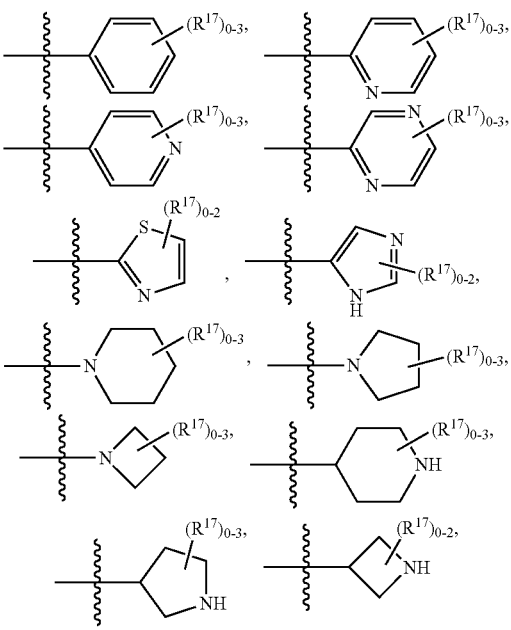

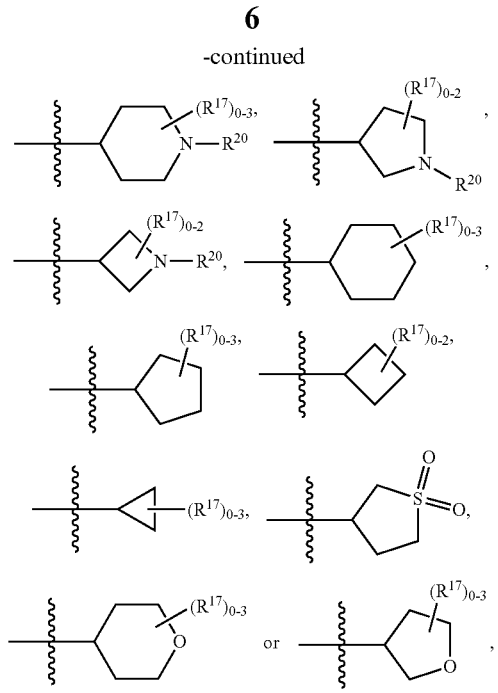

and each $R^{17}$ is independently selected from $C_1$-$C_6$alkyl, hydroxyl, hydroxyl-$C_1$-$C_6$alkyl, —CN, —$OR^9$, —$C(O)OR^9$, tetrazole, —$C(O)N(R^9)_2$, —$S(O)_2R^9$, —$(CR^9R^9)_m$ $R^{14}$, —$NR^9S(O)_2R^9$, —$N(R^9)_2$ and —$C(O)(CR^9R^9)_mR^{14}$ $R^{20}$ is H, $C_1$-$C_6$alkyl, —$(CR^9R^9)_mR^{14}$ or hydroxyl-$C_1$-$C_6$alkyl;

each m is independently 0, 1, 2, 3 or 4, and each n is independently 0, 1, 2, 3 or 4.

In certain embodiments of the aforementioned compounds of Formula (I), $R^6$ is —$(CR^{12}R^{12})_mR^{14}$.

In certain embodiments of the aforementioned compounds of Formula (I), $R^{14}$ is selected from H, halogen, hydroxyl, hydroxyl-$C_1$-$C_6$alkyl, $C_1$-$C_6$alkyl, $C_1$-$C_6$haloalkyl, —$OR^9$, —$N(R^9)_2$, —$C(O)N(R^9)_2$, —$C(O)R^9$, —$C(O)OR^9$, —$S(O)_2R^9$, —$N(R^9)S(O)_2R^9$, —$NR^9C(O)(R^9)$, —$N(R^9)C(O)(CR^9R^9)_nOR^9$, —$N(R^9)(CR^9R^9)_mOR^9$, and —$N(R^9)(CR^9R^9)_nR^{10}OR^{13}$, —$(CR^{12}R^{12})_nOR^{13}$, —$C(O)R^{10}$, —$OC(O)R^{13}$, —$C(O)OR^{13}$, —$N(R^{12})_2$, —CN, —$S(O)_2R^{13}$, —$N(R^{12}R^{10})$, —$(CR^{12}R^{12})_nN(R^{12})_2$, —$C(O)N(R^{12})_2$, —$N(R^{12})C(O)(CR^{12}R^{12})_nOR^{13}$, —$N(R^{12})C(O)OR^{13}$ and —$N(R^{12})(CR^{12}R^{12})_nOR^{13}$.

In certain embodiments of the aforementioned compounds of Formula (I), $R^1$ is a 4-6 membered heterocycloalkyl containing 1 to 2 heteroatoms independently selected from N, O and S, or $R^1$ is a 4-6 membered heterocycloalkyl containing 1 to 2 heteroatoms independently selected from N, O and S, substituted with 1 to 3 substituents independently selected from halogen, hydroxyl, hydroxyl-$C_1$-$C_6$alkyl, —$(CR^9R^9)_nOR^9$, =N—OH, =N—$OR^9$, —$(CR^9R^9)_m$ $SR^9$, —$(CR^9R^9)_mOS(O)_2N(R^9)_2$, —$(CR^9R^9)_nS(O)_2N(R^9)_2$, —$(CR^9R^9)_mN_3$, —$(CR^9R^9)_nNR^9R^9$, —$(CR^9R^9)_nC(O)NR^9R^9$ and —$(CR^9R^9)_nC(O)OR^9$.

In certain embodiments of the aforementioned compounds of Formula (I), $R^1$ is selected from

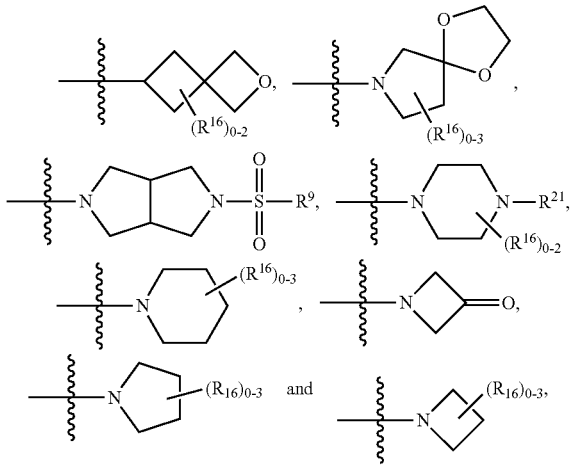

wherein
- each $R^{16}$ is independently selected from halogen, hydroxyl, hydroxyl-$C_1$-$C_6$alkyl, —$(CR^9R^9)_nOR^9$, =N—OH, =N—$OR^9$, —$(CR^9R^9)_mSR^9$, —$(CR^9R^9)_mOS(O)_2N(R^9)_2$, —$(CR^9R^9)_nS(O)_2N(R^9)_2$, —$(CR^9R^9)_mN_3$, —$(CR^9R^9)_nNR^9R^9$, —$(CR^9R^9)_nC(O)NR^9R^9$ and —$(CR^9R^9)_nC(O)OR^9$, and
- $R^{21}$ is H, hydroxyl-$C_1$-$C_6$alkyl, —$(CR^9R^9)_mOR^9$, —$(CR^9R^9)_mSR^9$, —$(CR^9R^9)_mOS(O)_2N(R^9)_2$, —$(CR^9R^9)_nS(O)_2N(R^9)_2$, —$(CR^9R^9)_mN_3$, —$(CR^9R^9)_nNR^9R^9$, —$(CR^9R^9)_nC(O)NR^9R^9$ and —$(CR^9R^9)_nC(O)OR^9$.

In certain embodiments of the aforementioned compounds of Formula (I), $R^1$ is selected from

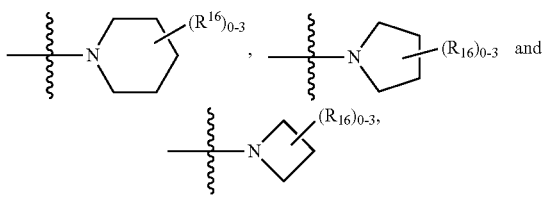

wherein each $R^{16}$ is independently selected from halogen, hydroxyl, hydroxyl-$C_1$-$C_6$alkyl, —$(CR^9R^9)_nOR^9$, =N—OH, =N—$OR^9$, —$(CR^9R^9)_mSR^9$, —$(CR^9R^9)_mOS(O)_2N(R^9)_2$, —$(CR^9R^9)_nS(O)_2N(R^9)_2$, —$(CR^9R^9)_mN_3$, —$(CR^9R^9)_nNR^9R^9$, —$(CR^9R^9)_nC(O)NR^9R^9$ and —$(CR^9R^9)_n C(O)OR^9$.

In certain embodiments of the aforementioned compounds of Formula (I),
- $R^1$ is a phenyl or a 5 or 6 membered heteroaryl containing 1 to 3 heteroatoms independently selected from N, O and S,
- or $R^1$ is a phenyl or a 5 or 6 membered heteroaryl containing 1 to 3 heteroatoms independently selected from N, O and S, each of which is substituted with 1 to 3 substituents independently selected from hydroxyl, hydroxyl-$C_1$-$C_6$alkyl and $R^{10}$.

In certain embodiments of the aforementioned compounds of Formula (I), $R^1$ is

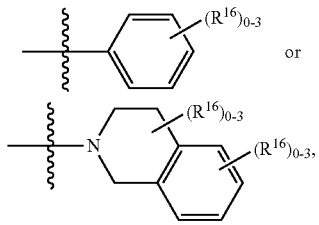

wherein each $R^{16}$ is independently selected from hydroxyl, hydroxyl-$C_1$-$C_6$alkyl and $R^{10}$.

In certain embodiments of the aforementioned compounds of Formula (I),
- $R^2$ is a phenyl or a 5, 6, or 9 membered heteroaryl containing 1 to 3 heteroatoms independently selected from N, O and S,
- or $R^2$ is selected from a phenyl and a 5, 6, or 9 membered heteroaryl containing 1 to 3 heteroatoms independently selected from N, O and S, each of which is substituted with 1 to 3 substituents independently selected from halogen, $R^{10}$, $R^{15}$, hydroxyl-$C_1$-$C_6$alkyl —CN, —$OR^9$, —$C(O)OR^9$, —$N(R^9)_2$, —$NR^9(CR^9R^9)_nR^{10}$, —$NR^9(CR^9R^9)_mR^{14}$, —$N(R^9)C(O)R^9$, —$(CR^9R^9)_mR^{10}$, —$(CR^9R^9)_mC(O)R^{10}$, —$O(CR^9R^9)_nR^{10}$, —$C(O)(CR^9R^9)_mR^{14}$, —$(CR^9R^9)_nR^{14}$, —$(CR^9R^9)_mR^{14}$, —$C(R^{36}R^{36})$, —$C(R^9R^9R^{14})$, —$O(CR^9R^9)_mR^{14}$, —$NR^9S(O)_2R^9$, —$S(O)_2R^9$, —$S(O)_2R^{10}$, —$S(O)_2N(R^9R^{10})$, —$S(O)_2N(R^9)_2$, —$S(O)_2(CR^9R^9)_mR^{10}$, —$S(O)_2NR^9(CR^9R^9)_mR^{14}$, —$S(O)_2(CR^9R^9)_mR^{14}$, —$(CR^9R^9)_nR^{15}$, $C_1$-$C_6$alkyl and

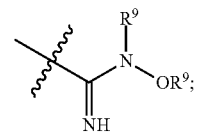

- each m is independently 0, 1, 2, 3 or 4, and
- each n is independently 0, 1, 2, 3 or 4.

In certain embodiments of the aforementioned compounds of Formula (I), $R^2$ is selected from

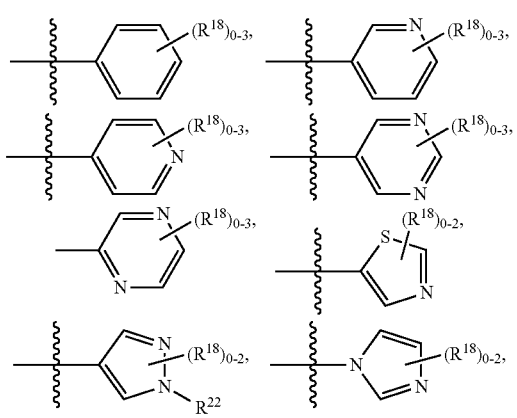

-continued

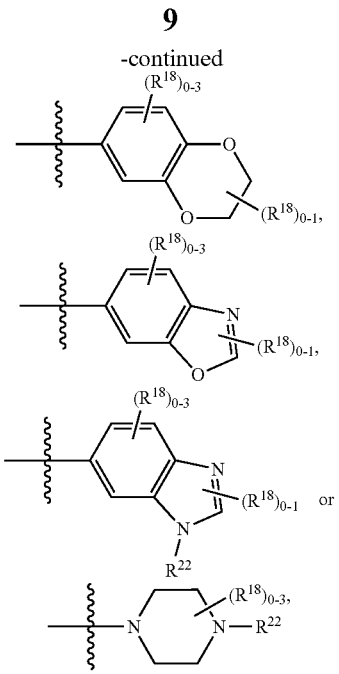

wherein
each R$^{18}$ is independently selected from halogen, R$^{10}$, R$^{15}$, hydroxyl-C$_1$-C$_6$alkyl —CN, —OR$^9$, —C(O)OR$^9$, —N(R$^9$)$_2$, —NR$^9$(CR$^9$R$^9$)$_n$R$^{10}$, —NR$^9$(CR$^9$R$^9$)$_m$R$^{14}$, —N(R$^9$)C(O)R$^9$, —(CR$^9$R$^9$)$_m$R$^{10}$, —(CR$^9$R$^9$)$_m$C(O)R$^{10}$, —O(CR$^9$R$^9$)$_n$R$^{10}$, —C(O)(CR$^9$R$^9$)$_m$R$^{14}$, —(CR$^9$R$^9$)$_n$R$^{14}$, —C(R$^9$R$^{36}$R$^{36}$), —C(R$^9$R$^9$R$^{14}$), —O(CR$^9$R$^9$)$_m$R$^{14}$, —NR$^9$S(O)$_2$R$^9$, —S(O)$_2$R$^9$, —S(O)$_2$ R$^{10}$, —S(O)$_2$N(R$^9$R$^{10}$), —S(O)$_2$N(R$^9$)$_2$, —S(O)$_2$(CR$^9$R$^9$)$_m$R$^{10}$, —S(O)$_2$NR$^9$(CR$^9$R$^9$)$_m$R$^{14}$, —S(O)$_2$(CR$^9$R$^9$)$_m$R$^{14}$, —(CR$^9$R$^9$)$_n$R$^{15}$, C$_1$-C$_6$alkyl and

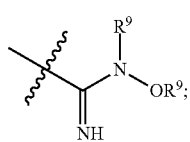

R$^{22}$ is H, C$_1$-C$_6$alkyl, —(CR$^9$R$^9$)$_m$R$^{14}$ or hydroxyl-C$_1$-C$_6$alkyl;
each m is independently 0, 1, 2, 3 or 4, and
each n is independently 0, 1, 2, 3 or 4.

In certain embodiments of the aforementioned compounds of Formula (I), is —NR$^8$(CR$^9$R$^9$)$_n$R$^{10}$ and n is 0, 1, 2, 3 or 4.

In certain embodiments of the aforementioned compounds of Formula (I),
R$^{10}$ is phenyl, a C$_3$-C$_8$cycloalkyl, a 5, 6 or 9 membered heteroaryl containing 1 to 3 heteroatoms independently selected from N, O and S, or a 4-6 membered heterocycloalkyl containing 1 to 2 heteroatoms independently selected from N, O and S;
or R$^{10}$ is selected from phenyl, a C$_3$-C$_8$cycloalkyl, 5, 6 or 9 membered heteroaryl containing 1 to 3 heteroatoms independently selected from N, O and S, and a 4-8 membered heterocycloalkyl containing 1 to 2 heteroatoms independently selected from N, O and S, each of which is substituted with 1 to 3 substituents independently selected from halogen, —C$_1$-C$_6$alkyl, hydroxyl, benzyl, hydroxyl-C$_1$-C$_6$alkyl, C$_3$-C$_8$cycloalkyl, —OR$^9$, —C(O)OR$^9$, —N(R$^9$)$_2$, —C(O)(CR$^9$R$^9$)$_n$N(R$^9$)$_2$, —C(O)(CR$^9$R$^9$)$_n$OR$^9$, —(CR$^9$R$^9$)$_n$R$^{14}$, —(CR$^9$R$^9$)$_m$R$^{14}$, —S(O)$_2$R$^9$, (CR$^9$R$^9$)$_n$S(O)$_2$R$^9$ and R$^{13}$.

In certain embodiments of the aforementioned compounds of Formula (I), R$^{10}$ is selected from

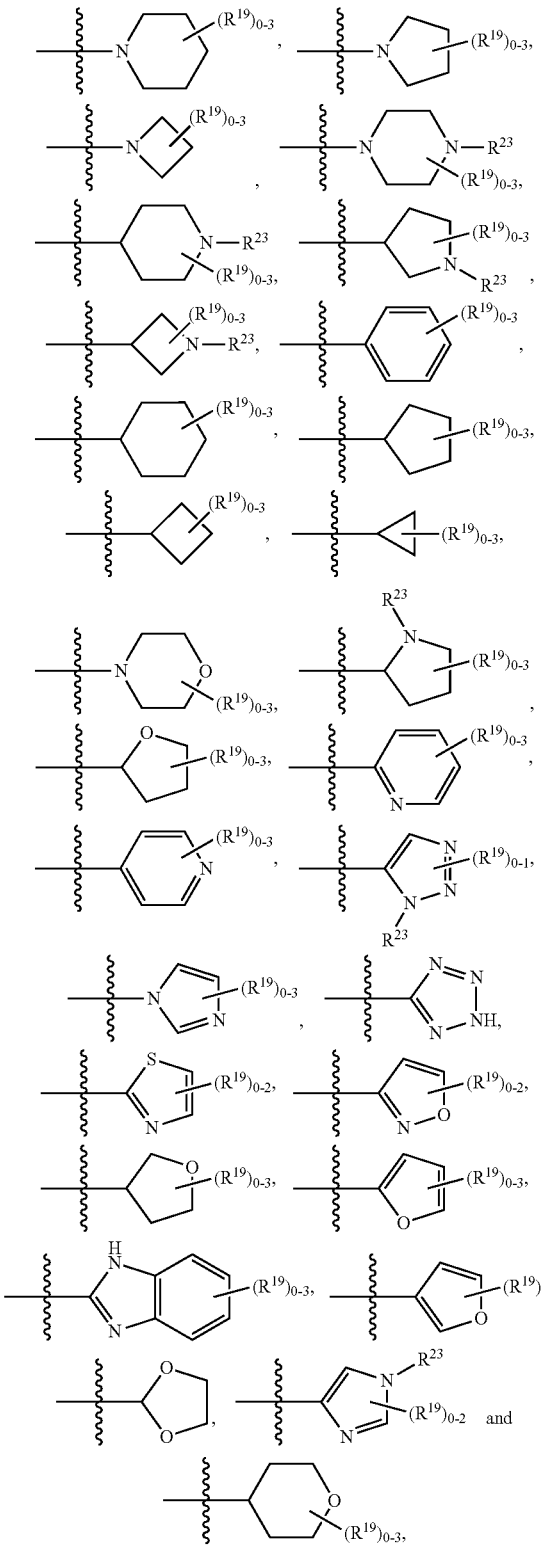

wherein;
    each $R^{19}$ is independently selected from halogen, —$C_1$-$C_6$alkyl, hydroxyl, benzyl, hydroxyl-$C_1$-$C_6$alkyl, $C_3$-$C_8$cycloalkyl, —$OR^9$, —$C(O)OR^9$, —$N(R^9)_2$, —$C(O)(CR^9R^9)_n N(R^9)_2$, —$C(O)(CR^9R^9)_n OR^9$, —$(CR^9R^9)_n R^{14}$, —$S(O)_2 R^9$, —$(CR^9R^9)_n S(O)_2 R^9$ and $R^{13}$;
    $R^{23}$ is H, $C_1$-$C_6$alkyl, —$(CR^9R^9)_m R^{14}$ or hydroxyl-$C_1$-$C_6$alkyl;
    each m is independently 0, 1, 2, 3 or 4, and
    each n is independently 0, 1, 2, 3 or 4.

In certain embodiments of the aforementioned compounds of Formula (I), $R^{10}$ is —$(CR^{12}R^{12})_n R^{11}$.

In certain embodiments of the aforementioned compounds of Formula (I),
    $R^{11}$ is $C_1$-$C_6$alkyl, phenyl, a 5, 6, 9, 10 or 14 membered heteroaryl containing 1 to 3 heteroatoms independently selected from N, O and S, or a 4-8 membered heterocycloalkyl containing 1 to 2 heteroatoms independently selected from N, O and S;
    or $R^{11}$ is selected from $C_3$-$C_8$cycloalkyl, and a 4-8 membered heterocycloalkyl containing 1 to 2 heteroatoms independently selected from N, O and S, each of which is substituted with 1 to 3 substituents independently selected from hydroxyl, —$C_1$-$C_6$alkyl, hydroxyl-$C_1$-$C_6$alkyl and —$(CR^9R^9)_n R^{14}$.

In certain embodiments of the aforementioned compounds of Formula (I), $R^3$ and $R^5$ are H.

In certain embodiments of the aforementioned compounds of Formula (I), $R^4$ is $C_1$-$C_6$alkyl, —$CD_3$, deuterated $C_1$-$C_6$alkyl or $C_1$-$C_6$haloalkyl. In certain embodiments of the aforementioned compounds of Formula (I), $R^4$ is $C_1$-$C_6$alkyl or $C_1$-$C_6$haloalkyl. In certain embodiments of the aforementioned compounds of Formula (I), $R^4$ is hydroxyl-$C_1$-$C_6$alkyl. In certain embodiments of the aforementioned compounds of Formula (I), $R^4$ is —$CD_3$.

In certain embodiments of the aforementioned compounds of Formula (I), $R^7$ is $C_1$-$C_6$alkyl.

In certain embodiments the compounds of Formula (I) are selected from: 5-[(3S)-3-(hydroxymethyl)pyrrolidin-1-yl]-3-methyl-7-[4-(methylamino)phenyl-3H,4H-pyrido[4,3-d]pyrimidin-4-one; 5-(cyclopropylamino)-7-(3-methanesulfonyl-4-{[2-(pyrrolidin-1-yl)ethyl]amino}phenyl)-3-methyl-3H,4H-pyrido[4,3-d]pyrimidin-4-one; 7-(3-methanesulfonyl-4-{[2-(pyrrolidin-1-yl)ethyl]amino}phenyl)-3-methyl-5-(propan-2-ylamino)-3H,4H-pyrido[4,3-d]pyrimidin-4-one; 5-(cyclopropylamino)-7-[3-methanesulfonyl-4-(methylamino)phenyl]-3-methyl-3H,4H-pyrido[4,3-d]pyrimidin-4-one; 5-(cyclopropylamino)-7-{3-methanesulfonyl-4-[(2-methoxyethyl)amino]phenyl}-3-methyl-3H,4H-pyrido[4,3-d]pyrimidin-4-one; 7-{3-methanesulfonyl-4-[(2-methoxyethyl)amino]phenyl}-3-methyl-5-(propan-2-ylamino)-3H,4H-pyrido[4,3-d]pyrimidin-4-one; 5-(cyclopropylamino)-7-{4-[(2-hydroxyethyl)amino]-3-methanesulfonylphenyl}-3-methyl-3H,4H-pyrido[4,3-d]pyrimidin-4-one; 7-{4-[(2-hydroxyethyl)amino]-3-methanesulfonylphenyl}-3-methyl-5-(propan-2-ylamino)-3H,4H-pyrido[4,3-d]pyrimidin-4-one; 5-(cyclopropylamino)-7-[4-(dimethylamino)-3-methanesulfonylphenyl]-3-methyl-3H,4H-pyrido[4,3-d]pyrimidin-4-one; 7-[4-(dimethylamino)-3-methanesulfonylphenyl]-3-methyl-5-(propan-2-ylamino)-3H,4H-pyrido[4,3-d]pyrimidin-4-one; 5-(cyclopropylamino)-7-{4-[4-(2-hydroxyethyl)piperazin-1-yl]-3-methanesulfonylphenyl}-3-methyl-3H,4H-pyrido[4,3-d]pyrimidin-4-one; 7-{4-[4-(2-hydroxyethyl)piperazin-1-yl]-3-methanesulfonylphenyl}-3-methyl-5-(propan-2-ylamino)-3H,4H-pyrido[4,3-d]pyrimidin-4-one; 5-[(2-methoxyethyl)amino]-3-methyl-7-{4-[(2R)-2-methylmorpholin-4-yl]phenyl}-3H,4H-pyrido[4,3-d]pyrimidin-4-one; 3-methyl-7-{4-[(2R)-2-methylmorpholin-4-yl]phenyl}-5-(propan-2-ylamino)-3H,4H-pyrido[4,3-d]pyrimidin-4-one; 7-(4-fluoro-3-methanesulfonylphenyl)-3-methyl-5-(propan-2-ylamino)-3H,4H-pyrido[4,3-d]pyrimidin-4-one; 5-(cyclopropylamino)-7-(4-fluoro-3-methanesulfonylphenyl)-3-methyl-3H,4H-pyrido[4,3-d]pyrimidin-4-one; 3-methyl-7-{[3-(4-methylpiperazin-1-yl)propyl]amino}-5-(propan-2-ylamino)-3H,4H-pyrido[4,3-d]pyrimidin-4-one; 3-methyl-7-[4-(morpholin-4-yl)phenyl]-5-{[(2S)-oxolan-2-ylmethyl]amino}-3H,4H-pyrido[4,3-d]pyrimidin-4-one; 5-(cyclopropylamino)-3-methyl-7-{4-[2-(morpholin-4-yl)ethoxy]phenyl}-3H,4H-pyrido[4,3-d]pyrimidin-4-one; 3-methyl-7-{4-[2-(morpholin-4-yl)ethoxy]phenyl}-5-(propan-2-ylamino)-3H,4H-pyrido[4,3-d]pyrimidin-4-one; 5-(cyclopropylamino)-3-methyl-7-{4-[2-(pyrrolidin-1-yl)ethoxy]phenyl}-3H,4H-pyrido[4,3-d]pyrimidin-4-one; 3-methyl-5-(propan-2-ylamino)-7-{4-[2-(pyrrolidin-1-yl)ethoxy]phenyl}-3H,4H-pyrido[4,3-d]pyrimidin-4-one; 5-(cyclopropylamino)-7-{3-methanesulfonyl-4-[(1-methylpiperidin-4-yl)amino]phenyl}-3-methyl-3H,4H-pyrido[4,3-d]pyrimidin-4-one; 7-{3-methanesulfonyl-4-[(1-methylpiperidin-4-yl)amino]phenyl}-3-methyl-5-(propan-2-ylamino)-3H,4H-pyrido[4,3-d]pyrimidin-4-one; 7-[3-methanesulfonyl-4-(methylamino)phenyl]-5-[(2-methoxyethyl)amino]-3-methyl-3H,4H-pyrido[4,3-d]pyrimidin-4-one; 7-{3-methanesulfonyl-4-[methyl(1-methylpiperidin-4-yl)amino]phenyl}-3-methyl-5-(propan-2-ylamino)-3H,4H-pyrido[4,3-d]pyrimidin-4-one; 5-(cyclopropylamino)-7-(3-methanesulfonyl-4-{[2-(4-methylpiperazin-1-yl)ethyl]amino}phenyl)-3-methyl-3H,4H-pyrido[4,3-d]pyrimidin-4-one; 7-(3-methanesulfonyl-4-{[2-(4-methylpiperazin-1-yl)ethyl]amino}phenyl)-3-methyl-5-(propan-2-ylamino)-3H,4H-pyrido[4,3-d]pyrimidin-4-one; 5-(cyclopropylamino)-7-(3-methanesulfonyl-4-{[3-(4-methylpiperazin-1-yl)propyl]amino}phenyl)-3-methyl-3H,4H-pyrido[4,3-d]pyrimidin-4-one; 7-(3-methanesulfonyl-4-{[3-(4-methylpiperazin-1-yl)propyl]amino}phenyl)-3-methyl-5-(propan-2-ylamino)-3H,4H-pyrido[4,3-d]pyrimidin-4-one; 3-methyl-7-[1-(2-methylpropyl)-1H-pyrazol-4-yl]-5-(propan-2-ylamino)-3H,4H-pyrido[4,3-d]pyrimidin-4-one; 3-methyl-7-[1-(3-methylbutyl)-1H-pyrazol-4-yl]-5-(propan-2-ylamino)-3H,4H-pyrido[4,3-d]pyrimidin-4-one; 3-methyl-5-(propan-2-ylamino)-7-(1-propyl-1H-pyrazol-4-yl)-3H,4H-pyrido[4,3-d]pyrimidin-4-one; 2-{4-[3-methyl-4-oxo-5-(propan-2-ylamino)-3H,4H-pyrido[4,3-d]pyrimidin-7-yl]-1H-pyrazol-1-yl}acetic acid; 7-[1-(2-methoxyethyl)-1H-pyrazol-4-yl]-3-methyl-5-(propan-2-ylamino)-3H,4H-pyrido[4,3-d]pyrimidin-4-one; 2-{4-[3-methyl-4-oxo-5-(propan-2-ylamino)-3H,4H-pyrido[4,3-d]pyrimidin-7-yl]-1H-pyrazol-1-yl}propanamide; 3-methyl-7-{1-[2-(morpholin-4-yl)ethyl]-1H-pyrazol-4-yl}-5-(propan-2-ylamino)-3H,4H-pyrido[4,3-d]pyrimidin-4-one; 3-methyl-7-{1-[2-(morpholin-4-yl)-2-oxoethyl]-1H-pyrazol-4-yl}-5-(propan-2-ylamino)-3H,4H-pyrido[4,3-d]pyrimidin-4-one; 7-{1-[2-(4-ethylpiperazin-1-yl)-2-oxoethyl]-1H-pyrazol-4-yl}-3-methyl-5-(propan-2-ylamino)-3H,4H-pyrido[4,3-d]pyrimidin-4-one; methyl 2-{4-[3-methyl-4-oxo-5-(propan-2-ylamino)-3H,4H-pyrido[4,3-d]pyrimidin-7-yl]-1H-pyrazol-1-yl}acetate; 3-methyl-7-(2-methyl-1,3-thiazol-5-yl)-5-(propan-2-ylamino)-3H,4H-pyrido[4,3-d]pyrimidin-4-one; 3-methyl-7-(4-methyl-1H-imidazol-1-yl)-5-(propan-2-ylamino)-3H,4H-pyrido[4,3-d]pyrimidin-4-one; 5-(cyclopropylamino)-3-methyl-7-[2-(morpholin-4-yl)pyrimidin-5-yl]-3H,4H-pyrido[4,3-d]pyrimidin-4-one; 3-methyl-7-[2-(morpholin-4-yl)pyrimidin-5-yl]-5-(propan-2-ylamino)-3H,4H-pyrido[4,3-d]pyrimidin-4-one; 2-{4-[5-(cyclopropylamino)-3-methyl-4-oxo-3H,4H-pyrido[4,3-d]pyrimidin-7-yl]phenyl}-2-methylpropanenitrile; 2-methyl-2-{4-[3-methyl-4-oxo-5-(propan-2-ylamino)-3H,4H-pyrido[4,3-d]pyrimidin-7-yl]phenyl}propanenitrile; 7-[4-(4-hydroxypiperidin-4-yl)phenyl]-3-methyl-5-(propan-2-ylamino)-3H,4H-pyrido[4,3-d]pyrimidin-4-one; 5-(cyclopropylamino)-7-(3-methanesulfonyl-4-{[2-(morpholin-4-yl)ethyl]amino}phenyl)-3-methyl-3H,4H-pyrido[4,3-d]pyrimidin-4-one; 7-(3-methanesulfonyl-4-{[2-(morpholin-4-yl)ethyl]amino}phenyl)-3-methyl-5-(propan-2-ylamino)-3H,4H-pyrido[4,3-d]pyrimidin-4-one; 5-(cyclopropylamino)-7-[3-methanesulfonyl-4-(morpholin-4-yl)phenyl]-3-methyl-3H,4H-pyrido[4,3-d]pyrimidin-4-one; 7-[3-methanesulfonyl-4-(morpholin-4-yl)phenyl]-3-methyl-5-(propan-2-ylamino)-3H,4H-pyrido[4,3-d]pyrimidin-4-one; 5-(cyclopropylamino)-7-[4-(4-ethylpiperazin-1-yl)-3-methanesulfonylphenyl]-3-methyl-3H,4H-pyrido[4,3-d]pyrimidin-4-one; 7-[4-(4-ethylpiperazin-1-yl)-3-methanesulfonylphenyl]-3-methyl-5-(propan-2-ylamino)-3H,4H-pyrido[4,3-d]pyrimidin-4-one; methyl 1-[3-methyl-4-oxo-5-(propan-2-ylamino)-3H,4H-pyrido[4,3-d]pyrimidin-7-yl]-1H-imidazole-4-carboxylate; 5-(cyclopropylamino)-7-{3-methanesulfonyl-4-[2-(pyrrolidin-1-yl)ethoxy]phenyl}-3-methyl-3H,4H-pyrido[4,3-d]pyrimidin-4-one; 7-{3-methanesulfonyl-4-[2-(pyrrolidin-1-yl)ethoxy]phenyl}-3-methyl-5-(propan-2-ylamino)-3H,4H-pyrido[4,3-d]pyrimidin-4-one; 5-(cyclopropylamino)-3-methyl-7-[4-(propane-2-sulfonyl)phenyl]-3H,4H-pyrido[4,3-d]pyrimidin-4-one; 3-methyl-5-(propan-2-ylamino)-7-[4-(propane-2-sulfonyl)phenyl]-3H,4H-pyrido[4,3-d]pyrimidin-4-one; 7-[3-methanesulfonyl-4-(morpholin-4-yl)phenyl]-3-methyl-5-{[(2S)-oxolan-2-ylmethyl]amino}-3H,4H-pyrido[4,3-d]pyrimidin-4-one; 7-[3-methanesulfonyl-4-(morpholin-4-yl)phenyl]-3-methyl-5-{[(5-methylfuran-2-yl)methyl]amino}-3H,4H-pyrido[4,3-d]pyrimidin-4-one; 5-(cyclopropylamino)-7-[3-methanesulfonyl-4-(pyrrolidin-1-yl)phenyl]-3-methyl-3H,4H-pyrido[4,3-d]pyrimidin-4-one; 7-[3-methanesulfonyl-4-(pyrrolidin-1-yl)phenyl]-3-methyl-5-(propan-2-ylamino)-3H,4H-pyrido[4,3-d]pyrimidin-4-one; 5-(cyclopropylamino)-7-[4-methanesulfonyl-3-(morpholin-4-yl)phenyl]-3-methyl-3H,4H-pyrido[4,3-d]pyrimidin-4-one; 7-[4-methanesulfonyl-3-(morpholin-4-yl)phenyl]-3-methyl-5-(propan-2-ylamino)-3H,4H-pyrido[4,3-d]pyrimidin-4-one; 5-(cyclopropylamino)-7-[3-(4-ethylpiperazin-1-yl)-4-methanesulfonylphenyl]-3-methyl-3H,4H-pyrido[4,3-d]pyrimidin-4-one; 7-[3-(4-ethylpiperazin-1-yl)-4-methanesulfonylphenyl]-3-methyl-5-(propan-2-ylamino)-3H,4H-pyrido[4,3-d]pyrimidin-4-one; 5-(cyclopropylamino)-7-(4-methanesulfonyl-3-{[2-(morpholin-4-yl)ethyl]amino}phenyl)-3-methyl-3H,4H-pyrido[4,3-d]pyrimidin-4-one; 7-(4-methanesulfonyl-3-{[2-(morpholin-4-yl)ethyl]amino}phenyl)-3-methyl-5-(propan-2-ylamino)-3H,4H-pyrido[4,3-d]pyrimidin-4-one; 7-[3-methanesulfonyl-4-(morpholin-4-yl)phenyl]-5-[(2-methoxyethyl)amino]-3-methyl-3H,4H-pyrido[4,3-d]pyrimidin-4-one; 7-[4-methanesulfonyl-3-(morpholin-4-yl)phenyl]-5-[(2-methoxyethyl)amino]-3-methyl-3H,4H-pyrido[4,3-d]pyrimidin-4-one; 7-(3-methanesulfonyl-4-{[2-(morpholin-4-yl)ethyl]amino}phenyl)-5-[(2-methoxyethyl)amino]-3-methyl-3H,4H-pyrido[4,3-d]pyrimidin-4-one; 7-[4-(4-ethylpiperazin-1-yl)-3-methanesulfonylphenyl]-5-[(2-methoxyethyl)amino]-3-methyl-3H,4H-pyrido[4,3-d]pyrimidin-4-one; 5-(cyclopropylamino)-3-methyl-7-{4-[2-(morpholin-4-yl)-2-oxoethyl]phenyl}-3H,4H-pyrido[4,3-d]pyrimidin-4-one; 3-methyl-7-{4-[2-(morpholin-4-yl)-2-oxoethyl]phenyl}-5-(propan-2-ylamino)-3H,4H-pyrido[4,3-d]pyrimidin-4-one; 5-(cyclopropylamino)-7-{4-[2-(4-ethylpiperazin-1-yl)-2-oxoethyl]phenyl}-3-methyl-3H,4H-pyrido[4,3-d]pyrimidin-4-one; 7-{4-[2-(4-ethylpiperazin-1-yl)-2-oxoethyl]phenyl}-3-methyl-5-(propan-2-ylamino)-3H,4H-pyrido[4,3-d]pyrimidin-4-one; 7-[3-methanesulfonyl-4-(methylamino)phenyl]-3-methyl-5-(propan-2-ylamino)-3H,4H-pyrido[4,3-d]pyrimidin-4-one; 3-methyl-7-[3-(4-methylpiperazin-1-yl)propoxy]-5-(propan-2-ylamino)-3H,4H-pyrido[4,3-d]pyrimidin-4-one; 5-[(2-hydroxyethyl)amino]-7-[3-methanesulfonyl-4-(methylamino)phenyl]-3-methyl-3H,4H-pyrido[4,3-d]pyrimidin-4-one; 5-[(3-hydroxypropyl)amino]-7-[3-methanesulfonyl-4-(methylamino)phenyl]-3-methyl-3H,4H-pyrido[4,3-d]pyrimidin-4-one; 7-[3-methanesulfonyl-4-(methylamino)phenyl]-3-methyl-5-[(3R)-oxolan-3-ylamino]-3H,4H-pyrido[4,3-d]pyrimidin-4-one; 5-[(3S)-3-(hydroxymethyl)pyrrolidin-1-yl]-7-[3-methanesulfonyl-4-(methylamino)phenyl]-3-methyl-3H,4H-pyrido[4,3-d]pyrimidin-4-one; 7-(3-methanesulfonyl-4-methoxyphenyl)-5-[(2-methoxyethyl)amino]-3-methyl-3H,4H-pyrido[4,3-d]pyrimidin-4-one; 5-(cyclopropylamino)-7-(3-methanesulfonyl-4-methoxyphenyl)-3-methyl-3H,4H-pyrido[4,3-d]pyrimidin-4-one; 7-(3-methanesulfonyl-4-methoxyphenyl)-3-methyl-5-(propan-2-ylamino)-3H,4H-pyrido[4,3-d]pyrimidin-4-one; 5-[(3-hydroxypropyl)amino]-7-{3-methanesulfonyl-4-[(1-methylpiperidin-4-yl)amino]phenyl}-3-methyl-3H,4H-pyrido[4,3-d]pyrimidin-4-one; 7-{3-methanesulfonyl-4-[(1-methylpiperidin-4-yl)amino]phenyl}-5-[(2-methoxyethyl)amino]-3-methyl-3H,4H-pyrido[4,3-d]pyrimidin-4-one; 7-{3-methanesulfonyl-4-[(1-methylpiperidin-4-yl)amino]phenyl}-3-methyl-5-[(3R)-oxolan-3-ylamino]-3H,4H-pyrido[4,3-d]pyrimidin-4-one; 5-(cyclopropylamino)-7-{4-[(3R)-3-hydroxypyrrolidin-1-yl]-3-methanesulfonylphenyl}-3-methyl-3H,4H-pyrido[4,3-d]pyrimidin-4-one; 7-{4-[(3R)-3-hydroxypyrrolidin-1-yl]-3-methanesulfonylphenyl}-3-methyl-5-(propan-2-ylamino)-3H,4H-pyrido[4,3-d]pyrimidin-4-one; 5-(cyclopropylamino)-7-{3-methanesulfonyl-4-[(3S)-pyrrolidin-3-ylamino]phenyl}-3-methyl-3H,4H-pyrido[4,3-d]pyrimidin-4-one; 7-{3-methanesulfonyl-4-[(3S)-pyrrolidin-3-ylamino]phenyl}-3-methyl-5-(propan-2-ylamino)-3H,4H-pyrido[4,3-d]pyrimidin-4-one; 5-(cyclopropylamino)-7-[3-methanesulfonyl-4-(pyrrolidin-3-ylamino)phenyl]-3-methyl-3H,4H-pyrido[4,3-d]pyrimidin-4-one; 7-[3-methanesulfonyl-4-(pyrrolidin-3-ylamino)phenyl]-3-methyl-5-(propan-2-ylamino)-3H,4H-pyrido[4,3-d]pyrimidin-4-one; 5-(cyclopropylamino)-7-{4-[(3S)-3-(hydroxymethyl)pyrrolidin-1-yl]-3-methanesulfonylphenyl}-3-methyl-3H,4H-pyrido[4,3-d]pyrimidin-4-one; 7-{4-[(3S)-3-(hydroxymethyl)pyrrolidin-1-yl]-3-methanesulfonylphenyl}-3-methyl-5-(propan-2-ylamino)-3H,4H-pyrido[4,3-d]pyrimidin-4-one; 5-(cyclopropylamino)-7-{4-[(3R)-3-(hydroxymethyl)pyrrolidin-1-yl]-3-methanesulfonylphenyl}-3-methyl-3H,4H-pyrido[4,3-d]pyrimidin-4-one; 7-{4-[(3R)-3-(hydroxymethyl)pyrrolidin-1-yl]-3-methanesulfonylphenyl}-3-methyl-5-(propan-2-ylamino)-3H,4H-pyrido[4,3-d]pyrimidin-4-one; 1-{4-[5-(cyclopropylamino)-3-methyl-4-oxo-3H,4H-pyrido[4,3-d]pyrimidin-7-yl]phenyl}pyrrolidin-2-one; 1-(4-{5-[(2-methoxyethyl)amino]-3-methyl-4-oxo-3H,4H-pyrido[4,3-d]pyrimidin-7-yl}phenyl)pyrrolidin-2-one; 1-{4-[3-methyl-4-oxo-5-(propan-2-ylamino)-3H,4H-pyrido[4,3-d]pyrimidin-7-yl]phenyl}pyrrolidin-2-one; 7-{4-[(3S)-3-(hydroxymethyl)pyrrolidin-1-yl]-3- methanesulfonylphenyl}-5-[(2-methoxyethyl)amino]-3-methyl-3H,4H-pyrido[4,3-d]pyrimidin-4-one; 7-{4-[(3R)-3-(hydroxymethyl)pyrrolidin-1-yl]-3-methanesulfonylphenyl}-5-[(2-methoxyethyl)amino]-3-methyl-3H,4H-pyrido[4,3-d]pyrimidin-4-one; 5-[(3S)-3-(hydroxymethyl)pyrrolidin-1-yl]-7-{3-methanesulfonyl-4-[(1-methylpiperidin-4-yl)amino]phenyl}-3-methyl-3H,4H-pyrido[4,3-d]pyrimidin-4-one; 1-(4-{5-[(2-hydroxyethyl)amino]-3-methyl-4-oxo-3H,4H-pyrido[4,3-d]pyrimidin-7-yl}phenyl)pyrrolidin-2-one; 1-(4-{5-[(3-hydroxypropyl)amino]-3-methyl-4-oxo-3H,4H-pyrido[4,3-d]pyrimidin-7-yl}phenyl)pyrrolidin-2-one; 1-(4-{5-[(3S)-3-(hydroxymethyl)pyrrolidin-1-yl]-3-methyl-4-oxo-3H,4H-pyrido[4,3-d]pyrimidin-7-yl}phenyl)pyrrolidin-2-one; 7-[4-(2-aminopropan-2-yl)phenyl]-3-methyl-5-(propan-2-ylamino)-3H,4H-pyrido[4,3-d]pyrimidin-4-one; 7-[4-(2-aminopropan-2-yl)phenyl]-5-(ethylamino)-3-methyl-3H,4H-pyrido[4,3-d]pyrimidin-4-one; 5-(ethylamino)-7-[4-methoxy-3-(morpholine-4-sulfonyl)phenyl]-3-methyl-3H,4H-pyrido[4,3-d]pyrimidin-4-one; 5-(cyclopropylamino)-7-[4-methoxy-3-(morpholine-4-sulfonyl)phenyl]-3-methyl-3H,4H-pyrido[4,3-d]pyrimidin-4-one; 7-[4-methoxy-3-(morpholine-4-sulfonyl)phenyl]-3-methyl-5-(propan-2-ylamino)-3H,4H-pyrido[4,3-d]pyrimidin-4-one; 5-(cyclopropylamino)-7-[3-fluoro-4-(piperidin-4-yl)phenyl]-3-methyl-3H,4H-pyrido[4,3-d]pyrimidin-4-one; 5-(cyclopropylamino)-7-[3-fluoro-4-(1-methylpiperidin-4-yl)phenyl]-3-methyl-3H,4H-pyrido[4,3-d]pyrimidin-4-one; 5-(cyclopropylamino)-7-[4-(1-ethylpiperidin-4-yl)-3-fluorophenyl]-3-methyl-3H,4H-pyrido[4,3-d]pyrimidin-4-one; 5-(ethylamino)-7-[4-(1-hydroxycyclobutyl)phenyl]-3-methyl-3H,4H-pyrido[4,3-d]pyrimidin-4-one; 5-(ethylamino)-3-methyl-7-(4-{[2-(morpholin-4-yl)ethane]sulfonyl}phenyl)-3H,4H-pyrido[4,3-d]pyrimidin-4-one; 5-(cyclopropylamino)-3-methyl-7-(4-{[2-(morpholin-4-yl)ethane]sulfonyl}phenyl)-3H,4H-pyrido[4,3-d]pyrimidin-4-one; 3-methyl-7-(4-{[2-(morpholin-4-yl)ethane]sulfonyl}phenyl)-5-(propan-2-ylamino)-3H,4H-pyrido[4,3-d]pyrimidin-4-one; 5-[(2-methoxyethyl)amino]-3-methyl-7-(4-{[2-(morpholin-4-yl)ethane]sulfonyl}phenyl)-3H,4H-pyrido[4,3-d]pyrimidin-4-one; 5-(ethylamino)-3-methyl-7-(4-{[2-(pyrrolidin-1-yl)ethane]sulfonyl}phenyl)-3H,4H-pyrido[4,3-d]pyrimidin-4-one; 5-(cyclopropylamino)-7-[4-(1-hydroxycyclobutyl)phenyl]-3-methyl-3H,4H-pyrido[4,3-d]pyrimidin-4-one; 7-[4-(1-hydroxycyclobutyl)phenyl]-3-methyl-5-(propan-2-ylamino)-3H,4H-pyrido[4,3-d]pyrimidin-4-one; 7-[4-(1-hydroxycyclobutyl)phenyl]-5-[(2-methoxyethyl)amino]-3-methyl-3H,4H-pyrido[4,3-d]pyrimidin-4-one; 5-(ethylamino)-3-methyl-7-(4-{[2-(pyrrolidin-1-yl)ethane]sulfonyl}phenyl)-3H,4H-pyrido[4,3-d]pyrimidin-4-one; 5-(cyclopropylamino)-3-methyl-7-(4-{[2-(pyrrolidin-1-yl)ethane]sulfonyl}phenyl)-3H,4H-pyrido[4,3-d]pyrimidin-4-one; 3-methyl-5-(propan-2-ylamino)-7-(4-{[2-(pyrrolidin-1-yl)ethane]sulfonyl}phenyl)-3H,4H-pyrido[4,3-d]pyrimidin-4-one; 5-[(2-methoxyethyl)amino]-3-methyl-7-(4-{[2-(pyrrolidin-1-yl)ethane]sulfonyl}phenyl)-3H,4H-pyrido[4,3-d]pyrimidin-4-one; 7-[4-(2-aminopropan-2-yl)phenyl]-5-(cyclopropylamino)-3-methyl-3H,4H-pyrido[4,3-d]pyrimidin-4-one; 7-[3-fluoro-4-(1-methylpiperidin-4-yl)phenyl]-5-[(2-methoxyethyl)amino]-3-methyl-3H,4H-pyrido[4,3-d]pyrimidin-4-one; 7-[3-fluoro-4-(1-methylpiperidin-4-yl)phenyl]-3-methyl-5-(propan-2-ylamino)-3H,4H-pyrido[4,3-d]pyrimidin-4-one; 5-(ethylamino)-7-[3-fluoro-4-(piperidin-4-yl)phenyl]-3-methyl-3H,4H-pyrido[4,3-d]pyrimidin-4-one; 5-(ethylamino)-7-[4-(1-hydroxycyclopentyl)phenyl]-3-methyl-3H,4H-pyrido[4,3-d]pyrimidin-4-one; 7-[4-(1-hydroxycyclopentyl)phenyl]-3-methyl-5-(propan-2-ylamino)-3H,4H-pyrido[4,3-d]pyrimidin-4-one; 5-(ethylamino)-7-[3-fluoro-4-(1-methylpiperidin-4-yl)phenyl]-3-methyl-3H,4H-pyrido[4,3-d]pyrimidin-4-one; 5-(ethylamino)-7-[4-(1-ethylpiperidin-4-yl)-3-fluorophenyl]-3-methyl-3H,4H-pyrido[4,3-d]pyrimidin-4-one; 5-(cyclopropylamino)-7-[4-(1-hydroxycyclopentyl)phenyl]-3-methyl-3H,4H-pyrido[4,3-d]pyrimidin-4-one; 5-(ethylamino)-7-{3-fluoro-4-[1-(propan-2-yl)piperidin-4-yl]phenyl}-3-methyl-3H,4H-pyrido[4,3-d]pyrimidin-4-one; 3-[5-(cyclopropylamino)-3-methyl-4-oxo-3H,4H-pyrido[4,3-d]pyrimidin-7-yl]-N-methylbenzene-1-sulfonamide; 7-(3,4-diaminophenyl)-3-methyl-5-(propan-2-ylamino)-3H,4H-pyrido[4,3-d]pyrimidin-4-one; 7-(1H-1,3-benzodiazol-6-yl)-3-methyl-5-(propan-2-ylamino)-3H,4H-pyrido[4,3-d]pyrimidin-4-one; 7-[6-(2-hydroxypropan-2-yl)pyridin-3-yl]-3-methyl-5-(propan-2-yloxy)-3H,4H-pyrido[4,3-d]pyrimidin-4-one; 5-(benzyloxy)-7-[6-(2-hydroxypropan-2-yl)pyridin-3-yl]-3-methyl-3H,4H-pyrido[4,3-d]pyrimidin-4-one; 5-(cyclobutylamino)-7-(4-methanesulfonylphenyl)-3-methyl-3H,4H-pyrido[4,3-d]pyrimidin-4-one; N-[2-({7-[4-(2-hydroxypropan-2-yl)phenyl]-3-methyl-4-oxo-3H,4H-pyrido[4,3-d]pyrimidin-5-yl}amino)ethyl]-2-methoxyacetamide; N-[2-({7-[6-(2-hydroxypropan-2-yl)pyridin-3-yl]-3-methyl-4-oxo-3H,4H-pyrido[4,3-d]pyrimidin-5-yl}amino)ethyl]-2-methoxyacetamide; N-(2-{[7-(3,4-dimethoxyphenyl)-3-methyl-4-oxo-3H,4H-pyrido[4,3-d]pyrimidin-5-yl]amino}ethyl)-2-methoxyacetamide; methyl N-[2-({7-[4-(2-hydroxypropan-2-yl)phenyl]-3-methyl-4-oxo-3H,4H-pyrido[4,3-d]pyrimidin-5-yl}amino)ethyl]carbamate; methyl N-[2-({7-[6-(2-hydroxypropan-2-yl)pyridin-3-yl]-3-methyl-4-oxo-3H,4H-pyrido[4,3-d]pyrimidin-5-yl}amino)ethyl]carbamate; methyl N-(2-{[7-(3,4-dimethoxyphenyl)-3-methyl-4-oxo-3H,4H-pyrido[4,3-d]pyrimidin-5-yl]amino}ethyl)carbamate; N-[(2S)-1-{[7-(3,4-dimethoxyphenyl)-3-methyl-4-oxo-3H,4H-pyrido[4,3-d]pyrimidin-5-yl]amino}propan-2-yl]-2-methoxyacetamide; 7-[6-(2-hydroxypropan-2-yl)pyridin-3-yl]-3-methyl-5-(pyridin-3-ylmethoxy)-3H,4H-pyrido[4,3-d]pyrimidin-4-one; 7-[6-(2-hydroxypropan-2-yl)pyridin-3-yl]-3-methyl-5-(pyridin-4-ylmethoxy)-3H,4H-pyrido[4,3-d]pyrimidin-4-one; N-[(2S)-1-({7-[4-(2-hydroxypropan-2-yl)phenyl]-3-methyl-4-oxo-3H,4H-pyrido[4,3-d]pyrimidin-5-yl}amino)propan-2-yl]-2-methoxyacetamide; N-[(2S)-1-({7-[6-(2-hydroxypropan-2-yl)pyridin-3-yl]-3-methyl-4-oxo-3H,4H-pyrido[4,3-d]pyrimidin-5-yl}amino)propan-2-yl]-2-methoxyacetamide; N-methyl-5-[3-methyl-4-oxo-5-(propan-2-ylamino)-3H,4H-pyrido[4,3-d]pyrimidin-7-yl]pyridine-2-sulfonamide; 2,2-dimethyl-7-[3-methyl-4-oxo-5-(propan-2-ylamino)-3H,4H-pyrido[4,3-d]pyrimidin-7-yl]-3,4-dihydro-2H-1,4-benzoxazin-3-one; 2,2-dimethyl-6-[3-methyl-4-oxo-5-(propan-2-ylamino)-3H,4H-pyrido[4,3-d]pyrimidin-7-yl]-3,4-dihydro-2H-1,4-benzoxazin-3-one; 5-(cyclopropylamino)-7-[3-methanesulfonyl-4-(morpholin-4-ylmethyl)phenyl]-3-methyl-3H,4H-pyrido[4,3-d]pyrimidin-4-one; 3-methyl-7-(2-methyl-1H-1,3-benzodiazol-6-yl)-5-(propan-2-ylamino)-3H,4H-pyrido[4,3-d]pyrimidin-4-one; 3-methyl-7-(6-{[2-(morpholin-4-yl)ethyl]amino}pyridin-3-yl)-5-(propan-2-ylamino)-3H,4H-pyrido[4,3-d]pyrimidin-4-one; 5-(cyclopropylamino)-3-methyl-7-(6-{[2-(morpholin-4-yl)ethyl]amino}pyridin-3-yl)-3H,4H-pyrido[4,3-d]pyrimidin-4-one; 5-(ethylamino)-7-[4-(2-hydroxypropan-2-yl)phenyl]-3-methyl-3H,4H-pyrido[4,3-d]pyrimidin-4-one; 3-[3-methyl-4-oxo-5-(propan-2-ylamino)-3H,4H-pyrido[4,3-d]pyrimidin-7-yl]benzene-1-sulfonamide; 3-[5-(cyclopropylamino)-3-methyl-4-oxo-3H,4H-pyrido[4,3-d]pyrimidin-7-yl]benzene-1-sulfonamide;

4-[3-methyl-4-oxo-5-(propan-2-ylamino)-3H,4H-pyrido[4,3-d]pyrimidin-7-yl]benzene-1-sulfonamide; 4-[5-(cyclopropylamino)-3-methyl-4-oxo-3H,4H-pyrido[4,3-d]pyrimidin-7-yl]benzene-1-sulfonamide; 5-(cyclopropylamino)-7-(6-methoxypyridin-3-yl)-3-methyl-3H,4H-pyrido[4,3-d]pyrimidin-4-one; 5-(cyclopropylamino)-7-(6-fluoropyridin-3-yl)-3-methyl-3H,4H-pyrido[4,3-d]pyrimidin-4-one; 5-(cyclopropylamino)-7-[4-(hydroxymethyl)phenyl]-3-methyl-3H,4H-pyrido[4,3-d]pyrimidin-4-one; 5-(cyclopropylamino)-7-[4-(methoxymethyl)phenyl]-3-methyl-3H,4H-pyrido[4,3-d]pyrimidin-4-one; 5-(cyclopropylamino)-7-[6-(dimethylamino)pyridin-3-yl]-3-methyl-3H,4H-pyrido[4,3-d]pyrimidin-4-one; N-{5-[5-(cyclopropylamino)-3-methyl-4-oxo-3H,4H-pyrido[4,3-d]pyrimidin-7-yl]pyridin-2-yl}acetamide; 7-[6-(dimethylamino)pyridin-3-yl]-3-methyl-5-(propan-2-ylamino)-3H,4H-pyrido[4,3-d]pyrimidin-4-one; N-{5-[3-methyl-4-oxo-5-(propan-2-ylamino)-3H,4H-pyrido[4,3-d]pyrimidin-7-yl]pyridin-2-yl}acetamide; 3-methyl-5-(propan-2-ylamino)-7-[6-(pyrrolidin-1-yl)pyridin-3-yl]-3H,4H-pyrido[4,3-d]pyrimidin-4-one; 5-(cyclopropylamino)-3-methyl-7-[6-(pyrrolidin-1-yl)pyridin-3-yl]-3H,4H-pyrido[4,3-d]pyrimidin-4-one; 5-(cyclopropylamino)-7-[4-(2-methoxypropan-2-yl)phenyl]-3-methyl-3H,4H-pyrido[4,3-d]pyrimidin-4-one; 7-(2-methoxypyridin-4-yl)-3-methyl-5-(propan-2-ylamino)-3H,4H-pyrido[4,3-d]pyrimidin-4-one; 5-(cyclopropylamino)-7-(2-methoxypyridin-4-yl)-3-methyl-3H,4H-pyrido[4,3-d]pyrimidin-4-one; 7-(5-methoxypyridin-3-yl)-3-methyl-5-(propan-2-ylamino)-3H,4H-pyrido[4,3-d]pyrimidin-4-one; 5-(cyclopropylamino)-7-(5-methoxypyridin-3-yl)-3-methyl-3H,4H-pyrido[4,3-d]pyrimidin-4-one; 5-[3-methyl-4-oxo-5-(propan-2-ylamino)-3H,4H-pyrido[4,3-d]pyrimidin-7-yl]pyridine-2-carbonitrile; 7-[4-(2-methoxypropan-2-yl)phenyl]-3-methyl-5-(propan-2-ylamino)-3H,4H-pyrido[4,3-d]pyrimidin-4-one; 3-methyl-7-[4-(morpholin-4-yl)phenyl]-5-(propan-2-ylamino)-3H,4H-pyrido[4,3-d]pyrimidin-4-one; 5-[5-(cyclopropylamino)-3-methyl-4-oxo-3H,4H-pyrido[4,3-d]pyrimidin-7-yl]pyridine-2-carbonitrile; 7-[6-(1-hydroxyethyl)pyridin-3-yl]-3-methyl-5-(propan-2-ylamino)-3H,4H-pyrido[4,3-d]pyrimidin-4-one; 7-[6-(hydroxymethyl)pyridin-3-yl]-3-methyl-5-(propan-2-ylamino)-3H,4H-pyrido[4,3-d]pyrimidin-4-one; 3-methyl-7-(6-methylpyridin-3-yl)-5-(propan-2-ylamino)-3H,4H-pyrido[4,3-d]pyrimidin-4-one; 7-[4-(1-hydroxyethyl)phenyl]-3-methyl-5-(propan-2-ylamino)-3H,4H-pyrido[4,3-d]pyrimidin-4-one; 7-[4-(hydroxymethyl)phenyl]-3-methyl-5-(propan-2-ylamino)-3H,4H-pyrido[4,3-d]pyrimidin-4-one; 7-(6-methoxypyridin-3-yl)-3-methyl-5-(propan-2-ylamino)-3H,4H-pyrido[4,3-d]pyrimidin-4-one; 7-[4-(2-hydroxyethyl)phenyl]-3-methyl-5-(propan-2-ylamino)-3H,4H-pyrido[4,3-d]pyrimidin-4-one; 7-[4-(methoxymethyl)phenyl]-3-methyl-5-(propan-2-ylamino)-3H,4H-pyrido[4,3-d]pyrimidin-4-one; S-{3-[5-(cyclopropylamino)-3-methyl-4-oxo-3H,4H-pyrido[4,3-d]pyrimidin-7-yl]phenyl}-2-hydroxyethane-1-sulfonamido; N-methyl-3-[3-methyl-4-oxo-5-(propan-2-ylamino)-3H,4H-pyrido[4,3-d]pyrimidin-7-yl]benzene-1-sulfonamide; N,N-dimethyl-3-[3-methyl-4-oxo-5-(propan-2-ylamino)-3H,4H-pyrido[4,3-d]pyrimidin-7-yl]benzene-1-sulfonamide; 2-hydroxy-S-{3-[3-methyl-4-oxo-5-(propan-2-ylamino)-3H,4H-pyrido[4,3-d]pyrimidin-7-yl]phenyl}ethane-1-sulfonamido; N-cyclopropyl-3-[3-methyl-4-oxo-5-(propan-2-ylamino)-3H,4H-pyrido[4,3-d]pyrimidin-7-yl]benzene-1-sulfonamide; 3-methyl-7-[3-(morpholine-4-sulfonyl)phenyl]-5-(propan-2-ylamino)-3H,4H-pyrido[4,3-d]pyrimidin-4-one; 5-(cyclopropylamino)-3-methyl-7-[4-(morpholin-4-yl)phenyl]-3H,4H-pyrido[4,3-d]pyrimidin-4-one; 5-(cyclopropylamino)-3-methyl-7-[6-(morpholin-4-yl)pyridin-3-yl]-3H,4H-pyrido[4,3-d]pyrimidin-4-one; 3-methyl-7-[6-(morpholin-4-yl)pyridin-3-yl]-5-(propan-2-ylamino)-3H,4H-pyrido[4,3-d]pyrimidin-4-one; 5-(ethylamino)-7-[4-(2-methoxypropan-2-yl)phenyl]-3-methyl-3H,4H-pyrido[4,3-d]pyrimidin-4-one; 5-(cyclopropylamino)-3-methyl-7-[4-(morpholin-4-ylmethyl)phenyl]-3H,4H-pyrido[4,3-d]pyrimidin-4-one; 3-methyl-7-[4-(morpholin-4-ylmethyl)phenyl]-5-(propan-2-ylamino)-3H,4H-pyrido[4,3-d]pyrimidin-4-one; 5-(cyclopropylamino)-7-[4-(1-hydroxycyclopropyl)phenyl]-3-methyl-3H,4H-pyrido[4,3-d]pyrimidin-4-one; 4-[5-(cyclopropylamino)-3-methyl-4-oxo-3H,4H-pyrido[4,3-d]pyrimidin-7-yl]-N-methylbenzene-1-sulfonamide; 3-[5-(cyclopropylamino)-3-methyl-4-oxo-3H,4H-pyrido[4,3-d]pyrimidin-7-yl]-N,N-dimethylbenzene-1-sulfonamide; 3-[5-(cyclopropylamino)-3-methyl-4-oxo-3H,4H-pyrido[4,3-d]pyrimidin-7-yl]-N-ethylbenzene-1-sulfonamide; N-methyl-4-[3-methyl-4-oxo-5-(propan-2-ylamino)-3H,4H-pyrido[4,3-d]pyrimidin-7-yl]benzene-1-sulfonamide; 2-hydroxy-S-{4-[3-methyl-4-oxo-5-(propan-2-ylamino)-3H,4H-pyrido[4,3-d]pyrimidin-7-yl]phenyl}ethane-1-sulfonamido; S-{4-[5-(cyclopropylamino)-3-methyl-4-oxo-3H,4H-pyrido[4,3-d]pyrimidin-7-yl]phenyl}-2-hydroxyethane-1-sulfonamido; 5-(cyclopropylamino)-7-(6-methoxypyrazin-2-yl)-3-methyl-3H,4H-pyrido[4,3-d]pyrimidin-4-one; 5-(ethylamino)-7-(6-methoxypyrazin-2-yl)-3-methyl-3H,4H-pyrido[4,3-d]pyrimidin-4-one; 5-(cyclopropylamino)-7-[4-(ethanesulfonyl)phenyl]-3-methyl-3H,4H-pyrido[4,3-d]pyrimidin-4-one; 5-(cyclopropylamino)-7-[6-(4-ethylpiperazin-1-yl)pyridin-3-yl]-3-methyl-3H,4H-pyrido[4,3-d]pyrimidin-4-one; 5-(cyclopropylamino)-7-{6-[(3-methoxypropyl)amino]pyridin-3-yl}-3-methyl-3H,4H-pyrido[4,3-d]pyrimidin-4-one; 5-(cyclopropylamino)-7-{4-[2-(4-ethylpiperazin-1-yl)ethyl]phenyl}-3-methyl-3H,4H-pyrido[4,3-d]pyrimidin-4-one; 5-(cyclopropylamino)-3-methyl-7-[6-(4-methyl-1H-imidazol-1-yl)pyridin-3-yl]-3H,4H-pyrido[4,3-d]pyrimidin-4-one; 5-(cyclopropylamino)-7-{6-[(2-hydroxyethyl)amino]pyridin-3-yl}-3-methyl-3H,4H-pyrido[4,3-d]pyrimidin-4-one; 5-(cyclopropylamino)-7-{6-[(2-methoxyethyl)amino]pyridin-3-yl}-3-methyl-3H,4H-pyrido[4,3-d]pyrimidin-4-one; 5-(cyclopropylamino)-3-methyl-7-[6-(piperidin-1-yl)pyridin-3-yl]-3H,4H-pyrido[4,3-d]pyrimidin-4-one; 5-(cyclopropylamino)-3-methyl-7-{6-[(1-methylpiperidin-4-yl)amino]pyridin-3-yl}-3H,4H-pyrido[4,3-d]pyrimidin-4-one; N-cyclopropyl-3-[5-(cyclopropylamino)-3-methyl-4-oxo-3H,4H-pyrido[4,3-d]pyrimidin-7-yl]benzene-1-sulfonamide; 7-[4-(ethanesulfonyl)phenyl]-5-(ethylamino)-3-methyl-3H,4H-pyrido[4,3-d]pyrimidin-4-one; 7-[4-(ethanesulfonyl)phenyl]-3-methyl-5-(propan-2-ylamino)-3H,4H-pyrido[4,3-d]pyrimidin-4-one; 5-(cyclopropylamino)-3-methyl-7-{4-[2-(morpholin-4-yl)ethyl]phenyl}-1-3H,4H-pyrido[4,3-d]pyrimidin-4-one; 7-{4-[2-(4-ethylpiperazin-1-yl)ethyl]phenyl}-3-methyl-5-(propan-2-ylamino)-3H,4H-pyrido[4,3-d]pyrimidin-4-one; 3-methyl-7-{4-[2-(morpholin-4-yl)ethyl]phenyl}-5-(propan-2-ylamino)-3H,4H-pyrido[4,3-d]pyrimidin-4-one; 5-(cyclopropylamino)-3-methyl-7-{4-[2-(piperidin-1-yl)ethyl]phenyl}-3H,4H-pyrido[4,3-d]pyrimidin-4-one; 3-methyl-7-{4-[2-(piperidin-1-yl)ethyl]phenyl}-5-(propan-2-ylamino)-3H,4H-pyrido[4,3-d]pyrimidin-4-one; 5-(cyclopropylamino)-3-methyl-7-{4-[2-(pyrrolidin-1-yl)ethyl]phenyl}-3H,4H-pyrido[4,3-d]pyrimidin-4-one; 3-methyl-5-(propan-2-ylamino)-7-{4-[2-(pyrrolidin-1-yl)ethyl]phenyl}-3H,4H-pyrido[4,3-d]pyrimidin-4-one; 5-(cyclopropylamino)-7-(4-{2-[(2-methoxyethyl)amino]ethyl}phenyl)-3-methyl-3H,4H-pyrido[4,3-d]pyrimidin-4-one; 7-(4-{2-[(2-methoxyethyl)

amino]ethyl}phenyl)-3-methyl-5-(propan-2-ylamino)-3H, 4H-pyrido[4,3-d]pyrimidin-4-one; 5-(cyclopropylamino)-3-methyl-7-(4-{2-[(1-methylpiperidin-4-yl)amino]ethyl}phenyl)-3H,4H-pyrido[4,3-d]pyrimidin-4-one; 3-methyl-7-(4-{2-[(1-methylpiperidin-4-yl)amino]ethyl}phenyl)-5-(propan-2-ylamino)-3H,4H-pyrido[4,3-d]pyrimidin-4-one; 7-(6-ethoxypyridin-3-yl)-3-methyl-5-(propan-2-ylamino)-3H,4H-pyrido[4,3-d]pyrimidin-4-one; 5-(cyclopropylamino)-3-methyl-7-(4-{2-[(2R)-2-methylmorpholin-4-yl]ethyl}phenyl)-3H,4H-pyrido[4,3-d]pyrimidin-4-one; 3-methyl-7-(4-{2-[(2R)-2-methylmorpholin-4-yl]ethyl}phenyl)-5-(propan-2-ylamino)-3H,4H-pyrido[4,3-d]pyrimidin-4-one; 5-(cyclopropylamino)-3-methyl-7-{6-[(2R)-2-methylmorpholin-4-yl]pyridin-3-yl}-3H,4H-pyrido[4,3-d]pyrimidin-4-one; 5-(cyclopropylamino)-7-(6-ethoxypyridin-3-yl)-3-methyl-3H,4H-pyrido[4,3-d]pyrimidin-4-one; N-{4-[5-(cyclopropylamino)-3-methyl-4-oxo-3H,4H-pyrido[4,3-d]pyrimidin-7-yl]phenyl}methanesulfonamide; N-{4-[3-methyl-4-oxo-5-(propan-2-ylamino)-3H,4H-pyrido[4,3-d]pyrimidin-7-yl]phenyl}methanesulfonamide; 4-(2-{4-[5-(cyclopropylamino)-3-methyl-4-oxo-3H,4H-pyrido[4,3-d]pyrimidin-7-yl]phenyl}ethyl)piperazin-2-one; 4-(2-{4-[3-methyl-4-oxo-5-(propan-2-ylamino)-3H,4H-pyrido[4,3-d]pyrimidin-7-yl]phenyl}ethyl)piperazin-2-one; 7-(4-{[2-(dimethylamino)ethane]sulfonyl}phenyl)-5-(ethylamino)-3-methyl-3H,4H-pyrido[4,3-d]pyrimidin-4-one; 5-(cyclopropylamino)-7-(4-{[2-(dimethylamino)ethane]sulfonyl}phenyl)-3-methyl-3H,4H-pyrido[4,3-d]pyrimidin-4-one; 3-methyl-7-[3-methyl-4-(piperidin-4-yl)phenyl]-5-(propan-2-ylamino)-3H,4H-pyrido[4,3-d]pyrimidin-4-one; 7-[4-(2-aminopropan-2-yl)phenyl]-5-[(3-hydroxypropyl)amino]-3-methyl-3H,4H-pyrido[4,3-d]pyrimidin-4-one; 7-[4-(2-aminopropan-2-yl)phenyl]-5-[(2-hydroxyethyl)amino]-3-methyl-3H,4H-pyrido[4,3-d]pyrimidin-4-one; 7-[4-(2-aminopropan-2-yl)phenyl]-3-methyl-5-(oxolan-3-ylamino)-3H,4H-pyrido[4,3-d]pyrimidin-4-one; 7-(4-{[2-(dimethylamino)ethane]sulfonyl}phenyl)-5-[(2-methoxyethyl)amino]-3-methyl-3H,4H-pyrido[4,3-d]pyrimidin-4-one; 7-(4-{[2-(dimethylamino)ethane]sulfonyl}phenyl)-5-[(3-hydroxypropyl)amino]-3-methyl-3H,4H-pyrido[4,3-d]pyrimidin-4-one; 3-methyl-7-[3-methyl-4-(1-methylpiperidin-4-yl)phenyl]-5-(propan-2-ylamino)-3H,4H-pyrido[4,3-d]pyrimidin-4-one; 7-[4-(1-ethylpiperidin-4-yl)-3-methylphenyl]-3-methyl-5-(propan-2-ylamino)-3H,4H-pyrido[4,3-d]pyrimidin-4-one; 5-(ethylamino)-3-methyl-7-[6-(piperidin-4-yl)pyridin-3-yl]-3H,4H-pyrido[4,3-d]pyrimidin-4-one; 5-(ethylamino)-3-methyl-7-[6-(1-methylpiperidin-4-yl)pyridin-3-yl]-3H,4H-pyrido[4,3-d]pyrimidin-4-one; 5-(ethylamino)-7-[6-(1-ethylpiperidin-4-yl)pyridin-3-yl]-3-methyl-3H,4H-pyrido[4,3-d]pyrimidin-4-one; 3-methyl-7-(4-{[2-(morpholin-4-yl)ethane]sulfonyl}phenyl)-5-(oxolan-3-ylamino)-3H,4H-pyrido[4,3-d]pyrimidin-4-one; 5-[(2-hydroxyethyl)amino]-3-methyl-7-(4-{[2-(morpholin-4-yl)ethane]sulfonyl}phenyl)-3H,4H-pyrido[4,3-d]pyrimidin-4-one; 5-[(3-hydroxypropyl)amino]-3-methyl-7-(4-{[2-(morpholin-4-yl)ethane]sulfonyl}phenyl)-3H,4H-pyrido[4,3-d]pyrimidin-4-one; 5-[(3S)-3-(hydroxymethyl)pyrrolidin-1-yl]-3-methyl-7-(4-{[2-(morpholin-4-yl)ethane]sulfonyl}phenyl)-3H,4H-pyrido[4,3-d]pyrimidin-4-one; 5-(ethylamino)-7-(4-{[2-(4-ethylpiperazin-1-yl)ethane]sulfonyl}phenyl)-3-methyl-3H,4H-pyrido[4,3-d]pyrimidin-4-one; 7-[4-(2-aminopropan-2-yl)phenyl]-5-[(3S)-3-(hydroxymethyl)pyrrolidin-1-yl]-3-methyl-3H,4H-pyrido[4,3-d]pyrimidin-4-one; 7-(4-{[2-(4-ethylpiperazin-1-yl)ethane]sulfonyl}phenyl)-5-[(3-hydroxypropyl)amino]-3-methyl-3H,4H-pyrido[4,3-d]pyrimidin-4-one; 7-[6-(2-aminopropan-2-yl)pyridin-3-yl]-5-(ethylamino)-3-methyl-3H,4H-pyrido[4,3-d]pyrimidin-4-one; 7-[6-(2-aminopropan-2-yl)pyridin-3-yl]-5-(cyclopropylamino)-3-methyl-3H,4H-pyrido[4,3-d]pyrimidin-4-one; 7-[6-(2-aminopropan-2-yl)pyridin-3-yl]-3-methyl-5-(propan-2-ylamino)-3H,4H-pyrido[4,3-d]pyrimidin-4-one; 7-(4-amino-3-methanesulfonylphenyl)-5-(ethylamino)-3-methyl-3H,4H-pyrido[4,3-d]pyrimidin-4-one; 7-(4-amino-3-methanesulfonylphenyl)-5-(cyclopropylamino)-3-methyl-3H,4H-pyrido[4,3-d]pyrimidin-4-one; 7-(4-amino-3-methanesulfonylphenyl)-5-[(2-methoxyethyl)amino]-3-methyl-3H,4H-pyrido[4,3-d]pyrimidin-4-one; 7-(4-amino-3-methanesulfonylphenyl)-5-[(3-hydroxypropyl)amino]-3-methyl-3H,4H-pyrido[4,3-d]pyrimidin-4-one; 5-(ethylamino)-7-(4-{[(2S)-1-hydroxypropan-2-yl]amino}-3-methanesulfonylphenyl)-3-methyl-3H,4H-pyrido[4,3-d]pyrimidin-4-one; 7-(4-{[(2S)-1-hydroxypropan-2-yl]amino}-3-methanesulfonylphenyl)-3-methyl-5-(propan-2-ylamino)-3H,4H-pyrido[4,3-d]pyrimidin-4-one; 5-(ethylamino)-7-(4-{[(2S)-2-hydroxypropyl]amino}-3-methanesulfonylphenyl)-3-methyl-3H,4H-pyrido[4,3-d]pyrimidin-4-one; 7-(4-{[(2S)-2-hydroxypropyl]amino}-3-methanesulfonylphenyl)-3-methyl-5-(propan-2-ylamino)-3H,4H-pyrido[4,3-d]pyrimidin-4-one; 7-(4-{[(2S)-2-hydroxypropyl]amino}-3-methanesulfonylphenyl)-5-[(2-methoxyethyl)amino]-3-methyl-3H,4H-pyrido[4,3-d]pyrimidin-4-one; 5-(ethylamino)-7-(4-{[(2R)-1-hydroxypropan-2-yl]amino}-3-methanesulfonylphenyl)-3-methyl-3H,4H-pyrido[4,3-d]pyrimidin-4-one; 5-(cyclopropylamino)-7-(4-{[(2R)-1-hydroxypropan-2-yl]amino}-3-methanesulfonylphenyl)-3-methyl-3H,4H-pyrido[4,3-d]pyrimidin-4-one; 5-(ethylamino)-7-(4-{[(2R)-2-hydroxypropyl]amino}-3-methanesulfonylphenyl)-3-methyl-3H,4H-pyrido[4,3-d]pyrimidin-4-one; 5-(cyclopropylamino)-7-(4-{[(2R)-2-hydroxypropyl]amino}-3-methanesulfonylphenyl)-3-methyl-3H,4H-pyrido[4,3-d]pyrimidin-4-one; 7-(4-{[(2R)-2-hydroxypropyl]amino}-3-methanesulfonylphenyl)-3-methyl-5-(propan-2-ylamino)-3H,4H-pyrido[4,3-d]pyrimidin-4-one; 7-(4-{[(2R)-2-hydroxypropyl]amino}-3-methanesulfonylphenyl)-5-[(2-methoxyethyl)amino]-3-methyl-3H,4H-pyrido[4,3-d]pyrimidin-4-one; 5-(cyclopropylamino)-7-(4-{[(2S)-1-hydroxypropan-2-yl]amino}-3-methanesulfonylphenyl)-3-methyl-3H,4H-pyrido[4,3-d]pyrimidin-4-one; 5-(cyclopropylamino)-7-(4-{[(2S)-2-hydroxypropyl]amino}-3-methanesulfonylphenyl)-3-methyl-3H,4H-pyrido[4,3-d]pyrimidin-4-one; 7-(4-{[(2R)-1-hydroxypropan-2-yl]amino}-3-methanesulfonylphenyl)-3-methyl-5-(propan-2-ylamino)-3H,4H-pyrido[4,3-d]pyrimidin-4-one; 7-(4-{[(2R)-1-hydroxypropan-2-yl]amino}-3-methanesulfonylphenyl)-5-[(2-methoxyethyl)amino]-3-methyl-3H,4H-pyrido[4,3-d]pyrimidin-4-one; 7-(4-{[(2S)-1-hydroxypropan-2-yl]amino}-3-methanesulfonylphenyl)-5-[(3-hydroxypropyl)amino]-3-methyl-3H,4H-pyrido[4,3-d]pyrimidin-4-one; 5-[(3-hydroxypropyl)amino]-7-(4-{[(2S)-2-hydroxypropyl]amino}-3-methanesulfonylphenyl)-3-methyl-3H,4H-pyrido[4,3-d]pyrimidin-4-one; 7-(4-{[(2R)-1-hydroxypropan-2-yl]amino}-3-methanesulfonylphenyl)-5-[(3-hydroxypropyl)amino]-3-methyl-3H,4H-pyrido[4,3-d]pyrimidin-4-one; 5-[(3-hydroxypropyl)amino]-7-(4-{[(2R)-2-hydroxypropyl]amino}-3-methanesulfonylphenyl)-3-methyl-3H,4H-pyrido[4,3-d]pyrimidin-4-one; 7-(4-{[(2S)-1-hydroxypropan-2-yl]amino}-3-methanesulfonylphenyl)-3-methyl-5-[(3R)-oxolan-3-ylamino]-3H,4H-pyrido[4,3-d]pyrimidin-4-one; 7-(4-{[(2S)-2-hydroxypropyl]amino}-3-methanesulfonylphenyl)-3-methyl-5-[(3R)-oxolan-3-ylamino]-3H,4H- pyrido[4,3-d]pyrimidin-4-one; 7-(4-{[(2R)-2-hydroxypropyl]amino}-3-methanesulfonylphenyl)-3-methyl-5-[(3R)-oxolan-3-ylamino]-3H,4H-pyrido[4,3-d]pyrimidin-4-one; 3-methyl-7-[4-(methylamino)phenyl]-5-(propan-2-ylamino)-3H,4H-pyrido[4,3-d]pyrimidin-4-one; 5-[(2-methoxyethyl)amino]-3-methyl-7-[4-(methylamino)phenyl]-3H,4H-pyrido[4,3-d]pyrimidin-4-one; 3-methyl-7-[4-(methylamino)phenyl]-5-[(3R)-oxolan-3-ylamino]-3H,4H-pyrido[4,3-d]pyrimidin-4-one; 7-{4-[(2R)-2-(hydroxymethyl)pyrrolidin-1-yl]-3-methanesulfonylphenyl}-3-methyl-5-(propan-2-ylamino)-3H,4H-pyrido[4,3-d]pyrimidin-4-one; 7-{4-[(2R)-2-(hydroxymethyl)pyrrolidin-1-yl]-3-methanesulfonylphenyl}-5-[(2-methoxyethyl)amino]-3-methyl-3H,4H-pyrido[4,3-d]pyrimidin-4-one; 7-{4-[(2R)-2-(hydroxymethyl)pyrrolidin-1-yl]-3-methanesulfonylphenyl}-3-methyl-5-[(3R)-oxolan-3-ylamino]-3H,4H-pyrido[4,3-d]pyrimidin-4-one; 5-[(3S)-3-(hydroxymethyl)pyrrolidin-1-yl]-7-{4-[(2R)-2-(hydroxymethyl)pyrrolidin-1-yl]-3-methanesulfonylphenyl}-3-methyl-3H,4H-pyrido[4,3-d]pyrimidin-4-one; 7-{4-[(2S)-2-(hydroxymethyl)pyrrolidin-1-yl]-3-methanesulfonylphenyl}-3-methyl-5-(propan-2-ylamino)-3H,4H-pyrido[4,3-d]pyrimidin-4-one; 7-{4-[(2S)-2-(hydroxymethyl)pyrrolidin-1-yl]-3-methanesulfonylphenyl}-5-[(2-methoxyethyl)amino]-3-methyl-3H,4H-pyrido[4,3-d]pyrimidin-4-one; 7-{4-[(2S)-2-(hydroxymethyl)pyrrolidin-1-yl]-3-methanesulfonylphenyl}-3-methyl-5-[(3R)-oxolan-3-ylamino]-3H,4H-pyrido[4,3-d]pyrimidin-4-one; 5-[(3S)-3-(hydroxymethyl)pyrrolidin-1-yl]-7-{4-[(2S)-2-(hydroxymethyl)pyrrolidin-1-yl]-3-methanesulfonylphenyl}-3-methyl-3H,4H-pyrido[4,3-d]pyrimidin-4-one; 5-(cyclopropylamino)-7-[4-(2-hydroxyethyl)phenyl]-3-methyl-3H,4H-pyrido[4,3-d]pyrimidin-4-one; 7-(6-methoxypyrazin-2-yl)-3-methyl-5-(propan-2-ylamino)-3H,4H-pyrido[4,3-d]pyrimidin-4-one; 5-(cyclopropylamino)-3-methyl-7-[3-(morpholine-4-sulfonyl)phenyl]-3H,4H-pyrido[4,3-d]pyrimidin-4-one; 7-(4-{[2-(dimethylamino)ethane]sulfonyl}phenyl)-3-methyl-5-(propan-2-ylamino)-3H,4H-pyrido[4,3-d]pyrimidin-4-one; 7-(3,4-dimethoxyphenyl)-3-methyl-5-[(3-methyl-1H-indazol-6-yl)amino]-3H,4H-pyrido[4,3-d]pyrimidin-4-one; 3-methyl-7-[5-(morpholin-4-ylmethyl)pyridin-3-yl]-5-(propan-2-ylamino)-3H,4H-pyrido[4,3-d]pyrimidin-4-one; 7-[3-methanesulfonyl-4-(morpholin-4-ylmethyl)phenyl]-3-methyl-5-(propan-2-ylamino)-3H,4H-pyrido[4,3-d]pyrimidin-4-one; 3-methyl-5-(propan-2-ylamino)-7-[6-(pyrrolidin-1-ylmethyl)pyridin-3-yl]-3H,4H-pyrido[4,3-d]pyrimidin-4-one; 5-(cyclopropylamino)-7-(5,6-diaminopyridin-3-yl)-3-methyl-3H,4H-pyrido[4,3-d]pyrimidin-4-one; 7-(3,4-dimethoxyphenyl)-3-methyl-5-{[(2R)-3,3,3-trifluoro-2-hydroxypropyl]amino}-3H,4H-pyrido[4,3-d]pyrimidin-4-one; 3-methyl-7-[4-(propan-2-yl)phenyl]-5-(propan-2-ylamino)-3H,4H-pyrido[4,3-d]pyrimidin-4-one; 5-(cyclopropylamino)-3-methyl-7-[4-(propan-2-yl)phenyl]-3H,4H-pyrido[4,3-d]pyrimidin-4-one; 7-(4-tert-butylphenyl)-3-methyl-5-(propan-2-ylamino)-3H,4H-pyrido[4,3-d]pyrimidin-4-one; 7-(4-tert-butylphenyl)-5-(cyclopropylamino)-3-methyl-3H,4H-pyrido[4,3-d]pyrimidin-4-one; 7-(3,4-dimethoxyphenyl)-3-methyl-5-[(pyridin-2-ylmethoxy)amino]-3H,4H-pyrido[4,3-d]pyrimidin-4-one; 7-(4-ethylphenyl)-3-methyl-5-(propan-2-ylamino)-3H,4H-pyrido[4,3-d]pyrimidin-4-one; 5-(cyclopropylamino)-7-(4-ethylphenyl)-3-methyl-3H,4H-pyrido[4,3-d]pyrimidin-4-one; 5-({7-[4-(2-hydroxypropan-2-yl)phenyl]-3-methyl-4-oxo-3H,4H-pyrido[4,3-d]pyrimidin-5-yl}amino)piperidin-2-one; 5-({7-[6-(2-hydroxypropan-2-yl)pyridin-3-yl]-3-methyl-4-oxo-3H,4H-pyrido[4,3-d]pyrimidin-5-yl}amino)piperidin-2-one; 5-{[7-(3,4-dimethoxyphenyl)-3-methyl-4-oxo-3H,4H-pyrido[4,3-d]pyrimidin-5-yl]amino}piperidin-2-one; N-[(2S)-1-({7-[4-(2-hydroxypropan-2-yl)phenyl]-3-methyl-4-oxo-3H,4H-pyrido[4,3-d]pyrimidin-5-yl}amino)propan-2-yl]methanesulfonamide; N-[(2S)-1-({7-[6-(2-hydroxypropan-2-yl)pyridin-3-yl]-3-methyl-4-oxo-3H,4H-pyrido[4,3-d]pyrimidin-5-yl}amino)propan-2-yl]methanesulfonamide; N-[(2S)-1-{[7-(3,4-dimethoxyphenyl)-3-methyl-4-oxo-3H,4H-pyrido[4,3-d]pyrimidin-5-yl]amino}propan-2-yl]methanesulfonamide; 5-(cyclopropylamino)-7-{1H-imidazo[4,5-b]pyridin-6-yl}-3-methyl-3H,4H-pyrido[4,3-d]pyrimidin-4-one; 5-(cyclopropylamino)-3-methyl-7-{2-methyl-1H-imidazo[4,5-b]pyridin-6-yl}-3H,4H-pyrido[4,3-d]pyrimidin-4-one; 5-amino-7-[4-(2-hydroxypropan-2-yl)phenyl]-3-methyl-3H,4H-pyrido[4,3-d]pyrimidin-4-one; 7-[6-(2-hydroxypropan-2-yl)pyridin-3-yl]-5-(2-methoxyethoxy)-3-methyl-3H,4H-pyrido[4,3-d]pyrimidin-4-one; 7-[6-(2-hydroxypropan-2-yl)pyridin-3-yl]-3-methyl-5-[(1-methylpiperidin-4-yl)oxy]-3H,4H-pyrido[4,3-d]pyrimidin-4-one; 5-[5-(cyclopropylamino)-3-methyl-4-oxo-3H,4H-pyrido[4,3-d]pyrimidin-7-yl]-N-methylpyridine-2-sulfonamide; methyl N-[(2S)-1-({7-[4-(2-hydroxypropan-2-yl)phenyl]-3-methyl-4-oxo-3H,4H-pyrido[4,3-d]pyrimidin-5-yl}amino)propan-2-yl]carbamate; methyl N-[(2S)-1-({7-[6-(2-hydroxypropan-2-yl)pyridin-3-yl]-3-methyl-4-oxo-3H,4H-pyrido[4,3-d]pyrimidin-5-yl}amino)propan-2-yl]carbamate; methyl N-[(2S)-1-{[7-(3,4-dimethoxyphenyl)-3-methyl-4-oxo-3H,4H-pyrido[4,3-d]pyrimidin-5-yl]amino}propan-2-yl]carbamate; 5-{[(2R)-1-hydroxybutan-2-yl]amino}-7-[6-(2-hydroxypropan-2-yl)pyridin-3-yl]-3-methyl-3H,4H-pyrido[4,3-d]pyrimidin-4-one; 5-{[(2R)-1-hydroxy-3-methylbutan-2-yl]amino}-7-[6-(2-hydroxypropan-2-yl)pyridin-3-yl]-3-methyl-3H,4H-pyrido[4,3-d]pyrimidin-4-one; 3-({7-[6-(2-hydroxypropan-2-yl)pyridin-3-yl]-3-methyl-4-oxo-3H,4H-pyrido[4,3-d]pyrimidin-5-yl}amino)-1-thiolane-1,1-dione; 7-[6-(2-hydroxypropan-2-yl)pyridin-3-yl]-3-methyl-5-(phenylamino)-3H,4H-pyrido[4,3-d]pyrimidin-4-one; 5-{[1-(2-hydroxyethyl)piperidin-4-yl]amino}-7-[6-(2-hydroxypropan-2-yl)pyridin-3-yl]-3-methyl-3H,4H-pyrido[4,3-d]pyrimidin-4-one; 5-[4-(2-hydroxyethyl)piperazin-1-yl]-7-[6-(2-hydroxypropan-2-yl)pyridin-3-yl]-3-methyl-3H,4H-pyrido[4,3-d]pyrimidin-4-one; 7-[6-(2-hydroxypropan-2-yl)pyridin-3-yl]-3-methyl-5-(oxan-4-ylamino)-3H,4H-pyrido[4,3-d]pyrimidin-4-one; 5-{[1-(4-chlorophenyl)propan-2-yl]amino}-7-[6-(2-hydroxypropan-2-yl)pyridin-3-yl]-3-methyl-3H,4H-pyrido[4,3-d]pyrimidin-4-one; 7-[6-(2-hydroxypropan-2-yl)pyridin-3-yl]-3-methyl-5-[methyl(propan-2-yl)amino]-3H,4H-pyrido[4,3-d]pyrimidin-4-one; 7-[6-(2-hydroxypropan-2-yl)pyridin-3-yl]-3-methyl-5-{[(1S)-1-phenylethyl]amino}-3H,4H-pyrido[4,3-d]pyrimidin-4-one; 5-[(3-aminopropyl)amino]-3-methyl-7-[4-(pyridin-2-yl)piperazin-1-yl]-3H,4H-pyrido[4,3-d]pyrimidin-4-one; 5-[(3-aminopropyl)amino]-3-methyl-7-[6-(morpholin-4-yl)pyridin-3-yl]-3H,4H-pyrido[4,3-d]pyrimidin-4-one; 7-[6-(2-hydroxypropan-2-yl)pyridin-3-yl]-5-[(3-hydroxypropyl)amino]-3-methyl-3H,4H-pyrido[4,3-d]pyrimidin-4-one; 7-[6-(2-hydroxypropan-2-yl)pyridin-3-yl]-3-methyl-5-{[(2S)-pyrrolidin-2-ylmethyl]amino}-3H,4H-pyrido[4,3-d]pyrimidin-4-one; 7-[6-(2-hydroxypropan-2-yl)pyridin-3-yl]-3-methyl-5-[(2-phenylethyl)amino]-3H,4H-pyrido[4,3-d]pyrimidin-4-one; 7-[6-(2-hydroxypropan-2-yl)pyridin-3-yl]-3-methyl-5-[(3R)-pyrrolidin-3-ylamino]-3H,4H-pyrido[4,3-d]pyrimidin-4-one; 5-[(1H-1,3-benzodiazol-2-ylmethyl)amino]-7-[6-(2-hydroxypropan-2-yl)pyridin-3- yl]-3-methyl-3H,4H-pyrido[4,3-d]pyrimidin-4-one; ethyl 2-({7-[6-(2-hydroxypropan-2-yl)pyridin-3-yl]-3-methyl-4-oxo-3H,4H-pyrido[4,3-d]pyrimidin-5-yl}amino)pyridine-4-carboxylate; 5-{[(1R,2S)-2-hydroxycyclopentyl]amino}-7-[6-(2-hydroxypropan-2-yl)pyridin-3-yl]-3-methyl-3H,4H-pyrido[4,3-d]pyrimidin-4-one; 5-{[(1R,2R)-2-hydroxycyclopentyl]amino}-7-[6-(2-hydroxypropan-2-yl)pyridin-3-yl]-3-methyl-3H,4H-pyrido[4,3-d]pyrimidin-4-one; 5-[(1-hydroxy-2-methylpropan-2-yl)amino]-7-[6-(2-hydroxypropan-2-yl)pyridin-3-yl]-3-methyl-3H,4H-pyrido[4,3-d]pyrimidin-4-one; methyl 4-({7-[6-(2-hydroxypropan-2-yl)pyridin-3-yl]-3-methyl-4-oxo-3H,4H-pyrido[4,3-d]pyrimidin-5-yl}amino)butanoate; 2-({7-[6-(2-hydroxypropan-2-yl)pyridin-3-yl]-3-methyl-4-oxo-3H,4H-pyrido[4,3-d]pyrimidin-5-yl}amino)pyridine-4-carboxylic acid; 3[({7-[6-(2-hydroxypropan-2-yl)pyridin-3-yl]-3-methyl-4-oxo-3H,4H-pyrido[4,3-d]pyrimidin-5-yl}amino)methyl]benzoic acid; 4-({7-[6-(2-hydroxypropan-2-yl)pyridin-3-yl]-3-methyl-4-oxo-3H,4H-pyrido[4,3-d]pyrimidin-5-yl}amino)butanoic acid; 7-[6-(2-hydroxypropan-2-yl)pyridin-3-yl]-5-[(3-methoxypropyl)amino]-3-methyl-3H,4H-pyrido[4,3-d]pyrimidin-4-one; 5-[(4-hydroxybutyl)amino]-7-[6-(2-hydroxypropan-2-yl)pyridin-3-yl]-3-methyl-3H,4H-pyrido[4,3-d]pyrimidin-4-one; 7-[6-(2-hydroxypropan-2-yl)pyridin-3-yl]-3-methyl-5-[(oxan-4-ylmethyl)amino]-3H,4H-pyrido[4,3-d]pyrimidin-4-one; 3-({7-[6-(2-hydroxypropan-2-yl)pyridin-3-yl]-3-methyl-4-oxo-3H,4H-pyrido[4,3-d]pyrimidin-5-yl}amino)propanenitrile; 7-[6-(2-hydroxypropan-2-yl)pyridin-3-yl]-3-methyl-5-[(3-methyl-1H-pyrazol-5-yl)amino]-3H,4H-pyrido[4,3-d]pyrimidin-4-one; 7-[6-(2-hydroxypropan-2-yl)pyridin-3-yl]-3-methyl-5-(pyrazin-2-ylamino)-3H,4H-pyrido[4,3-d]pyrimidin-4-one; 5-[4-(hydroxymethyl)piperidin-1-yl]-7-[6-(2-hydroxypropan-2-yl)pyridin-3-yl]-3-methyl-3H,4H-pyrido[4,3-d]pyrimidin-4-one; 5-[3-(hydroxymethyl)piperidin-1-yl]-7-[6-(2-hydroxypropan-2-yl)pyridin-3-yl]-3-methyl-3H,4H-pyrido[4,3-d]pyrimidin-4-one; 5-[4-(2-hydroxyethyl)piperidin-1-yl]-7-[6-(2-hydroxypropan-2-yl)pyridin-3-yl]-3-methyl-3H,4H-pyrido[4,3-d]pyrimidin-4-one; 5-[(furan-3-ylmethyl)amino]-7-[6-(2-hydroxypropan-2-yl)pyridin-3-yl]-3-methyl-3H,4H-pyrido[4,3-d]pyrimidin-4-one; 5-[(2,3-dihydroxypropyl)amino]-7-[6-(2-hydroxypropan-2-yl)pyridin-3-yl]-3-methyl-3H,4H-pyrido[4,3-d]pyrimidin-4-one; 7-[6-(2-hydroxypropan-2-yl)pyridin-3-yl]-5-[(3-methanesulfonylphenyl)amino]-3-methyl-3H,4H-pyrido[4,3-d]pyrimidin-4-one; 7-[6-(2-hydroxypropan-2-yl)pyridin-3-yl]-5-{[(3-methanesulfonylphenyl)methyl]amino}-3-methyl-3H,4H-pyrido[4,3-d]pyrimidin-4-one; 7-[6-(2-hydroxypropan-2-yl)pyridin-3-yl]-5-{[(4-methanesulfonylphenyl)methyl]amino}-3-methyl-3H,4H-pyrido[4,3-d]pyrimidin-4-one; 3-({7-[6-(2-hydroxypropan-2-yl)pyridin-3-yl]-3-methyl-4-oxo-3H,4H-pyrido[4,3-d]pyrimidin-5-yl}amino)benzonitrile; 7-[6-(2-hydroxypropan-2-yl)pyridin-3-yl]-3-methyl-5-{[3-(2H-1,2,3,4-tetrazol-5-yl)phenyl]amino}-3H,4H-pyrido[4,3-d]pyrimidin-4-one; methyl 2-{7-[6-(2-hydroxypropan-2-yl)pyridin-3-yl]-3-methyl-4-oxo-3H,4H-pyrido[4,3-d]pyrimidin-5-yl}-1,2,3,4-tetrahydroisoquinoline-5-carboxylate; methyl 2-{7-[6-(2-hydroxypropan-2-yl)pyridin-3-yl]-3-methyl-4-oxo-3H,4H-pyrido[4,3-d]pyrimidin-5-yl}-1,2,3,4-tetrahydroisoquinoline-8-carboxylate; 2-{7-[6-(2-hydroxypropan-2-yl)pyridin-3-yl]-3-methyl-4-oxo-3H,4H-pyrido[4,3-d]pyrimidin-5-yl}-1,2,3,4-tetrahydroisoquinoline-5-carboxylic acid; 2-{7-[6-(2-hydroxypropan-2-yl)pyridin-3-yl]-3-methyl-4-oxo-3H,4H-pyrido[4,3-d]pyrimidin-5-yl}-1,2,3,4-tetrahydroisoquinoline-8-carboxylic acid; 2-{7-[6-(2-hydroxypropan-2-yl)pyridin-3-yl]-3-methyl-4-oxo-3H,4H-pyrido[4,3-d]pyrimidin-5-yl}-1,2,3,4-tetrahydroisoquinoline-7-carboxylic acid; 5-[(3-hydroxy-2,2-dimethylpropyl)amino]-7-[6-(2-hydroxypropan-2-yl)pyridin-3-yl]-3-methyl-3H,4H-pyrido[4,3-d]pyrimidin-4-one; 7-[6-(2-hydroxypropan-2-yl)pyridin-3-yl]-5-[(1H-imidazol-4-ylmethyl)amino]-3-methyl-3H,4H-pyrido[4,3-d]pyrimidin-4-one; 5-[3-methyl-4-oxo-5-(propan-2-ylamino)-3H,4H-pyrido[4,3-d]pyrimidin-7-yl]-2-(morpholin-4-yl)-1-oxidopyridin-1-ium; 7-[6-(2-hydroxypropan-2-yl)pyridin-3-yl]-3-methyl-5-[(1H-1,2,3-triazol-4-ylmethyl)amino]-3H,4H-pyrido[4,3-d]pyrimidin-4-one; 3-methyl-7-[4-(4-methylpiperazin-1-yl)phenyl]-5-[(1H-1,2,3-triazol-4-ylmethyl)amino]-3H,4H-pyrido[4,3-d]pyrimidin-4-one; 5-[7-(hydroxymethyl)-1,2,3,4-tetrahydroisoquinolin-2-yl]-3-methyl-7-[4-(piperazin-1-yl)phenyl]-3H,4H-pyrido[4,3-d]pyrimidin-4-one; 5-[5-(hydroxymethyl)-1,2,3,4-tetrahydroisoquinolin-2-yl]-3-methyl-7-[4-(piperazin-1-yl)phenyl]-3H,4H-pyrido[4,3-d]pyrimidin-4-one; 5-[8-(hydroxymethyl)-1,2,3,4-tetrahydroisoquinolin-2-yl]-3-methyl-7-[4-(piperazin-1-yl)phenyl]-3H,4H-pyrido[4,3-d]pyrimidin-4-one; 5-[(3Z)-3-(hydroxyimino)pyrrolidin-1-yl]-3-methyl-7-[4-(piperazin-1-yl)phenyl]-3H,4H-pyrido[4,3-d]pyrimidin-4-one; 5-[(3S)-3-(hydroxymethyl)pyrrolidin-1-yl]-3-methyl-7-[4-(oxolan-2-ylmethoxy)phenyl]-3H,4H-pyrido[4,3-d]pyrimidin-4-one; 7-(4-{[(2R)-1-benzylpyrrolidin-2-yl]methoxy}phenyl)-5-[(3S)-3-(hydroxymethyl)pyrrolidin-1-yl]-3-methyl-3H,4H-pyrido[4,3-d]pyrimidin-4-one; 7-(4-{[(2S)-1-benzylpyrrolidin-2-yl]methoxy}phenyl)-5-[(3S)-3-(hydroxymethyl)pyrrolidin-1-yl]-3-methyl-3H,4H-pyrido[4,3-d]pyrimidin-4-one; 7-[4-(2-hydroxyethoxy)phenyl]-5-[(3S)-3-(hydroxymethyl)pyrrolidin-1-yl]-3-methyl-3H,4H-pyrido[4,3-d]pyrimidin-4-one; 5-[(3R)-3-aminopyrrolidin-1-yl]-3-methyl-7-[4-(4-methylpiperazin-1-yl)phenyl]-3H,4H-pyrido[4,3-d]pyrimidin-4-one; 5-[(3S)-3-aminopyrrolidin-1-yl]-3-methyl-7-[4-(4-methylpiperazin-1-yl)phenyl]-3H,4H-pyrido[4,3-d]pyrimidin-4-one; 5-[3-(1-hydroxyethyl)pyrrolidin-1-yl]-3-methyl-7-[4-(4-methylpiperazin-1-yl)phenyl]-3H,4H-pyrido[4,3-d]pyrimidin-4-one; 5-[3-(2-hydroxypropan-2-yl)pyrrolidin-1-yl]-3-methyl-7-[4-(4-methylpiperazin-1-yl)phenyl]-3H,4H-pyrido[4,3-d]pyrimidin-4-one; 5-[(3S)-3-(hydroxymethyl)pyrrolidin-1-yl]-3-methyl-7-{4-[(2R)-pyrrolidin-2-ylmethoxy]phenyl}-3H,4H-pyrido[4,3-d]pyrimidin-4-one; 5-[(3S)-3-(hydroxymethyl)pyrrolidin-1-yl]-3-methyl-7-{4-[(2S)-pyrrolidin-2-ylmethoxy]phenyl}-3H,4H-pyrido[4,3-d]pyrimidin-4-one; 4-hydroxy-1-{3-methyl-7-[4-(4-methylpiperazin-1-yl)phenyl]-4-oxo-3H,4H-pyrido[4,3-d]pyrimidin-5-yl}pyrrolidine-3-carboxylic acid; 5-[(3S,4R)-3-hydroxy-4-(hydroxymethyl)pyrrolidin-1-yl]-3-methyl-7-[4-(4-methylpiperazin-1-yl)phenyl]-3H,4H-pyrido[4,3-d]pyrimidin-4-one; 5-[(3S,4S)-3-hydroxy-4-(hydroxymethyl)pyrrolidin-1-yl]-3-methyl-7-[4-(4-methylpiperazin-1-yl)phenyl]-3H,4H-pyrido[4,3-d]pyrimidin-4-one; 5-[(3Z)-3-(hydroxyimino)pyrrolidin-1-yl]-3-methyl-7-[4-(4-methylpiperazin-1-yl)phenyl]-3H,4H-pyrido[4,3-d]pyrimidin-4-one; 5-[9-(hydroxymethyl)-1,4-dioxa-7-azaspiro[4.4]nonan-7-yl]-3-methyl-7-[4-(4-methylpiperazin-1-yl)phenyl]-3H,4H-pyrido[4,3-d]pyrimidin-4-one; 3-methyl-7-[4-(4-methylpiperazin-1-yl)phenyl]-5-(3-propanoylpyrrolidin-1-yl)-3H,4H-pyrido[4,3-d]pyrimidin-4-one; 7-(2,3-dihydro-1,4-benzodioxin-6-yl)-5-[(2-methoxyethyl)amino]-3-methyl-3H,4H-pyrido[4,3-d]pyrimidin-4-one; 7-(3-fluoro-4-methoxyphenyl)-5-[(2-methoxyethyl)amino]-3-methyl-3H,4H-pyrido[4,3-d]pyrimidin-4-one; 2-({3-methyl-7-[4-(morpholin-4-yl)

phenyl]-4-oxo-3H,4H-pyrido[4,3-d]pyrimidin-5-yl}amino) acetonitrile; 3-({3-methyl-7-[4-(morpholin-4-yl)phenyl]-4-oxo-3H,4H-pyrido[4,3-d]pyrimidin-5-yl}amino) propanenitrile; 3-methyl-7-[4-(morpholin-4-yl)phenyl]-5-[(pyridin-4-ylmethyl)amino]-3H,4H-pyrido[4,3-d]pyrimidin-4-one; 5-[(2-methoxyethyl)amino]-3-methyl-7-[4-(morpholin-4-yl)phenyl]-3H,4H-pyrido[4,3-d]pyrimidin-4-one; 7-(3,4-dimethoxyphenyl)-5-[(2-methoxyethyl)amino]-3-methyl-3H,4H-pyrido[4,3-d]pyrimidin-4-one; 7-[6-(2-hydroxypropan-2-yl)pyridin-3-yl]-3-methyl-5-(1,3-thiazol-2-ylamino)-3H,4H-pyrido[4,3-d]pyrimidin-4-one; 3-methyl-7-[4-(morpholin-4-yl)phenyl]-5-(1,3-thiazol-2-ylamino)-3H,4H-pyrido[4,3-d]pyrimidin-4-one; 7-[6-(2-hydroxypropan-2-yl)pyridin-3-yl]-5-[(2-methanesulfonylethyl)amino]-3-methyl-3H,4H-pyrido[4,3-d]pyrimidin-4-one; 5-[(2-methanesulfonylethyl)amino]-3-methyl-7-[4-(morpholin-4-yl)phenyl]-3H,4H-pyrido[4,3-d]pyrimidin-4-one; 7-[6-(2-hydroxypropan-2-yl)pyridin-3-yl]-3-methyl-5-(pyridin-4-ylamino)-3H,4H-pyrido[4,3-d]pyrimidin-4-one; 3-methyl-7-[4-(morpholin-4-yl)phenyl]-5-{[(1S)-1-phenylethyl]amino}-3H,4H-pyrido[4,3-d]pyrimidin-4-one; 5-[(1-methoxypropan-2-yl)amino]-3-methyl-7-[4-(morpholin-4-yl)phenyl]-3H,4H-pyrido[4,3-d]pyrimidin-4-one; 5-(dimethylamino)-3-methyl-7-[4-(morpholin-4-yl)phenyl]-3H,4H-pyrido[4,3-d]pyrimidin-4-one; 3-methyl-7-[4-(morpholin-4-yl)phenyl]-5-{[(1S)-1-phenylethyl]amino}-1H,2H,3H,4H-pyrido[4,3-d]pyrimidin-4-one; 5-[(1-methoxypropan-2-yl)amino]-3-methyl-7-[4-(morpholin-4-yl)phenyl]-1H,2H,3H,4H-pyrido[4,3-d]pyrimidin-4-one; 3-methyl-7-[4-(morpholin-4-yl)phenyl]-5-(propan-2-ylamino)-3H,4H-pyrido[4,3-d]pyrimidin-4-one; 5-[(3-hydroxypropyl)amino]-3-methyl-7-[4-(morpholin-4-yl)phenyl]-3H,4H-pyrido[4,3-d]pyrimidin-4-one; 5-[(3-methoxypropyl)amino]-3-methyl-7-[4-(morpholin-4-yl)phenyl]-3H,4H-pyrido[4,3-d]pyrimidin-4-one; 5-{[3-(dimethylamino)propyl]amino}-3-methyl-7-[4-(morpholin-4-yl)phenyl]-3H,4H-pyrido[4,3-d]pyrimidin-4-one; 5-[(cyclopropylmethyl)amino]-3-methyl-7-[4-(morpholin-4-yl)phenyl]-3H,4H-pyrido[4,3-d]pyrimidin-4-one; 3-methyl-7-[4-(morpholin-4-yl)phenyl]-5-{[2-(pyridin-4-yl)ethyl]amino}-3H,4H-pyrido[4,3-d]pyrimidin-4-one; 3-methyl-7-[4-(morpholin-4-yl)phenyl]-5-(oxolan-3-ylamino)-3H,4H-pyrido[4,3-d]pyrimidin-4-one; 3-methyl-7-[4-(morpholin-4-yl)phenyl]-5-[(oxan-4-ylmethyl)amino]-3H,4H-pyrido[4,3-d]pyrimidin-4-one; 5-[(2-methoxyethyl)amino]-3-methyl-7-[2-(morpholin-4-yl)pyrimidin-5-yl]-3H,4H-pyrido[4,3-d]pyrimidin-4-one; 3-{5-[(2-methoxyethyl)amino]-3-methyl-4-oxo-3H,4H-pyrido[4,3-d]pyrimidin-7-yl}benzene-1-sulfonamide; 5-[(2-hydroxyethyl)amino]-3-methyl-7-[4-(morpholin-4-yl)phenyl]-3H,4H-pyrido[4,3-d]pyrimidin-4-one; 5-{[2-(dimethylamino)ethyl]amino}-3-methyl-7-[4-(morpholin-4-yl)phenyl]-3H,4H-pyrido[4,3-d]pyrimidin-4-one; tert-butyl 4-(4-{5-[(2-methoxyethyl)amino]-3-methyl-4-oxo-3H,4H-pyrido[4,3-d]pyrimidin-7-yl}phenyl)piperidine-1-carboxylate; 5-[(2-methoxyethyl)amino]-3-methyl-7-[4-(piperidin-4-yl)phenyl]-3H,4H-pyrido[4,3-d]pyrimidin-4-one; 7-(6-fluoropyridin-3-yl)-5-[(2-methoxyethyl)amino]-3-methyl-3H,4H-pyrido[4,3-d]pyrimidin-4-one; 7-{6-[(2-hydroxyethyl)amino]pyridin-3-yl}-5-[(2-methoxyethyl)amino]-3-methyl-3H,4H-pyrido[4,3-d]pyrimidin-4-one; 7-[6-(4-ethylpiperazin-1-yl)pyridin-3-yl]-5-[(2-methoxyethyl)amino]-3-methyl-3H,4H-pyrido[4,3-d]pyrimidin-4-one; 5-[(2-methoxyethyl)amino]-3-methyl-7-(6-{[2-(morpholin-4-yl)ethyl]amino}pyridin-3-yl)-3H,4H-pyrido[4,3-d]pyrimidin-4-one; 3-methyl-7-[4-(morpholin-4-yl)phenyl]-5-[(3R)-oxolan-3-ylamino]-3H,4H-pyrido[4,3-d]pyrimidin-4-one; 3-methyl-7-[4-(morpholin-4-yl)phenyl]-5-[(3S)-oxolan-3-ylamino]-3H,4H-pyrido[4,3-d]pyrimidin-4-one; 5-{[(2S)-2-hydroxy-2-phenylethyl]amino}-3-methyl-7-[4-(morpholin-4-yl)phenyl]-3H,4H-pyrido[4,3-d]pyrimidin-4-one; 5-{[(3R)-1-methanesulfonylpyrrolidin-3-yl]amino}-3-methyl-7-[4-(morpholin-4-yl)phenyl]-3H,4H-pyrido[4,3-d]pyrimidin-4-one; 5-{[(3R)-1-[2-(dimethylamino)acetyl]pyrrolidin-3-yl]amino}-3-methyl-7-[4-(morpholin-4-yl)phenyl]-3H,4H-pyrido[4,3-d]pyrimidin-4-one; 5-{[(3R)-1-(2-hydroxyacetyl)pyrrolidin-3-yl]amino}-3-methyl-7-[4-(morpholin-4-yl)phenyl]-3H,4H-pyrido[4,3-d]pyrimidin-4-one; 3-methyl-7-[4-(morpholin-4-yl)phenyl]-5-[(3R)-pyrrolidin-3-ylamino]-3H,4H-pyrido[4,3-d]pyrimidin-4-one; 5-{[(1S,2R)-2-hydroxycyclopentyl]amino}-3-methyl-7-[4-(morpholin-4-yl)phenyl]-3H,4H-pyrido[4,3-d]pyrimidin-4-one; 5-{[(1S,2S)-2-hydroxycyclopentyl]amino}-3-methyl-7-[4-(morpholin-4-yl)phenyl]-3H,4H-pyrido[4,3-d]pyrimidin-4-one; 5-{[(1S,2R)-2-hydroxycyclopentyl]amino}-3-methyl-7-[4-(morpholin-4-yl)phenyl]-3H,4H-pyrido[4,3-d]pyrimidin-4-one; 5-{[(1S,2S)-2-hydroxycyclopentyl]amino}-3-methyl-7-[4-(morpholin-4-yl)phenyl]-3H,4H-pyrido[4,3-d]pyrimidin-4-one; 5-{[4-(hydroxymethyl)-1,3-thiazol-2-yl]amino}-3-methyl-7-[4-(4-methylpiperazin-1-yl)phenyl]-3H,4H-pyrido[4,3-d]pyrimidin-4-one; 1-{3-methyl-7-[4-(morpholin-4-yl)phenyl]-4-oxo-3H,4H-pyrido[4,3-d]pyrimidin-5-yl}piperidine-3-carboxamide; 3-methyl-5-[(4-methyl-1,3-thiazol-2-yl)amino]-7-[4-(morpholin-4-yl)phenyl]-3H,4H-pyrido[4,3-d]pyrimidin-4-one; 3-methyl-5-[(5-methyl-1,3-thiazol-2-yl)amino]-7-[4-(morpholin-4-yl)phenyl]-3H,4H-pyrido[4,3-d]pyrimidin-4-one; 3-methyl-7-[4-(morpholin-4-yl)phenyl]-5-[(1,3-thiazol-2-ylmethyl)amino]-3H,4H-pyrido[4,3-d]pyrimidin-4-one; 3-methyl-5-{[(5-methyl-1,2-oxazol-3-yl)methyl]amino}-7-[4-(morpholin-4-yl)phenyl]-3H,4H-pyrido[4,3-d]pyrimidin-4-one; 5-[(1,3-dioxolan-2-ylmethyl)amino]-3-methyl-7-[4-(morpholin-4-yl)phenyl]-3H,4H-pyrido[4,3-d]pyrimidin-4-one; 1-{3-methyl-7-[4-(morpholin-4-yl)phenyl]-4-oxo-3H,4H-pyrido[4,3-d]pyrimidin-5-yl}pyrazolidin-3-one; 7-[6-(2-hydroxypropan-2-yl)pyridin-3-yl]-3-methyl-5-[(3S)-oxolan-3-ylamino]-3H,4H-pyrido[4,3-d]pyrimidin-4-one; 5-(cyclopentylamino)-7-[6-(2-hydroxypropan-2-yl)pyridin-3-yl]-3-methyl-3H,4H-pyrido[4,3-d]pyrimidin-4-one; 7-[4-(morpholin-4-yl)phenyl]-5-(propan-2-ylamino)-3H,4H-pyrido[4,3-d]pyrimidin-4-one; 7-[6-(2-hydroxypropan-2-yl)pyridin-3-yl]-3-methyl-5-[(3R)-oxolan-3-ylamino]-3H,4H-pyrido[4,3-d]pyrimidin-4-one; 5-{[(1R,2S)-2-(hydroxymethyl)cyclopentyl]amino}-7-[6-(2-hydroxypropan-2-yl)pyridin-3-yl]-3-methyl-3H,4H-pyrido[4,3-d]pyrimidin-4-one; 3-methyl-7-[4-(piperazin-1-yl)phenyl]-5-(propan-2-ylamino)-3H,4H-pyrido[4,3-d]pyrimidin-4-one; 3-methyl-7-[4-(4-methylpiperazin-1-yl)phenyl]-5-[(3R)-oxolan-3-ylamino]-3H,4H-pyrido[4,3-d]pyrimidin-4-one; 3-methyl-7-{4-[4-(propan-2-yl)piperazin-1-yl]phenyl}-5-(propan-2-ylamino)-3H,4H-pyrido[4,3-d]pyrimidin-4-one; 3-methyl-7-[4-(4-methylpiperazin-1-yl)phenyl]-5-(propan-2-ylamino)-3H,4H-pyrido[4,3-d]pyrimidin-4-one; 5-[3-(hydroxymethyl)azetidin-1-yl]-7-[6-(2-hydroxypropan-2-yl)pyridin-3-yl]-3-methyl-3H,4H-pyrido[4,3-d]pyrimidin-4-one; 3-methyl-5-[(3R)-oxolan-3-ylamino]-7-[4-(piperazin-1-yl)phenyl]-3H,4H-pyrido[4,3-d]pyrimidin-4-one; 3-methyl-7-[4-(piperidin-4-yl)phenyl]-5-(propan-2-ylamino)-3H,4H-pyrido[4,3-d]pyrimidin-4-one; 5-[(2-hydroxyethyl)amino]-3-methyl-7-[4-(4-methylpiperazin-1-yl)phenyl]-3H,4H-pyrido[4,3-d]pyrimidin-4-one; 5-[(3-hydroxypropyl)amino]-3-methyl-7-[4-(4-methylpiperazin-1-yl)phenyl]-3H,4H-pyrido[4,3-d]

pyrimidin-4-one; 7-[6-(2-hydroxypropan-2-yl)pyridin-3-yl]-5-{[(2R)-1-hydroxypropan-2-yl]amino}-3-methyl-3H,4H-pyrido[4,3-d]pyrimidin-4-one; 7-[6-(2-hydroxypropan-2-yl)pyridin-3-yl]-5-{[(2S)-1-hydroxypropan-2-yl]amino}-3-methyl-3H,4H-pyrido[4,3-d]pyrimidin-4-one; 5-[(2-hydroxyethyl)amino]-3-methyl-7-[4-(piperidin-4-yl)phenyl]-3H,4H-pyrido[4,3-d]pyrimidin-4-one; 5-[(3-hydroxypropyl)amino]-3-methyl-7-[4-(piperidin-4-yl)phenyl]-3H,4H-pyrido[4,3-d]pyrimidin-4-one; 5-{[(2R)-1-hydroxypropan-2-yl]amino}-3-methyl-7-[4-(4-methylpiperazin-1-yl)phenyl]-3H,4H-pyrido[4,3-d]pyrimidin-4-one; 5-{[(2S)-1-hydroxypropan-2-yl]amino}-3-methyl-7-[4-(4-methylpiperazin-1-yl)phenyl]-3H,4H-pyrido[4,3-d]pyrimidin-4-one; 5-[(2-hydroxyethyl)amino]-3-methyl-7-[4-(piperazin-1-yl)phenyl]-3H,4H-pyrido[4,3-d]pyrimidin-4-one; 5-[(3-hydroxypropyl)amino]-3-methyl-7-[4-(piperazin-1-yl)phenyl]-3H,4H-pyrido[4,3-d]pyrimidin-4-one; 5-{[(2R)-1-hydroxypropan-2-yl]amino}-3-methyl-7-[4-(piperazin-1-yl)phenyl]-3H,4H-pyrido[4,3-d]pyrimidin-4-one; 5-{[(2S)-1-hydroxypropan-2-yl]amino}-3-methyl-7-[4-(piperazin-1-yl)phenyl]-3H,4H-pyrido[4,3-d]pyrimidin-4-one; 5-(3-hydroxyazetidin-1-yl)-7-[6-(2-hydroxypropan-2-yl)pyridin-3-yl]-3-methyl-3H,4H-pyrido[4,3-d]pyrimidin-4-one; 1-{7-[6-(2-hydroxypropan-2-yl)pyridin-3-yl]-3-methyl-4-oxo-3H,4H-pyrido[4,3-d]pyrimidin-5-yl}azetidin-3-one; 7-[6-(2-hydroxypropan-2-yl)pyridin-3-yl]-3-methyl-5-{2-oxa-6-azaspiro[3.3]heptan-6-yl}-3H,4H-pyrido[4,3-d]pyrimidin-4-one; 7-[6-(2-hydroxypropan-2-yl)pyridin-3-yl]-5-[(3R)-3-hydroxypyrrolidin-1-yl]-3-methyl-3H,4H-pyrido[4,3-d]pyrimidin-4-one; 5-[(3R)-3-(hydroxymethyl)pyrrolidin-1-yl]-7-[6-(2-hydroxypropan-2-yl)pyridin-3-yl]-3-methyl-3H,4H-pyrido[4,3-d]pyrimidin-4-one; 5-[(3S)-3-(hydroxymethyl)pyrrolidin-1-yl]-7-[6-(2-hydroxypropan-2-yl)pyridin-3-yl]-3-methyl-3H,4H-pyrido[4,3-d]pyrimidin-4-one; 5-[(3R)-3-(hydroxymethyl)pyrrolidin-1-yl]-3-methyl-7-[4-(4-methylpiperazin-1-yl)phenyl]-3H,4H-pyrido[4,3-d]pyrimidin-4-one; 5-[(3S)-3-(hydroxymethyl)pyrrolidin-1-yl]-3-methyl-7-[4-(4-methylpiperazin-1-yl)phenyl]-3H,4H-pyrido[4,3-d]pyrimidin-4-one; 7-[4-(azetidin-3-yl)phenyl]-3-methyl-5-(propan-2-ylamino)-3H,4H-pyrido[4,3-d]pyrimidin-4-one; 7-[4-(azetidin-3-yl)phenyl]-3-methyl-5-[(3R)-oxolan-3-ylamino]-3H,4H-pyrido[4,3-d]pyrimidin-4-one; 5-[(3R)-3-(hydroxymethyl)pyrrolidin-1-yl]-3-methyl-7-{4-[4-(propan-2-yl)piperazin-1-yl]phenyl}-3H,4H-pyrido[4,3-d]pyrimidin-4-one; 5-[(3S)-3-(hydroxymethyl)pyrrolidin-1-yl]-3-methyl-7-{4-[4-(propan-2-yl)piperazin-1-yl]phenyl}-3H,4H-pyrido[4,3-d]pyrimidin-4-one; 3-methyl-5-[(3R)-oxolan-3-ylamino]-7-{4-[4-(propan-2-yl)piperazin-1-yl]phenyl}-3H,4H-pyrido[4,3-d]pyrimidin-4-one; 5-{[(2R)-1-hydroxypropan-2-yl]amino}-3-methyl-7-{4-[4-(propan-2-yl)piperazin-1-yl]phenyl}-3H,4H-pyrido[4,3-d]pyrimidin-4-one; 5-{[(2R)-1-hydroxypropan-2-yl]amino}-3-methyl-7-[4-(morpholin-4-yl)phenyl]-3H,4H-pyrido[4,3-d]pyrimidin-4-one; 5-[(3R)-3-(hydroxymethyl)pyrrolidin-1-yl]-3-methyl-7-[4-(morpholin-4-yl)phenyl]-3H,4H-pyrido[4,3-d]pyrimidin-4-one; 5-[(3S)-3-(hydroxymethyl)pyrrolidin-1-yl]-3-methyl-7-[4-(morpholin-4-yl)phenyl]-3H,4H-pyrido[4,3-d]pyrimidin-4-one; 3-methyl-5-[(3R)-oxolan-3-ylamino]-7-[4-(piperidin-4-yl)phenyl]-3H,4H-pyrido[4,3-d]pyrimidin-4-one; 5-[(3R)-3-(hydroxymethyl)pyrrolidin-1-yl]-3-methyl-7-[4-(piperidin-4-yl)phenyl]-3H,4H-pyrido[4,3-d]pyrimidin-4-one; 5-[(3S)-3-(hydroxymethyl)pyrrolidin-1-yl]-3-methyl-7-[4-(piperidin-4-yl)phenyl]-3H,4H-pyrido[4,3-d]pyrimidin-4-one; 3-methyl-7-[4-(4-methylpiperazin-1-yl)phenyl]-5-[(oxolan-3-ylmethyl)amino]-3H,4H-pyrido[4,3-d]pyrimidin-4-one; 5-[(3R)-3-hydroxypyrrolidin-1-yl]-3-methyl-7-[4-(4-methylpiperazin-1-yl)phenyl]-3H,4H-pyrido[4,3-d]pyrimidin-4-one; 5-[(3S,4S)-3,4-dihydroxypyrrolidin-1-yl]-3-methyl-7-[4-(4-methylpiperazin-1-yl)phenyl]-3H,4H-pyrido[4,3-d]pyrimidin-4-one; 3-methyl-7-[4-(4-methylpiperazin-1-yl)phenyl]-5-(pyrrolidin-1-yl)-3H,4H-pyrido[4,3-d]pyrimidin-4-one; 5-[3-(dimethylamino)pyrrolidin-1-yl]-3-methyl-7-[4-(4-methylpiperazin-1-yl)phenyl]-3H,4H-pyrido[4,3-d]pyrimidin-4-one; 5-[(3R)-3-fluoropyrrolidin-1-yl]-3-methyl-7-[4-(4-methylpiperazin-1-yl)phenyl]-3H,4H-pyrido[4,3-d]pyrimidin-4-one; 3-methyl-7-[4-(4-methylpiperazin-1-yl)phenyl]-5-{[(2R)-oxolan-2-ylmethyl]amino}-3H,4H-pyrido[4,3-d]pyrimidin-4-one; 5-[(3S)-3-(hydroxymethyl)pyrrolidin-1-yl]-3-methyl-7-[4-(piperazin-1-yl)phenyl]-3H,4H-pyrido[4,3-d]pyrimidin-4-one; 5-{[(1R,2S)-2-(hydroxymethyl)cyclopentyl]amino}-3-methyl-7-[4-(4-methylpiperazin-1-yl)phenyl]-3H,4H-pyrido[4,3-d]pyrimidin-4-one; 5-{5-methanesulfonyl-octahydropyrrolo[3,4-c]pyrrol-2-yl}-3-methyl-7-[4-(4-methylpiperazin-1-yl)phenyl]-3H,4H-pyrido[4,3-d]pyrimidin-4-one; 5-{[(1R,2S)-2-(hydroxymethyl)cyclohexyl]amino}-3-methyl-7-[4-(4-methylpiperazin-1-yl)phenyl]-3H,4H-pyrido[4,3-d]pyrimidin-4-one; 1-{3-methyl-7-[4-(4-methylpiperazin-1-yl)phenyl]-4-oxo-3H,4H-pyrido[4,3-d]pyrimidin-5-yl}piperidine-3-carboxamide; 5-(3-hydroxypiperidin-1-yl)-3-methyl-7-[4-(4-methylpiperazin-1-yl)phenyl]-3H,4H-pyrido[4,3-d]pyrimidin-4-one; 7-[4-(4-ethylpiperazin-1-yl)phenyl]-5-[(3S)-3-(hydroxymethyl)pyrrolidin-1-yl]-3-methyl-3H,4H-pyrido[4,3-d]pyrimidin-4-one; [(3S)-1-{3-methyl-7-[4-(4-methylpiperazin-1-yl)phenyl]-4-oxo-3H,4H-pyrido[4,3-d]pyrimidin-5-yl}pyrrolidin-3-yl]methyl sulfamate; 5-[3-(hydroxymethyl)azetidin-1-yl]-3-methyl-7-[4-(4-methylpiperazin-1-yl)phenyl]-3H,4H-pyrido[4,3-d]pyrimidin-4-one; 5-{[(1R,2R)-2-(hydroxymethyl)-1-methylcyclopentyl]amino}-3-methyl-7-[4-(4-methylpiperazin-1-yl)phenyl]-3H,4H-pyrido[4,3-d]pyrimidin-4-one; 3-methyl-7-[4-(4-methylpiperazin-1-yl)phenyl]-5-{2-oxa-6-azaspiro[3.3]heptan-6-yl}-3H,4H-pyrido[4,3-d]pyrimidin-4-one; 3-methyl-7-[4-(morpholin-4-yl)phenyl]-5-{[(2R)-oxolan-2-ylmethyl]amino}-3H,4H-pyrido[4,3-d]pyrimidin-4-one; 7-[4-(4-ethylpiperazin-1-yl)phenyl]-3-methyl-5-[(3R)-oxolan-3-ylamino]-3H,4H-pyrido[4,3-d]pyrimidin-4-one; 7-[4-(4-ethylpiperazin-1-yl)phenyl]-5-[(2-hydroxyethyl)amino]-3-methyl-3H,4H-pyrido[4,3-d]pyrimidin-4-one; 7-[4-(4-ethylpiperazin-1-yl)phenyl]-5-[(3-hydroxypropyl)amino]-3-methyl-3H,4H-pyrido[4,3-d]pyrimidin-4-one; 7-[4-(4-ethylpiperazin-1-yl)phenyl]-5-{[(2R)-1-hydroxypropan-2-yl]amino}-3-methyl-3H,4H-pyrido[4,3-d]pyrimidin-4-one; 7-[4-(1-ethylpiperidin-4-yl)phenyl]-3-methyl-5-(propan-2-ylamino)-3H,4H-pyrido[4,3-d]pyrimidin-4-one; 7-[4-(1-ethylpiperidin-4-yl)phenyl]-5-[(2-hydroxyethyl)amino]-3-methyl-3H,4H-pyrido[4,3-d]pyrimidin-4-one; 7-[4-(1-ethylpiperidin-4-yl)phenyl]-5-[(3-hydroxypropyl)amino]-3-methyl-3H,4H-pyrido[4,3-d]pyrimidin-4-one; 7-[4-(1-ethylpiperidin-4-yl)phenyl]-3-methyl-5-[(3R)-oxolan-3-ylamino]-3H,4H-pyrido[4,3-d]pyrimidin-4-one; 7-[4-(1-ethylpiperidin-4-yl)phenyl]-5-[(3S)-3-(hydroxymethyl)pyrrolidin-1-yl]-3-methyl-3H,4H-pyrido[4,3-d]pyrimidin-4-one; 7-{4-[4-(2-hydroxyacetyl)piperazin-1-yl]phenyl}-3-methyl-5-(propan-2-ylamino)-3H,4H-pyrido[4,3-d]pyrimidin-4-one; 7-(4-{4-[2-(ethylamino)acetyl]piperazin-1-yl}phenyl)-3-methyl-5-(propan-2-ylamino)-3H,4H-pyrido[4,3-d]pyrimidin-4-one; 5-[(3S)-3-(azidomethyl)pyrrolidin-1-yl]-3-methyl-7-[4-(4-methylpiperazin-1-yl)phenyl]-3H,4H-pyrido[4,3-d]pyrimidin-4-one; 7-[4-(1-ethylazetidin-3-yl)phenyl]-3- methyl-5-(propan-2-ylamino)-3H,4H-pyrido[4,3-d]pyrimidin-4-one; 7-[4-(1-ethylazetidin-3-yl)phenyl]-3-methyl-5-[(3R)-oxolan-3-ylamino]-3H,4H-pyrido[4,3-d]pyrimidin-4-one; 5-[(3S)-3-(hydroxymethyl)pyrrolidin-1-yl]-7-{4-[4-(2-methanesulfonylethyl)piperazin-1-yl]phenyl}-3-methyl-3H,4H-pyrido[4,3-d]pyrimidin-4-one; 5-[(3S)-3-(hydroxymethyl)pyrrolidin-1-yl]-3-methyl-7-{4-[(2R)-2-methylmorpholin-4-yl]phenyl}-3H,4H-pyrido[4,3-d]pyrimidin-4-one; 7-{4-[4-(2-hydroxyacetyl)piperazin-1-yl]phenyl}-5-[(3S)-3-(hydroxymethyl)pyrrolidin-1-yl]-3-methyl-3H,4H-pyrido[4,3-d]pyrimidin-4-one; 7-{4-[(2R,6S)-2,6-dimethylmorpholin-4-yl]phenyl}-5-[(3S)-3-(hydroxymethyl)pyrrolidin-1-yl]-3-methyl-3H,4H-pyrido[4,3-d]pyrimidin-4-one; 7-[4-(4-cyclopropylpiperazin-1-yl)phenyl]-5-[(3S)-3-(hydroxymethyl)pyrrolidin-1-yl]-3-methyl-3H,4H-pyrido[4,3-d]pyrimidin-4-one; 4-(4-{5-[(3S)-3-(hydroxymethyl)pyrrolidin-1-yl]-3-methyl-4-oxo-3H,4H-pyrido[4,3-d]pyrimidin-7-yl}phenyl)-1,4-thiomorpholine-1,1-dione; 7-(4-{4-[2-(ethylamino)acetyl]piperazin-1-yl}phenyl)-5-[(3S)-3-(hydroxymethyl)pyrrolidin-1-yl]-3-methyl-3H,4H-pyrido[4,3-d]pyrimidin-4-one; 5-[(3S)-3-(methanesulfonylmethyl)pyrrolidin-1-yl]-3-methyl-7-[4-(4-methylpiperazin-1-yl)phenyl]-3H,4H-pyrido[4,3-d]pyrimidin-4-one; 5-[(3S)-3-(hydroxymethyl)piperidin-1-yl]-3-methyl-7-[4-(morpholin-4-yl)phenyl]-3H,4H-pyrido[4,3-d]pyrimidin-4-one; 5-[(3R)-3-(hydroxymethyl)piperidin-1-yl]-3-methyl-7-[4-(morpholin-4-yl)phenyl]-3H,4H-pyrido[4,3-d]pyrimidin-4-one; 7-[3-fluoro-4-(morpholin-4-yl)phenyl]-5-[(3S)-3-(hydroxymethyl)pyrrolidin-1-yl]-3-methyl-3H,4H-pyrido[4,3-d]pyrimidin-4-one; 7-[3-chloro-4-(morpholin-4-yl)phenyl]-5-[(3S)-3-(hydroxymethyl)pyrrolidin-1-yl]-3-methyl-3H,4H-pyrido[4,3-d]pyrimidin-4-one; 7-[2-chloro-4-(morpholin-4-yl)phenyl]-5-[(3S)-3-(hydroxymethyl)pyrrolidin-1-yl]-3-methyl-3H,4H-pyrido[4,3-d]pyrimidin-4-one; 5-[(1S,4S)-4-(hydroxymethyl)-2-azabicyclo[2.2.1]heptan-2-yl]-3-methyl-7-[4-(morpholin-4-yl)phenyl]-3H,4H-pyrido[4,3-d]pyrimidin-4-one; 5-[(3S)-3-(hydroxymethyl)pyrrolidin-1-yl]-3-methyl-7-[4-(morpholin-4-yl)phenyl]-3H,4H-pyrido[4,3-d]pyrimidin-4-one; 5-[(3S)-3-(hydroxymethyl)pyrrolidin-1-yl]-7-[4-(morpholin-4-yl)phenyl]-3H,4H-pyrido[4,3-d]pyrimidin-4-one; 7-[4-(4-ethylpiperazin-1-yl)-3-fluorophenyl]-5-[(3S)-3-(hydroxymethyl)pyrrolidin-1-yl]-3-methyl-3H,4H-pyrido[4,3-d]pyrimidin-4-one; 5-{[(1S,3S)-3-hydroxycyclopentyl]amino}-3-methyl-7-[4-(morpholin-4-yl)phenyl]-3H,4H-pyrido[4,3-d]pyrimidin-4-one; 5-{[(1R,3R)-3-hydroxycyclopentyl]amino}-3-methyl-7-[4-(morpholin-4-yl)phenyl]-3H,4H-pyrido[4,3-d]pyrimidin-4-one; 5-{[(1R,3S)-3-hydroxycyclopentyl]amino}-3-methyl-7-[4-(morpholin-4-yl)phenyl]-3H,4H-pyrido[4,3-d]pyrimidin-4-one; 5-{[(1S,3R)-3-hydroxycyclopentyl]amino}-3-methyl-7-[4-(morpholin-4-yl)phenyl]-3H,4H-pyrido[4,3-d]pyrimidin-4-one; 5-[(3R)-3-hydroxypyrrolidin-1-yl]-3-methyl-7-[4-(morpholin-4-yl)phenyl]-3H,4H-pyrido[4,3-d]pyrimidin-4-one; 5-[3-(hydroxymethyl)azetidin-1-yl]-3-methyl-7-[4-(morpholin-4-yl)phenyl]-3H,4H-pyrido[4,3-d]pyrimidin-4-one; 5-[3-(hydroxymethyl)piperidin-1-yl]-3-methyl-7-[4-(4-methylpiperazin-1-yl)phenyl]-3H,4H-pyrido[4,3-d]pyrimidin-4-one; 5-[(3R)-3-(hydroxymethyl)piperidin-1-yl]-3-methyl-7-[4-(4-methylpiperazin-1-yl)phenyl]-3H,4H-pyrido[4,3-d]pyrimidin-4-one; 2-({3-methyl-4-oxo-7-[4-(piperidin-4-yl)phenyl]-3H,4H-pyrido[4,3-d]pyrimidin-5-yl}amino)ethyl 2,2,2-trifluoroacetate; 3-({3-methyl-4-oxo-7-[4-(piperidin-4-yl)phenyl]-3H,4H-pyrido[4,3-d]pyrimidin-5-yl}amino)propyl 2,2,2-trifluoroacetate; 7-[6-(hydroxypropan-2-yl)pyridin-3-yl]-5-[(3S)-3-hydroxypyrrolidin-1-yl]-3-methyl-3H,4H-pyrido[4,3-d]pyrimidin-4-one; 3-(2-fluoroethyl)-7-[4-(morpholin-4-yl)phenyl]-5-(propan-2-ylamino)-3H,4H-pyrido[4,3-d]pyrimidin-4-one; 5-{[(1R,2R)-2-(hydroxymethyl)cyclohexyl]amino}-3-methyl-7-[4-(4-methylpiperazin-1-yl)phenyl]-3H,4H-pyrido[4,3-d]pyrimidin-4-one; 5-[(3S)-3-(methoxymethyl)pyrrolidin-1-yl]-3-methyl-7-[4-(4-methylpiperazin-1-yl)phenyl]-3H,4H-pyrido[4,3-d]pyrimidin-4-one; 3-methyl-7-[4-(4-methylpiperazin-1-yl)phenyl]-5-[(3S)-3-[(methylsulfanyl)methyl]pyrrolidin-1-yl]-3H,4H-pyrido[4,3-d]pyrimidin-4-one; 5-[(3S)-3-hydroxypyrrolidin-1-yl]-3-methyl-7-[4-(morpholin-4-yl)phenyl]-3H,4H-pyrido[4,3-d]pyrimidin-4-one; N-ethyl-3-[3-methyl-4-oxo-5-(propan-2-ylamino)-3H,4H-pyrido[4,3-d]pyrimidin-7-yl]benzene-1-sulfonamide; 5-({7-[4-(2-hydroxypropan-2-yl)phenyl]-3-methyl-4-oxo-3H,4H-pyrido[4,3-d]pyrimidin-5-yl}amino)piperidin-2-one; 5-({7-[4-(2-hydroxypropan-2-yl)phenyl]-3-methyl-4-oxo-3H,4H-pyrido[4,3-d]pyrimidin-5-yl}amino)piperidin-2-one; 7-[6-(2-hydroxypropan-2-yl)pyridin-3-yl]-3-methyl-5-(pyridin-2-ylamino)-3H,4H-pyrido[4,3-d]pyrimidin-4-one; 3-methyl-5,7-bis[4-(morpholin-4-yl)phenyl]-3H,4H-pyrido[4,3-d]pyrimidin-4-one; N-(2-hydroxy-5-{5-[(2-methoxyethyl)amino]-3-methyl-4-oxo-3H,4H-pyrido[4,3-d]pyrimidin-7-yl}phenyl)formamide; 5-[(2-methoxyethyl)amino]-3-methyl-7-(2-methyl-1,3-benzoxazol-6-yl)-3H,4H-pyrido[4,3-d]pyrimidin-4-one; N-(2-hydroxy-4-{5-[(2-methoxyethyl)amino]-3-methyl-4-oxo-3H,4H-pyrido[4,3-d]pyrimidin-7-yl}phenyl)acetamide; 5-{[4-(hydroxymethyl)-1,3-thiazol-2-yl]amino}-3-methyl-7-[4-(morpholin-4-yl)phenyl]-3H,4H-pyrido[4,3-d]pyrimidin-4-one; (3R)-3-({3-methyl-7-[4-(morpholin-4-yl)phenyl]-4-oxo-3H,4H-pyrido[4,3-d]pyrimidin-5-yl}amino)pyrrolidine-1-carboxamide; 3-methyl-7-{4-[4-(morpholin-4-yl)cyclohexyl]phenyl}-5-[(3R)-oxolan-3-ylamino]-3H,4H-pyrido[4,3-d]pyrimidin-4-one; 5-[(3S)-3-(hydroxymethyl)pyrrolidin-1-yl]-3-methyl-7-{4-[4-(morpholin-4-yl)cyclohexyl]phenyl}-3H,4H-pyrido[4,3-d]pyrimidin-4-one; 3-methyl-7-(1-methyl-1H-pyrazol-4-yl)-5-[(3R)-oxolan-3-ylamino]-3H,4H-pyrido[4,3-d]pyrimidin-4-one; 7-[4-(4-hydroxy-4-methylpiperidin-1-yl)phenyl]-3-methyl-5-[(3R)-oxolan-3-ylamino]-3H,4H-pyrido[4,3-d]pyrimidin-4-one; 5-[(4-aminocyclohexyl)amino]-3-methyl-7-[4-(morpholin-4-yl)phenyl]-3H,4H-pyrido[4,3-d]pyrimidin-4-one; 5-[(4-aminocyclohexyl)amino]-7-[4-(4-hydroxy-4-methylpiperidin-1-yl)phenyl]-3-methyl-3H,4H-pyrido[4,3-d]pyrimidin-4-one; 5-[(4-aminocyclohexyl)amino]-3-methyl-7-[4-(morpholin-4-yl)phenyl]-3H,4H-pyrido[4,3-d]pyrimidin-4-one; N-[4-({3-methyl-7-[4-(morpholin-4-yl)phenyl]-4-oxo-3H,4H-pyrido[4,3-d]pyrimidin-5-yl}amino)cyclohexyl]methanesulfonamide; 5-[(4-hydroxycyclohexyl)amino]-3-methyl-7-(pyrazin-2-ylamino)-3H,4H-pyrido[4,3-d]pyrimidin-4-one; 5-[(4-hydroxycyclohexyl)amino]-3-methyl-7-[(4-methylpyridin-2-yl)amino]-3H,4H-pyrido[4,3-d]pyrimidin-4-one; 4-({3-methyl-7-[4-(morpholin-4-yl)phenyl]-4-oxo-3H,4H-pyrido[4,3-d]pyrimidin-5-yl}amino)cyclohexane-1-carboxylic acid; 4-({3-methyl-7-[4-(morpholin-4-yl)phenyl]-4-oxo-3H,4H-pyrido[4,3-d]pyrimidin-5-yl}amino)cyclohexane-1-carboxamide; 5-[5-(hydroxymethyl)thiophen-2-yl]-3-methyl-7-[4-(morpholin-4-yl)phenyl]-3H,4H-pyrido[4,3-d]pyrimidin-4-one; 5-[5-(hydroxymethyl)furan-2-yl]-3-methyl-7-[4-(morpholin-4-yl)phenyl]-3H,4H-pyrido[4,3-d]pyrimidin-4-one; 5-[(3Z)-3-(methoxyimino)pyrrolidin-1-yl]-3-methyl-7-[4-(morpholin-4-yl)phenyl]-3H,4H-pyrido[4,3-d]pyrimidin-4-one; 5-[(3R)-3-(2-hydroxyethyl)pyrrolidin-1-yl]-3-methyl-7-[4-(morpholin-4-yl)phenyl]-3H,4H-pyrido[4,3-d]pyrimidin-4- one; 5-{[(2S)-2,3-dihydroxypropyl]amino}-3-methyl-7-[4-(morpholin-4-yl)phenyl]-3H,4H-pyrido[4,3-d]pyrimidin-4-one; 5-{[(2R)-2,3-dihydroxypropyl]amino}-3-methyl-7-[4-(morpholin-4-yl)phenyl]-3H,4H-pyrido[4,3-d]pyrimidin-4-one; 5-[4-(hydroxymethyl)furan-2-yl]-3-methyl-7-[4-(morpholin-4-yl)phenyl]-3H,4H-pyrido[4,3-d]pyrimidin-4-one; 5-[(3R)-3-(2-hydroxyethyl)pyrrolidin-1-yl]-3-methyl-7-[4-(4-methylpiperazin-1-yl)phenyl]-3H,4H-pyrido[4,3-d]pyrimidin-4-one; 7-[4-(4-cyclopropylpiperazin-1-yl)phenyl]-5-[(3R)-3-(2-hydroxyethyl)pyrrolidin-1-yl]-3-methyl-3H,4H-pyrido[4,3-d]pyrimidin-4-one; 5-[(3R)-3-(2-hydroxyethyl)pyrrolidin-1-yl]-3-methyl-7-{4-[(2R)-2-methylmorpholin-4-yl]phenyl}-3H,4H-pyrido[4,3-d]pyrimidin-4-one; 7-[1-(2-hydroxyethyl)-1H-pyrazol-4-yl]-5-[(2-methoxyethyl)amino]-3-methyl-3H,4H-pyrido[4,3-d]pyrimidin-4-one; 5-{[2-(1H-imidazol-4-yl)ethyl]amino}-3-methyl-7-[4-(morpholin-4-yl)phenyl]-3H,4H-pyrido[4,3-d]pyrimidin-4-one; 5-{1-azabicyclo[2.2.2]octan-3-ylamino}-3-methyl-7-[4-(morpholin-4-yl)phenyl]-3H,4H-pyrido[4,3-d]pyrimidin-4-one; 5-{[4-(2-hydroxyethyl)-1,3-thiazol-2-yl]amino}-3-methyl-7-[4-(morpholin-4-yl)phenyl]-3H,4H-pyrido[4,3-d]pyrimidin-4-one; 5-(2-methoxyethoxy)-3-methyl-7-[4-(morpholin-4-yl)phenyl]-3H,4H-pyrido[4,3-d]pyrimidin-4-one; 3-methyl-7-[4-(morpholin-4-yl)phenyl]-5-[2-(1H-pyrazol-4-yl)ethoxy]-3H,4H-pyrido[4,3-d]pyrimidin-4-one; 3-methyl-7-[4-(morpholin-4-yl)phenyl]-5-[2-(1H-1,2,3-triazol-4-yl)ethoxy]-3H,4H-pyrido[4,3-d]pyrimidin-4-one; 5-(2-aminoethoxy)-3-methyl-7-[4-(morpholin-4-yl)phenyl]-3H,4H-pyrido[4,3-d]pyrimidin-4-one; 5-(3-aminopropoxy)-3-methyl-7-[4-(morpholin-4-yl)phenyl]-3H,4H-pyrido[4,3-d]pyrimidin-4-one; 5-[2-(1H-imidazol-1-yl)ethoxy]-3-methyl-7-[4-(morpholin-4-yl)phenyl]-3H,4H-pyrido[4,3-d]pyrimidin-4-one; 5-[(4-aminocyclohexyl)oxy]-3-methyl-7-[4-(morpholin-4-yl)phenyl]-3H,4H-pyrido[4,3-d]pyrimidin-4-one; 5-(2-hydroxyethoxy)-3-methyl-7-[4-(morpholin-4-yl)phenyl]-3H,4H-pyrido[4,3-d]pyrimidin-4-one; 3-methyl-7-[4-(morpholin-4-yl)phenyl]-5-[(3S)-pyrrolidin-3-ylmethoxy]-3H,4H-pyrido[4,3-d]pyrimidin-4-one; 3-methyl-7-[4-(4-methylpiperazin-1-yl)phenyl]-5-[2-(1H-1,2,3-triazol-4-yl)ethoxy]-3H,4H-pyrido[4,3-d]pyrimidin-4-one; 3-methyl-7-[4-(morpholin-4-yl)phenyl]-5-{2-[3-(trifluoromethyl)-1H-pyrazol-4-yl]ethoxy}-3H,4H-pyrido[4,3-d]pyrimidin-4-one; 3-methyl-5-(propan-2-ylamino)-7-{4-[4-(pyrrolidin-1-yl)piperidin-1-yl]phenyl}-3H,4H-pyrido[4,3-d]pyrimidin-4-one; 3-methyl-5-[(3R)-oxolan-3-ylamino]-7-{4-[4-(pyrrolidin-1-yl)piperidin-1-yl]phenyl}-3H,4H-pyrido[4,3-d]pyrimidin-4-one; 5-[(3S)-3-(hydroxymethyl)pyrrolidin-1-yl]-3-methyl-7-{4-[4-(pyrrolidin-1-yl)piperidin-1-yl]phenyl}-1-3H,4H-pyrido[4,3-d]pyrimidin-4-one; 7-{4-[(3S)-3-hydroxypyrrolidin-1-yl]phenyl}-3-methyl-5-(propan-2-ylamino)-3H,4H-pyrido[4,3-d]pyrimidin-4-one; 7-{4-[(3S)-3-hydroxypyrrolidin-1-yl]phenyl}-3-methyl-5-[(3R)-oxolan-3-ylamino]-3H,4H-pyrido[4,3-d]pyrimidin-4-one; 5-{3-methyl-4-oxo-5-[(3R)-oxolan-3-ylamino]-3H,4H-pyrido[4,3-d]pyrimidin-7-yl}-2,3-dihydro-1H-indol-2-one; 5-{5-[(3S)-3-(hydroxymethyl)pyrrolidin-1-yl]-3-methyl-4-oxo-3H,4H-pyrido[4,3-d]pyrimidin-7-yl}-2,3-dihydro-1H-indol-2-one; N-[(1R)-1-{4-[3-methyl-4-oxo-5-(propan-2-ylamino)-3H,4H-pyrido[4,3-d]pyrimidin-7-yl]phenyl}ethyl]methanesulfonamide; N-[(1R)-1-(4-{5-[(3S)-3-(hydroxymethyl)pyrrolidin-1-yl]-3-methyl-4-oxo-3H,4H-pyrido[4,3-d]pyrimidin-7-yl}phenyl)ethyl]methanesulfonamide; N-[(1S)-1-{4-[3-methyl-4-oxo-5-(propan-2-ylamino)-3H,4H-pyrido[4,3-d]pyrimidin-7-yl]phenyl}ethyl]acetamide; N-[(1S)-1-(4-{5-[(3S)-3-(hydroxymethyl)pyrrolidin-1-yl]-3-methyl-4-oxo-3H,4H-pyrido[4,3-d]pyrimidin-7-yl}-phenyl)ethyl]acetamide; 5-{[(1R,3R)-3-(hydroxymethyl)cyclopentyl]amino}-3-methyl-7-[4-(morpholin-4-yl)phenyl]-3H,4H-pyrido[4,3-d]pyrimidin-4-one; 5-{[(1S,3R)-3-(hydroxymethyl)cyclopentyl]amino}-3-methyl-7-[4-(morpholin-4-yl)phenyl]-3H,4H-pyrido[4,3-d]pyrimidin-4-one; 5-{[(1R,3S)-3-(hydroxymethyl)cyclopentyl]amino}-3-methyl-7-[4-(morpholin-4-yl)phenyl]-3H,4H-pyrido[4,3-d]pyrimidin-4-one; 5-{[(1S,3S)-3-(hydroxymethyl)cyclopentyl]amino}-3-methyl-7-[4-(morpholin-4-yl)phenyl]-3H,4H-pyrido[4,3-d]pyrimidin-4-one; (5S)-5-[({3-methyl-7-[4-(morpholin-4-yl)phenyl]-4-oxo-3H,4H-pyrido[4,3-d]pyrimidin-5-yl}amino)methyl]-1,3-oxazolidin-2-one; 5-({[(1S,3S)-3-hydroxycyclopentyl]methyl}amino)-3-methyl-7-[4-(morpholin-4-yl)phenyl]-3H,4H-pyrido[4,3-d]pyrimidin-4-one; 5-({[(1R,3R)-3-hydroxycyclopentyl]methyl}amino)-3-methyl-7-[4-(morpholin-4-yl)phenyl]-3H,4H-pyrido[4,3-d]pyrimidin-4-one; 5-({[(1R,3S)-3-hydroxy-3-methylcyclopentyl]methyl}amino)-3-methyl-7-[4-(morpholin-4-yl)phenyl]-3H,4H-pyrido[4,3-d]pyrimidin-4-one; 5-({[(1S,3R)-3-hydroxy-3-methylcyclopentyl]methyl}amino)-3-methyl-7-[4-(morpholin-4-yl)phenyl]-3H,4H-pyrido[4,3-d]pyrimidin-4-one; 7-(1-acetyl-2,3-dihydro-1H-indol-5-yl)-3-methyl-5-(propan-2-ylamino)-3H,4H-pyrido[4,3-d]pyrimidin-4-one; 7-(1-acetyl-2,3-dihydro-1H-indol-5-yl)-5-[(3S)-3-(hydroxymethyl)pyrrolidin-1-yl]-3-methyl-3H,4H-pyrido[4,3-d]pyrimidin-4-one; 5-[(3S)-3-(hydroxymethyl)pyrrolidin-1-yl]-3-methyl-7-(1-methyl-2,3-dihydro-1H-indol-5-yl)-3H,4H-pyrido[4,3-d]pyrimidin-4-one; 3-methyl-7-(1-methyl-2,3-dihydro-1H-indol-5-yl)-5-(propan-2-ylamino)-3H,4H-pyrido[4,3-d]pyrimidin-4-one; 3-methyl-7-[4-(morpholin-4-yl)phenyl]-5-[(1H-1,2,3-triazol-4-ylmethyl)amino]-3H,4H-pyrido[4,3-d]pyrimidin-4-one; 5-[(3S)-3-[(1R)-1-hydroxyethyl]pyrrolidin-1-yl]-3-methyl-7-[4-(4-methylpiperazin-1-yl)phenyl]-3H,4H-pyrido[4,3-d]pyrimidin-4-one; 5-[(3R)-3-[(1S)-1-hydroxyethyl]pyrrolidin-1-yl]-3-methyl-7-[4-(4-methylpiperazin-1-yl)phenyl]-3H,4H-pyrido[4,3-d]pyrimidin-4-one; 5-[(3R)-3-[(1R)-1-hydroxyethyl]pyrrolidin-1-yl]-3-methyl-7-[4-(4-methylpiperazin-1-yl)phenyl]-3H,4H-pyrido[4,3-d]pyrimidin-4-one; 3-hydroxy-1-{3-methyl-7-[4-(morpholin-4-yl)phenyl]-4-oxo-3H,4H-pyrido[4,3-d]pyrimidin-5-yl}pyrrolidine-3-carboxamide; 5-[3-hydroxy-3-(hydroxymethyl)pyrrolidin-1-yl]-3-methyl-7-[4-(morpholin-4-yl)phenyl]-3H,4H-pyrido[4,3-d]pyrimidin-4-one; 3-fluoro-1-{3-methyl-7-[4-(morpholin-4-yl)phenyl]-4-oxo-3H,4H-pyrido[4,3-d]pyrimidin-5-yl}pyrrolidine-3-carboxamide; 3-methyl-7-[4-(morpholin-4-yl)phenyl]-5-[(1H-pyrazol-4-ylmethyl)amino]-3H,4H-pyrido[4,3-d]pyrimidin-4-one; 5-[3-fluoro-3-(hydroxymethyl)pyrrolidin-1-yl]-3-methyl-7-[4-(morpholin-4-yl)phenyl]-3H,4H-pyrido[4,3-d]pyrimidin-4-one; 3-(2-hydroxyethyl)-5-(propan-2-ylamino)-7-(pyrazin-2-ylamino)-3H,4H-pyrido[4,3-d]pyrimidin-4-one; 7-(6-aminopyridin-3-yl)-3-methyl-5-(propan-2-ylamino)-3H,4H-pyrido[4,3-d]pyrimidin-4-one; 7-(2-aminopyridin-3-yl)-3-methyl-5-(propan-2-ylamino)-3H,4H-pyrido[4,3-d]pyrimidin-4-one; 7-(2-aminopyrimidin-5-yl)-5-(tert-butylamino)-3-(2-hydroxyethyl)-3H,4H-pyrido[4,3-d]pyrimidin-4-one; 7-(2-aminopyrimidin-5-yl)-3-methyl-5-(propan-2-ylamino)-3H,4H-pyrido[4,3-d]pyrimidin-4-one; 7-{4-[(3S)-3-hydroxypyrrolidin-1-yl]-3-methanesulfonylphenyl}-3-methyl-5-(propan-2-ylamino)-3H,4H-pyrido[4,3-d]pyrimidin-4-one; 7-{4-[(3S)-3-hydroxypyrrolidin-1-yl]-3-methanesulfonylphenyl}-5-[(2-methoxyethyl)amino]-3-methyl-3H,4H-pyrido[4,3-d]pyrimidin-4-one; 7-{4-[(3S)-3-hydroxypyrrolidin-1-yl]-3-methanesulfonylphenyl}-3-methyl-5-[(3R)-oxolan-3- ylamino]-3H,4H-pyrido[4,3-d]pyrimidin-4-one; 5-[(3S)-3-(hydroxymethyl)pyrrolidin-1-yl]-7-{4-[(3S)-3-hydroxypyrrolidin-1-yl]-3-methanesulfonylphenyl}-3-methyl-3H,4H-pyrido[4,3-d]pyrimidin-4-one; 4-methyl-7-[3-methyl-4-oxo-5-(propan-2-ylamino)-3H,4H-pyrido[4,3-d]pyrimidin-7-yl]-3,4-dihydro-2H-1,1-dioxo-2H-benzo[b][1,4]thiazin-3(4H)-one; 7-{5-[(2-methoxyethyl)amino]-3-methyl-4-oxo-3H,4H-pyrido[4,3-d]pyrimidin-7-yl}-4-methyl-3,4-dihydro-2H-1,1-dioxo-2H-benzo[b][1,4]thiazin-3(4H)-one; 4-methyl-7-{3-methyl-4-oxo-5-[(3R)-oxolan-3-ylamino]-3H,4H-pyrido[4,3-d]pyrimidin-7-yl}-3,4-dihydro-2H-1,1-dioxo-2H-benzo[b][1,4]thiazin-3(4H)-one; 7-{5-[(3S)-3-(hydroxymethyl)pyrrolidin-1-yl]-3-methyl-4-oxo-3H,4H-pyrido[4,3-d]pyrimidin-7-yl}-4-methyl-3,4-dihydro-2H-1,1-dioxo-2H-benzo[b][1,4]thiazin-3(4H)-one; N-hydroxy-4-[3-methyl-4-oxo-5-(propan-2-ylamino)-3H,4H-pyrido[4,3-d]pyrimidin-7-yl]benzene-1-carboximidamide; N-hydroxy-4-{5-[(2-methoxyethyl)amino]-3-methyl-4-oxo-3H,4H-pyrido[4,3-d]pyrimidin-7-yl}benzene-1-carboximidamide; N-hydroxy-4-{3-methyl-4-oxo-5-[(3R)-oxolan-3-ylamino]-3H,4H-pyrido[4,3-d]pyrimidin-7-yl}benzene-1-carboximidamide; N-hydroxy-4-{5-[(3S)-3-(hydroxymethyl)pyrrolidin-1-yl]-3-methyl-4-oxo-3H,4H-pyrido[4,3-d]pyrimidin-7-yl}benzene-1-carboximidamide; 5-(cyclopropylamino)-7-[4-(dimethylamino)phenyl]-3-methyl-3H,4H-pyrido[4,3-d]pyrimidin-4-one; 7-[4-(dimethylamino)phenyl]-5-[(3-hydroxypropyl)amino]-3-methyl-3H,4H-pyrido[4,3-d]pyrimidin-4-one; 7-[4-(dimethylamino)phenyl]-3-methyl-5-[(3R)-oxolan-3-ylamino]-3H,4H-pyrido[4,3-d]pyrimidin-4-one; 7-[4-(dimethylamino)phenyl]-5-[(3S)-3-(hydroxymethyl)pyrrolidin-1-yl]-3-methyl-3H,4H-pyrido[4,3-d]pyrimidin-4-one; 7-[4-(aminomethyl)phenyl]-3-methyl-5-(propan-2-ylamino)-3H,4H-pyrido[4,3-d]pyrimidin-4-one; 7-[4-(aminomethyl)phenyl]-5-[(2-methoxyethyl)amino]-3-methyl-3H,4H-pyrido[4,3-d]pyrimidin-4-one; 7-[4-(aminomethyl)phenyl]-3-methyl-5-[(3R)-oxolan-3-ylamino]-3H,4H-pyrido[4,3-d]pyrimidin-4-one; 7-{4-[(1R)-1-aminoethyl]phenyl}-3-methyl-5-(propan-2-ylamino)-3H,4H-pyrido[4,3-d]pyrimidin-4-one; 7-{4-[(1R)-1-aminoethyl]phenyl}-5-[(3-hydroxypropyl)amino]-3-methyl-3H,4H-pyrido[4,3-d]pyrimidin-4-one; 7-{4-[(1R)-1-aminoethyl]phenyl}-3-methyl-5-[(3R)-oxolan-3-ylamino]-3H,4H-pyrido[4,3-d]pyrimidin-4-one; 7-{4-[(1R)-1-aminoethyl]phenyl}-5-[(3S)-3-(hydroxymethyl)pyrrolidin-1-yl]-3-methyl-3H,4H-pyrido[4,3-d]pyrimidin-4-one; 7-{4-[(1S)-1-aminoethyl]phenyl}-3-methyl-5-(propan-2-ylamino)-3H,4H-pyrido[4,3-d]pyrimidin-4-one; 7-{4-[(1S)-1-aminoethyl]phenyl}-5-[(3-hydroxypropyl)amino]-3-methyl-3H,4H-pyrido[4,3-d]pyrimidin-4-one; 7-{4-[(1S)-1-aminoethyl]phenyl}-3-methyl-5-[(3R)-oxolan-3-ylamino]-3H,4H-pyrido[4,3-d]pyrimidin-4-one; 7-{4-[(1S)-1-aminoethyl]phenyl}-5-[(3S)-3-(hydroxymethyl)pyrrolidin-1-yl]-3-methyl-3H,4H-pyrido[4,3-d]pyrimidin-4-one; 7-{4-[(1R)-1-aminoethyl]phenyl}-5-(cyclopropylamino)-3-methyl-3H,4H-pyrido[4,3-d]pyrimidin-4-one; 7-{4-[(1S)-1-aminoethyl]phenyl}-5-(cyclopropylamino)-3-methyl-3H,4H-pyrido[4,3-d]pyrimidin-4-one; 4-methyl-7-[3-methyl-4-oxo-5-(propan-2-ylamino)-3H,4H-pyrido[4,3-d]pyrimidin-7-yl]-3,4-dihydro-2H-1,1-dioxo-2H-benzo[b][1,4]thiazine; 7-{5-[(2-methoxyethyl)amino]-3-methyl-4-oxo-3H,4H-pyrido[4,3-d]pyrimidin-7-yl}-4-methyl-3,4-dihydro-2H-1,1-dioxo-2H-benzo[b][1,4]thiazine; 4-methyl-7-{3-methyl-4-oxo-5-[(3R)-oxolan-3-ylamino]-3H,4H-pyrido[4,3-d]pyrimidin-7-yl}-3,4-dihydro-2H-1,1-dioxo-2H-benzo[b][1,4]thiazine; 7-{5-[(3S)-3-(hydroxymethyl)pyrrolidin-1-yl]-3-methyl-4-oxo-3H,4H-pyrido[4,3-d]pyrimidin-7-yl}-4-methyl-3,4-dihydro-2H-1,1-dioxo-2H-benzo[b][1,4]thiazine; N-[(1R)-1-{4-[3-methyl-4-oxo-5-(propan-2-ylamino)-3H,4H-pyrido[4,3-d]pyrimidin-7-yl]phenyl}ethyl]acetamide; N-[(1R)-1-{4-[5-(cyclopropylamino)-3-methyl-4-oxo-3H,4H-pyrido[4,3-d]pyrimidin-7-yl]phenyl}ethyl]acetamide; N-[(1R)-1-(4-{5-[(3-hydroxypropyl)amino]-3-methyl-4-oxo-3H,4H-pyrido[4,3-d]pyrimidin-7-yl}phenyl)ethyl]acetamide; N-[(1R)-1-(4-{3-methyl-4-oxo-5-[(3R)-oxolan-3-ylamino]-3H,4H-pyrido[4,3-d]pyrimidin-7-yl}phenyl)ethyl]acetamide; N-[(1S)-1-{4-[5-(cyclopropylamino)-3-methyl-4-oxo-3H,4H-pyrido[4,3-d]pyrimidin-7-yl]phenyl}ethyl]methanesulfonamide; N-[(1S)-1-(4-{5-[(3-hydroxypropyl)amino]-3-methyl-4-oxo-3H,4H-pyrido[4,3-d]pyrimidin-7-yl}phenyl)ethyl]methanesulfonamide; N-[(1S)-1-(4-{3-methyl-4-oxo-5-[(3R)-oxolan-3-ylamino]-3H,4H-pyrido[4,3-d]pyrimidin-7-yl}phenyl)ethyl]methanesulfonamide; N-[(1S)-1-(4-{5-[(3S)-3-(hydroxymethyl)pyrrolidin-1-yl]-3-methyl-4-oxo-3H,4H-pyrido[4,3-d]pyrimidin-7-yl}phenyl)ethyl]methanesulfonamide; 5-[(3S)-3-(hydroxymethyl)pyrrolidin-1-yl]-3-methyl-7-[3-methyl-4-(piperidin-4-yl)phenyl]-3H,4H-pyrido[4,3-d]pyrimidin-4-one; 3-methyl-7-[3-methyl-4-(piperidin-4-yl)phenyl]-5-[(3R)-oxolan-3-ylamino]-3H,4H-pyrido[4,3-d]pyrimidin-4-one; 5-[(3-hydroxypropyl)amino]-3-methyl-7-[3-methyl-4-(piperidin-4-yl)phenyl]-3H,4H-pyrido[4,3-d]pyrimidin-4-one; 3-methyl-7-[3-methyl-4-(1-methylpiperidin-4-yl)phenyl]-5-[(3R)-oxolan-3-ylamino]-3H,4H-pyrido[4,3-d]pyrimidin-4-one; 5-[(3S)-3-(hydroxymethyl)pyrrolidin-1-yl]-3-methyl-7-[3-methyl-4-(1-methylpiperidin-4-yl)phenyl]-3H,4H-pyrido[4,3-d]pyrimidin-4-one; 7-[3-fluoro-4-(1-methylpiperidin-4-yl)phenyl]-3-methyl-5-[(3R)-oxolan-3-ylamino]-3H,4H-pyrido[4,3-d]pyrimidin-4-one; 7-[3-fluoro-4-(1-methylpiperidin-4-yl)phenyl]-5-[(3S)-3-(hydroxymethyl)pyrrolidin-1-yl]-3-methyl-3H,4H-pyrido[4,3-d]pyrimidin-4-one; 7-[3-fluoro-4-(1-methylpiperidin-4-yl)phenyl]-5-[(3-hydroxypropyl)amino]-3-methyl-3H,4H-pyrido[4,3-d]pyrimidin-4-one; 7-[4-(1-ethylpiperidin-4-yl)-3-methylphenyl]-3-methyl-5-[(3R)-oxolan-3-ylamino]-3H,4H-pyrido[4,3-d]pyrimidin-4-one; 7-[4-(1-ethylpiperidin-4-yl)-3-methylphenyl]-5-[(3S)-3-(hydroxymethyl)pyrrolidin-1-yl]-3-methyl-3H,4H-pyrido[4,3-d]pyrimidin-4-one; 7-[4-(1-ethylpiperidin-4-yl)-3-methylphenyl]-5-[(3-hydroxypropyl)amino]-3-methyl-3H,4H-pyrido[4,3-d]pyrimidin-4-one; 5-[2-(hydroxymethyl)morpholin-4-yl]-3-methyl-7-[4-(morpholin-4-yl)phenyl]-3H,4H-pyrido[4,3-d]pyrimidin-4-one; 7-[4-(1-ethylpiperidin-4-yl)-3-methylphenyl]-5-[2-(hydroxymethyl)morpholin-4-yl]-3-methyl-3H,4H-pyrido[4,3-d]pyrimidin-4-one; ethyl 4-(4-{3-methyl-4-oxo-5-[(3R)-oxolan-3-ylamino]-3H,4H-pyrido[4,3-d]pyrimidin-7-yl}phenyl)-4-oxobutanoate; ethyl 4-(4-{5-[(3S)-3-(hydroxymethyl)pyrrolidin-1-yl]-3-methyl-4-oxo-3H,4H-pyrido[4,3-d]pyrimidin-7-yl}phenyl)-4-oxobutanoate; 5-{4-[3-methyl-4-oxo-5-(propan-2-ylamino)-3H,4H-pyrido[4,3-d]pyrimidin-7-yl]phenyl}pyrrolidin-2-one; 5-(4-{3-methyl-4-oxo-5-[(3R)-oxolan-3-ylamino]-3H,4H-pyrido[4,3-d]pyrimidin-7-yl}phenyl)pyrrolidin-2-one; 5-(4-{5-[(3S)-3-(hydroxymethyl)pyrrolidin-1-yl]-3-methyl-4-oxo-3H,4H-pyrido[4,3-d]pyrimidin-7-yl}phenyl)pyrrolidin-2-one; 5-[(3S)-3-(hydroxymethyl)pyrrolidin-1-yl]-3-methyl-7-[4-(2,2,2-trifluoro-1-hydroxyethyl)phenyl]-3H,4H-pyrido[4,3-d]pyrimidin-4-one; 3-methyl-5-[(3R)-oxolan-3-ylamino]-7-[4-(2,2,2-trifluoro-1-hydroxyethyl)phenyl]-3H,4H-pyrido[4,3-d]pyrimidin-4-one; 1-methyl-5-[3-methyl-4-oxo-5-(propan-2-ylamino)-3H,4H-pyrido[4,3-d]pyrimidin-7-yl]-2,3-dihydro-1H-indole-2,3-dione; 5-{5-[(3-hydroxypropyl)amino]-3-methyl-4-oxo-3H,4H-pyrido[4,3-d]pyrimidin-7- yl}-1-methyl-2,3-dihydro-1H-indole-2,3-dione; 1-methyl-5-{3-methyl-4-oxo-5-[(3R)-oxolan-3-ylamino]-3H,4H-pyrido[4,3-d]pyrimidin-7-yl}-2,3-dihydro-1H-indole-2,3-dione; 5-{5-[(3S)-3-(hydroxymethyl)pyrrolidin-1-yl]-3-methyl-4-oxo-3H,4H-pyrido[4,3-d]pyrimidin-7-yl}-1-methyl-2,3-dihydro-1H-indole-2,3-dione; 7-[4-(1-aminocyclopropyl)phenyl]-5-(cyclopropylamino)-3-methyl-3H,4H-pyrido[4,3-d]pyrimidin-4-one; 7-[4-(1-aminocyclopropyl)phenyl]-5-[(3-hydroxypropyl)amino]-3-methyl-3H,4H-pyrido[4,3-d]pyrimidin-4-one; 7-[4-(1-aminocyclopropyl)phenyl]-3-methyl-5-[(3R)-oxolan-3-ylamino]-3H,4H-pyrido[4,3-d]pyrimidin-4-one; 7-[4-(1-aminocyclopropyl)phenyl]-5-[(3S)-3-(hydroxymethyl)pyrrolidin-1-yl]-3-methyl-3H,4H-pyrido[4,3-d]pyrimidin-4-one; 5-(ethylamino)-3-methyl-7-[6-(morpholin-4-yl)pyridin-3-yl]-3H,4H-pyrido[4,3-d]pyrimidin-4-one; 7-[6-(1-aminocyclopropyl)pyridin-3-yl]-5-(ethylamino)-3-methyl-3H,4H-pyrido[4,3-d]pyrimidin-4-one; 7-[6-(1-aminocyclopropyl)pyridin-3-yl]-5-(cyclopropylamino)-3-methyl-3H,4H-pyrido[4,3-d]pyrimidin-4-one; 7-[6-(1-aminocyclopropyl)pyridin-3-yl]-3-methyl-5-(propan-2-ylamino)-3H,4H-pyrido[4,3-d]pyrimidin-4-one; 7-[6-(1-aminocyclopropyl)pyridin-3-yl]-3-methyl-5-[(2S)-oxolan-2-ylamino]-3H,4H-pyrido[4,3-d]pyrimidin-4-one, and 7-[6-(1-aminocyclopropyl)pyridin-3-yl]-5-[(3S)-3-(hydroxymethyl)pyrrolidin-1-yl]-3-methyl-3H,4H-pyrido[4,3-d]pyrimidin-4-one.

Another aspect provided herein are pharmaceutical compositions for treating a Syk kinase mediated disease comprising a therapeutically effective amount of any aforementioned compound of Formula (I) and a pharmaceutically acceptable excipient.

Another aspect provided herein are medicaments for treating a Syk kinase mediated disease, wherein the medicament comprises a therapeutically effective amount of any aforementioned compound of Formula (I).

Another aspect provided herein is the use of any of the aforementioned compounds of a Formula (I) in the manufacture of a medicament for treating a Syk-mediated disease in a subject in need thereof.

Another aspect provided herein is a method for inhibiting a Syk kinase, comprising administering to a system or a subject in need thereof a therapeutically effective amount of any aforementioned compound of Formula (I).

Another aspect provided herein is a method for treating a Syk-mediated disease comprising administering to a subject in need thereof a therapeutically effective amount of any aforementioned compound of Formula (I).

In certain embodiments of such aspects the Syk kinase mediated disease is an inflammatory disease, an allergic disease, a cell-proliferative disease, an autoimmune disease or cytopenia.

In certain embodiments of such aspects the Syk kinase mediated disease is allergic asthma, allergic rhinitis, rheumatoid arthritis, multiple sclerosis, lupus, systemic lupus erythematosus, lymphoma, B cell lymphoma, T cell lymphoma, myelodysplasic syndrome, anemia, leucopenia, neutropenia, thrombocytopenia, granuloctopenia, pancytoia or idiopathic thrombocytopenic purpura.

Another aspect provided herein is a compound for use in a method of medical treatment, wherein the method of medical treatment is for treating a Syk kinase mediated disease, wherein the disease is selected from allergic asthma, allergic rhinitis, rheumatoid arthritis, multiple sclerosis, lupus, systemic lupus erythematosus, lymphoma, B cell lymphoma, T cell lymphoma, myelodysplasic syndrome, anemia, leucopenia, neutropenia, thrombocytopenia, granuloctopenia, pancytoia and idiopathic thrombocytopenic purpura, and wherein the compound is any aforementioned compound of Formula (I).

DETAILED DESCRIPTION OF THE INVENTION

Definitions

The terms "alkenyl" or "alkene", as used herein, refers to a partially unsaturated branched or straight chain hydrocarbon having at least one carbon-carbon double bond. Atoms oriented about the double bond are in either the cis (Z) or trans (E) conformation. As used herein, the terms "$C_2$-$C_4$alkenyl", "$C_2$-$C_5$alkenyl", "$C_2$-$C_6$alkenyl", "$C_2$-$C_7$alkenyl", "$C_2$-$C_8$alkenyl", "$C_2$-$C_4$alkene", "$C_2$-$C_5$alkene", "$C_2$-$C_6$alkene", "$C_2$-$C_7$alkene", and "$C_2$-$C_8$alkene" refer to an alkyenyl group containing at least 2, and at most 4, 5, 6, 7 or 8 carbon atoms, respectively. Non-limiting examples of alkenyl groups, as used herein, include ethenyl, ethane, propenyl, propene, allyl (2-propenyl), 2-propene, butenyl, pentenyl, pentene, hexenyl, heptenyl, heptene, octenyl, nonenyl, nonene, decenyl, decene and the like.

The term "alkyl", as used herein, refers to a saturated branched or straight chain hydrocarbon. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene", as used herein, refers to a saturated branched or straight chain divalent hydrocarbon radical, wherein the radical is derived by the removal of one hydrogen atom from each of two carbon atoms. As used herein, the terms "$C_1$-$C_3$alkylene", "$C_1$-$C_4$alkylene", "$C_1$-$C_5$alkylene", and "$C_1$-$C_6$alkylene" refer to an alkylene group containing at least 1, and at most 3, 4, 5 or 6 carbon atoms respectively. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkynyl", as used herein, refers to a partially unsaturated branched or straight chain hydrocarbon radical having at least one carbon-carbon triple bond. As used herein, the terms "$C_2$-$C_4$alkynyl", "$C_2$-$C_5$alkynyl", "$C_2$-$C_6$alkynyl", "$C_2$-$C_7$alkynyl", and "$C_2$-$C_8$alkynyl" refer to an alkynyl group containing at least 2, and at most 4, 5, 6, 7 or 8 carbon atoms, respectively. Non-limiting examples of alkynyl groups, as used herein, include ethynyl, propynyl, butynyl, pentynyl, hexynyl, heptynyl, octynyl, nonynyl, decynyl and the like.

The term "alkoxy", as used herein, refers to the group —$OR_a$, where $R_a$ is an alkyl group as defined herein. As used herein, the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butoxy, t-butoxy, pentoxy, hexoxy, heptoxy, and the like.

The term "aryl", as used herein, refers to monocyclic, bicyclic, and tricyclic ring systems having a total of six to fourteen ring members, wherein at least one ring in the system is aromatic. Non-limiting examples of aryl groups, as used herein, include phenyl, naphthyl, fluorenyl, indenyl, azulenyl, anthracenyl and the like. An aryl group may contain one or more substituents and thus may be "optionally substituted". Unless otherwise defined herein, suitable substituents on the unsaturated carbon atom of an aryl group are generally selected from halogen; —R, —OR, —SR, —NO$_2$, —CN, —N(R)$_2$, —NRC(O)R, —NRC(S)R, —NRC(O)N(R)$_2$, —NRC(S)N(R)$_2$, —NRCO$_2$R, —NRNRC(O)R, —NRNRC(O)N(R)$_2$, —NRNRCO$_2$R, —C(O)C(O)R, —C(O)CH$_2$C(O)R, —CO$_2$R, —C(O)R°, —C(S)R, —C(O)N(R)$_2$, —C(S)N(R)$_2$, —OC(O)N(R)$_2$, —OC(O)R, —C(O)N(OR)R, —C(NOR)R, —S(O)$_2$R, —S(O)$_3$R, —SO$_2$N(R)$_2$, —S(O)R, —NRSO$_2$N(R)$_2$, —NRSO$_2$R, —N(OR)R, —C(=NH)—N(R)$_2$, —P(O)$_2$R, —PO(R)$_2$, —OPO(R)$_2$, —(CH$_2$)$_{0-2}$NHC(O)R, phenyl (Ph) optionally substituted with R, —O(Ph) optionally substituted with R, —(CH$_2$)$_{1-2}$(Ph), optionally substituted with R, or —CH=CH(Ph), optionally substituted with R, wherein each independent occurrence of R is selected from hydrogen, optionally substituted C$_1$-C$_6$alkyl, optionally substituted C$_1$-C$_6$alkoxy, an unsubstituted 5-6 membered heteroaryl, phenyl, —O(Ph), or —CH$_2$(Ph), or two independent occurrences of R, on the same substituent or different substituents, taken together with the atom(s) to which each R is bound, to form an optionally substituted 3-12 membered saturated, partially unsaturated, or fully unsaturated monocyclic or bicyclic ring having 0-4 heteroatoms independently selected from nitrogen, oxygen, or sulfur.

The term "arylene", as used means a divalent radical derived from an aryl group.

The term "cyano", as used herein, refers to a —CN group.

The term "cycloalkyl", as used herein, refers to a saturated monocyclic, fused bicyclic, fused tricyclic or bridged polycyclic ring assembly. As used herein, the terms "C$_3$-C$_5$cycloalkyl", "C$_3$-C$_6$cycloalkyl", "C$_3$-C$_7$cycloalkyl", "C$_3$-C$_8$cycloalkyl, "C$_3$-C$_9$cycloalkyl and "C$_3$-C$_{10}$cycloalkyl refer to a cycloalkyl group wherein the saturated or partially unsaturated, monocyclic, fused bicyclic or bridged polycyclic ring assembly contain at least 3, and at most 5, 6, 7, 8, 9 or 10, carbon atoms. Non-limiting examples of cycloalkyl groups, as used herein, include cyclopropyl, cyclobutyl, cyclopentyl, cyclohexyl, cycloheptyl, cyclooctyl, cyclononyl, cyclodecyl, decahydronaphthalenyl, 2,3,4,5,6,7-hexahydro-1H-indenyl and the like.

The term "halogen", as used herein, refers to fluorine (F), chlorine (Cl), bromine (Br), or iodine (I).

The term "halo", as used herein, refers to the halogen radicals: fluoro (—F), chloro (—CO, bromo (—Br), and iodo (—I).

The terms "haloalkyl" or "halo-substituted alkyl", as used herein, refers to an alkyl group as defined herein, substituted with at least one halo group or combinations thereof. Non-limiting examples of such branched or straight chained haloalkyl groups, as used herein, include methyl, ethyl, propyl, isopropyl, isobutyl and n-butyl substituted with one or more halo groups or combinations thereof, and include, but are not limited to, trifluoromethyl, pentafluoroethyl, and the like.

The term "heteroalkyl", as used herein, refers to refers to an alkyl group as defined herein wherein one or more carbon atoms are independently replaced by one or more of oxygen, sulfur, nitrogen, or combinations thereof.

The term "heteroaryl", as used herein, refers to monocyclic, bicyclic, and tricyclic ring systems having a total of five to fourteen ring members, wherein at least one ring in the system is aromatic and at least one ring in the system contains one or more heteroatoms selected from nitrogen, oxygen and sulfur. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl. Unless otherwise defined above and herein, suitable substituents on the unsaturated carbon atom of a heteroaryl group are generally selected from halogen; —R, —OR, —SR, —NO$_2$, —CN, —N(R)$_2$, —NRC(O)R, —NRC(S)R, —NRC(O)N(R)$_2$, —NRC(S)N(R)$_2$, —NRCO$_2$R, —NRNRC(O)R, —NRNRC(O)N(R)$_2$, —NRNRCO$_2$R, —C(O)C(O)R, —C(O)CH$_2$C(O)R, —CO$_2$R, —C(O)R°, —C(S)R, —C(O)N(R)$_2$, —C(S)N(R)$_2$, —OC(O)N(R)$_2$, —OC(O)R, —C(O)N(OR)R, —C(NOR)R, —S(O)$_2$R, —S(O)$_3$R, —SO$_2$N(R)$_2$, —S(O)R, —NRSO$_2$N(R)$_2$, —NRSO$_2$R, —N(OR)R, —C(=NH)—N(R)$_2$, —P(O)$_2$R, —PO(R)$_2$, —OPO(R)$_2$, —(CH$_2$)$_{0-2}$NHC(O)R, phenyl (Ph) optionally substituted with R, —O(Ph) optionally substituted with R, —(CH$_2$)$_{1-2}$(Ph), optionally substituted with R, or —CH=CH(Ph), optionally substituted with R, wherein each independent occurrence of R is selected from hydrogen, optionally substituted C$_1$-C$_6$alkyl, optionally substituted C$_1$-C$_6$alkoxy, an unsubstituted 5-6 membered heteroaryl, phenyl, —O(Ph), or —CH$_2$(Ph), or two independent occurrences of R, on the same substituent or different substituents, taken together with the atom(s) to which each R is bound, to form an optionally substituted 3-12 membered saturated, partially unsaturated, or fully unsaturated monocyclic or bicyclic ring having 0-4 heteroatoms independently selected from nitrogen, oxygen, or sulfur.

The term "heterocycloalkyl", as used herein, refers to a cycloalkyl, as defined herein, wherein one or more of the ring carbons are replaced by a moiety selected from —O—, —N=, —NR—, —C(O)—, —S—, —S(O)— or —S(O)$_2$—, wherein R is hydrogen or an N substituent provided herein, with the proviso that the ring does not contain two adjacent O or S atoms. Non-limiting examples of heterocycloalkyl groups, as used herein, include morpholino, pyrrolidinyl, pyrrolidinyl-2-one, piperazinyl, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

The term "heteroatom", as used herein, refers to one or more of oxygen, sulfur, nitrogen, phosphorus, or silicon.

The term "hydroxyl", as used herein, refers to the group —OH.

The term "hydroxyalkyl", as used herein refers to an alkyl group as defined herein substituted with at least one hydroxyl, hydroxyl being as defined herein. Non-limiting examples of branched or straight chained "C$_1$-C$_6$ hydroxyalkyl groups as used herein include methyl, ethyl, propyl, isopropyl, isobutyl and n-butyl substituted independently with one or more hydroxyl groups.

The term "isocyanato", as used herein, refers to a —N=C=O group.

The term "isothiocyanato", as used herein, refers to a —N=C=S group.

The term "mercaptyl", as used herein, refers to an (alkyl)S— group.

The term "optionally substituted", as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN, —OR, —C(O)R, ⁻OC(O)R, —C(O)OR, OC(O)NHR, —C(O)N(R)$_2$, —SR—, —S(=O)R, —S(=O)$_2$R, —NHR, —N(R)$_2$, —NHC(O)—, NHC(O)O—, —C(O)NH—, S(=O)$_2$NHR, —S(O)$_2$N(R)$_2$, —NHS(=O)$_2$, —NHS(O)$_2$R, $C_1$-$C_6$ alkyl, $C_1$-$C_6$ alkoxy, aryl, heteroaryl, cycloalkyl, heterocycloalkyl, halo-substituted $C_1$-$C_6$alkyl, halo-substituted $C_1$-$C_6$alkoxy, where each R is independently selected from H, halo, $C_1$-$C_6$ alkyl, $C_1$-$C_6$ alkoxy, aryl, heteroaryl, cycloalkyl, heterocycloalkyl, halo-substituted $C_1$-$C_6$alkyl, halo-substituted $C_1$-$C_6$alkoxy.

The term "solvate", as used herein, refers to a complex of variable stoichiometry formed by a solute (in this invention, a compound of Formula (I), or a salt thereof) and a solvent. Such solvents for the purpose provided herein may not interfere with the biological activity of the solute. Non-limiting examples of suitable solvents include water, acetone, methanol, ethanol and acetic acid. Preferably the solvent used is a pharmaceutically acceptable solvent. Non-limiting examples of suitable pharmaceutically acceptable solvents include water, ethanol and acetic acid.

The term "acceptable" with respect to a formulation, composition or ingredient, as used herein, means having no persistent detrimental effect on the general health of the subject being treated.

The term "administration" or "administering" of the subject compound means providing a compound provided herein and prodrugs thereof to a subject in need of treatment.

The term "bone disease," as used herein, refers to a disease or condition of the bone, including, but not limited to, inappropriate bone remodeling, loss or gain, osteopenia, osteomalacia, osteofibrosis, and Paget's disease.

The term "cardiovascular disease," as used herein refers to diseases affecting the heart or blood vessels or both, including but not limited to: arrhythmia; atherosclerosis and its sequelae; angina; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to chemical compounds or agents that facilitate the incorporation of a compound provided herein into cells or tissues.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, and urticaria.

The term "diluent" as used herein, refers to chemical compounds that are used to dilute a compound provided herein prior to delivery. Diluents can also be used to stabilize compounds provided herein.

The terms "effective amount" or "therapeutically effective amount," as used herein, refer to a sufficient amount of a compound provided herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "iatrogenic", as used herein, means a condition, disorder, or disease created or worsened by medical or surgical therapy.

The term "inflammatory disorders", as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arteritis);

joints (arthritis: crystalline, osteo-, psoriatic, reactive, rheumatoid, Reiter's); gastrointestinal tract (Disease); skin (dermatitis); or multiple organs and tissues (systemic lupus erythematosus).

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The terms "neurogenerative disease" or "nervous system disorder," as used herein, refers to conditions that alter the structure or function of the brain, spinal cord or peripheral nervous system, including but not limited to Alzheimer's Disease, cerebral edema, cerebral ischemia, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica. The acronym "CNS" refers to disorders of the central nervous system (brain and spinal cord).

The terms "ocular disease" or "ophthalmic disease," as used herein, refer to diseases which affect the eye or eyes and potentially the surrounding tissues as well. Ocular or ophthalmic diseases include, but are not limited to, conjunctivitis, retinitis, scleritis, uveitis, allergic conjunctivitis, vernal conjunctivitis, papillary conjunctivitis.

The term "pharmaceutically acceptable," as used herein, refers a material, such as a carrier or diluent, which does not abrogate the biological activity or properties of the compounds provided herein. Such materials are administered to an individual without causing undesirable biological effects or interacting in a deleterious manner with any of the components of the composition in which it is contained.

The term "pharmaceutically acceptable salt", as used herein, refers to a formulation of a compound that does not cause significant irritation to an organism to which it is administered and does not abrogate the biological activity and properties of the compounds provided herein.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a coagent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The term "pharmaceutical composition", as used herein, refers to a mixture of a compound provided herein with other chemical components, such as carriers, stabilizers, diluents, dispersing agents, suspending agents, thickening agents, and/or excipients.

The term "prodrug", as used herein, refers to an agent that is converted into the parent drug in vivo. Prodrugs are often useful because, in some situations, they may be easier to administer than the parent drug. Prodrugs are bioavailable by oral administration whereas the parent is not. Prodrugs improve solubility in pharmaceutical compositions over the parent drug. A non-limiting example of a prodrug of the compounds provided herein is a compound provided herein administered as an ester which is then metabolically hydrolyzed to a carboxylic acid, the active entity, once inside the cell. A further example of a prodrug is a short peptide bonded to an acid group where the peptide is metabolized to reveal the active moiety.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient", as used herein, encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

The term "Syk inhibitor", as used herein, refers to a compound which inhibits the Syk receptor.

The term "Syk mediated disease" or a "disorder or disease or condition mediated by inappropriate Syk activity", as used herein, refers to any disease state mediated or modulated by Syk kinase mechanisms. Such disease states include, but are not limited to, an inflammatory disease, an allergic disease, a cell-proliferative disease, an autoimmune disease and cytopenia, such as, by way of example only, allergic asthma, allergic rhinitis, rheumatoid arthritis, multiple sclerosis, lupus, systemic lupus erythematosus, lymphoma, B cell lymphoma, T cell lymphoma, myelodysplasic syndrome, anemia, leucopenia, neutropenia, thrombocytopenia, granuloctopenia, pancytoia or idiopathic thrombocytopenic purpura.

The term "therapeutically effective amount", as used herein, refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treat", "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The compound names provided herein were obtained using ChemDraw Ultra 10.0 (CambridgeSoft®) or JChem version 5.2.2 (ChemAxon).

Other objects, features and advantages of the methods and compositions provided herein will become apparent from the following detailed description. It should be understood, however, that the detailed description and the specific examples, while indicating specific embodiments, are given by way of illustration only.

DESCRIPTION OF THE PREFERRED EMBODIMENTS

Provided herein are compounds and pharmaceutical compositions thereof, which are Syk kinase inhibitors. Also provided herein are compounds, pharmaceutical compositions and methods for the treatment and/or prevention of Syk kinase mediated diseases or conditions/disorders, including diseases or conditions/disorders associated with abnormal or deregulated Syk kinase activity.

The Syk kinase inhibitors provided herein are compounds having a structure of Formula (I), and pharmaceutically acceptable salts, pharmaceutically acceptable solvates (e.g. hydrates), the N-oxide derivatives, diastereomers, individual isomers and mixture of isomers thereof:

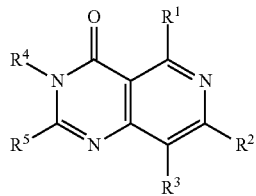

Formula (I)

wherein:
$R^1$ is $-NR^6R^7$, $-O(CR^9R^9)_nR^{11}$, $-O(CR^9R^9)_mR^{14}$, $R^{15}$, phenyl, $C_{10}$aryl, $C_{14}$aryl, a 5, 6, 9, 10 or 14 membered heteroaryl containing 1 to 3 heteroatoms independently selected from N, O and S, or a 4-8 membered heterocycloalkyl containing 1 to 2 heteroatoms independently selected from N, O and S, or $R^1$ is selected from phenyl, $C_{10}$aryl, $C_{14}$aryl, and a 5, 6, 9, 10 or 14 membered heteroaryl containing 1 to 3 heteroatoms independently selected from N, O and S, each of which is substituted with 1 to 3 substituents independently selected from halogen, hydroxyl, hydroxyl-$C_1$-$C_6$alkyl, $-(CR^9R^9)_nOR^9$, $-(CR^9R^9)_mOR^9$, $R^{10}$, $-(CR^9R^9)_mSR^9$, $-(CR^9R^9)_nSR^9$, $-(CR^9R^9)_mOS(O)_2N(R^9)_2$, $-(CR^9R^9)_nOS(O)_2N(R^9)_2$, $-(CR^9R^9)_mS(O)_2N(R^9)_2$, $-(CR^9R^9)_nS(O)_2N(R^9)_2$, $-(CR^9R^9)_nN_3$, $-(CR^9R^9)_mN_3$, $-(CR^9R^9)_nNR^9R^9$, $-(CR^9R^9)_mNR^9R^9$, $-(CR^9R^9)_nC(O)NR^9R^9$, $-(CR^9R^9)_nC(O)OR^9$ and $-(CR^9R^9)_nC(O)R^9$;

or $R^1$ is a 4-8 membered heterocycloalkyl containing 1 to 2 heteroatoms independently selected from N, O and S, substituted with 1 to 3 substituents independently selected from halogen, hydroxyl, hydroxyl-$C_1$-$C_6$alkyl, $-(CR^9R^9)_nOR^9$, $-(CR^9R^9)_mOR^9$, $R^{10}$, $=$N$-$OH, $=$N$-$OR$^9$, $-(CR^9R^9)_mSR^9$, $-(CR^9R^9)_nSR^9$, $-(CR^9R^9)_mOS(O)_2N(R^9)_2$, $-(CR^9R^9)_nOS(O)_2N(R^9)_2$, $-(CR^9R^9)_nS(O)_2N(R^9)_2$, $-(CR^9R^9)_mS(O)_2N(R^9)_2$, $-(CR^9R^9)_nN_3$, $-(CR^9R^9)_mN_3$, $-(CR^9R^9)_nNR^9R^9$, $-(CR^9R^9)_mNR^9R^9$, $-(CR^9R^9)_nC(O)NR^9R^9$, $-(CR^9R^9)_nC(O)OR^9$ and $-(CR^9R^9)_nC(O)R^9$;

$R^2$ is selected from $-NR^8(CR^9R^9)_nR^{10}$, $-O(CR^{12}R^{12})_nR^{10}$, $R^{15}$, $-NR^8(CR^{12}R^{12})_nR^{10}$, $O(CR^{12}R^{12})_nR^{10}$, phenyl, $C_{10}$aryl, $C_{14}$aryl, a 5, 6, 9, 10 or 14 membered heteroaryl containing 1 to 3 heteroatoms independently selected from N, O and S, and a 4-8 membered heterocycloalkyl containing 1 to 2 heteroatoms independently selected from N, O and S, or $R^2$ is selected from phenyl, $C_{10}$aryl, $C_{14}$aryl, a 5, 6, 9, 10 or 14 membered heteroaryl containing 1 to 3 heteroatoms independently selected from N, O and S, or a 4-8 membered heterocycloalkyl containing 1 to 2 heteroatoms independently selected from N, O and S, each of which is substituted with 1 to 3 substituents independently selected from halogen, $-CN$, $-OR^9$, $-OR^{10}$, $-OR^{12}$, $-C(O)R^{12}$, $-C(O)OR^9$, $-C(O)OR^{12}$, $-N(R^9)_2$, $-N(R^{12})_2$, $-NR^9(CR^9R^9)_nR^{10}$, $-NR^9(CR^9R^9)_mR^{14}$, $-NR^{12}(CR^{12}R^{12})_nR^{10}$, $NR^{12}(CR^{12}R^{12})_n R^{14}$, $-NR^{12}S(O)_2R^{13}$, $-N(R^{12})C(O)R^{13}$, $-N(R^9)C(O)R^9$, $-(CR^9R^9)_mR^{10}$, $-(CR^{12}R^{12})_nR^{10}$, $-(CR^9R^9)_m$ $C(O)R^{10}$, $-O(CR^9R^9)_nR^{10}$, $-O(CR^{12}R^{12})_nR^{10}$, $-C(O)(CR^9R^9)_mR^{14}$, $-(CR^9R^9)_n R^{14}$, $-(CR^9R^9)_m$ $R^{14}$, $-(CR^{12}R^{12})_n R^{14}$, $-C(R^9R^{36}R^{36})$, $-C(R^9R^9R^{14})$, $-C(R^{12}R^{12}R^{14})$, $-O(CR^9R^9)_mR^{14}$, $-O(CR^{12}R^{12})_nR^{14}$, $-NR^9S(O)_2$ $R^9$, $-S(O)_2R^9$, $-S(O)_2R^{12}$, $-S(O)_2R^{10}$, $-S(O)_2N(R^9R^{10})$, $-S(O)_2N(R^9)_2$, $-S(O)_2N(R^{12})_2$, $-S(O)_2(CR^9R^9)_mR^{10}$, $-S(O)_2(CR^{12}R^{12})_nR^{10}$, $-S(O)_2NR^9(CR^9R^9)_mR^{14}$, $-S(O)_2NR^5(CR^{12}R^{12})_nR^{14}$, $-S(O)_2(CR^9R^9)_mR^{14}-S(O)_2(CR^{12}R^{12})_nR^{14}$, $-(CR^9R^9)_nR^{15}$, $-(CR^{12}R^{12})_nR^{15}$, $R^{15}$, $R^{10}$, $C_1$-$C_6$alkyl, hydroxyl-$C_1$-$C_6$alkyl, halo-substituted $C_1$-$C_6$alkyl and

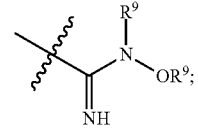

$R^4$ is H, $C_1$-$C_6$alkyl, hydroxyl-$C_1$-$C_6$alkyl, $-CD_3$, deuterated $C_1$-$C_6$alkyl or $C_1$-$C_6$haloalkyl;
$R^3$ and $R^5$ are independently selected from H or $C_1$-$C_6$alkyl;
$R^6$ is H, $-(CR^9R^9)_nR^{15}$, $-(CR^9R^9)_nR^{10}$, $-O(CR^9R^9)_n$ $R^{10}$, $-(CR^9R^9)_mR^{14}$, $-(CR^9R^9)_n(CR^9R^{14})_nR^{10}$, $R^{15}$, $-(CR^{12}R^{12})_n(CR^{12}R^{14})_nR^{10}$, $-(CR^{12}R^{12})_mR^{14}$, $C_1$-$C_6$ alkyl, $C_1$-$C_6$alkyl substituted with 1-4 hydroxyl groups, $C_3$-$C_8$cycloalkyl, phenyl, $C_{10}$aryl, $C_{14}$aryl, a 5, 6, 9, 10 or 14 membered heteroaryl containing 1 to 3 heteroatoms independently selected from N, O and S, or a 4-8 membered heterocycloalkyl containing 1 to 2 heteroatoms independently selected from N, O and S;
or $R^6$ is selected from phenyl, $C_{10}$aryl, $C_{14}$aryl, a 5, 6, 9, 10 or 14 membered heteroaryl containing 1 to 3 heteroatoms independently selected from N, O and S, a 4-8 membered heterocycloalkyl containing 1 to 2 heteroatoms independently selected from N, O and S, and $C_3$-$C_8$cycloalkyl, each of which is substituted with 1 to 3 substituents independently selected from halogen, $C_1$-$C_6$alkyl, hydroxyl, hydroxyl-$C_1$-$C_6$alkyl, $-(CR^{12}R^{12})_nR^{14}$, $(CR^9R^9)_mR^{14}$, $-CN$, $-OR^9$, $-OR^{12}$, $-C(O)OR^{12}$, $-C(O)OR^9$, tetrazole, $R^{10}$, $-C(O)N(R^9)_2$, $-C(O)N(R^{12})_2$, $-S(O)_2R^9$, $-S(O)_2 R^{12}$, $-NR^9S(O)_2R^9$, $-N(R^9)_2$, $-N(R^{12})_2$, $-N(R^{12})C(O)OR^{12}$, $-N(R^{12})C(O)(CR^{12}R^{12})_nOR^{12}$, $-C(O)(CR^{12}R^{12})_nOR^{11}$, $-C(O)(CR^9R^9)_mR^{14}$, $C(O)(CR^{12}R^{12})_nR^{14}$ and $-OC(O)R^{13}$;
$R^7$ is H or $C_1$-$C_6$ alkyl;
$R^8$ is H or $C_1$-$C_6$ alkyl;

each $R^9$ is independently selected from H and $C_1$-$C_6$alkyl $R^{10}$ is phenyl, $C_{10}$aryl, $C_{14}$aryl, a 5, 6, 9, 10 or 14 membered heteroaryl containing 1 to 3 heteroatoms independently selected from N, O and S, or a 4-8 membered heterocycloalkyl containing 1 to 2 heteroatoms independently selected from N, O and S, $C_3$-$C_8$cycloalkyl or —$(CR^{12}R^{12})_nR^{11}$;

or $R^{10}$ is phenyl, $C_{10}$ aryl, $C_{14}$aryl, a 5, 6, 9, 10 or 14 membered heteroaryl containing 1 to 3 heteroatoms independently selected from N, O and S, a 4-8 membered heterocycloalkyl containing 1 to 2 heteroatoms independently selected from N, O and S, or a $C_3$-$C_8$cycloalkyl, each of which is substituted with 1 to 3 substituents independently selected from halogen, —CN, hydroxyl, —$C_1$-$C_6$alkyl, benzyl, hydroxyl-$C_1$-$C_6$alkyl, $C_3$-$C_8$cycloalkyl, —$OR^{12}$, —$OR^{11}$, —$C(O)R^{14}$, —$C(O)OR^9$, —$C(O)OR^{12}$, —$N(R^9)_2$, —$N(R^{12})_2$, —$C(O)N(R^{12}R^{11})$, —$C(O)(CR^{12}R^{12})_nN(R^{12})_2$, —$C(O)(CR^{12}R^{12})_nOR^{12}$, —$(CR^{12}R^{12})_nR^{14}$, $(CR^9R^9)_mR^{14}$, $OR^9$, —$C(O)OR^9$, —$C(O)(CR^9R^9)_nN(R^9)_2$, —$C(O)(CR^9R^9)_nOR^9$, —$(CR^9R^9)_nR^{14}$, —$S(O)_2R^9$, —$(CR^9R^9)_nS(O)_2R^9$, —$S(O)_2R^{10}$, —$S(O)_2R^{12}$, —$S(O)_2R^9$, —$(CR^{12}R^{12})_nS(O)_2R^{12}$, —$(CR^{12}R^{12})_nS(O)_2R^{10}$, $R^{15}$, $R^{13}$ and —$C(O)OR^{13}$;

$R^{11}$ is $C_1$-$C_6$alkyl, $C_3$-$C_8$cycloalkyl, phenyl, $C_{10}$aryl, $C_{14}$aryl, a 5, 6, 9, 10 or 14 membered heteroaryl containing 1 to 3 heteroatoms independently selected from N, O and S, or a 4-8 membered heterocycloalkyl containing 1 to 2 heteroatoms independently selected from N, O and S;

or $R^{11}$ is selected from $C_1$-$C_6$alkyl, $C_3$-$C_8$cycloalkyl, phenyl, $C_{10}$aryl, $C_{14}$aryl, a 5, 6, 9, 10 or 14 membered heteroaryl containing 1 to 3 heteroatoms independently selected from N, O and S, and a 4-8 membered heterocycloalkyl containing 1 to 2 heteroatoms independently selected from N, O and S, each of which is substituted with 1 to 3 substituents independently selected from hydroxyl, —$C_1$-$C_6$alkyl, hydroxyl-$C_1$-$C_6$alkyl, —$(CR^{12}R^{12})_nR^{14}$ and —$(CR^9R^9)_nR^{14}$;

each $R^{12}$ is independently selected from H, $C_1$-$C_6$alkyl, and $C_3$-$C_8$cycloalkyl, or each $R^{12}$ is independently a $C_1$-$C_6$alkyl that together with N they are attached to form a heterocycloalkyl;

$R^{13}$ is H, $C_1$-$C_6$alkyl, halo-substituted $C_1$-$C_6$alkyl, $C_3$-$C_8$cycloalkyl, phenyl, $C_{10}$aryl, $C_{14}$aryl, a 5, 6, 9, 10 or 14 membered heteroaryl containing 1 to 3 heteroatoms independently selected from N, O and S, or a 4-8 membered heterocycloalkyl containing 1 to 2 heteroatoms independently selected from N, O and S;

$R^{14}$ is H, $C_1$-$C_6$alkyl, halogen, hydroxyl, hydroxyl-$C_1$-$C_6$alkyl, $C_1$-$C_6$haloalkyl, —$OR^9$, —$N(R^9)_2$, —$C(O)N(R^9)_2$, —$C(O)R^9$, —$C(O)OR^9$, —$OR^{13}$, —$(CR^9R^9)_nOR^{13}$, —$(CR^{12}R^{12})_nOR^{13}$, —$C(O)R^{10}$, —$OC(O)R^{13}$, —$C(O)OR^{13}$, —$N(R^{12})_2$, —CN, —$S(O)_2R^9$, —$S(O)_2N(R^{12})_2$, —$S(O)_2R^{13}$, —$N(R^9)S(O)_2R^9$, —$N(R^{12}R^{10})$, —$(CR^9R^9)_nN(R^{12})_2$, —$(CR^{12}R^{12})_nN(R^{12})_2$, —$C(O)N(R^{12})_2$, —$NR^9C(O)(R^9)$, —$NR^{12}C(O)(R^{12})$, —$(CR^9R^9)_nR^{13}$, —$(CR^{12}R^{12})_nR^{13}$, —$N(R^9)C(O)(CR^9R^9)_nOR^9$, —$(CR^9R^9)_nOR^9$, —$N(R^{12})C(O)(CR^{12}R^{12})_nOR^{13}$, —$N(R^{12})(CR^{12}R^{12})_nOR^{13}$, —$N(R^9)(CR^9R^9)_nR^{10}$, —$N(R^{12})(CR^{12}R^{12})_nR^{10}$, —$C(O)N(R^{12})_2$, —$N(R^{12})C(O)R^{13}$, —$N(R^{12})C(O)OR^{13}$, —$(CR^9R^9)_nR^{10}$, $R^{13}$ and $R^{15}$;

$R^{15}$ is

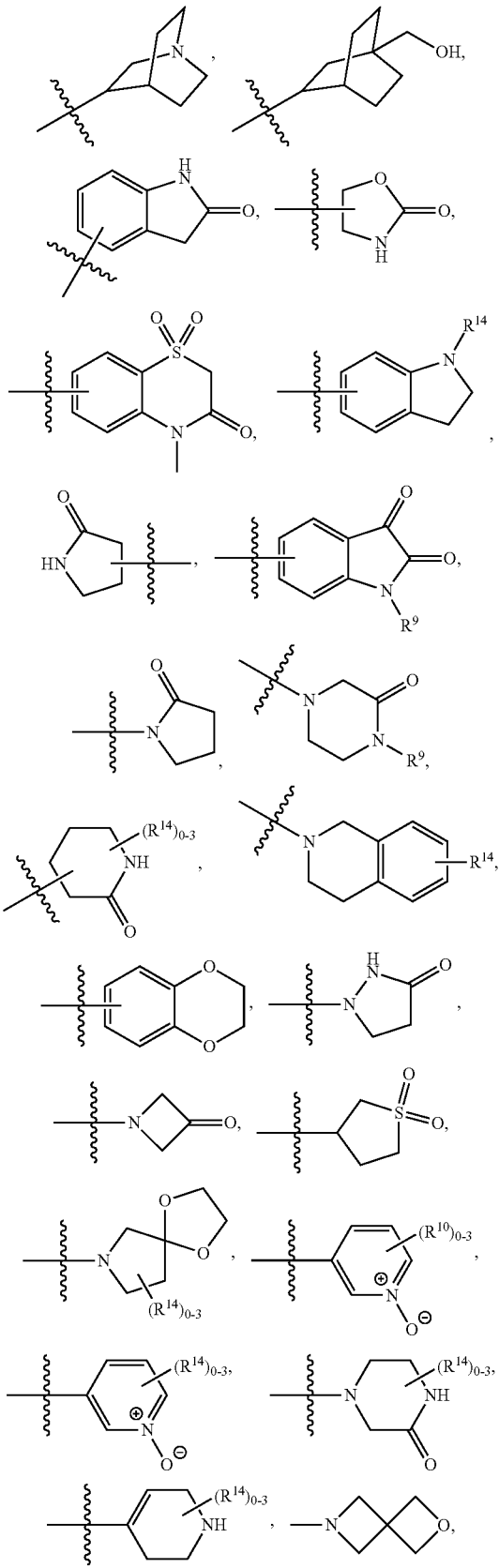

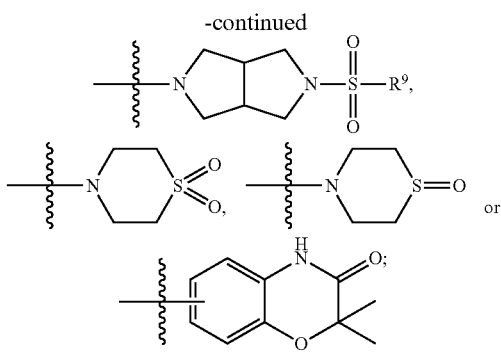

each $R^{36}$ is independently hydroxyl or $C_1$-$C_6$haloalkyl,
each m is independently 1, 2, 3, 4, 5 or 6, and
each n is independently 0, 1, 2, 3, 4, 5 or 6

In certain embodiments of such compounds of Formula (I), $R^1$ is —$NR^6R^7$, and the Syk kinase inhibitors provided herein are compounds having a structure of Formula (II), and pharmaceutically acceptable salts, pharmaceutically acceptable solvates (e.g. hydrates), the N-oxide derivatives, diastereomers, individual isomers and mixture of isomers thereof:

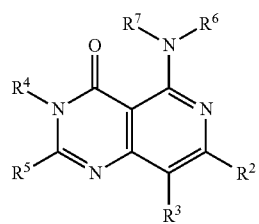

Formula (II)

In certain embodiments of such compounds of Formulas (I) and Formula (II), $R^7$ is $C_1$-$C_6$alkyl.

In certain embodiments of the Syk kinase inhibitors provided herein having the structure of Formula (I) and Formula (II),
$R^6$ is H, —$(CR^9R^9)_nR^{15}$, —$(CR^9R^9)_nR^{10}$, —$O(CR^9R^9)_n$ $R^{10}$, —$(CR^9R^9)_mR^{14}$, —$(CR^9R^9)_n(CR^9R^{14})_nR^{10}$, $R^{15}$, —$(CR^{12}R^{12})_n(CR^{12}R^{14})_nR^{10}$, —$(CR^{12}R^{12})_mR^{14}$, $C_1$-$C_6$ alkyl, $C_1$-$C_6$alkyl substituted with 1-4 hydroxyl groups, $C_3$-$C_8$cycloalkyl, phenyl, $C_{10}$aryl, $C_{14}$aryl, a 5, 6, 9, 10 or 14 membered heteroaryl containing 1 to 3 heteroatoms independently selected from N, O and S, or a 4-8 membered heterocycloalkyl containing 1 to 2 heteroatoms independently selected from N, O and S;
or $R^6$ is selected from phenyl, $C_{10}$aryl, $C_{14}$aryl, a 5, 6, 9, 10 or 14 membered heteroaryl containing 1 to 3 heteroatoms independently selected from N, O and S, a 4-8 membered heterocycloalkyl containing 1 to 2 heteroatoms independently selected from N, O and S, and $C_3$-$C_8$cycloalkyl, each of which is substituted with 1 to 3 substituents independently selected from halogen, $C_1$-$C_6$alkyl, hydroxyl, hydroxyl-$C_1$-$C_6$alkyl, —$(CR^{12}R^{12})_nR^{14}$, —$(CR^9R^9)_mR^{14}$, —CN, —$OR^9$, —$OR^{12}$, —$C(O)OR^{12}$, —$C(O)OR^9$, tetrazole, $R^{10}$, —$C(O)N(R^9)_2$, —$C(O)N(R^{12})_2$, —$S(O)_2R^9$, —$S(O)_2R^{12}$, —$NR^9S(O)_2R^9$, —$N(R^9)_2$, —$N(R^{12})_2$, —$N(R^{12})C(O)OR^{12}$, —$N(R^{12})C(O)(CR^{12}R^{12})_nOR^{12}$, —$C(O)(CR^{12}R^{12})_nR^{11}$, —$C(O)(CR^9R^9)_mR^{14}$, —$C(O)(CR^{12}R^{12})_nR^{14}$ and —$OC(O)R^{13}$;
each m is independently 0, 1, 2, 3 or, and each n is independently 0, 1, 2, 3 or 4.

In certain embodiments of the Syk kinase inhibitors provided herein having the structure of Formula (I) and Formula (II), $R^6$ is

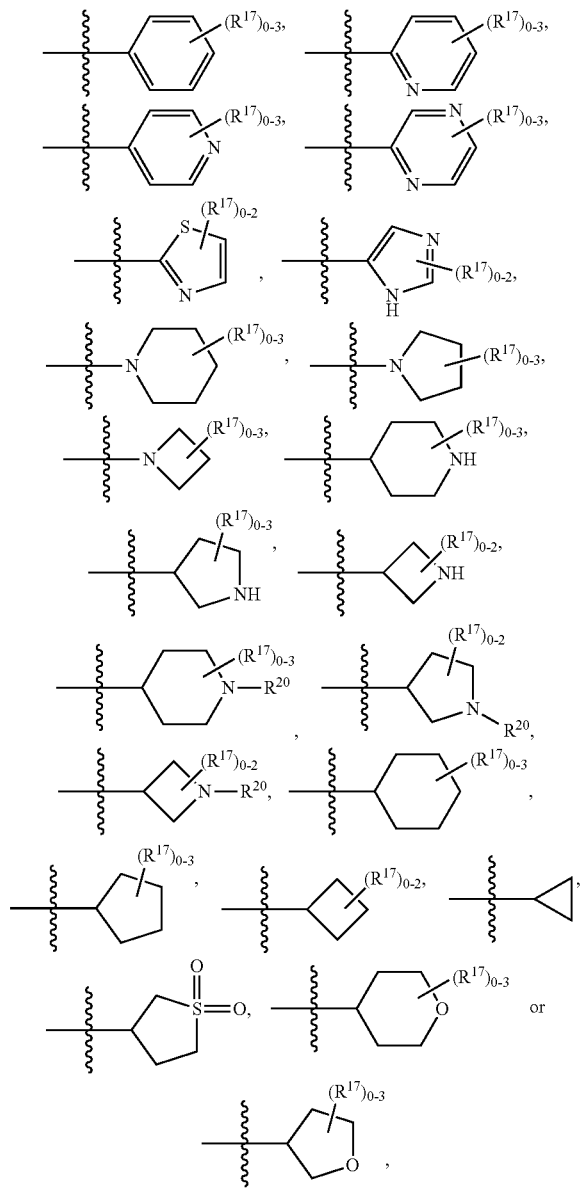

and each $R^{17}$ is independently selected from halogen, $C_1$-$C_6$alkyl, hydroxyl, hydroxyl-$C_1$-$C_6$alkyl, —$(CR^{12}R^{12})_nR^{14}$, —CN, —$OR^9$, —$C(O)OR^{12}$, —$C(O)OR^9$, tetrazole, $R^{10}$, —$C(O)N(R^9)_2$, —$C(O)N(R^{12})_2$, —$S(O)_2R^9$, —$S(O)_2R^{12}$, —$NR^9S(O)_2R^9$, —$N(R^9)_2$, —$N(R^{12})_2$, —$N(R^{12})C(O)OR^{12}$, —$N(R^{12})C(O)(CR^{12}R^{12})_nOR^{12}$, —$C(O)(CR^{12}R^{12})_nR^{11}$, —$C(O)(CR^9R^9)_mR^{14}$, —$C(O)(CR^{12}R^{12})_nR^{14}$ and —$OC(O)R^{13}$;

$R^{20}$ is H, hydroxyl, $C_1$-$C_6$alkyl, —$(CR^{12}R^{12})_nR^{14}$, —$(CR^9R^9)_mR^{14}$, hydroxyl-$C_1$-$C_6$alkyl, —$(CR^9R^9)_m$ $R^{14}$, —$C(O)OR^{12}$, $R^{10}$, —$C(O)N(R^{12})_2$, —$S(O)_2R^{12}$, —$C(O)(CR^{12}R^{12})_nR^{11}$, —$C(O)(CR^{12}R^{12})_nR^{14}$ or —$OC(O)R^{13}$, each m is independently 0, 1, 2, 3 or 4, and
each n is independently 0, 1, 2, 3 or 4.

In certain embodiments of the Syk kinase inhibitors provided herein having the structure of Formula (I) and Formula (II), $R^6$ is $—(CR^{12}R^{12})_mR^{14}$. In certain embodiments of such Syk kinase inhibitors provided herein having the structure of Formula (I) and Formula (II), $R^{14}$ is selected from H, $C_1$-$C_6$alkyl, halogen, hydroxyl, hydroxyl-$C_1$-$C_6$alkyl, $C_1$-$C_6$haloalkyl, $—OR^9$, $—N(R^9)_2$, $—C(O)N(R^9)_2$, $—C(O)R^9$, $—C(O)OR^9$, $—(CR^9R^9)_nOR^{13}$, $—(CR^{12}R^{12})_nOR^{13}$, $—C(O)R^{13}$, $—C(O)R^{10}$, $—OC(O)R^{13}$, $—C(O)OR^{13}$, $—N(R^{12})_2$, $—CN$, $—S(O)_2R^9$, $—S(O)_2N(R^{12})_2$, $—S(O)_2R^{13}$, $—N(R^9)S(O)_2R^9$, $—N(R^{12}R^{10})$, $(CR^9R^9)_nN(R^{12})_2$, $—(CR^{12}R^{12})_nN(R^{12})_2$, $—C(O)N(R^{12})_2$, $—NR^9C(O)(R^9)$, $—NR^{12}C(O)(R^{12})$, $—(CR^9R^9)_nR^{13}$, $—(CR^{12}R^{12})_nR^{13}$, $—N(R^9)C(O)(CR^9R^9)_nOR^9$, $—N(R^9)(CR^9R^9)_mOR^9$, $—N(R^{12})(CR^9R^9)_nOR^{13}$, $—N(R^{12})C(O)(CR^{12}R^{12})_nOR^{13}$, $—N(R^{12})(CR^{12}R^{12})_nOR^{13}$, $—N(R^9)(CR^9R^9)_nR^{10}$, $—N(R^{12})(CR^{12}R^{12})_nR^{10}$, $—C(O)N(R^{12})_2$, $—N(R^{12})C(O)R^{13}$, $—N(R^{12})C(O)OR^{13}$, $—(CR^9R^9)_nR^{10}$, $—(CR^{12}R^{12})_nR^{10}$, $R^{13}$ and $R^{15}$.

In certain embodiments of the Syk kinase inhibitors provided herein having the structure of Formula (I), $R^1$ is a 4-8 membered heterocycloalkyl containing 1 to 2 heteroatoms independently selected from N, O and S, or $R^1$ is a 4-8 membered heterocycloalkyl containing 1 to 2 heteroatoms independently selected from N, O and S, substituted with 1 to 3 substituents independently selected from halogen, hydroxyl, hydroxyl-$C_1$-$C_6$alkyl, $—(CR^9R^9)_nOR^9$, $—(CR^9R^9)_mOR^9$, $=N—OH$, $=N—OR^9$, $—(CR^9R^9)_mSR^9$, $—(CR^9R^9)_nSR^9$, $—(CR^9R^9)_mOS(O)_2N(R^9)_2$, $—(CR^9R^9)_nOS(O)_2N(R^9)_2$, $—(CR^9R^9)_nS(O)_2N(R^9)_2$, $—(CR^9R^9)_mS(O)_2N(R^9)_2$, $—(CR^9R^9)_nN_3$, $—(CR^9R^9)_mN_3$, $—(CR^9R^9)_nNR^9R^9$, $—(CR^9R^9)_nNR^9R^9$, $—(CR^9R^9)_nC(O)NR^9R^9$, $—(CR^9R^9)_nC(O)OR^9$ and $—(CR^9R^9)_nC(O)R^9$.

In other embodiments of the Syk kinase inhibitors provided herein having the structure of Formula (I), $R^1$ is selected from

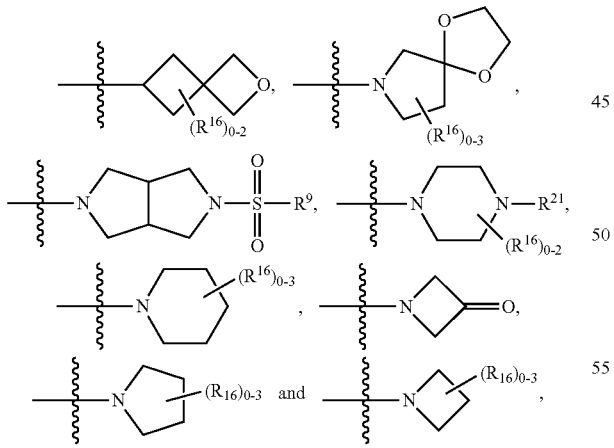

wherein
each $R^{16}$ is independently selected from halogen, hydroxyl, hydroxyl-$C_1$-$C_6$alkyl, $—(CR^9R^9)_nOR^9$, $—(CR^9R^9)_mOR^9$, $R^{10}$, $=N—OH$, $=N—OR^9$, $—(CR^9R^9)_mSR^9$, $—(CR^9R^9)_nSR^9$, $—(CR^9R^9)_mOS(O)_2N(R^9)_2$, $—(CR^9R^9)_nOS(O)_2N(R^9)_2$, $—(CR^9R^9)_nS(O)_2N(R^9)_2$, $—(CR^9R^9)_mS(O)_2N(R^9)_2$, $—(CR^9R^9)_nN_3$, $—(CR^9R^9)_mN_3$, $—(CR^9R^9)_nNR^9R^9$, $—(CR^9R^9)_mNR^9R^9$, $—(CR^9R^9)_nC(O)NR^9R^9$, $—(CR^9R^9)_nC(O)OR^9$ and $—(CR^9R^9)_nC(O)R^9$, and $R^{21}$ is H, hydroxyl-$C_1$-$C_6$alkyl, $—(CR^9R^9)_mOR^9$, $R^{10}$, $—(CR^9R^9)_mSR^9$, $—(CR^9R^9)_mOS(O)_2N(R^9)_2$, $—(CR^9R^9)_mS(O)_2N(R^9)_2$, $—(CR^9R^9)_mN_3$, $—(CR^9R^9)_mNR^9R^9$, $—(CR^9R^9)_nC(O)NR^9R^9$, $—(CR^9R^9)_nC(O)OR^9$ and $—(CR^9R^9)_nC(O)R^9$.

In certain embodiments of the Syk kinase inhibitors provided herein having the structure of Formula (I), $R^1$ is selected from

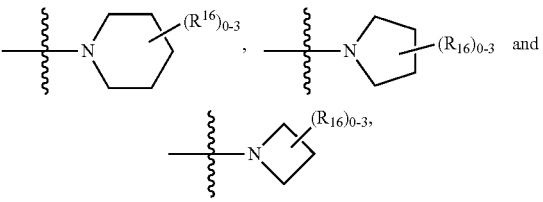

wherein each $R^{16}$ is independently selected from halogen, hydroxyl, hydroxyl-$C_1$-$C_6$alkyl, $—(CR^9R^9)_nOR^9$, $—(CR^9R^9)_mOR^9$, $R^{10}$, $=N—OH$, $=N—OR^9$, $—(CR^9R^9)_mSR^9$, $—(CR^9R^9)_nSR^9$, $—(CR^9R^9)_mOS(O)_2N(R^9)_2$, $—(CR^9R^9)_nOS(O)_2N(R^9)_2$, $—(CR^9R^9, S(O)_2N(R^9)_2$, $—(CR^9R^9)_mS(O)_2N(R^9)_2$, $—(CR^9R^9)_nN_3$, $—(CR^9R^9)_mN_3$, $—(CR^9R^9)_nNR^9R^9$, $—(CR^9R^9)_mNR^9R^9$, $—(CR^9R^9)_nC(O)NR^9R^9$, $—(CR^9R^9)_nC(O)OR^9$ and $—(CR^9R^9)_nC(O)R^9$, and in other embodiments, the Syk kinase inhibitors provided herein are compounds having a structure of Formula (III), and pharmaceutically acceptable salts, pharmaceutically acceptable solvates (e.g. hydrates), the N-oxide derivatives, diastereomers, individual isomers and mixture of isomers thereof:

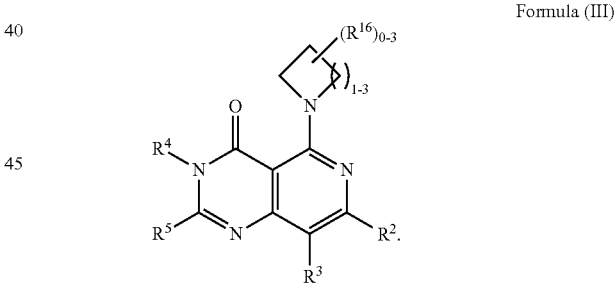

Formula (III)

In other embodiments of the Syk kinase inhibitors provided herein having the structure of Formula (I), $R^1$ is selected from phenyl, $C_{10}$aryl, $C_{14}$aryl, and a 5, 6, 9, 10 or 14 membered heteroaryl containing 1 to 3 heteroatoms independently selected from N, O and S, each of which is substituted with 1 to 3 substituents independently selected from halogen, hydroxyl, hydroxyl-$C_1$-$C_6$alkyl, $—(CR^9R^9)_nOR^9$, $—(CR^9R^9)_mOR^9$, $—(CR^9R^9)_mSR^9$, $—(CR^9R^9)_nSR^9$, $—(CR^9R^9)_mOS(O)_2N(R^9)_2$, $—(CR^9R^9)_nOS(O)_2N(R^9)_2$, $—(CR^9R^9)_nS(O)_2N(R^9)_2$, $—(CR^9R^9)_mS(O)_2N(R^9)_2$, $—(CR^9R^9)_nN_3$, $—(CR^9R^9)_mN_3$, $—(CR^9R^9)_nNR^9R^9$, $—(CR^9R^9)_mNR^9R^9$, $—(CR^9R^9)_nC(O)NR^9R^9$, $—(CR^9R^9)_nC(O)OR^9$ and $—(CR^9R^9)_nC(O)R^9$.

In certain embodiments of the Syk kinase inhibitors provided herein having the structure of Formula (I), $R^1$ is

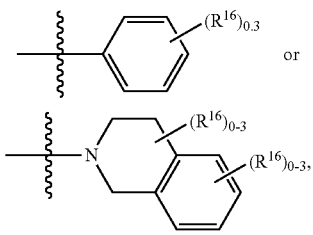 or

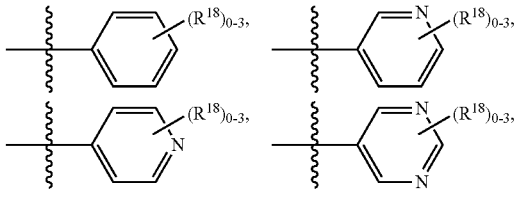

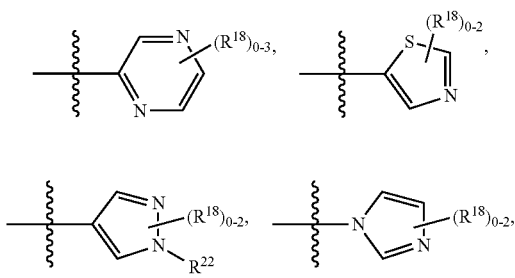

wherein each $R^6$ is independently selected from halogen, hydroxyl, hydroxyl-$C_1$-$C_6$alkyl, —$(CR^9R^9)_nOR^9$, —$(CR^9R^9)_mOR^9$, $R^{10}$, —$(CR^9R^9)_mSR^9$, —$(CR^9R^9)_nSR^9$, —$(CR^9R^9)_mOS(O)_2N(R^9)_2$, —$(CR^9R^9)_nOS(O)_2N(R^9)_2$, —$(CR^9R^9)_nS(O)_2N(R^9)_2$, —$(CR^9R^9)_mS(O)_2N(R^9)_2$, —$(CR^9R^9)_nN_3$, —$(CR^9R^9)_mN_3$, —$(CR^9R^9)_nNR^9R^9$, —$(CR^9R^9)_mNR^9R^9$, —$(CR^9R^9)_nC(O)NR^9R^9$, —$(CR^9R^9)_nC(O)OR^9$ and —$(CR^9R^9)_nC(O)R^9$.

In certain embodiments of the Syk kinase inhibitors provided herein having the structure of Formula (I), Formula (II) and Formula (III), $R^2$ is selected from phenyl, $C_{10}$aryl, $C_{14}$aryl, a 5, 6, 9, 10 or 14 membered heteroaryl containing 1 to 3 heteroatoms independently selected from N, O and S, and a 4-8 membered heterocycloalkyl containing 1 to 2 heteroatoms independently selected from N, O and S. In certain embodiments of the Syk kinase inhibitors provided herein having the structure of Formula (I), Formula (II) and Formula (III), $R^2$ is selected from phenyl, $C_{10}$aryl, $C_{14}$aryl, a 5, 6, 9, 10 or 14 membered heteroaryl containing 1 to 3 heteroatoms independently selected from N, O and S, or a 4-8 membered heterocycloalkyl containing 1 to 2 heteroatoms independently selected from N, O and S, each of which is substituted with 1 to 3 substituents independently selected from halogen, —CN, —$OR^9$, —$OR^{12}$, —$C(O)R^{12}$, —$C(O)OR^9$, —$C(O)OR^{12}$, —$N(R^9)_2$, —$N(R^{12})_2$, —$NR^9(CR^9R^9)_nR^{10}$, —$NR^9(CR^9R^9)_mR^{14}$, $NR^{12}(CR^{12}R^{12})_nR^{10}$, —$NR^{12}(CR^{12}R^{12})_nR^{14}$, —$NR^{12}S(O)_2R^{13}$, $N(R^{12})C(O)R^{13}$, —$N(R^9)C(O)R^9$, —$(CR^9R^9)_mR^{10}$, —$(CR^{12}R^{12})_nR^{10}$, —$(CR^9R^9)_mC(O)R^{10}$, —$O(CR^9R^9)_nR^{10}$, —$O(CR^{12}R^{12})_nR^{10}$, $C(O)(CR^9R^9)_mR^{14}$, —$(CR^9R^9)_nR^{14}$, —$(CR^9R^9)_mR^{14}$, —$(CR^{12}R^{12})_nR^{14}$, —$C(R^9R^{36}R^{36})$, —$C(R^9R^9R^{14})$, —$C(R^{12}R^{12}R^{14})$, —$O(CR^9R^9)_mR^{14}$, —$O(CR^{12}R^{12})_nR^{14}$, —$NR^9S(O)_2R^9$, —$S(O)_2R^9$, —$S(O)_2R^{12}$, —$S(O)_2R^{10}$, —$S(O)_2N(R^9R^{10})$, —$S(O)_2N(R^9)_2$, —$S(O)_2N(R^{12})_2$, —$S(O)_2(CR^9R^9)_mR^{10}$, —$S(O)_2(CR^{12}R^{12})_nR^{10}$, —$S(O)_2NR^9(CR^9R^9)_mR^{14}$, —$S(O)_2NR^5(CR^{12}R^{12})_nR^{14}$, —$(CR^9R^9)_mR^{14}$, —$S(O)_2(CR^{12}R^{12})_nR^{14}$, $R(CR^9R^9)_nR^{15}$, —$(CR^{12}R^{12})_nR^{15}$, $R^{15}$, $R^{15}$, $R^{10}$, $C_1$-$C_6$alkyl, hydroxyl-$C_1$-$C_6$alkyl, halo-substituted $C_1$-$C_6$alkyl and

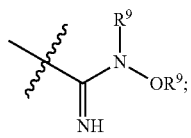

each m is independently 0, 1, 2, 3 or 4, and each n is independently 0, 1, 2, 3 or 4.

In certain embodiments of the Syk kinase inhibitors provided herein having the structure of Formula (I), Formula (II) and Formula (III), $R^2$ is selected from

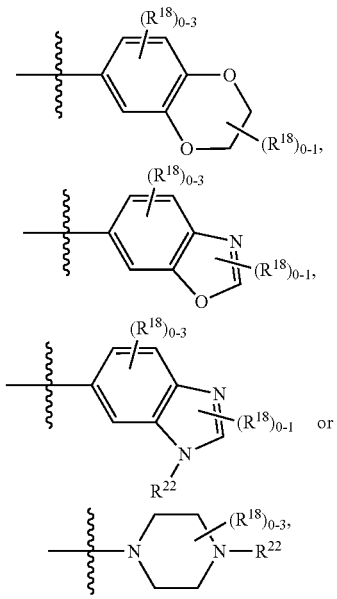

wherein each $R^{18}$ is independently selected from halogen, —CN, —$OR^9$, —$OR^{12}$, —$C(O)R^{12}$, —$C(O)OR^9$, —$C(O)OR^{12}$, —$N(R^9)_2$, —$N(R^{12})_2$, —$NR^9(CR^9R^9)_nR^{10}$, —$NR^9(CR^9R^9)_mR^{14}$, —$NR^{12}(CR^{12}R^{12})_nR^{10}$, —$NR^{12}(CR^{12}R^{12})_nR^{14}$, —$NR^{12}S(O)_2R^{13}$, —$N(R^{12})C(O)R^{13}$, —$N(R^9)C(O)R^9$, —$(CR^9R^9)_mR^{10}$, —$(CR^{12}R^{12})_nR^{10}$, —$(CR^9R^9)_mC(O)R^{10}$, —$O(CR^9R^9)_nR^{10}$, —$O(CR^{12}R^{12})_nR^{10}$, —$C(O)(CR^9R^9)_mR^{14}$, —$(CR^9R^9)_nR^{14}$, —$(CR^9R^9)_mR^{14}$, —$(CR^{12}R^{12})_nR^{14}$, —$C(R^9R^{36}R^{36})$, —$C(R^9R^9R^{14})$, —$C(R^{12}R^{12}R^{14})$, —$O(CR^9R^9)_mR^{14}$, —$O(CR^{12}R^{12})_nR^{14}$, —$NR^9S(O)_2R^9$, —$S(O)_2R^9$, —$S(O)_2R^{12}$, —$S(O)_2N(R^9R^{10})$, —$S(O)_2N(R^9)_2$, —$S(O)_2N(R^{12})_2$, —$S(O)_2(CR^9R^9)_mR^{10}$, —$S(O)_2(CR^{12}R^{12})_nR^{10}$, —$S(O)_2NR^9(CR^9R^9)_mR^{14}$, —$S(O)_2NR^5(CR^{12}R^{12})_nR^{14}$, —$S(O)_2(CR^9R^9)_mR^{14}$, —$S(O)_2(CR^{12}R^{12})_nR^{14}$, —$(CR^9R^9)_nR^{15}$, —$(CR^{12}R^{12})_nR^{15}$, $R^{15}$, $R^{10}$, $C_1$-$C_6$ alkyl, hydroxyl-$C_1$-$C_6$alkyl, halo-substituted $C_1$-$C_6$alkyl and

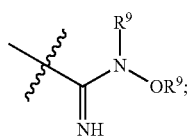

$R^{22}$ is H, $C_1$-$C_6$alkyl, —$(CR^9R^9)_mR^{14}$, hydroxyl-$C_1$-$C_6$alkyl, —$C(O)R^{12}$, —$C(O)OR^{12}$, —$(CR^{12}R^{12})_nR^{10}$, —$(CR^{12}R^{12})_mR^{14}$, —$S(O)_2R^{12}$, —$S(O)_2R^{10}$, —$S(O)_2N(R^{12}R^{10})$, —$S(O)_2N(R^{12})_2$, $S(O)_2(CR^{12}R^{12})R^{10}$, $S(O)_2$ $NR^5(CR^{12}R^{12})_nR^{14}$, —$S(O)_2(CR^{12}R^{12})_nR^{14}$, —$(CR^{12}R^{12})_nR^{15}$, $R^{10}$, and halo-substituted $C_1$-$C_6$ alkyl;

each m is independently 0, 1, 2, 3 or 4, and each n is independently 0, 1, 2, 3 or 4.

In certain embodiments of the Syk kinase inhibitors provided herein having the structure of Formula (I), Formula (II) and Formula (III), $R^{10}$ is selected from phenyl, $C_{10}$aryl, $C_{14}$aryl, a 5, 6, 9, 10 or 14 membered heteroaryl containing 1 to 3 heteroatoms independently selected from N, O and S, or a 4-8 membered heterocycloalkyl containing 1 to 2 heteroatoms independently selected from N, O and S, and $C_3$-$C_8$cycloalkyl.

In certain embodiments of the Syk kinase inhibitors provided herein having the structure of Formula (I), Formula (II) and Formula (III), $R^{10}$ is phenyl, $C_{10}$aryl, $C_{14}$aryl, a 5, 6, 9, 10 or 14 membered heteroaryl containing 1 to 3 heteroatoms independently selected from N, O and S, a 4-8 membered heterocycloalkyl containing 1 to 2 heteroatoms independently selected from N, O and S, or a $C_3$-$C_8$cycloalkyl, each of which is substituted with 1 to 3 substituents independently selected from halogen, —CN, hydroxyl, —$C_1$-$C_6$alkyl, benzyl, hydroxyl-$C_1$-$C_6$alkyl, $C_3$-$C_8$cycloalkyl, —$OR^{12}$, —$OR^{11}$, —$C(O)R^{14}$, —$C(O)OR^9$, —$C(O)OR^{12}$, —$N(R^9)_2$, —$N(R^{12})_2$, —$C(O)N(R^{12}R^{11})$, —$C(O)(CR^{12}R^{12})_nN(R^{12})_2$, $C(O)(CR^{12}R^{12})_nOR^{12}$, —$(CR^{12}R^{12})_nR^{14}$, —$OR^9$, —$C(O)OR^9$, —$C(O)(CR^9R^9)_nN(R^9)_2$, —$C(O)(CR^9R^9)_nOR^9$, —$(CR^9R^9)_nR^{14}$, —$(CR^9R^9)_mR^{14}$, —$S(O)_2R^9$, —$(CR^9R^9)_nS(O)_2R^9$, —$S(O)_2R^{10}$, —$S(O)_2R^{12}$, —$S(O)_2R^9$, —$(CR^{12}R^{12})_nS(O)_2R^{12}$, —$(CR^{12}R^{12})_nS(O)_2R^{10}$, $R^{15}$, $R^{13}$ and —$C(O)OR^{13}$.

In certain embodiments of the Syk kinase inhibitors provided herein having the structure of Formula (I), Formula (II) and Formula (III), $R^{10}$ is selected from

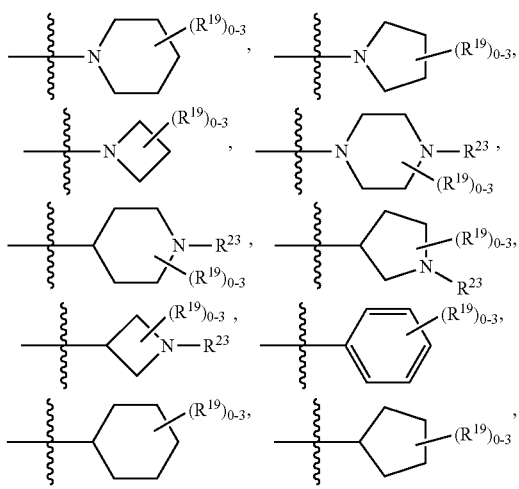

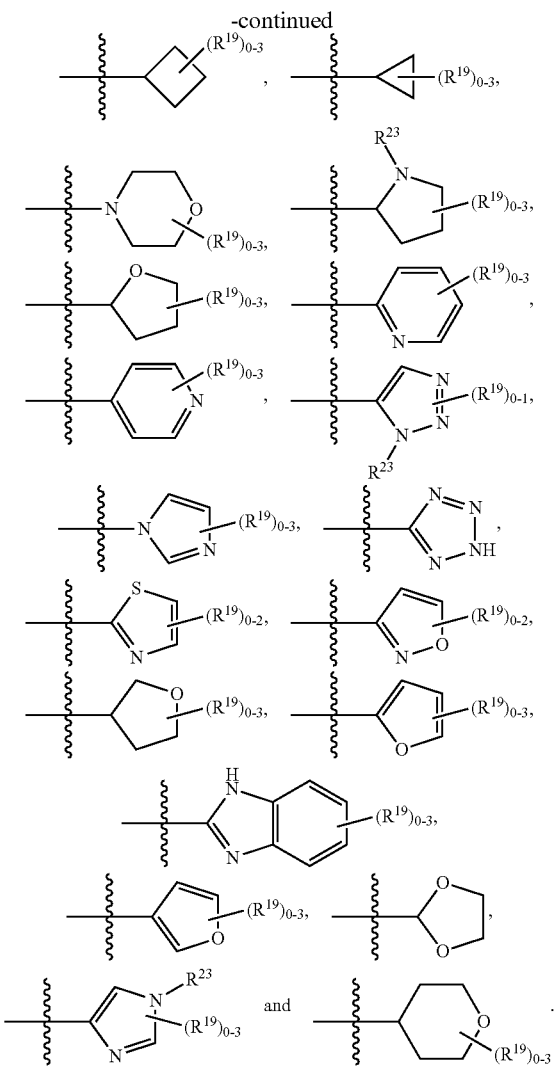

wherein;

each $R^{19}$ is independently selected from halogen, —CN, hydroxyl, —$C_1$-$C_6$alkyl, benzyl, hydroxyl-$C_1$-$C_6$alkyl, $C_3$-$C_8$cycloalkyl, —$OR^{12}$, —$OR^{11}$, —$C(O)R^{14}$, —$C(O)OR^9$, —$C(O)OR^{12}$, —$N(R^9)_2$, —$N(R^{12})_2$, —$C(O)N(R^{12}R^{11})$, —$C(O)(CR^{12}R^{12})_nN(R^{12})_2$, —$C(O)(CR^{12}R^{12})_nOR^{12}$, —$(CR^{12}R^{12})_nR^{14}$, —$OR^9$, —$C(O)OR^9$, —$C(O)(CR^9R^9)_nN(R^9)_2$, —$C(O)(CR^9R^9)_n$ $OR^9$, —$(CR^9R^9)_nR^{14}$, —$S(O)_2R^9$, —$(CR^9R^9)_nS(O)_2R^9$, —$S(O)_2R^{10}$, —$S(O)_2R^{12}$, —$S(O)_2R^9$, —$(CR^{12}R^{12})_nS(O)_2R^{12}$, $(CR^{12}R^{12})_nS(O)_2R^{10}$, $R^{15}$, $R^{13}$ and —$C(O)OR^{13}$;

$R^{23}$ is H, —$C_1$-$C_6$alkyl, hydroxyl-$C_1$-$C_6$alkyl, —$C(O)R^{14}$, —$C(O)OR^{12}$, —$C(O)N(R^{12}R^{11})$, —$C(O)(CR^{12}R^{12})_nN(R^{12})_2$, —$C(O)(CR^{12}R^{12})_nOR^{12}$, —$(CR^{12}R^{12})_mR^{14}$, —$(CR^9R^9)_mR^{14}$, —$S(O)_2R^{10}$, —$S(O)_2R^{12}$— $(CR^{12}R^{12})_nS(O)_2R^{12}$, —$(CR^{12}R^{12})_nS(O)_2R^{10}$, $R^{13}$ and —$C(O)OR^{13}$;

each m is independently 0, 1, 2, 3 or 4, and each n is independently 0, 1, 2, 3 or 4.

In certain embodiments of the Syk kinase inhibitors provided herein having the structure of Formula (I), Formula (II) and Formula (III), $R^{10}$ is —$(CR^{12}R^{12})_nR^{11}$.

In certain embodiments of the Syk kinase inhibitors provided herein having the structure of Formula (I), Formula (II)

and Formula (III), $R^{11}$ is $C_1$-$C_6$alkyl, phenyl, a 5, 6, 9, 10 or 14 membered heteroaryl containing 1 to 3 heteroatoms independently selected from N, O and S, or a 4-8 membered heterocycloalkyl containing 1 to 2 heteroatoms independently selected from N, O and S.

In certain embodiments of the Syk kinase inhibitors provided herein having the structure of Formula (I), Formula (II) and Formula (III), $R^{11}$ is selected from $C_3$-$C_8$cycloalkyl, and a 4-8 membered heterocycloalkyl containing 1 to 2 heteroatoms independently selected from N, O and S, each of which is substituted with 1 to 3 substituents independently selected from hydroxyl, —$C_1$-$C_6$alkyl, hydroxyl-$C_1$-$C_6$alkyl and —$(CR^9R^9)_nR^{14}$.

In certain embodiments of the Syk kinase inhibitors provided herein having the structure of Formula (I), Formula (II) and Formula (III), $R^3$ and $R^5$ are H. In certain embodiments of the Syk kinase inhibitors provided herein having the structure of Formula (I), Formula (II) and Formula (III), $R^4$ is $C_1$-$C_6$alkyl, —$CD_3$, deuterated $C_1$-$C_6$alkyl or $C_1$-$C_6$haloalkyl. In certain embodiments of the Syk kinase inhibitors provided herein having the structure of Formula (I), Formula (II) and Formula (III), $R^4$ is $C_1$-$C_6$alkyl or $C_1$-$C_6$haloalkyl. In certain embodiments of the Syk kinase inhibitors provided herein having the structure of Formula (I), Formula (II) and Formula (III), $R^4$ is —$CD_3$. In certain embodiments of the Syk kinase inhibitors provided herein having the structure of Formula (I), Formula (II) and Formula (III), $R^4$ is hydroxyl-$C_1$-$C_6$alkyl.

The present invention also includes all suitable isotopic variations of the compounds provided herein, or pharmaceutically acceptable salts thereof. An isotopic variation of a compound provided herein or a pharmaceutically acceptable salt thereof is defined as one in which at least one atom is replaced by an atom having the same atomic number but an atomic mass different from the atomic mass usually found in nature. Examples of isotopes that may be incorporated into the compounds provided herein and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$, and $^{123}I$. Certain isotopic variations of the compounds provided herein and pharmaceutically acceptable salts thereof, for example, those in which a radioactive isotope such as or $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds provided herein or pharmaceutically acceptable salts thereof can generally be prepared by conventional procedures using appropriate isotopic variations of suitable reagents.

The compounds and compositions provided herein are useful for treating or preventing a variety of disorders, including, but not limited to, cytopenias, inflammatory disease, allergic diseases, cell-proliferative diseases, and autoimmune diseased, including, but not limited to, allergic asthma, allergic rhinitis, rheumatoid arthritis, multiple sclerosis, lupus, systemic lupus erythematosus, lymphoma, B cell lymphoma, T cell lymphoma, myelodysplasic syndrome, anemia, leucopenia, neutropenia, thrombocytopenia, granuloctopenia, pancytoia or idiopathic thrombocytopenic purpura.

Certain embodiments of compounds of Formula (I) are useful for treating or preventing a variety of disorders, including, but not limited to, heart disease, diabetes, Alzheimer's disease, immunodeficiency disorders, inflammatory diseases, neurological inflammation, chronic arthritis inflammation, hypertension, respiratory diseases, autoimmune diseases, destructive bone disorders such as osteoporosis, proliferative disorders, infectious diseases, immunologically-mediated diseases, and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), acute myeloid leukemia (AML), acute promyelocytic leukemia (APL), rheumatoid arthritis, asthma, osteoarthritis, ischemia, cancer (including, but not limited to, prostate cancer, ovarian cancer, breast cancer and endometrial cancer), liver disease including hepatic ischemia, heart disease such as myocardial infarction and congestive heart failure, pathologic immune conditions involving T cell activation, and neurodegenerative disorders.

Pharmacology and Utility

Protein kinases (PTK) play a central role in the regulation of a wide variety of cellular processes and maintaining control over cellular function. Protein kinases catalyze and regulate the process of phosphorylation, whereby the kinases covalently attach phosphate groups to proteins or lipid targets in response to a variety of extracellular signals. Examples of such stimuli include hormones, neurotransmitters, growth and differentiation factors, cell cycle events, environmental stresses and nutritional stresses. An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include, but are not limited to, autoimmune diseases, inflammatory diseases, bone diseases, metabolic diseases, neurological and neurodegenerative diseases, cancer, cardiovascular diseases, respiratory diseases, allergies and asthma, Alzheimer's disease, and hormone-related diseases.

Examples of protein-tyrosine kinases include, but are not limited to, (a) tyrosine kinases such as Irk, IGFR-1, Zap-70, Bmx, Btk, CHK (Csk homologous kinase), CSK (C-terminal Src Kinase), Itk-1, Src (c-Src, Lyn, Fyn, Lck, Hck, Yes, Blk, Fgr and Frk), Syk, Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-I or c-MET), PDGFR (.alpha. and .beta.), Tie-1, Tie-2 (also Tek-1 or Tek), VEGFR1 (also FLT-1), VEGFR2 (also KDR), FLT-3, FLT-4, c-KIT, JAK1, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1), and (b) and serine/threonine kinases such as Aurora, c-RAF, SGK, MAP kinases (e.g., MKK4, MKK6, etc.), SAPK2α, SAPK2β, Ark, ATM (1-3), CamK (1-IV), CamKK, Chk1 and 2 (Checkpoint kinases), CK1, CK2, Erk, IKK-I (also IKK-ALPHA or CHUK), IKK-2 (also IKK-BETA), Ilk, Jnk (1-3), LimK (1 and 2), MLK3Raf (A, B, and C), CDK (1-10), PKC (including all PKC subtypes), Plk (1-3), NIK, Pak (1-3), PDK1, PKR, RhoK, RIP, RIP-2, GSK3 (α and β), PKA, P38, Erk (1-3), PKB (including all PKB subtypes) (also AKT-1, AKT-2, AKT-3 or AKT3-1), IRAK1, FRK, SGK, TAK1 and Tp1-2 (also COT).

Phosphorylation modulates or regulates a variety of cellular processes such as proliferation, growth, differentiation, metabolism, apoptosis, motility, transcription, translation and other signaling processes. Aberrant or excessive PTK activity has been observed in many disease states including, but not limited to, benign and malignant proliferative disorders, diseases resulting from inappropriate activation of the immune system and diseases resulting from inappropriate activation of the nervous systems. Specific diseases and disease conditions include, but are not limited to, autoimmune disorders, allograft rejection, graft vs. host disease, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, diabetes mellitus, diabetic angiopathy, retinopathy of prematurity, infantile hemangiomas, non-small cell lung, bladder and head and neck cancers, prostate cancer, breast cancer, ovarian cancer, gastric and pancreatic cancer, psoriasis, fibrosis, rheumatoid arthritis, atherosclerosis, restenosis, auto-immune disease, allergy, respiratory diseases, asthma, transplantation rejection, inflammation, thrombosis, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases and bronchitis.

Tyrosine kinases can be broadly classified as receptor-type (having extracellular, transmembrane and intracellular domains) or the non-receptor type (being wholly intracellular) protein tyrosine kinases. Inappropriate or uncontrolled activation of many of these kinase (aberrant protein tyrosine kinase activity), for example by over-expression or mutation, results in uncontrolled cell growth. Many of the protein tyrosine kinases, whether a receptor or non-receptor tyrosine kinase have been found to be involved in cellular signaling pathways involved in numerous pathogenic conditions, including, but not limited to, immunomodulation, inflammation, or proliferative disorders such as cancer.

Compounds provided herein are inhibitors of Syk kinase activity and as such, the compounds and compositions provided herein are useful for treating diseases or disorders in which Syk kinase contributes to the pathology and/or symptomology of a disease or disorder associated with Syk kinase. Such diseases or disorders include, but are not limited to, lymphomas (by way of example only, B and T cell lymphomas), myelodysplasic syndrome, autoimmune diseases (by way of example only, rheumatoid arthritis and multiple scherosis), cytopenias (by way of example only, anemia, leucopenia, neutropenia, thrombocytopenia, granuloctopenia, pancytoia and idiopathic thrombocytopenic purpura), lupus (by way of example, systemic lupus erythematosus), cancer and allergic disorders (by way of example only, allergic asthma and allergic rhinitis).

In certain embodiments, compounds provided herein are inhibitors of one or more kinases selected from ZAP70, KDR, FMS, FLT3, c-Kit, RET, TrkA, TrkB, TrkC, IGR-1R, Alk and c-FMS kinases, and such compounds are useful for treating diseases or disorders in which ZAP70, KDR, FMS, FLT3, c-Kit, RET, TrkA, TrkB, TrkC, IGR-1R, Alk and c-FMS kinase contributes to the pathology and/or symptomology of a disease or disorder. Non-limiting examples of diseases or disorders associated with ZAP70, KDR, FMS, FLT3, c-Kit, RET, TrkA, TrkB, TrkC, IGR-1R, Alk or c-FMS kinases are provided herein, including, but not limited to, chronic obstructive pulmonary disease (COPD), adult respiratory distress syndrome (ARDS), ulcerative colitis, Crohns disease, bronchitis, dermatitis, psoriasis, scleroderma, urticaria, cancer, breast cancer, HIV, pancreatic cancer, papillary thyroid carcinoma, ovarian carcinoma, human adenoid cystic carcinoma, non small cell lung cancer, secretory breast carcinoma, congenital fibrosarcoma, congenital mesoblastic nephroma, acute myelogenous leukemia, metastasis, cancer-related pain, neuroblastoma, osteosarcoma, melanoma, or a tumor of breast, renal, prostate, colorectal, thyroid, ovarian, pancreatic, neuronal, lung, uterine or gastrointestinal tumor.

Receptor Tyrosine Kinases (RTKs).

The Receptor Tyrosine Kinases (RTKs) comprise a large family of transmembrane receptors with diverse biological activities. A number of distinct RTK subfamilies have been identified including, but not limited to, EGF receptor family, the Insulin receptor family, the PDGF receptor family, the FGF receptor family, the VEGF receptor family, the HGF receptor family, the Trk receptor family), the EPH receptor family, the AXL receptor family, the LTK receptor family, the TIE receptor family), the ROR receptor family, the DDR receptor family, the RET receptor family, the KLG receptor family, the RYK receptor family and the MuSK receptor family.

Receptor tyrosine kinases have been shown to be not only key regulators of normal cellular processes but also to have a critical role in the development and progression of many types of cancer. The receptor tyrosine kinase (RTK) family includes receptors that are crucial for the growth and differentiation of a variety of cell types. The intrinsic function of RTK mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response such as, by way of example only, cell division, differentiation, metabolic effects, and changes in the extracellular microenvironment.

Tropomyosin-Receptor-Kinase (Trk) Family

The Trk family receptor tyrosine kinases, TrkA (NTRK1), TrkB (NTRK2), and TrkC (NTRK3), are the signaling receptors that mediate the biological actions of the peptide hormones of the neurotrophin family. Trk receptors are membrane-bound receptor that, through several signal cascades, controls neuronal growth and survival, and differentiation, migration and metastasis of tumor cells. The neurotrophin family of growth factors includes nerve growth factor (NGF), brain-derived neurotrophic factor (BDNF), and two neurotrophins (NT), NT-3, and NT-4. Neurotrophins are critical to the functioning of the nervous system, and the activation of Trk receptors by neurotrophin binding leads to activation of signal cascades resulting in promoting survival and other functional regulation of cells. Each type of neurotrophin has a different binding affinity toward its corresponding Trk receptor, and upon neurotrophin binding, the Trk receptors phosphorylates themselves and members of the MAPK pathway.

The differences in the signaling initiated by these distinct types of receptors are important for generating diverse biological responses.

The Trk receptors are implicated in the development and progression of cancer, possibly by upregulation of either the receptor, their ligand (NGF), BDNF, NT-3, and NT-4, or both. In many cases high Trk expression is associated with aggressive tumor behavior, poor prognosis and metastasis. Thus, diseases and disorders related to Trk receptors result from 1) expression of a Trk receptor(s) in cells which normally do not express such a receptor(s); 2) expression of a Trk receptor(s) by cells which normally do not express such a receptor(s); 3) increased expression of Trk receptor(s) leading to unwanted cell proliferation; 4) increased expression of Trk receptor(s) leading to adhesion independent cell survival; 5) mutations leading to constitutive activation of Trk receptor (s); 6) over stimulation of Trk receptor(s) due to abnormally high amount of, or mutations in, Trk receptor(s), and/or 7) abnormally high amount of Trk receptor(s) activity due to abnormally high amount of, or mutations in, Trk receptor(s).

Genetic abnormalities, i.e. point mutations and chromosomal rearrangements involving both the genes expressing TrkB and TrkC have been found in a variety of cancer types. In a kinome-wide approach to identify point mutants in tyrosine kinases, mutations in the genes expressing TrkB and TrkC were found in cell lines and primary samples from patients with colorectal cancer. In addition, chromosomal translocations involving the genes expressing TrkA and TrkB have been found in several different types of tumors. Gene rearrangements involving the genes expressing TrkA and a set of different fusion partners (TPM3, TPR, TFG) are a hallmark of a subset of papillary thyroid cancers. Moreover, secretary breast cancer, infant fibrosarcoma and congenital mesoblastic nephroma have been shown to be associated with a chromosomal rearrangement t(12; 15) generating a ETV6-NTRK3 fusion gene that was shown to have constitutive kinase activity and transforming potential in several different cell lines including fibroblasts, hematopoietic cells and breast epithelial cells.

TrkA has the highest affinity to the binding nerve growth factor (NGF). NGF is important in both local and nuclear actions, regulating growth cones, motility, and expression of genes encoding the biosynthesis enzymes for neurotransmitters. Nocireceptive sensory neurons express mostly trkA and not trkB or trkC.

TrkB serves as a receptor for both BDNF and NT-4, and is expressed in neuroendocrine-type cells in the small intestine and the colon, in the alpha cells of the pancreas, in the monocytes and macrophages of the lymph nodes and of the spleen, and in the granular layers of the epidermis. TrkB is also expressed in cancerous prostate cells but not in normal cells.

The binding of BDNF to TrkB receptor causes activation of intercellular cascades which regulate neuronal development and plasticity, long-term potentiation, and apoptosis. BDNF promotes the proliferation, differentiation and growth and survival of normal neural components such as retinal cells and glial cells. In addition, TrkB activation is a potent and specific suppressor of anchorage independent cell death (anoikis), which is apoptosis induced by loss of attachment of a cell to its matrix. By way of example, activation of the Phosphatidylinositol-3kinase/Protein Kinase B signaling axis by TrkB promotes the survival of non-transformed epithelial cells in 3-dimensional cultures and induces tumor formation and metastasis of those cells in immuno-compromised mice. Anchorage independent cell survival is a metastatic process allowing tumor cells to migrate through the systemic circulation and grow at distant organs. Agonism of TrkB results in the failure of induced cell death by cancer treatments. Thus, TrkB modulation is a target for treatment of benign and malignant proliferative diseases, especially tumor diseases.

Diseases and disorders related to the TrkB receptor include, but are not limited to, cancers, such as, by way of example only, neuroblastoma progression, Wilm's tumor progression, breast cancer, pancreatic cancer, colon cancer, prostate cancer, and lung cancer. The TrkB receptor has been shown to be associated with Alzheimer's disease.

TrkC is activated by binding with NT-3 and is expressed by proprioceptive sensory neurons. The axons of these proprioceptive sensory neurons are much thicker than those of nocireceptive sensory neurons, which express TrkA. Signalling through TrkC leads to cell differentiation and development of proprioceptive neurons that sense body position. Mutations in this gene expressing TrkC is associated with medulloblastomas, secretory breast carcinomas and other cancers. In addition, high expression of TrkC is a hallmark of melanoma, especially in cases with brain metastasis.

Certain embodiments of compounds of Formula (I) are also used for the treatment of diseases which respond to an inhibition of the Trk receptor tyrosine kinases (TrkA, TrkB, and TrkC). Certain embodiments of compounds of Formula (I) inhibit Trk receptor tyrosine kinases (TrkA, TrkB, and TrkC) activity and are, therefore, suitable for the treatment of diseases, such as, neuroblastoma, Wilm's tumor, breast cancer, pancreatic cancer, colon cancer, prostate cancer, and lung cancer.

Platelet-Derived Growth Factor (PDGF) Receptor Family

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. The PDGF growth factor family consists of PDGF-A, PDGF-B, PDGF-C and PDGF-D, which form either homo- or heterodimers (AA, AB, BB, CC, DD) that bind to the protein tyrosine kinase receptors PDGFR-$\alpha$ and PDGFR-$\beta$. Dimerization of the growth factors is a prerequisite for activation of the kinase, as the monomeric forms are inactive. The two receptor isoforms dimerize upon binding resulting in three possible receptor combinations, PDGFR-$\alpha\alpha$, PDGFR-$\beta\beta$ and PDGFR-$\alpha\beta$. Growth factor AA binds only to -$\alpha\alpha$, growth factor BB can bind with -$\alpha\alpha$, -$\beta\beta$ and -$\alpha\beta$, growth factors CC and AB specifically interact with -$\alpha\alpha$ and -$\alpha\beta$, and growth factor DD binds to -$\beta\beta$.

Key downstream mediators of PDGFR signaling are Ras/mitogen-activated protein kinase (MAPK), PI-3 kinase and phospholipase-$\gamma$ (PLC$\gamma$) pathways. MAPK family members regulate various biological functions by phosphorylation of target molecules (transcription factors and other kinases) and thus contribute to regulation of cellular processes such as proliferation, differentiation, apoptosis and immunoresponses. PI-3 kinase activation generated PIPS which functions as a second messenger to activate downstream tyrosine kinases Btk and Itk, the Ser/Thr kinases PDK1 and Akt (PKB). Akt activation is involved in survival, proliferation and cell growth. After activation PLC$\gamma$ hydrolyses its substrate, PtdIns(4,5)P2, and forms two secondary messengers, diacylglycerol and Ins(1,4,5)P3 which stimulates intracellular processes such as proliferation, angiogenesis and cell motility. The PDGF-receptor plays an important role in the maintenance, growth and development of hematopoietic and non-hematopoietic cells.

PDGFR is expressed on early stem cells, mast cells, myeloid cells, mesenchymal cells and smooth muscle cells.

Only PDGFR-β is implicated in myeloid leukemias-usually as a translocation partner with Tel, Huntingtin interacting protein (HIP1) or Rabaptin5. Activation mutations in PDGFR-α kinase domain are associated with gastrointestinal stromal tumors (GIST).

Vascular Endothelial Growth Factor (VEGF) Receptor Family

VEGF, also known as fms-related tyrosine kinase-1 (FLT1), is an important signaling protein involved in both vasculogenesis (formation of embryonic circulatory system) and angiogenesis (growth of blood vessels from pre-existing vasculature). Structurally VEGF belongs to the PDGF family of cytokine-knot growth factors. The VEGF sub-family of growth factors includes VEGF-A, VEGF-B, VEGF-C and VEGF-D. VEGF-A binds to receptor VEGFR-1 (Flt-1) and to VEGFR-2 (KDR/Flk-1). VEGF-C and VEGF-D bind to receptor VEGFR-3 and mediate lymphangiogenesis. The VGFR receptors mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

Fms-Like Tyrosine Kinase

The fms-like tyrosine kinase-3 (FLT3) ligand (FLT3L) is one of the cytokines that affects the development of multiple hematopoietic lineages. These effects occur through the binding of FLT3L to the FLT3 receptor, also referred to as fetal liver tkinase-2 (flk-2) and STK-1, a receptor tyrosine kinase (RTK) expressed on hematopoietic stem and progenitor cells. FLT3 is a member of the type III receptor tyrosine kinase (RTK) family. The ligand for FLT3 is expressed by the marrow stromal cells and other cells and synergizes with other growth factors to stimulate proliferation of stem cells, progenitor cells, dendritic cells, and natural killer cells. Flt3 plays an important role in the maintenance, growth and development of hematopoietic and non-hematopoietic cells.

The FLT3 gene encodes a membrane-bound RTK that plays an important role in proliferation, differentiation and apoptosis of cells during normal hematopoiesis. The FLT3 gene is mainly expressed by early meyloid and lymphoid progenitor cells. Hematopoietic disorders are pre-malignant disorders and include, for instance, the myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes. Hematological malignancies include leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma.

Aberrant expression of the Flt3 gene has been documented in both adult and childhood leukemias including acute myeloid leukemia (AML), AML with trilineage myelodysplasia (AML/TMDS), acute lymphoblastic leukemia (ALL), and myelodysplastic syndrome (MDS). Activating mutations of the Flt3 receptor have been found in about 35% of patients with acute myeloblastic leukemia (AML), and are associated with a poor prognosis. The most common mutation involves in-frame duplication within the juxtamembrane domain, with an additional 5-10% of patients having a point mutation at asparagine 835. Both of these mutations are associated with constitutive activation of the tyrosine kinase activity of Flt3, and result in proliferation and viability signals in the absence of ligand. Patients expressing the mutant form of the receptor have been shown to have a decreased chance for cure. Thus, there is accumulating evidence for a role for hyper-activated (mutated) Flt3 kinase activity in human leukemias and myelodysplastic syndrome.

FLT-3 and c-Kit regulate maintenance of stem cell/early progenitor pools as well the development of mature lymphoid and myeloid cells. Both receptors contain an intrinsic kinase domain that is activated upon ligand-mediated dimerization of the receptors. Upon activation, the kinase domain induces autophosphorylation of the receptor as well as the phosphorylation of various cytoplasmic proteins that help propogate the activation signal leading to growth, differentiation and survival. Some of the downstream regulators of FLT-3 and c-Kit receptor signaling include, PLCγ, PI3-kinase, Grb-2, SHIP and Src related kinases. Both receptor tyrosine kinases have been shown to play a role in a variety of hematopoietic and non-hematopoietic malignancies. Mutations that induce ligand independent activation of FLT-3 and c-Kit have been implicated acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type FLT-3 or c-Kit can contribute to the malignant phenotype.

c-Fms encodes for macrophage colony stimulating factor receptor (M-CSF-1R) which is expressed predominately in the monocytes/macrophage lineage. MCSF-1R and its ligand regulate macrophage lineage growth and differentiation. Like the other family members, MCSF-1R contains an intrinsic kinase domain that is activated upon ligand-induced dimerization of the receptor. MCSF-1R is also expressed in non-hematopoietic cells including mammary gland epithelial cells and neurons. Mutations in this receptor are potentially linked to myeloid leukemias and its expression is correlated with metastatic breast, ovarian and endometrial carcinomas. Another possible indication for antagonists of MCSF-1R is osteoporosis.

Certain embodiments of compounds of Formula (I) are inhibitors of FLT-3 and c-kit and are used for the treatment of diseases which respond to an inhibition of the FLT-3 c-kit receptors.

Insulin-Like Growth Factor 1 (IGF-1) Receptor

The Insulin-like Growth Factor 1 (IGF-1) Receptor is a transmembrane receptor that is activated by IGF-1 and by the related growth factor IGF-2. IGF-1R mediates the effects of IGF-1, which is a polypeptide protein hormone similar in molecular structure to insulin. IGF-1 plays an important role in survival and proliferation in mitosis-competent cells, and growth (hypertrophy) in tissues such as skeletal muscle and cardiac muscle. The IGFR signalling pathway is of critical importance during normal development of mammary gland tissue during pregnancy and lactation. During pregnancy, there is intense proliferation of epithelial cells which form the duct and gland tissue. Following weaning, the cells undergo apoptosis and all the tissue is destroyed. Several growth factors and hormones are involved in this overall process, and IGF-1R is believed to have roles in the differentiation of the cells and a key role in inhibiting apoptosis until weaning is complete.

The IGF-1R is implicated in several cancers including, but not limited to, breast cancer. In some instances its anti-apoptotic properties allow cancerous cells to resist the cytotoxic properties of chemotherapeutic drugs or radiotherapy. It is further implicated in breast cancer by increasing the metastatic potential of the original tumour by inferring the ability to promote vascularisation.

RET Receptor Family

The RET proto-oncogene encodes a receptor tyrosine kinase for members of the glial cell line derived neurotrophic factor (GDNF) family of extracellular signalling molecules. RET loss of function mutations are associated with the development of Hirschsprung's disease, while gain of function mutations are associated with development of various types of cancer, including medullar thyroid carcinoma and multiple endocrine neoplasias type II and III.

RET is the receptor for members of the glial cell line derived neurotrophic factor (GDNF) family of extracellular signalling molecules (GFL's). There are three different isoforms, RET51, RET43 and RET9, containing 51, 43 and 9 amino acids in their C-terminal tail, respectively. RET signal transduction is key to the development of normal kidneys and the enteric nervous system.

In order to activate RET GFLs first need to form a complex with a glycosylphosphatidylinositol (GPI)-anchored co-receptor. The co-receptors themselves are classified as members of the GDNF receptor-α (GFRα) protein family. Different members of the GFRα family (GFRα1-GFRα4) exhibit a specific binding activity for a specific GFLs. Upon GFL-GFRα complex formation, the complex then brings together two molecules of RET, triggering trans-autophosphorylation of specific tyrosine residues within the tyrosine kinase domain of each RET molecule. Tyr900 and Tyr905 within the activation loop (A-loop) of the kinase domain have been shown to be autophosphorylation sites by mass spectrometry. Phosphorylation of Tyr905 stabilizes the active conformation of the kinase which in turn results in the autophosphorylation of other tyrosine residues mainly located in the C-terminal tail region of the molecule.

c-Kit Receptor

Certain embodiments of compounds of Formula (I) inhibit cellular processes involving stem-cell factor (SCF, also known as the c-kit ligand or steel factor), such as inhibiting SCF receptor (kit) autophosphorylation and SCF-stimulated activation of MAPK kinase (mitogen-activated protein kinase). MO7e cells are a human promegakaryocytic leukemia cell line, which depends on SCF for proliferation.

c-Kit has a substantial homology to the PDGF receptor and to the CSF-1 receptor (c-Fms). Investigations on various erythroid and myeloid cell lines indicate an expression of the c-Kit gene in early stages of differentiation. Certain tumors such as glioblastoma cells likewise exhibit a pronounced expression of the c-Kit gene.

Anaplastic Lymphoma Kinase (Ki-1 or ALK)

ALK is a receptor protein-tyrosine kinase having a putative transmembrane domain and an extracellular domain. ALK plays an important role in the development of the brain and exerts its effects on specific neurons in the nervous system.

Anaplastic lymphoma kinase (ALK), a member of the insulin receptor superfamily of receptor tyrosine kinases, has been implicated in oncogenesis in hematopoietic and non-hematopoietic tumors. The aberrant expression of full-length ALK receptor proteins has been reported in neuroblastomas and glioblastomas; and ALK fusion proteins have occurred in anaplastic large cell lymphoma.

Non-Receptor Tyrosine Kinases.

Non-receptor tyrosine kinases represent a collection of cellular enzymes that lack extracellular and transmembrane sequences. Over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. The Src subfamily of non-receptor tyrosine kinases is comprised of the largest number of PTKs and includes Src, Yes, Fyn, Lyn, Lck, Blk, Hck, Fgr and Yrk. The Src subfamily of enzymes has been linked to oncogenesis and immune responses.

The Src family of kinases is implicated in cancer, immune system dysfunction osteopetrosis, and bone remodeling diseases, and therefore Src kinases are considered as potential therapeutic targets for various human diseases. Src expression is linked to cancers such as colon, breast, hepatic and pancreatic cancer, certain B-cell leukemias and lymphomas. In addition, antisense Src expressed in ovarian and colon tumor cells inhibits tumor growth.

Csk, or C-terminal Src kinase, phosphorylates and thereby inhibits Src catalytic activity. Suppression of arthritic bone destruction has been achieved by the overexpression of Csk in rheumatoid synoviocytes and osteoclasts. This implies that Src inhibition may prevent joint destruction that is characteristic in patients suffering from rheumatoid arthritis. Src also plays a role in the replication of hepatitis B virus. The virally encoded transcription factor HBx activates Src in a step required for propagation of the virus.

Other Src family kinases are also potential therapeutic targets. Lck plays a role in T-cell signaling, and mice that lack the Lck gene have a poor ability to develop thymocytes. The function of Lck as a positive activator of T-cell signaling suggests that Lck inhibitors may be useful for treating autoimmune disease such as rheumatoid arthritis. Hck, Fgr and Lyn are important mediators of integrin signaling in myeloid leukocytes. Inhibition of these kinase mediators may therefore be useful for treating inflammation.

Spleen Tyrosine Kinase (Syk)

Spleen tyrosine kinase (Syk) and Zap-70 are members of the Syk family of tyrosine kinases. These non-receptor cytoplasmic tyrosine kinases share a characteristic by a carboxy terminal kinase domain and a dual SH2 domain separated by a linker domain. Syk is a non-receptor linked protein tyrosine kinase which plays a critical role in mediator of immunoreceptor signalling in a host of inflammatory cells including mast cells, B-cells, macrophages and neutrophils. These immunoreceptors, including Fc receptors (such as FcεRI) and the B-cell receptor, are important for both allergic diseases and antibody-mediated autoimmune diseases. Syk also plays a role in FcεRI mediated mast cell degranulation and eosiniphil activation. Accordingly, Syk kinase is implicated in various allergic disorders, in particular asthma.

Inhibition of eosinophil apoptosis has been proposed as key mechanisms for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. Syk kinase is required for the prevention of eosinophil apoptosis by cytokines.

While Syk and Zap-70 are primarily expressed in hematopoietic tissues, Syk is also expressed in a variety of other tissues. Within B and T cells respectively, Syk and Zap-70 transmit signals from the B-cell receptor and T-cell receptor.

Syk plays a similar role in transmitting signals from a variety of cell surface receptors including CD74, Fc Receptor, and integrins.

Abnormal function of Syk has been implicated in several instances of hematopoeitic malignancies including translocations involving Itk and Tel. Constitutive Syk activity can transform B cells. Several transforming viruses contain "Immunoreceptor Tyrosine Activation Motifs" (ITAMs) which lead to activation of Syk including Epstein Barr virus, bovine leukemia virus, and mouse mammary tumor virus.

Syk kinase is known to play a critical role in other signaling cascades. For example, Syk kinase is an effector of B-cell receptor (BCR) signaling and is an essential component of integrin beta(1), beta(2) and beta(3) signaling in neutrophils.

Syk kinase is important in transducing the downstream cellular signals associated with cross-linking Fc epsilon RI (Fcer1) and or Fc epsilon RI (Fcer1) receptors, and is positioned early in the signalling cascade. In mast cells, for example, the early sequence of Fc epsilon RI (Fcer1) signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE (Fc epsilon RI) and IgG (Fc epsilon.RI) become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesised lipid mediators including prostaglandins and leukotrienes.

Rheumatoid Arthritis (RA) is an auto-immune disease affecting approximately 1% of the population. It is characterised by inflammation of articular joints leading to debilitating destruction of bone and cartilage. Targeting B cell function is a therapeutic strategy in auto-immune diseases such as RA, with B cell function and auto-antibody production being central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development. These studies, along with studies on mature B cells deficient in Syk, demonstrate that Syk is required for the differentiation and activation of B cells. Hence, inhibition of Syk in RA patients is likely to block B cell function and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

Syk also plays a role in FcγR dependent and independent response in bone marrow derived macrophages. Syk deficient macrophages are defective in phagocytosis induced by FcγR, but have normal phagocytosis in response to complement. Aerosolized Syk antisense suppresses Syk expression and mediator release from macrophages.

Loss of Syk was found in childhood pro-B cell ALL. Syk is an important suppressor of breast cancer cell growth and metastasis. Tel-Syk fusion protein was found in patients with atypical myelodysplastic syndrome and constitutively activates PI3-K/Akt, MAPK and Jak2 independent STAT5 signaling. Overexpression of Tel-Syk fusion protein causes B-cell lymphoma in mice (differentiation defect in pre-B-cells). ITK-Syk fusion protein was found in 17% of patients with unspecified peripheral T-cell lymphomas. Syk overexpression is associated with mantle cell lymphoma and Waldenstroem's makroglobulinaemia.

The compounds provided herein are inhibitors of Syk kinase activity and have therapeutic benefit in the treatment of disorders associated with inappropriate Syk activity, in particular in the treatment and prevention of disease states mediated by Syk. Such disease states include cytopenias, inflammatory disease, allergic diseases, cell-proliferative diseases, and autoimmune diseased, including, but not limited to, allergic asthma, allergic rhinitis, rheumatoid arthritis, multiple sclerosis, lupus, systemic lupus erythematosus, lymphoma, B cell lymphoma, T cell lymphoma, myelodysplasic syndrome, anemia, leucopenia, neutropenia, thrombocytopenia, granuloctopenia, pancytoia or idiopathic thrombocytopenic purpura.

Furthermore, the compounds, compositions and methods provided herein include methods of regulating, and in particular inhibiting, signal transduction cascades in which Syk plays a role. The method generally involves contacting a Syk-dependent receptor or a cell expressing a Syk-dependent receptor with an amount of a compound provided herein, or prodrug a compound provided herein, or an acceptable salt, hydrate, solvate, N-oxide and/or composition thereof, effective to regulate or inhibit the signal transduction cascade. The methods are used to regulate, and in particular inhibit, downstream processes or cellular responses elicited by activation of the particular Syk-dependent signal transduction cascade. The methods are practiced to regulate any signal transduction cascade where Syk is not known or later discovered to play a role. The methods are practiced in in-vitro contexts or in in-vivo contexts as a therapeutic approach towards the treatment or prevention of diseases characterized by, caused by or associated with activation of the Syk-dependent signal transduction cascade. Non-limited examples of such diseases include those provided above.

The compounds and compositions provided herein are inhibitors of Syk kinase, and therefore regulate, and in particular inhibit, any signaling cascade where Syk plays a role, such as, fore example, the Fc receptor, BCR and integrin signaling cascades, as well as the cellular responses elicited through these signaling cascades. The particular cellular response regulated or inhibited will depend, in part, on the specific cell type and receptor signaling cascade. Non-limiting examples of cellular responses that may be regulated or inhibited with the compounds provided herein include a respiratory burst, cellular adhesion, cellular degranulation, cell spreading, cell migration, phagocytosis (e.g., in macrophages), calcium ion flux (e.g., in mast, basophil, neutrophil, eosinophil and B-cells), platelet aggregation, and cell maturation (e.g., in B-cells).

Zeta-Chain-Associated Protein Kinase 70 (ZAP70) Kinase

ZAP-70 is normally expressed in T cells and natural killer cells and has a critical role in the initiation of T-cell signaling. ZAP-70 in B cells is used as a prognostic marker in identifying different forms of chronic lymphocytic leukemia (CLL).

T lymphocytes are activated by engagement of the T cell receptor with processed antigen fragments presented by professional antigen presenting cells (e.g. macrophages, dendritic cells and B cells). Upon this activation, the tyrosine kinase Lck becomes activated and phosphorylates the intracellular portions of the CD3 complex (called ITAMs). The most important member of the CD3 family is CD3-zeta to which ZAP-70 binds. The tandem SH2-domains of ZAP-70 are engaged by the doubly phosphorylated ITAMs of CD3-zeta, which positions ZAP-70 to phosphorylate the transmembrane protein LAT (Linker of Activated T cells). Phosphorylated LAT in turn serves as a docking site to which a number of signaling proteins bind. The final outcome of T cell activation is the transcription of several gene products which allow the T cells to differentiate, proliferate and secrete a number of cytokines.

Certain embodiments of compounds of Formula (I) are inhibitors of ZAP-70 kinase activity and have therapeutic benefit in the treatment of disorders associated with inappropriate ZAP-70 activity, in particular in the treatment and prevention of disease states mediated by ZAP-70.

In accordance with the foregoing, further provided herein are methods for preventing or treating any of the diseases or disorders provided above in a subject in need of such treatment, which method comprises administering to said subject a therapeutically effective amount (See, "*Administration and Pharmaceutical Compositions*", infra) of a compound of Formula (I), Formula (II) or Formula (III), or a pharmaceutically acceptable salts, pharmaceutically acceptable solvates (e.g. hydrates), the N-oxide derivatives, individual isomers and mixture of isomers thereof. For any of the above uses, the required dosage will vary depending on the mode of administration, the particular condition to be treated and the effect desired.

Administration and Pharmaceutical Compositions

For the therapeutic uses of compounds provided herein, including compounds of Formula (I Formula (II) and Formula (III), or a pharmaceutically acceptable salts, pharmaceutically acceptable solvates (e.g. hydrates), the N-oxide derivatives, individual isomers and mixture of isomers thereof, such compounds are administered in therapeutically effective amounts either alone or as part of a pharmaceutical composition. Accordingly, provided herein are pharmaceutical compositions, which comprise at least one compound provided herein, including at least one compound of Formulas (I), Formula (II) or Formula (III), or a pharmaceutically acceptable salts, pharmaceutically acceptable solvates (e.g. hydrates), the N-oxide derivatives, individual isomers and mixture of isomers thereof, and one or more pharmaceutically acceptable carriers, diluents, adjuvant or excipients. In addition, such compounds and compositions are administered singly or in combination with one or more additional therapeutic agents. The method of administration of such compounds and compositions include, but are not limited to, oral administration, rectal administration, parenteral, intravenous administration, intravitreal administration, subcutaneous administration, intramuscular administration, inhalation, intranasal administration, dermal administration, topical administration, ophthalmic administration or buccal administration, tracheal administration, bronchial administration, sublingual administration or otic administration.

The therapeutically effective amount will vary depending on, among others, the disease indicated, the severity of the disease, the age and relative health of the subject, the potency of the compound administered, the mode of administration and the treatment desired. In certain embodiments, the daily dosage of a compound of Formula (I), Formula (II) or Formula (III), satisfactory results are indicated to be obtained systemically at daily dosages of from about 0.03 to 2.5 mg/kg per body weight. In certain embodiments, the daily dosage of a compound of Formula (I), Formula (II) or Formula (III), administered by inhalation, is in the range from 0.05 micrograms per kilogram body weight ($\mu$g/kg) to 100 micrograms per kilogram body weight ($\mu$g/kg). In other embodiments, the daily dosage of a compound of Formula (I), Formula (II) or Formula (III), administered orally, is in the range from 0.01 micrograms per kilogram body weight ($\mu$g/kg) to 100 milligrams per kilogram body weight (mg/kg). An indicated daily dosage in the larger mammal, e.g. humans, is in the range from about 0.5 mg to about 100 mg of a compound of Formula (I), Formula (II) or Formula (III), conveniently administered, e.g. in divided doses up to four times a day or in controlled release form. In certain embodiment, unit dosage forms for oral administration comprise from about 1 to 50 mg of a compound of Formula (I), Formula (II) or Formula (III).

In certain embodiments, compounds provided herein, and pharmaceutically acceptable salts, pharmaceutically acceptable solvates (e.g. hydrates), the N-oxide derivatives, individual isomers and mixture of isomers thereof, are administered as the raw chemical, while in other embodiments the compounds provided herein, and pharmaceutically acceptable salts, pharmaceutically acceptable solvates (e.g. hydrates), the N-oxide derivatives, individual isomers and mixture of isomers thereof, are administered as a pharmaceutical composition. Accordingly, provided herein are pharmaceutical compositions, which comprise at least one compound of Formulas (I), Formula (II) or Formula (III), pharmaceutically acceptable salts, pharmaceutically acceptable solvates (e.g. hydrates), the N-oxide derivatives, individual isomers and mixture of isomers thereof, and one or more pharmaceutically acceptable carriers, diluents, or excipients. Furthermore, another aspect provided herein is a process for the preparation of such pharmaceutical composition including admixing a compound of the Formula (I), Formula (II) or Formula (III) provided herein, and pharmaceutically acceptable salts, pharmaceutically acceptable solvates (e.g. hydrates), the N-oxide derivatives, individual isomers and mixture of isomers thereof, with one or more pharmaceutically acceptable carriers, diluents or excipients. Pharmaceutical compositions comprising a compound provided herein in free form or in a pharmaceutically acceptable salt form in association with at least one pharmaceutically acceptable carrier or diluent can be manufactured in a conventional manner by mixing, granulating or coating methods. The compositions may be sterilized and/or contain adjuvants, such as preserving, stabilizing, wetting or emulsifying agents, solution promoters, salts for regulating the osmotic pressure and/or buffers.

Compounds provided herein, and pharmaceutically acceptable salts, pharmaceutically acceptable solvates (e.g. hydrates), the N-oxide derivatives, individual isomers and mixture of isomers thereof, can be administered as pharmaceutical compositions by any conventional route including, but not limited to, intravenous administration (parenteral), oral administration, rectal administration, inhalation, nasal administration, topical administration, ophthalmic administration or otic administration.

Compounds provided herein are administered alone, or are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like.

In certain embodiments, pharmaceutical formulations (pharmaceutical compositions) provided herein include those in which the active ingredient is present in at least 1% by weight. In certain embodiments, pharmaceutical formulations (pharmaceutical compositions) provided herein include those in which the active ingredient is present in at least 5% by weight. In certain embodiments, pharmaceutical formulations (pharmaceutical compositions) provided herein include those in which the active ingredient is present in at least 10% by weight. In certain embodiments, pharmaceutical formulations (pharmaceutical compositions) provided herein include those in which the active ingredient is present in at least 20% by weight. In certain embodiments, pharmaceutical formulations (pharmaceutical compositions) provided herein include those in which the active ingredient is present in at least 20% by weight. In certain embodiments, pharmaceutical formulations (pharmaceutical compositions) provided herein include those in which the active ingredient is present in at least 40% by weight. In certain embodiments, pharmaceutical formulations (pharmaceutical compositions) provided herein include those in which the active ingredient is present in at least 50% by weight. That is, the ratio of active ingredient to the other components (by way of example, the addition of adjuvant, diluent and carrier) of the pharmaceutical composition is at least 1:99, 5:95, 10:90, 20:80, 30:70, 40:60 or at least 50:50 by weight.

Oral Dosage Forms

In certain embodiments, the pharmaceutical compositions containing at least one compound of Formula (I), Formula (II) or Formula (III) are administered orally as discrete dosage forms, wherein such dosage forms include, but are not limited to, capsules, gelatin capsules, caplets, tablets, chewable tablets, powders, granules, syrups, flavored syrups, solutions or suspensions in aqueous or non-aqueous liquids, edible foams or whips, and oil-in-water liquid emulsions or water-in-oil liquid emulsions.

The capsules, gelatin capsules, caplets, tablets, chewable tablets, powders or granules, used for the oral administration of at least one compound of Formula (I), Formula (II) or Formula (III) are prepared by admixing at least one compound of Formula (I), Formula (II) or Formula (III) (active ingredient) together with at least one excipient using conventional pharmaceutical compounding techniques. Non-limiting examples of excipients used in oral dosage forms provided herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing at least one compound of Formula (I), Formula (II) or Formula (III) (active ingredients) with liquid carriers, finely divided solid carriers, or both, and then shaping the product into the desired presentation if necessary. In certain embodiments, tablets are prepared by compression. In other embodiments, tablets are prepared by molding.

In certain embodiments, at least one compound of Formula (I), Formula (II) or Formula (III) is orally administered as a controlled release dosage form. Such dosage forms are used to provide slow or controlled-release of one or more compounds of Formula (I), Formula (II) or Formula (III). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I), Formula (II) or Formula (III), reduce dosage frequency, and increase patient compliance.

Administration of compounds of Formula (I), Formula (II) or Formula (III) as oral fluids such as solution, syrups and elixirs are prepared in unit dosage forms such that a given quantity of solution, syrups or elixirs contains a predetermined amount of a compound of Formula (I), Formula (II) or Formula (III). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing at least one compound of Formula (I), Formula (II) or Formula (III) are administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Transdermal Dosage Forms

In certain embodiments pharmaceutical compositions containing at least one compound of Formula (I), Formula (II) or Formula (III) are administered transdermally. Such transdermal dosage forms include "reservoir type" or "matrix type" patches, which are applied to the skin and worn for a specific period of time to permit the penetration of a desired amount of a compound of Formula (I), Formula (II) or Formula (III). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used.

Formulations for transdermal delivery of a compound of Formula (I), Formula (II) or Formula (III) include an effective amount of a compound of Formula (I), Formula (II) or Formula (III), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compounds of Formula (I), Formula (II) or Formula (III) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I), Formula (II) or Formula (III). In other embodiments, the polarity of a solvent carrier, its ionic strength, or tonicity are adjusted to improve delivery. In other embodiments, compounds such as stearates are added to advantageously alter the hydrophilicity or lipophilicity of one or more compounds of Formula (I), Formula (II) or Formula (III) so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of the compounds of Formula (I), Formula (II) or Formula (III) are used to further adjust the properties of the resulting composition.

Topical Dosage Forms

In certain embodiments at least one compound of Formula (I), Formula (II) or Formula (III) is administered by topical application of pharmaceutical composition containing at least one compound of Formula (I), Formula (II) or Formula (III) in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compounds of Formula (I), Formula (II) or Formula (III) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In certain embodiments pharmaceutical compositions containing at least one compound of Formula (I), Formula (II) or Formula (III) are administered by inhalation. Dosage forms for inhaled administration are formulated as aerosols or dry powders. Aerosol formulations for inhalation administration comprise a solution or fine suspension of at least one compound of Formula (I), Formula (II) or Formula (III) in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain embodiments, compounds of Formula (I), Formula (II) or Formula (III) are be administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I), Formula (II) or Formula (III) and a powder base such as lactose or starch. In certain embodiments, compounds of Formula (I), Formula (II) or Formula (III) are delivered to the lung using a liquid spray device, wherein such devices use extremely small nozzle holes to aerosolize liquid drug formulations that can then be directly inhaled into the lung. In other embodiments, compounds of Formula (I), Formula (II) or Formula (III) are delivered to the lung using a nebulizer device, wherein a nebulizers creates an aerosols of liquid drug formulations by using ultrasonic energy to form fine particles that can be readily inhaled. In other embodiments, compounds of Formula (I), Formula (II) or Formula (III) are delivered to the lung using an electrohydrodynamic ("EHD") aerosol device wherein such EHD aerosol devices use electrical energy to aerosolize liquid drug solutions or suspensions.

In certain embodiments, the pharmaceutical composition containing at least one compound of Formula (I), Formula (II) or Formula (III), or pharmaceutically acceptable salts and solvates thereof, provided herein, also contain one or more absorption enhancers. In certain embodiments, such absorption enhancers include, but are not limited to, sodium glycocholate, sodium caprate, N-lauryl-β-D-maltopyranoside, EDTA, and mixed micelles.

In certain embodiments pharmaceutical compositions containing at least one compound of Formula (I), Formula (II) or Formula (III) are administered nasally. The dosage forms for nasal administration are formulated as aerosols, solutions, drops, gels or dry powders.

In certain embodiments pharmaceutical compositions containing at least one compound of Formula (I), Formula (II) or Formula (III) are administered rectally in the form of suppositories, enemas, ointment, creams rectal foams or rectal gels. In certain embodiments such suppositories are prepared from fatty emulsions or suspensions, cocoa butter or other glycerides.

In certain embodiments pharmaceutical compositions containing at least one compound of Formula (I), Formula (II) or Formula (III) are administered opthamically as eye drops. Such formulations are aqueous solutions that optionally contain solubilizers, stabilizers, tonicity enhancing agents, buffers and preservatives.

In certain embodiments pharmaceutical compositions containing at least one compound of Formula (I), Formula (II) or Formula (III) are administered otically as ear drops. Such formulations are aqueous solutions that optionally contain solubilizers, stabilizers, tonicity enhancing agents, buffers and preservatives.

In certain embodiments pharmaceutical compositions containing at least one compound of Formula (I), Formula (II) or Formula (III) are formulated as a depot preparation. Such long acting formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

In other embodiments, a compound of Formula (I), Formula (II) or Formula (III) provided herein, or a pharmaceutically acceptable salt, N-oxide, isomer or solvate thereof, or a pharmaceutical composition containing such compounds of Formula (I), Formula (II) or Formula (III), is administered to a patient who has not previously undergone or is not currently undergoing treatment with another therapeutic agent.

In certain embodiments pharmaceutical compositions containing at least one compound of Formula (I), Formula (II) or Formula (III) are administered in the form of liposome delivery systems, such as small unilamellar vesicles, large unilamellar vesicles and multilamellar vesicles. Liposomes are formed from a variety of phospholipids, such as cholesterol, stearylamine or phosphatidylcholines.

Provided herein are compounds of Formula (I), Formula (II) or Formula (III) and salts, solvates and pharmaceutical compositions thereof for use in modulating Syk activity, including inhibiting Syk activity. Provided herein are compounds of Formula (I), Formula (II) or Formula (III) and salts, solvates and pharmaceutical compositions thereof for use in the treatment of diseases and conditions mediated by inappropriate Syk activity. By way of example only, this inappropriate Syk activity is any Syk activity that deviates from the normal Syk activity expected in a particular mammalian subject. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk, using compounds of Formula (I), Formula (II) or Formula (III) or a pharmaceutically acceptable salt or solvate thereof, for the prevention and/or treatment of disorders related to unregulated Syk activity.

In a further embodiment, the present invention provides a method of treatment of a mammal suffering from a disorder mediated by Syk activity, which includes administering to said subject an effective amount of a compound of Formula (I), Formula (II) or Formula (III) or a pharmaceutically acceptable salt, solvate, or a physiologically functional derivative thereof.

In a further embodiment, the present invention provides for the use of a compound of Formula (I), Formula (II) or Formula (III), or a pharmaceutically acceptable salt or solvate thereof, in the preparation of a medicament for the treatment of a disease or condition/disorder mediated by Syk activity.

In a further embodiment, the disease or condition mediated by inappropriate Syk activity is rheumatoid arthritis. In a further embodiment, the disease or condition mediated by inappropriate Syk activity is allergic rhinitis. In a further embodiment, the disease or condition mediated by inappropriate Syk activity is rheumatoid arthritis. In a further embodiment, the disease or condition mediated by inappropriate Syk activity is asthma or allergic rhinitis. In a further embodiment, the disease or condition mediated by inappropriate Syk activity is lymphoma.

In a further embodiment, the present invention provides a pharmaceutical composition comprising at least one compound of Formula (I), Formula (II) or Formula (III) adapted for administration by the oral route, for treating, for example, rheumatoid arthritis. In a further embodiment, the present invention provides a pharmaceutical composition comprising at least one compound of Formula (I), Formula (II) or Formula (III) adapted for administration by the nasal route, for treating, for example, allergic rhinitis. In a further embodiment, the present invention provides a pharmaceutical composition comprising at least one compound of Formula (I), Formula (II) or Formula (III) adapted for administration by the inhaled route, for treating, for example, asthma or allergic rhinitis.

Combination Therapies

In certain embodiments, a compound of Formula (I), Formula (II) or Formula (III) is used in combination with a second therapeutic agent, for ameliorating a condition mediated by a protein kinase, such as a Syk-mediated condition. In certain embodiments, the compounds provided herein are used in combination with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor. In certain embodiments, the compounds provided herein are used in combination with an agent to treat respiratory diseases.

In certain embodiments, compounds of the present invention, and their salts and solvates thereof, are administered alone or in combination with other therapeutic agents (pharmaceutical combinations) for the treatment of diseases and conditions associated with inappropriate Syk activity. In certain embodiment, the compounds and pharmaceutically acceptable compositions provided herein are administered concurrently with one or more other desired therapeutics or medical procedures. In other embodiment, the compounds and pharmaceutically acceptable compositions provided herein are administered prior to one or more other desired therapeutics or medical procedures. In certain embodiment, the compounds and pharmaceutically acceptable compositions provided herein are administered subsequent to one or more other desired therapeutics or medical procedures.

Chemotherapeutic agents or other anti-proliferative agents used in combination with the compounds provided herein to treat proliferative diseases and cancer include, but are not limited to, surgery, radiotherapy (gamma.-radiation, neutron beam radiotherapy, electron beam radiotherapy, proton therapy, brachytherapy, and systemic radioactive isotopes), endocrine therapy, biologic response modifiers (interferons, interleukins, and tumor necrosis factor (TNF)), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), GLEEVEC™, adriamycin, dexamethasone, and cyclophosphamide.

Other chemotherapeutic agents which are used in the compositions and methods provided herein include but are not limited to anthracyclines, alkylating agents (e.g., mitomycin C), alkyl sulfonates, aziridines, ethylenimines, methylmelamines, nitrogen mustards, nitrosoureas, antibiotics, antimetabolites, folic acid analogs (e.g., dihydrofolate reductase inhibitors such as methotrexate), purine analogs, pyrimidine analogs, enzymes, podophyllotoxins, platinum-containing agents, interferons, and interleukins Particular examples of known chemotherapeutic agents which may be used in the compositions and methods provided herein include, but are not limited to, busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elformithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, paclitaxel, tamoxifen, teniposide, tenuazonic acid, triaziquone, 2,2',2"-trichlorotriethylamine, urethane, vinblastine, vincristine, and vindesine.

Other agents used in combination with the compounds provided herein include, but are not limited to: treatments for Alzheimer's Disease such as ARRICEPT™ and EXCELON™; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., AVONEX™ and REBIF™), COPAXONE™, and mitoxantrone; treatments for asthma such as albuterol and SINGULAIR™; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Other agents having synergic effects when used in combination with the compounds include, but are not limited to, immunomodulatory or anti-inflammatory substances, for example cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA41g. Where the compounds provided herein are administered in conjunction with other therapies, dosages of the co-administered compounds will of course vary depending on the type of co-drug employed, on the specific drug employed, on the condition being treated and so forth.

Also provided herein are pharmaceutical combinations, e.g. a kit, comprising a) a first agent which is a compound provided herein as disclosed herein, in free form or in pharmaceutically acceptable salt form, and b) at least one co-agent. The kit can comprise instructions for its administration.

Processes for Making Compounds of the Invention

General procedures for preparing compounds provided herein are provided in the Examples, infra. In the reactions provided, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry", John Wiley and Sons, 1991).

In certain embodiments compounds provided herein are prepared as a pharmaceutically acceptable acid addition salt by reacting the free base form of the compound with a pharmaceutically acceptable inorganic or organic acid. In other embodiments, a pharmaceutically acceptable base addition salt of a compound provided herein is prepared by reacting the free acid form of the compound with a pharmaceutically acceptable inorganic or organic base. Alternatively, the salt forms of the compounds provided herein are prepared using salts of the starting materials or intermediates. In certain embodiments, the compounds provided herein are in the form of other salts including, but not limited to, oxalates or trifluoroacetates.

A pharmaceutically acceptable acid addition salt is formed by reaction of the free base form a compound of Formula (I), Formula (II) or Formula (III) with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

The free acid or free base forms of the compounds provided herein may be prepared from the corresponding base addition salt or acid addition salt from, respectively. For example a compound provided herein in an acid addition salt form may be converted to the corresponding free base by treating with a suitable base (e.g., ammonium hydroxide solution, sodium hydroxide, and the like). A compound provided herein in a base addition salt form may be converted to the corresponding free acid by treating with a suitable acid (e.g., hydrochloric acid, etc.).

Compounds provided herein in unoxidized form may be prepared from N-oxides of compounds provided herein by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds provided herein may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound provided herein with a suitable carbamylating agent (e.g., 1,1-acyloxyalkylcarbanochloridate, para-nitrophenyl carbonate, or the like).

Protected derivatives of the compounds provided herein may be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention may be conveniently prepared or formed during the process provided herein, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds provided herein may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds provided herein, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

Compounds of Formula (I) are made by processes provided herein and in the Examples. In certain embodiments, compounds of Formula (I) are made by:

(a) optionally converting a compound provided herein into a pharmaceutically acceptable salt;

(c) optionally converting a salt form of a compound provided herein to a non-salt form;

(d) optionally converting an unoxidized form of a compound provided herein into a pharmaceutically acceptable N-oxide;

(e) optionally converting an N-oxide form of a compound provided herein to its unoxidized form;

(f) optionally resolving an individual isomer of a compound provided herein from a mixture of isomers;

(g) optionally converting a non-derivatized compound provided herein into a pharmaceutically acceptable prodrug derivative; and (h) optionally converting a prodrug derivative of a compound provided herein to its non-derivatized form.

One of skill in the art will appreciate that the above transformations are only representative of methods for preparation of the compounds of the present invention, and that other well known methods can similarly be used.

Certain methods for the synthesis of compounds of Formula (I) is provided in reaction schemes (I)-(XII), wherein schemes (I)-(VI) illustrate the synthesis of intermediates used to make compounds of Formula (I), and schemes (VII)-(XII) illustrate the use of these intermediates to make certain compounds of Formula (I).

Scheme (I)

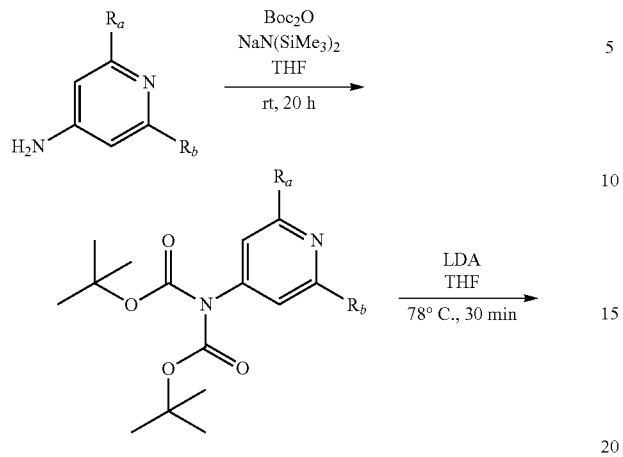

$R_a$ = H, Cl, Br or t-Bu
$R_b$ = H, Cl or Br

Scheme (I) illustrates the general synthesis of the intermediates used to make compounds of Formula (I).

Scheme (II) illustrates the synthesis of the tert-butyl 4-(tert-butoxycarbonylamino)-2,6-dichloronicotinate (3) intermediate compound used in the synthesis of compounds of Formula (I).

Scheme (II)

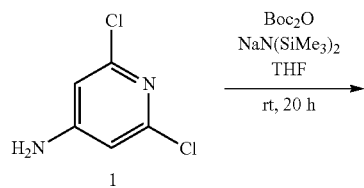

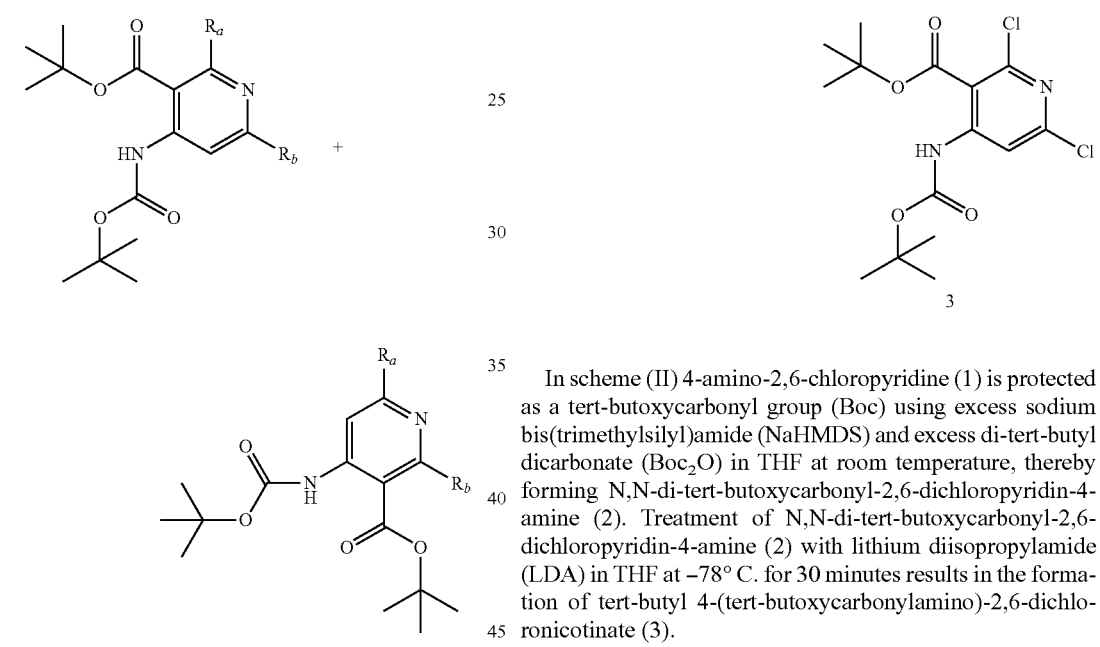

In scheme (II) 4-amino-2,6-chloropyridine (1) is protected as a tert-butoxycarbonyl group (Boc) using excess sodium bis(trimethylsilyl)amide (NaHMDS) and excess di-tert-butyl dicarbonate (Boc$_2$O) in THF at room temperature, thereby forming N,N-di-tert-butoxycarbonyl-2,6-dichloropyridin-4-amine (2). Treatment of N,N-di-tert-butoxycarbonyl-2,6-dichloropyridin-4-amine (2) with lithium diisopropylamide (LDA) in THF at −78° C. for 30 minutes results in the formation of tert-butyl 4-(tert-butoxycarbonylamino)-2,6-dichloronicotinate (3).

Alternatively, the tert-butyl 4-(tert-butoxycarbonylamino)-2,6-dichloronicotinate (3) intermediate compound used in the synthesis of compounds of Formula (I) is synthesized according to scheme (III), wherein 4-amino-2,6-chloropyridine (1) is treated with excess sodium bis(trimethylsilyl)amide (NaHMDS) and excess di-tert-butyl dicarbonate (Boc$_2$O) in THF at room temperature for 96 hours, thereby forming tert-butyl 4-(tert-butoxycarbonylamino)-2,6-dichloronicotinate (3).

Scheme (III)

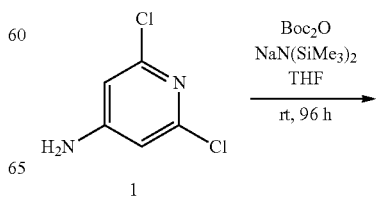

The synthesis of the 5-(tert-butoxycarbonyl)-4-(tert-butoxycarbonylamino)-2,6-dichloronicotinic acid (4) intermediate compound used in the synthesis of certain compounds of Formula (I) is illustrated in scheme (IV).

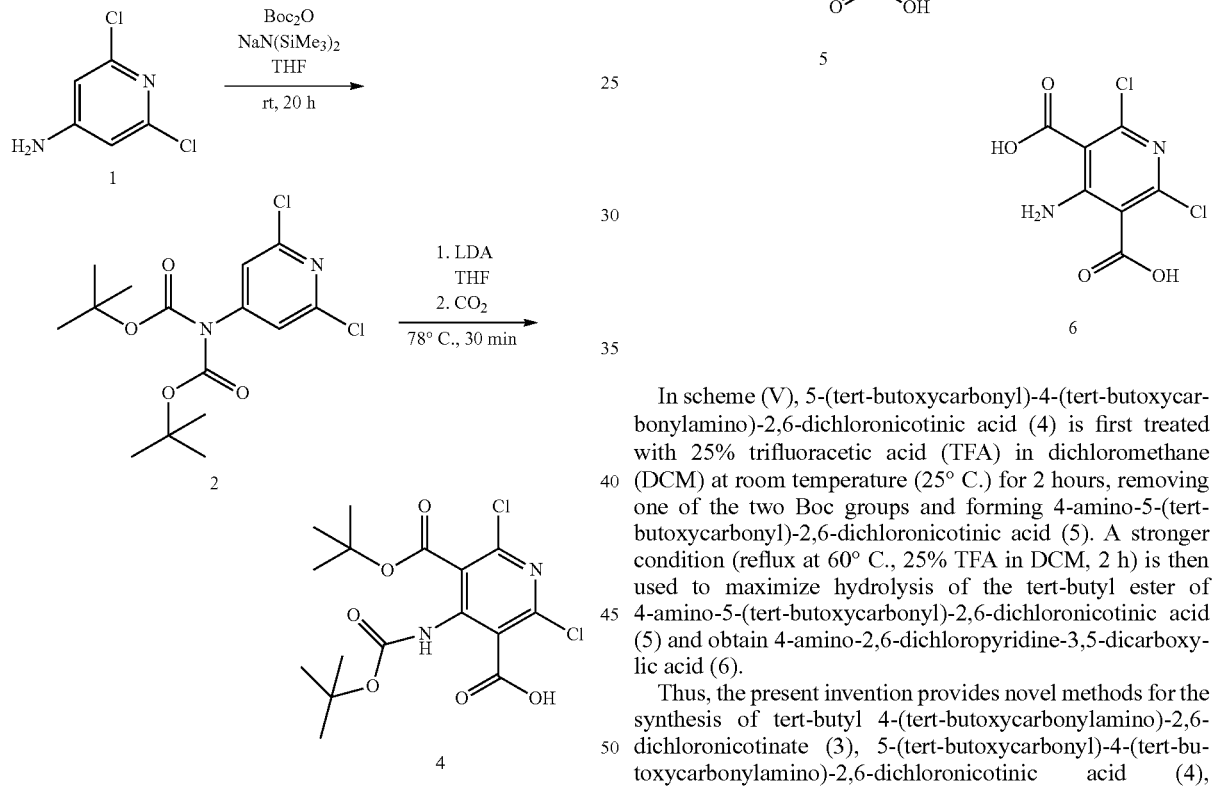

In scheme (IV), 4-amino-2,6-chloropyridine (1) is protected as a tert-butoxycarbonyl group (Boc) using excess sodium bis(trimethylsilyl)amide (NaHMDS) and excess di-tert-butyl dicarbonate (Boc₂O) in THF at room temperature, thereby forming N,N-di-tert-butoxycarbonyl-2,6-dichloropyridin-4-amine (2). Treatment of N,N-di-tert-butoxycarbonyl-2,6-dichloropyridin-4-amine (2) with lithium diisopropylamide (LDA) in THF at −78° C. for 30 minutes, followed by quenching with excess of dry ice results in the formation of 5-(tert-butoxycarbonyl)-4-(tert-butoxycarbonylamino)-2,6-dichloronicotinic acid (4).

The synthesis of the 4-amino-2,6-dichloropyridine-3,5-dicarboxylic acid (6) intermediate compound used in the synthesis of certain compounds of Formula (I) is illustrated in scheme (V).

In scheme (V), 5-(tert-butoxycarbonyl)-4-(tert-butoxycarbonylamino)-2,6-dichloronicotinic acid (4) is first treated with 25% trifluoracetic acid (TFA) in dichloromethane (DCM) at room temperature (25° C.) for 2 hours, removing one of the two Boc groups and forming 4-amino-5-(tert-butoxycarbonyl)-2,6-dichloronicotinic acid (5). A stronger condition (reflux at 60° C., 25% TFA in DCM, 2 h) is then used to maximize hydrolysis of the tert-butyl ester of 4-amino-5-(tert-butoxycarbonyl)-2,6-dichloronicotinic acid (5) and obtain 4-amino-2,6-dichloropyridine-3,5-dicarboxylic acid (6).

Thus, the present invention provides novel methods for the synthesis of tert-butyl 4-(tert-butoxycarbonylamino)-2,6-dichloronicotinate (3), 5-(tert-butoxycarbonyl)-4-(tert-butoxycarbonylamino)-2,6-dichloronicotinic acid (4), 4-amino-5-(tert-butoxycarbonyl)-2,6-dichloronicotinic acid (5) and 4-amino-2,6-dichloropyridine-3,5-dicarboxylic acid (6) intermediate compounds, and although not wishing to be bound by any theory, it is believed such intermediate compounds are formed in the process provided herein by a novel rearrangement of N,N-di(tert-butoxycarbonyl)-2,6-dichloropyridin-4-amine (2). This novel rearrangement is a directed ortho metalation by a strong base (LDA or NaHMDS) that occurs at the ortho carbon to the di-Boc-amino group of N,N-di(tert-butoxycarbonyl)-2,6-dichloropyridin-4-amine (2), thereby leading to the intramolecular migration of a Boc group to afford the rearranged product.

Scheme (VI) illustrates the synthesis of the tert-pentyl 4-(tert-pentoxycarbonylamino)-2,6-dichloronicotinate intermediate compound via reaarangement of di-tert-pentoxycarbonyl-pyridin-4-amine. The tert-pentyl 4-(tert-pentoxycarbonylamino)-2,6-dichloronicotinate intermediate is used in the synthesis of certain compounds of Formula (I).

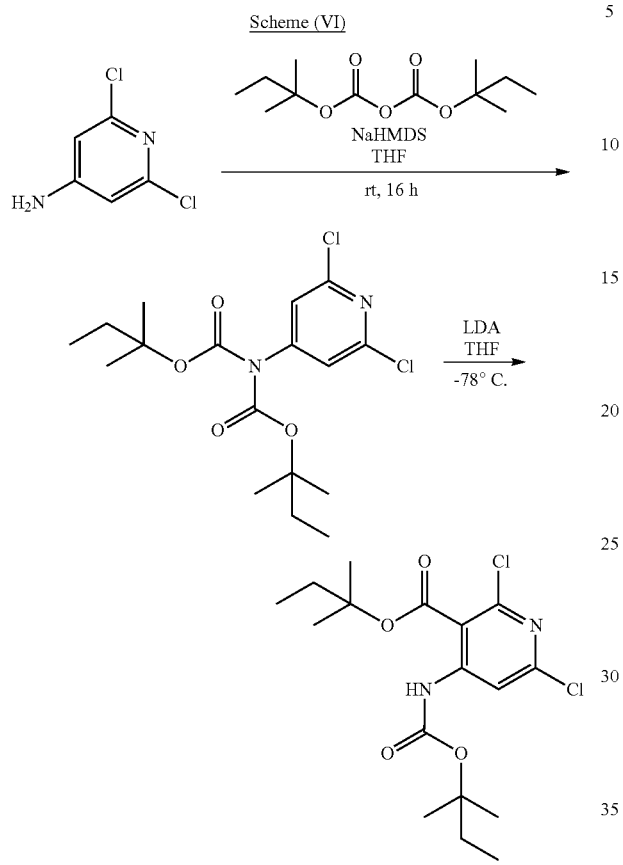

In scheme (VI), 2,6-dichloropyridin-4-amine is reacted with di-tert-pentyl dicarbonate using sodium bis(trimethylsilyl)amide (NaHMDS) in THF at room temperature. Treatment of di-tert-pentoxycarbonyl-pyridin-4-amine with lithium diisopropylamide (LDA) in THF at −78° C. for results in the formation of tert-pentyl 4-(tert-pentoxycarbonylamino)-2,6-dichloronicotinate.

The synthesis of certain compounds of Formula (I) using the tert-butyl 4-(tert-butoxycarbonylamino)-2,6-dichloronicotinate (3) intermediate compound is illustrated in scheme (VII).

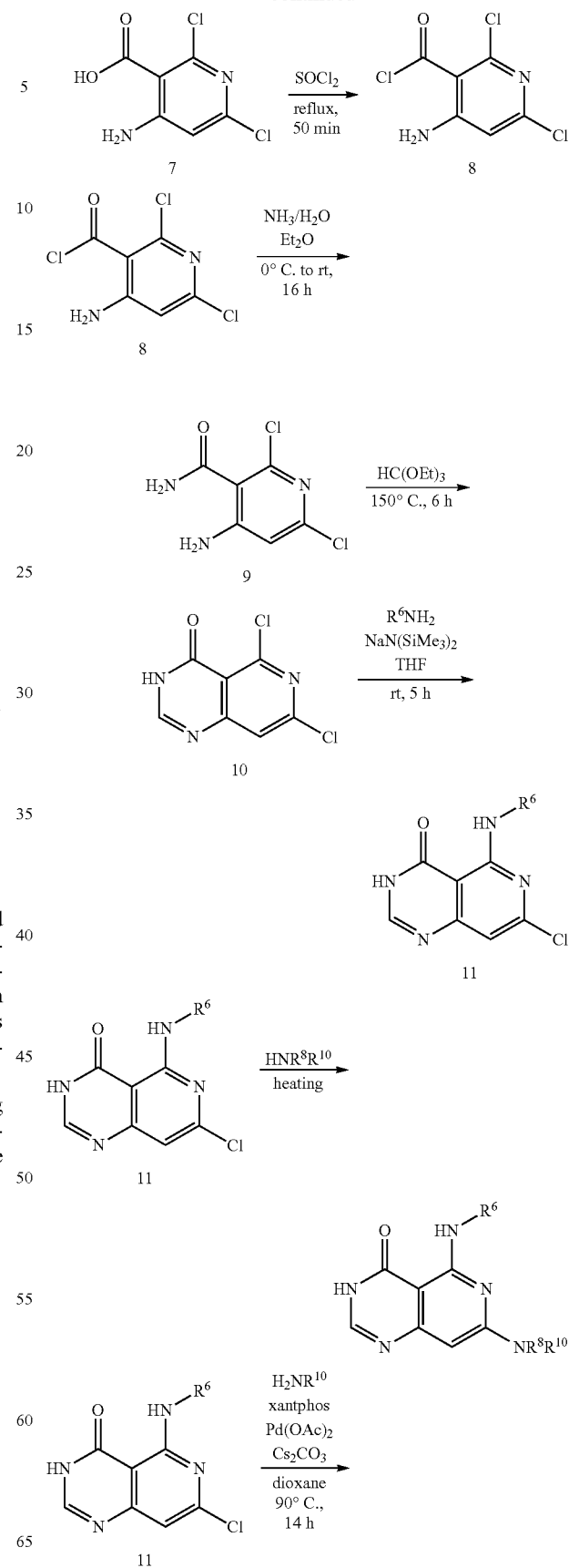

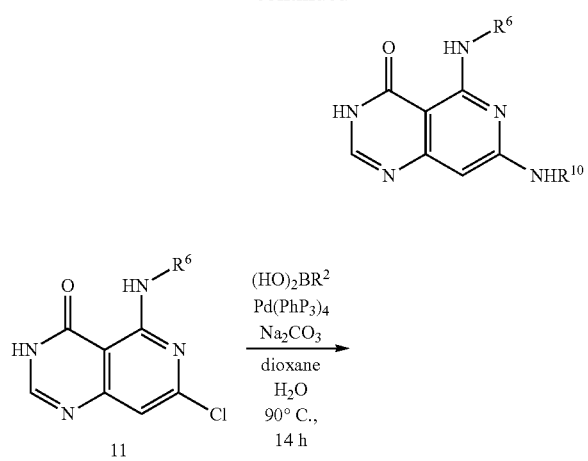

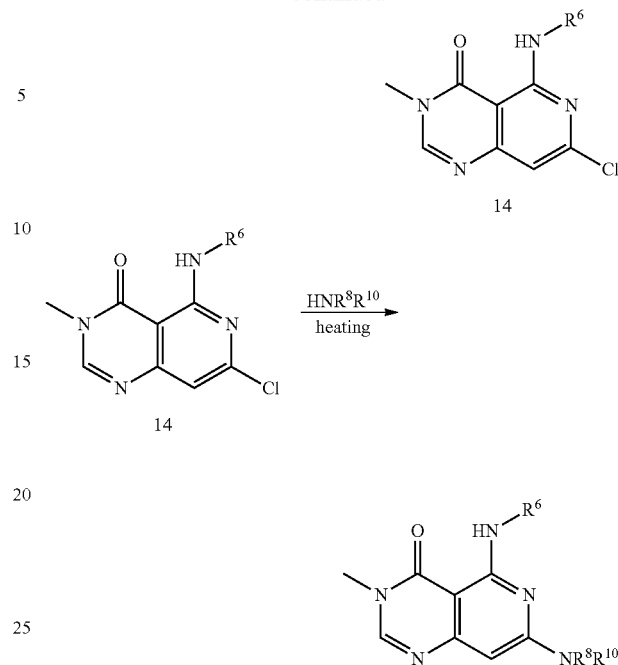

In scheme (VII), the tert-butyl 4-(tert-butoxycarbonylamino)-2,6-dichloronicotinate (3) the Boc groups are removed by treatment with trifluoracetic acid (TFA) in dichloromethane (DCM) at room temperature (60° C.) for 3 hours thereby forming the carboxylic acid, 4-amino-2,6-dichloronicotinic acid (7). Subsequent treatment with thionyl chloride under reflux conditions for 50 minutes gives the acid chloride, 4-amino-2,6-dichloronicotinoyl chloride (8). Treatment of the acid chloride (8) with ammonia gives the amide, 4-amino-2,6-dichloronicotinamide (9). Heating the amide (9) with triethylorthoformate for 6 hours gives 5,7-dichloropyrido[4,3-d]pyrimidin-4(3H)-one (10), which is then used to obtain various compounds of Formula (I) as illustrated in scheme (VII).

The synthesis of certain compounds of Formula (I) using the 5,7-dichloropyrido[4,3-d]pyrimidin-4(3H)-one (10) intermediate compound is illustrated in scheme (VIII).

Scheme (VIII)

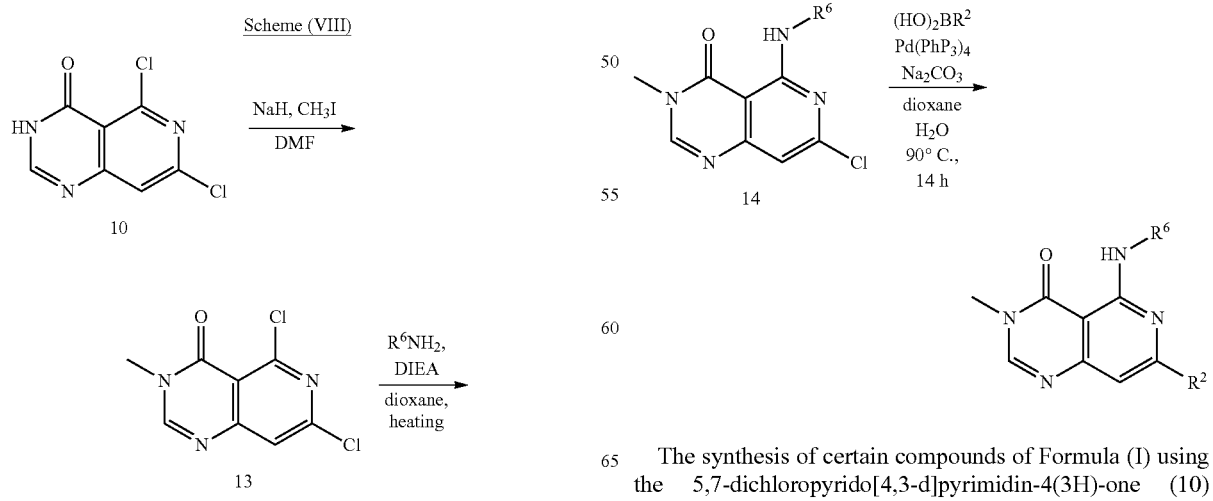

The synthesis of certain compounds of Formula (I) using the 5,7-dichloropyrido[4,3-d]pyrimidin-4(3H)-one (10) intermediate compound is illustrated in scheme (IX).

Scheme (IX)

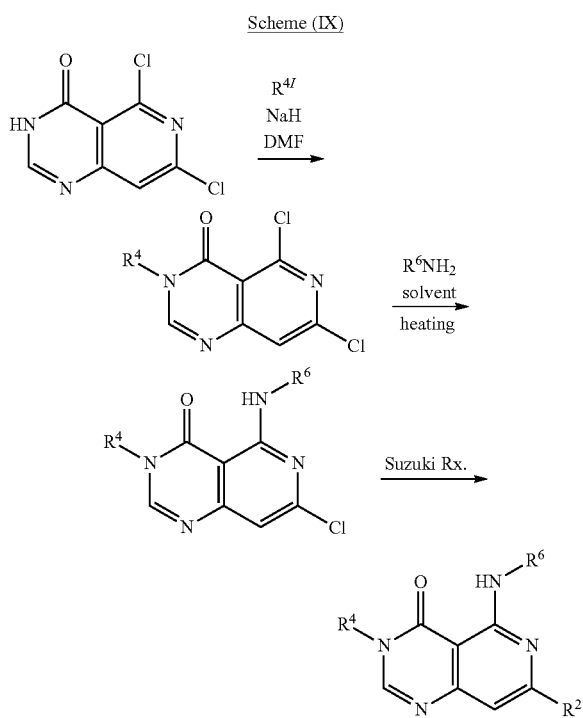

The synthesis of certain compounds of Formula (I) using the 5,7-dichloropyrido[4,3-d]pyrimidin-4(3H)-one (10) intermediate compound is illustrated in scheme (X).

Scheme (X)

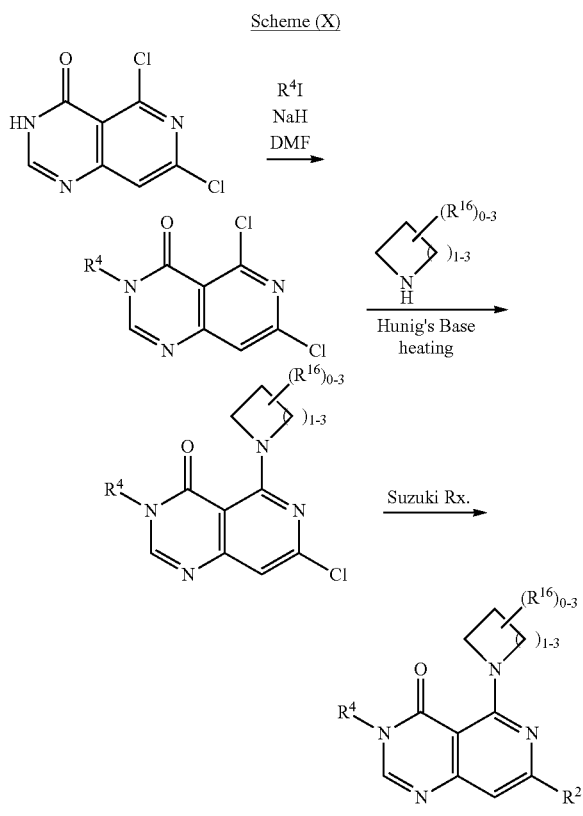

The synthesis of certain compounds of Formula (I) using the 5,7-dichloropyrido[4,3-d]pyrimidin-4(3H)-one (10) intermediate compound is illustrated in scheme (XI).

Scheme (XI)

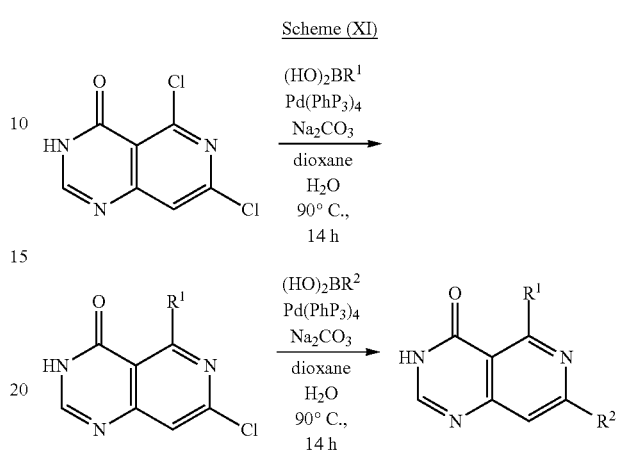

The synthesis of certain compounds of Formula (I) using the 5,7-dichloropyrido[4,3-d]pyrimidin-4(3H)-one (10) intermediate compound is illustrated in scheme (XII).

Scheme (XII)

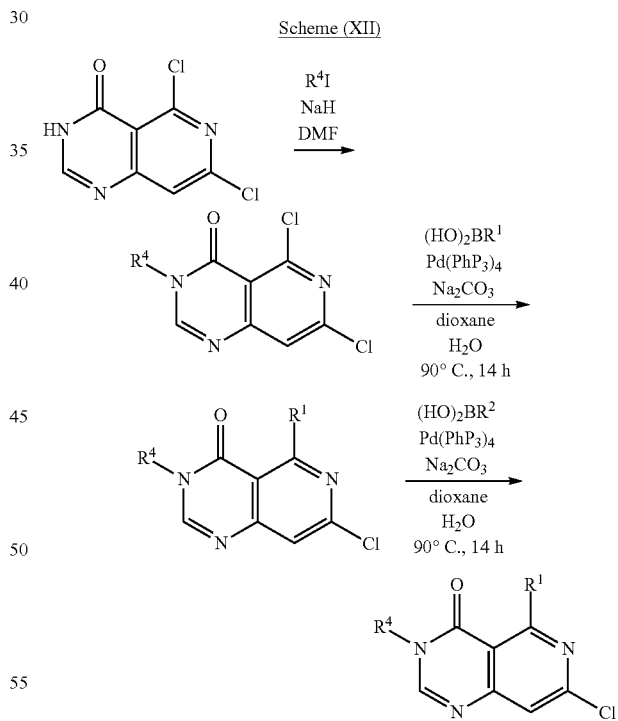

The $R^1$, $R^2$, $R^4$, $R^8$, $R^{10}$, and $R^{16}$ of Schemes (VII) to (XII) are as defined herein.

EXAMPLES

The present invention is further exemplified, but not limited, by the following examples that illustrate the preparation of compounds of Formula (I) according to the invention.

Example 1

Preparation of 7-(4-(2-Aminopropan-2-yl)phenyl)-5-(ethylamino)-3-methylpyrido[4,3-d]pyrimidin-4(3H)-one

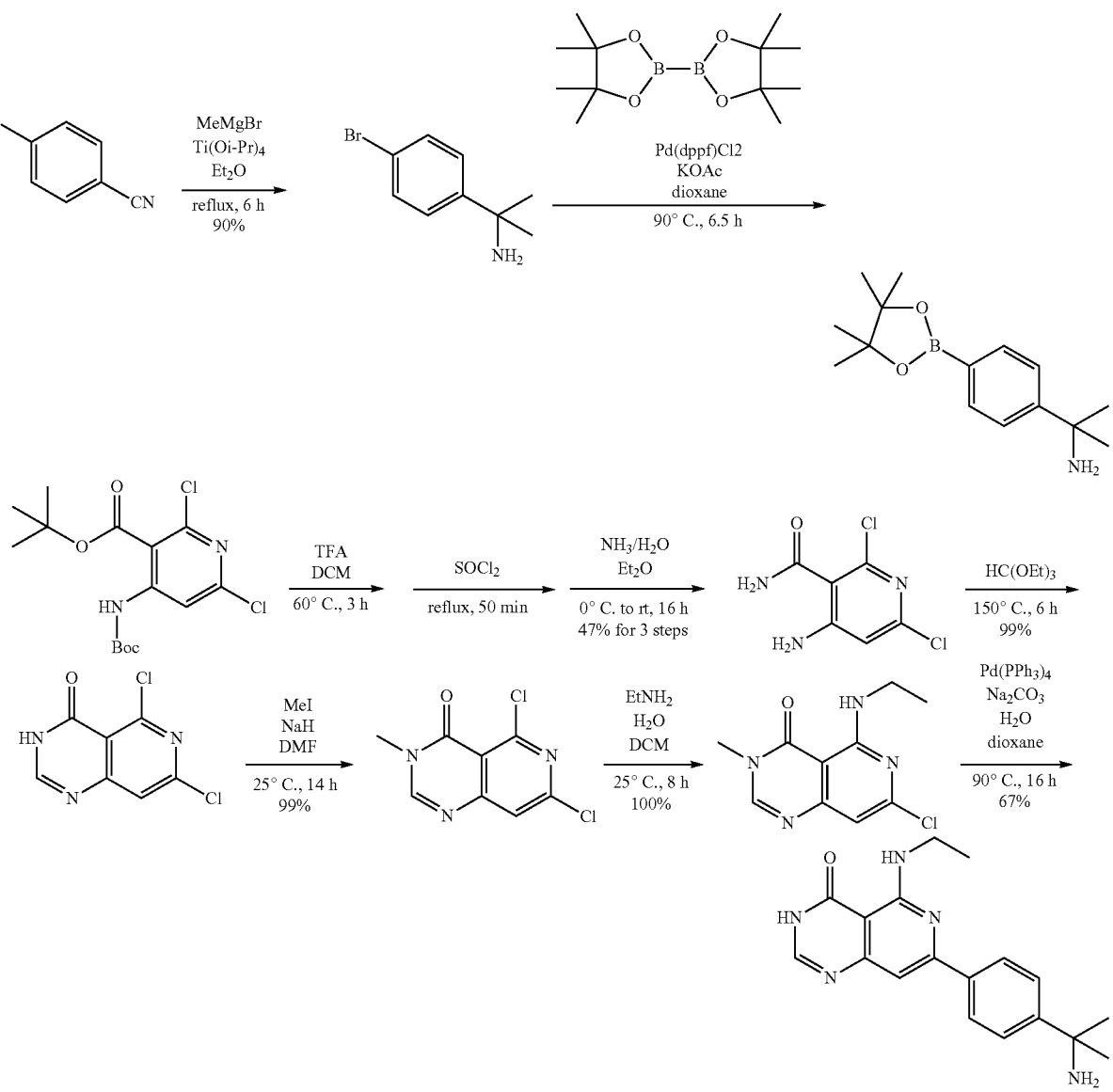

Example 1a 2-(4-Bromophenyl)propan-2-amine

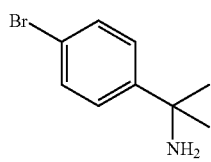

2-(4-Bromophenyl)propan-2-amine was synthesized according to the procedure of Tomashenko, O.; Sokolov, V.; Tomashevskiy, A.; de Meijere, A. *Synlett* 2007, 652-654). Specifically, to a solution of the 4-bromobenzonitrile (3.64 g, 20 mmol) in Et$_2$O (100 mL) was added a methylmagnesium bromide solution (3.0 M in Et$_2$O, 20 mL, 60 mmol). After the reaction mixture was stirred for 30 minutes, Ti(Oi-Pr)$_4$ (5.86 mL, 5.685 g, 20 mmol) was added. The mixture was heated under reflux for 6 hours (bath temperature 48° C.), and a 10% aqueous solution of NaOH (200 mL) was then added slowly at 0° C. The reaction mixture was stirred for 30 minutes at room temperature, and then diluted with 5% aqueous Na$_2$CO$_3$ solution (400 mL) and extracted with Et$_2$O (3×100 mL). The combined Et$_2$O layers were concentrated under reduced pressure and the residue was extracted with dilute 5% aqueous HCl solution. The combined aqueous layers were washed with Et$_2$O (2×50 mL), cooled to 0° C., basified by addition of aqueous 20% NaOH solution and extracted with Et$_2$O (3×100 mL). Evaporation of solvent afforded the title compound. $^1$H NMR (DMSO-$d_6$) δ 1.96 (s, 6H, 2CH$_3$), 8.06 (d, J=6.8 Hz, 2H), 8.10 (d, J=6.8 Hz, 2H); ESI-MS m/z 214.0 (MH$^+$).

Example 1b 2-(4-(4,4,5,5-Tetramethyl-1,3,2-dioxaborolan-2-yl)phenyl)propan-2-amine

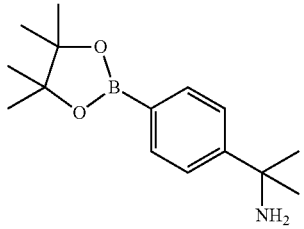 [SMILES: CC(C)(N)c1ccc(B2OC(C)(C)C(C)(C)O2)cc1]

A mixture of 2-(4-bromophenyl)propan-2-amine (1.90 g, 8.78 mmol), bis(pinacolate)diboron (3.35 g, 13.2 mmol), Pd(dppf)Cl$_2$ (358 mg, 0.44 mmol), and KOAc (2.58 g, 26.3 mmol) in dioxane (24.0 mL) was purged with N$_2$ and heated at 90° C. for 6.5 hours. The reaction mixture was poured into H$_2$O (200 mL) and extracted with EtOAc (3×50 mL). The combined EtOAc extracts were washed with brine (20 mL), dried over MgSO$_4$ and evaporated to afford the crude title compound that was used in the next step directly without purification.

Example 1c

4-Amino-2,6-dichloronicotinamide

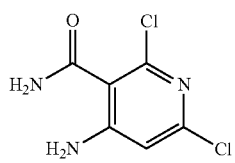 [SMILES: NC(=O)c1c(N)cc(Cl)nc1Cl]

To a solution of tert-butyl 4-(tert-butoxycarbonylamino)-2,6-dichloronicotinate (7.98 g, 22.0 mmol) (see: Liu, Y.; Ding, Q.; Wu, X. *J. Org. Chem.* 2008, 73, 6025) in DCM (75 mL) was added TFA (25 mL). After it was stirred at the room temperature for 30 minutes, the reaction mixture was heated at 60° C. in a ChemGlass pressure vessel (heavy wall, 350 mL) for 3 hours and evaporated under reduced pressure to result in a residue which was refluxed in thionyl chloride (80 mL) for 50 minutes and evaporated under reduced pressure. The residue was diluted with ethyl ether (100 mL) and cooled to 0° C., to which 28% aqueous NH$_4$OH (10 mL) solution was added slowly and dropwise followed by addition of more 28% aqueous NH$_4$OH solution (40 mL). The mixture was then stirred at 0° C. for 1 hour and at the room temperature for another 16 hours. The reaction mixture was concentrated under reduced pressure, diluted with a mixed solvent of DCM/MeOH (9:1), loaded on silica gel (60 mL). Chromatography of the mixture with gradient mixed solvents from DCM/MeOH/28% aqueous NH$_4$OH (190:10:1) to (90:10:1) afforded the title compound. $^1$H NMR (MeOH-$d_4$) δ 6.55 (s, 1H); ESI-MS m/z 206.0 (MH$^+$).

Example 1d 5,7-Dichloropyrido[4,3-d]pyrimidin-4(3H)-one

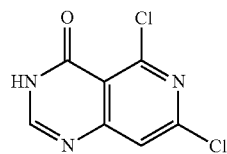 [SMILES: O=c1[nH]cnc2cc(Cl)nc(Cl)c12]

A mixture of 4-Amino-2,6-dichloronicotinamide (2.06 g, 10.0 mmol) and triethyl orthoformate (20 mL) was heated at 150° C. in a ChemGlass pressure vessel (heavy wall, 150 mL) for 6 hours and evaporated under reduced pressure to afford the crude title compound. $^1$H NMR (DMSO-$d_6$) δ 7.72 (s, 1H), 8.31 (1H); ESI-MS m/z 216.0 (MH$^+$).

Example 1e 5,7-Dichloro-3-methylpyrido[4,3-d]pyrimidin-4(3H)-one

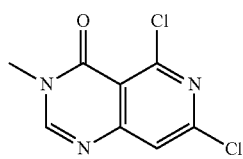

To a solution of 5,7-dichloropyrido[4,3-d]pyrimidin-4(3H)-one (1.73 g, 8.0 mmol) in dry DMF (25 mL) was added NaH (352 mg, 60% in mineral oil, 8.8 mmol) at 0° C. and the resulting mixture was stirred under N$_2$ at 0° C. for 30 min. MeI (0.6 mL, 1.36 g, 9.6 mmol) was added via a syringe and the reaction mixture was stirred at room temperature for 14 hours and was cooled to 0° C. MeOH (2.0 mL) was added slowly and the reaction mixture was stirred for 20 minutes at room temperature and then concentrated under reduced pressure. The resulting residue was partitioned between 10% aqueous NH$_4$Cl solution (80 mL) and EtOAc (40 mL). The aqueous phase was separated and extracted with EtOAc (3×30 mL). The combined EtOAc extracts were washed with brine (8 mL), dried over MgSO$_4$ and evaporated to afford the title compound. $^1$H NMR (DMSO-$d_6$) δ 3.46 (s, 3H), 7.74 (s, 1H), 8.64 (s, 1H); ESI-MS m/z 230.1 (MH$^+$).

Example 1f

7-Chloro-5-(ethylamino)-3-methylpyrido[4,3-d]pyrimidin-4(3H)-one

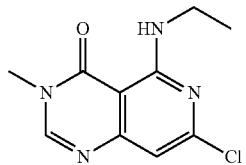 [SMILES: CCNc1nc(Cl)cc2ncn(C)c(=O)c12]

To a solution of 5,7-dichloro-3-methylpyrido[4,3-d]pyrimidin-4(3H)-one (1.5 g, 6.5 mmol) in DCM (10 mL) was added an aqueous ethylamine solution (70%, 8 mL, 6.368 g, 141.3 mmol). After stirring for 8 hours at room temperature, the reaction mixture was evaporated under reduced pressure to afford the title compound. ESI-MS m/z 239.1 (MH$^+$).

Example 1g 7-(4-(2-Aminopropan-2-yl)phenyl)-5-(ethylamino)-3-methylpyrido[4,3-d]pyrimidin-4(3H)-one

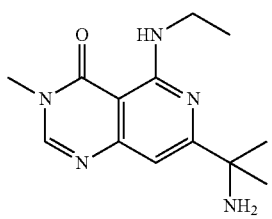 [SMILES: CCNc1nc(C(C)(C)N)cc2ncn(C)c(=O)c12]

A mixture of 7-chloro-5-(ethylamino)-3-methylpyrido[4,3-d]pyrimidin-4(3H)-one (48.7 mg, 0.2 mmol), crude 2-(4-(4,4,5,5-tetramethyl-1,3,2-dioxaborolan-2-yl)phenyl)propan-2-amine (estimated 0.5 mmol), Pd(PPh$_3$)$_4$ (3.4 mg, 0.003 mmol) and Na$_2$CO$_3$ (63.6 mg, 0.6 mol) in a mixed solvent of dioxane (1.5 mL) and H$_2$O (0.5 mL) was purged with N$_2$, heated at 90° C. for 16 hours, evaporated to result in a residue which was diluted with DMSO, acidified with TFA, and subjected to HPLC purification to afford the TFA salt of the title compound. The TFA salt was dissolved in 5 mL of a mixed solvent of MeOH/DCM (1:4) and basified with aqueous NH$_4$OH solution (28%, 0.3 mL) and was further purified by chromatography (DCM:MeOH:28% aqueous NH$_4$OH=90:10:1) to furnish the free base form the title compound that was 45.2 mg (0.147 mmol) after being dried thoroughly under reduced pressure. The free base form compound was diluted with 5 mL of a mixed solvent of MeOH/DCM (1:4) and acidified with aqueous HCl solution (1.0 M, 0.147 mL, 0.147 mmol) and was evaporated to afford the HCl salt form of the title compound. $^1$H NMR (DMSO-$d_6$) δ 1.20 (t, J=7.0 Hz, 3H), 1.61 (s, 6H), 3.39 (s, 3H), 3.56 (q, J=7.0 Hz, 2H), 7.16 (s, 1H), 7.61 (d, J=8.4 Hz, 2H), 8.13 (d, J=8.4 Hz, 2H), 8.44 (s, 1H); ESI-MS m/z 338.2 (MH$^+$).

Example 2

Preparation of 7-(4-(2-morpholinoethylamino)-3-(methylsulfonyl)phenyl)-5-(isopropylamino)-3-methylpyrido[4,3-d]pyrimidin-4(3H)-one

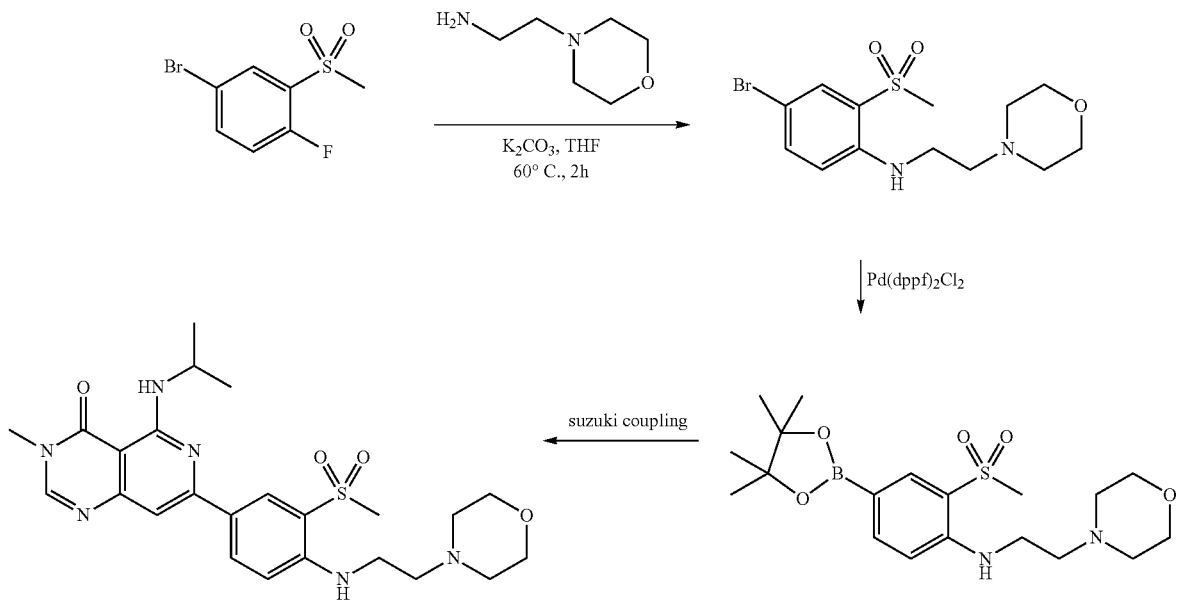

Example 2a

7-Chloro-5-(isopropylamino)-3-methylpyrido[4,3-d]pyrimidin-4(3H)-one

A mixture of 5,7-dichloro-3-methylpyrido[4,3-d]pyrimidin-4(3H)-one (920.2 mg, 4.0 mmol) and isopropylamine (1.7 mL, 1.182 g, 20.0 mmol) in dioxane (10 mL) was heated at 80° C. for 26 hours and evaporated to result in a residue which was partitioned between saturated NH$_4$Cl solution (200 mL) and EtOAc (100 mL). The aqueous phase was extracted with EtOAc (2×50 mL) and the combined organic phases were washed with brine (20 mL), dried over Na$_2$SO$_4$, and evaporated to afford crude title product (872 mg, 86%). $^1$H NMR (DMSO-d$_6$) δ 1.22 (d, J=6.4 Hz, 6H, 2CH$_3$), 3.42 (s, 3H, NCH$_3$), 4.19 (m, 1H), 6.59 (s, 1H), 8.45 (s, 1H), 8.90 (d, J=7.6 Hz, 1H, NH); ESI-MS m/z 253.1 (MH$^+$).

Example 2b

4-bromo-2-(methylsulfonyl)-N-(2-morpholinoethyl)benzenamine 4-bromo-1-fluoro-2-(methylsulfonyl)benzene (250 mg, 1 mmol), K$_2$CO$_3$ (240 mg, 2 mmol) and 10 mL THF was added to a 20 mL vial. The vial was then sealed vial and heated to 60° C. for 2 hours. The solution was cooled to the room temperature and the solvent was removed under vacuum. The crude product was purified by silica column using 50% EA in Hexane yielding a white solid. ESI-MS m/z 363.2 (MH$^+$).

Example 2c

4-(4,4,5,5-tetramethyl-1,3,2-dioxaborolan-2-yl)-2-(methylsulfonyl)-N-(2-morpholinoethyl)benzenamine 4-bromo-2-(methylsulfonyl)-N-(2-morpholinoethyl)benzenamine (200 mg, 0.55 mmol), bis(pinacolato)diboron (210 mg, 0.82 mmol), KOAc (215 mg, 2.2 mmol), and Pd(dppf)$_2$Cl$_2$ (41 mg, 0.05 mmol) and anhydrous 1,4-dioxane (10 mL) were added to a 20 mL vial. The reaction mixture was purged with N$_2$ and heated at 100° C. overnight. After cooling to room temperature, the reaction mixture was passed through a short silica gel plug using 10% MeOH in dichloromethane (DCM). The solvent was removed to give the final product as a dark brown solid, ESI-MS m/z 411.2 (MH$^+$), which was used in the next step reaction without further purification.

Example 2d

7-(4-(2-morpholinoethylamino)-3-(methylsulfonyl)phenyl)-5-(isopropylamino)-3-methylpyrido[4,3-d]pyrimidin-4(3H)-one 7-Chloro-5-(isopropylamino)-3-methylpyrido[4,3-d]pyrimidin-4(3H)-one (60 mg, 0.24 mmol), crude 4-(4,4,5,5-tetramethyl-1,3,2-dioxaborolan-2-yl)-2-(methylsulfonyl)-N-(2-morpholinoethyl)benzenamine (240 mg, ~0.28 mmol), Pd(PPh$_3$)$_4$ (28 mg, 0.024 mmol) and Na$_2$CO$_3$ (102 mg, 0.96 mol) in a mixed solvent of acetonitrile (4 mL) and H$_2$O (4 mL) were added to a 20 mL microwave tube and sealed. The tube was then heated in a Microwave Reactor at 140° C. for 10 minutes. The solvent was removed and the crude product purified by silica column using 7% MeOH in DCM to give the final product as a pale solid. ESI-MS m/z 501.2 (MH$^+$); $^1$H NMR (DMSO-d$_6$) δ 8.71 (d, J=7.2 Hz, 1H), 8.46 (d, J=2.4 HZ, 1H), 8.40 (s, 1H), 8.26 (d, J=8.8 Hz, 1H), 7.04 (s, 1H), 6.97 (d, J=8.8 Hz, 1H), 6.77 (t, J=4.8 Hz, 1H), 3.59 (m, 4H), 3.42 (s, 3H), 3.33 (m, 4H), 3.20 (s, 3H), 2.62 (m, 2H), 2.44 (s, 3H), 1.29 (d, J=6.4 Hz, 6H).

Example 3

Preparation of (R)-3-methyl-7-(4-(4-methylpiperazin-1-yl)phenyl)-5-(tetrahydrofuran-3-ylamino)pyrido[4,3-d]pyrimidin-4(3H)-one

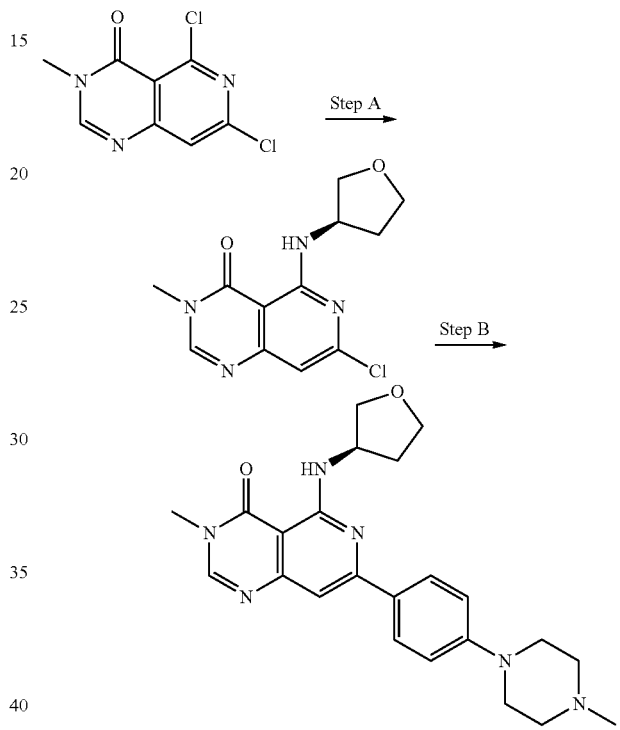

Example 3

Step A

A mixture of 5,7-dichloro-3-methylpyrido[4,3-d]pyrimidin-4(3H)-one (75 mg, 0.33 mmol), (R)-3-aminotetrahydrofuran toluene-4-sulfonate (101 mg, 0.39 mmol), Hunig's base (0.23 mL, 1.32 mmol) and dioxane (4 mL) was stirred at 90° C. overnight. The reaction mixture was cooled to room temperature and worked-up. The residue was purified using slilica gel flash column chromatography (eluent: 0-10% methanol in dichloromethane) to afford (R)-7-chloro-3-methyl-5-(tetrahydrofuran-3-ylamino)pyrido[4,3-d]pyrimidin-4(3H)-one as a white solid.

Example 3

Step B

A mixture of (R)-7-chloro-3-methyl-5-(tetrahydrofuran-3-ylamino)pyrido[4,3-d]pyrimidin-4(3H)-one (16 mg, 0.057 mmol), 1-methyl-4-(4-(4,4,5,5-tetramethyl-1,3,2-dioxaborolan-2-yl)phenyl)piperazine (19 mg, 0.063 mmol), Pd(PPh$_3$)$_4$ (6.6 mg, 0.0057 mmol), K$_2$CO$_3$ (24 mg, 0.17 mmol), 2-propanol (3 mL) and H$_2$O (1 mL) was stirred at 90° C. overnight. The reaction mixture was cooled to room temperature and worked-up. The residue was purified using slilica gel flash column chromatography (eluent: 0-10% methanol in dichloromethane) to afford (R)-3-methyl-7-(4-(4-methylpiperazin-1-yl)phenyl)-5-(tetrahydrofuran-3-ylamino)pyrido[4,3-d]pyrimidin-4(3H)-one as a slightly yellow solid. HPLC-MS calculated C$_{23}$H$_{28}$N$_6$O$_2$(M+H$^+$): 421.24, found: 421.20.

Example 4

Preparation of (S)-5-(3-(hydroxymethyl)pyrrolidin-1-yl)-3-methyl-7-(4-morpholinophenyl)pyrido[4,3-d]pyrimidin-4(3H)-one

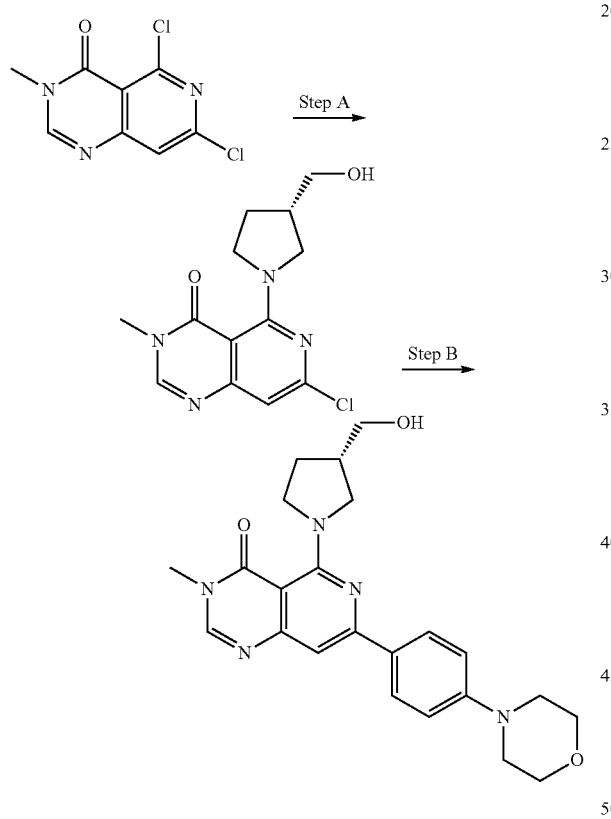

Example 4

Step A

A mixture of 5,7-dichloro-3-methylpyrido[4,3-d]pyrimidin-4(3H)-one (270 mg, 1.17 mmol), (S)-pyrrolidin-3-ylmethanol (1.40 mmol), Hunig's base (1.02 mL, 5.85 mmol) and dioxane (4 mL) was stirred at 100° C. overnight. The reaction mixture was cooled to room temperature and worked-up. The residue was purified using slilica gel flash column chromatography (eluent: 0-10% methanol in dichloromethane) to afford (S)-7-chloro-5-(3-(hydroxymethyl)pyrrolidin-1-yl)-3-methylpyrido[4,3-d]pyrimidin-4(3H)-one as a white solid.

Example 4

Step B

A mixture of (S)-7-chloro-5-(3-(hydroxymethyl)pyrrolidin-1-yl)-3-methylpyrido[4,3-d]pyrimidin-4(3H)-one (26 mg, 0.088 mmol), 4-(4-(4,4,5,5-tetramethyl-1,3,2-dioxaborolan-2-yl)phenyl)morpholine (28 mg, 0.097 mmol), Pd(PPh$_3$)$_4$ (10.2 mg, 0.0088 mmol), K$_2$CO$_3$ (36 mg, 0.26 mmol), 2-propanol (3 mL) and H$_2$O (1 mL) was stirred at 90° C. overnight. The reaction mixture was cooled to room temperature and worked-up. The residue was purified on slilica gel flash column chromatography (eluent: 0-10% methanol in dichloromethane) to afford (S)-5-(3-(hydroxymethyl)pyrrolidin-1-yl)-3-methyl-7-(4-morpholinophenyl)pyrido[4,3-d]pyrimidin-4(3H)-one as a slightly yellow solid. $^1$H NMR (CDCl$_3$) δ (ppm) 8.06 (d, 2H), 8.01 (s, 1H), 7.19 (s, 1H), 6.96 (d, 2H), 3.91-3.81 (m, 5H), 3.78-3.65 (m, 4H), 3.65-3.58 (m, 1H), 3.50 (s, 3H), 3.27-3.24 (m, 4H), 2.57-2.47 (m, 1H), 2.15-2.07 (m, 1H), 1.90 (s, br, 1H), 1.82-1.72 (m, 1H); HPLC-MS calculated C$_{23}$H$_{27}$N$_5$O$_3$ (M+H$^+$): 422.22, found: 422.20.

Example 5

Preparation of (S)-5-(3-(hydroxymethyl)pyrrolidin-1-yl)-3-methyl-7-(4-(thiomorpholino-1,1-dioxide)phenyl)pyrido[4,3-d]pyrimidin-4(3H)-one

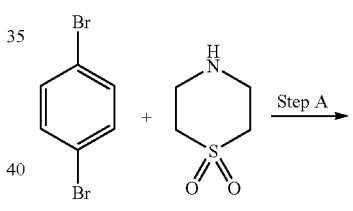

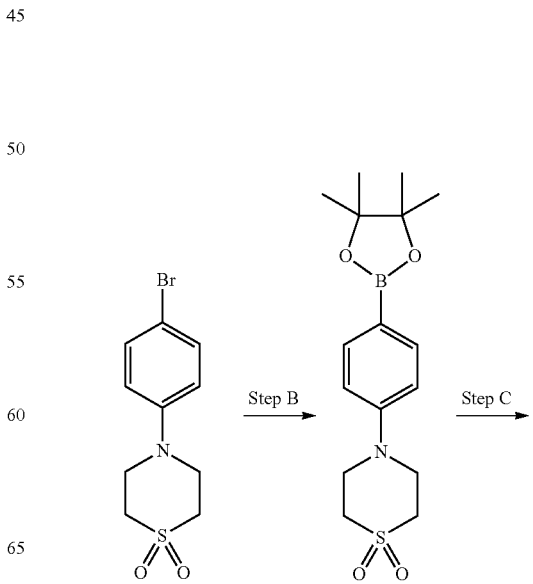

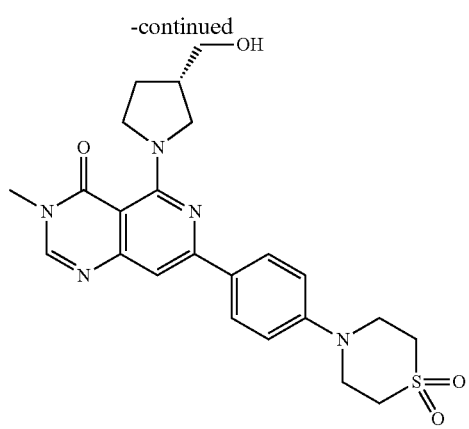

Example 5

Step A

A mixture of 1,4-dibromobenzene (118 mg, 0.5 mmol), thiomorpholine-1,1-dioxide (68 mg, 0.5 mmol), Pd2 dba3 (12 mg, 2.5 mol %), BINAP (24 mg, 7.5 mol %), sodium 2-methylpropan-2-olate (72 mg, 0.75 mmol) and toluene (2 mL) was stirred at 80° C. for overnight. The reaction mixture was cooled down to room temperature and worked-up. The residue was purified on slilica gel flash column chromatography (eluent: 0-50% EtOAc in hexane) to afford 4-(4-bromophenyl)thiomorpholine-1,1-dioxide as a white solid.

Example 5

Step B

A mixture of 4-(4-bromophenyl)thiomorpholine-1,1-dioxide (104 mg, 0.36 mmol), Pd(dppf)$_2$Cl$_2$ (31 mg, 10 mol %), KOAc (139 mg, 1.08 mmol), 4,4,4',4',5,5,5',5'-octamethyl-2,2'-bi(1,3,2-dioxaborolane) (139 mg, 0.54 mmol) and DMSO (2 mL) was stirred at 90° C. overnight. The reaction mixture was cooled to room temperature and worked-up. The residue was purified using slilica gel flash column chromatography (eluent: 0-50% EtOAc in hexane) to afford 4-(4-(4,4,5,5-tetramethyl-1,3,2-dioxaborolan-2-yl)phenyl)thiomorpholine-1,1-dioxide as a white solid.

Example 5

Step C

A mixture of (S)-7-chloro-5-(3-(hydroxymethyl)pyrrolidin-1-yl)-3-methylpyrido[4,3-d]pyrimidin-4(3H)-one (19.8 mg, 0.067 mmol), 4-(4-(4,4,5,5-tetramethyl-1,3,2-dioxaborolan-2-yl)phenyl)thiomorpholine-1,1-dioxide (25 mg, 0.074 mmol), Pd(PPh$_3$)$_4$ (7.8 mg, 0.0067 mmol), K$_2$CO$_3$ (28 mg, 0.20 mmol), 2-propanol (3 mL) and H$_2$O (1 mL) was stirred at 90° C. overnight. The reaction mixture was cooled to room temperature and worked-up. The residue was purified using slilica gel flash column chromatography (eluent: 0-10% methanol in dichloromethane) to afford (S)-5-(3-(hydroxymethyl)pyrrolidin-1-yl)-3-methyl-7-(4-(thiomorpholino-1,1-dioxide)phenyl)pyrido[4,3-d]pyrimidin-4(3H)-one as a slightly yellow solid. $^1$H NMR (CDCl$_3$) δ (ppm) 8.08 (d, 2H), 8.02 (s, 1H), 7.18 (s, 1H), 6.97 (d, 2H), 3.98-3.92 (m, 4H), 3.90-3.80 (m, 1H), 3.78-3.58 (m, 5H), 3.51 (s, 5H), 3.14-3.08 (m, 4H), 2.55-2.46 (m, 1H), 2.15-2.07 (m, 1H), 1.91 (s, br, 1H), 1.82-1.72 (m, 1H); HPLC-MS calculated C$_{23}$H$_{27}$N$_5$O$_4$S (M+H$^+$): 470.19, found: 470.10.

Example 6

Preparation of 5-(4-(hydroxymethyl)thiazol-2-ylamino)-3-methyl-7-(4-morpholinophenyl)pyrido[4,3-d]pyrimidin-4(3H)-one

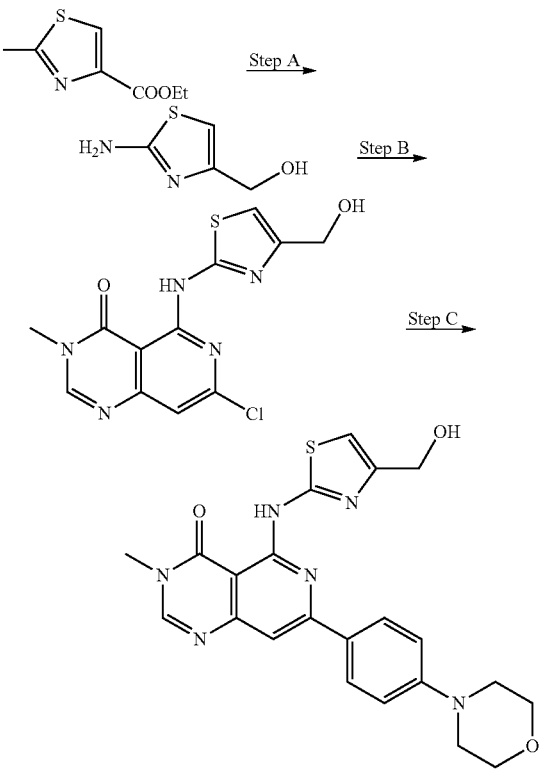

Example 6

Step A

Ethyl 2-aminothiazole-4-carboxylate (0.86 g, 5.0 mmol) was slowly added to 2.0 M LiBH$_4$ in THF solution (3.0 mL, 6.0 mmol) at 0° C. The reaction mixture was allowed to warm up to room temperature and then stirred overnight. The mixture was then quenched with H$_2$O (30 mL) at 0° C. and extracted with ethyl acetate (3×15 mL). The combined organic layers were washed with brine, dried over MgSO$_4$, filtered, concentrated, and purified by silica gel chromatography (10% methanol/dichloromethane) to give (2-aminothiazol-4-yl)methanol as a white solid product.

Example 6

Step B (2-aminothiazol-4-yl)methanol (70.0 mg, 0.54 mmol) and K$_2$CO$_3$ (148.6 mg, 1.08 mmol) were added to a solution of 5,7-dichloro-3-methylpyrido[4,3-d]pyrimidin-4(3H)-one (123.7 mg, 0.54 mmol) in 1,4-dioxane (2.7 mL). The reaction mixture was heated at 80° C. overnight, cooled down, quenched with H$_2$O (20 mL) and extracted with ethyl acetate (3×5 mL). The combined organic layers were washed with brine, dried over MgSO$_4$, filtered, concentrated, and purified by silica gel chromatography (10% methanol/dichloromethane) to give 7-chloro-5-(4-(hydroxymethyl)thiazol-2-ylamino)-3-methylpyrido[4,3-d]pyrimidin-4(3H)-one as a white solid product.

Example 6

Step C 4-morpholinophenylboronic acid pinacol ester (28.8 mg, 0.099 mmol), 2M aqueous Na$_2$CO$_3$ solution (149 μL, 0.298 mmol), and a catalytic amount of Pd(PPh$_3$)$_4$ were added to a solution of 7-chloro-5-(4-(hydroxymethyl)thiazol-2-ylamino)-3-methylpyrido[4,3-d]pyrimidin-4(3H)-one (32.2 mg, 0.099 mmol) in 1,4-dioxane (1.0 mL). The reaction mixture was purged with N$_2$ and heated at 140° C. by a microwave reactor for 15 minutes. The mixture was then cooled, quenched with H$_2$O (5 mL) and extracted with ethyl acetate (3×2.5 mL). The combined organic layers were evaporated under vacuo and the residue was purified by preparatory LC/MS to provide the title compound; $^1$H NMR (CD$_3$OD, 400 MHz) δ 8.58 (s, 1H), 8.27 (d, J=8.8 Hz, 2H), 7.75 (s, 1H), 7.40 (d, J=8.8 Hz, 2H), 7.26 (s, 1H), 4.70 (s, 2H), 3.97 (t, J=4.8 Hz, 4H), 3.67 (s, 3H), 3.49 (t, J=4.8 Hz, 4H); HPLC-MS calculated for C$_{22}$H$_{22}$N$_6$O$_3$S (M+H$^+$) 451.1, found 451.1.

Example 7

Preparation of 7-(6-(2-hydroxypropan-2-yl)pyridin-3-yl)-3-methyl-5-(pyridin-2-ylamino)pyrido[4,3-d]pyrimidin-4(3H)-one

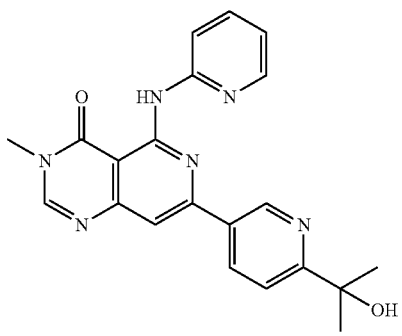 [SMILES: Cn1cnc2cc(-c3ccc(C(C)(C)O)nc3)nc(Nc3ccccn3)c2c1=O]

2-iodopyridine (7.51 μL, 0.071 mmol), Cs$_2$CO$_3$ (41.9 mg, 0.129 mmol), and a catalytic amount of Pd(OAc)$_2$ and xant phos ligand were added to a solution of 5-amino-7-(6-(2-hydroxypropan-2-yl)pyridin-3-yl)-3-methylpyrido[4,3-d]pyrimidin-4(3H)-one (20.0 mg, 0.064 mmol) in anhydrous THF (0.5 mL). The reaction mixture was purged with N$_2$ and heated at 85° C. overnight. The mixture was then cooled, quenched with H$_2$O (5 mL) and extracted with ethyl acetate (3×2.5 mL). The combined organic layers were evaporated under vacuo and the residue was purified by preparatory LC/MS to provide the title compound; HPLC-MS calculated for C$_{21}$H$_{20}$N$_6$O$_2$ (M+H$^+$) 389.2, found 389.2.

Example 8

Preparation of 3-methyl-5,7-bis(4-morpholinophenyl)pyrido[4,3-d]pyrimidin-4(3H)-one

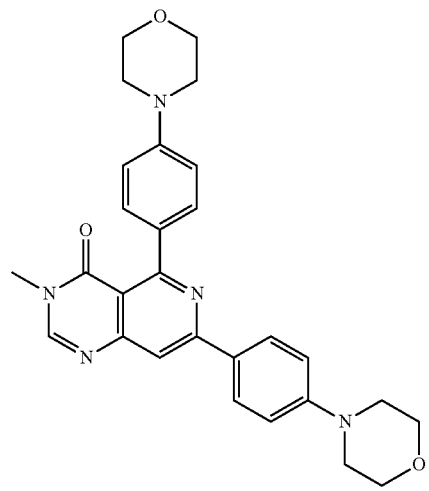 [SMILES: Cn1cnc2cc(-c3ccc(N4CCOCC4)cc3)nc(-c3ccc(N4CCOCC4)cc3)c2c1=O]

To a solution of 5,7-dichloro-3-methylpyrido[4,3-d]pyrimidin-4(3H)-one (23.0 mg, 0.10 mmol) in 1,4-dioxane (0.5 mL) were added 4-morpholinophenylboronic acid pinacol ester (57.8 mg, 0.20 mmol), 2M aqueous Na$_2$CO$_3$ solution (150 μL, 0.30 mmol), and a catalytic amount of Pd(PPh$_3$)$_4$. The reaction mixture was purged with N$_2$ and heated at 140° C. by a microwave reactor for 15 minutes. The mixture was then cooled, quenched with H$_2$O (5 mL) and extracted with ethyl acetate (3×2.5 mL). The combined organic layers were evaporated under vacuo and the residue was purified by preparatory LC/MS to provide the title compound; HPLC-MS calculated for C$_{28}$H$_{29}$N$_5$O$_3$ (M+H$^+$) 484.2, found 484.2.

Example 9

Preparation of N-(2-hydroxy-5-(5-(2-methoxyethylamino)-3-methyl-4-oxo-3,4-dihydropyrido[4,3-d]pyrimidin-7-yl)phenyl)formamide

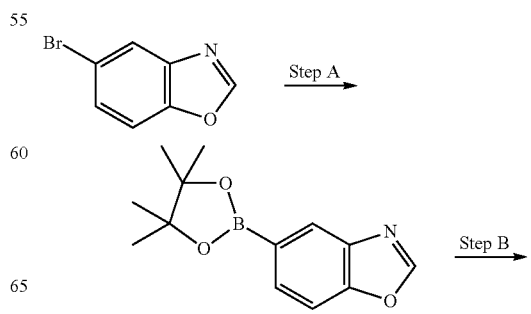

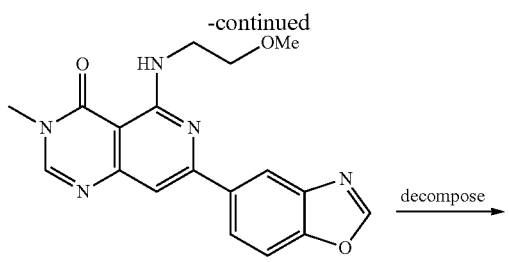

decompose

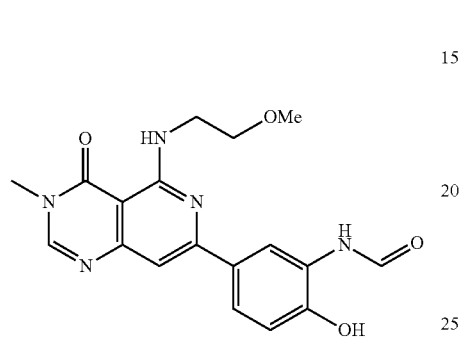

Example 9

Step A

To a solution of 5-bromobenzo[d]oxazole (198.0 mg, 1.00 mmol) in anhydrous DMF (4.0 mL) were added bis(pinacolato)diboron (279.3 mg, 1.10 mmol), KOAc (294.5 mg, 3.00 mmol), and Pd(dppf)$_2$Cl$_2$ (40.8 mg, 0.05 mmol). The reaction mixture was purged with N$_2$ and heated at 100° C. overnight. The mixture was then cooled, quenched with H$_2$O (40 mL) and extracted with ethyl acetate (3×20 mL). The combined organic layers were washed with brine, dried over MgSO$_4$, filtered, concentrated, and purified by silica gel chromatography (0-40% EtOAc/Hexanes) to give 5-(4,4,5,5-tetramethyl-1,3,2-dioxaborolan-2-yl)benzo[d]oxazole as a white solid product.

Example 9

Step B

To a solution of 7-chloro-5-(2-methoxyethylamino)-3-methylpyrido[4,3-d]pyrimidin-4(3H)-one (15.0 mg, 0.0559 mmol) in 1,4-dioxane (0.5 mL) were added 5-(4,4,5,5-tetramethyl-1,3,2-dioxaborolan-2-yl)benzo[d]oxazole (15.0 mg, 0.0612 mmol), 2M aqueous Na$_2$CO$_3$ solution (83.7 μL, 0.167 mmol), and a catalytic amount of Pd(PPh$_3$)$_4$. The reaction mixture was purged with N$_2$ and heated at 140° C. by a microwave reactor for 15 minutes. The mixture was then cooled, quenched with H$_2$O (5 mL) and extracted with ethyl acetate (3×2.5 mL). The combined organic layers were evaporated under vacuum and the residue was purified by preparatory LC/MS to provide 7-(benzo[d]oxazol-5-yl)-5-(2-methoxyethylamino)-3-methylpyrido[4,3-d]pyrimidin-4(3H)-one, which was completely decomposed to the title compound at room temperature; HPLC-MS calculated for C$_{18}$H$_{19}$N$_5$O$_4$ (M+H$^+$) 370.1, found 370.1.

Example 10

Preparation of 5-(2-methoxyethylamino)-3-methyl-7-(2-methylbenzo[d]oxazol-6-yl)pyrido[4,3-d]pyrimidin-4(3H)-one

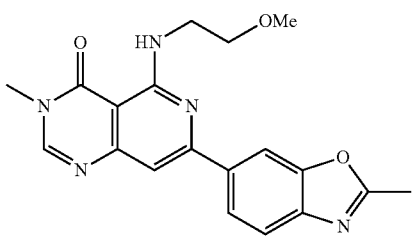

Example 10a

N-(2-hydroxy-4-(5-(2-methoxyethylamino)-3-methyl-4-oxo-3,4-dihydropyrido[4,3-d]pyrimidin-7-yl)phenyl)acetamide

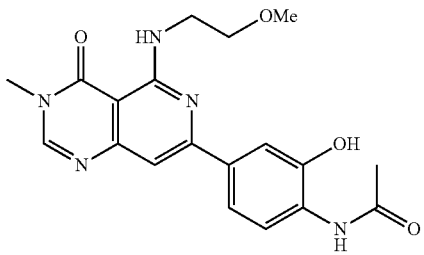 [SMILES: COCCNc1nc(-c2ccc(NC(C)=O)c(O)c2)cc2ncn(C)c(=O)c12]

5-(2-Methoxyethylamino)-3-methyl-7-(2-methylbenzo[d]oxazol-6-yl)pyrido[4,3-d]pyrimidin-4(3H)-one was synthesized, as described in Example 9, from 6-bromo-2-methylbenzo[d]oxazole and 7-chloro-5-(2-methoxyethylamino)-3-methylpyrido[4,3-d]pyrimidin-4(3H)-one. After purification by preparatory LC/MS, it was partially decomposed to N-(2-hydroxy-4-(5-(2-methoxyethylamino)-3-methyl-4-oxo-3,4-dihydropyrido[4,3-d]pyrimidin-7-yl)phenyl)acetamide. The two compounds are separated again by preparatory TLC.

5-(2-Methoxyethylamino)-3-methyl-7-(2-methylbenzo[d]oxazol-6-yl)pyrido[4,3-d]pyrimidin-4(3H)-one; $^1$H NMR (CD$_3$OD, 400 MHz) δ 8.29 (s, 1H), 8.26 (d, J=1.6 Hz, 1H), 8.07 (dd, J=8.4, 1.6 Hz, 1H), 7.62 (d, J=8.4 Hz, 1H), 7.10 (s, 1H), 3.87 (t, J=5.6 Hz, 2H), 3.71 (t, J=5.6 Hz, 2H), 3.51 (s, 3H), 3.45 (s, 3H), 2.67 (s, 3H); HPLC-MS calculated for C$_{19}$H$_{19}$N$_5$O$_3$ (M+H$^+$) 366.1, found 366.1.

N-(2-Hydroxy-4-(5-(2-methoxyethylamino)-3-methyl-4-oxo-3,4-dihydropyrido[4,3-d]pyrimidin-7-yl)phenyl)acetamide; $^1$H NMR (CD$_3$OD with a drop of CDCl$_3$, 400 MHz) δ 8.25 (s, 1H), 7.84 (d, J=8.4 Hz, 1H), 7.66 (d, J=1.6 Hz, 1H), 7.55 (dd, J=8.4, 1.6 Hz, 1H), 7.01 (s, 1H), 3.86 (t, J=5.6 Hz, 2H), 3.69 (t, J=5.6 Hz, 2H), 3.50 (s, 3H), 3.43 (s, 3H), 2.21 (s, 3H); HPLC-MS calculated for $C_{19}H_{21}N_5O_4$ (M+H⁺) 384.2, found 384.2.

Example 11

Preparation of (R)-3-(3-methyl-7-(4-morpholinophenyl)-4-oxo-3,4-dihydropyrido[4,3-d]pyrimidin-5-ylamino)pyrrolidine-1-carboxamide

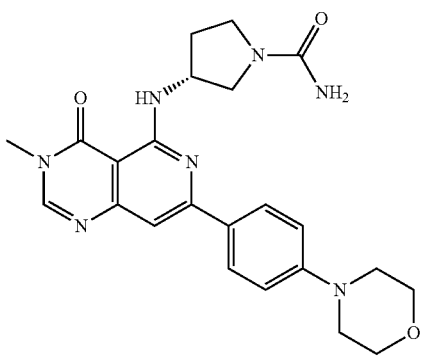 [SMILES: Cn1cnc2cc(-c3ccc(N4CCOCC4)cc3)nc(N[C@@H]3CCN(C(N)=O)C3)c2c1=O]

To a solution of (R)-3-methyl-7-(4-morpholinophenyl)-5-(pyrrolidin-3-ylamino)pyrido[4,3-d]pyrimidin-4(3H)-one (8.0 mg, 0.0197 mmol) in methanol (0.2 mL) were added KOCN (2.9 mg, 0.0354 mmol) and 1N aqueous HCl solution (19.7 μL, 0.0197 mmol). The reaction mixture was stirred at room temperature overnight, evaporated under vacuo, and purified by preparatory LC/MS to provide the title compound; HPLC-MS calculated for $C_{23}H_{27}N_7O_3$ (M+H⁺) 450.2, found 450.2.

Example 12

Preparation of (R)-7-(4-(4-isopropylpiperazin-1-yl)phenyl)-3-methyl-5-(tetrahydrofuran-3-ylamino)pyrido[4,3-d]pyrimidin-4(3H)-one

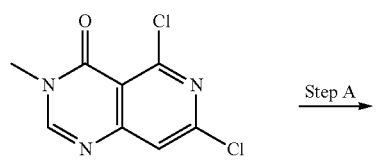

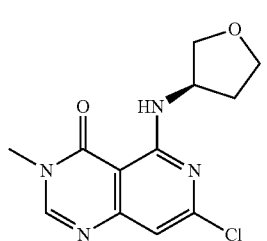

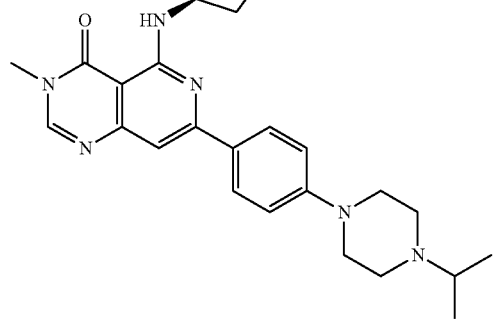

Step A

A mixture of 5,7-dichloro-3-methylpyrido[4,3-d]pyrimidin-4(3H)-one (75 mg, 0.33 mmol), (R)-3-aminotetrahydrofuran toluene-4-sulfonate (101 mg, 0.39 mmol), Hunig's base (0.23 mL, 1.32 mmol) and dioxane (4 mL) was stirred at 90° C. overnight. The reaction mixture was cooled to room temperature and worked-up. The residue was purified using slilica gel flash column chromatography (eluent: 0-10% methanol in dichloromethane) to afford (R)-7-chloro-3-methyl-5-(tetrahydrofuran-3-ylamino)pyrido[4,3-d]pyrimidin-4(3H)-one as a white solid.

A mixture of (R)-7-chloro-3-methyl-5-(tetrahydrofuran-3-ylamino)pyrido[4,3-d]pyrimidin-4(3H)-one (15 mg, 0.053 mmol), 1-methyl-4-(4-(4,4,5,5-tetramethyl-1,3,2-dioxaborolan-2-yl)phenyl)piperazine (19.4 mg, 0.059 mmol), Pd(PPh₃)₄ (6.1 mg, 0.0053 mmol), K₂CO₃ (22 mg, 0.16 mmol), 2-propanol (3 mL) and H₂O (1 mL) was stirred at 90° C. overnight. The reaction mixture was cooled to room temperature and worked-up. The residue was purified on slilica gel flash column chromatography (eluent: 0-10% methanol in dichloromethane) to afford (R)-7-(4-(4-isopropylpiperazin-1-yl)phenyl)-3-methyl-5-(tetrahydrofuran-3-ylamino)pyrido[4,3-d]pyrimidin-4(3H)-one as a slightly yellow solid. ¹H NMR (CDCl₃) δ (ppm) 8.80 (d, 1H), 8.04 (d, 2H), 8.00 (s, 1H), 7.10 (s, 1H), 6.98 (d, 2H), 4.92-4.84 (m, 1H), 4.22 (dd, 1H), 4.06-3.99 (m, 1H), 3.95-3.89 (m, 1H), 3.80 (dd, 1H), 3.51 (s, 3H), 3.34-3.31 (m, 4H), 3.77-3.68 (m, 5H), 2.46-2.36 (m, 1H), 2.06-1.96 (m, 1H), 1.10 (d, 6H); HPLC-MS calculated $C_{25}H_{32}N_6O_2$ (M+H⁺): 449.27, found: 449.20.

Example 13

Preparation of 5-(5-(hydroxymethyl)thiophen-2-yl)-3-methyl-7-(4-morpholinophenyl)pyrido[4,3-d]pyrimidin-4(3H)-one

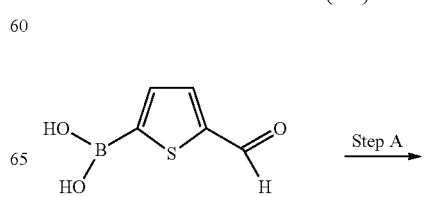

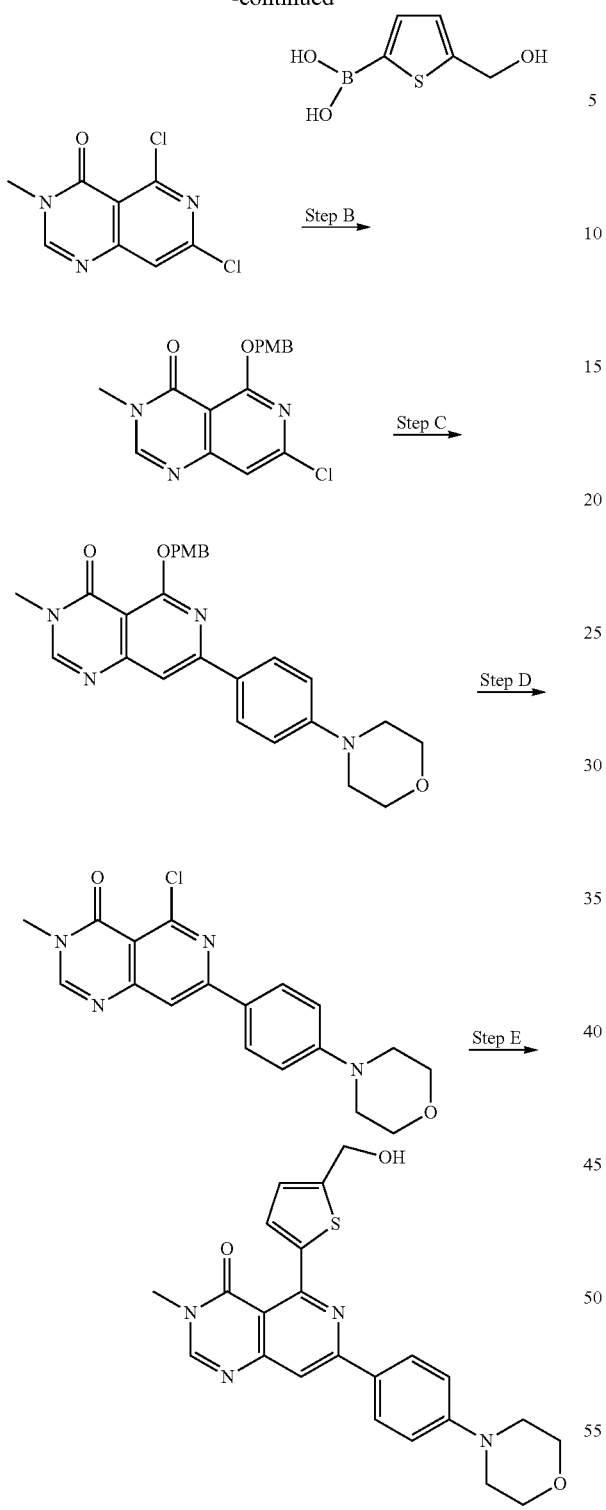

Step B

To a solution of 4-methoxybenzylalcohol (596 μL, 4.78 mmol) in anhydrous DMF (20 mL) was added NaH (208 mg, 60% dispersion in mineral oil, 5.20 mmol) at 0° C. The mixture was stirred at 0° C. for 10 minutes before 5,7-dichloro-3-methylpyrido[4,3-d]pyrimidin-4(3H)-one (1.00 g, 4.35 mmol) was slowly added. The resulting mixture was heated at 80° C. overnight, cooled down, quenched with $H_2O$ (200 mL), and extracted with EtOAc (3×100 mL). The combined organic layer was dried over $MgSO_4$ and evaporated under reduced pressure to afford crude 7-chloro-5-(4-methoxybenzyloxy)-3-methylpyrido[4,3-d]pyrimidin-4(3H)-one as a yellow solid.

Step C

To a solution of 7-chloro-5-(4-methoxybenzyloxy)-3-methylpyrido[4,3-d]pyrimidin-4(3H)-one (750 mg, 2.26 mmol) in 1,4-dioxane (11 mL) were added 4-morpholinophenylboronic acid pinacol ester (654 mg, 2.26 mmol), 2M aqueous $Na_2CO_3$ solution (3.39 mL, 6.78 mmol), and $Pd(dppf)_2Cl_2$ (36.9 mg, 0.045 mmol). The reaction mixture was purged with $N_2$ and heated at 140° C. by a microwave reactor for 15 minutes. The mixture was then cooled, quenched with $H_2O$ (100 mL) and extracted with $CH_2Cl_2$ (3×50 mL). The combined organic layer was dried over $MgSO_4$ and evaporated under reduced pressure to afford crude 5-(4-methoxybenzyloxy)-3-methyl-7-(4-morpholinophenyl)pyrido[4,3-d]pyrimidin-4(3H)-one.

Step D

The crude 5-(4-methoxybenzyloxy)-3-methyl-7-(4-morpholinophenyl)pyrido[4,3-d]pyrimidin-4(3H)-one from Step C was dissolved in TFA (3.5 mL) and heated at 80° C. overnight. After removal of TFA under reduced pressure, the residue was taken in $POCl_3$ (5 mL) and heated at 100° C. for 2 hours. After removal of most $POCl_3$ under reduced pressure, the residue was basified with cold 1N aqueous NaOH at 0° C., extracted with $CH_2Cl_2$, and purified by reverse phase HPLC to provide 5-chloro-3-methyl-7-(4-morpholinophenyl)pyrido[4,3-d]pyrimidin-4(3H)-one as a yellow solid.

Step E

To a solution of 5-chloro-3-methyl-7-(4-morpholinophenyl)pyrido[4,3-d]pyrimidin-4(3H)-one (6.0 mg, 0.017 mmol) in 1,4-dioxane (0.5 mL) were added crude 5-(hydroxymethyl)thiophen-2-ylboronic acid from Step A, 2M aqueous $Na_2CO_3$ solution (0.1 mL, 0.2 mmol), and a catalytic amount of $Pd(PPh_3)_4$. The reaction mixture was purged with $N_2$ and heated at 140° C. by a microwave reactor for 15 minutes. The mixture was then cooled, quenched with $H_2O$, extracted with EtOAc, and purified by preparatory LC/MS to provide the title compound; ESI-MS m/z 435.1 (MH⁺).

Example 14

Preparation of 5-(2-(1H-pyrazol-4-yl)ethoxy)-3-methyl-7-(4-morpholinophenyl)pyrido[4,3-d]pyrimidin-4(3H)-one

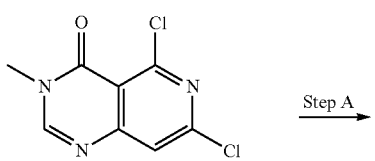

Step A

To a solution of 5-formylthiophen-2-ylboronic acid (15.6 mg, 0.1 mmol) in MeOH (0.5 mL) was added excess amount of $NaBH_4$. The mixture was stirred at room temperature for 2 hours and evaporated under reduced pressure to afford crude 5-(hydroxymethyl)thiophen-2-ylboronic acid, which was used in step E without further purification.

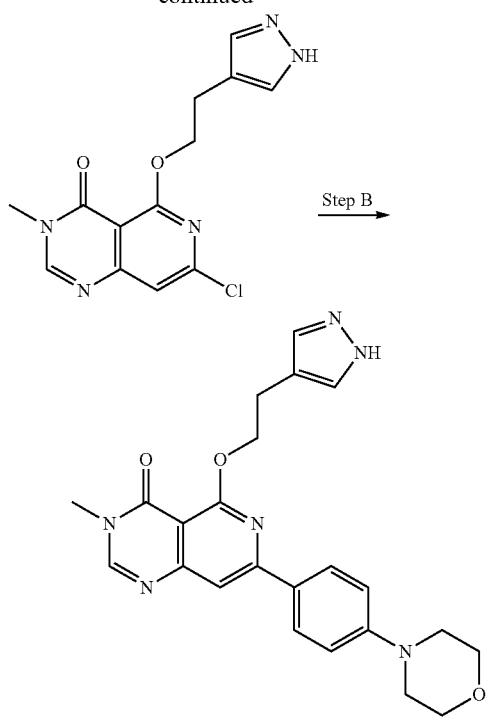

Step A

A mixture of 5,7-dichloro-3-methylpyrido[4,3-d]pyrimidin-4(3H)-one (115.0 mg, 0.50 mmol), 2-(1H-pyrazol-4-yl)ethanol (112.1 mg, 1.00 mmol) and $K_2CO_3$ (138.2 mg, 1.00 mmol) in 1,4-dioxane (5 mL) was heated at 80° C. overnight, cooled down, quenched with $H_2O$ (25 mL) and extracted with EtOAc (3×12.5 mL). The combined organic layer was evaporated under reduced pressure and purified by reverse phase HPLC to afford 5-(2-(1H-pyrazol-4-yl)ethoxy)-7-chloro-3-methylpyrido[4,3-d]pyrimidin-4(3H)-one.

Step B

To a solution of 5-(2-(1H-pyrazol-4-yl)ethoxy)-7-chloro-3-methylpyrido[4,3-d]pyrimidin-4(3H)-one (31.6 mg, 0.10 mmol) in 1,4-dioxane (1 mL) were added 4-morpholinophenylboronic acid pinacol ester (29.9 mg, 0.10 mmol), 2M aqueous $Na_2CO_3$ solution (155 µL, 0.30 mmol), and a catalytic amount of $Pd(dppf)_2Cl_2$. The reaction mixture was purged with $N_2$ and heated at 140° C. by a microwave reactor for 15 minutes. The mixture was then cooled, quenched with $H_2O$ and extracted with EtOAc. The combined organic layer was dried over $MgSO_4$, concentrated, and purified by silica gel chromatography (eluent: 0-10% MeOH in DCM) to provide the title compound as a yellow solid. $^1$H NMR (CD$_3$OD, 400 MHz) δ 8.37 (s, 1H), 8.06 (d, J=9.2 Hz, 2H), 7.71 (s, 2H), 7.43 (s, 1H), 7.04 (d, J=9.2 Hz, 2H), 4.71 (t, J=6.4 Hz, 2H), 3.85 (t, J=4.8 Hz, 4H), 3.55 (s, 3H), 3.27 (t, J=4.8 Hz, 4H), 3.10 (t, J=6.4 Hz, 2H); ESI-MS m/z 433.1 (MH$^+$).

By repeating the procedures provided in the above examples, using appropriate starting materials, the following compounds of Formula I, in particular compounds of Formula (I) as identified in Table 1, were obtained.

TABLE 1

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 1 | 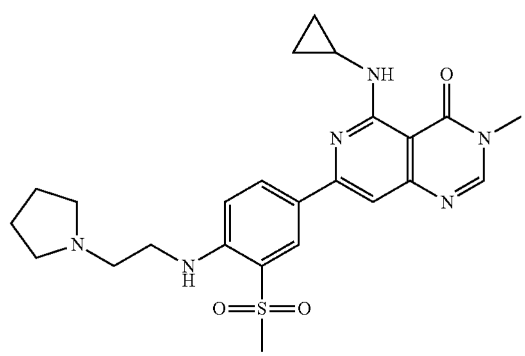 [SMILES: Cn1cnc2cc(-c3ccc(NCCN4CCCC4)c(S(C)(=O)=O)c3)nc(NC3CC3)c2c1=O] | ESI-MS m/z 483.2 (MH$^+$) | 0.013 |
| 2 | 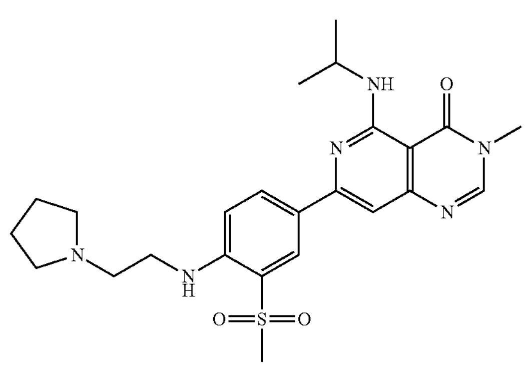 [SMILES: CC(C)Nc1nc(-c2ccc(NCCN3CCCC3)c(S(C)(=O)=O)c2)cc2ncn(C)c(=O)c12] | ESI-MS m/z 485.2 (MH$^+$) | 0.01 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 3 | 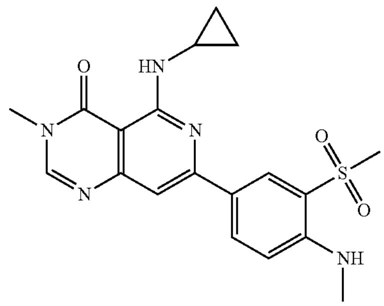 | ESI-MS m/z 400.2 (MH$^+$) | 0.1 |
| 4 | 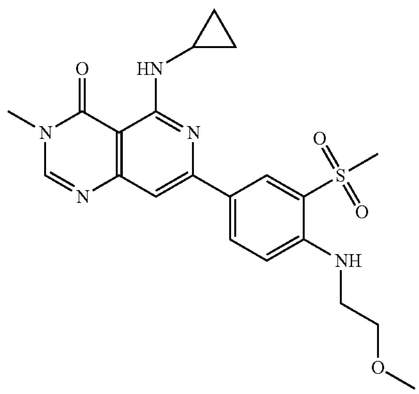 | ESI-MS m/z 444.2 (MH$^+$) | 0.167 |
| 5 | 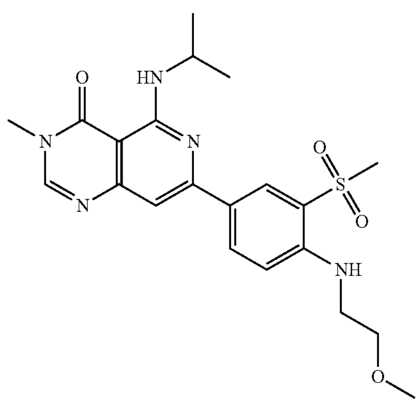 | ESI-MS m/z 446.2 (MH$^+$) | 0.114 |
| 6 | 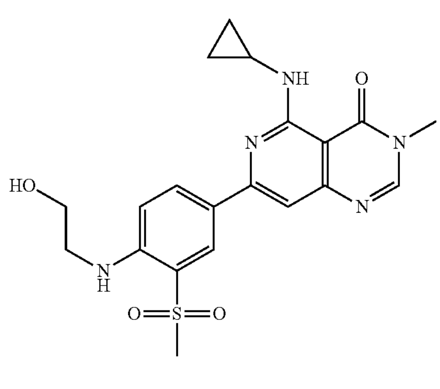 [SMILES: Cn1cnc2cc(-c3ccc(NCCO)c(S(C)(=O)=O)c3)nc(NC3CC3)c2c1=O] | ESI-MS m/z 430.2 (MH$^+$) | 0.114 |

TABLE 1-continued

| Compound Number | Structure | Physical Data <br> ¹H NMR 400 MHz (CDCl₃), HPLC Retention Time, and/or MS (m/z) | Syk Enzyme IC$_{50}$ (uM) |
| --- | --- | --- | --- |
| 7 | 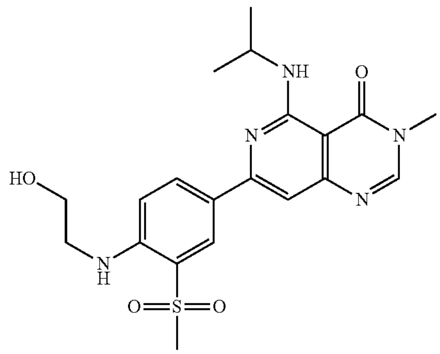 [SMILES: CC(C)Nc1nc(-c2ccc(NCCO)c(S(C)(=O)=O)c2)cc2ncn(C)c(=O)c12] | ESI-MS m/z 432.2 (MH⁺) | 0.114 |
| 8 | 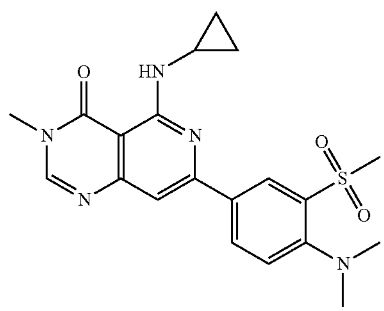 | ESI-MS m/z 414.2 (MH⁺) | 0.114 |
| 9 | 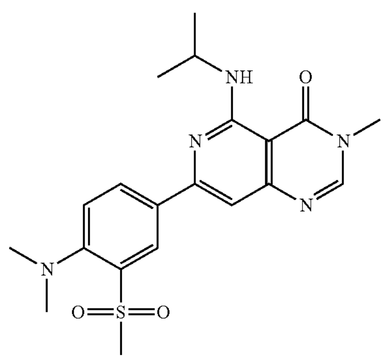 | ESI-MS m/z 416.2 (MH⁺) | 0.204 |
| 10 | 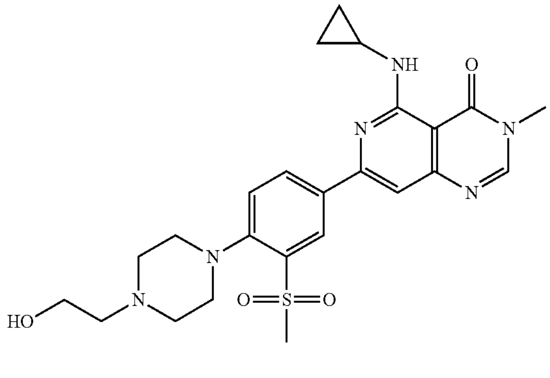 [SMILES: Cn1cnc2cc(-c3ccc(N4CCN(CCO)CC4)c(S(C)(=O)=O)c3)nc(NC3CC3)c2c1=O] | ESI-MS m/z 499.2 (MH⁺) | 0.085 |

TABLE 1-continued
| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 11 | 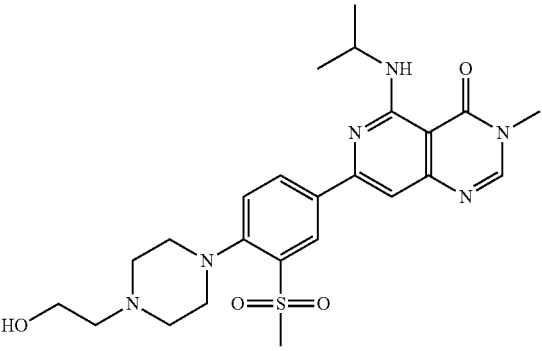 [SMILES: CC(C)Nc1nc(-c2ccc(N3CCN(CCO)CC3)c(S(C)(=O)=O)c2)cc2ncn(C)c(=O)c12] | ESI-MS m/z 501.2 (MH⁺) | 0.052 |
| 12 | 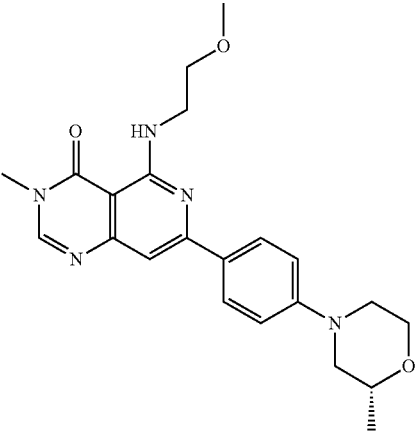 [SMILES: COCCNc1nc(-c2ccc(N3CCO[C@H](C)C3)cc2)cc2ncn(C)c(=O)c12] | ESI-MS m/z 410.2 (MH⁺) | 0.17 |
| 13 | 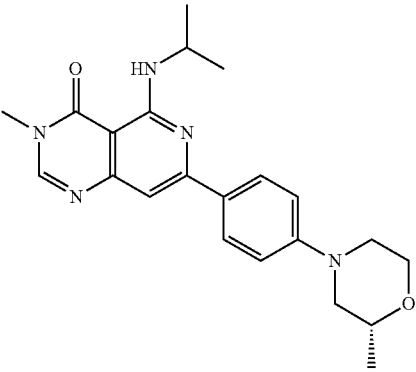 [SMILES: CC(C)Nc1nc(-c2ccc(N3CCO[C@H](C)C3)cc2)cc2ncn(C)c(=O)c12] | ESI-MS m/z 394.2 (MH⁺) | 0.581 |
| 14 | 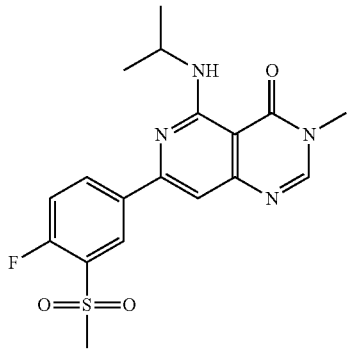 [SMILES: CC(C)Nc1nc(-c2ccc(F)c(S(C)(=O)=O)c2)cc2ncn(C)c(=O)c12] | ESI-MS m/z 391.2 (MH⁺) | 0.572 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
| --- | --- | --- | --- |
| 15 | 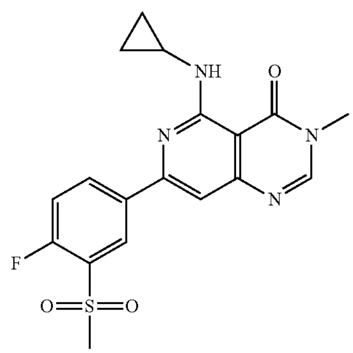 [SMILES: Cn1cnc2cc(-c3ccc(F)c(S(C)(=O)=O)c3)nc(NC3CC3)c2c1=O] | ESI-MS m/z 389.2 (MH⁺) | 0.533 |
| 16 | 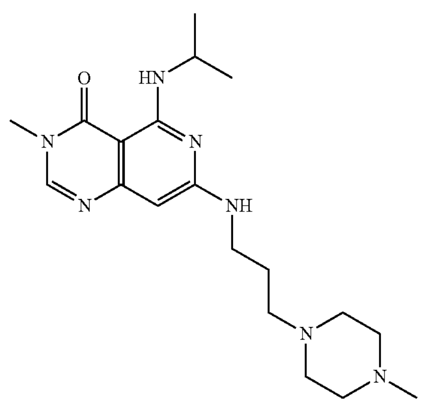 | ESI-MS m/z 374.2 (MH⁺) | 1.86 |
| 17 | 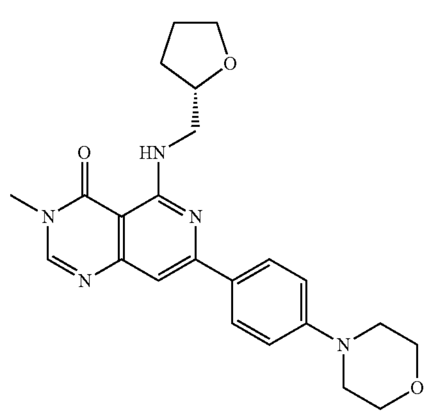 [SMILES: Cn1cnc2cc(-c3ccc(N4CCOCC4)cc3)nc(NC[C@@H]3CCCO3)c2c1=O] | ESI-MS m/z 422.2 (MH⁺) | 0.411 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 18 | 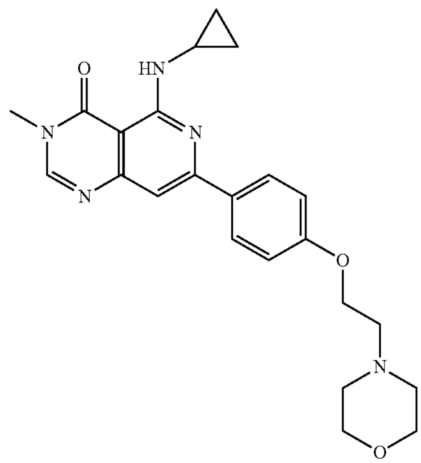 [SMILES: Cn1cnc2cc(-c3ccc(OCCN4CCOCC4)cc3)nc(NC3CC3)c2c1=O] | ESI-MS m/z 422.2 (MH$^+$) | 0.273 |
| 19 | 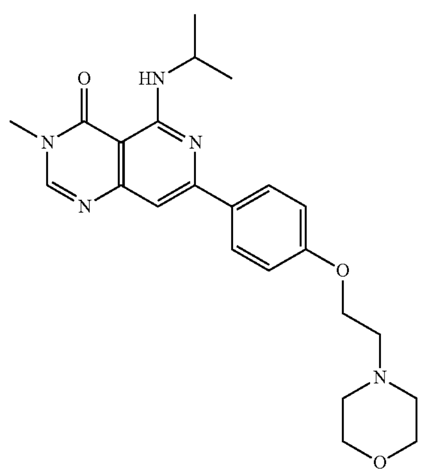 [SMILES: CC(C)Nc1nc(-c2ccc(OCCN3CCOCC3)cc2)cc2ncn(C)c(=O)c12] | ESI-MS m/z 424.2 (MH$^+$) | 0.44 |
| 20 | 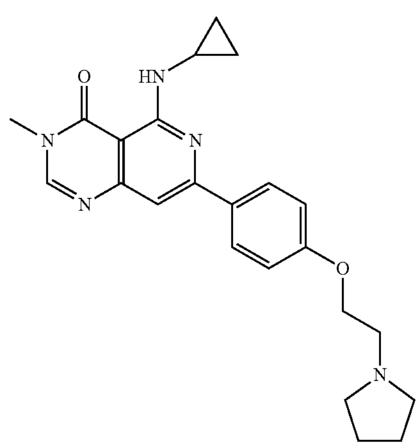 [SMILES: Cn1cnc2cc(-c3ccc(OCCN4CCCC4)cc3)nc(NC3CC3)c2c1=O] | ESI-MS m/z 406.2 (MH$^+$) | 0.14 |

TABLE 1-continued
| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 21 | 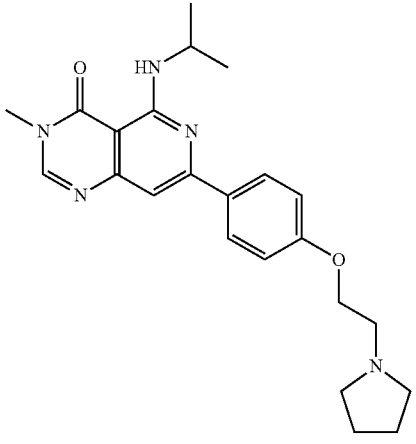 | ESI-MS m/z 424.2 (MH$^+$), $^1$H NMR (DMSO-d$_6$) δ 10.85 (s, 1H), 8.72 (s, 1H), 8.51 (s, 1H), 8.13 (d, J = 8.8 Hz, 2H), 7.13 (d, J = 8.8 Hz, 2H), 4.34 (m, 4H), 3.60 (m, 4H), 3.44 (s, 3H), 3.11 (m, 2H), 1.95 (m, 4H), 1.29 (d, J = 6.4 Hz, 6H) | 0.115 |
| 22 | 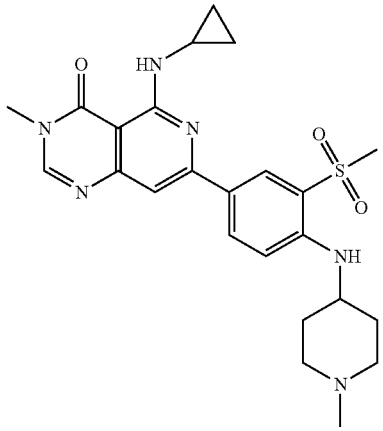 | ESI-MS m/z 483.2 (MH$^+$) | 0.03 |
| 23 | 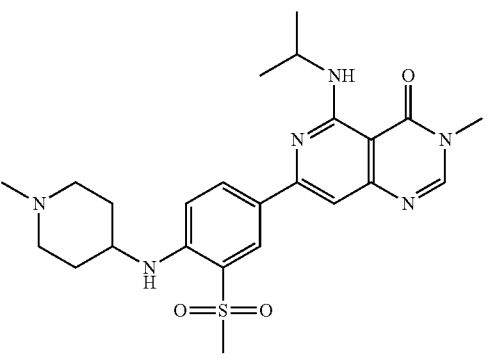 | ESI-MS m/z 485.2 (MH$^+$) | 0.027 |
| 24 | 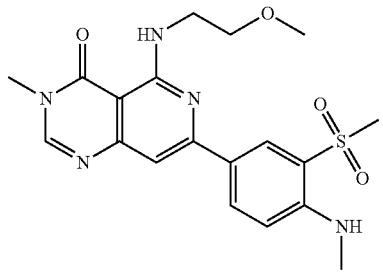 | ESI-MS m/z 418.2 (MH$^+$), $^1$H NMR (DMSO-d$_6$) δ 8.91 (t, J = 5.2 Hz, 1H), 8.45 (d, J = 2.4 Hz, 1H), 8.40 (s, 1H), 8.27 (d, J = 8.8 Hz, 1H), 7.06 (s, 1H), 6.90 (d, J = 8.8 Hz, 1H), 6.50 (m, 1H), 3.76 (m, 2H), 3.61 (t, J = 5.6 Hz, 2H), 3.43 (s, 3H), 3.33 (s, 3H), 3.19 (s, 3H), 2.91 (d, J = 4.8 Hz, 3H) | 0.076 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
| --- | --- | --- | --- |
| 25 | 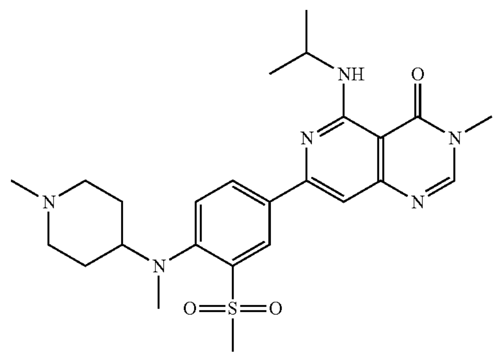 | ESI-MS m/z 499.2 (MH⁺) | 0.076 |
| 26 | 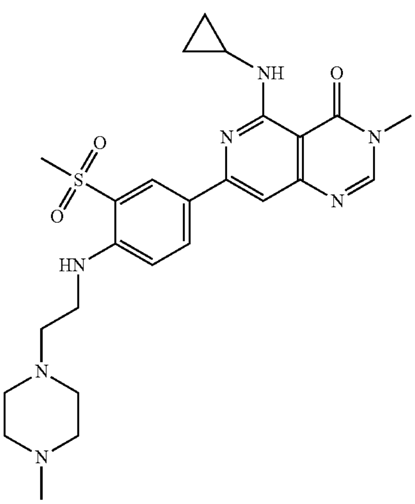 [SMILES: CN1CCN(CCNc2ccc(-c3cc4ncn(C)c(=O)c4c(NC4CC4)n3)cc2S(C)(=O)=O)CC1] | ESI-MS m/z 512.3 (MH⁺) | 0.06 |
| 27 | 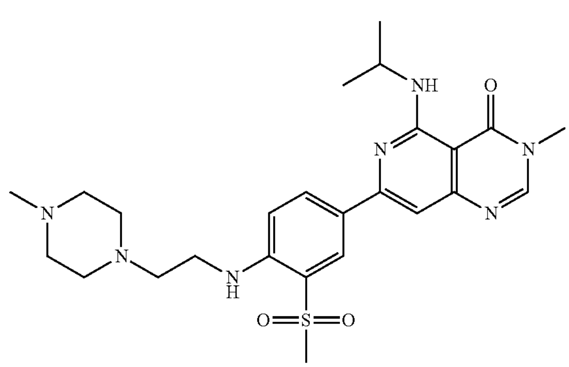 | ESI-MS m/z 514.3 (MH⁺) | 0.054 |

TABLE 1-continued
| Compound Number | Structure | Physical Data<br>$^1$H NMR 400 MHz (CDCl$_3$),<br>HPLC Retention Time, and/or<br>MS (m/z) | Syk Enzyme IC$_{50}$ (uM) |
|---|---|---|---|
| 28 | 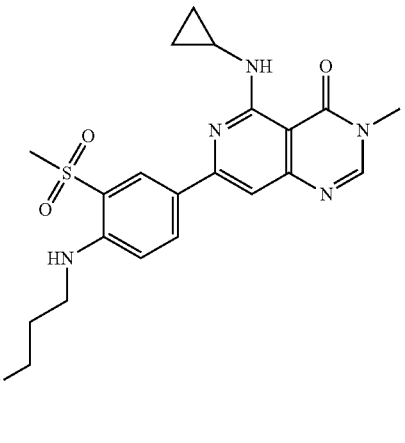 | ESI-MS m/z 526.3 (MH$^+$) | 0.084 |
| 29 | 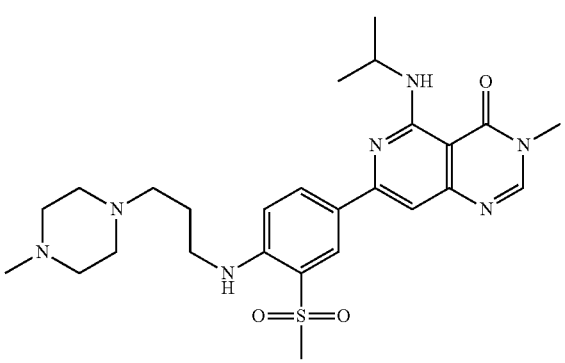 | ESI-MS m/z 528.3 (MH$^+$) | 0.122 |
| 30 | 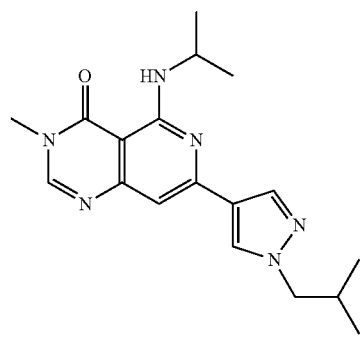 [SMILES: CC(C)Cn1cc(-c2cc3ncn(C)c(=O)c3c(NC(C)C)n2)cn1] | ESI-MS m/z 341.2 (MH$^+$) | 0.359 |
| 31 | 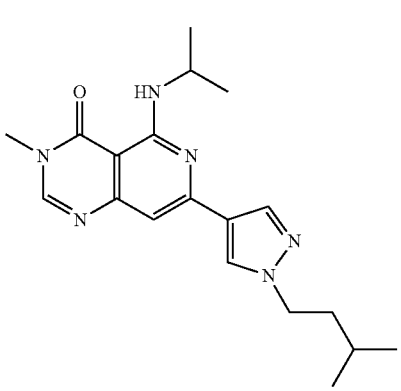 [SMILES: CC(C)CCn1cc(-c2cc3ncn(C)c(=O)c3c(NC(C)C)n2)cn1] | ESI-MS m/z 355.2 (MH$^+$) | 0.595 |

TABLE 1-continued

| Compound Number | Structure | Physical Data <br> $^1$H NMR 400 MHz (CDCl$_3$), HPLC Retention Time, and/or MS (m/z) | Syk Enzyme IC$_{50}$ (uM) |
| --- | --- | --- | --- |
| 32 | 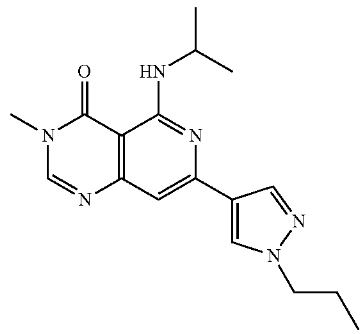 [SMILES: CCCn1cc(-c2cc3ncn(C)c(=O)c3c(NC(C)C)n2)cn1] | ESI-MS m/z 327.2 (MH$^+$) | 0.123 |
| 33 | 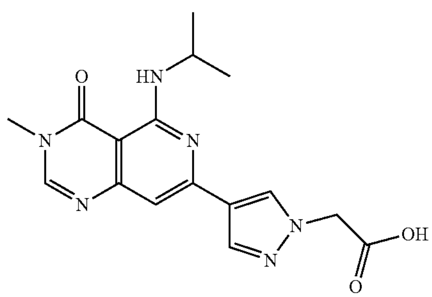 [SMILES: CC(C)Nc1nc(-c2cnn(CC(=O)O)c2)cc2ncn(C)c(=O)c12] | ESI-MS m/z 343.2 (MH$^+$) | 0.159 |
| 34 | 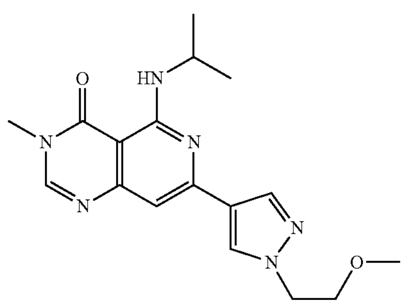 | ESI-MS m/z 343.2 (MH$^+$) | 0.136 |
| 35 | 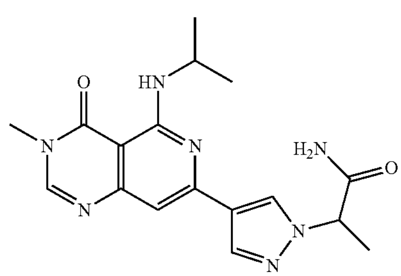 [SMILES: CC(C)Nc1nc(-c2cnn(C(C)C(N)=O)c2)cc2ncn(C)c(=O)c12] | ESI-MS m/z 356.2 (MH$^+$) | 0.133 |
| 36 | 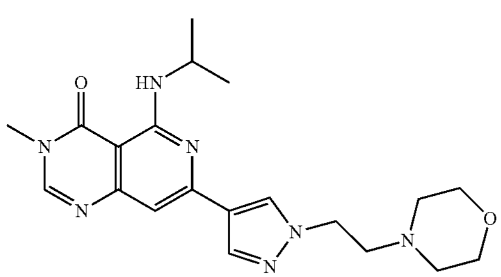 [SMILES: CC(C)Nc1nc(-c2cnn(CCN3CCOCC3)c2)cc2ncn(C)c(=O)c12] | ESI-MS m/z 398.2 (MH$^+$) | 0.2 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 37 | 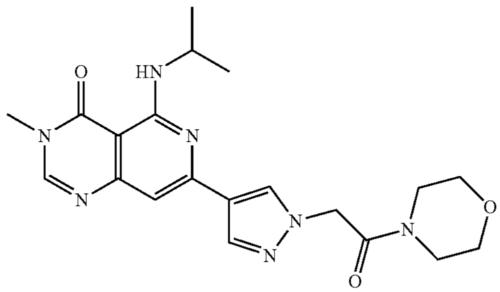 [SMILES: CC(C)Nc1nc(-c2cnn(CC(=O)N3CCOCC3)c2)cc2ncn(C)c(=O)c12] | ESI-MS m/z 412.2 (MH⁺) | 0.101 |
| 38 | 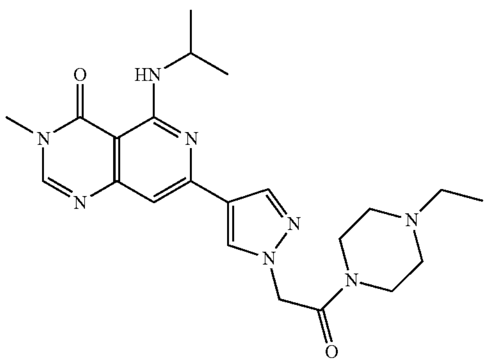 [SMILES: CCN1CCN(C(=O)Cn2cc(-c3cc4ncn(C)c(=O)c4c(NC(C)C)n3)cn2)CC1] | ESI-MS m/z 439.2 (MH⁺) | 0.167 |
| 39 | 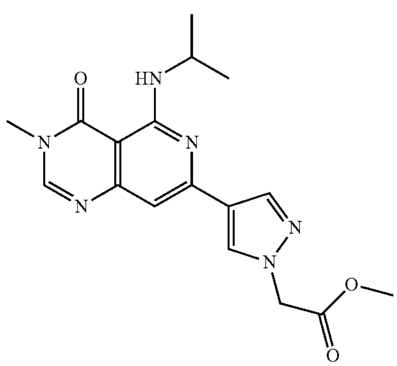 | ESI-MS m/z 357.2 (MH⁺) | 0.124 |
| 40 | 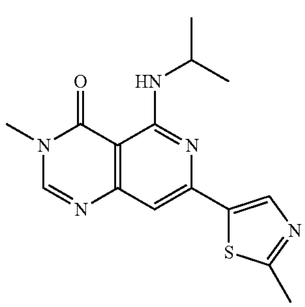 [SMILES: Cc1ncc(-c2cc3ncn(C)c(=O)c3c(NC(C)C)n2)s1] | ESI-MS m/z 316.2 (MH⁺) | 0.565 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 41 | 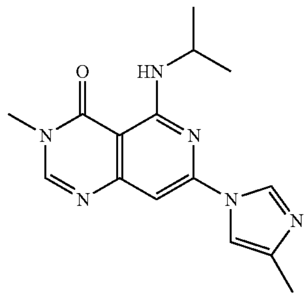 [SMILES: Cc1cn(-c2cc3ncn(C)c(=O)c3c(NC(C)C)n2)cn1] | ESI-MS m/z 299.2 (MH⁺) | 0.683 |
| 42 | 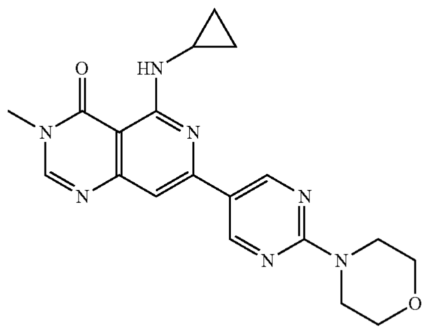 [SMILES: Cn1cnc2cc(-c3cnc(N4CCOCC4)nc3)nc(NC3CC3)c2c1=O] | ESI-MS m/z 380.2 (MH⁺) | 1.347 |
| 43 | 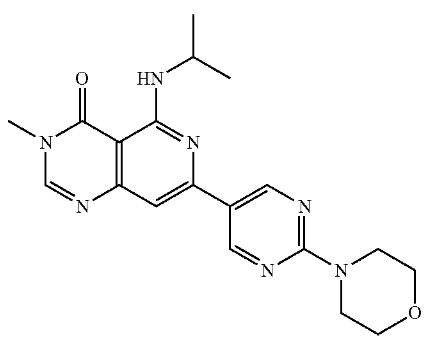 [SMILES: CC(C)Nc1nc(-c2cnc(N3CCOCC3)nc2)cc2ncn(C)c(=O)c12] | ESI-MS m/z 382.2 (MH⁺) | 1.042 |
| 44 | 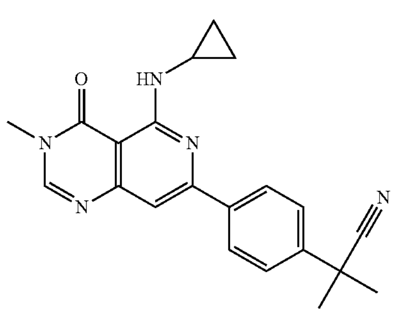 [SMILES: Cn1cnc2cc(-c3ccc(C(C)(C)C#N)cc3)nc(NC3CC3)c2c1=O] | ESI-MS m/z 360.2 (MH⁺) | 0.454 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 45 | 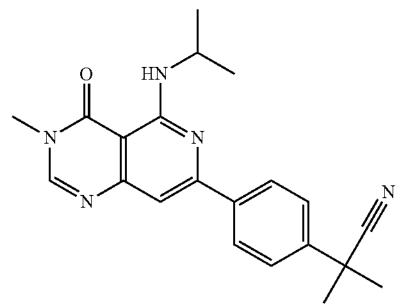 [SMILES: CC(C)Nc1nc(-c2ccc(C(C)(C)C#N)cc2)cc2ncn(C)c(=O)c12] | ESI-MS m/z 362.2 (MH$^+$) | 0.82 |
| 46 | 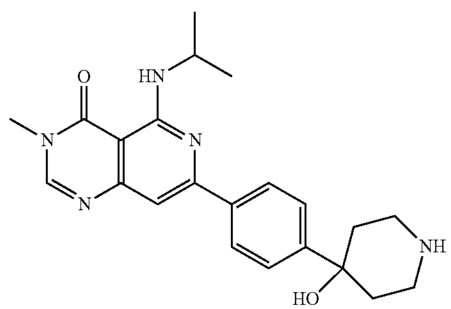 [SMILES: CC(C)Nc1nc(-c2ccc(C3(O)CCNCC3)cc2)cc2ncn(C)c(=O)c12] | ESI-MS m/z 394.2 (MH$^+$) | 0.065 |
| 47 | 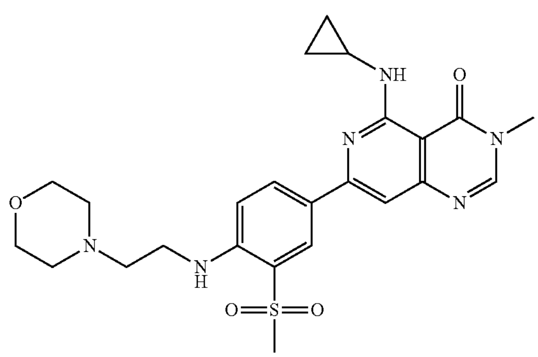 [SMILES: Cn1cnc2cc(-c3ccc(NCCN4CCOCC4)c(S(C)(=O)=O)c3)nc(NC3CC3)c2c1=O] | ESI-MS m/z 499.2 (MH$^+$) | 0.094 |
| 48 | 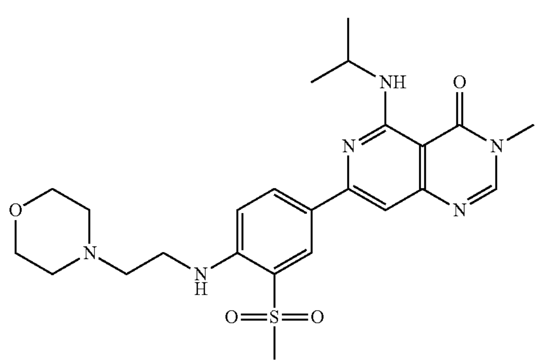 [SMILES: CC(C)Nc1nc(-c2ccc(NCCN3CCOCC3)c(S(C)(=O)=O)c2)cc2ncn(C)c(=O)c12] | ESI-MS m/z 501.2 (MH$^+$), $^1$H NMR (DMSO-d$_6$) δ 8.71 (d, J = 7.2 Hz, 1H), 8.46 (d, J = 2.4 HZ, 1H), 8.40 (s, 1H), 8.26 (d, J = 8.8 Hz, 1H), 7.04 (s, 1H), 6.97 (d, J = 8.8 Hz, 1H), 6.77 (t, J = 4.8 Hz, 1H), 3.59 (m, 4H), 3.42 (s, 3H), 3.33 (m, 4H), 3.20 (s, 3H), 2.62 (m, 2H), 2.44 (s, 3H), 1.29 (d, J = 6.4 Hz, 6H). | 0.111 |

TABLE 1-continued
| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 49 | 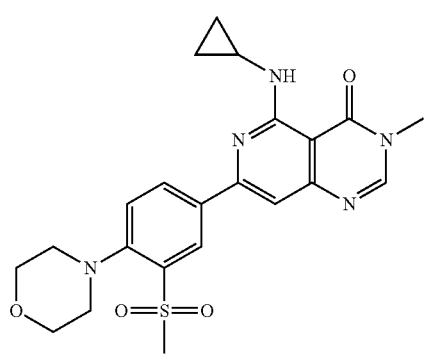 [SMILES: Cn1cnc2cc(-c3ccc(N4CCOCC4)c(S(C)(=O)=O)c3)nc(NC3CC3)c2c1=O] | ESI-MS m/z 456.2 (MH⁺) | 0.103 |
| 50 | 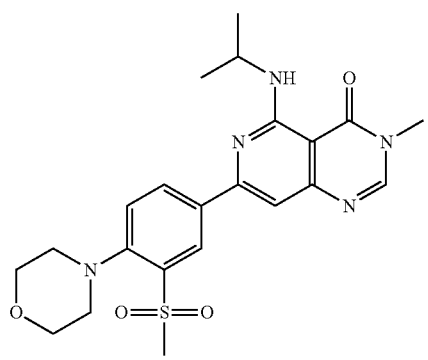 [SMILES: CC(C)Nc1nc(-c2ccc(N3CCOCC3)c(S(C)(=O)=O)c2)cc2ncn(C)c(=O)c12] | ESI-MS m/z 458.2 (MH⁺) | 0.18 |
| 51 | 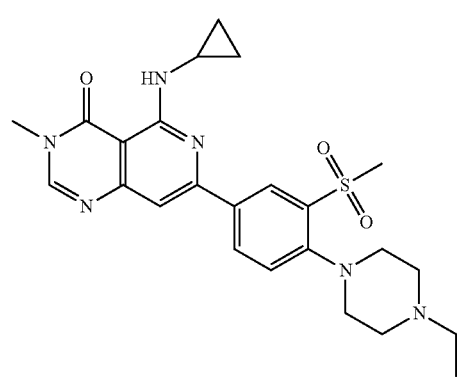 [SMILES: CCN1CCN(c2ccc(-c3cc4ncn(C)c(=O)c4c(NC4CC4)n3)cc2S(C)(=O)=O)CC1] | ESI-MS m/z 483.2 (MH⁺) | 0.056 |
| 52 | 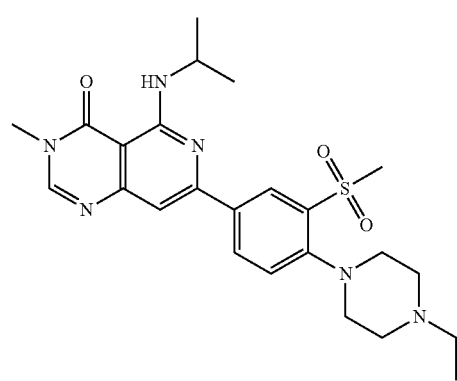 [SMILES: CCN1CCN(c2ccc(-c3cc4ncn(C)c(=O)c4c(NC(C)C)n3)cc2S(C)(=O)=O)CC1] | ESI-MS m/z 485.2 (MH⁺) | 0.102 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 53 | 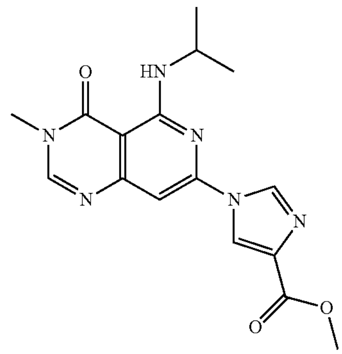 | ESI-MS m/z 343.2 (MH⁺) | 0.665 |
| 54 | 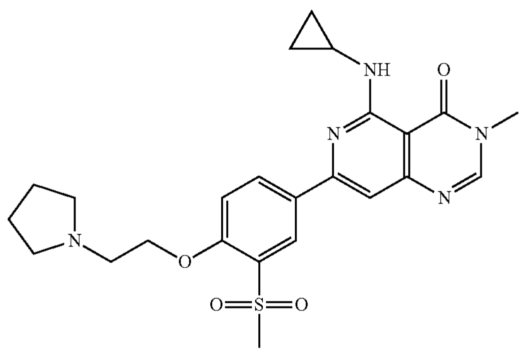 [SMILES: Cn1cnc2cc(-c3ccc(OCCN4CCCC4)c(S(C)(=O)=O)c3)nc(NC3CC3)c2c1=O] | ESI-MS m/z 484.2 (MH⁺) | 0.084 |
| 55 | 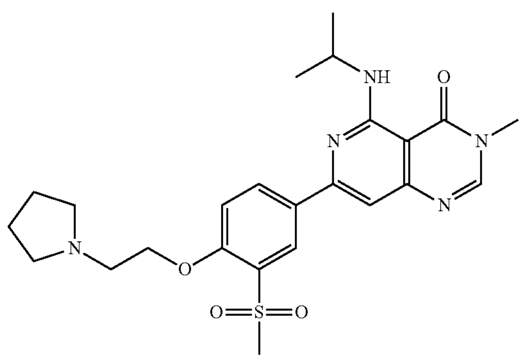 [SMILES: CC(C)Nc1nc(-c2ccc(OCCN3CCCC3)c(S(C)(=O)=O)c2)cc2ncn(C)c(=O)c12] | ESI-MS m/z 486.2 (MH⁺) | 0.065 |
| 56 | 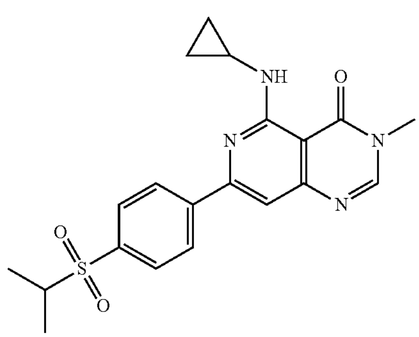 [SMILES: CC(C)S(=O)(=O)c1ccc(-c2cc3ncn(C)c(=O)c3c(NC3CC3)n2)cc1] | ESI-MS m/z 399.2 (MH⁺) | 0.351 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 57 | 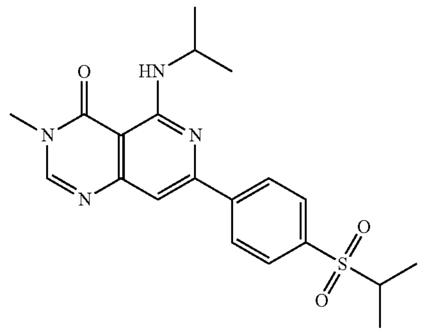 [SMILES: CC(C)Nc1nc(-c2ccc(S(=O)(=O)C(C)C)cc2)cc2ncn(C)c(=O)c12] | ESI-MS m/z 401.2 (MH⁺) | 1.103 |
| 58 | 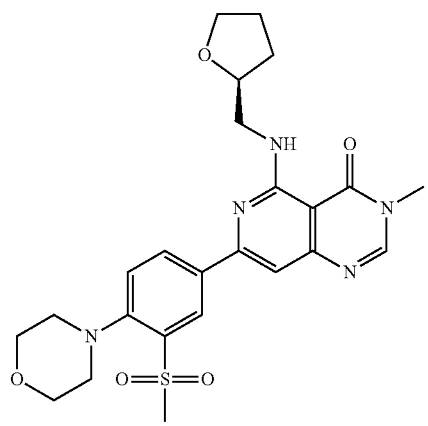 [SMILES: Cn1cnc2cc(-c3ccc(N4CCOCC4)c(S(C)(=O)=O)c3)nc(NC[C@@H]3CCCO3)c2c1=O] | ESI-MS m/z 500.2 (MH⁺) | 0.141 |
| 59 | 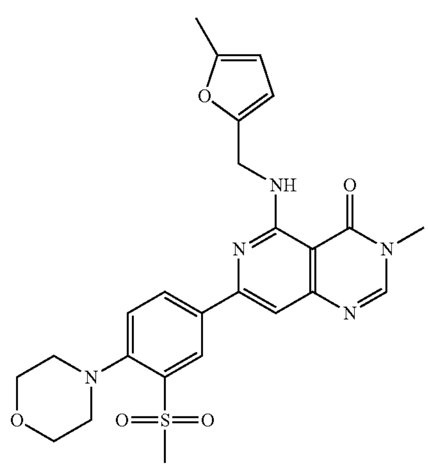 [SMILES: Cc1ccc(CNc2nc(-c3ccc(N4CCOCC4)c(S(C)(=O)=O)c3)cc3ncn(C)c(=O)c23)o1] | ESI-MS m/z 510.3 (MH⁺) | 0.496 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 60 | 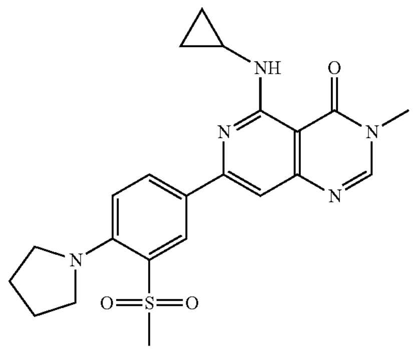 [SMILES: Cn1cnc2cc(-c3ccc(N4CCCC4)c(S(C)(=O)=O)c3)nc(NC3CC3)c2c1=O] | ESI-MS m/z 440.2 (MH⁺) | 0.098 |
| 61 | 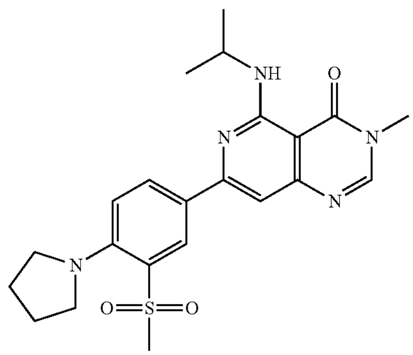 [SMILES: CC(C)Nc1nc(-c2ccc(N3CCCC3)c(S(C)(=O)=O)c2)cc2ncn(C)c(=O)c12] | ESI-MS m/z 442.2 (MH⁺) | 0.213 |
| 62 | 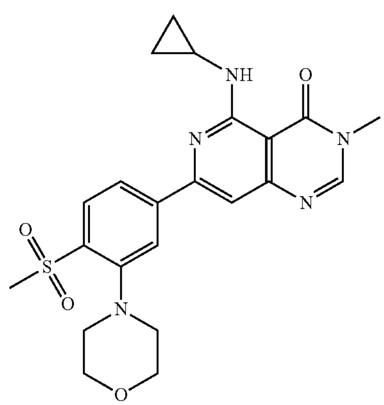 | ESI-MS m/z 456.2 (MH⁺) | 0.559 |
| 63 | 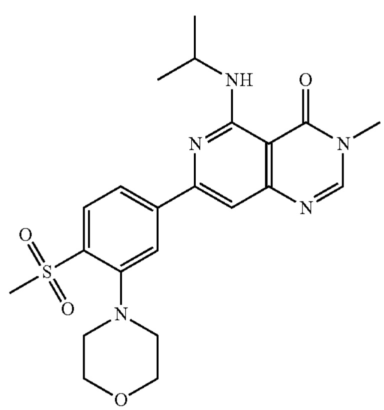 | ESI-MS m/z 458.2 (MH⁺) | 0.751 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 64 | 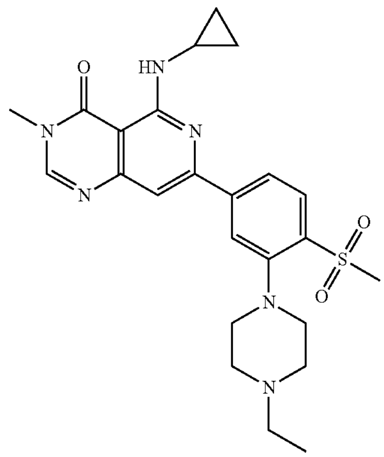 | ESI-MS m/z 483.2 (MH⁺) | 0.696 |
| 65 | 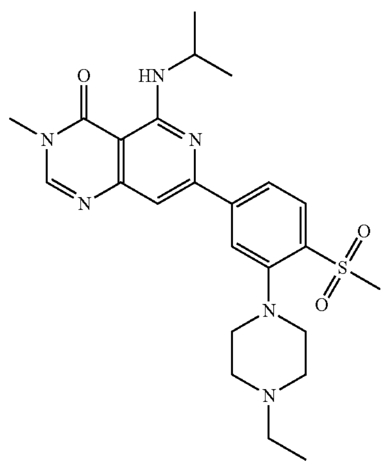 | ESI-MS m/z 485.2 (MH⁺) | 0.304 |
| 66 | 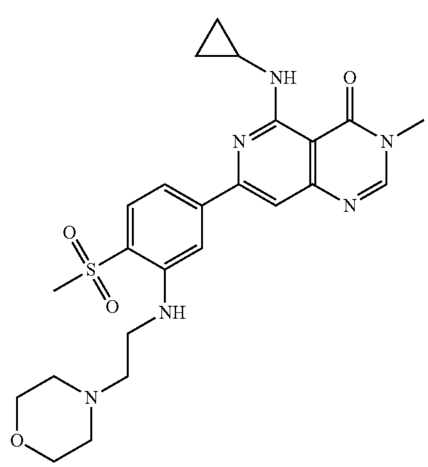 [SMILES: Cn1cnc2cc(-c3ccc(S(C)(=O)=O)c(NCCN4CCOCC4)c3)nc(NC3CC3)c2c1=O] | ESI-MS m/z 499.2 (MH⁺) | 0.643 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
| --- | --- | --- | --- |
| 67 | 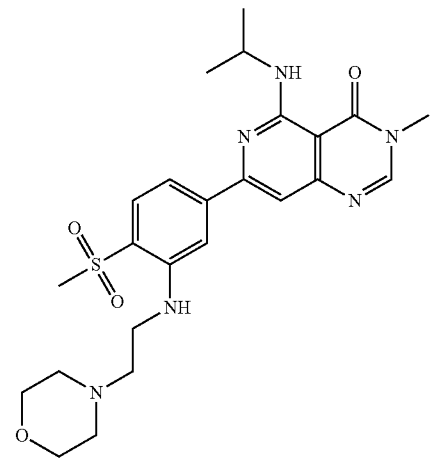 [SMILES: CC(C)Nc1nc(-c2ccc(S(C)(=O)=O)c(NCCN3CCOCC3)c2)cc2ncn(C)c(=O)c12] | ESI-MS m/z 501.2 (MH$^+$) | 1.677 |
| 68 | 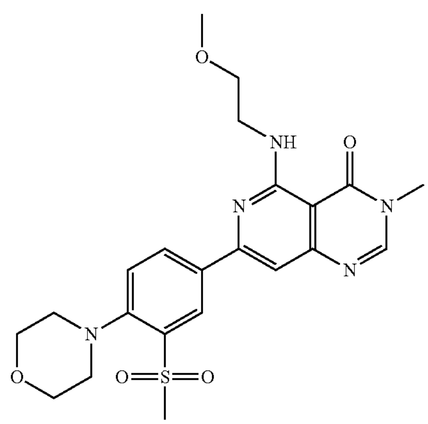 [SMILES: COCCNc1nc(-c2ccc(N3CCOCC3)c(S(C)(=O)=O)c2)cc2ncn(C)c(=O)c12] | ESI-MS m/z 474.2 (MH$^+$) | 0.056 |
| 69 | 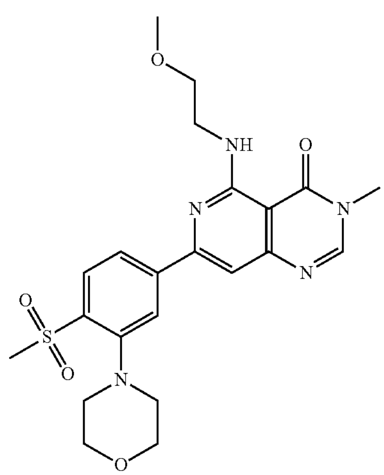 | ESI-MS m/z 474.2 (MH$^+$) | 0.227 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 70 | 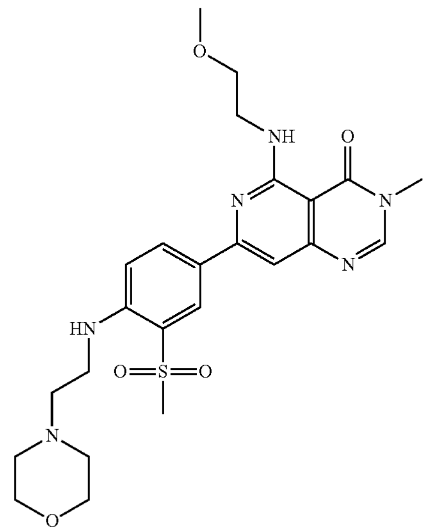 [SMILES: COCCNc1nc(-c2ccc(NCCN3CCOCC3)c(S(C)(=O)=O)c2)cc2ncn(C)c(=O)c12] | ESI-MS m/z 517.3 (MH⁺) | 0.026 |
| 71 | 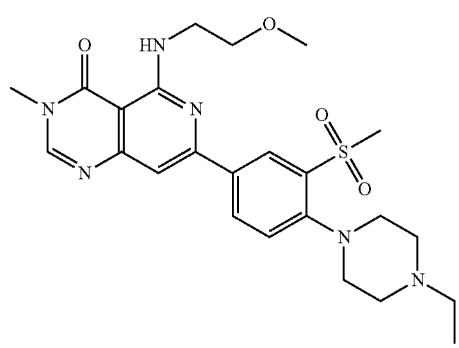 [SMILES: CCN1CCN(c2ccc(-c3cc4ncn(C)c(=O)c4c(NCCOC)n3)cc2S(C)(=O)=O)CC1] | ESI-MS m/z 501.2 (MH⁺) | 0.065 |
| 72 | 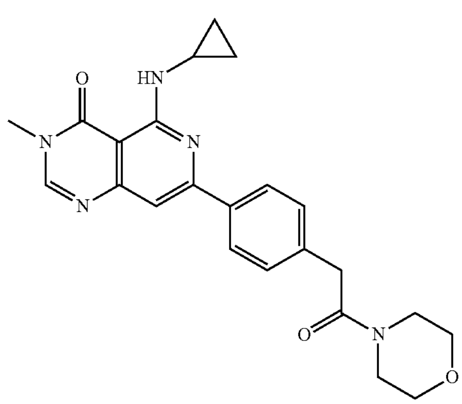 [SMILES: Cn1cnc2cc(-c3ccc(CC(=O)N4CCOCC4)cc3)nc(NC3CC3)c2c1=O] | ESI-MS m/z 420.2 (MH⁺) | 0.153 |

TABLE 1-continued

| Compound Number | Structure | Physical Data <br> ¹H NMR 400 MHz (CDCl₃), HPLC Retention Time, and/or MS (m/z) | Syk Enzyme IC$_{50}$ (uM) |
| --- | --- | --- | --- |
| 73 | 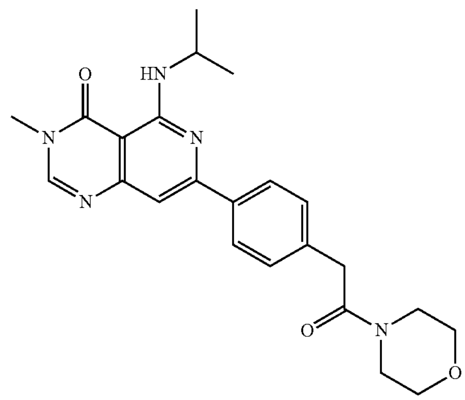 [SMILES: CC(C)Nc1nc(-c2ccc(CC(=O)N3CCOCC3)cc2)cc2ncn(C)c(=O)c12] | ESI-MS m/z 422.2 (MH⁺) | 0.136 |
| 74 | 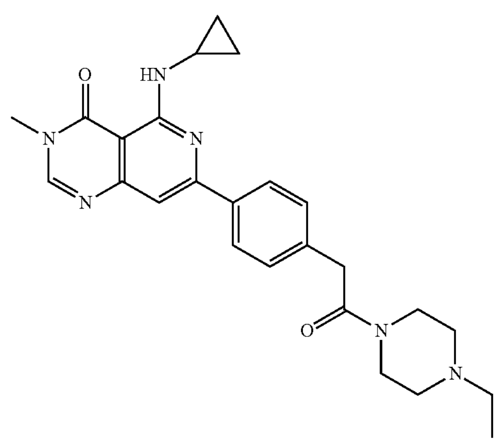 [SMILES: CCN1CCN(C(=O)Cc2ccc(-c3cc4ncn(C)c(=O)c4c(NC4CC4)n3)cc2)CC1] | ESI-MS m/z 447.2 (MH⁺) | 0.278 |
| 75 | 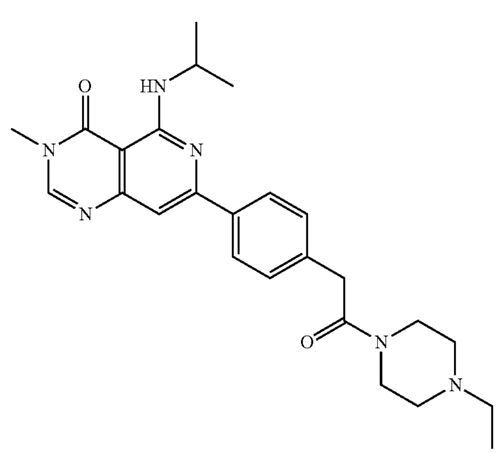 [SMILES: CCN1CCN(C(=O)Cc2ccc(-c3cc4ncn(C)c(=O)c4c(NC(C)C)n3)cc2)CC1] | ESI-MS m/z 449.2 (MH⁺) | 0.25 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 76 | 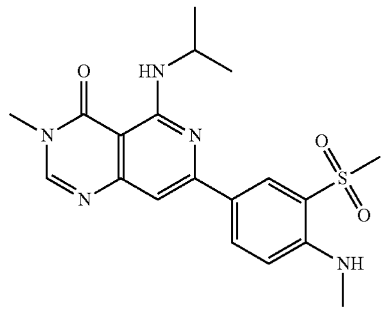 | ESI-MS m/z 402.2 (MH⁺) | 0.14 |
| 77 | 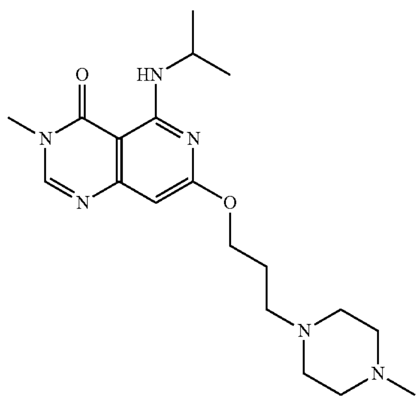 | ESI-MS m/z 374.2 (MH⁺) | 4.09 |
| 78 | 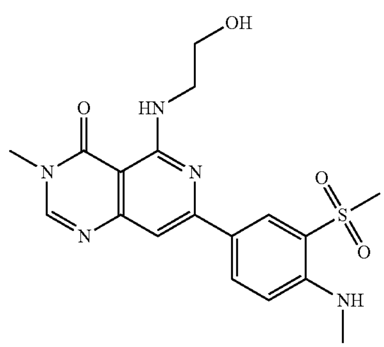 | ESI-MS m/z 404.2 (MH⁺) | 0.067 |
| 79 | 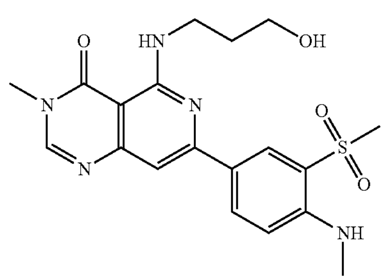 | ESI-MS m/z 418.2 (MH⁺) | 0.053 |

TABLE 1-continued

| Compound Number | Structure | Physical Data <sup>1</sup>H NMR 400 MHz (CDCl$_3$), HPLC Retention Time, and/or MS (m/z) | Syk Enzyme IC$_{50}$ (uM) |
|---|---|---|---|
| 80 | 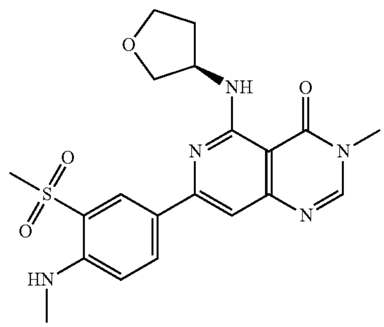 | ESI-MS m/z 430.2 (MH$^+$) | 0.021 |
| 81 | 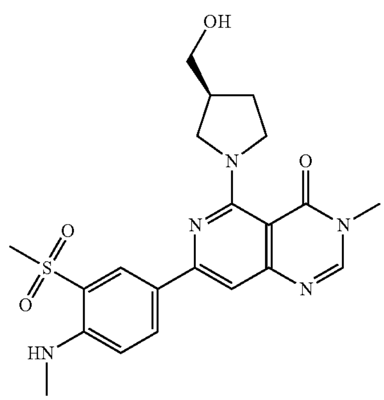 | ESI-MS m/z 444.2 (MH$^+$) | 0.126 |
| 82 | 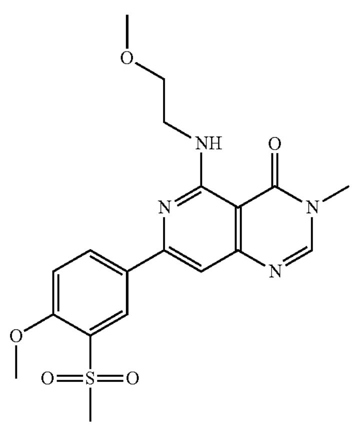 [SMILES: COCCNc1nc(-c2ccc(OC)c(S(C)(=O)=O)c2)cc2ncn(C)c(=O)c12] | ESI-MS m/z 419.2 (MH$^+$) | 0.196 |
| 83 | 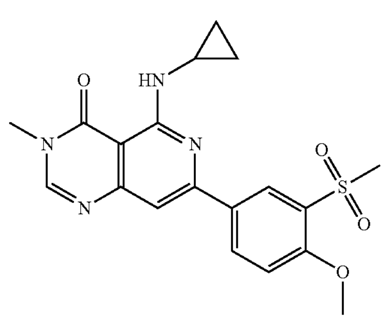 | ESI-MS m/z 401.2 (MH$^+$) | 0.181 |

TABLE 1-continued

| Compound Number | Structure | Physical Data <br> ¹H NMR 400 MHz (CDCl₃), HPLC Retention Time, and/or MS (m/z) | Syk Enzyme IC₅₀ (uM) |
| --- | --- | --- | --- |
| 84 | 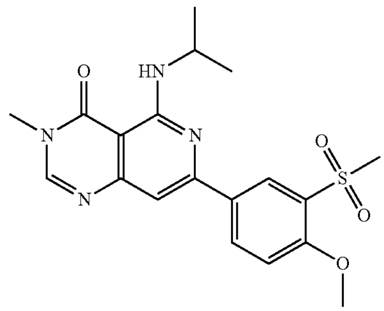 | ESI-MS m/z 403.2 (MH⁺) | 0.272 |
| 85 | 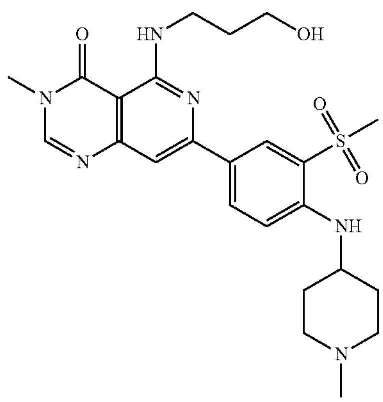 [SMILES: CN1CCC(Nc2ccc(-c3cc4ncn(C)c(=O)c4c(NCCCO)n3)cc2S(C)(=O)=O)CC1] | ESI-MS m/z 501.2 (MH⁺) | 0.064 |
| 86 | 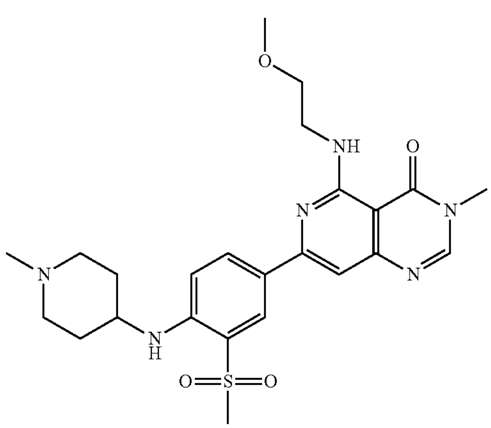 | ESI-MS m/z 501.2 (MH⁺) | 0.045 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
| --- | --- | --- | --- |
| 87 | 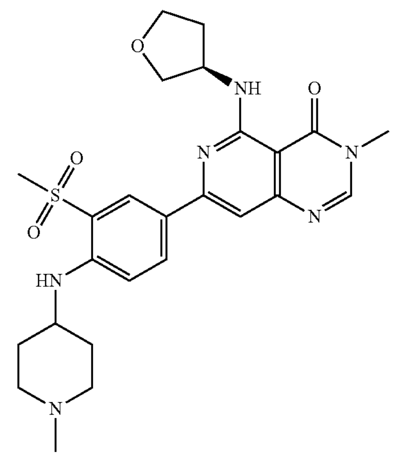 [SMILES: CN1CCC(Nc2ccc(-c3cc4ncn(C)c(=O)c4c(N[C@@H]4CCOC4)n3)cc2S(C)(=O)=O)CC1] | ESI-MS m/z 513.2 (MH⁺) | 0.011 |
| 88 | 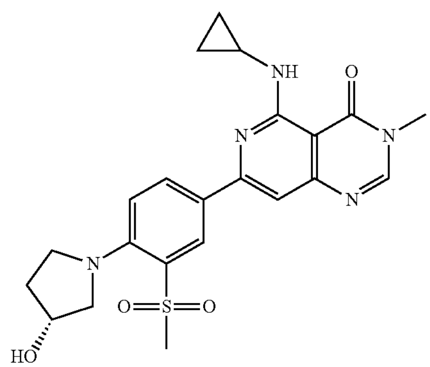 [SMILES: Cn1cnc2cc(-c3ccc(N4CC[C@@H](O)C4)c(S(C)(=O)=O)c3)nc(NC3CC3)c2c1=O] | ESI-MS m/z 456.2 (MH⁺) | 0.123 |
| 89 | 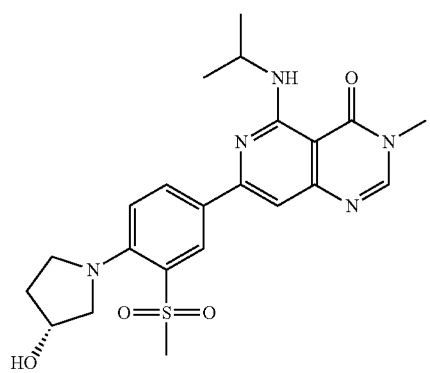 [SMILES: CC(C)Nc1nc(-c2ccc(N3CC[C@@H](O)C3)c(S(C)(=O)=O)c2)cc2ncn(C)c(=O)c12] | ESI-MS m/z 458.2 (MH⁺) | 0.156 |
| 90 | 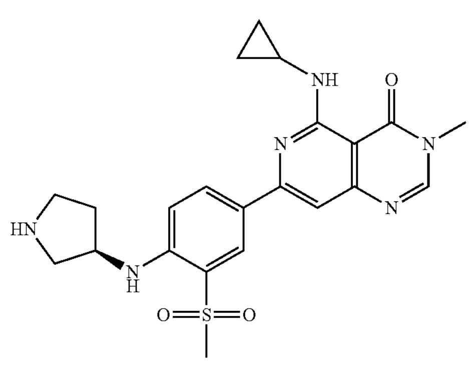 [SMILES: Cn1cnc2cc(-c3ccc(N[C@@H]4CCNC4)c(S(C)(=O)=O)c3)nc(NC3CC3)c2c1=O] | ESI-MS m/z 455.2 (MH⁺) | 0.051 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 91 | 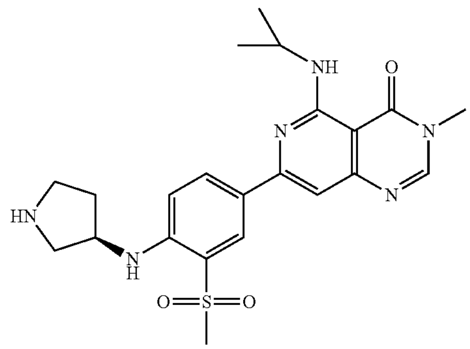 [SMILES: CC(C)Nc1nc(-c2ccc(N[C@@H]3CCNC3)c(S(C)(=O)=O)c2)cc2ncn(C)c(=O)c12] | ESI-MS m/z 457.2 (MH⁺) | 0.051 |
| 92 | 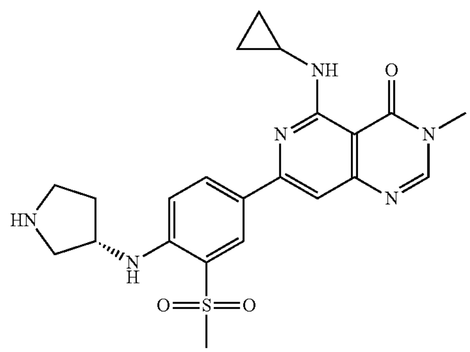 [SMILES: Cn1cnc2cc(-c3ccc(N[C@H]4CCNC4)c(S(C)(=O)=O)c3)nc(NC3CC3)c2c1=O] | ESI-MS m/z 455.2 (MH⁺) | 0.048 |
| 93 | 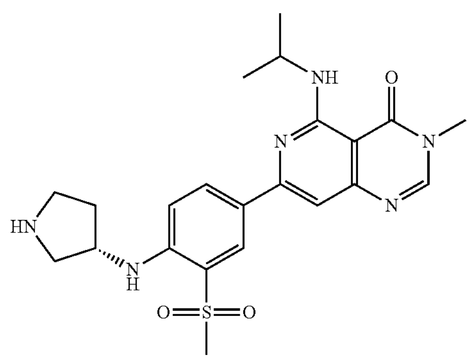 [SMILES: CC(C)Nc1nc(-c2ccc(N[C@H]3CCNC3)c(S(C)(=O)=O)c2)cc2ncn(C)c(=O)c12] | ESI-MS m/z 457.2 (MH⁺) | 0.034 |
| 94 | 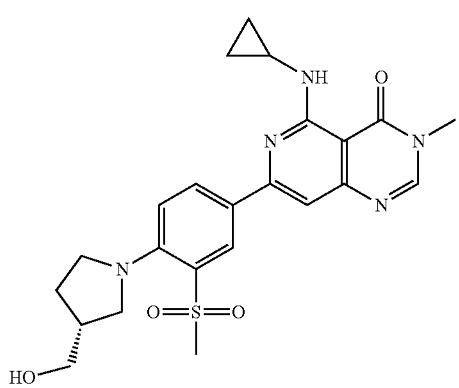 [SMILES: Cn1cnc2cc(-c3ccc(N4CC[C@@H](CO)C4)c(S(C)(=O)=O)c3)nc(NC3CC3)c2c1=O] | ESI-MS m/z 470.2 (MH⁺) | 0.187 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
| --- | --- | --- | --- |
| 95 | 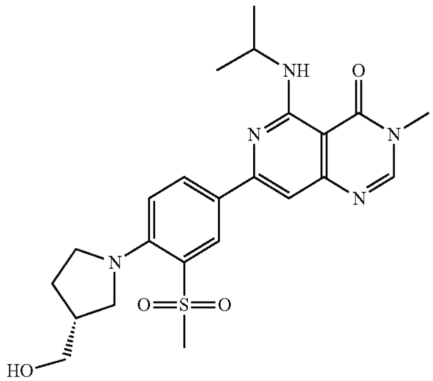 | ESI-MS m/z 472.2 (MH⁺) | 0.218 |
| 96 | 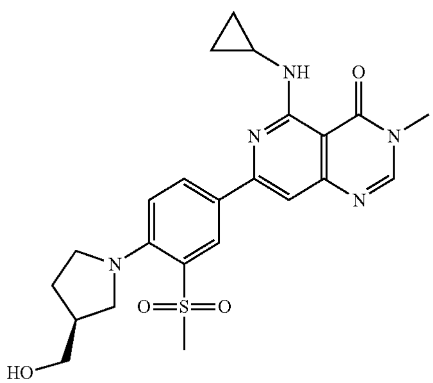 | ESI-MS m/z 470.2 (MH⁺) | 0.245 |
| 97 | 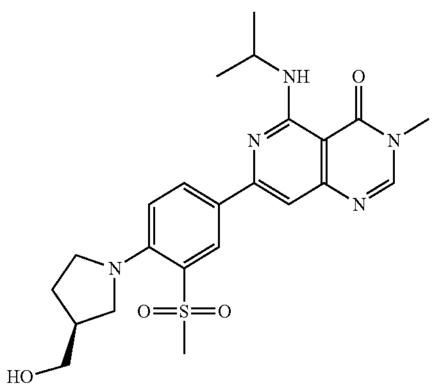 | ESI-MS m/z 472.2 (MH⁺) | 0.194 |
| 98 | 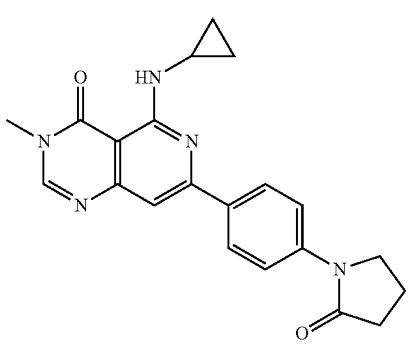 [SMILES: Cn1cnc2cc(-c3ccc(N4CCCC4=O)cc3)nc(NC3CC3)c2c1=O] | ESI-MS m/z 376.2 (MH⁺) | 0.646 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 99 | 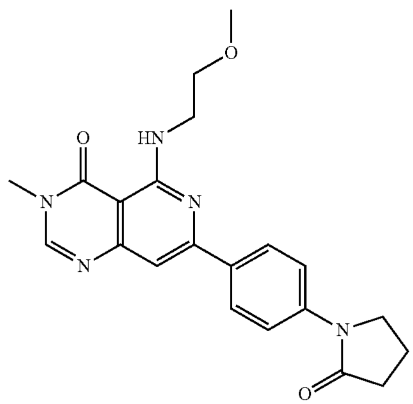 [SMILES: COCCNc1nc(-c2ccc(N3CCCC3=O)cc2)cc2ncn(C)c(=O)c12] | ESI-MS m/z 394.2 (MH⁺) | 0.797 |
| 100 | 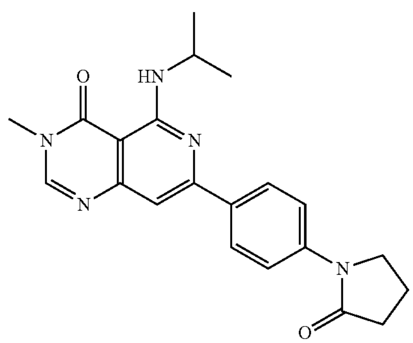 [SMILES: CC(C)Nc1nc(-c2ccc(N3CCCC3=O)cc2)cc2ncn(C)c(=O)c12] | ESI-MS m/z 378.2 (MH⁺) | 0.614 |
| 101 | 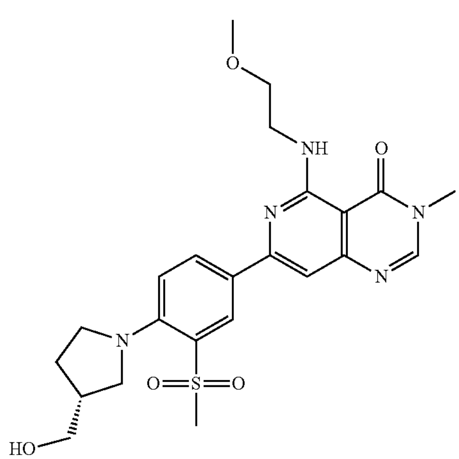 [SMILES: COCCNc1nc(-c2ccc(N3CC[C@@H](CO)C3)c(S(C)(=O)=O)c2)cc2ncn(C)c(=O)c12] | ESI-MS m/z 488.2 (MH⁺) | 0.097 |

TABLE 1-continued
| Compound Number | Structure | Physical Data<br>¹H NMR 400 MHz (CDCl₃), HPLC Retention Time, and/or MS (m/z) | Syk Enzyme IC₅₀ (uM) |
| --- | --- | --- | --- |
| 102 | 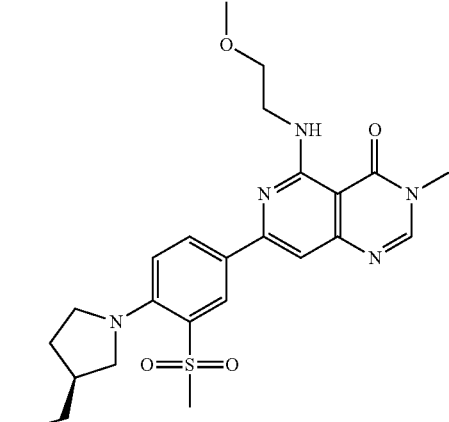 | ESI-MS m/z 488.2 (MH⁺) | 0.074 |
| 103 | 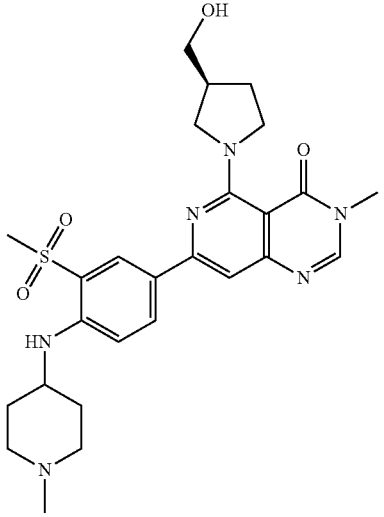 | ESI-MS m/z 527.3 (MH⁺) | 0.127 |
| 104 | 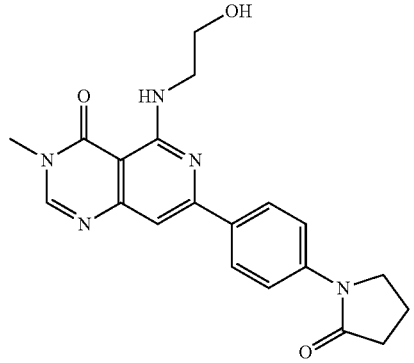 [SMILES: Cn1cnc2cc(-c3ccc(N4CCCC4=O)cc3)nc(NCCO)c2c1=O] | ESI-MS m/z 380.2 (MH⁺) | 0.586 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 105 | 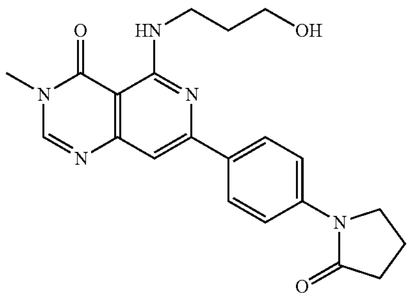 [SMILES: Cn1cnc2cc(-c3ccc(N4CCCC4=O)cc3)nc(NCCCO)c2c1=O] | ESI-MS m/z 393.2 (MH⁺) | 0.466 |
| 106 | 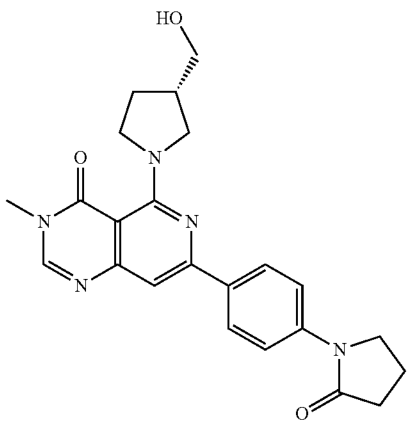 [SMILES: Cn1cnc2cc(-c3ccc(N4CCCC4=O)cc3)nc(N3CC[C@H](CO)C3)c2c1=O] | ESI-MS m/z 420.2 (MH⁺) | 0.65 |
| 107 | 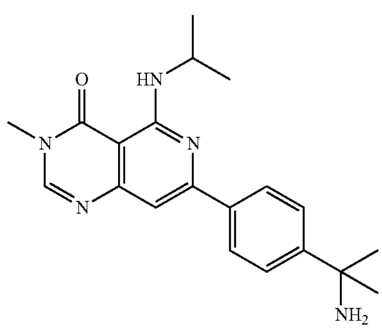 [SMILES: CC(C)Nc1nc(-c2ccc(C(C)(C)N)cc2)cc2ncn(C)c(=O)c12] | ESI-MS m/z 352.2 (MH⁺) | 0.117 |
| 108 | 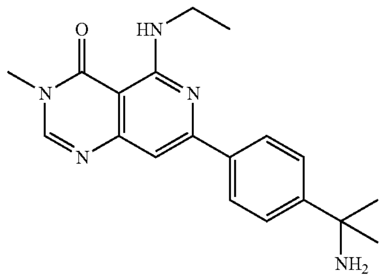 [SMILES: CCNc1nc(-c2ccc(C(C)(C)N)cc2)cc2ncn(C)c(=O)c12] | ¹H NMR (400 MHz, DMSO-d₆) of the HCl salt of the compound: δ 1.20 (t, J = 7.0 Hz, 3H), 1.61 (s, 6H), 3.39 (s, 3H), 3.56 (q, J = 7.0 Hz, 2H), 7.16 (s, 1H), 7.61 (d, J = 8.4 Hz, 2H), 8.13 (d, J = 8.4 Hz, 2H), 8.44 (s, 1H);<br>ESI-MS m/z 338.2 (MH⁺). | 0.066 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 109 | 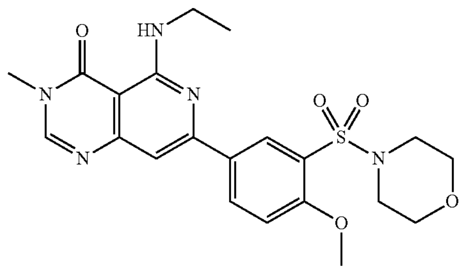 [SMILES: CCNc1nc(-c2ccc(OC)c(S(=O)(=O)N3CCOCC3)c2)cc2ncn(C)c(=O)c12] | ESI-MS m/z 460.5 (MH⁺) | 0.147 |
| 110 | 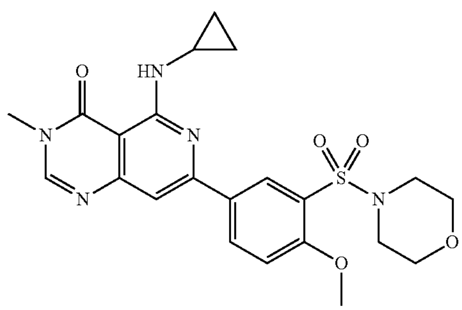 [SMILES: COc1ccc(-c2cc3ncn(C)c(=O)c3c(NC3CC3)n2)cc1S(=O)(=O)N1CCOCC1] | ESI-MS m/z 472.1 (MH⁺) | 0.337 |
| 111 | 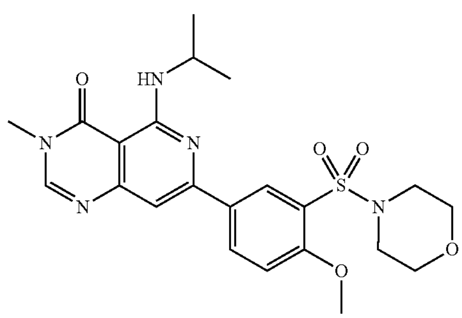 [SMILES: COc1ccc(-c2cc3ncn(C)c(=O)c3c(NC(C)C)n2)cc1S(=O)(=O)N1CCOCC1] | ¹H NMR (400 MHz, DMSO-d₆) of the HCl salt of the compound: δ 1.30 (d, J = 6.4 Hz, 6H), 3.10-3.12 (4H), 3.45 (s, 3H), 3.59-3.61 (4H), 3.98 (s, 3H), 4.38 (m, 1H), 7.16 (s, 1H), 7.38 (d, J = 8.8 Hz, 1H), 8.41 (d, J = 8.8 Hz, 1H), 8.46 (s, 1H), 8.56 (s, 1H), 8.74 (br s, 1H, NH);<br>ESI-MS m/z 474.2 (MH⁺) | 0.195 |
| 112 | 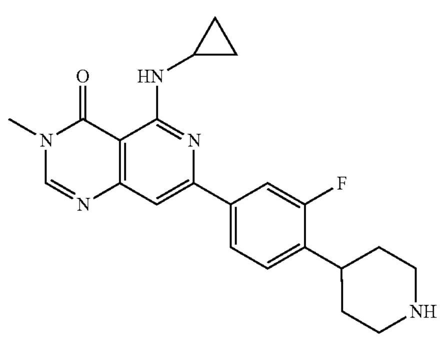 [SMILES: Cn1cnc2cc(-c3ccc(C4CCNCC4)c(F)c3)nc(NC3CC3)c2c1=O] | ESI-MS m/z 394.2 (MH⁺) | 0.237 |

TABLE 1-continued
| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 113 | 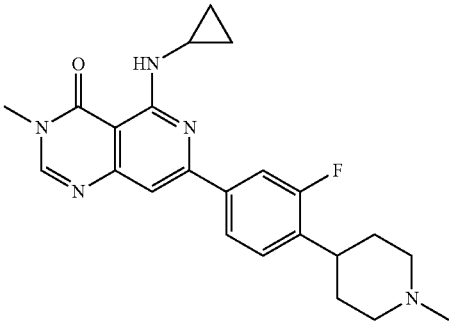 | ESI-MS m/z 408.2 (MH⁺) | 0.329 |
| 114 | 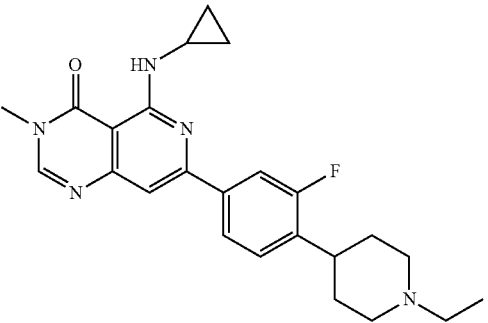 [SMILES: CCN1CCC(c2ccc(-c3cc4ncn(C)c(=O)c4c(NC4CC4)n3)cc2F)CC1] | ESI-MS m/z 422.2 (MH⁺) | 0.181 |
| 115 | 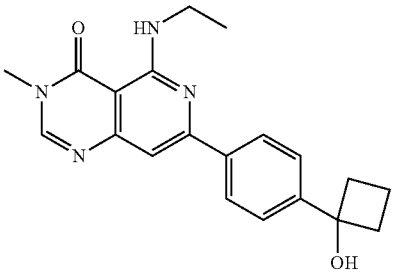 [SMILES: CCNc1nc(-c2ccc(C3(O)CCC3)cc2)cc2ncn(C)c(=O)c12] | ¹H NMR (400 MHz, DMSO-d₆) of the TFA salt of the compound: δ 1.20 (t, J = 7.2 Hz, 3H), 1.63 (m, 1H), 1.87 (m, 1H), 2.24 (m, 2H), 2.34 (m, 2H), 3.38 (s, 3H), 3.56 (m, 2H), 7.09 (s, 1H), 7.52 (d, J = 8.4 Hz, 1H), 8.06 (d, J = 8.4 Hz, 1H) 8.37 (s, 1H), 8.71 (br s, 1H, NH);<br>ESI-MS m/z 351.2 (MH⁺) | 0.271 |
| 116 | 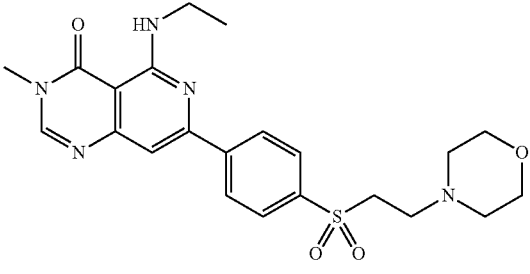 [SMILES: CCNc1nc(-c2ccc(S(=O)(=O)CCN3CCOCC3)cc2)cc2ncn(C)c(=O)c12] | ESI-MS m/z 458.2 (MH⁺) | 0.082 |
| 117 | 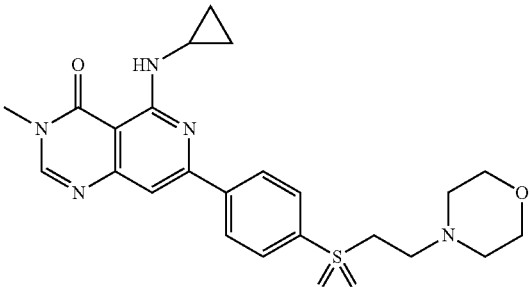 | ESI-MS m/z 470.2 (MH⁺) | 0.179 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 118 | 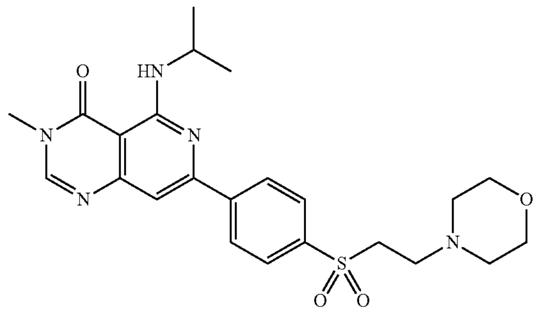 [SMILES: CC(C)Nc1nc(-c2ccc(S(=O)(=O)CCN3CCOCC3)cc2)cc2ncn(C)c(=O)c12] | ESI-MS m/z 472.2 (MH⁺) | 0.217 |
| 119 | 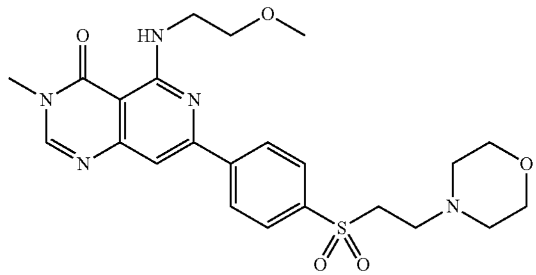 [SMILES: COCCNc1nc(-c2ccc(S(=O)(=O)CCN3CCOCC3)cc2)cc2ncn(C)c(=O)c12] | ESI-MS m/z 488.2 (MH⁺) | 0.16 |
| 120 | 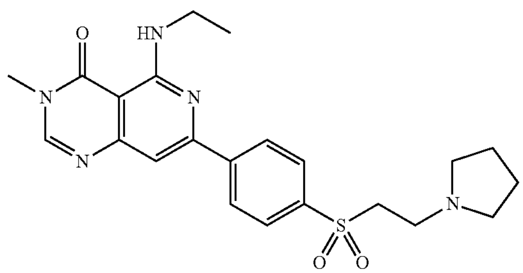 [SMILES: CCNc1nc(-c2ccc(S(=O)(=O)CCN3CCCC3)cc2)cc2ncn(C)c(=O)c12] | ESI-MS m/z 442.2 (MH⁺) | 0.222 |
| 121 | 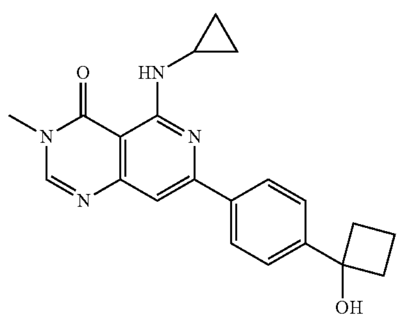 [SMILES: Cn1cnc2cc(-c3ccc(C4(O)CCC4)cc3)nc(NC3CC3)c2c1=O] | ESI-MS m/z 363.2 (MH⁺) | 0.296 |
| 122 | 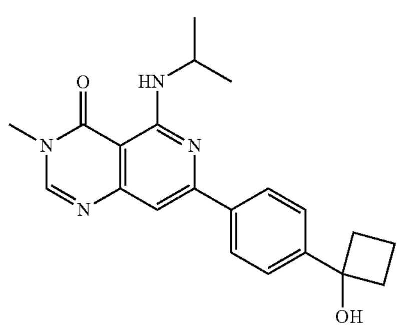 [SMILES: CC(C)Nc1nc(-c2ccc(C3(O)CCC3)cc2)cc2ncn(C)c(=O)c12] | ESI-MS m/z 365.2 (MH⁺) | 1.046 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
| --- | --- | --- | --- |
| 123 | 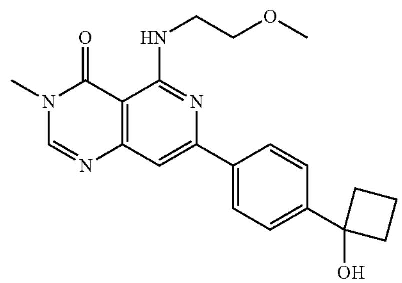 [SMILES: COCCNc1nc(-c2ccc(C3(O)CCC3)cc2)cc2ncn(C)c(=O)c12] | ESI-MS m/z 381.2 (MH$^+$) | 0.116 |
| 124 | 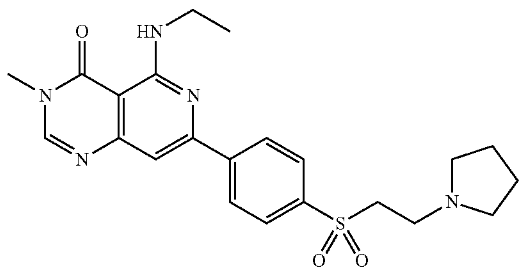 [SMILES: CCNc1nc(-c2ccc(S(=O)(=O)CCN3CCCC3)cc2)cc2ncn(C)c(=O)c12] | ESI-MS m/z 442.2 (MH$^+$) | 0.222 |
| 125 | 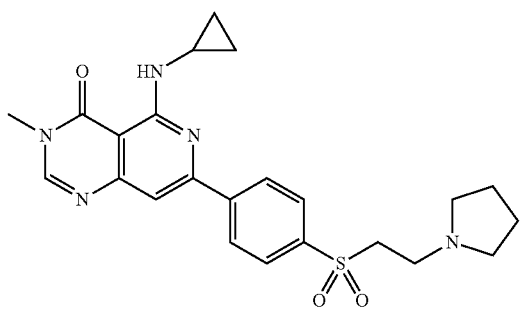 [SMILES: Cn1cnc2cc(-c3ccc(S(=O)(=O)CCN4CCCC4)cc3)nc(NC3CC3)c2c1=O] | ESI-MS m/z 454.2 (MH$^+$) | 0.392 |
| 126 | 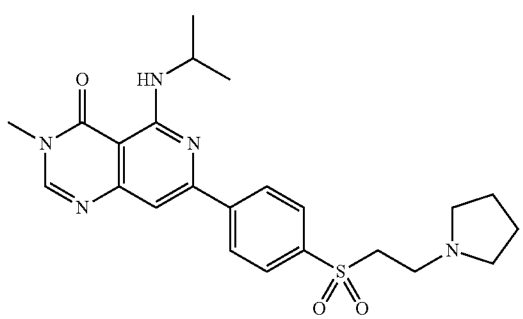 [SMILES: CC(C)Nc1nc(-c2ccc(S(=O)(=O)CCN3CCCC3)cc2)cc2ncn(C)c(=O)c12] | ESI-MS m/z 456.2 (MH$^+$) | 0.555 |
| 127 | 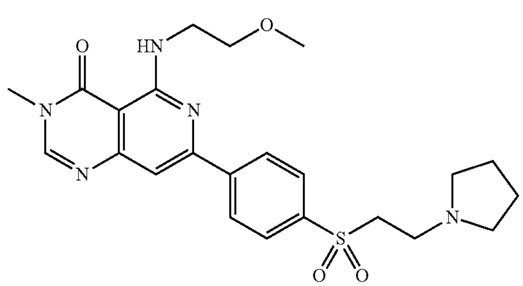 [SMILES: COCCNc1nc(-c2ccc(S(=O)(=O)CCN3CCCC3)cc2)cc2ncn(C)c(=O)c12] | ESI-MS m/z 472.2 (MH$^+$) | 0.374 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
| --- | --- | --- | --- |
| 128 | 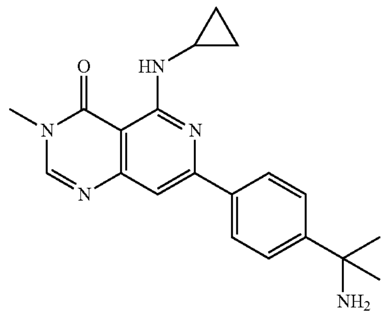 | ¹H NMR (400 MHz, DMSO-d$_6$) of the HCl salt of the compound: δ 0.57 (m, 2H), 0.87 (m, 2H), 1.68 (s, 6H), 3.07 (m, 1H), 3.39 (s, 3H), 7.31 (s, 1H), 7.66 (d, J = 8.8 Hz, 2H), 8.28 (d, J = 8.8 Hz, 2H), 8.47 (s, 1H); ESI-MS m/z 350.2 (MH⁺) | 0.128 |
| 129 | 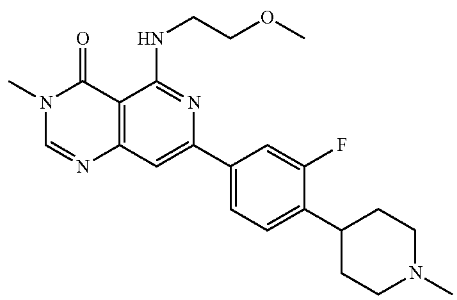 | ESI-MS m/z 426.2 (MH⁺) | 0.141 |
| 130 | 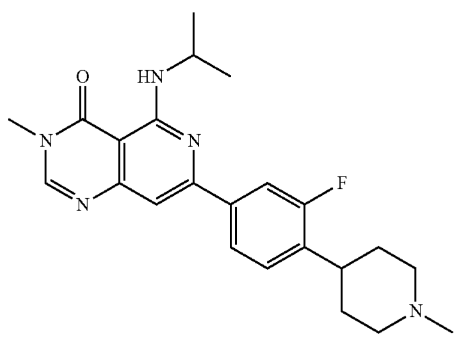 | ESI-MS m/z 410.20 (MH⁺) | 0.247 |
| 131 | 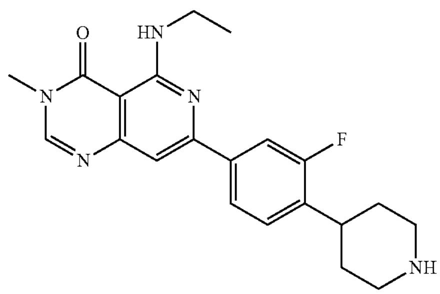 [SMILES: CCNc1nc(-c2ccc(C3CCNCC3)c(F)c2)cc2ncn(C)c(=O)c12] | ESI-MS m/z 382.2 (MH⁺) | 0.069 |
| 132 | 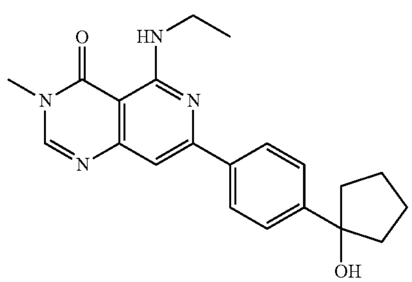 [SMILES: CCNc1nc(-c2ccc(C3(O)CCCC3)cc2)cc2ncn(C)c(=O)c12] | ESI-MS m/z 365.2 (MH⁺) | 0.346 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 133 | 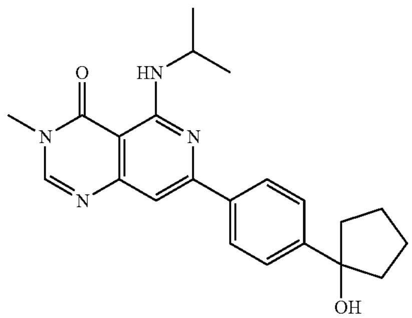 [SMILES: CC(C)Nc1nc(-c2ccc(C3(O)CCCC3)cc2)cc2ncn(C)c(=O)c12] | ESI-MS m/z 379.2 (MH⁺) | 0.872 |
| 134 | 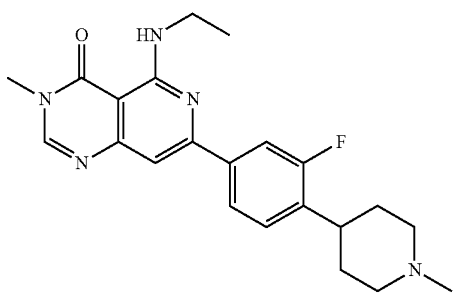 | ESI-MS m/z 396.2 (MH⁺) | 0.084 |
| 135 | 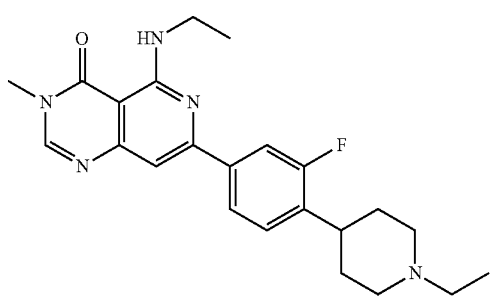 [SMILES: CCNc1nc(-c2ccc(C3CCN(CC)CC3)c(F)c2)cc2ncn(C)c(=O)c12] | ESI-MS m/z 410.2 (MH⁺) | 0.112 |
| 136 | 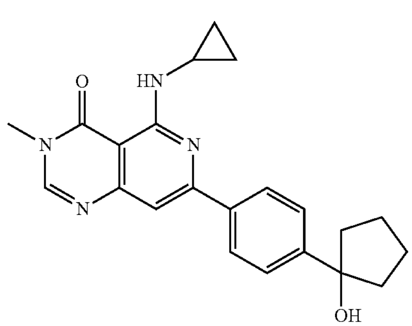 [SMILES: Cn1cnc2cc(-c3ccc(C4(O)CCCC4)cc3)nc(NC3CC3)c2c1=O] | ESI-MS m/z 376.2 (MH⁺) | 0.936 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 137 | 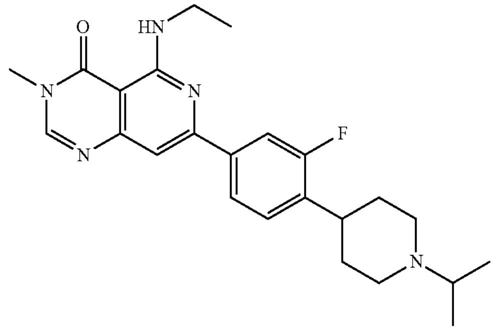 [SMILES: CCNc1nc(-c2ccc(C3CCN(C(C)C)CC3)c(F)c2)cc2ncn(C)c(=O)c12] | ESI-MS m/z 423.2 (MH⁺) | 0.086 |
| 138 | 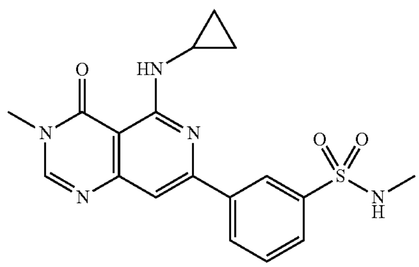 | ESI-MS m/z 386.1 (MH⁺) | 0.167 |
| 139 | 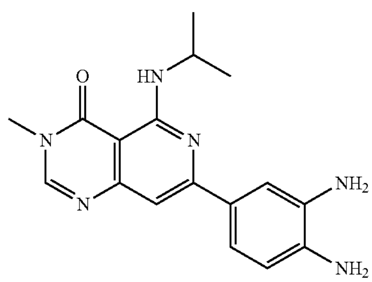 [SMILES: CC(C)Nc1nc(-c2ccc(N)c(N)c2)cc2ncn(C)c(=O)c12] | ESI-MS m/z 325.2 (MH⁺) | 0.228 |
| 140 | 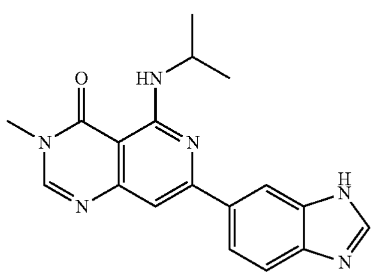 [SMILES: CC(C)Nc1nc(-c2ccc3nc[nH]c3c2)cc2ncn(C)c(=O)c12] | ESI-MS m/z 335.2 (MH⁺) | 0.346 |
| 141 | 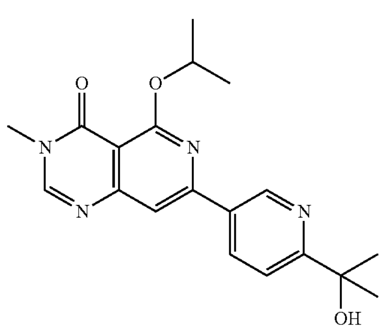 [SMILES: CC(C)Oc1nc(-c2ccc(C(C)(C)O)nc2)cc2ncn(C)c(=O)c12] | ESI-MS m/z 355.2 (MH⁺) | 0.238 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 142 | 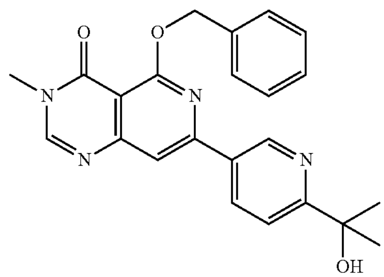 [SMILES: Cn1cnc2cc(-c3ccc(C(C)(C)O)nc3)nc(OCc3ccccc3)c2c1=O] | ESI-MS m/z 403.2 (MH⁺) | 0.181 |
| 143 | 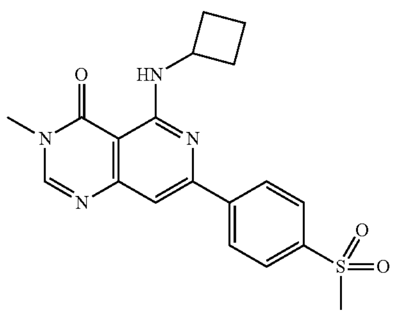 [SMILES: Cn1cnc2cc(-c3ccc(S(C)(=O)=O)cc3)nc(NC3CCC3)c2c1=O] | ESI-MS m/z 385.1 (MH⁺) | 0.391 |
| 144 | 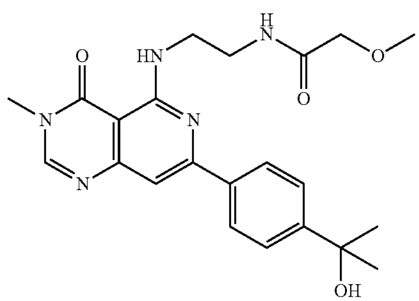 | ESI-MS m/z 426.2 (MH⁺) | 0.43 |
| 145 | 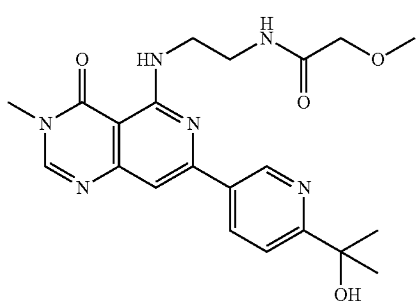 | ESI-MS m/z 427.2 (MH⁺) | 0.086 |
| 146 | 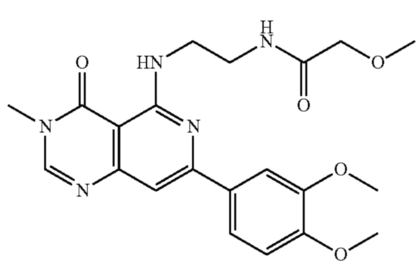 | ESI-MS m/z 428.2 (MH⁺) | 0.572 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 147 | 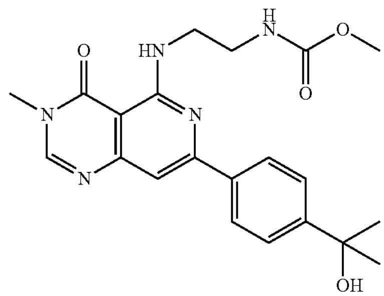 [SMILES: COC(=O)NCCNc1nc(-c2ccc(C(C)(C)O)cc2)cc2ncn(C)c(=O)c12] | ESI-MS m/z 412.2 (MH⁺) | 0.102 |
| 148 | 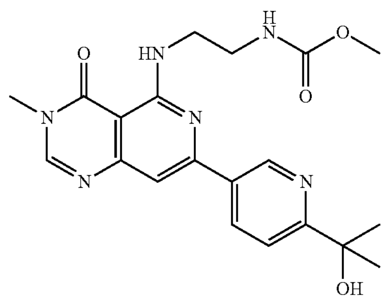 [SMILES: COC(=O)NCCNc1nc(-c2ccc(C(C)(C)O)nc2)cc2ncn(C)c(=O)c12] | ESI-MS m/z 413.2 (MH⁺) | 0.091 |
| 149 | 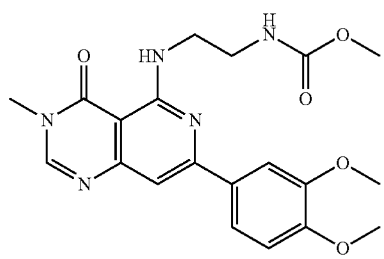 | ESI-MS m/z 414.2 (MH⁺) | 0.391 |
| 150 | 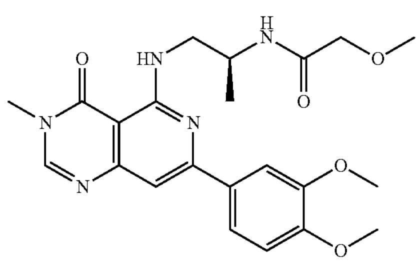 | ESI-MS m/z 442.2 (MH⁺) | 1.966 |
| 151 | 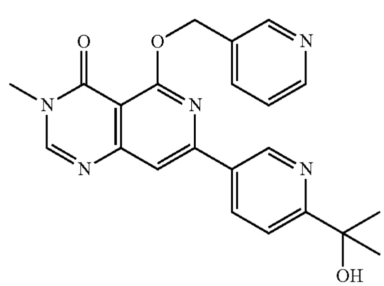 [SMILES: Cn1cnc2cc(-c3ccc(C(C)(C)O)nc3)nc(OCc3cccnc3)c2c1=O] | ESI-MS m/z 404.2 (MH⁺) | 0.7 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 152 | 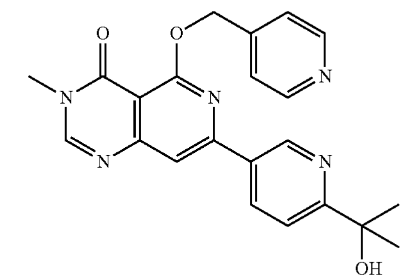 [SMILES: Cn1cnc2cc(-c3ccc(C(C)(C)O)nc3)nc(OCc3ccncc3)c2c1=O] | ESI-MS m/z 404.2 (MH⁺) | 0.7 |
| 153 | 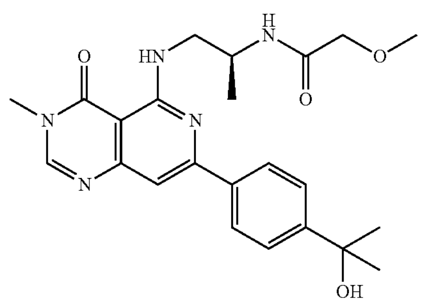 | ESI-MS m/z 440.2 (MH⁺) | 2.615 |
| 154 | 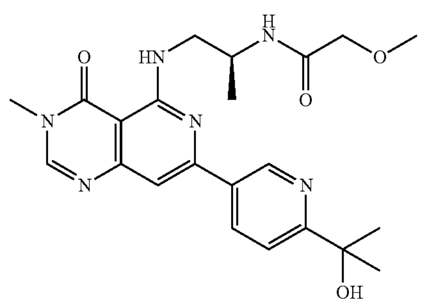 | ESI-MS m/z 441.2 (MH⁺) | 0.182 |
| 155 | 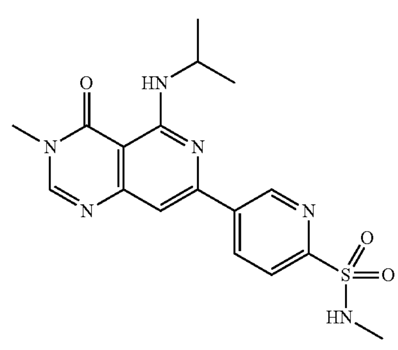 [SMILES: CNS(=O)(=O)c1ccc(-c2cc3ncn(C)c(=O)c3c(NC(C)C)n2)cn1] | ESI-MS m/z 389.2 (MH⁺) | 0.989 |
| 156 | 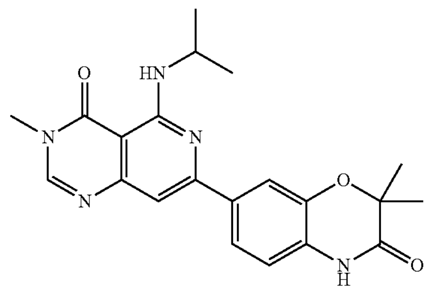 | ESI-MS m/z 394.2 (MH⁺) | 2.472 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 157 | 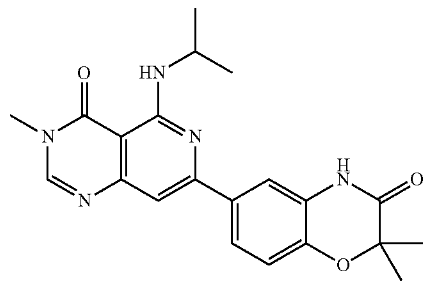 | ESI-MS m/z 394.2 (MH⁺) | 1.11 |
| 158 | 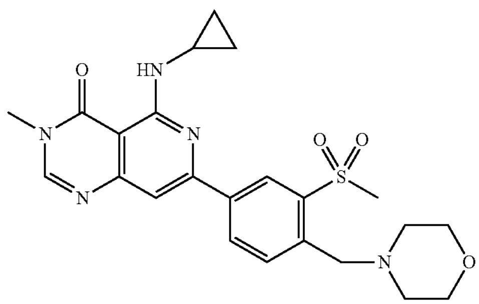 [SMILES: Cn1cnc2cc(-c3ccc(CN4CCOCC4)c(S(C)(=O)=O)c3)nc(NC3CC3)c2c1=O] | ESI-MS m/z 470.2 (MH⁺) | 0.155 |
| 159 | 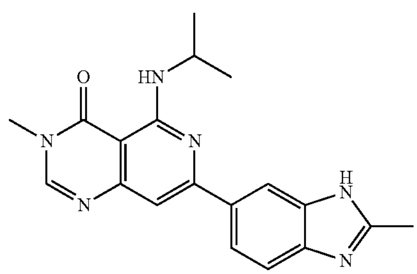 | ESI-MS m/z 349.2 (MH⁺) | 0.208 |
| 160 | 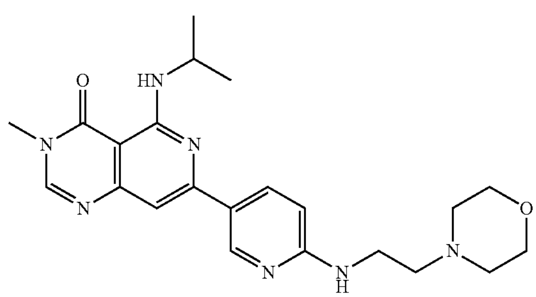 [SMILES: CC(C)Nc1nc(-c2ccc(NCCN3CCOCC3)nc2)cc2ncn(C)c(=O)c12] | ESI-MS m/z 424.2 (MH⁺) | 0.116 |
| 161 | 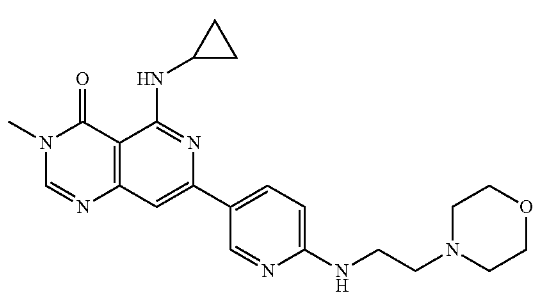 [SMILES: Cn1cnc2cc(-c3ccc(NCCN4CCOCC4)nc3)nc(NC3CC3)c2c1=O] | ESI-MS m/z 422.2 (MH⁺) | <0.00686 |

TABLE 1-continued

| Compound Number | Structure | Physical Data <br> $^1$H NMR 400 MHz (CDCl$_3$), HPLC Retention Time, and/or MS (m/z) | Syk Enzyme IC$_{50}$ (uM) |
| --- | --- | --- | --- |
| 162 | 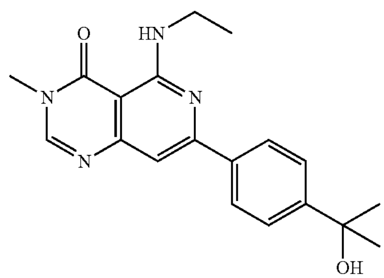 [SMILES: CCNc1nc(-c2ccc(C(C)(C)O)cc2)cc2ncn(C)c(=O)c12] | ESI-MS m/z 339.2 (MH$^+$) | 0.147 |
| 163 | 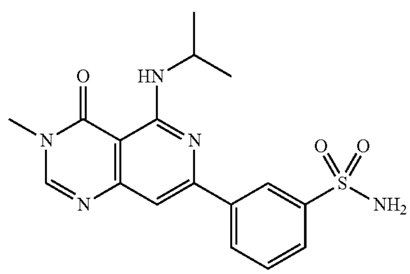 | $^1$H NMR (400 MHz, DMSO-d$_6$) of the HCl salt of the compound: δ 0.60 (m, 2H), 0.89 (m, 2H), 3.10 (m, 1H), 3.46 (s, 3H), 7.33 (s, 1H), 7.48 (br s, 1H, NH$_2$), 7.70 (dd, J = 8.0 Hz and 8.0 Hz, 1H), 7.91 (d, J = 8.0 Hz, 1H), 8.41 (d, J = 7.6 Hz, 1H), 8.53 (s, 1H), 8.69 (s, 1H), 8.86 (br s, 1H, NH); ESI-MS m/z 324.1 (MH$^+$) | 0.086 |
| 164 | 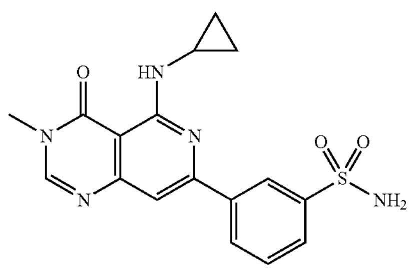 [SMILES: Cn1cnc2cc(-c3cccc(S(N)(=O)=O)c3)nc(NC3CC3)c2c1=O] | ESI-MS m/z 372.1 (MH$^+$) | 0.038 |
| 165 | 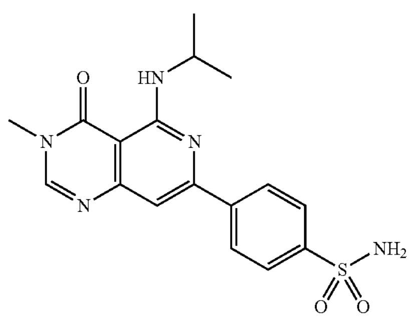 [SMILES: CC(C)Nc1nc(-c2ccc(S(N)(=O)=O)cc2)cc2ncn(C)c(=O)c12] | ESI-MS m/z 374.1 (MH$^+$) | 0.422 |
| 166 | 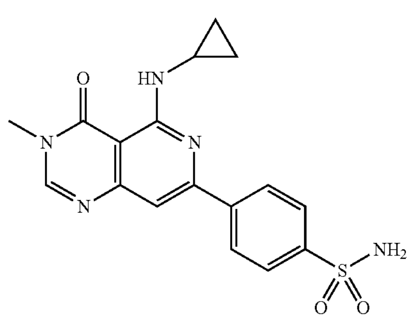 [SMILES: Cn1cnc2cc(-c3ccc(S(N)(=O)=O)cc3)nc(NC3CC3)c2c1=O] | ESI-MS m/z 372.1 (MH$^+$) | 0.219 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 167 | 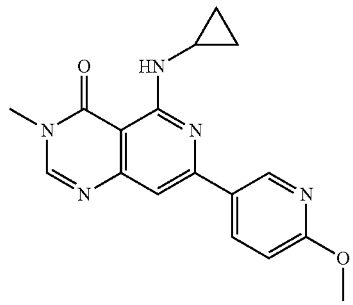 | ESI-MS m/z 324.1 (MH⁺) | 0.348 |
| 168 | 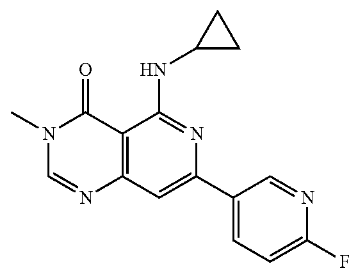 [SMILES: Cn1cnc2cc(-c3ccc(F)nc3)nc(NC3CC3)c2c1=O] | ESI-MS m/z 312.1 (MH⁺) | 0.472 |
| 169 | 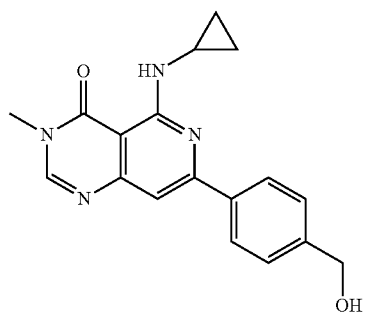 [SMILES: Cn1cnc2cc(-c3ccc(CO)cc3)nc(NC3CC3)c2c1=O] | ESI-MS m/z 323.1 (MH⁺) | 0.277 |
| 170 | 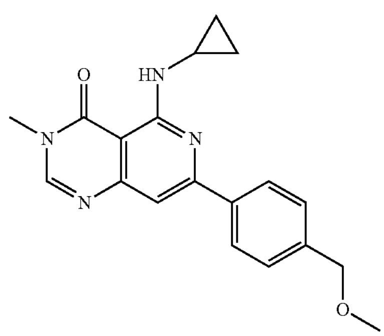 | ESI-MS m/z 337.2 (MH⁺) | 0.422 |
| 171 | 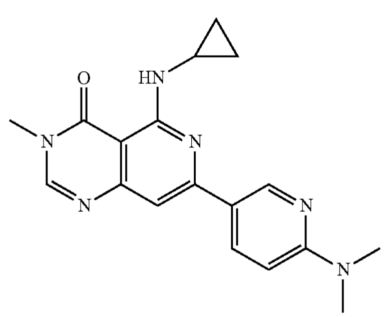 | ESI-MS m/z 337.2 (MH⁺) | 0.182 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 172 | 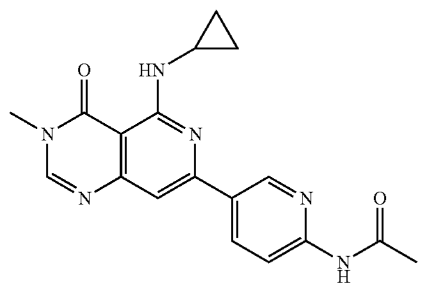 [SMILES: CC(=O)Nc1ccc(-c2cc3ncn(C)c(=O)c3c(NC3CC3)n2)cn1] | ESI-MS m/z 351.1 (MH$^+$) | 0.353 |
| 173 | 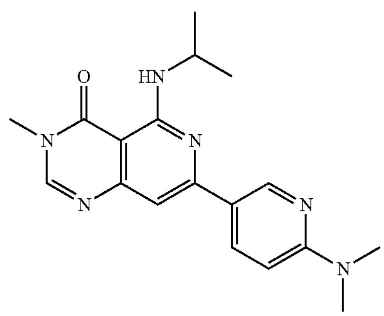 | ESI-MS m/z 339.2 (MH$^+$) | 0.159 |
| 174 | 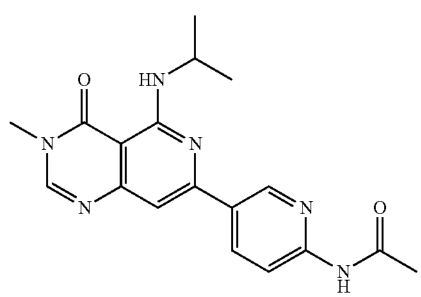 [SMILES: CC(=O)Nc1ccc(-c2cc3ncn(C)c(=O)c3c(NC(C)C)n2)cn1] | ESI-MS m/z 353.2 (MH$^+$) | 0.533 |
| 175 | 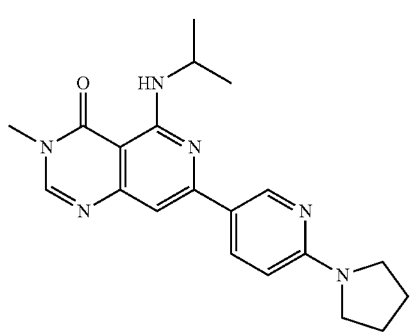 [SMILES: CC(C)Nc1nc(-c2ccc(N3CCCC3)nc2)cc2ncn(C)c(=O)c12] | ESI-MS m/z 365.2 (MH$^+$) | 0.621 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 176 | 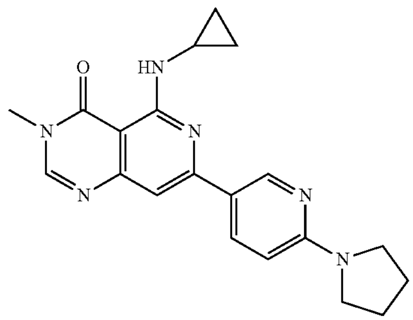 [SMILES: Cn1cnc2cc(-c3ccc(N4CCCC4)nc3)nc(NC3CC3)c2c1=O] | ESI-MS m/z 363.2 (MH⁺) | 0.249 |
| 177 | 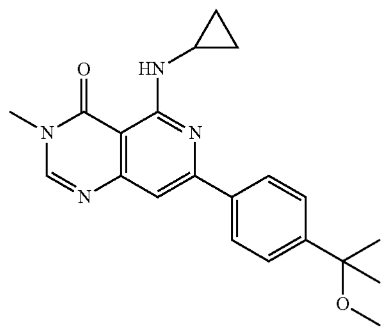 | ¹H NMR (400 MHz, DMSO-d₆) of the TFA salt of the compound: δ 0.58 (m, 2H), 0.87 (m, 2H), 1.49 (s, 6H), 3.02 (s, 3H), 3.11 (m, 1H), 3.44 (s, 3H), 7.24 (s, 1H), 7.50 (d, J = 8.4 Hz, 2H), 8.18 (d, J = 8.4 Hz, 2H), 8.45 (s, 1H), 8.81 (br s, 1H, NH);<br>ESI-MS m/z 365.2 (MH⁺) | 0.317 |
| 178 | 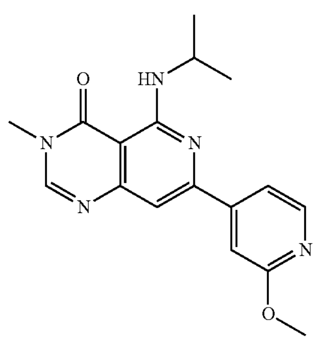 | ¹H NMR (400 MHz, DMSO-d₆) of the TFA salt of the compound: δ 1.23 (d, J = 6.8 Hz, 6H), 3.39 (s, 3H), 3.84 (s, 3H), 4.33 (m, 1H), 7.24 (s, 1H), 7.44 (s, 1H), 7.63 (d, J = 5.4 Hz, 1H), 8.21 (d, J = 5.4 Hz, 1H) 8.42 (s, 1H), 8.70 (br s, 1H, NH);<br>ESI-MS m/z 326.2 (MH⁺) | 2.017 |
| 179 | 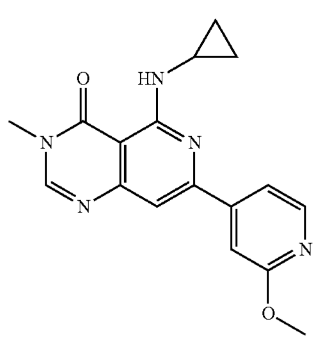 | ESI-MS m/z 324.1 (MH⁺) | 0.843 |

TABLE 1-continued

| Compound Number | Structure | Physical Data<br>¹H NMR 400 MHz (CDCl₃),<br>HPLC Retention Time, and/or<br>MS (m/z) | Syk Enzyme IC₅₀ (uM) |
|---|---|---|---|
| 180 | 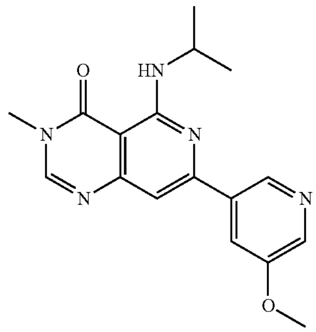 | ¹H NMR (400 MHz, DMSO-d₆) of the TFA salt of the compound: δ 1.30 (d, J = 6.4 Hz, 6H), 3.45 (s, 3H), 3.93 (s, 3H), 4.40 (m, 1H), 7.34 (s, 1H), 8.06 (s, 1H), 8.39 (s, 1H), 8.47 (s, 1H), 8.77 (br s, 1H, NH), 8.95 (s, 1H); ESI-MS m/z 326.2 (MH⁺) | 1.864 |
| 181 | 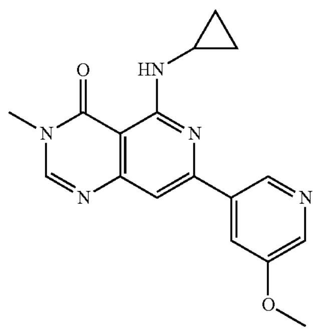 | ¹H NMR (400 MHz, DMSO-d₆) of TFA salt of the compound: δ 0.51 (m, 2H), 0.80 (m, 2H), 2.99 (m, 1H), 3.38 (s, 3H), 3.87 (s, 3H), 7.37 (s, 1H), 8.08 (s, 1H), 8.33 (s, 1H), 8.41 (s, 1H), 8.77 (br s, 1H, NH), 8.95 (s, 1H); ESI-MS m/z 324.1 (MH⁺) | 1.236 |
| 182 | 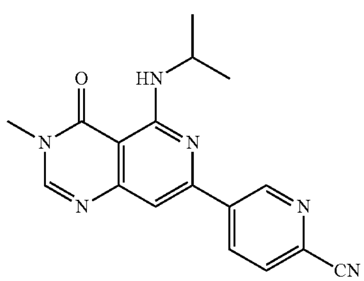 [SMILES: CC(C)Nc1nc(-c2ccc(C#N)nc2)cc2ncn(C)c(=O)c12] | ESI-MS m/z 321.1 (MH⁺) | 2.8 |
| 183 | 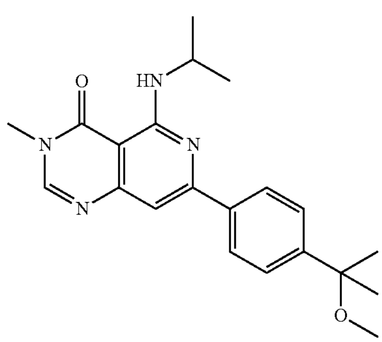 | ¹H NMR (400 MHz, DMSO-d₆) of the HCl salt of the compound: δ 1.30 (d, J = 6.4 Hz, 6H), 1.48 (s, 6H), 3.01 (s, 3H), 3.45 (s, 3H), 4.42 (m, 1H), 7.16 (s, 1H), 7.50 (d, J = 8.4 Hz, 2H), 8.11 (d, J = 8.4 Hz, 2H), 8.51 (s, 1H), 8.74 (br s, 1H, NH); ESI-MS m/z 367.2 (MH⁺) | 0.575 |

TABLE 1-continued
| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 184 | 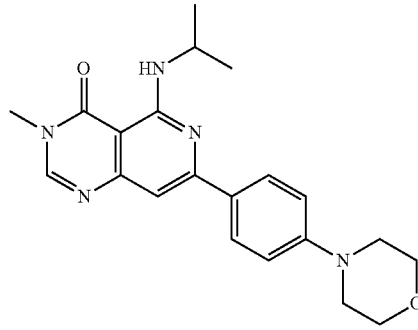 | ESI-MS m/z 380.2 (MH$^+$) | 0.558 |
| 185 | 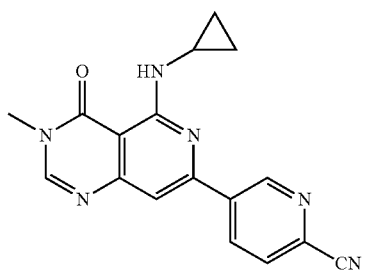 [SMILES: Cn1cnc2cc(-c3ccc(C#N)nc3)nc(NC3CC3)c2c1=O] | ESI-MS m/z 319.1 (MH$^+$) | 2.543 |
| 186 | 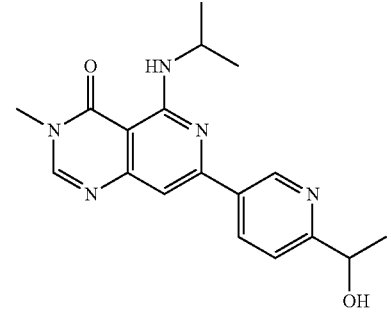 [SMILES: CC(C)Nc1nc(-c2ccc(C(C)O)nc2)cc2ncn(C)c(=O)c12] | ESI-MS m/z 340.2 (MH$^+$) | 0.523 |
| 187 | 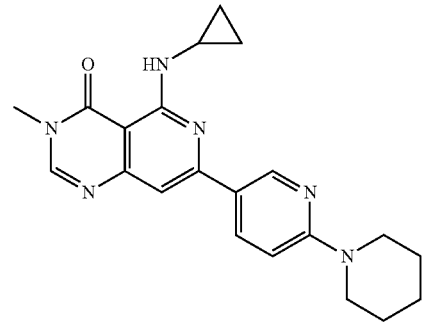 | ESI-MS m/z 326.2 (MH$^+$) | 0.417 |
| 188 | 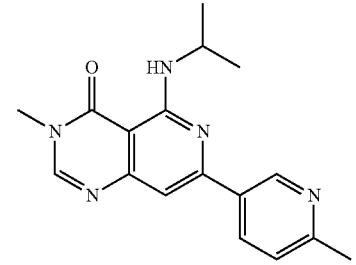 | ESI-MS m/z 310.2 (MH$^+$) | 0.483 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 189 | 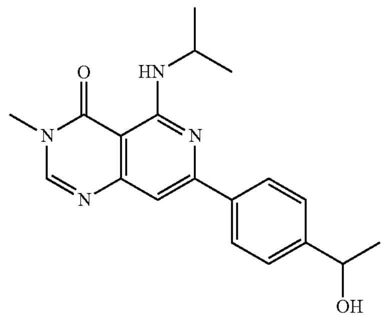 [SMILES: CC(C)Nc1nc(-c2ccc(C(C)O)cc2)cc2ncn(C)c(=O)c12] | ESI-MS m/z 339.2 (MH⁺) | 0.39 |
| 190 | 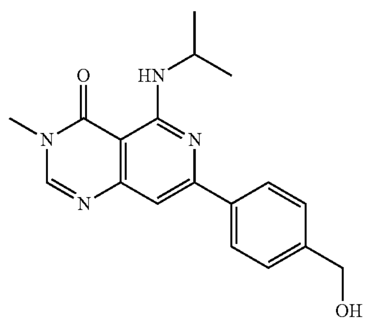 [SMILES: CC(C)Nc1nc(-c2ccc(CO)cc2)cc2ncn(C)c(=O)c12] | ESI-MS m/z 325.2 (MH⁺) | 0.215 |
| 191 | 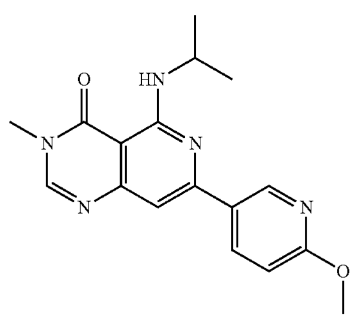 | ESI-MS m/z 326.2 (MH⁺) | 0.739 |
| 192 | 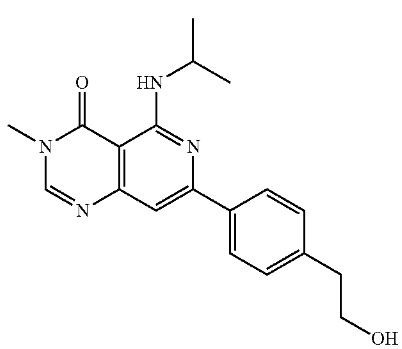 [SMILES: CC(C)Nc1nc(-c2ccc(CCO)cc2)cc2ncn(C)c(=O)c12] | ¹H NMR (400 MHz, DMSO-d₆) of the TFA salt of the compound: δ 1.29 (d, J = 6.4 Hz, 6H), 2.79 (m, 2H), 3.43 (s, 3H), 3.63 (m, 2H), 4.42 (m, 1H), 4.73 (m, 1H, OH), 7.14 (s, 1H), 7.33 (d, J = 8.4 Hz, 2H), 8.05 (d, J = 8.4 Hz, 2H), 8.43 (s, 1H), 8.72 (br s, 1H, NH); ESI-MS m/z 339.2 (MH⁺) | 0.473 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 193 | 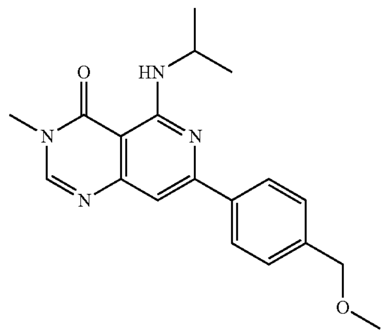 | ESI-MS m/z 339.2 (MH⁺) | 2.207 |
| 194 | 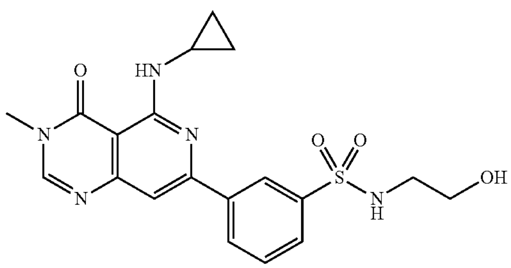 [SMILES: Cn1cnc2cc(-c3cccc(S(=O)(=O)NCCO)c3)nc(NC3CC3)c2c1=O] | ESI-MS m/z 416.1 (MH⁺) | 0.082 |
| 195 | 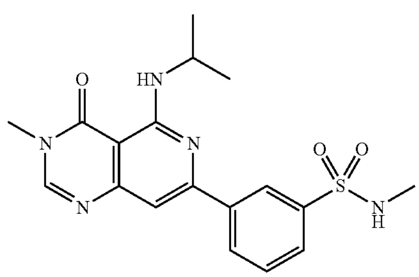 | ESI-MS m/z 388.1 (MH⁺) | 0.321 |
| 196 | 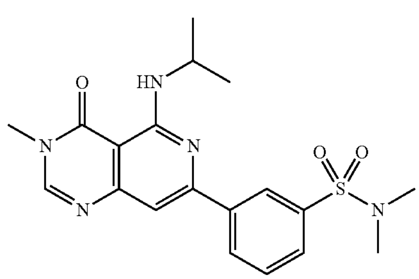 | ESI-MS m/z 402.2 (MH⁺) | 1.203 |
| 197 | 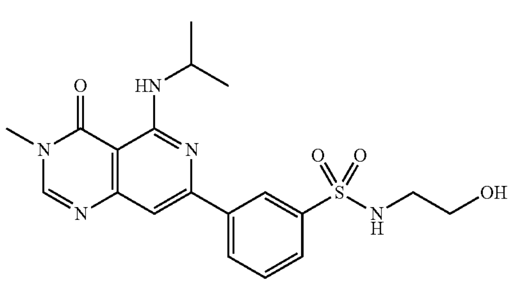 [SMILES: CC(C)Nc1nc(-c2cccc(S(=O)(=O)NCCO)c2)cc2ncn(C)c(=O)c12] | ESI-MS m/z 418.1 (MH⁺) | 0.118 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 198 | 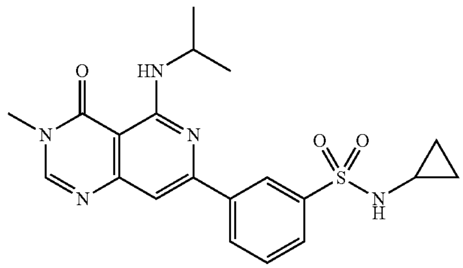 [SMILES: CC(C)Nc1nc(-c2cccc(S(=O)(=O)NC3CC3)c2)cc2ncn(C)c(=O)c12] | ESI-MS m/z 414.2 (MH⁺) | 0.443 |
| 199 | 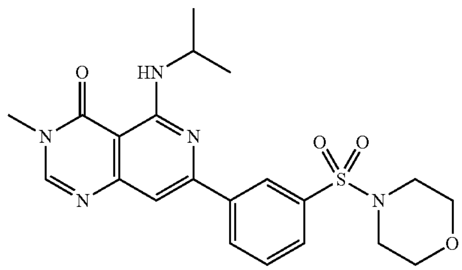 [SMILES: CC(C)Nc1nc(-c2cccc(S(=O)(=O)N3CCOCC3)c2)cc2ncn(C)c(=O)c12] | ESI-MS m/z 444.2 (MH⁺) | 1.055 |
| 200 | 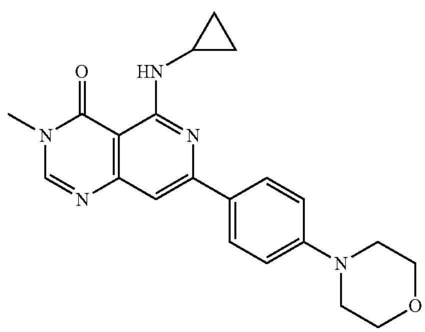 [SMILES: Cn1cnc2cc(-c3ccc(N4CCOCC4)cc3)nc(NC3CC3)c2c1=O] | ESI-MS m/z 378.2 (MH⁺) | 0.145 |
| 201 | 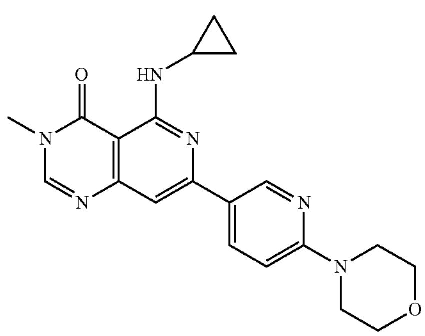 [SMILES: Cn1cnc2cc(-c3ccc(N4CCOCC4)nc3)nc(NC3CC3)c2c1=O] | ESI-MS m/z 379.2 (MH⁺) | 0.397 |
| 202 | 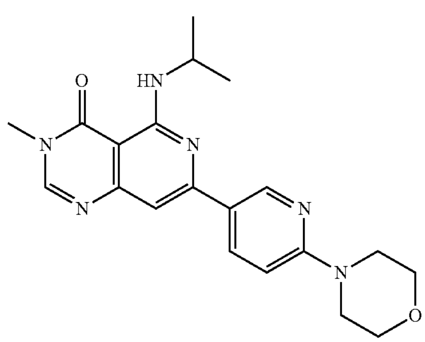 [SMILES: CC(C)Nc1nc(-c2ccc(N3CCOCC3)nc2)cc2ncn(C)c(=O)c12] | ESI-MS m/z 381.2 (MH⁺) | 0.296 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 203 | 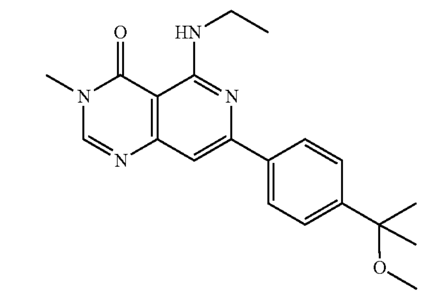 | ESI-MS m/z 353.2 (MH⁺) | 0.314 |
| 204 | 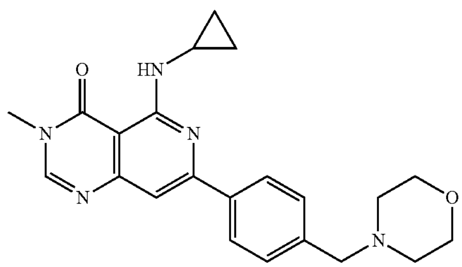 [SMILES: Cn1cnc2cc(-c3ccc(CN4CCOCC4)cc3)nc(NC3CC3)c2c1=O] | ESI-MS m/z 392.2 (MH⁺) | 0.46 |
| 205 | 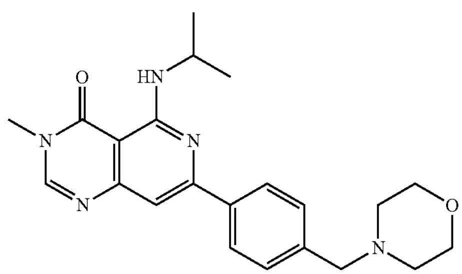 [SMILES: CC(C)Nc1nc(-c2ccc(CN3CCOCC3)cc2)cc2ncn(C)c(=O)c12] | ESI-MS m/z 394.2 (MH⁺) | 0.626 |
| 206 | 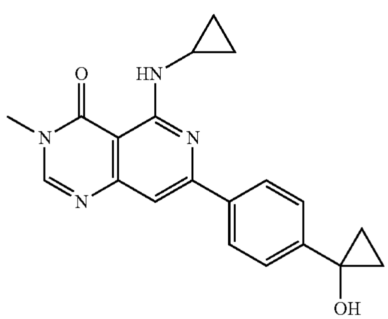 [SMILES: Cn1cnc2cc(-c3ccc(C4(O)CC4)cc3)nc(NC3CC3)c2c1=O] | ESI-MS m/z 349.2 (MH⁺) | 0.231 |
| 207 | 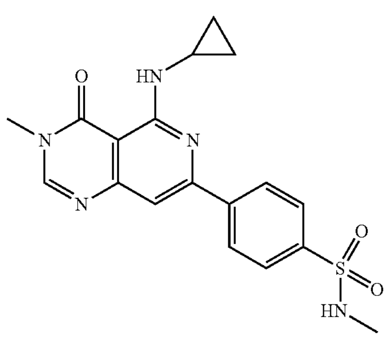 | ¹H NMR (400 MHz, DMSO-d₆) of the TFA salt of the compound: δ 0.57 (m, 2H), 0.88 (m, 2H), 2.55 (d, J = 5.2 Hz, 3H), 3.08 (m, 1H), 3.45 (s, 3H), 7.36 (s, 1H), 7.56 (d, J = 5.2 Hz, 1H, NH), 7.88 (d, J = 8.8 Hz, 2H), 8.43 (d, J = 8.8 Hz, 2H), 8.48 (s, 1H), 8.83 (br s, 1H, NH);<br>ESI-MS m/z 386.1 (MH⁺) | 0.543 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 208 | 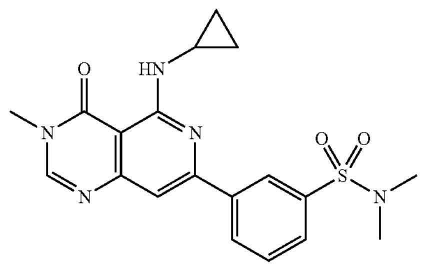 | ESI-MS m/z 400.1 (MH⁺) | 2.971 |
| 209 | 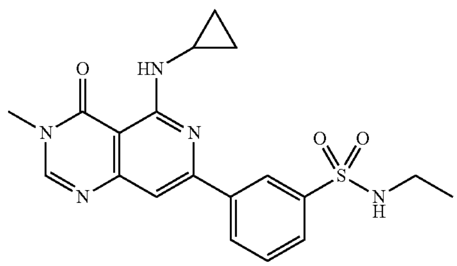 [SMILES: CCNS(=O)(=O)c1cccc(-c2cc3ncn(C)c(=O)c3c(NC3CC3)n2)c1] | ESI-MS m/z 400.1 (MH⁺) | 0.2 |
| 210 | 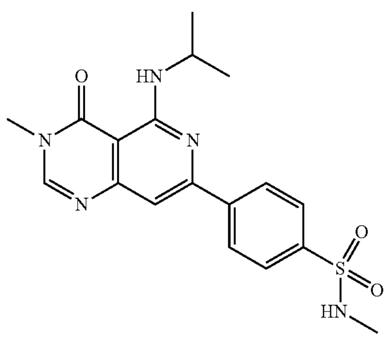 [SMILES: CNS(=O)(=O)c1ccc(-c2cc3ncn(C)c(=O)c3c(NC(C)C)n2)cc1] | ESI-MS m/z 388.1 (MH⁺) | 0.754 |
| 211 | 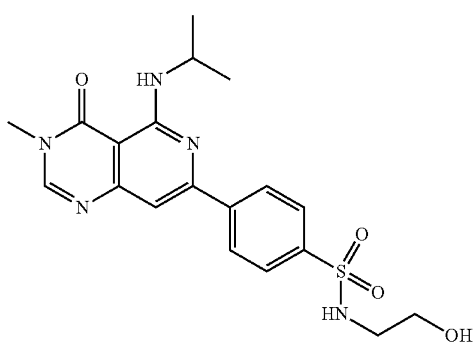 [SMILES: CC(C)Nc1nc(-c2ccc(S(=O)(=O)NCCO)cc2)cc2ncn(C)c(=O)c12] | ESI-MS m/z 418.1 (MH⁺) | 0.544 |
| 212 | 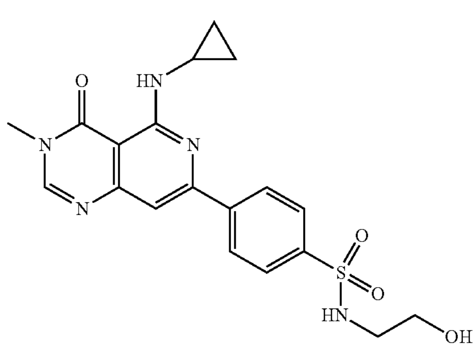 [SMILES: Cn1cnc2cc(-c3ccc(S(=O)(=O)NCCO)cc3)nc(NC3CC3)c2c1=O] | ESI-MS m/z 416.1 (MH⁺) | 0.222 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 213 | 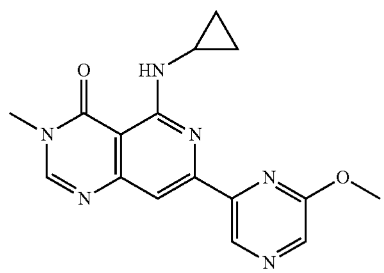 | ¹H NMR (400 MHz, DMSO-d₆) of the TFA salt of the compound: δ 0.59 (m, 2H), 0.89 (m, 2H), 3.09 (m, 1H), 3.46 (s, 3H), 4.06 (s, 3H), 7.62 (s, 1H), 8.41 (s, 1H), 8.50 (s, 1H), 8.86 (br s, 1H, NH), 9.20 (s, 1H);<br>ESI-MS m/z 325.1 (MH⁺) | 0.674 |
| 214 | 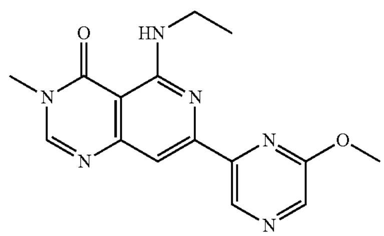 | ESI-MS m/z 313.1 (MH⁺) | 3.368 |
| 215 | 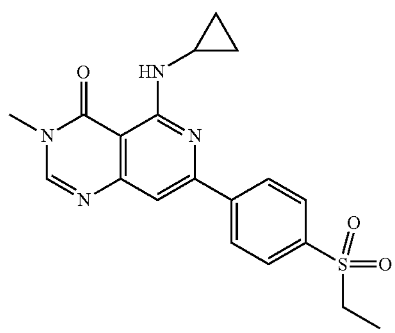 [SMILES: CCS(=O)(=O)c1ccc(-c2cc3ncn(C)c(=O)c3c(NC3CC3)n2)cc1] | ESI-MS m/z 385.1 (MH⁺) | 0.761 |
| 216 | 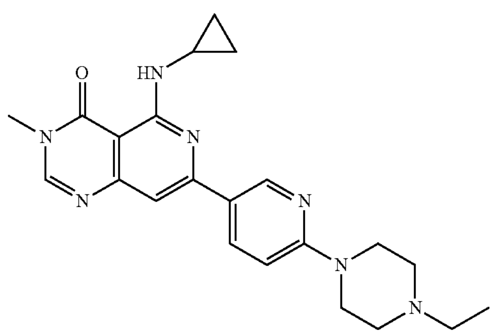 [SMILES: CCN1CCN(c2ccc(-c3cc4ncn(C)c(=O)c4c(NC4CC4)n3)cn2)CC1] | ESI-MS m/z 406.2 (MH⁺) | 0.158 |
| 217 | 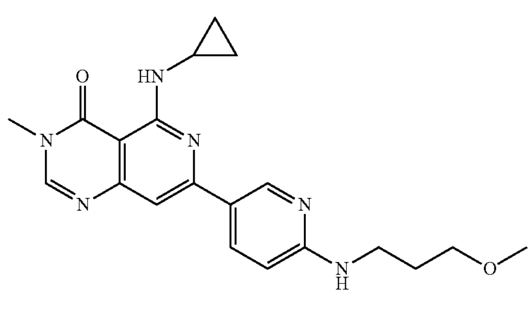 | ESI-MS m/z 381.2 (MH⁺) | 0.238 |

//
TABLE 1-continued
| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 218 | 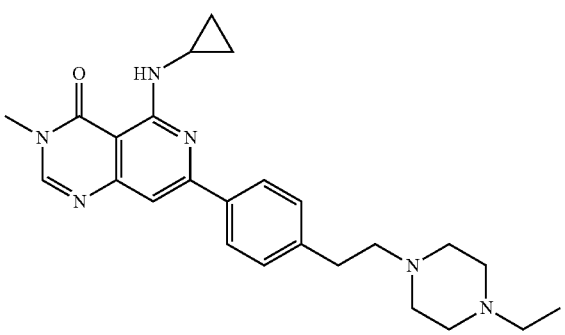 [SMILES: CCN1CCN(CCc2ccc(-c3cc4ncn(C)c(=O)c4c(NC4CC4)n3)cc2)CC1] | ESI-MS m/z 433.3 (MH⁺) | 0.265 |
| 219 | 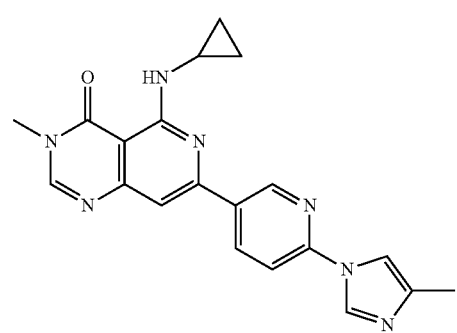 | ESI-MS m/z 374.2 (MH⁺) | 1.442 |
| 220 | 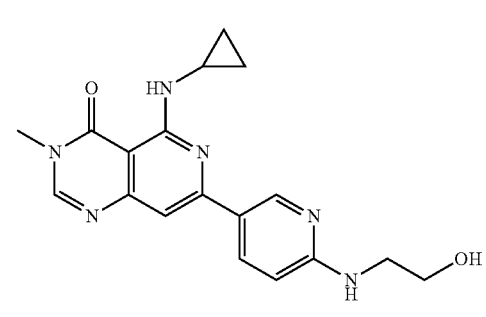 [SMILES: Cn1cnc2cc(-c3ccc(NCCO)nc3)nc(NC3CC3)c2c1=O] | ESI-MS m/z 353.2 (MH⁺) | 0.135 |
| 221 | 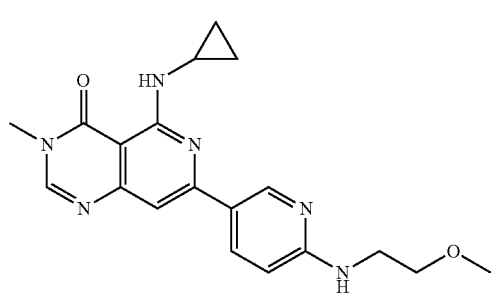 | ¹H NMR (400 MHz, DMSO-d₆) of the TFA salt of the compound: δ 0.56 (m, 2H), 0.86 (m, 2H), 3.01 (m, 1H), 3.31 (s, 3H), 3.43 (s, 3H), 3.56-3.58 (4H), 7.03 (d, J = 9.2 Hz, 1H), 7.23 (s, 1H), 8.44 (s, 1H), 8.51 (d, J = 9.2 Hz, 1H) 8.73 (s, 1H), 8.86 (br s, 1H, NH); ESI-MS m/z 367.2 (MH⁺) | 0.21 |

TABLE 1-continued

| Compound Number | Structure | Physical Data<br>¹H NMR 400 MHz (CDCl₃),<br>HPLC Retention Time, and/or<br>MS (m/z) | Syk Enzyme IC₅₀ (uM) |
|---|---|---|---|
| 222 | 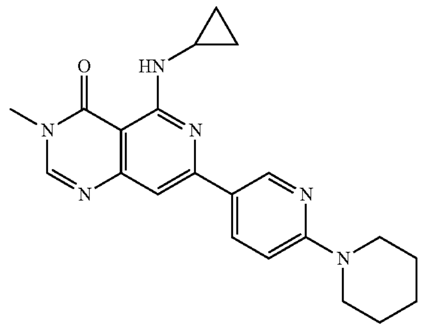 [SMILES: Cn1cnc2cc(-c3ccc(N4CCCCC4)nc3)nc(NC3CC3)c2c1=O] | ESI-MS m/z 377.2 (MH⁺) | 0.765 |
| 223 | 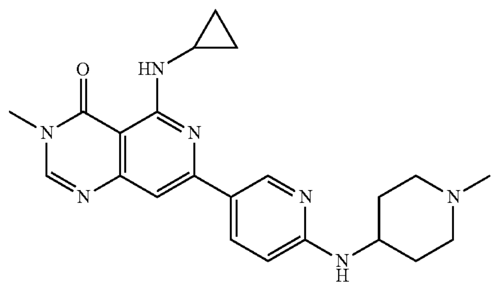 | ESI-MS m/z 406.2 (MH⁺) | 0.232 |
| 224 | 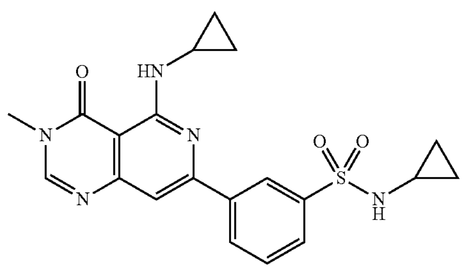 [SMILES: Cn1cnc2cc(-c3cccc(S(=O)(=O)NC4CC4)c3)nc(NC3CC3)c2c1=O] | ESI-MS m/z 412.1 (MH⁺) | 0.366 |
| 225 | 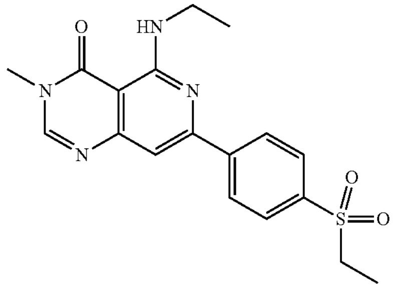 [SMILES: CCNc1nc(-c2ccc(S(=O)(=O)CC)cc2)cc2ncn(C)c(=O)c12] | ESI-MS m/z 373.1 (MH⁺) | 0.362 |
| 226 | 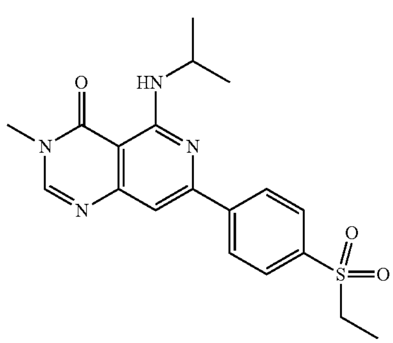 [SMILES: CCS(=O)(=O)c1ccc(-c2cc3ncn(C)c(=O)c3c(NC(C)C)n2)cc1] | ESI-MS m/z 387.1 (MH⁺) | 0.685 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 227 | 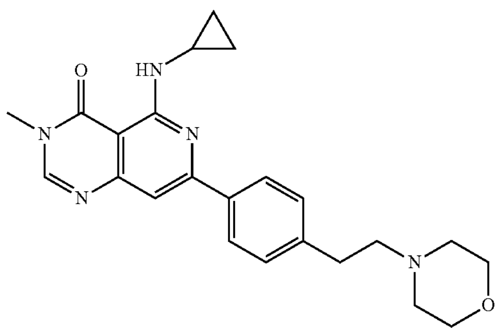 [SMILES: Cn1cnc2cc(-c3ccc(CCN4CCOCC4)cc3)nc(NC3CC3)c2c1=O] | ESI-MS m/z 406.2 (MH⁺) | 0.23 |
| 228 | 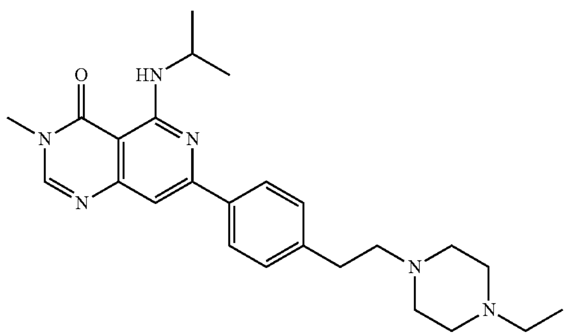 [SMILES: CCN1CCN(CCc2ccc(-c3cc4ncn(C)c(=O)c4c(NC(C)C)n3)cc2)CC1] | ESI-MS m/z 435.3 (MH⁺) | 0.269 |
| 229 | 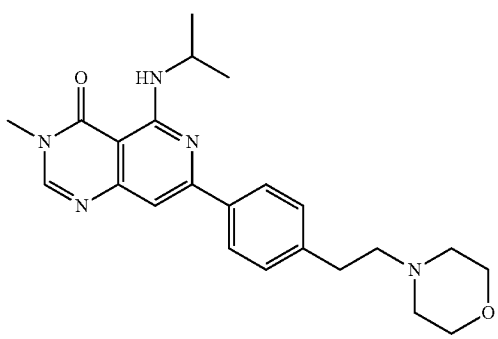 [SMILES: CC(C)Nc1nc(-c2ccc(CCN3CCOCC3)cc2)cc2ncn(C)c(=O)c12] | ESI-MS m/z 408.2 (MH⁺) | 0.38 |
| 230 | 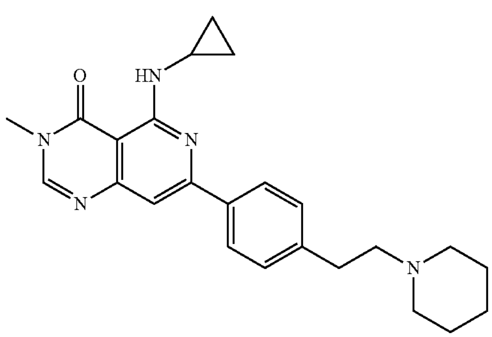 [SMILES: Cn1cnc2cc(-c3ccc(CCN4CCCCC4)cc3)nc(NC3CC3)c2c1=O] | ESI-MS m/z 404.2 (MH⁺) | 0.141 |

TABLE 1-continued

| Compound Number | Structure | Physical Data<br>$^1$H NMR 400 MHz (CDCl$_3$),<br>HPLC Retention Time, and/or<br>MS (m/z) | Syk Enzyme IC$_{50}$ (uM) |
|---|---|---|---|
| 231 | 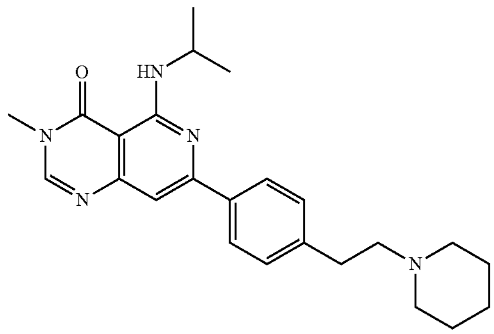 [SMILES: CC(C)Nc1nc(-c2ccc(CCN3CCCCC3)cc2)cc2ncn(C)c(=O)c12] | ESI-MS m/z 406.3 (MH$^+$) | 0.143 |
| 232 | 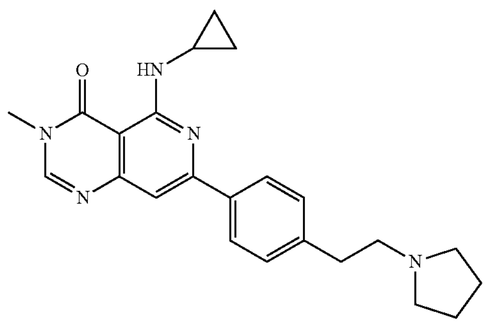 [SMILES: Cn1cnc2cc(-c3ccc(CCN4CCCC4)cc3)nc(NC3CC3)c2c1=O] | ESI-MS m/z 390.2 (MH$^+$) | 0.139 |
| 233 | 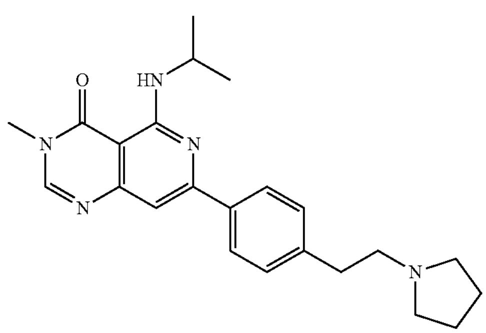 [SMILES: CC(C)Nc1nc(-c2ccc(CCN3CCCC3)cc2)cc2ncn(C)c(=O)c12] | ESI-MS m/z 392.2 (MH$^+$) | 0.101 |
| 234 | 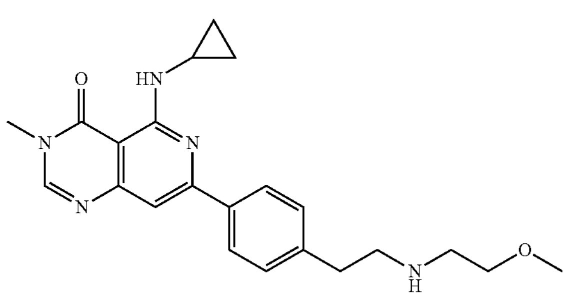 | ESI-MS m/z 394.2 (MH$^+$) | 0.156 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
| --- | --- | --- | --- |
| 235 | 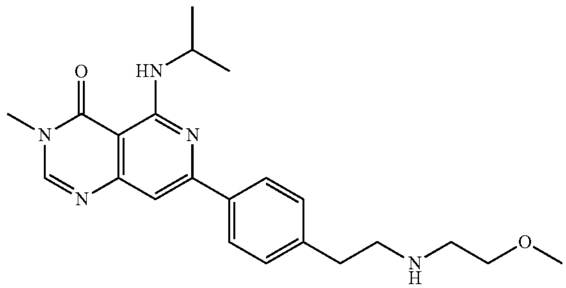 | ESI-MS m/z 396.2 (MH⁺) | 0.135 |
| 236 | 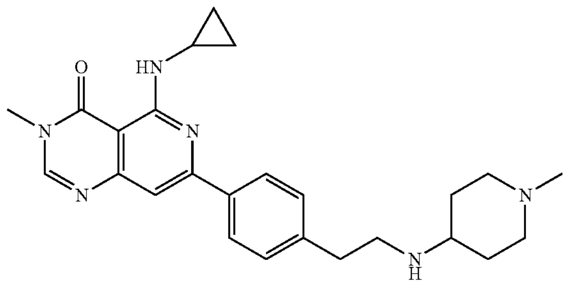 | ESI-MS m/z 433.3 (MH⁺) | 0.146 |
| 237 | 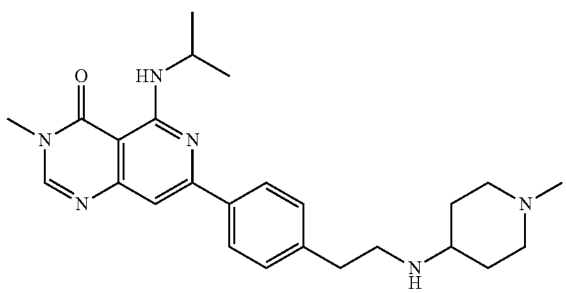 | ESI-MS m/z 435.3 (MH⁺) | 0.177 |
| 238 | 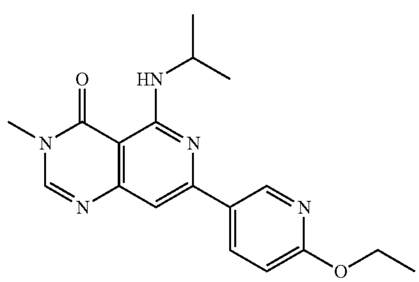 [SMILES: CCOc1ccc(-c2cc3ncn(C)c(=O)c3c(NC(C)C)n2)cn1] | ESI-MS m/z 340.2 (MH⁺) | 0.977 |
| 239 | 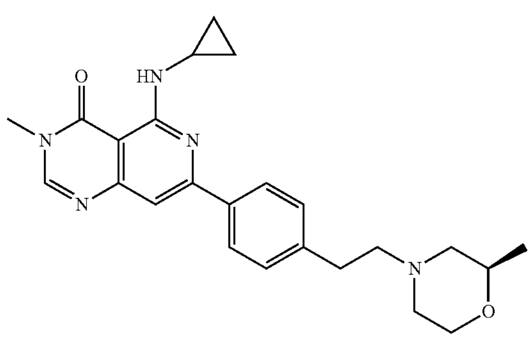 | ESI-MS m/z 420.2 (MH⁺) | 0.403 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 240 | 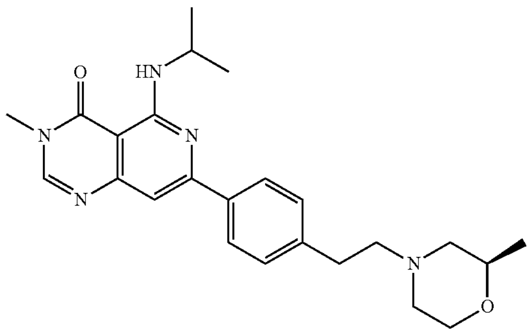 | ESI-MS m/z 422.2 (MH⁺) | 0.525 |
| 241 | 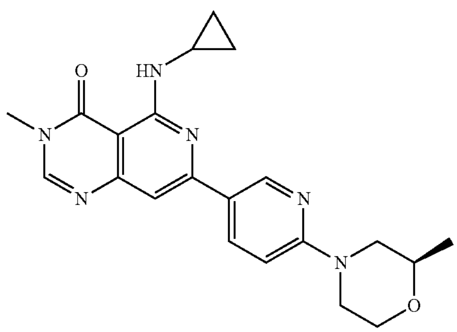 | ESI-MS m/z 393.2 (MH⁺) | 0.411 |
| 242 | 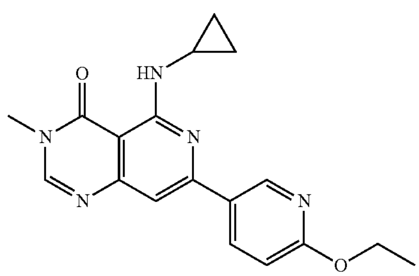 [SMILES: CCOc1ccc(-c2cc3ncn(C)c(=O)c3c(NC3CC3)n2)cn1] | ESI-MS m/z 339.2 (MH⁺) | 1.372 |
| 243 | 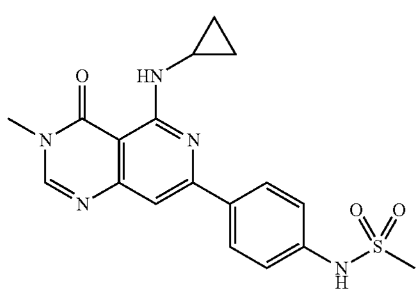 | ¹H NMR (400 MHz, DMSO-d₆) of the TFA salt of the compound: δ 0.57 (m, 2H), 0.87 (m, 2H), 3.07 (s, 3H), 3.08 (m, 1H), 3.43 (s, 3H), 7.21 (s, 1H), 7.31 (d, J = 8.8 Hz, 2H), 8.20 (d, J = 8.8 Hz, 2H), 8.44 (s, 1H), 8.79 (br s, 1H, NH); ESI-MS m/z 386.1 (MH⁺) | 0.345 |
| 244 | 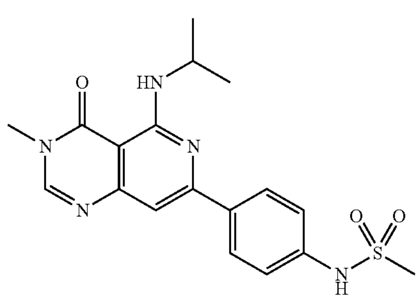 | ESI-MS m/z 388.1 (MH⁺) | 0.62 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 245 | 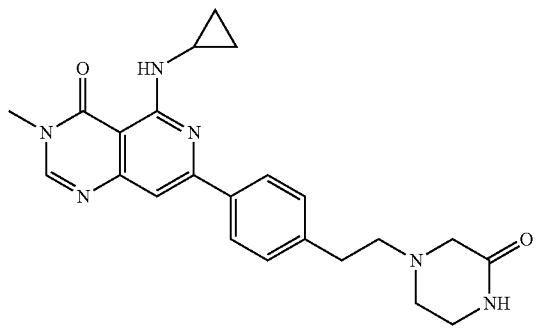 [SMILES: Cn1cnc2cc(-c3ccc(CCN4CCNC(=O)C4)cc3)nc(NC3CC3)c2c1=O] | ESI-MS m/z 419.2 (MH⁺) | 0.225 |
| 246 | 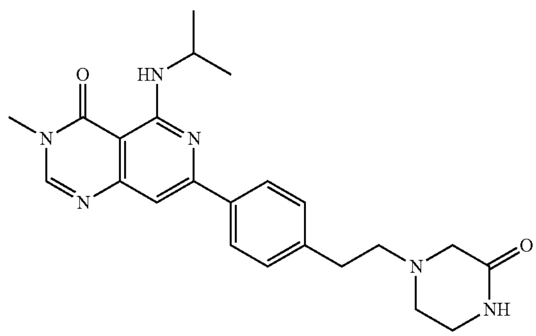 [SMILES: CC(C)Nc1nc(-c2ccc(CCN3CCNC(=O)C3)cc2)cc2ncn(C)c(=O)c12] | ESI-MS m/z 421.2 (MH⁺) | 0.288 |
| 247 | 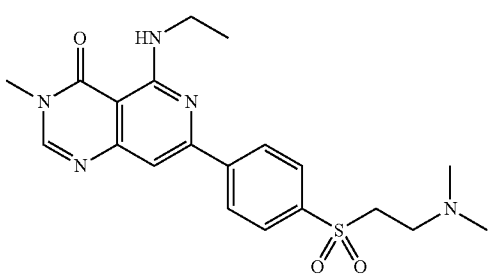 | ESI-MS m/z 416.2 (MH⁺) | 0.286 |
| 248 | 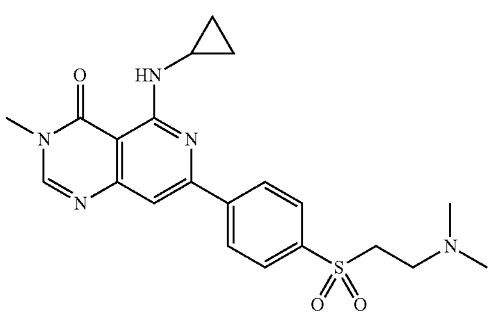 | ¹H NMR (400 MHz, DMSO-d₆) of the TFA salt of the compound: δ 0.53 (m, 2H), 0.81 (m, 2H), 2.72 (s, 6H), 3.00 (s, 3H), 3.32 (m, 2H), 3.39 (s, 3H), 3.83 (m, 2H), 7.36 (s, 1H), 7.98 (d, J = 8.8 Hz, 2H), 8.44 (d, J = 8.8 Hz, 2H), 8.48 (s, 1H), 8.79 (br s, 1H, NH);<br>ESI-MS m/z 428.2 (MH⁺) | 0.281 |

US 8,722,692 B2

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 249 | 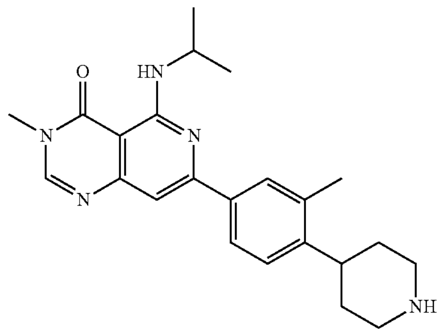 [SMILES: Cc1cc(-c2cc3ncn(C)c(=O)c3c(NC(C)C)n2)ccc1C1CCNCC1] | ESI-MS m/z 392.2 (MH⁺) | 0.089 |
| 250 | 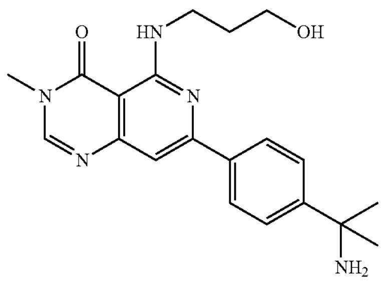 [SMILES: Cn1cnc2cc(-c3ccc(C(C)(C)N)cc3)nc(NCCCO)c2c1=O] | ESI-MS m/z 368.2 (MH⁺) | 0.1 |
| 251 | 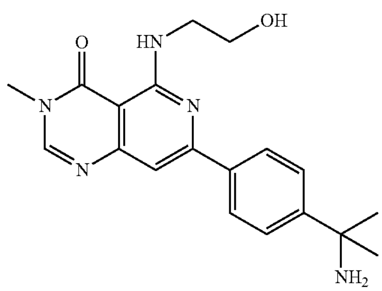 [SMILES: Cn1cnc2cc(-c3ccc(C(C)(C)N)cc3)nc(NCCO)c2c1=O] | ESI-MS m/z 354.2 (MH⁺) | 0.2 |
| 252 | 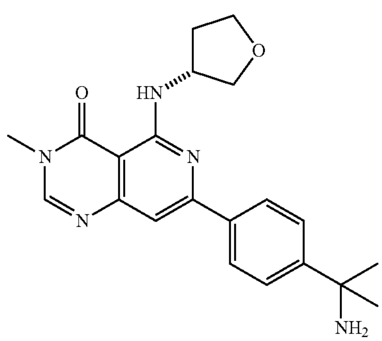 | ESI-MS m/z 380.2 (MH⁺) | 0.133 |
| 253 | 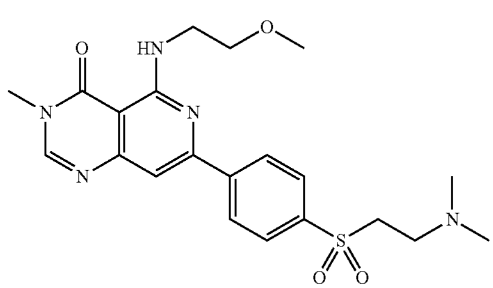 | ESI-MS m/z 446.2 (MH⁺) | 0.426 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 254 | 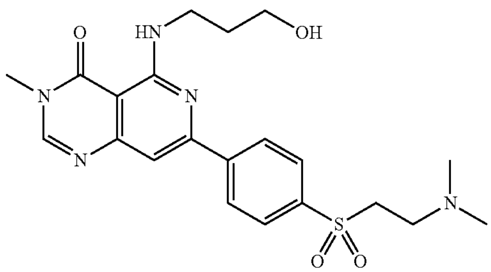 | ESI-MS m/z 446.2 (MH⁺) | 0.245 |
| 255 | 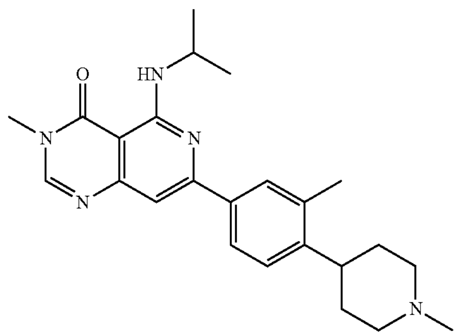 | ESI-MS m/z 406.3 (MH⁺) | 0.11 |
| 256 | 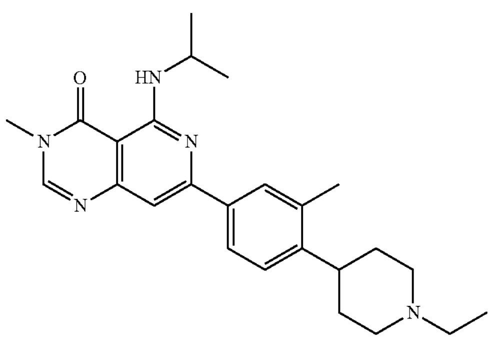 [SMILES: CCN1CCC(c2ccc(-c3cc4ncn(C)c(=O)c4c(NC(C)C)n3)cc2C)CC1] | ESI-MS m/z 420.3 (MH⁺) | 0.176 |
| 257 | 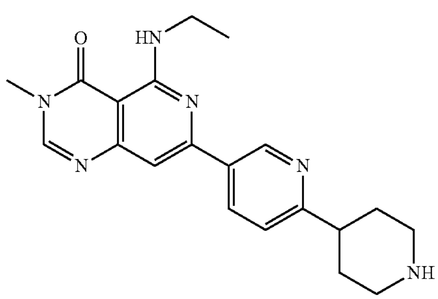 [SMILES: CCNc1nc(-c2ccc(C3CCNCC3)nc2)cc2ncn(C)c(=O)c12] | ESI-MS m/z 365.2 (MH⁺) | 0.18 |
| 258 | 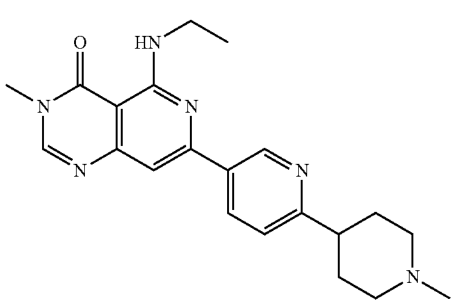 | ESI-MS m/z 379.2 (MH⁺) | 0.938 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 259 | 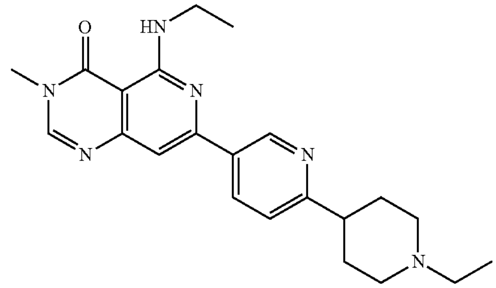 [SMILES: CCNc1nc(-c2ccc(C3CCN(CC)CC3)nc2)cc2ncn(C)c(=O)c12] | ESI-MS m/z 393.2 (MH⁺) | 0.925 |
| 260 | 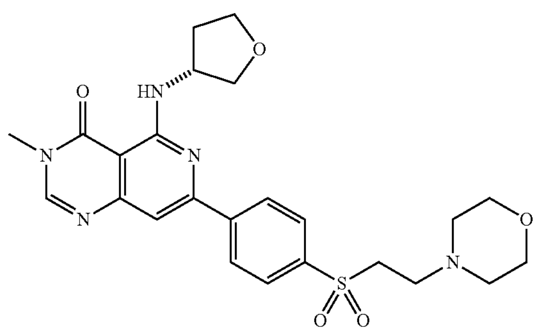 | ESI-MS m/z 490.2 (MH⁺) | 0.097 |
| 261 | 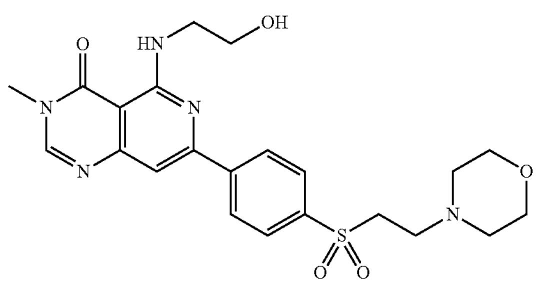 [SMILES: Cn1cnc2cc(-c3ccc(S(=O)(=O)CCN4CCOCC4)cc3)nc(NCCO)c2c1=O] | ESI-MS m/z 474.2 (MH⁺) | 0.168 |
| 262 | 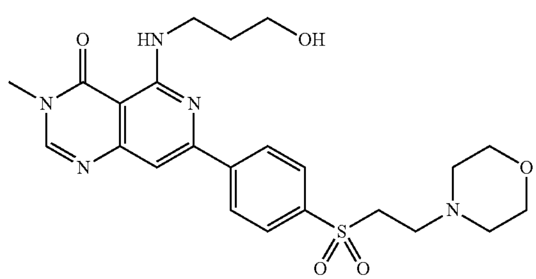 [SMILES: Cn1cnc2cc(-c3ccc(S(=O)(=O)CCN4CCOCC4)cc3)nc(NCCCO)c2c1=O] | ESI-MS m/z 488.2 (MH⁺) | 0.112 |
| 263 | 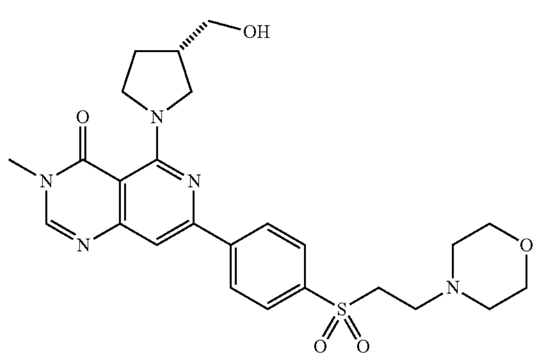 [SMILES: Cn1cnc2cc(-c3ccc(S(=O)(=O)CCN4CCOCC4)cc3)nc(N3CC[C@H](CO)C3)c2c1=O] | ESI-MS m/z 514.2 (MH⁺) | 0.083 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 264 | 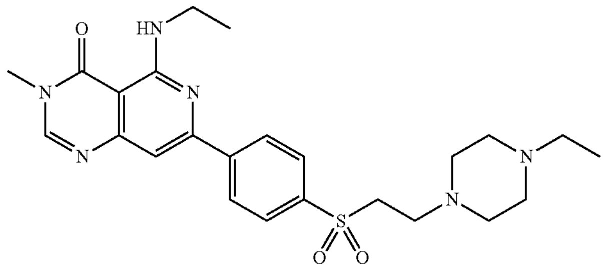 [SMILES: CCNc1nc(-c2ccc(S(=O)(=O)CCN3CCN(CC)CC3)cc2)cc2ncn(C)c(=O)c12] | ESI-MS m/z 485.2 (MH⁺) | 0.689 |
| 265 | 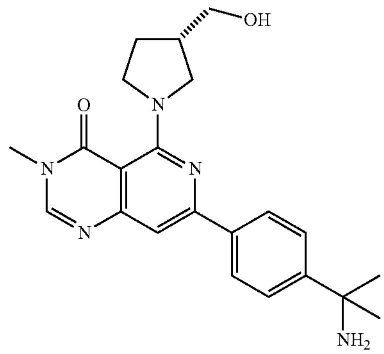 [SMILES: Cn1cnc2cc(-c3ccc(C(C)(C)N)cc3)nc(N3CC[C@H](CO)C3)c2c1=O] | ESI-MS m/z 394.2 (MH⁺) | 0.102 |
| 266 | 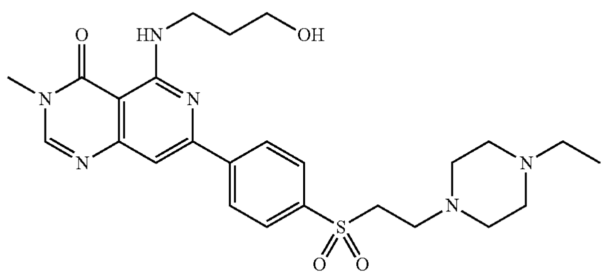 [SMILES: CCN1CCN(CCS(=O)(=O)c2ccc(-c3cc4ncn(C)c(=O)c4c(NCCCO)n3)cc2)CC1] | ESI-MS m/z 515.2 (MH⁺) | 0.694 |
| 267 | 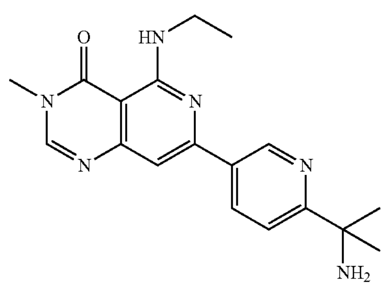 [SMILES: CCNc1nc(-c2ccc(C(C)(C)N)nc2)cc2ncn(C)c(=O)c12] | ESI-MS m/z 339.2 (MH⁺) | 0.269 |
| 268 | 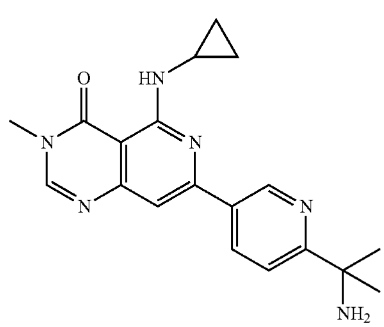 [SMILES: Cn1cnc2cc(-c3ccc(C(C)(C)N)nc3)nc(NC3CC3)c2c1=O] | ESI-MS m/z 351.2 (MH⁺) | 0.46 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 269 | 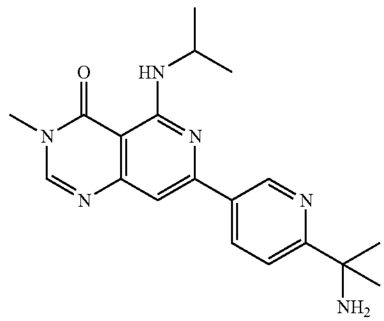 [SMILES: CC(C)Nc1nc(-c2ccc(C(C)(C)N)nc2)cc2ncn(C)c(=O)c12] | ESI-MS m/z 353.2 (MH⁺) | 0.387 |
| 270 | 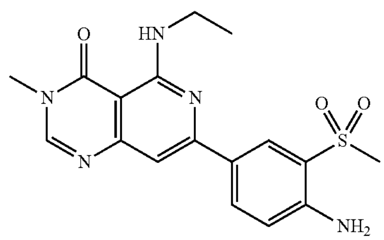 | ESI-MS m/z 374.1 (MH⁺) | 0.496 |
| 271 | 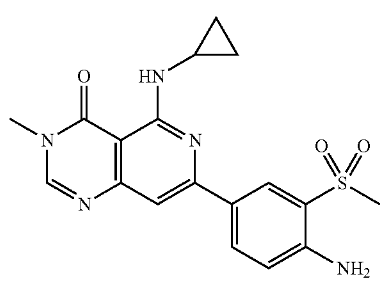 | ESI-MS m/z 386.1 (MH⁺) | 0.246 |
| 272 | 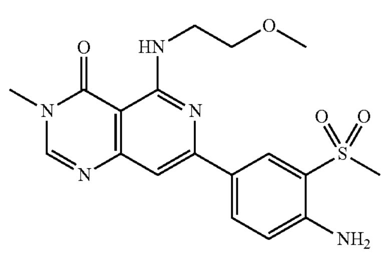 | ESI-MS m/z 404.1 (MH⁺) | 0.21 |
| 273 | 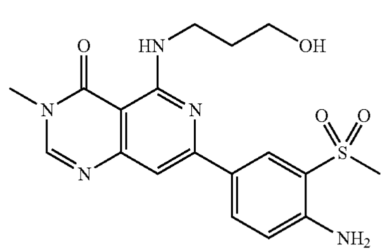 | ESI-MS m/z 404.1 (MH⁺) | 0.248 |

US 8,722,692 B2
239                                                                                                     240
TABLE 1-continued
| Compound Number | Structure | Physical Data<br>$^1$H NMR 400 MHz (CDCl$_3$),<br>HPLC Retention Time, and/or<br>MS (m/z) | Syk<br>Enzyme<br>IC$_{50}$ (uM) |
|---|---|---|---|
| 274 | 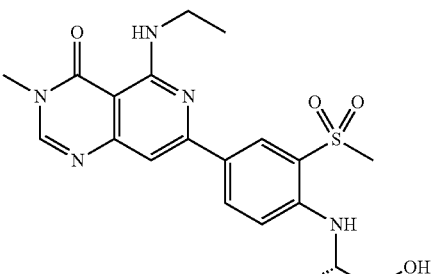 | ESI-MS m/z 432.2 (MH$^+$) | 0.132 |
| 275 | 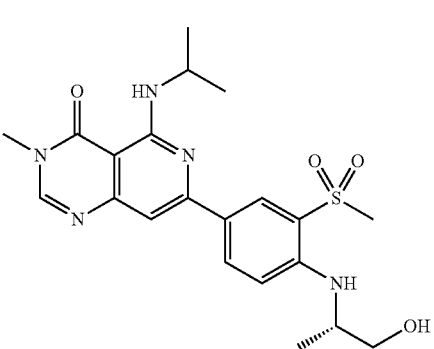 [SMILES: CC(C)Nc1nc(-c2ccc(N[C@@H](C)CO)c(S(C)(=O)=O)c2)cc2ncn(C)c(=O)c12] | ESI-MS m/z 446.2 (MH$^+$) | 0.564 |
| 276 | 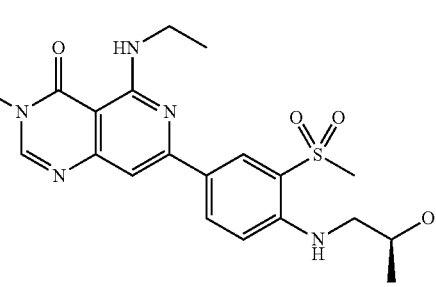 | ESI-MS m/z 432.2 (MH$^+$) | 0.066 |
| 277 | 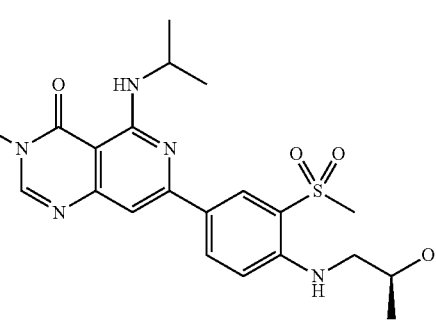 | ESI-MS m/z 446.2 (MH$^+$) | 0.161 |
| 278 | 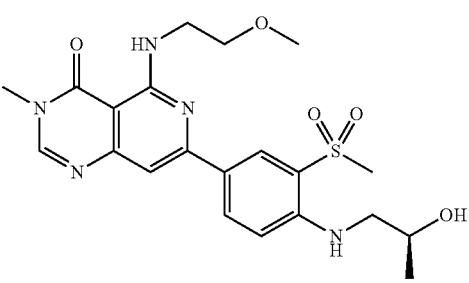 [SMILES: COCCNc1nc(-c2ccc(NC[C@H](C)O)c(S(C)(=O)=O)c2)cc2ncn(C)c(=O)c12] | ESI-MS m/z 462.2 (MH$^+$) | 0.194 |

TABLE 1-continued
| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 279 | 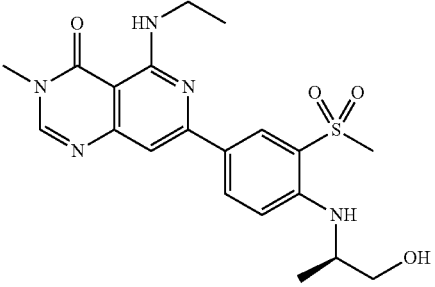 [SMILES: CCNc1nc(-c2ccc(N[C@H](C)CO)c(S(C)(=O)=O)c2)cc2ncn(C)c(=O)c12] | ESI-MS m/z 432.2 (MH⁺) | 0.137 |
| 280 | 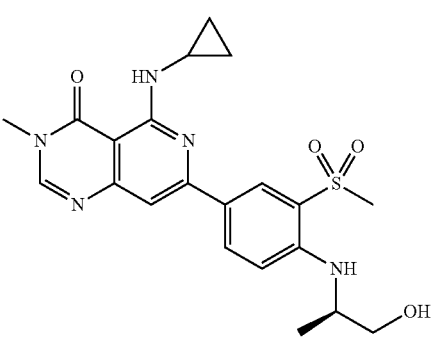 [SMILES: C[C@H](CO)Nc1ccc(-c2cc3ncn(C)c(=O)c3c(NC3CC3)n2)cc1S(C)(=O)=O] | ESI-MS m/z 444.2 (MH⁺) | 0.097 |
| 281 | 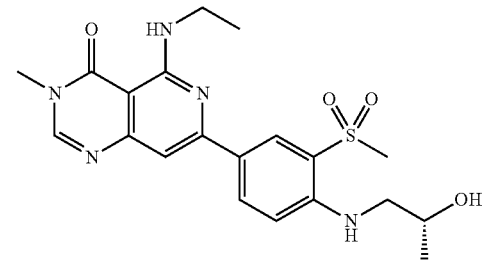 | ESI-MS m/z 432.2 (MH⁺) | 0.088 |
| 282 | 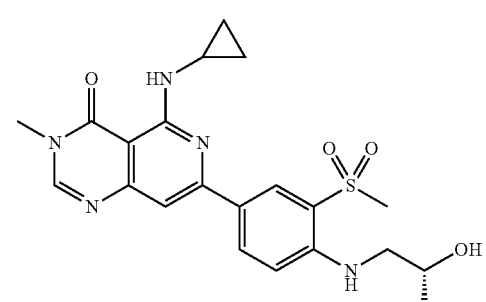 | ESI-MS m/z 444.2 (MH⁺) | 0.168 |
| 283 | 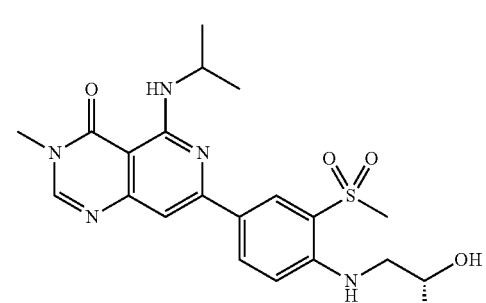 | ESI-MS m/z 446.2 (MH⁺) | 0.277 |

TABLE 1-continued
| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 284 | 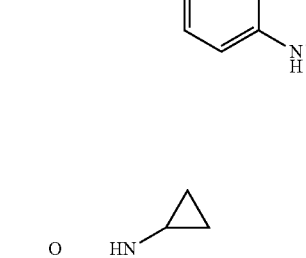 | ESI-MS m/z 462.2 (MH⁺) | 0.086 |
| 285 | 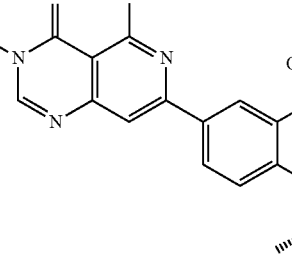 | ESI-MS m/z 444.2 (MH⁺) | 0.875 |
| 286 | 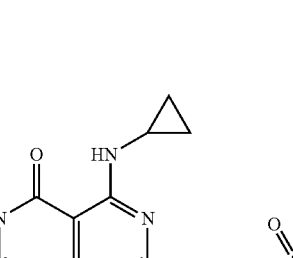 | ESI-MS m/z 444.2 (MH⁺) | 0.168 |
| 287 | 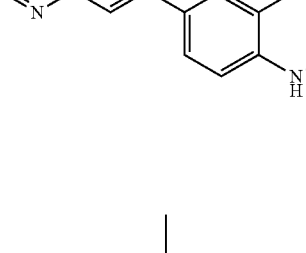 | ESI-MS m/z 446.2 (MH⁺) | 0.357 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 288 | 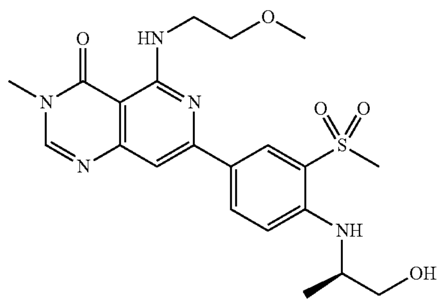 [SMILES: COCCNc1nc(-c2ccc(N[C@H](C)CO)c(S(C)(=O)=O)c2)cc2ncn(C)c(=O)c12] | ESI-MS m/z 462.2 (MH$^+$) | 0.277 |
| 289 | 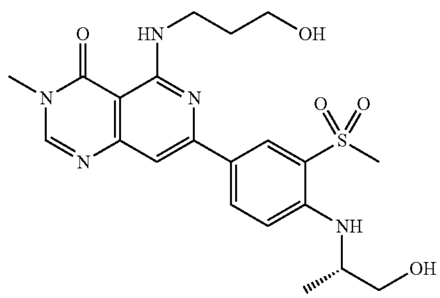 [SMILES: C[C@@H](CO)Nc1ccc(-c2cc3ncn(C)c(=O)c3c(NCCCO)n2)cc1S(C)(=O)=O] | ESI-MS m/z 462.2 (MH$^+$) | 0.287 |
| 290 | 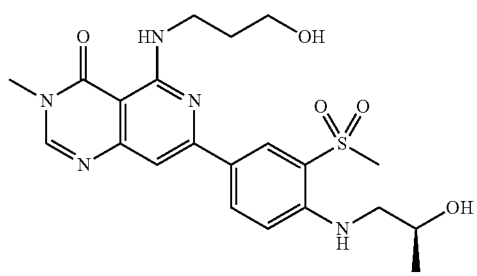 [SMILES: C[C@H](O)CNc1ccc(-c2cc3ncn(C)c(=O)c3c(NCCCO)n2)cc1S(C)(=O)=O] | ESI-MS m/z 462.2 (MH$^+$) | 0.162 |
| 291 | 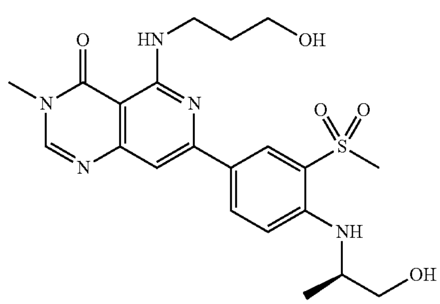 [SMILES: C[C@H](CO)Nc1ccc(-c2cc3ncn(C)c(=O)c3c(NCCCO)n2)cc1S(C)(=O)=O] | ESI-MS m/z 462.2 (MH$^+$) | 0.222 |
| 292 | 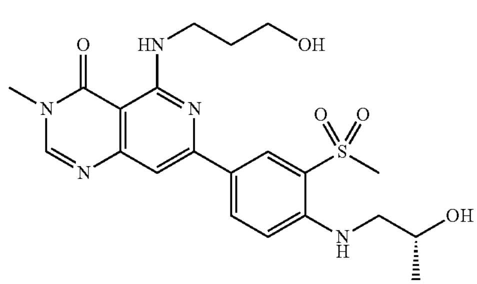 [SMILES: C[C@@H](O)CNc1ccc(-c2cc3ncn(C)c(=O)c3c(NCCCO)n2)cc1S(C)(=O)=O] | ESI-MS m/z 462.2 (MH$^+$) | 0.255 |

TABLE 1-continued

| Compound Number | Structure | Physical Data ¹H NMR 400 MHz (CDCl$_3$), HPLC Retention Time, and/or MS (m/z) | Syk Enzyme IC$_{50}$ (uM) |
|---|---|---|---|
| 293 | 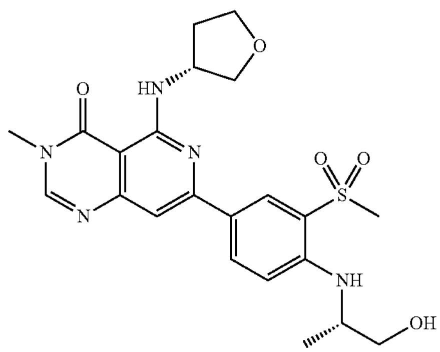 [SMILES: C[C@@H](CO)Nc1ccc(-c2cc3ncn(C)c(=O)c3c(N[C@@H]3CCOC3)n2)cc1S(C)(=O)=O] | ESI-MS m/z 474.2 (MH$^+$) | 0.037 |
| 294 | 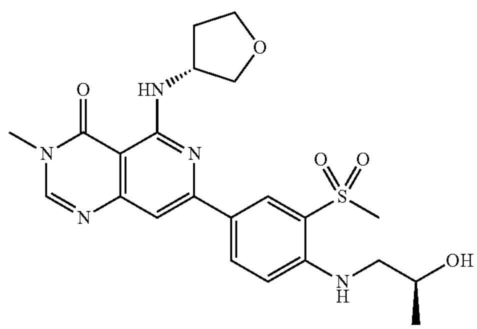 [SMILES: C[C@H](O)CNc1ccc(-c2cc3ncn(C)c(=O)c3c(N[C@@H]3CCOC3)n2)cc1S(C)(=O)=O] | ESI-MS m/z 474.2 (MH$^+$) | 0.027 |
| 295 | 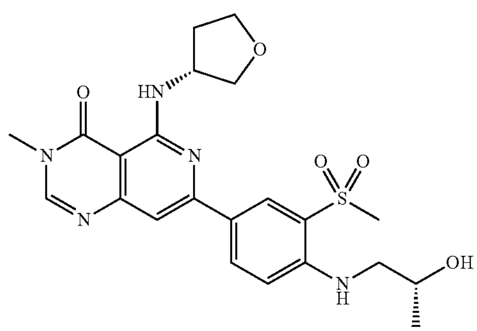 [SMILES: C[C@@H](O)CNc1ccc(-c2cc3ncn(C)c(=O)c3c(N[C@@H]3CCOC3)n2)cc1S(C)(=O)=O] | ESI-MS m/z 474.2 (MH$^+$) | 0.045 |
| 296 | 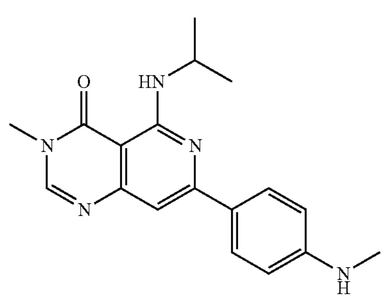 | ESI-MS m/z 324.20 (MH$^+$) | 0.927 |
| 297 | 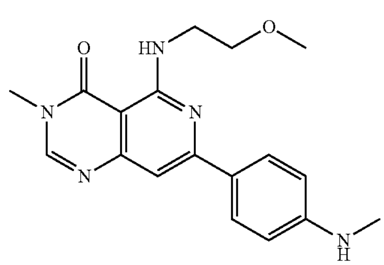 | ESI-MS m/z 340.2 (MH$^+$) | 0.317 |

TABLE 1-continued
| Compound Number | Structure | Physical Data<br>$^1$H NMR 400 MHz (CDCl$_3$),<br>HPLC Retention Time, and/or<br>MS (m/z) | Syk Enzyme IC$_{50}$ (uM) |
|---|---|---|---|
| 298 | 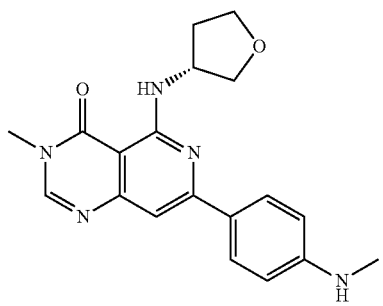 | ESI-MS m/z 352.2 (MH$^+$) | 0.093 |
| 299 | 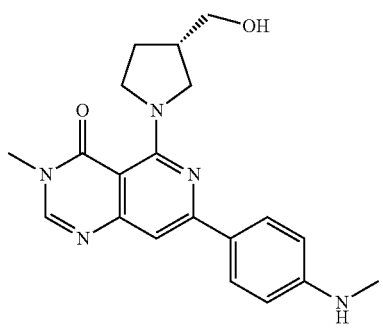 | $^1$H NMR (400 MHz, DMSO-d$_6$) of the HCl salt of the compound: δ 1.66 (m, 1H), 1.99 (m, 1H), 2.53 (m, 1H), 2.82 (s, 3H), 3.84-3.76 (5H), 3.48 (s, 3H), 7.02 (d, J = 8.4 Hz, 2H), 7.72 (s, 1H), 8.01 (d, J = 8.4 Hz, 2H), 8.99 (s, 1H); ESI-MS m/z 366.2 (MH$^+$) | 0.165 |
| 300 | 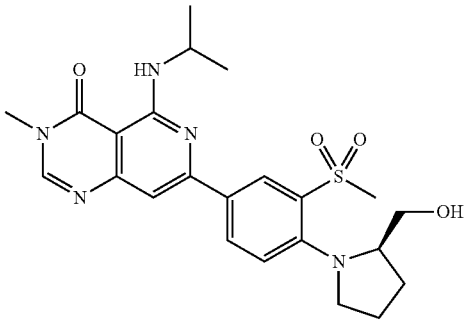 [SMILES: CC(C)Nc1nc(-c2ccc(N3CCC[C@@H]3CO)c(S(C)(=O)=O)c2)cc2ncn(C)c(=O)c12] | ESI-MS m/z 472.2 (MH$^+$) | 0.24 |
| 301 | 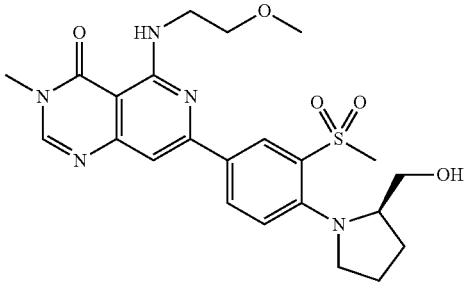 [SMILES: COCCNc1nc(-c2ccc(N3CCC[C@@H]3CO)c(S(C)(=O)=O)c2)cc2ncn(C)c(=O)c12] | ESI-MS m/z 488.2 (MH$^+$) | 0.109 |

TABLE 1-continued

| Compound Number | Structure | Physical Data <br> ¹H NMR 400 MHz (CDCl₃), HPLC Retention Time, and/or MS (m/z) | Syk Enzyme IC$_{50}$ (uM) |
|---|---|---|---|
| 302 | 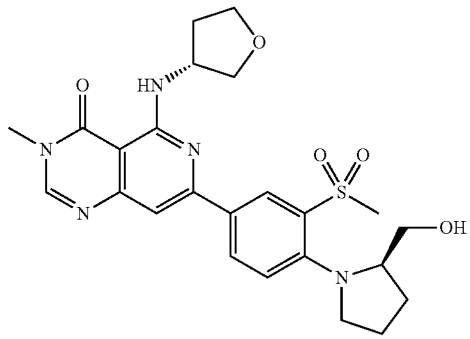 [SMILES: Cn1cnc2cc(-c3ccc(N4CCC[C@@H]4CO)c(S(C)(=O)=O)c3)nc(N[C@@H]3CCOC3)c2c1=O] | ESI-MS m/z 500.2 (MH⁺) | 0.048 |
| 303 | 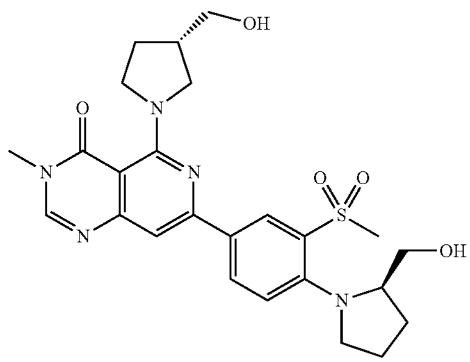 [SMILES: Cn1cnc2cc(-c3ccc(N4CCC[C@@H]4CO)c(S(C)(=O)=O)c3)nc(N3CC[C@H](CO)C3)c2c1=O] | ESI-MS m/z 514.2 (MH⁺) | 0.122 |
| 304 | 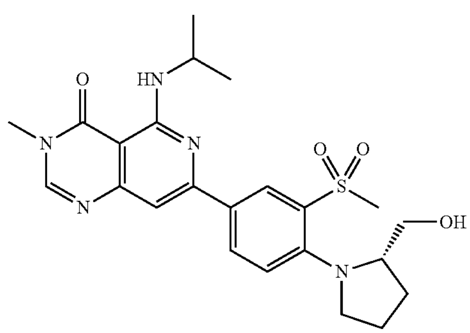 [SMILES: CC(C)Nc1nc(-c2ccc(N3CCC[C@H]3CO)c(S(C)(=O)=O)c2)cc2ncn(C)c(=O)c12] | ESI-MS m/z 472.2 (MH⁺) | 0.217 |
| 305 | 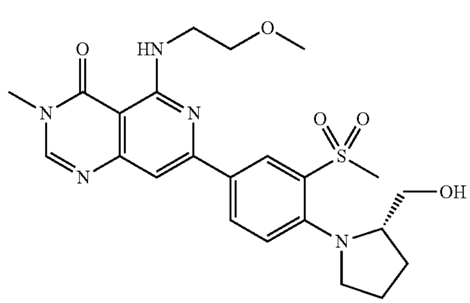 [SMILES: COCCNc1nc(-c2ccc(N3CCC[C@H]3CO)c(S(C)(=O)=O)c2)cc2ncn(C)c(=O)c12] | ESI-MS m/z 488.2 (MH⁺) | 0.064 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 306 | 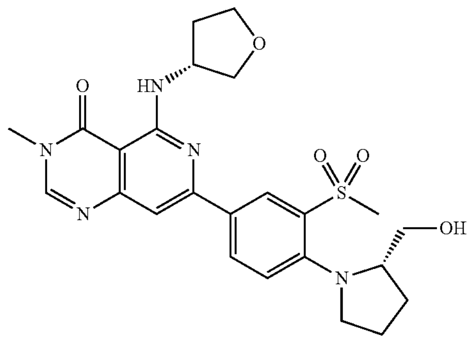 [SMILES: Cn1cnc2cc(-c3ccc(N4CCC[C@H]4CO)c(S(C)(=O)=O)c3)nc(N[C@@H]3CCOC3)c2c1=O] | ESI-MS m/z 500.2 (MH⁺) | 0.062 |
| 307 | 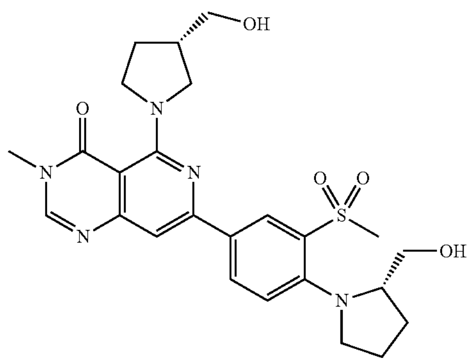 [SMILES: Cn1cnc2cc(-c3ccc(N4CCC[C@H]4CO)c(S(C)(=O)=O)c3)nc(N3CC[C@H](CO)C3)c2c1=O] | ESI-MS m/z 514.2 (MH⁺) | 0.162 |
| 308 | 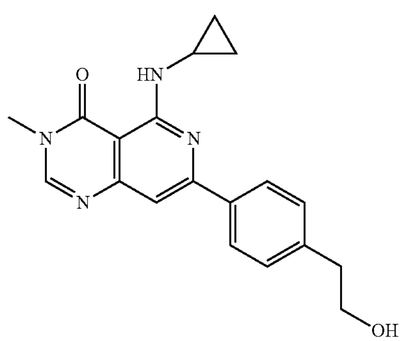 [SMILES: Cn1cnc2cc(-c3ccc(CCO)cc3)nc(NC3CC3)c2c1=O] | ¹H NMR (400 MHz, DMSO-d₆) of the TFA salt of the compound: δ 0.56 (m, 2H), 0.85 (m, 2H), 2.79 (m, 2H), 3.06 (m, 1H), 3.42 (s, 3H), 3.65 (m, 2H), 4.64 (m, 1H, OH), 7.20 (s, 1H), 7.33 (d, J = 8.4 Hz, 2H), 8.12 (d, J = 8.4 Hz, 2H), 8.41 (s, 1H), 8.77 (br s, 1H, NH); ESI-MS m/z 337.2 (MH⁺) | 0.289 |
| 309 | 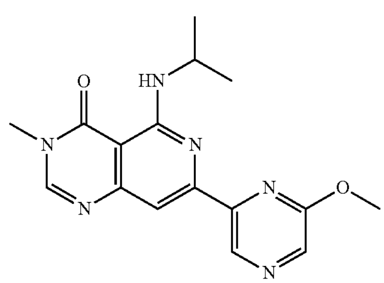 | ESI-MS m/z 327.1 (MH⁺) | 5.783 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 310 | 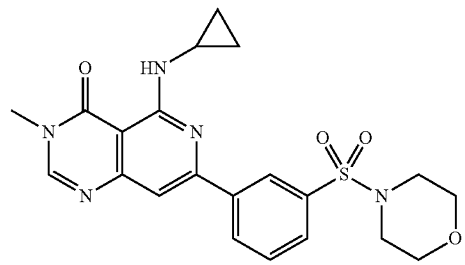 [SMILES: Cn1cnc2cc(-c3cccc(S(=O)(=O)N4CCOCC4)c3)nc(NC3CC3)c2c1=O] | ESI-MS m/z 442.1 (MH⁺) | 4.962 |
| 311 | 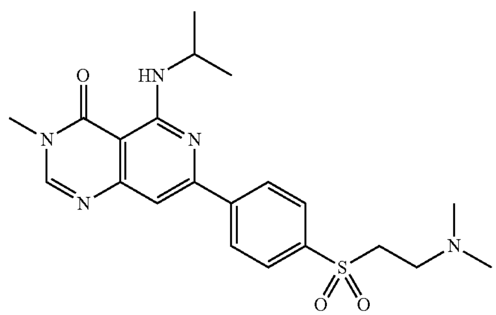 | ESI-MS m/z 430.2 (MH⁺) | 0.316 |
| 312 | 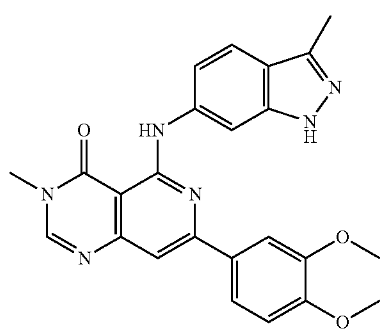 | ESI-MS m/z 443.2 (MH⁺) | 0.907 |
| 313 | 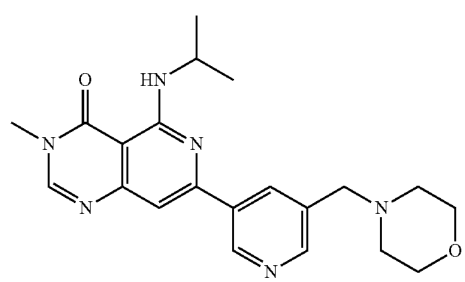 [SMILES: CC(C)Nc1nc(-c2cncc(CN3CCOCC3)c2)cc2ncn(C)c(=O)c12] | ESI-MS m/z 395.2 (MH⁺) | 0.771 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 314 | 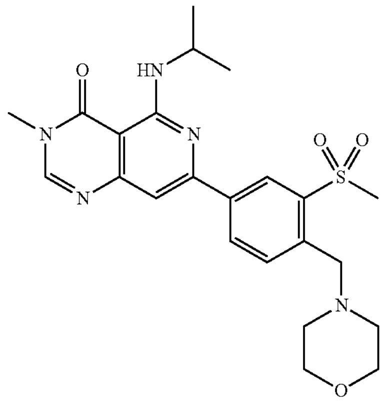 | ESI-MS m/z 472.2 (MH⁺) | 0.183 |
| 315 | 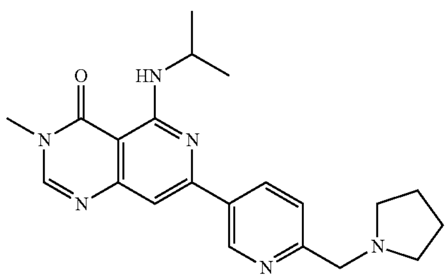 [SMILES: CC(C)Nc1nc(-c2ccc(CN3CCCC3)nc2)cc2ncn(C)c(=O)c12] | ESI-MS m/z 379.2 (MH⁺) | 0.262 |
| 316 | 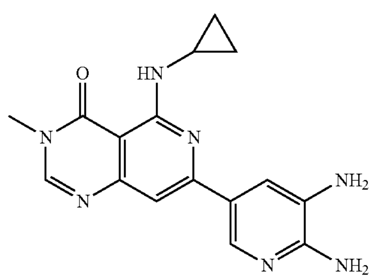 [SMILES: Cn1cnc2cc(-c3cnc(N)c(N)c3)nc(NC3CC3)c2c1=O] | ESI-MS m/z 324.1 (MH⁺) | 0.198 |
| 317 | 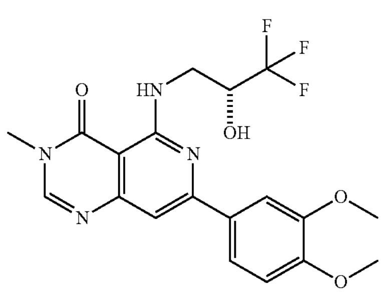 | ESI-MS m/z 424.1 (MH⁺) | >50 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 318 | 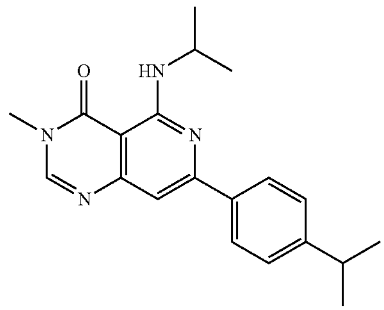 [SMILES: CC(C)Nc1nc(-c2ccc(C(C)C)cc2)cc2ncn(C)c(=O)c12] | ESI-MS m/z 337.2 (MH⁺) | 9.34 |
| 319 | 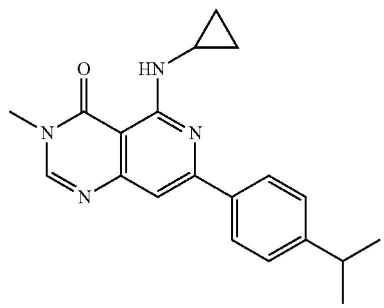 [SMILES: CC(C)c1ccc(-c2cc3ncn(C)c(=O)c3c(NC3CC3)n2)cc1] | ESI-MS m/z 335.2 (MH⁺) | 3.055 |
| 320 | 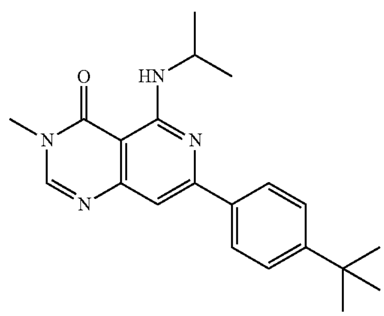 [SMILES: CC(C)Nc1nc(-c2ccc(C(C)(C)C)cc2)cc2ncn(C)c(=O)c12] | ESI-MS m/z 351.2 (MH⁺) | 6.736 |
| 321 | 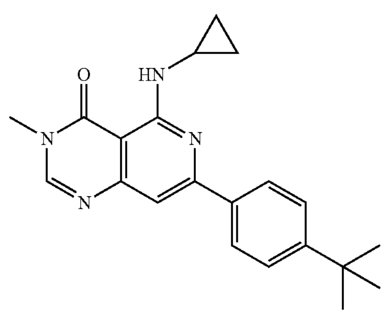 [SMILES: Cn1cnc2cc(-c3ccc(C(C)(C)C)cc3)nc(NC3CC3)c2c1=O] | ESI-MS m/z 349.2 (MH⁺) | 3.97 |
| 322 | 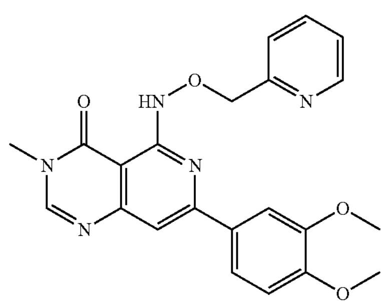 | ESI-MS m/z 320.2 (MH⁺) | 0.158 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 323 | 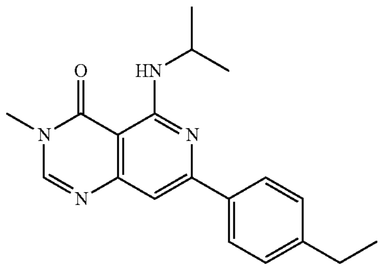 [SMILES: CCc1ccc(-c2cc3ncn(C)c(=O)c3c(NC(C)C)n2)cc1] | ESI-MS m/z 323.2 (MH⁺) | 5.067 |
| 324 | 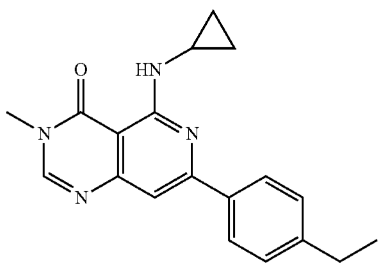 [SMILES: CCc1ccc(-c2cc3ncn(C)c(=O)c3c(NC3CC3)n2)cc1] | ESI-MS m/z 321.2 (MH⁺) | *** |
| 325 | 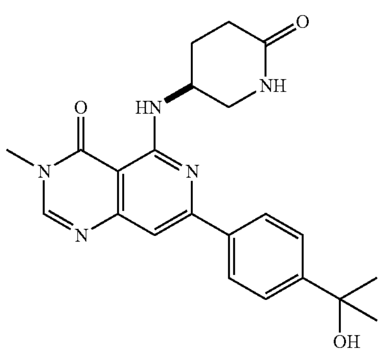 | ESI-MS m/z 408.2 (MH⁺) | 1.311 |
| 326 | 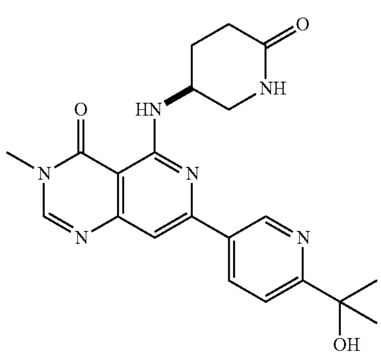 | ESI-MS m/z 409.2 (MH⁺) | 0.169 |

TABLE 1-continued

| Compound Number | Structure | Physical Data<br>¹H NMR 400 MHz (CDCl₃), HPLC Retention Time, and/or MS (m/z) | Syk Enzyme IC$_{50}$ (uM) |
|---|---|---|---|
| 327 | 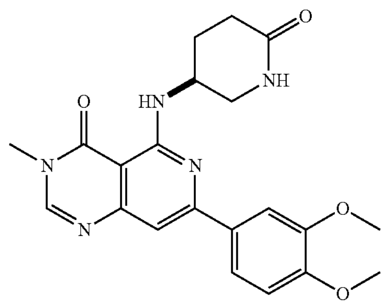 | ESI-MS m/z 410.2 (MH⁺) | 0.214 |
| 328 | 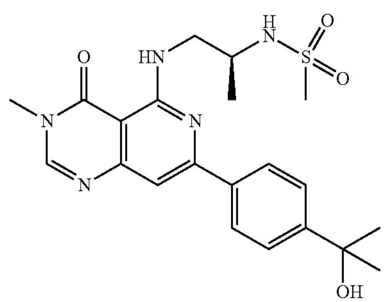 [SMILES: C[C@@H](CNc1nc(-c2ccc(C(C)(C)O)cc2)cc2ncn(C)c(=O)c12)NS(C)(=O)=O] | ESI-MS m/z 446.2 (MH⁺) | 0.087 |
| 329 | 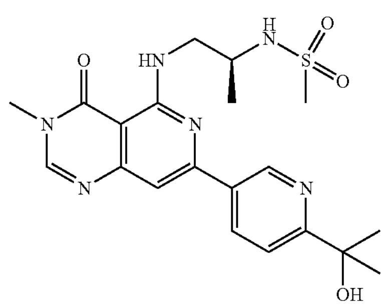 [SMILES: C[C@@H](CNc1nc(-c2ccc(C(C)(C)O)nc2)cc2ncn(C)c(=O)c12)NS(C)(=O)=O] | ESI-MS m/z 447.2 (MH⁺) | 0.156 |
| 330 | 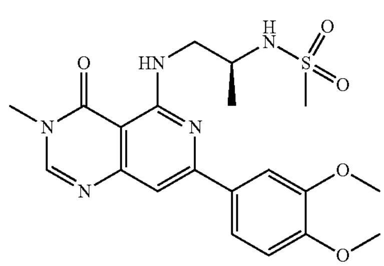 | ESI-MS m/z 448.2 (MH⁺) | 0.145 |
| 331 | 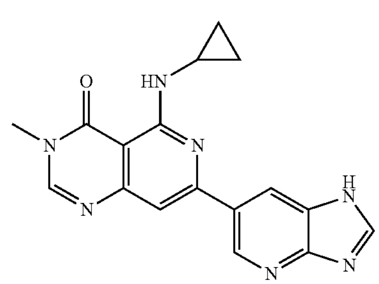 [SMILES: Cn1cnc2cc(-c3cnc4nc[nH]c4c3)nc(NC3CC3)c2c1=O] | ¹H NMR (400 MHz, DMSO-d₆) of the HCl salt of the compound: δ 0.55 (m, 2H), 0.84 (m, 2H), 3.01 (m, 1H), 3.39 (s, 3H), 7.32 (s, 1H), 7.88 (d, J = 8.8 Hz, 1H), 8.36 (d, J = 8.8 Hz, 1H), 8.46 (s, 1H), 8.62 (s, 1H), 8.79 (br s, 1H, NH), 9.60 (s, 1H);<br>ESI-MS m/z 334.1 (MH⁺) | 0.231 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
| --- | --- | --- | --- |
| 332 | 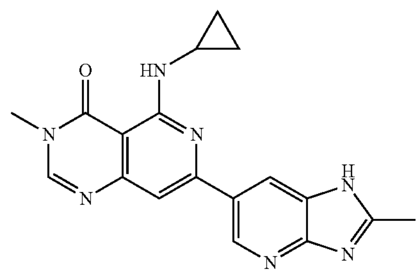 | ¹H NMR (400 MHz, DMSO-d₆) of the HCl salt of the compound: δ 0.68 (m, 2H), 0.95 (m, 2H), 2.89 (s, 3H), 3.16 (m, 1H), 3.52 (s, 3H), 7.47 (s, 1H), 7.92 (d, J = 8.8 Hz, 1H), 8.46 (d, J = 8.8 Hz, 1H), 8.55 (s, 1H), 8.66 (s, 1H), 8.92 (br s, 1H, NH); ESI-MS m/z 348.1 (MH⁺) | 0.404 |
| 333 | 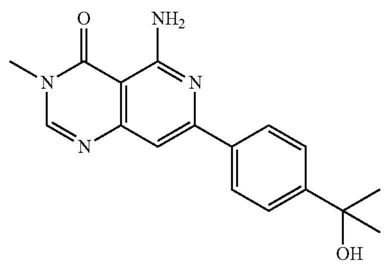 [SMILES: Cn1cnc2cc(-c3ccc(C(C)(C)O)cc3)nc(N)c2c1=O] | ESI-MS m/z 311.1 (MH⁺) | 0.864 |
| 334 | 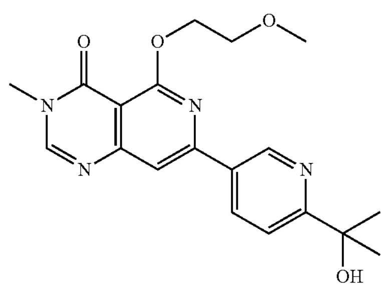 [SMILES: COCCOc1nc(-c2ccc(C(C)(C)O)nc2)cc2ncn(C)c(=O)c12] | ESI-MS m/z 371.2 (MH⁺) | 1.096 |
| 335 | 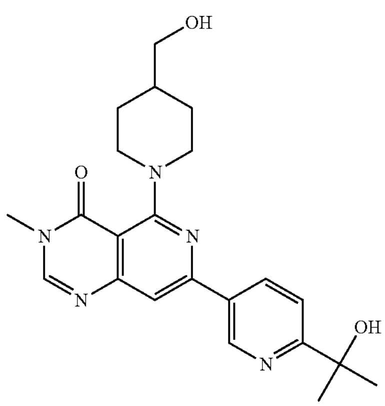 [SMILES: Cn1cnc2cc(-c3ccc(C(C)(C)O)nc3)nc(N3CCC(CO)CC3)c2c1=O] | ESI-MS m/z 410.2 (MH⁺) | 0.196 |
| 336 | 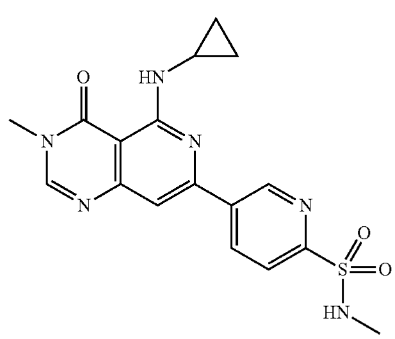 [SMILES: CNS(=O)(=O)c1ccc(-c2cc3ncn(C)c(=O)c3c(NC3CC3)n2)cn1] | ESI-MS m/z 387.1 (MH⁺) | 0.581 |

TABLE 1-continued
| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 337 | 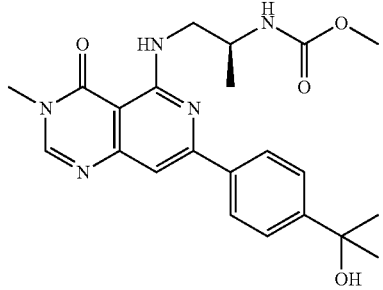 [SMILES: COC(=O)N[C@@H](C)CNc1nc(-c2ccc(C(C)(C)O)cc2)cc2ncn(C)c(=O)c12] | ESI-MS m/z 426.2 (MH⁺) | 0.646 |
| 338 | 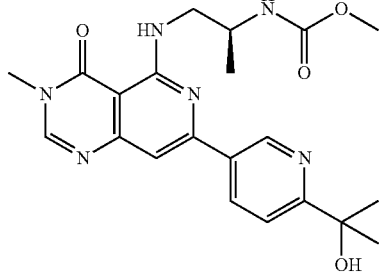 | ESI-MS m/z 427.2 (MH⁺) | 0.064 |
| 339 | 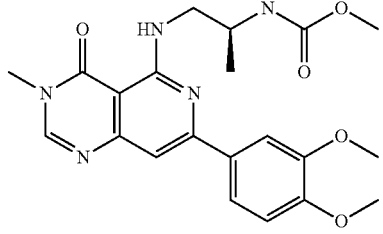 | ESI-MS m/z 428.2 (MH⁺) | 0.709 |
| 340 | 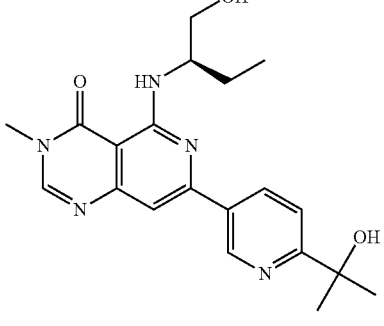 | HPLC-MS calculated for C$_{20}$H$_{25}$N$_5$O$_3$ (M + H⁺) 384.2, found 384.2. | 0.438 |
| 341 | 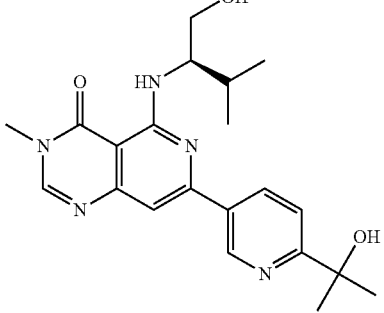 | HPLC-MS calculated for C$_{21}$H$_{27}$N$_5$O$_3$ (M + H⁺) 398.2, found 398.2. | 1.413 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
| --- | --- | --- | --- |
| 342 | 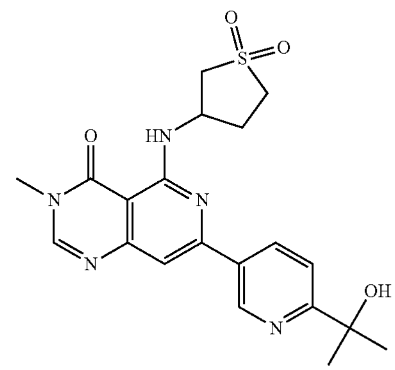 [SMILES: Cn1cnc2cc(-c3ccc(C(C)(C)O)nc3)nc(NC3CCS(=O)(=O)C3)c2c1=O] | HPLC-MS calculated for C$_{20}$H$_{23}$N$_5$O$_4$S (M + H$^+$) 430.1, found 430.1. | 2.22 |
| 343 | 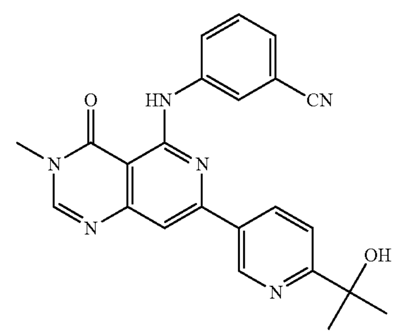 | HPLC-MS calculated for C$_{22}$H$_{21}$N$_5$O$_2$ (M + H$^+$) 388.2, found 388.2. | 2.492 |
| 344 | 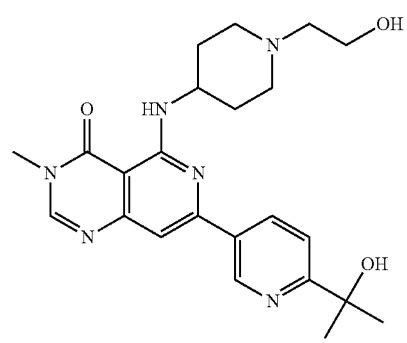 [SMILES: Cn1cnc2cc(-c3ccc(C(C)(C)O)nc3)nc(NC3CCN(CCO)CC3)c2c1=O] | HPLC-MS calculated for C$_{23}$H$_{30}$N$_6$O$_3$ (M + H$^+$) 439.2, found 439.2. | 20.91 |
| 345 | 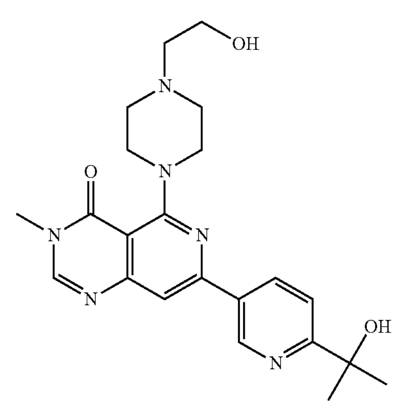 [SMILES: Cn1cnc2cc(-c3ccc(C(C)(C)O)nc3)nc(N3CCN(CCO)CC3)c2c1=O] | HPLC-MS calculated for C$_{22}$H$_{28}$N$_6$O$_3$ (M + H$^+$) 425.2, found 425.2. | 3.327 |

TABLE 1-continued

| Compound Number | Structure | Physical Data <br> ¹H NMR 400 MHz (CDCl₃), HPLC Retention Time, and/or MS (m/z) | Syk Enzyme IC₅₀ (uM) |
|---|---|---|---|
| 346 | 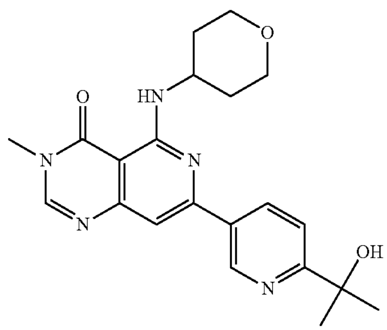 [SMILES: Cn1cnc2cc(-c3ccc(C(C)(C)O)nc3)nc(NC3CCOCC3)c2c1=O] | HPLC-MS calculated for $C_{21}H_{25}N_5O_3$ (M + H⁺) 396.2, found 396.2. | 1.437 |
| 347 | 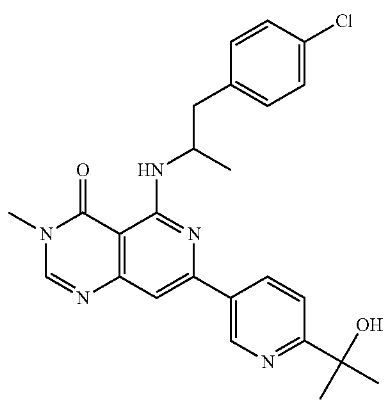 [SMILES: CC(Cc1ccc(Cl)cc1)Nc1nc(-c2ccc(C(C)(C)O)nc2)cc2ncn(C)c(=O)c12] | HPLC-MS calculated for $C_{25}H_{26}ClN_5O_2$ (M + H⁺) 464.2, found 464.2. | 2.226 |
| 348 | 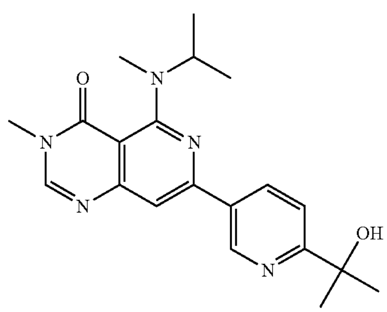 [SMILES: CC(C)N(C)c1nc(-c2ccc(C(C)(C)O)nc2)cc2ncn(C)c(=O)c12] | HPLC-MS calculated for $C_{20}H_{25}N_5O_2$ (M + H⁺) 368.2, found 368.2. | 2.004 |
| 349 | 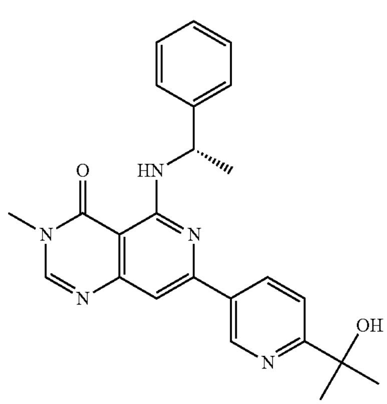 [SMILES: C[C@H](Nc1nc(-c2ccc(C(C)(C)O)nc2)cc2ncn(C)c(=O)c12)c1ccccc1] | HPLC-MS calculated for $C_{24}H_{25}N_5O_2$ (M + H⁺) 416.2, found 416.2. | 4.464 |

TABLE 1-continued
| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 350 | 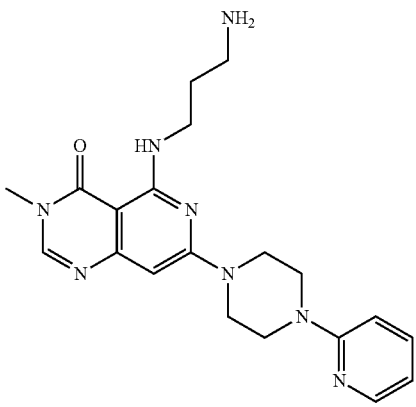 [SMILES: Cn1cnc2cc(N3CCN(c4ccccn4)CC3)nc(NCCCN)c2c1=O] | HPLC-MS calculated for C$_{20}$H$_{26}$N$_8$O (M + H$^+$) 395.2, found 395.2. | 3.918 |
| 351 | 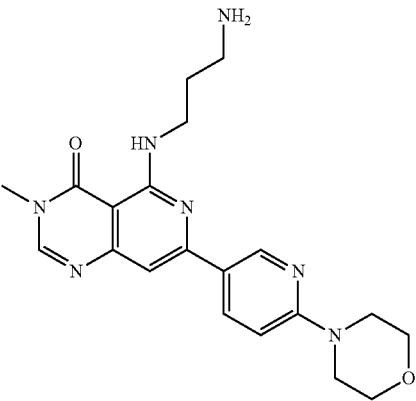 [SMILES: Cn1cnc2cc(-c3ccc(N4CCOCC4)nc3)nc(NCCCN)c2c1=O] | HPLC-MS calculated for C$_{20}$H$_{25}$N$_7$O$_2$ (M + H$^+$) 396.2, found 396.2. | 0.303 |
| 352 | 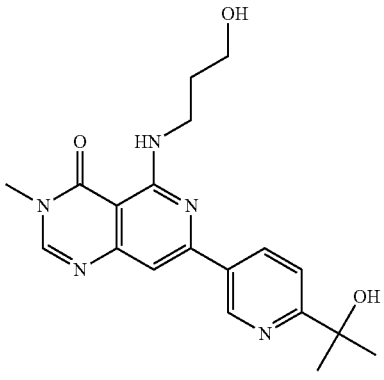 [SMILES: Cn1cnc2cc(-c3ccc(C(C)(C)O)nc3)nc(NCCCO)c2c1=O] | HPLC-MS calculated for C$_{19}$H$_{23}$N$_5$O$_3$ (M + H$^+$) 370.2, found 370.2. | 0.142 |
| 353 | 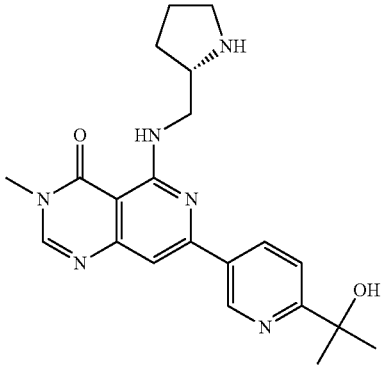 [SMILES: Cn1cnc2cc(-c3ccc(C(C)(C)O)nc3)nc(NC[C@@H]3CCCN3)c2c1=O] | HPLC-MS calculated for C$_{21}$H$_{26}$N$_6$O$_2$ (M + H$^+$) 395.2, found 395.2. | 2.769 |

TABLE 1-continued

| Compound Number | Structure | Physical Data <br> $^1$H NMR 400 MHz (CDCl$_3$), HPLC Retention Time, and/or MS (m/z) | Syk Enzyme IC$_{50}$ (uM) |
| --- | --- | --- | --- |
| 354 | 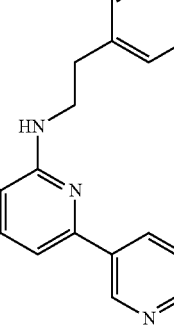 | HPLC-MS calculated for C$_{24}$H$_{25}$N$_5$O$_2$ (M + H$^+$) 416.2, found 416.2. | 1.554 |
| 355 | 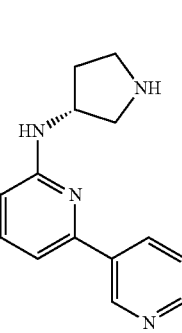 | $^1$H NMR (MeOD, 400 MHz) δ 9.37 (s, 1H), 9.30 (dd, 1H), 8.61 (s, 1H), 8.27 (d, 1H), 7.52 (s, 1H), 5.07 (m, 1H), 3.83 (m, 1H), 3.66 (m, 1H), 3.61 (s, 3H), 3.56 (m, 1H), 3.44 (dd, 1H), 2.60 (m, 1H), 2.25 (m, 1H), 1.74 (s, 6H); HPLC-MS calculated for C$_{20}$H$_{24}$N$_6$O$_2$ (M + H$^+$) 381.2, found 381.2. | 1.598 |
| 356 | 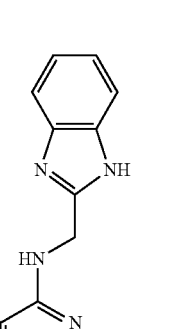 | HPLC-MS calculated for C$_{24}$H$_{23}$N$_7$O$_2$ (M + H$^+$) 442.2, found 442.2. | 3.347 |
| 357 | 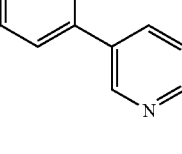 | HPLC-MS calculated for C$_{24}$H$_{24}$N$_6$O$_4$ (M + H$^+$) 461.2, found 461.2. | 2.452 |

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 358 | 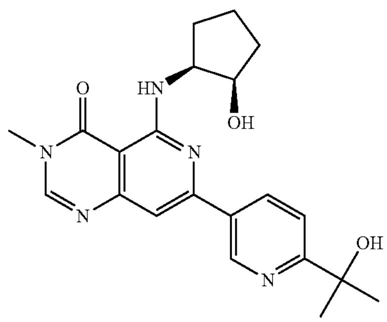 [SMILES: Cn1cnc2cc(-c3ccc(C(C)(C)O)nc3)nc(N[C@H]3CCC[C@H]3O)c2c1=O] | HPLC-MS calculated for C$_{21}$H$_{25}$N$_5$O$_3$ (M + H$^+$) 396.2, found 396.2. | 0.334 |
| 359 | 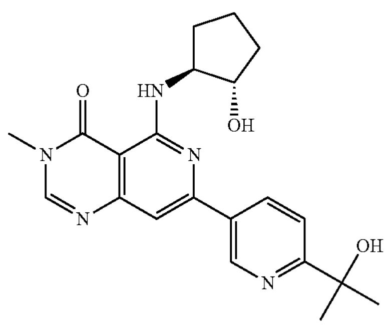 [SMILES: Cn1cnc2cc(-c3ccc(C(C)(C)O)nc3)nc(N[C@H]3CCC[C@@H]3O)c2c1=O] | HPLC-MS calculated for C$_{21}$H$_{25}$N$_5$O$_3$ (M + H$^+$) 396.2, found 396.2. | 0.395 |
| 360 | 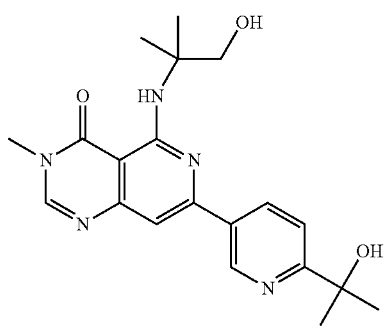 [SMILES: Cn1cnc2cc(-c3ccc(C(C)(C)O)nc3)nc(NC(C)(C)CO)c2c1=O] | HPLC-MS calculated for C$_{20}$H$_{25}$N$_5$O$_3$ (M + H$^+$) 384.2, found 384.2. | 0.219 |
| 361 | 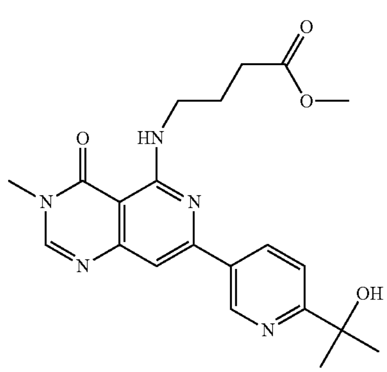 [SMILES: COC(=O)CCCNc1nc(-c2ccc(C(C)(C)O)nc2)cc2ncn(C)c(=O)c12] | HPLC-MS calculated for C$_{21}$H$_{25}$N$_5$O$_4$ (M + H$^+$) 412.2, found 412.2. | 1.803 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 362 | 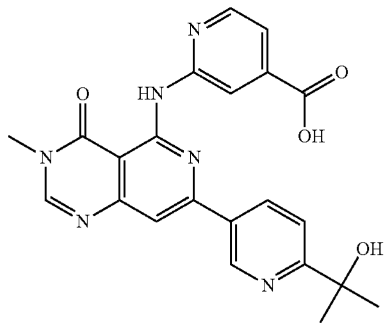 [SMILES: Cn1cnc2cc(-c3ccc(C(C)(C)O)nc3)nc(Nc3cc(C(=O)O)ccn3)c2c1=O] | HPLC-MS calculated for C$_{22}$H$_{20}$N$_6$O$_4$ (M + H$^+$) 433.2, found 433.2. | 0.215 |
| 363 | 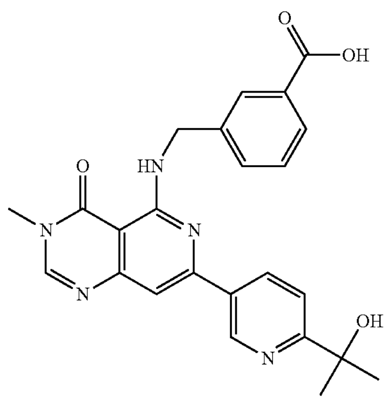 [SMILES: Cn1cnc2cc(-c3ccc(C(C)(C)O)nc3)nc(NCc3cccc(C(=O)O)c3)c2c1=O] | HPLC-MS calculated for C$_{24}$H$_{23}$N$_5$O$_4$ (M + H$^+$) 446.2, found 446.2. | 0.195 |
| 364 | 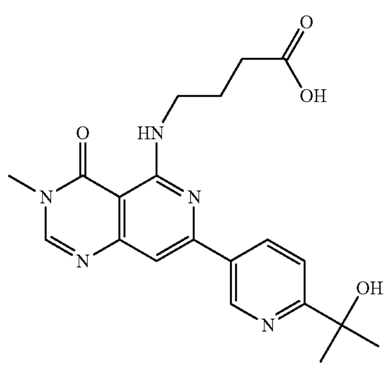 [SMILES: Cn1cnc2cc(-c3ccc(C(C)(C)O)nc3)nc(NCCCC(=O)O)c2c1=O] | HPLC-MS calculated for C$_{20}$H$_{23}$N$_5$O$_4$ (M + H$^+$) 398.2, found 398.2. | 2.707 |
| 365 | 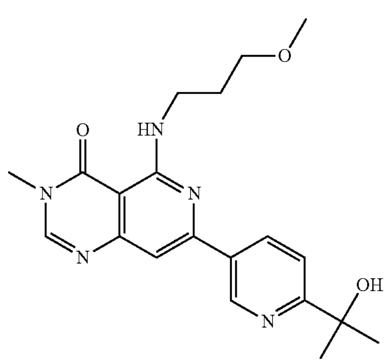 [SMILES: COCCCNc1nc(-c2ccc(C(C)(C)O)nc2)cc2ncn(C)c(=O)c12] | HPLC-MS calculated for C$_{20}$H$_{25}$N$_5$O$_4$ (M + H$^+$) 384.2, found 384.2. | 0.299 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 366 | 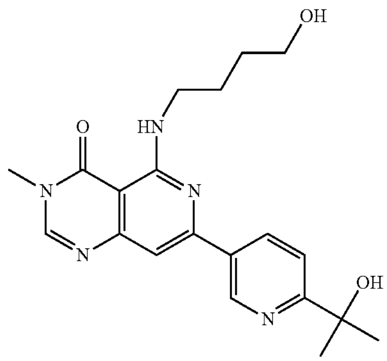 [SMILES: Cn1cnc2cc(-c3ccc(C(C)(C)O)nc3)nc(NCCCCO)c2c1=O] | HPLC-MS calculated for C$_{20}$H$_{25}$N$_5$O$_4$ (M + H$^+$) 384.2, found 384.2. | 0.29 |
| 367 | 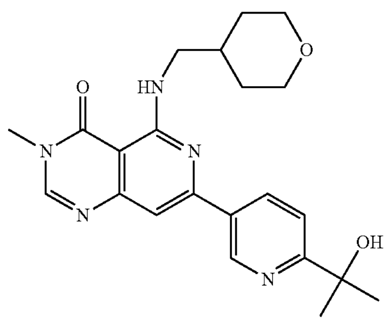 [SMILES: Cn1cnc2cc(-c3ccc(C(C)(C)O)nc3)nc(NCC3CCOCC3)c2c1=O] | HPLC-MS calculated for C$_{22}$H$_{27}$N$_5$O$_4$ (M + H$^+$) 410.2, found 410.2. | 1.178 |
| 368 | 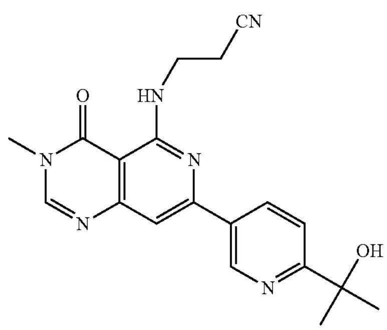 [SMILES: Cn1cnc2cc(-c3ccc(C(C)(C)O)nc3)nc(NCCC#N)c2c1=O] | HPLC-MS calculated for C$_{19}$H$_{20}$N$_6$O$_4$ (M + H$^+$) 365.2, found 365.2. | 2.825 |
| 369 | 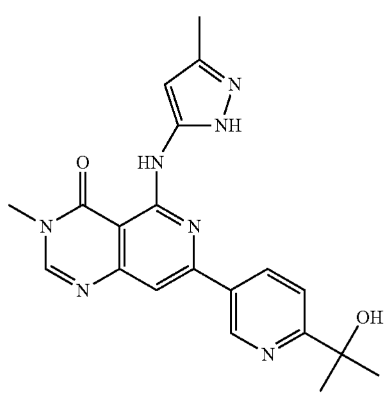 [SMILES: Cc1cc(Nc2nc(-c3ccc(C(C)(C)O)nc3)cc3ncn(C)c(=O)c23)[nH]n1] | HPLC-MS calculated for C$_{20}$H$_{21}$N$_7$O$_2$ (M + H$^+$) 392.2, found 392.2. | 3.798 |

TABLE 1-continued

| Compound Number | Structure | Physical Data <br> ¹H NMR 400 MHz (CDCl₃), HPLC Retention Time, and/or MS (m/z) | Syk Enzyme IC$_{50}$ (uM) |
| --- | --- | --- | --- |
| 370 | 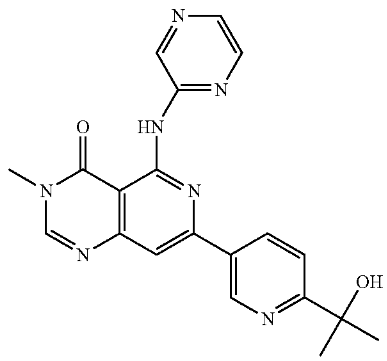 [SMILES: Cn1cnc2cc(-c3ccc(C(C)(C)O)nc3)nc(Nc3cnccn3)c2c1=O] | HPLC-MS calculated for $C_{20}H_{19}N_7O_2$ (M + H⁺) 390.2, found 390.2. | 0.856 |
| 371 | 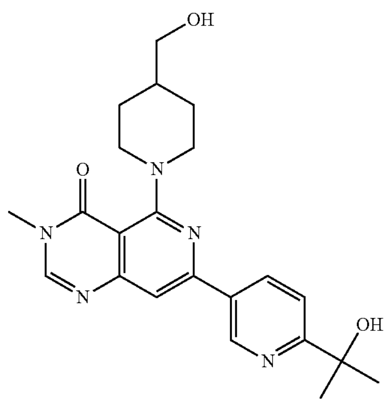 [SMILES: Cn1cnc2cc(-c3ccc(C(C)(C)O)nc3)nc(N3CCC(CO)CC3)c2c1=O] | HPLC-MS calculated for $C_{22}H_{27}N_7O_2$ (M + H⁺) 410.2, found 410.2. | 0.724 |
| 372 | 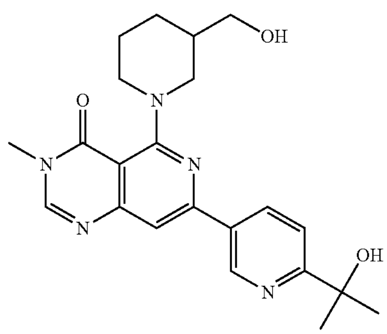 [SMILES: Cn1cnc2cc(-c3ccc(C(C)(C)O)nc3)nc(N3CCCC(CO)C3)c2c1=O] | HPLC-MS calculated for $C_{22}H_{27}N_7O_2$ (M + H⁺) 410.2, found 410.2. | 0.313 |
| 373 | 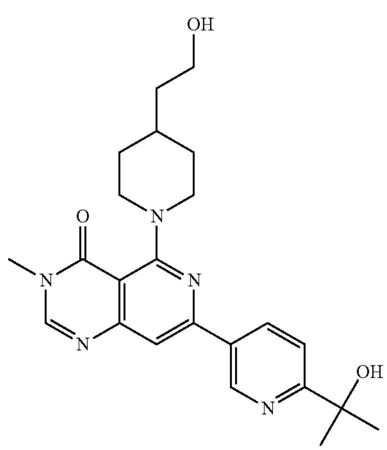 [SMILES: Cn1cnc2cc(-c3ccc(C(C)(C)O)nc3)nc(N3CCC(CCO)CC3)c2c1=O] | HPLC-MS calculated for $C_{23}H_{29}N_5O_2$ (M + H⁺) 424.2, found 424.2. | 1.037 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 374 | 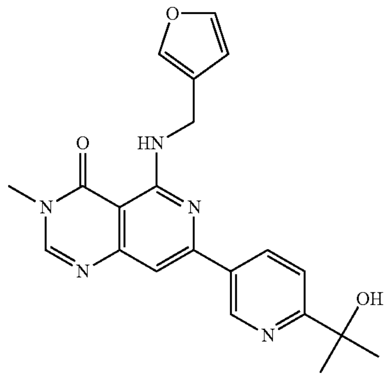 [SMILES: Cn1cnc2cc(-c3ccc(C(C)(C)O)nc3)nc(NCc3ccoc3)c2c1=O] | HPLC-MS calculated for<br>$C_{21}H_{21}N_5O_2$ (M + H⁺) 392.2,<br>found 392.2. | 1.051 |
| 375 | 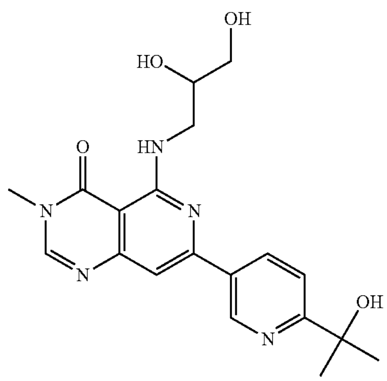 [SMILES: Cn1cnc2cc(-c3ccc(C(C)(C)O)nc3)nc(NCC(O)CO)c2c1=O] | HPLC-MS calculated for<br>$C_{19}H_{23}N_5O_4$ (M + H⁺) 386.2,<br>found 386.2. | 0.464 |
| 376 | 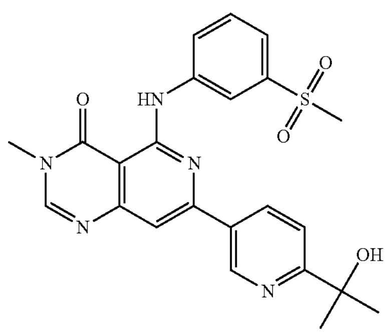 [SMILES: Cn1cnc2cc(-c3ccc(C(C)(C)O)nc3)nc(Nc3cccc(S(C)(=O)=O)c3)c2c1=O] | HPLC-MS calculated for<br>$C_{23}H_{23}N_5O_4S$ (M + H⁺) 466.1,<br>found 466.1. | 1.422 |
| 377 | 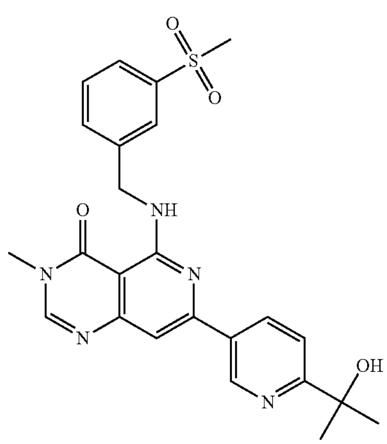 [SMILES: Cn1cnc2cc(-c3ccc(C(C)(C)O)nc3)nc(NCc3cccc(S(C)(=O)=O)c3)c2c1=O] | HPLC-MS calculated for<br>$C_{24}H_{25}N_5O_4S$ (M + H⁺) 480.2,<br>found 480.2. | 0.947 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 378 | 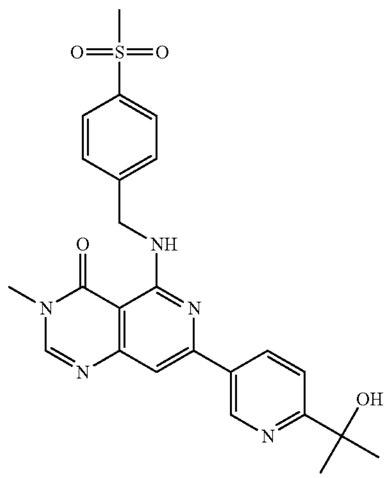 [SMILES: Cn1cnc2cc(-c3ccc(C(C)(C)O)nc3)nc(NCc3ccc(S(C)(=O)=O)cc3)c2c1=O] | HPLC-MS calculated for $C_{24}H_{25}N_5O_4S$ (M + H⁺) 480.2, found 480.2. | 3.961 |
| 379 | 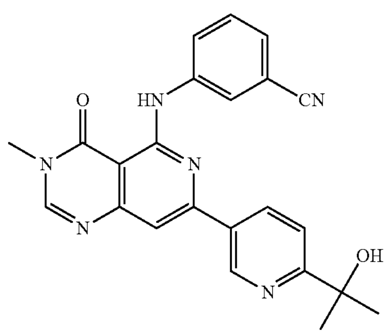 [SMILES: Cn1cnc2cc(-c3ccc(C(C)(C)O)nc3)nc(Nc3cccc(C#N)c3)c2c1=O] | HPLC-MS calculated for $C_{23}H_{20}N_6O_2$ (M + H⁺) 413.2, found 413.2. | 1.28 |
| 380 | 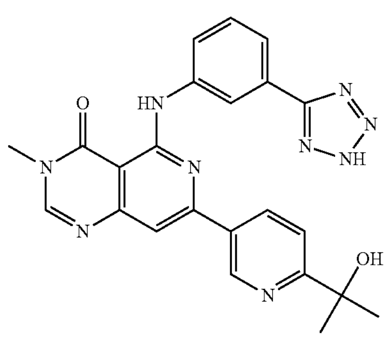 [SMILES: Cn1cnc2cc(-c3ccc(C(C)(C)O)nc3)nc(Nc3cccc(-c4nn[nH]n4)c3)c2c1=O] | HPLC-MS calculated for $C_{24}H_{21}N_9O_2$ (M + H⁺) 456.2, found 456.2. | 0.602 |

TABLE 1-continued
| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 381 | 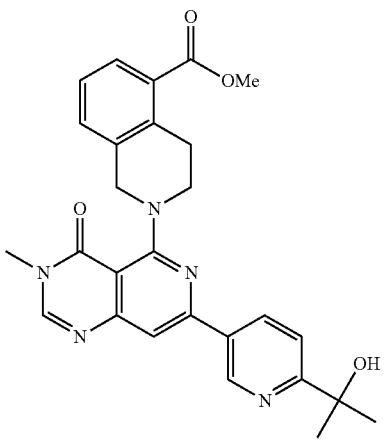 [SMILES: COC(=O)c1cccc2c1CCN(c1nc(-c3ccc(C(C)(C)O)nc3)cc3ncn(C)c(=O)c13)C2] | HPLC-MS calculated for C$_{27}$H$_{27}$N$_5$O$_4$ (M + H$^+$) 486.2, found 486.2. | 0.959 |
| 382 | 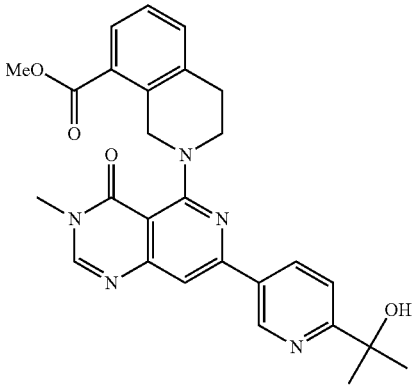 [SMILES: COC(=O)c1cccc2c1CN(c1nc(-c3ccc(C(C)(C)O)nc3)cc3ncn(C)c(=O)c13)CC2] | HPLC-MS calculated for C$_{27}$H$_{27}$N$_5$O$_4$ (M + H$^+$) 486.2, found 486.2. | 2.288 |
| 383 | 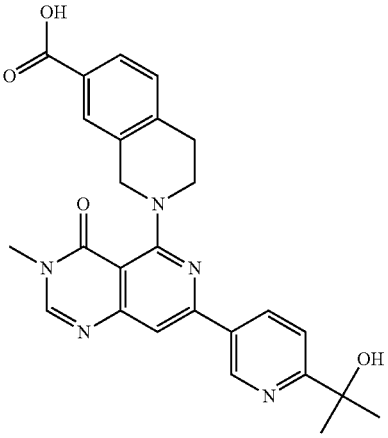 [SMILES: Cn1cnc2cc(-c3ccc(C(C)(C)O)nc3)nc(N3CCc4ccc(C(=O)O)cc4C3)c2c1=O] | HPLC-MS calculated for C$_{26}$H$_{25}$N$_5$O$_4$ (M + H$^+$) 472.2, found 472.2. | 0.952 |

TABLE 1-continued
| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 384 | 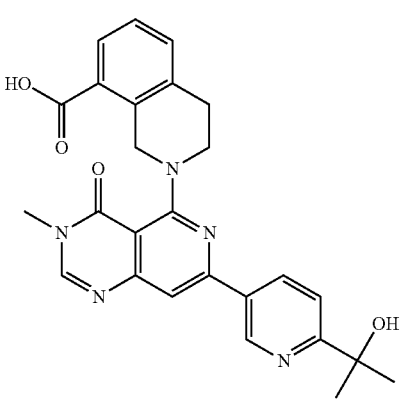 [SMILES: Cn1cnc2cc(-c3ccc(C(C)(C)O)nc3)nc(N3CCc4cccc(C(=O)O)c4C3)c2c1=O] | HPLC-MS calculated for $C_{26}H_{25}N_5O_4$ (M + H⁺) 472.2, found 472.2. | 0.611 |
| 385 | 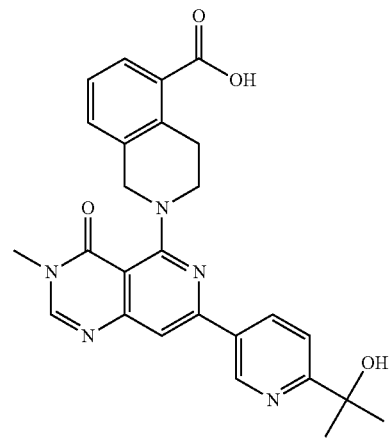 [SMILES: Cn1cnc2cc(-c3ccc(C(C)(C)O)nc3)nc(N3CCc4c(cccc4C(=O)O)C3)c2c1=O] | HPLC-MS calculated for $C_{26}H_{25}N_5O_4$ (M + H⁺) 472.2, found 472.2. | 0.72 |
| 386 | 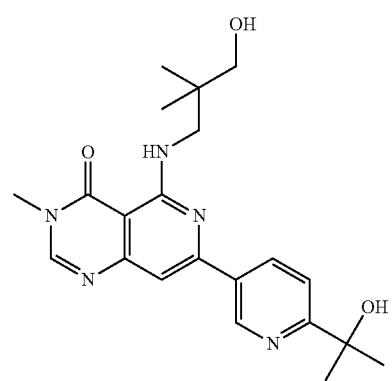 [SMILES: Cn1cnc2cc(-c3ccc(C(C)(C)O)nc3)nc(NCC(C)(C)CO)c2c1=O] | HPLC-MS calculated for $C_{21}H_{27}N_5O_3$ (M + H⁺) 398.2, found 398.2. | 0.446 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 387 | 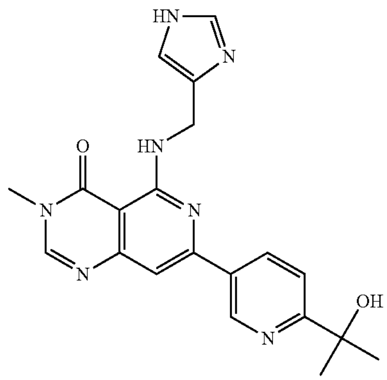 [SMILES: Cn1cnc2cc(-c3ccc(C(C)(C)O)nc3)nc(NCc3c[nH]cn3)c2c1=O] | HPLC-MS calculated for C$_{20}$H$_{21}$N$_7$O$_2$ (M + H$^+$) 392.2, found 392.2. | 0.196 |
| 388 | 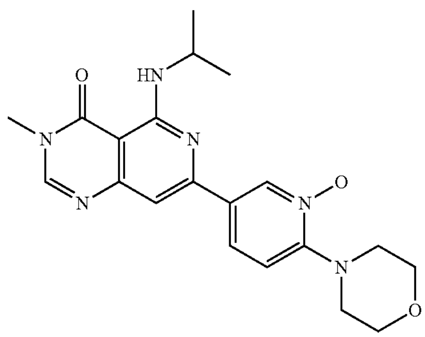 | HPLC-MS calculated for C$_{20}$H$_{24}$N$_6$O$_3$ (M + H$^+$) 397.2, found 397.2. | 0.598 |
| 389 | 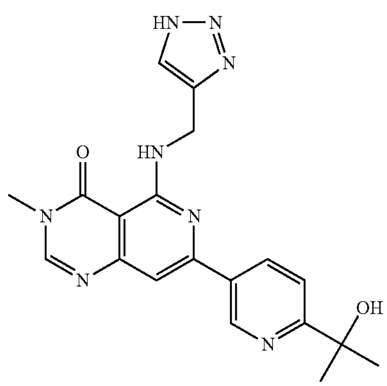 [SMILES: Cn1cnc2cc(-c3ccc(C(C)(C)O)nc3)nc(NCc3c[nH]nn3)c2c1=O] | HPLC-MS calculated for C$_{19}$H$_{20}$N$_8$O$_2$ (M + H$^+$) 393.2, found 393.2. | 0.202 |
| 390 | 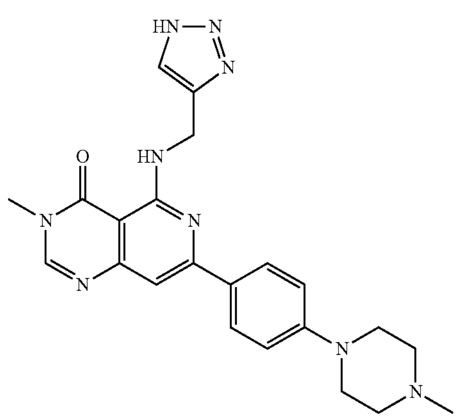 | HPLC-MS calculated for C$_{22}$H$_{25}$N$_9$O (M + H$^+$) 432.2, found 432.2. | 0.024 |

TABLE 1-continued
| Compound Number | Structure | Physical Data<br>$^1$H NMR 400 MHz (CDCl$_3$),<br>HPLC Retention Time, and/or<br>MS (m/z) | Syk Enzyme IC$_{50}$ (uM) |
|---|---|---|---|
| 391 | 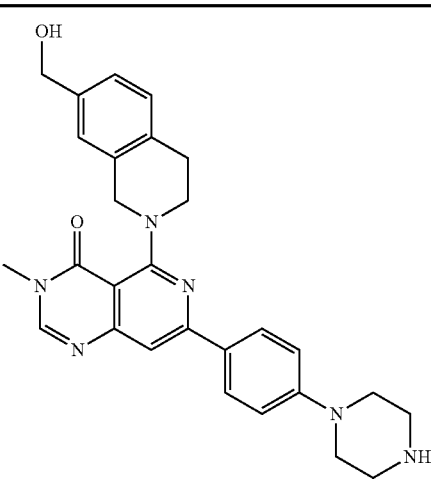 | HPLC-MS calculated for C$_{28}$H$_{30}$N$_6$O$_2$ (M + H$^+$) 483.2, found 483.2. | 2.092 |
| 392 | 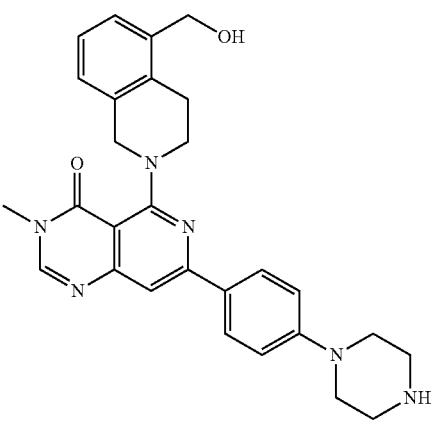 [SMILES: Cn1cnc2cc(-c3ccc(N4CCNCC4)cc3)nc(N3CCc4c(CO)cccc4C3)c2c1=O] | HPLC-MS calculated for C$_{28}$H$_{30}$N$_6$O$_2$ (M + H$^+$) 483.2, found 483.2. | 0.565 |
| 393 | 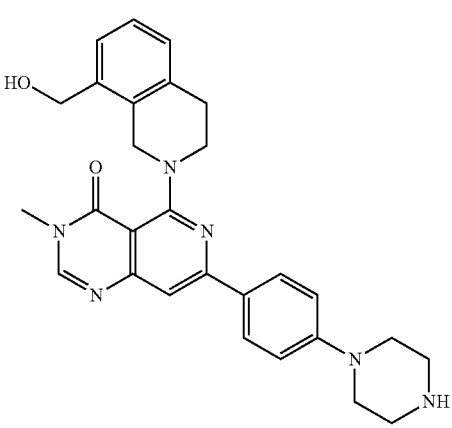 [SMILES: Cn1cnc2cc(-c3ccc(N4CCNCC4)cc3)nc(N3CCc4cccc(CO)c4C3)c2c1=O] | HPLC-MS calculated for C$_{28}$H$_{30}$N$_6$O$_2$ (M + H$^+$) 483.2, found 483.2. | 0.733 |

TABLE 1-continued

| Compound Number | Structure | Physical Data<br>¹H NMR 400 MHz (CDCl₃), HPLC Retention Time, and/or MS (m/z) | Syk Enzyme IC$_{50}$ (uM) |
|---|---|---|---|
| 394 | 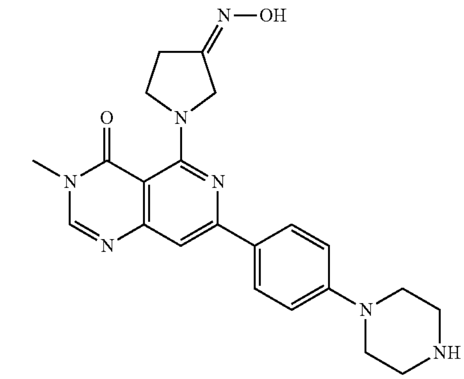 [SMILES: Cn1cnc2cc(-c3ccc(N4CCNCC4)cc3)nc(N3CC/C(=N/O)C3)c2c1=O] | ¹H NMR (MeOD, 400 MHz) δ 8.29 (s, 1H), 8.05 (d, 2H), 7.24 (s, 1H), 7.03 (d, 2H), 4.48 (s, 2H), 3.92 (t, 2H), 3.52 (s, 3H), 3.27 (m, 4H), 3.00 (m, 4H), 2.74 (t, 2H); HPLC-MS calculated for C$_{22}$H$_{25}$N$_7$O$_2$ (M + H⁺) 420.2, found 420.2. | 0.065 |
| 395 | 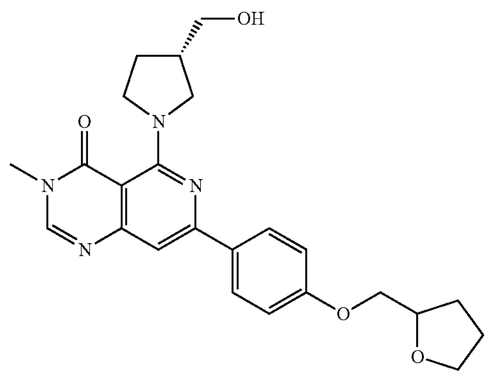 [SMILES: Cn1cnc2cc(-c3ccc(OCC4CCCO4)cc3)nc(N3CC[C@H](CO)C3)c2c1=O] | HPLC-MS calculated for C$_{24}$H$_{28}$N$_4$O$_4$ (M + H⁺) 437.2, found 437.2. | 0.265 |
| 396 | 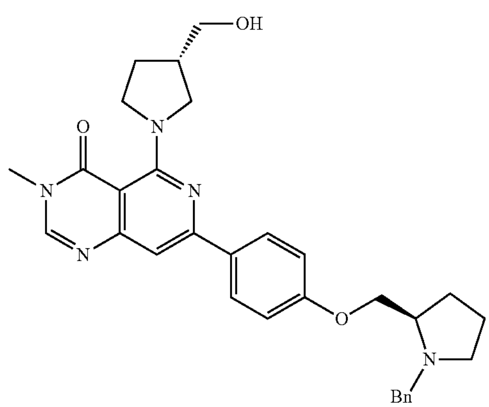 [SMILES: Cn1cnc2cc(-c3ccc(OC[C@H]4CCCN4Cc4ccccc4)cc3)nc(N3CC[C@H](CO)C3)c2c1=O] | HPLC-MS calculated for C$_{31}$H$_{35}$N$_5$O$_3$ (M + H⁺) 526.2, found 526.2. | 0.791 |
| 397 | 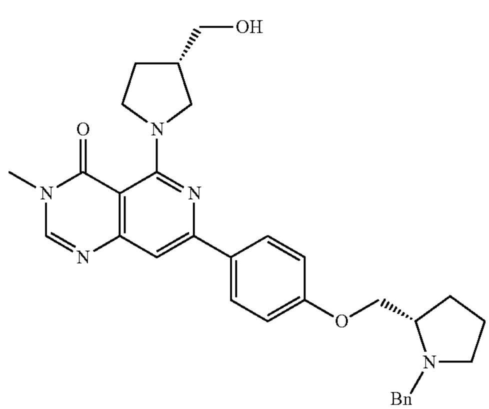 [SMILES: Cn1cnc2cc(-c3ccc(OC[C@@H]4CCCN4Cc4ccccc4)cc3)nc(N3CC[C@H](CO)C3)c2c1=O] | HPLC-MS calculated for C$_{31}$H$_{35}$N$_5$O$_3$ (M + H⁺) 526.2, found 526.2. | 0.63 |

TABLE 1-continued

| Compound Number | Structure | Physical Data <sup>1</sup>H NMR 400 MHz (CDCl₃), HPLC Retention Time, and/or MS (m/z) | Syk Enzyme IC$_{50}$ (uM) |
| --- | --- | --- | --- |
| 398 | 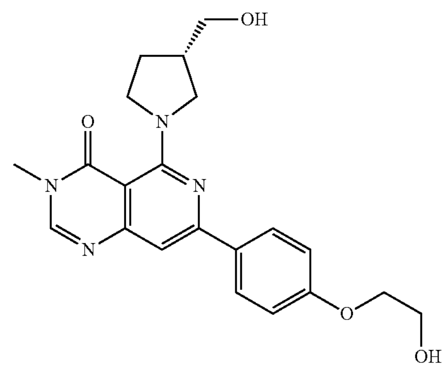 [SMILES: Cn1cnc2cc(-c3ccc(OCCO)cc3)nc(N3CC[C@H](CO)C3)c2c1=O] | HPLC-MS calculated for C$_{21}$H$_{24}$N$_4$O$_4$ (M + H⁺) 397.2, found 397.2. | 0.294 |
| 399 | 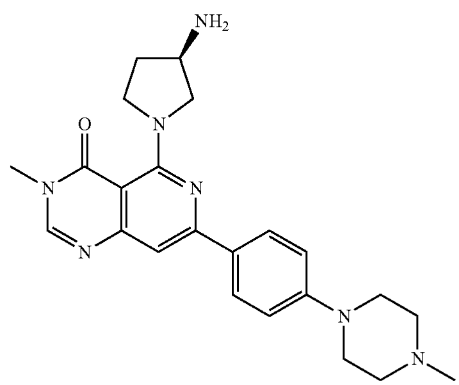 | HPLC-MS calculated for C$_{23}$H$_{29}$N$_7$O (M + H⁺) 420.2, found 420.2. | 0.518 |
| 400 | 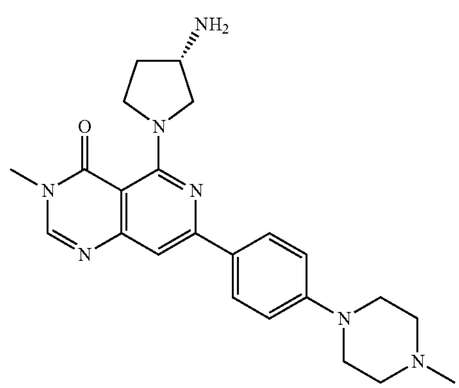 | HPLC-MS calculated for C$_{23}$H$_{29}$N$_7$O (M + H⁺) 420.2, found 420.2. | 0.139 |
| 401 | 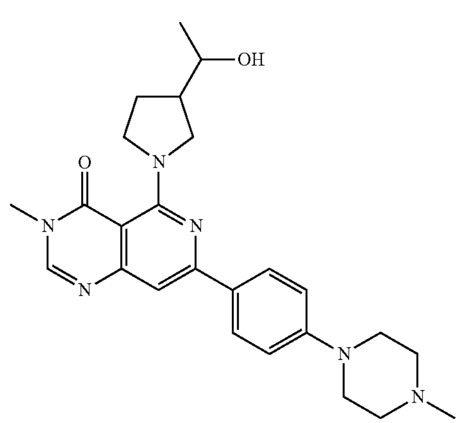 | HPLC-MS calculated for C$_{25}$H$_{32}$N$_6$O$_2$ (M + H⁺) 449.2, found 449.2. | 0.295 |

TABLE 1-continued
| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 402 | 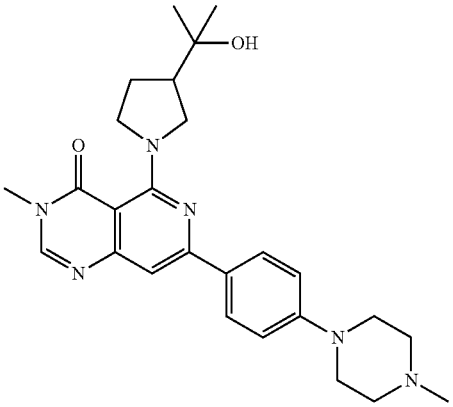 | HPLC-MS calculated for C$_{26}$H$_{34}$N$_6$O$_2$ (M + H$^+$) 463.2, found 463.2. | 0.327 |
| 403 | 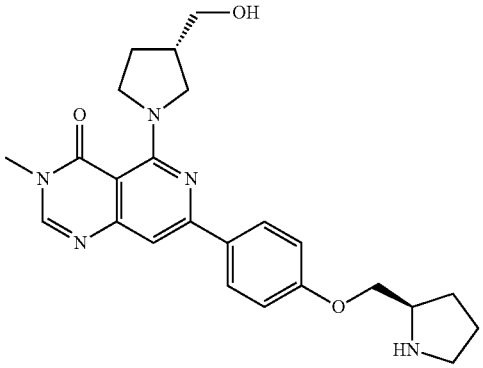 [SMILES: Cn1cnc2cc(-c3ccc(OC[C@H]4CCCN4)cc3)nc(N3CC[C@H](CO)C3)c2c1=O] | HPLC-MS calculated for C$_{24}$H$_{29}$N$_5$O$_3$ (M + H$^+$) 436.2, found 436.2. | 0.274 |
| 404 | 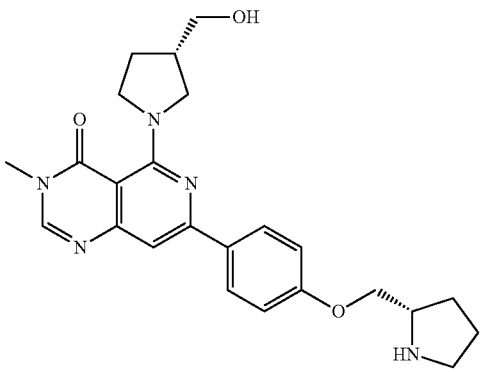 [SMILES: Cn1cnc2cc(-c3ccc(OC[C@@H]4CCCN4)cc3)nc(N3CC[C@H](CO)C3)c2c1=O] | HPLC-MS calculated for C$_{24}$H$_{29}$N$_5$O$_3$ (M + H$^+$) 436.2, found 436.2. | 0.202 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 405 | 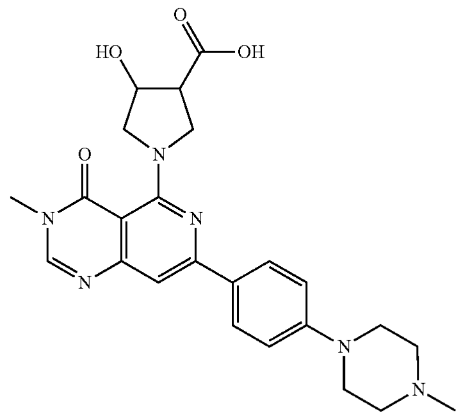 | HPLC-MS calculated for C$_{24}$H$_{28}$N$_6$O$_4$ (M + H⁺) 465.2, found 465.2. | 1.313 |
| 406 | 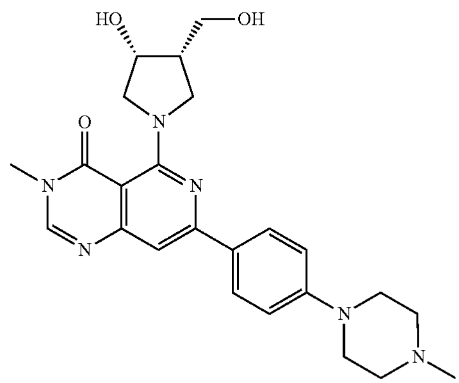 | HPLC-MS calculated for C$_{24}$H$_{30}$N$_6$O$_3$ (M + H⁺) 451.2, found 451.2. | 0.598 |
| 407 | 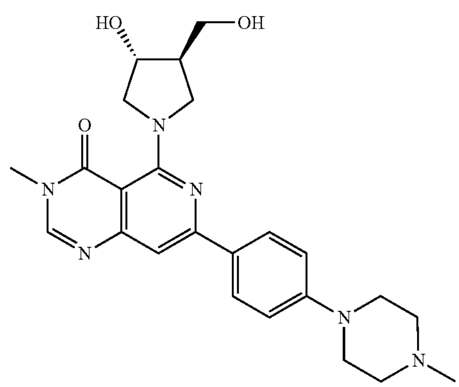 | HPLC-MS calculated for C$_{24}$H$_{30}$N$_6$O$_3$ (M + H⁺) 451.2, found 451.2. | 0.198 |
| 408 | 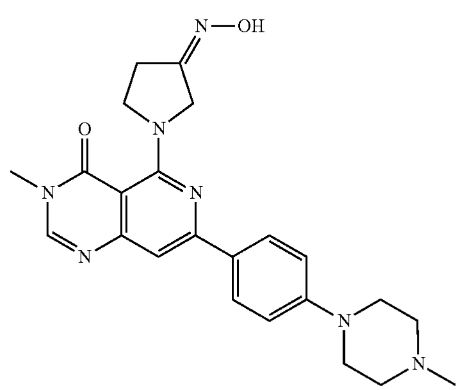 | HPLC-MS calculated for C$_{23}$H$_{27}$N$_7$O$_2$ (M + H⁺) 434.2, found 434.2. | 0.079 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 409 | 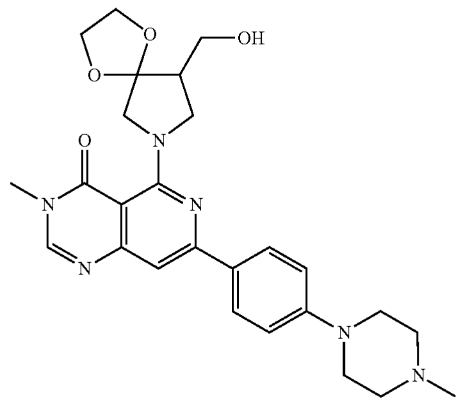 | HPLC-MS calculated for C$_{26}$H$_{32}$N$_6$O$_4$ (M + H$^+$) 493.2, found 493.2. | 0.328 |
| 410 | 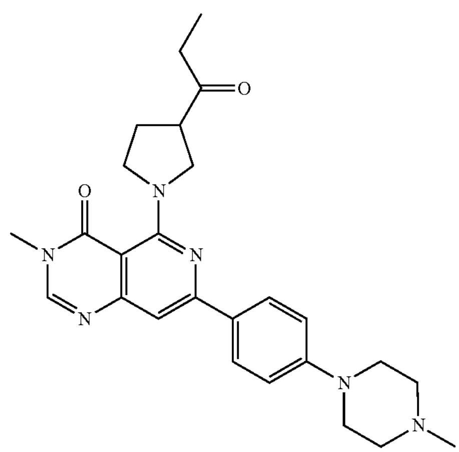 | ¹H NMR (MeOD, 400 MHz) δ 8.05 (d, 2H), 8.04 (s, 1H), 7.20 (s, 1H), 6.96 (d, 2H), 3.95 (m, 2H), 3.82 (m, 1H), 3.59 (m, 1H), 3.50 (s, 3H), 3.27-3.80 (b, 4H), 3.26 (m, 1H), 2.90-3.20 (b, 2H), 2.86 (s, 3H), 2.57 (m, 2H), 2.22 (m, 1H), 2.12 (m, 1H), 1.70-2.0 (b, 2H), 1.08 (t, 3H); HPLC-MS calculated for C$_{26}$H$_{32}$N$_6$O$_2$ (M + H$^+$) 461.3, found 461.3. | 1.755 |
| 411 | 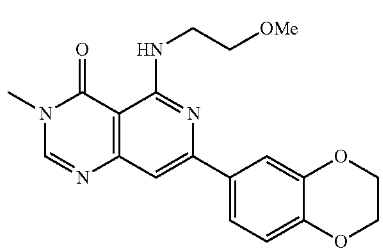 [SMILES: COCCNc1nc(-c2ccc3c(c2)OCCO3)cc2ncn(C)c(=O)c12] | HPLC-MS calculated for C$_{19}$H$_{20}$N$_4$O$_4$ (M + H$^+$) 369.2, found 369.2. | 0.384 |
| 412 | 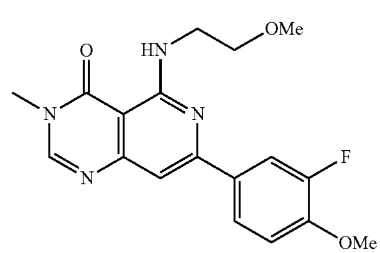 [SMILES: COCCNc1nc(-c2ccc(OC)c(F)c2)cc2ncn(C)c(=O)c12] | HPLC-MS calculated for C$_{18}$H$_{19}$FN$_4$O$_3$ (M + H$^+$) 359.1, found 359.1. | 0.337 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 413 | 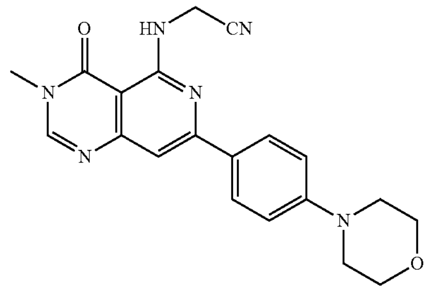 [SMILES: Cn1cnc2cc(-c3ccc(N4CCOCC4)cc3)nc(NCC#N)c2c1=O] | HPLC-MS calculated for C$_{20}$H$_{20}$N$_6$O$_2$ (M + H⁺) 377.2, found 377.2. | 0.341 |
| 414 | 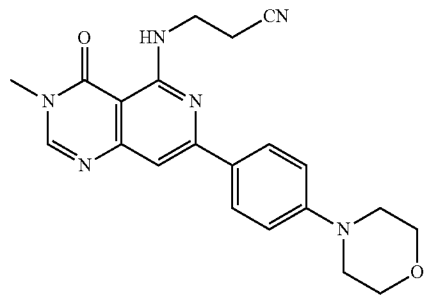 | HPLC-MS calculated for C$_{21}$H$_{22}$N$_6$O$_2$ (M + H⁺) 391.2, found 391.2. | 0.133 |
| 415 | 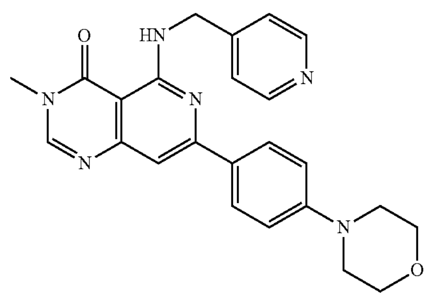 [SMILES: Cn1cnc2cc(-c3ccc(N4CCOCC4)cc3)nc(NCc3ccncc3)c2c1=O] | HPLC-MS calculated for C$_{24}$H$_{24}$N$_6$O$_2$ (M + H⁺) 429.2, found 429.2. | 0.305 |
| 416 | 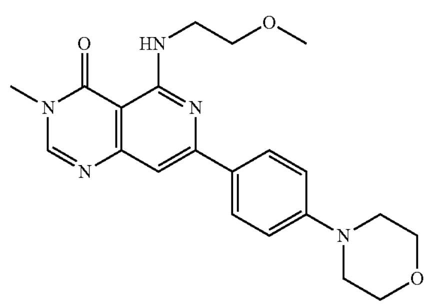 [SMILES: COCCNc1nc(-c2ccc(N3CCOCC3)cc2)cc2ncn(C)c(=O)c12] | ¹H NMR (CD₃OD, 400 MHz) δ 8.28 (s, 1H), 8.04 (d, J = 8.8 Hz, 2H), 7.04 (m, 3H), 3.86 (m, 6H), 3.69 (t, J = 5.2 Hz, 2H), 3.51 (s, 3H), 3.43 (s, 3H), 3.26 (t, J = 4.8 Hz, 4H); HPLC-MS calculated for C$_{21}$H$_{25}$N$_5$O$_3$ (M + H⁺) 396.2, found 396.2. | 0.048 |
| 417 | 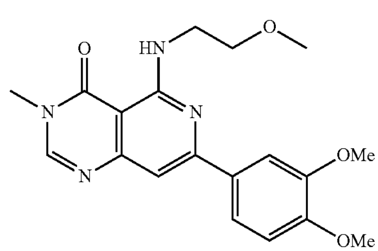 [SMILES: COCCNc1nc(-c2ccc(OC)c(OC)c2)cc2ncn(C)c(=O)c12] | HPLC-MS calculated for C$_{19}$H$_{22}$N$_4$O$_4$ (M + H⁺) 371.2, found 371.2. | 0.071 |

TABLE 1-continued
| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 418 | 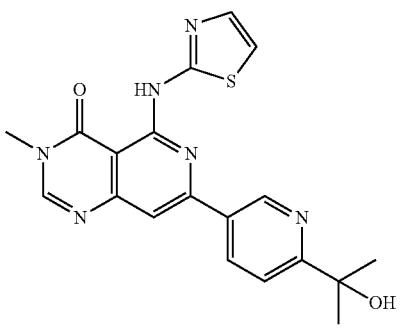 [SMILES: Cn1cnc2cc(-c3ccc(C(C)(C)O)nc3)nc(Nc3nccs3)c2c1=O] | HPLC-MS calculated for C$_{19}$H$_{18}$N$_6$O$_2$S (M + H$^+$) 395.1, found 395.1. | 0.382 |
| 419 | 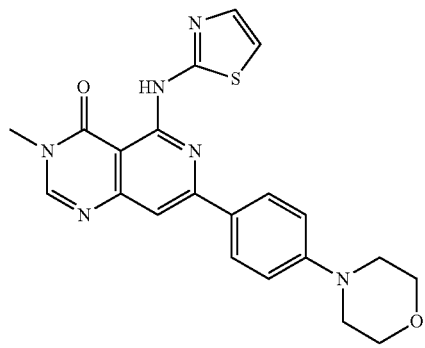 [SMILES: Cn1cnc2cc(-c3ccc(N4CCOCC4)cc3)nc(Nc3nccs3)c2c1=O] | HPLC-MS calculated for C$_{21}$H$_{20}$N$_6$O$_2$S (M + H$^+$) 421.1, found 421.1. | 0.387 |
| 420 | 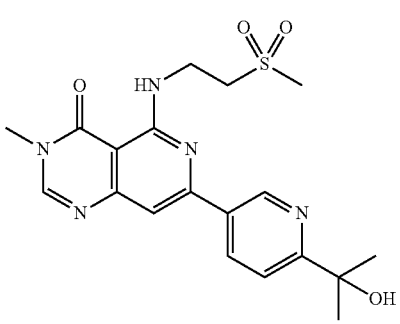 [SMILES: Cn1cnc2cc(-c3ccc(C(C)(C)O)nc3)nc(NCCS(C)(=O)=O)c2c1=O] | HPLC-MS calculated for C$_{19}$H$_{23}$N$_5$O$_4$S (M + H$^+$) 418.1, found 418.1. | 0.904 |
| 421 | 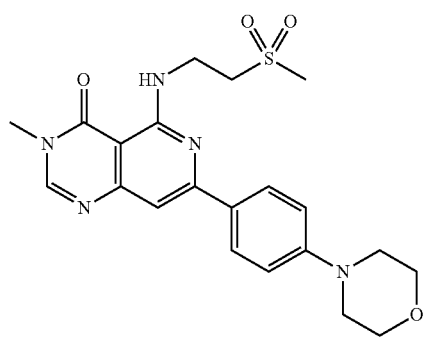 [SMILES: Cn1cnc2cc(-c3ccc(N4CCOCC4)cc3)nc(NCCS(C)(=O)=O)c2c1=O] | HPLC-MS calculated for C$_{21}$H$_{25}$N$_5$O$_4$S (M + H$^+$) 444.2, found 444.2. | 0.19 |

TABLE 1-continued

| Compound Number | Structure | Physical Data <br> $^1$H NMR 400 MHz (CDCl$_3$), HPLC Retention Time, and/or MS (m/z) | Syk Enzyme IC$_{50}$ (uM) |
|---|---|---|---|
| 422 | 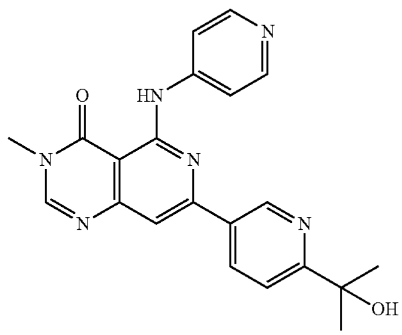 | HPLC-MS calculated for C$_{21}$H$_{20}$N$_6$O$_2$ (M + H$^+$) 389.2, found 389.2. | 0.706 |
| 423 | 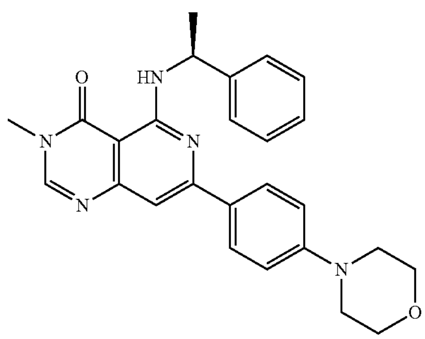 [SMILES: C[C@H](Nc1nc(-c2ccc(N3CCOCC3)cc2)cc2ncn(C)c(=O)c12)c1ccccc1] | HPLC-MS calculated for C$_{26}$H$_{27}$N$_5$O$_2$ (M + H$^+$) 442.2, found 442.2. | 2.814 |
| 424 | 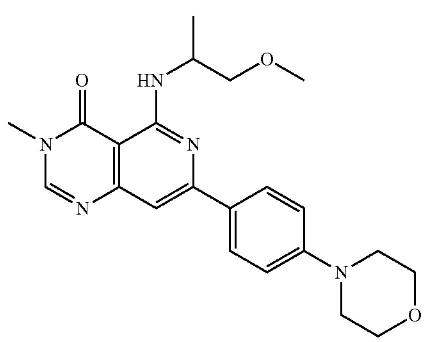 | HPLC-MS calculated for C$_{22}$H$_{27}$N$_5$O$_3$ (M + H$^+$) 410.2, found 410.2. | 0.233 |
| 425 | 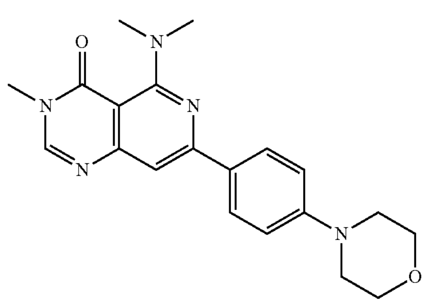 [SMILES: CN(C)c1nc(-c2ccc(N3CCOCC3)cc2)cc2ncn(C)c(=O)c12] | HPLC-MS calculated for C$_{20}$H$_{23}$N$_5$O$_2$ (M + H$^+$) 366.2, found 366.2. | 0.508 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 426 | 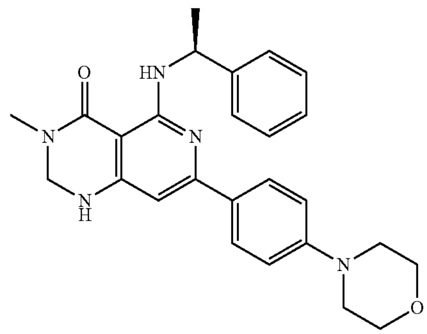 [SMILES: C[C@H](Nc1nc(-c2ccc(N3CCOCC3)cc2)cc2c1C(=O)N(C)CN2)c1ccccc1] | HPLC-MS calculated for $C_{26}H_{29}N_5O_2$ (M + H⁺) 444.2, found 444.2. | 3.752 |
| 427 | 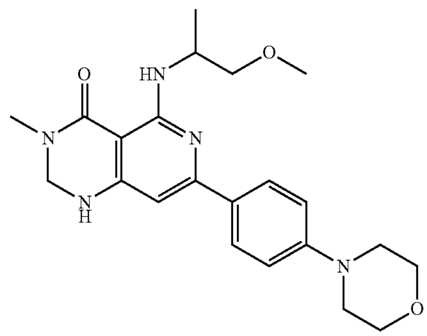 [SMILES: COCC(C)Nc1nc(-c2ccc(N3CCOCC3)cc2)cc2c1C(=O)N(C)CN2] | HPLC-MS calculated for $C_{22}H_{29}N_5O_3$ (M + H⁺) 412.2, found 412.2. | 0.897 |
| 428 | 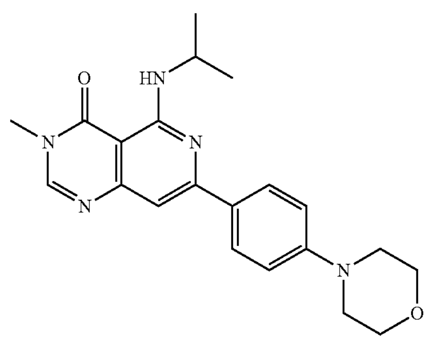 [SMILES: CC(C)Nc1nc(-c2ccc(N3CCOCC3)cc2)cc2ncn(C)c(=O)c12] | HPLC-MS calculated for $C_{21}H_{25}N_5O_2$ (M + H⁺) 380.2, found 380.2. | 0.315 |
| 429 | 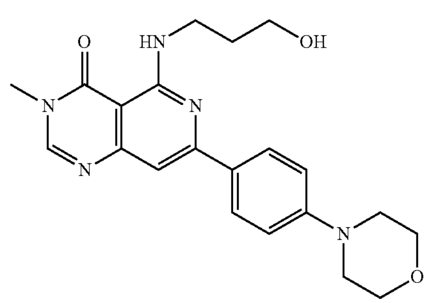 [SMILES: Cn1cnc2cc(-c3ccc(N4CCOCC4)cc3)nc(NCCCO)c2c1=O] | ¹H NMR (CD₃OD, 400 MHz) δ 8.28 (s, 1H), 8.02 (d, J = 8.8 Hz, 2H), 7.04 (d, J = 8.8 Hz, 2H), 7.01 (s, 1H), 3.85 (t, J = 4.8 Hz, 4H), 3.79 (m, 2H), 3.69 (t, J = 6.0 Hz, 2H), 3.51 (s, 3H), 3.25 (t, J = 4.8 Hz, 4H), 1.93 (m, 2H); HPLC-MS calculated for $C_{21}H_{25}N_5O_3$ (M + H⁺) 396.2, found 396.2. | 0.166 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 430 | 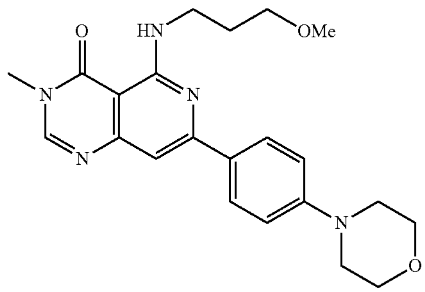 [SMILES: COCCCNc1nc(-c2ccc(N3CCOCC3)cc2)cc2ncn(C)c(=O)c12] | HPLC-MS calculated for<br>$C_{22}H_{27}N_5O_3$ (M + H⁺) 410.2,<br>found 410.2. | 0.179 |
| 431 | 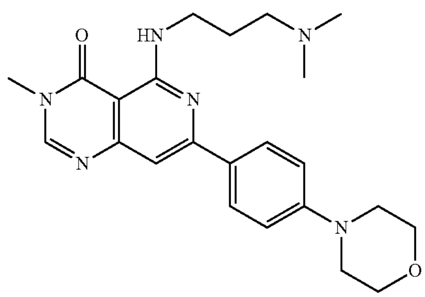 [SMILES: CN(C)CCCNc1nc(-c2ccc(N3CCOCC3)cc2)cc2ncn(C)c(=O)c12] | HPLC-MS calculated for<br>$C_{23}H_{30}N_6O_2$ (M + H⁺) 423.2,<br>found 423.2. | 1.988 |
| 432 | 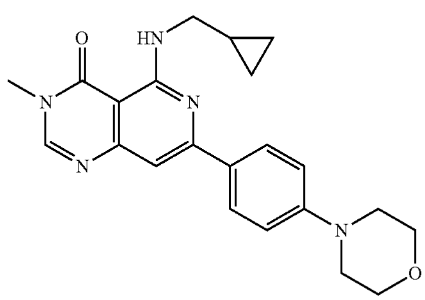 [SMILES: Cn1cnc2cc(-c3ccc(N4CCOCC4)cc3)nc(NCC3CC3)c2c1=O] | HPLC-MS calculated for<br>$C_{22}H_{25}N_5O_2$ (M + H⁺) 392.2,<br>found 392.2. | 0.461 |
| 433 | 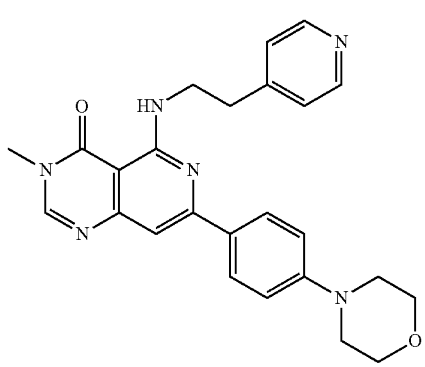 [SMILES: Cn1cnc2cc(-c3ccc(N4CCOCC4)cc3)nc(NCCc3ccncc3)c2c1=O] | HPLC-MS calculated for<br>$C_{25}H_{26}N_6O_2$ (M + H⁺) 443.2,<br>found 443.2. | 0.496 |

TABLE 1-continued

| Compound Number | Structure | Physical Data<br>$^1$H NMR 400 MHz (CDCl$_3$), HPLC Retention Time, and/or MS (m/z) | Syk Enzyme IC$_{50}$ (uM) |
|---|---|---|---|
| 434 | 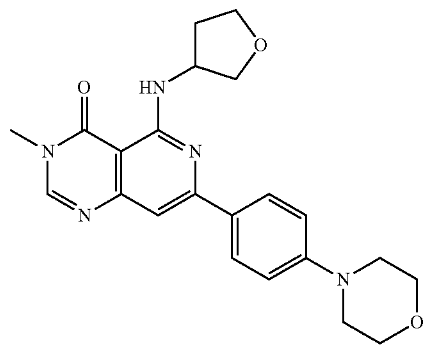 | HPLC-MS calculated for C$_{22}$H$_{25}$N$_5$O$_3$ (M + H$^+$) 408.2, found 408.2. | 0.072 |
| 435 | 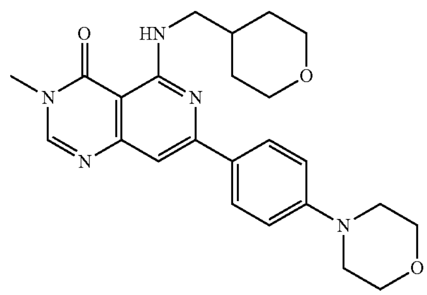 [SMILES: Cn1cnc2cc(-c3ccc(N4CCOCC4)cc3)nc(NCC3CCOCC3)c2c1=O] | HPLC-MS calculated for C$_{24}$H$_{29}$N$_5$O$_3$ (M + H$^+$) 436.2, found 436.2. | 0.553 |
| 436 | 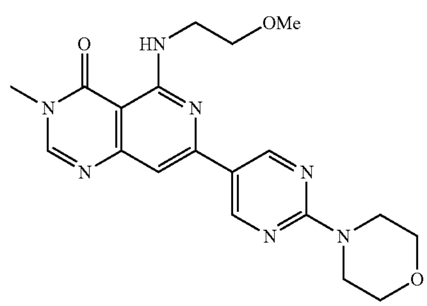 [SMILES: COCCNc1nc(-c2cnc(N3CCOCC3)nc2)cc2ncn(C)c(=O)c12] | HPLC-MS calculated for C$_{19}$H$_{23}$N$_7$O$_3$ (M + H$^+$) 398.2, found 398.2. | 1.536 |
| 437 | 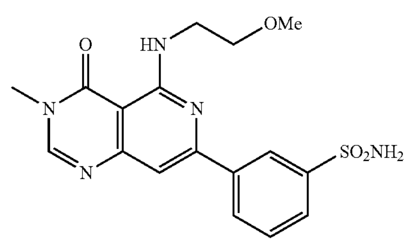 [SMILES: COCCNc1nc(-c2cccc(S(N)(=O)=O)c2)cc2ncn(C)c(=O)c12] | HPLC-MS calculated for C$_{17}$H$_{19}$N$_5$O$_4$S (M + H$^+$) 390.1, found 390.1. | 0.092 |
| 438 | 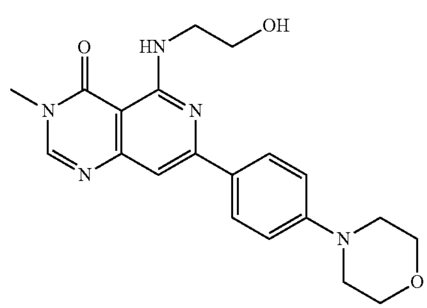 [SMILES: Cn1cnc2cc(-c3ccc(N4CCOCC4)cc3)nc(NCCO)c2c1=O] | $^1$H NMR (CD$_3$OD, 400 MHz) δ 8.29 (s, 1H), 8.03 (d, J = 8.8 Hz, 2H), 7.04 (m, 3H), 3.84 (m, 8H), 3.52 (s, 3H), 3.26 (t, J = 4.8 Hz, 4H); HPLC-MS calculated for C$_{20}$H$_{23}$N$_5$O$_3$ (M + H$^+$) 382.2, found 382.2. | 0.099 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 439 | 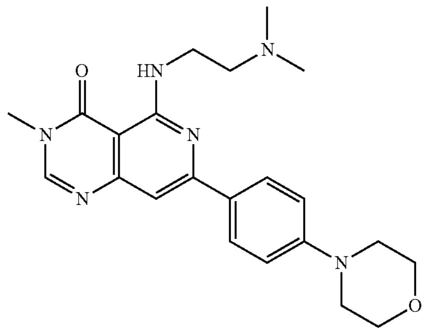 [SMILES: CN(C)CCNc1nc(-c2ccc(N3CCOCC3)cc2)cc2ncn(C)c(=O)c12] | HPLC-MS calculated for C$_{22}$H$_{28}$N$_6$O$_2$ (M + H$^+$) 409.2, found 409.2. | 0.687 |
| 440 | 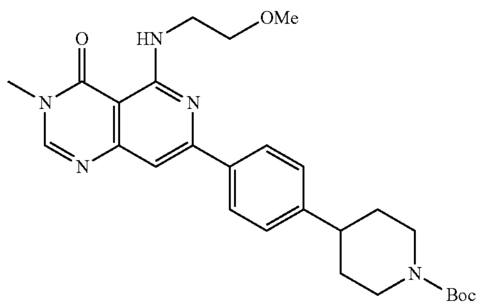 [SMILES: COCCNc1nc(-c2ccc(C3CCN(C(=O)OC(C)(C)C)CC3)cc2)cc2ncn(C)c(=O)c12] | HPLC-MS calculated for C$_{27}$H$_{35}$N$_5$O$_4$ (M + H$^+$) 494.3, found 494.3. | 0.942 |
| 441 | 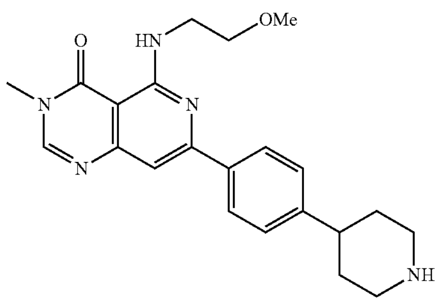 [SMILES: COCCNc1nc(-c2ccc(C3CCNCC3)cc2)cc2ncn(C)c(=O)c12] | HPLC-MS calculated for C$_{22}$H$_{27}$N$_5$O$_2$ (M + H$^+$) 394.2, found 394.2. | 0.032 |
| 442 | 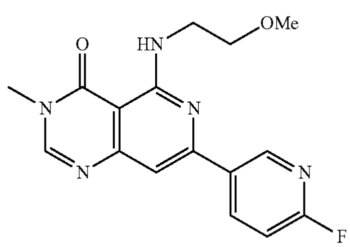 [SMILES: COCCNc1nc(-c2ccc(F)nc2)cc2ncn(C)c(=O)c12] | HPLC-MS calculated for C$_{16}$H$_{16}$FN$_5$O$_2$ (M + H$^+$) 330.1, found 330.1. | 0.43 |
| 443 | 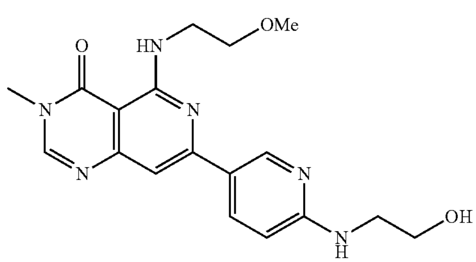 [SMILES: COCCNc1nc(-c2ccc(NCCO)nc2)cc2ncn(C)c(=O)c12] | HPLC-MS calculated for C$_{18}$H$_{22}$N$_6$O$_3$ (M + H$^+$) 371.2, found 371.2. | 0.148 |

TABLE 1-continued

| Compound Number | Structure | Physical Data<br>¹H NMR 400 MHz (CDCl₃),<br>HPLC Retention Time, and/or<br>MS (m/z) | Syk Enzyme IC₅₀ (uM) |
|---|---|---|---|
| 444 | 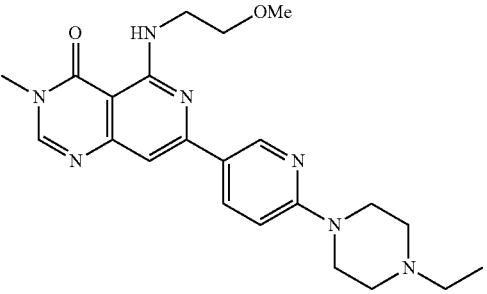 [SMILES: CCN1CCN(c2ccc(-c3cc4ncn(C)c(=O)c4c(NCCOC)n3)cn2)CC1] | HPLC-MS calculated for $C_{22}H_{29}N_7O_2$ (M + H⁺) 424.2, found 424.2. | 0.075 |
| 445 | 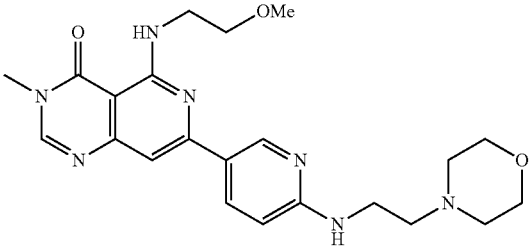 [SMILES: COCCNc1nc(-c2ccc(NCCN3CCOCC3)nc2)cc2ncn(C)c(=O)c12] | HPLC-MS calculated for $C_{22}H_{29}N_7O_3$ (M + H⁺) 440.2, found 440.2. | 0.053 |
| 446 | 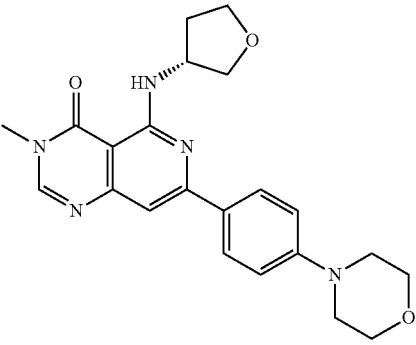 [SMILES: Cn1cnc2cc(-c3ccc(N4CCOCC4)cc3)nc(N[C@@H]3CCOC3)c2c1=O] | ¹H NMR (CD₃OD, 400 MHz) δ 8.29 (s, 1H), 8.05 (d, J = 8.8 Hz, 2H), 7.05 (m, 3H), 4.14 (dd, J = 8.8, 2.4 Hz, 1H), 4.03 (dd, J = 16.0, 3.6 Hz, 1H), 3.94-3.79 (m, 7H), 3.52 (s, 3H), 3.26 (t, J = 4.8 Hz, 4H), 2.44 (m, 1H), 2.02 (m, 1H); HPLC-MS calculated for $C_{22}H_{25}N_5O_3$ (M + H⁺) 408.2, found 408.2. | 0.051 |
| 447 | 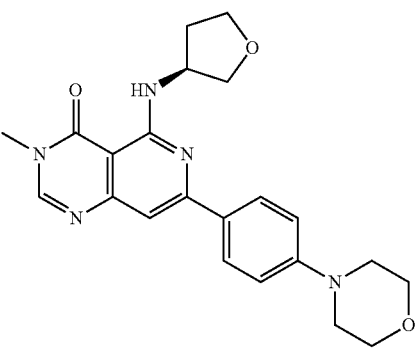 [SMILES: Cn1cnc2cc(-c3ccc(N4CCOCC4)cc3)nc(N[C@H]3CCOC3)c2c1=O] | HPLC-MS calculated for $C_{22}H_{25}N_5O_3$ (M + H⁺) 408.2, found 408.2. | 0.216 |

TABLE 1-continued

| Compound Number | Structure | Physical Data<br>¹H NMR 400 MHz (CDCl₃),<br>HPLC Retention Time, and/or<br>MS (m/z) | Syk Enzyme IC₅₀ (uM) |
|---|---|---|---|
| 448 | 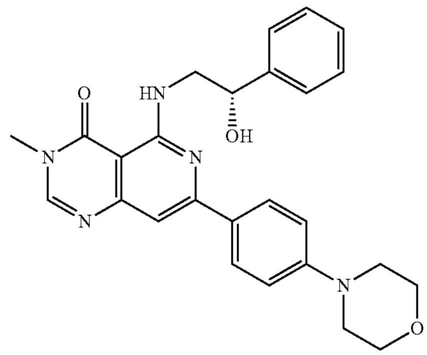 [SMILES: Cn1cnc2cc(-c3ccc(N4CCOCC4)cc3)nc(NC[C@@H](O)c3ccccc3)c2c1=O] | HPLC-MS calculated for<br>$C_{26}H_{27}N_5O_3$ (M + H⁺) 458.2,<br>found 458.2. | 0.286 |
| 449 | 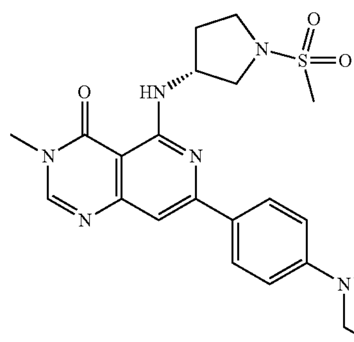 | HPLC-MS calculated for<br>$C_{23}H_{28}N_6O_4S$ (M + H⁺) 485.2,<br>found 485.2. | 0.253 |
| 450 | 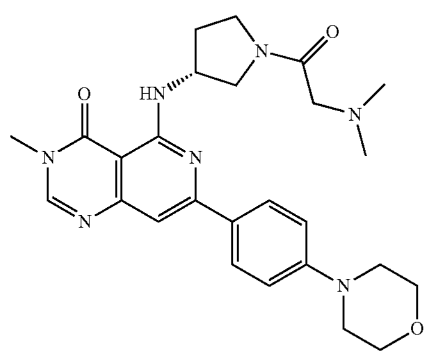 [SMILES: CN(C)CC(=O)N1CC[C@@H](Nc2nc(-c3ccc(N4CCOCC4)cc3)cc3ncn(C)c(=O)c23)C1] | HPLC-MS calculated for<br>$C_{26}H_{33}N_7O_3$ (M + H⁺) 492.3,<br>found 492.3. | 3.947 |
| 451 | 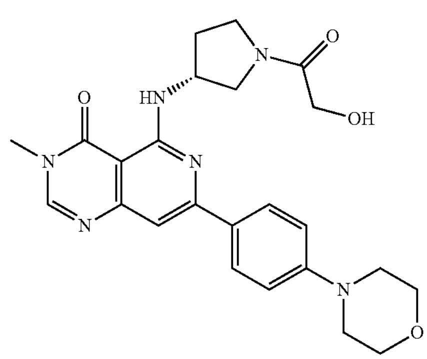 [SMILES: Cn1cnc2cc(-c3ccc(N4CCOCC4)cc3)nc(N[C@@H]3CCN(C(=O)CO)C3)c2c1=O] | HPLC-MS calculated for<br>$C_{24}H_{28}N_6O_4$ (M + H⁺) 465.2,<br>found 465.2. | 0.795 |

TABLE 1-continued

| Compound Number | Structure | Physical Data<br>¹H NMR 400 MHz (CDCl₃),<br>HPLC Retention Time, and/or<br>MS (m/z) | Syk Enzyme IC₅₀ (uM) |
|---|---|---|---|
| 452 | 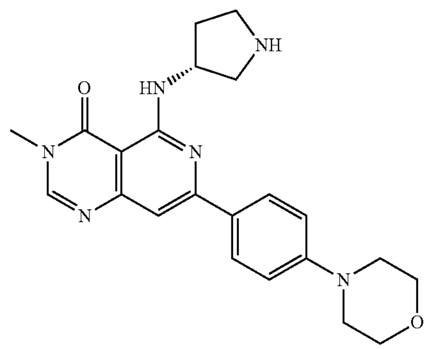 [SMILES: Cn1cnc2cc(-c3ccc(N4CCOCC4)cc3)nc(N[C@@H]3CCNC3)c2c1=O] | HPLC-MS calculated for $C_{22}H_{26}N_6O_2$ (M + H⁺) 407.2, found 407.2. | 0.116 |
| 453 | 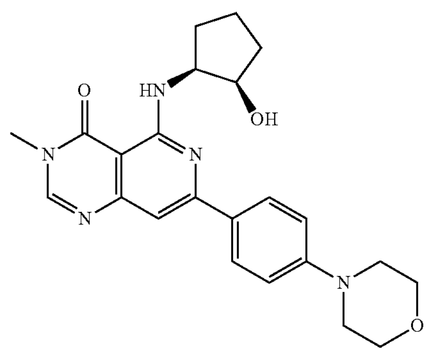 [SMILES: Cn1cnc2cc(-c3ccc(N4CCOCC4)cc3)nc(N[C@H]3CCC[C@H]3O)c2c1=O] | HPLC-MS calculated for $C_{23}H_{27}N_5O_3$ (M + H⁺) 422.2, found 422.2. | 0.28 |
| 454 | 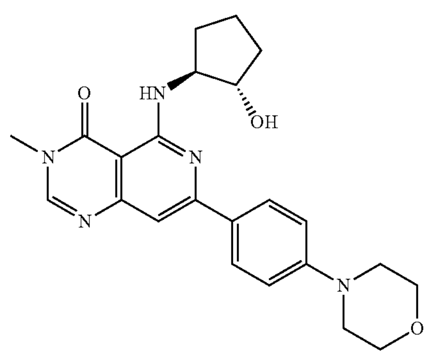 [SMILES: Cn1cnc2cc(-c3ccc(N4CCOCC4)cc3)nc(N[C@H]3CCC[C@@H]3O)c2c1=O] | HPLC-MS calculated for $C_{23}H_{27}N_5O_3$ (M + H⁺) 422.2, found 422.2. | 0.893 |
| 455 | 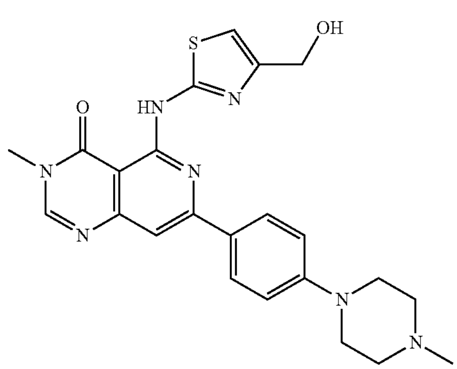 | HPLC-MS calculated for $C_{23}H_{25}N_7O_2S$ (M + H⁺) 464.2, found 464.2. | 0.161 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 456 | 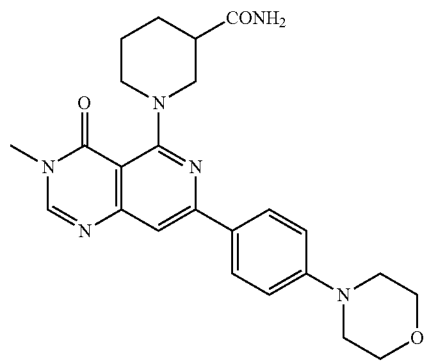 [SMILES: Cn1cnc2cc(-c3ccc(N4CCOCC4)cc3)nc(N3CCCC(C(N)=O)C3)c2c1=O] | HPLC-MS calculated for C$_{24}$H$_{28}$N$_6$O$_3$ (M + H⁺) 449.2, found 449.2. | 0.336 |
| 457 | 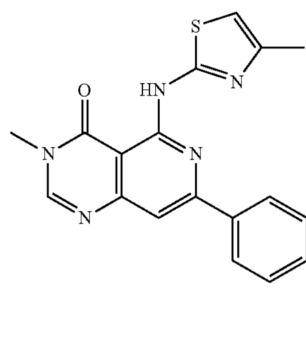 | HPLC-MS calculated for C$_{22}$H$_{22}$N$_6$O$_2$S (M + H⁺) 435.2, found 435.2. | 0.6 |
| 458 | 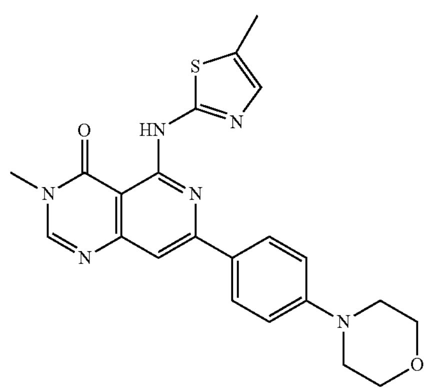 [SMILES: Cc1cnc(Nc2nc(-c3ccc(N4CCOCC4)cc3)cc3ncn(C)c(=O)c23)s1] | HPLC-MS calculated for C$_{22}$H$_{22}$N$_6$O$_2$S (M + H⁺) 435.2, found 435.2. | 1.698 |
| 459 | 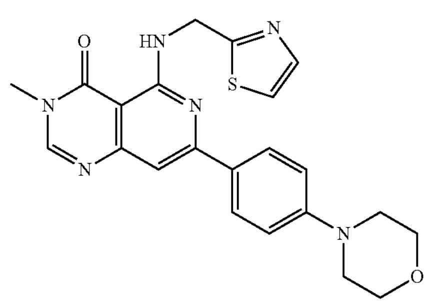 [SMILES: Cn1cnc2cc(-c3ccc(N4CCOCC4)cc3)nc(NCc3nccs3)c2c1=O] | HPLC-MS calculated for C$_{22}$H$_{22}$N$_6$O$_2$S (M + H⁺) 435.2, found 435.2. | 0.736 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 460 | 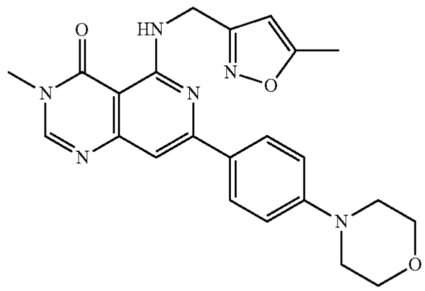 [SMILES: Cc1cc(CNc2nc(-c3ccc(N4CCOCC4)cc3)cc3ncn(C)c(=O)c23)no1] | HPLC-MS calculated for $C_{23}H_{24}N_6O_3$ (M + H⁺) 433.2, found 433.2. | 0.697 |
| 461 | 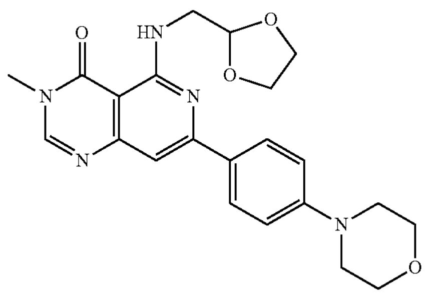 [SMILES: Cn1cnc2cc(-c3ccc(N4CCOCC4)cc3)nc(NCC3OCCO3)c2c1=O] | HPLC-MS calculated for $C_{22}H_{25}N_5O_4$ (M + H⁺) 424.2, found 424.2. | 0.432 |
| 462 | 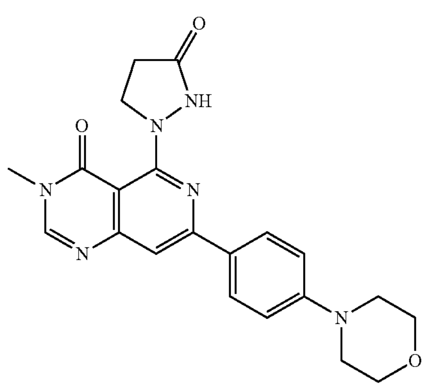 [SMILES: Cn1cnc2cc(-c3ccc(N4CCOCC4)cc3)nc(N3CCC(=O)N3)c2c1=O] | HPLC-MS calculated for $C_{21}H_{22}N_6O_3$ (M + H⁺) 407.2, found 407.2. | 2.502 |
| 463 | 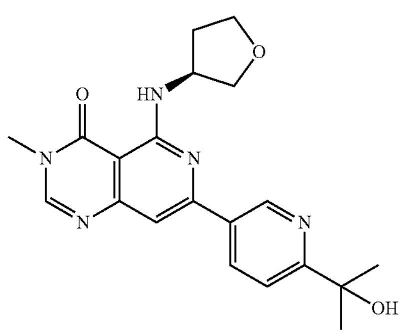 [SMILES: Cn1cnc2cc(-c3ccc(C(C)(C)O)nc3)nc(N[C@H]3CCOC3)c2c1=O] | HPLC-MS calculated $C_{20}H_{23}N_5O_3$ (M + H⁺): 382.19, found: 382.20. | 0.463 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 464 | 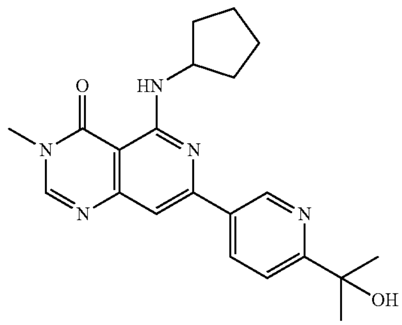 [SMILES: Cn1cnc2cc(-c3ccc(C(C)(C)O)nc3)nc(NC3CCCC3)c2c1=O] | HPLC-MS calculated $C_{21}H_{25}N_5O_3$ (M + H⁺): 380.21, found: 380.20. | 0.857 |
| 465 | 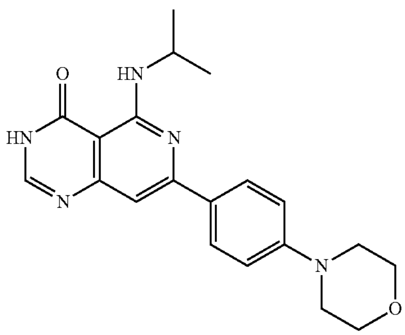 [SMILES: CC(C)Nc1nc(-c2ccc(N3CCOCC3)cc2)cc2nc[nH]c(=O)c12] | HPLC-MS calculated $C_{20}H_{23}N_5O_3$ (M + H⁺): 366.20, found: 366.10. | 1.593 |
| 466 | 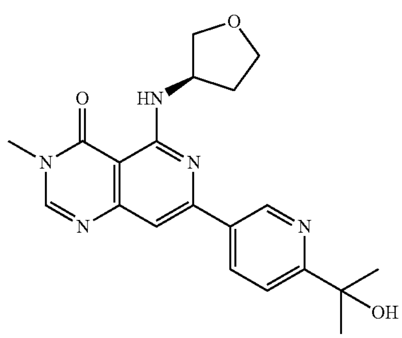 [SMILES: Cn1cnc2cc(-c3ccc(C(C)(C)O)nc3)nc(N[C@@H]3CCOC3)c2c1=O] | HPLC-MS calculated $C_{20}H_{23}N_5O_3$ (M + H⁺): 382.19, found: 382.20. | 0.199 |
| 467 | 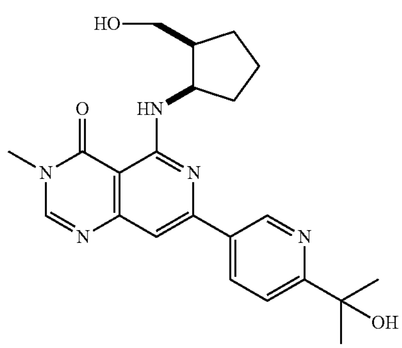 | HPLC-MS calculated $C_{22}H_{27}N_5O_3$ (M + H⁺): 410.22, found: 410.20. | 0.553 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 468 | 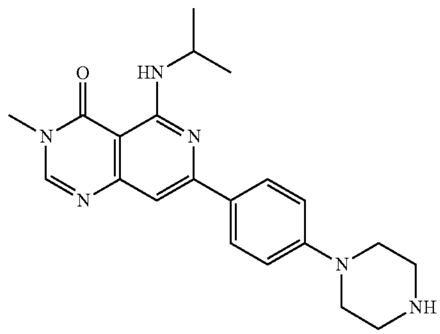 [SMILES: CC(C)Nc1nc(-c2ccc(N3CCNCC3)cc2)cc2ncn(C)c(=O)c12] | HPLC-MS calculated $C_{21}H_{26}N_6O$ (M + H⁺): 379.23, found: 379.10. | 0.049 |
| 469 | 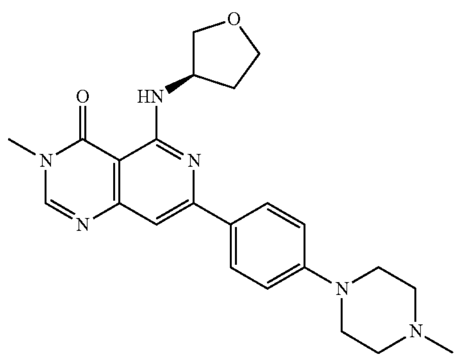 | HPLC-MS calculated $C_{23}H_{28}N_6O_2$ (M + H⁺): 421.24, found: 421.20. | 0.028 |
| 470 | 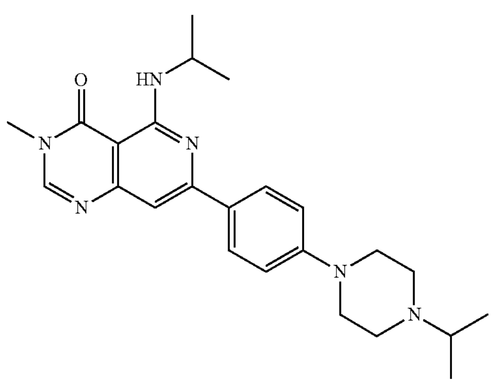 [SMILES: CC(C)Nc1nc(-c2ccc(N3CCN(C(C)C)CC3)cc2)cc2ncn(C)c(=O)c12] | HPLC-MS calculated $C_{24}H_{32}N_6O$ (M + H⁺): 421.27, found: 421.30. | 0.068 |
| 471 | 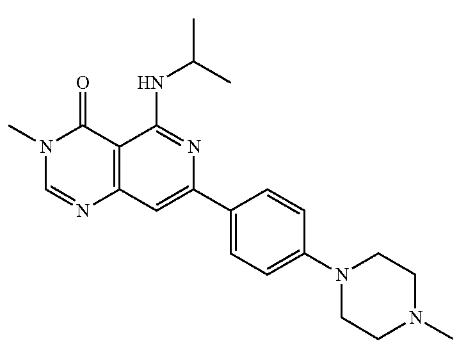 | HPLC-MS calculated $C_{23}H_{28}N_6O$ (M + H⁺): 393.24, found: 393.20. | 0.051 |

TABLE 1-continued

| Compound Number | Structure | Physical Data <sup>1</sup>H NMR 400 MHz (CDCl<sub>3</sub>), HPLC Retention Time, and/or MS (m/z) | Syk Enzyme IC$_{50}$ (uM) |
|---|---|---|---|
| 472 | 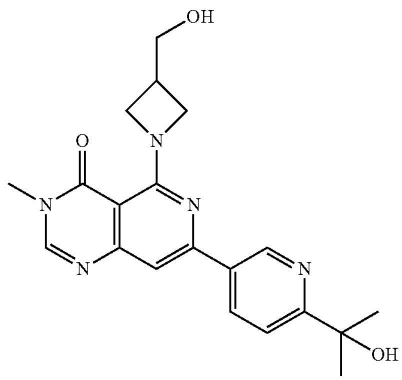 [SMILES: Cn1cnc2cc(-c3ccc(C(C)(C)O)nc3)nc(N3CC(CO)C3)c2c1=O] | HPLC-MS calculated C$_{20}$H$_{23}$N$_5$O$_3$ (M + H$^+$): 382.19, found: 382.10. | 0.435 |
| 473 | 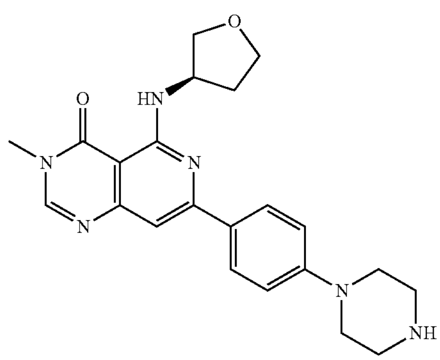 | HPLC-MS calculated C$_{22}$H$_{26}$N$_6$O$_2$ (M + H$^+$): 407.22, found: 407.10. | 0.019 |
| 474 | 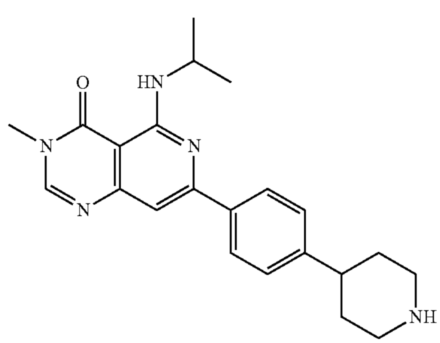 [SMILES: CC(C)Nc1nc(-c2ccc(C3CCNCC3)cc2)cc2ncn(C)c(=O)c12] | HPLC-MS calculated C$_{22}$H$_{27}$N$_5$O (M + H$^+$): 378.23, found: 378.10. | 0.035 |
| 475 | 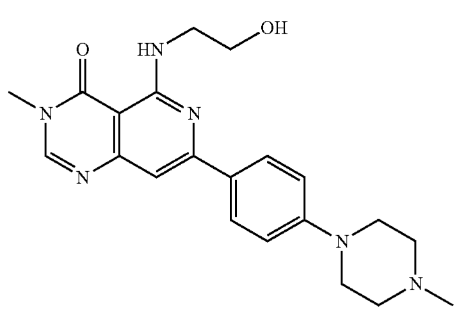 | HPLC-MS calculated C$_{21}$H$_{26}$N$_6$O$_2$ (M + H$^+$): 395.22, found: 395.20. | 0.044 |

TABLE 1-continued

| Compound Number | Structure | Physical Data<br>¹H NMR 400 MHz (CDCl₃),<br>HPLC Retention Time, and/or<br>MS (m/z) | Syk Enzyme IC₅₀ (uM) |
|---|---|---|---|
| 476 | 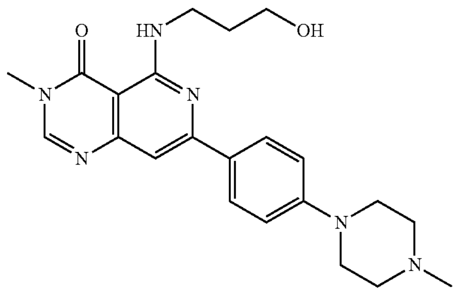 | HPLC-MS calculated $C_{22}H_{28}N_6O_2$ (M + H⁺): 409.24, found: 409.30. | 0.045 |
| 477 | 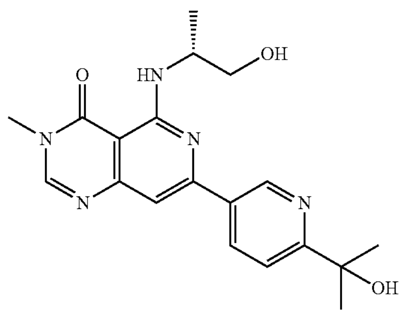 [SMILES: C[C@H](CO)Nc1nc(-c2ccc(C(C)(C)O)nc2)cc2ncn(C)c(=O)c12] | HPLC-MS calculated $C_{19}H_{23}N_5O_3$ (M + H⁺): 370.19, found: 370.00. | 0.177 |
| 478 | 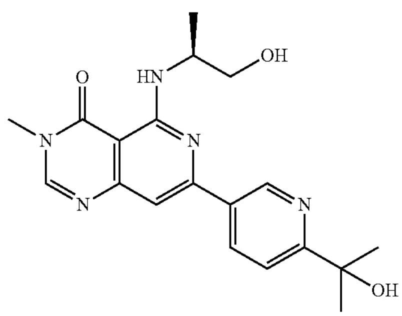 [SMILES: C[C@@H](CO)Nc1nc(-c2ccc(C(C)(C)O)nc2)cc2ncn(C)c(=O)c12] | HPLC-MS calculated $C_{19}H_{23}N_5O_3$ (M + H⁺): 370.19, found: 370.10. | 0.754 |
| 479 | 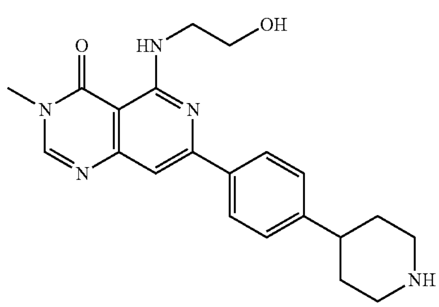 | HPLC-MS calculated $C_{21}H_{24}N_5O_2$ (M + H⁺): 380.21, found: 380.10. | 0.047 |
| 480 | 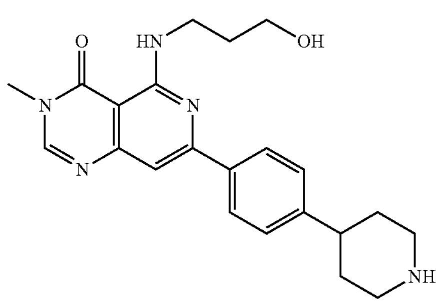 | HPLC-MS calculated $C_{22}H_{27}N_5O_2$ (M + H⁺): 394.23, found: 394.10. | 0.042 |

TABLE 1-continued

| Compound Number | Structure | Physical Data <br> ¹H NMR 400 MHz (CDCl₃), HPLC Retention Time, and/or MS (m/z) | Syk Enzyme IC$_{50}$ (uM) |
| --- | --- | --- | --- |
| 481 | 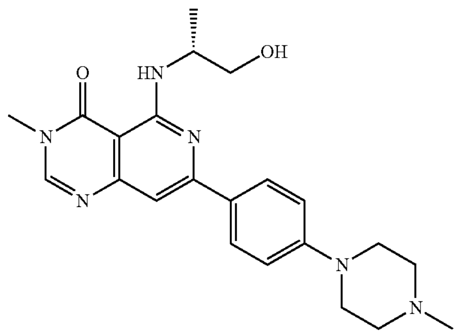 | HPLC-MS calculated C$_{22}$H$_{28}$N$_6$O$_2$ (M + H⁺): 409.24, found: 409.10. | 0.026 |
| 482 | 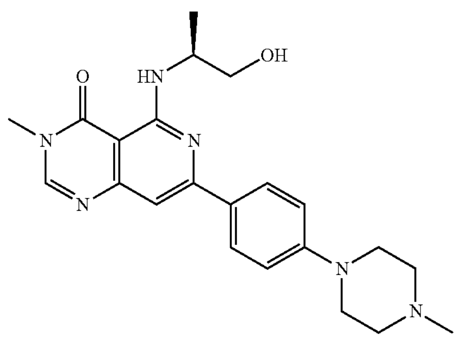 | HPLC-MS calculated C$_{22}$H$_{28}$N$_6$O$_2$ (M + H⁺): 409.24, found: 409.10. | 0.147 |
| 483 | 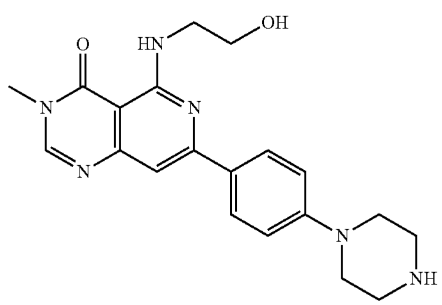 [SMILES: Cn1cnc2cc(-c3ccc(N4CCNCC4)cc3)nc(NCCO)c2c1=O] | HPLC-MS calculated C$_{20}$H$_{24}$N$_6$O$_2$ (M + H⁺): 381.21, found: 381.10. | 0.051 |
| 484 | 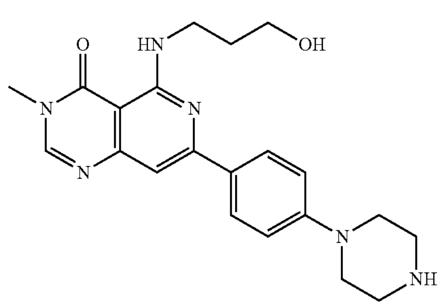 [SMILES: Cn1cnc2cc(-c3ccc(N4CCNCC4)cc3)nc(NCCCO)c2c1=O] | HPLC-MS calculated C$_{21}$H$_{26}$N$_6$O$_2$ (M + H⁺): 395.22, found: 395.10. | 0.042 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 485 | 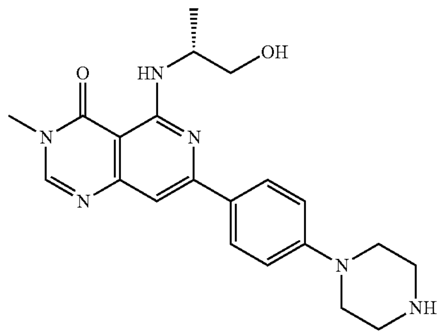 [SMILES: C[C@H](CO)Nc1nc(-c2ccc(N3CCNCC3)cc2)cc2ncn(C)c(=O)c12] | HPLC-MS calculated C$_{21}$H$_{26}$N$_6$O$_2$ (M + H⁺): 395.22, found: 395.10. | 0.019 |
| 486 | 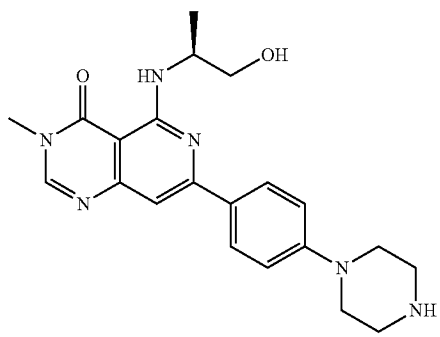 [SMILES: C[C@@H](CO)Nc1nc(-c2ccc(N3CCNCC3)cc2)cc2ncn(C)c(=O)c12] | HPLC-MS calculated C$_{21}$H$_{26}$N$_6$O$_2$ (M + H⁺): 395.22, found: 395.10. | 0.111 |
| 487 | 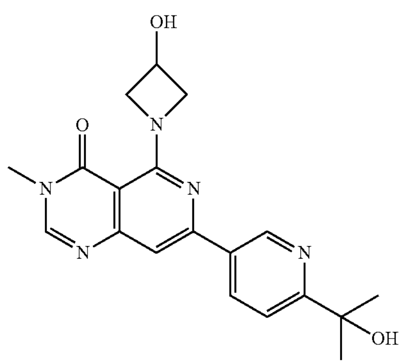 [SMILES: Cn1cnc2cc(-c3ccc(C(C)(C)O)nc3)nc(N3CC(O)C3)c2c1=O] | HPLC-MS calculated C$_{19}$H$_{21}$N$_5$O$_3$ (M + H⁺): 368.17, found: 368.10. | 1.119 |
| 488 | 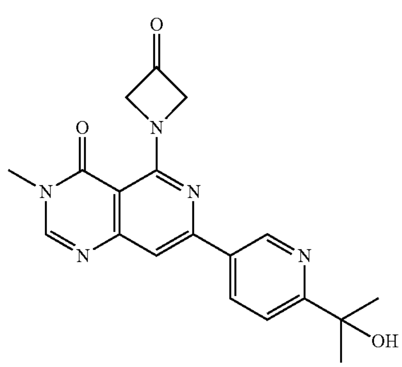 [SMILES: Cn1cnc2cc(-c3ccc(C(C)(C)O)nc3)nc(N3CC(=O)C3)c2c1=O] | HPLC-MS calculated C$_{19}$H$_{19}$N$_5$O$_3$ (M + H⁺): 366.16, found: 366.10. | 0.632 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 489 | 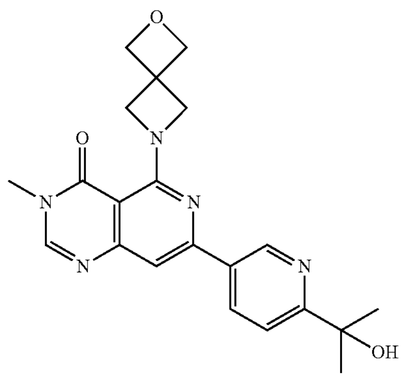 [SMILES: Cn1cnc2cc(-c3ccc(C(C)(C)O)nc3)nc(N3CC4(COC4)C3)c2c1=O] | HPLC-MS calculated C$_{21}$H$_{23}$N$_5$O$_3$ (M + H⁺): 394.19, found: 394.10. | 0.662 |
| 490 | 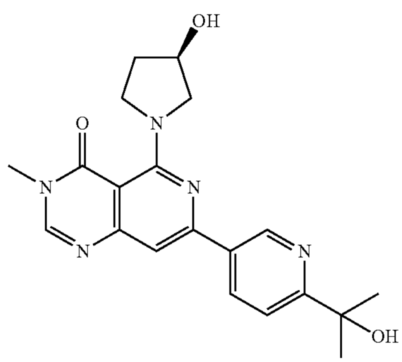 [SMILES: Cn1cnc2cc(-c3ccc(C(C)(C)O)nc3)nc(N3CC[C@@H](O)C3)c2c1=O] | HPLC-MS calculated C$_{20}$H$_{23}$N$_5$O$_3$ (M + H⁺): 382.19, found: 382.10. | 0.658 |
| 491 | 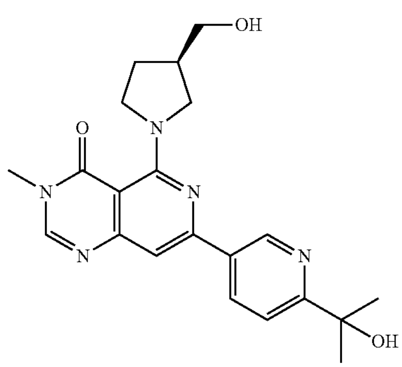 [SMILES: Cn1cnc2cc(-c3ccc(C(C)(C)O)nc3)nc(N3CC[C@@H](CO)C3)c2c1=O] | HPLC-MS calculated C$_{21}$H$_{25}$N$_5$O$_3$ (M + H⁺): 396.21, found: 396.10. | 0.8 |
| 492 | 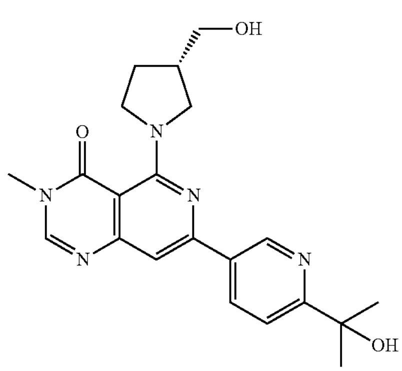 [SMILES: Cn1cnc2cc(-c3ccc(C(C)(C)O)nc3)nc(N3CC[C@H](CO)C3)c2c1=O] | HPLC-MS calculated C$_{21}$H$_{25}$N$_5$O$_3$ (M + H⁺): 396.21, found: 396.10. | 0.252 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 493 | 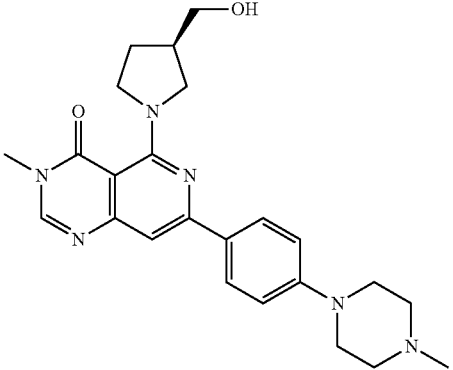 | $^1$H NMR (CDCl$_3$) δ (ppm) 8.05 (d, 2H), 8.00 (s, 1H), 7.18 (s, 1H), 6.97 (d, 2H), 3.90-3.81 (m, 1H), 3.77-3.65 (m, 4H), 3.64-3.58 (m, 1H), 3.49 (s, 3H), 3.33-3.30 (m, 4H), 2.61-2.57 (m, 4H), 2.54-2.47 (m, 1H), 2.36 (s, 3H), 2.15-2.06 (m, 1H), 1.82-1.72 (m, 2H); HPLC-MS calculated C$_{24}$H$_{30}$N$_6$O$_2$ (M + H$^+$): 435.25, found: 435.10. | 0.205 |
| 494 | 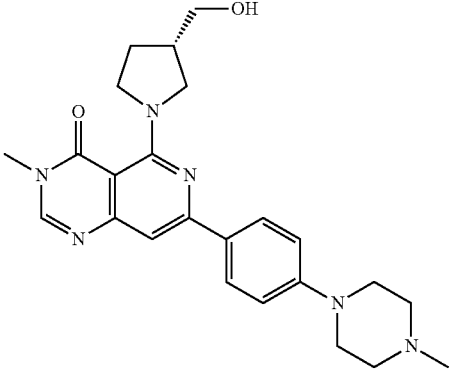 | $^1$H NMR (CDCl$_3$) δ (ppm) 8.05 (d, 2H), 8.00 (s, 1H), 7.18 (s, 1H), 6.97 (d, 2H), 3.90-3.81 (m, 1H), 3.77-3.65 (m, 4H), 3.64-3.58 (m, 1H), 3.49 (s, 3H), 3.33-3.30 (m, 4H), 2.61-2.57 (m, 4H), 2.54-2.47 (m, 1H), 2.36 (s, 3H), 2.15-2.06 (m, 1H), 1.82-1.72 (m, 2H); HPLC-MS calculated C$_{24}$H$_{30}$N$_6$O$_2$ (M + H$^+$): 435.25, found: 435.10. | 0.057 |
| 495 | 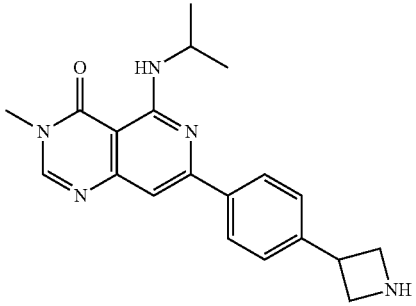 [SMILES: CC(C)Nc1nc(-c2ccc(C3CNC3)cc2)cc2ncn(C)c(=O)c12] | HPLC-MS calculated C$_{20}$H$_{23}$N$_6$O (M + H$^+$): 350.20, found: 350.10. | 0.122 |
| 496 | 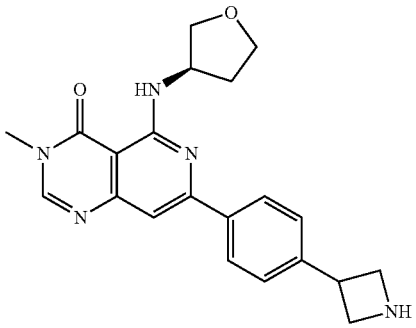 [SMILES: Cn1cnc2cc(-c3ccc(C4CNC4)cc3)nc(N[C@@H]3CCOC3)c2c1=O] | HPLC-MS calculated C$_{21}$H$_{23}$N$_5$O$_2$ (M + H$^+$): 378.20, found: 378.10. | 0.048 |

TABLE 1-continued

| Compound Number | Structure | Physical Data<br>¹H NMR 400 MHz (CDCl₃), HPLC Retention Time, and/or MS (m/z) | Syk Enzyme IC$_{50}$ (uM) |
| --- | --- | --- | --- |
| 497 | 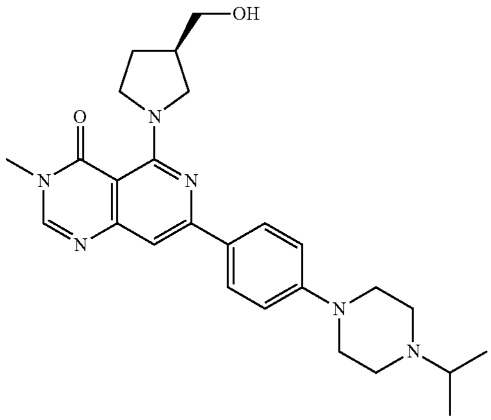 [SMILES: CC(C)N1CCN(c2ccc(-c3cc4ncn(C)c(=O)c4c(N4CC[C@@H](CO)C4)n3)cc2)CC1] | HPLC-MS calculated C$_{26}$H$_{34}$N$_6$O$_2$ (M + H$^+$): 463.28, found: 463.20. | 0.162 |
| 498 | 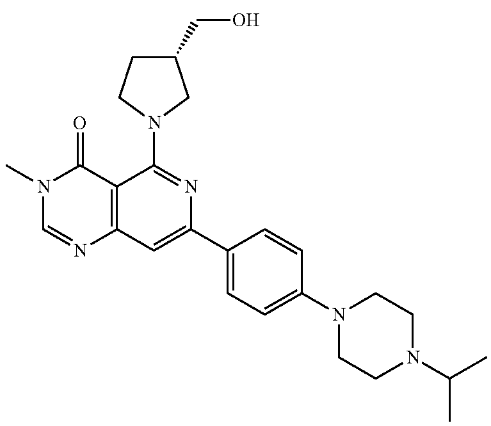 [SMILES: CC(C)N1CCN(c2ccc(-c3cc4ncn(C)c(=O)c4c(N4CC[C@H](CO)C4)n3)cc2)CC1] | HPLC-MS calculated C$_{26}$H$_{34}$N$_6$O$_2$ (M + H$^+$): 463.28, found: 463.20. | 0.044 |
| 499 | 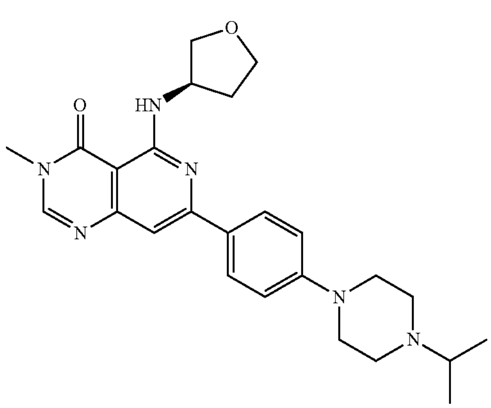 [SMILES: CC(C)N1CCN(c2ccc(-c3cc4ncn(C)c(=O)c4c(N[C@@H]4CCOC4)n3)cc2)CC1] | ¹H NMR (CDCl₃) δ (ppm) 8.80 (d, 1H), 8.04 (d, 2H), 8.00 (s, 1H), 7.10 (s, 1H), 6.98 (d, 2H), 4.92-4.84 (m, 1H), 4.22 (dd, 1H), 4.06-3.99 (m, 1H), 3.95-3.89 (m, 1H), 3.80 (dd, 1H), 3.51 (s, 3H), 3.34-3.31 (m, 4H), 3.77-3.68 (m, 5H), 2.46-2.36 (m, 1H), 2.06-1.96 (m, 1H), 1.10 (d, 6H); HPLC-MS calculated C$_{25}$H$_{32}$N$_6$O$_2$ (M + H$^+$): 449.27, found: 449.20. | 0.032 |

TABLE 1-continued

| Compound Number | Structure | Physical Data <sup>1</sup>H NMR 400 MHz (CDCl<sub>3</sub>), HPLC Retention Time, and/or MS (m/z) | Syk Enzyme IC$_{50}$ (uM) |
|---|---|---|---|
| 500 | 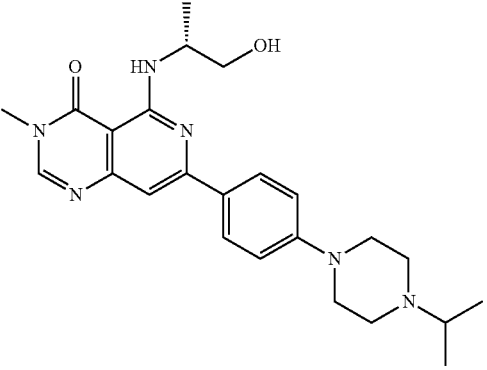 [SMILES: CC(C)N1CCN(c2ccc(-c3cc4ncn(C)c(=O)c4c(N[C@H](C)CO)n3)cc2)CC1] | HPLC-MS calculated C$_{24}$H$_{32}$N$_6$O$_2$ (M + H$^+$): 437.27, found: 437.20. | 0.024 |
| 501 | 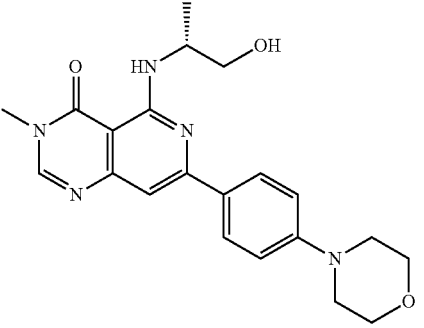 [SMILES: C[C@H](CO)Nc1nc(-c2ccc(N3CCOCC3)cc2)cc2ncn(C)c(=O)c12] | $^1$H NMR (CDCl$_3$) δ (ppm) 8.87 (d, 1H), 8.02 (s, 1H), 7.96 (d, 2H), 7.06 (s, 1H), 6.96 (d, 2H), 5.06 (s, br, 1H), 4.57-4.47 (m, 1H), 3.89-3.85 (m, 5H), 3.71 (dd, 1H), 3.51 (s, 3H), 3.26-3.23 (m, 4H), 1.36 (d, 3H); HPLC-MS calculated C$_{21}$H$_{25}$N$_5$O$_3$ (M + H$^+$): 396.21, found: 396.20. | 0.057 |
| 502 | 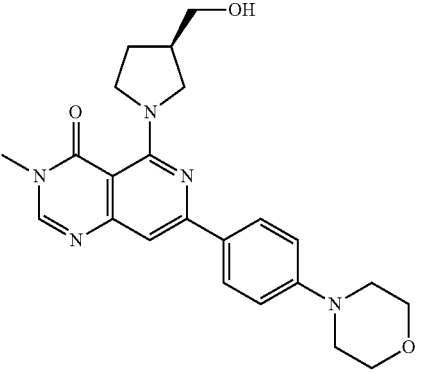 [SMILES: Cn1cnc2cc(-c3ccc(N4CCOCC4)cc3)nc(N3CC[C@@H](CO)C3)c2c1=O] | $^1$H NMR (CDCl$_3$) δ (ppm) 8.06 (d, 2H), 8.01 (s, 1H), 7.19 (s, 1H), 6.96 (d, 2H), 3.91-3.81 (m, 5H), 3.78-3.65 (m, 4H), 3.65-3.58 (m, 1H), 3.50 (s, 3H), 3.27-3.24 (m, 4H), 2.57-2.47 (m, 1H), 2.15-2.07 (m, 1H), 1.90 (s, br, 1H), 1.82-1.72 (m, 1H); HPLC-MS calculated C$_{23}$H$_{27}$N$_5$O$_3$ (M + H$^+$): 422.22, found: 422.20. | 0.19 |
| 503 | 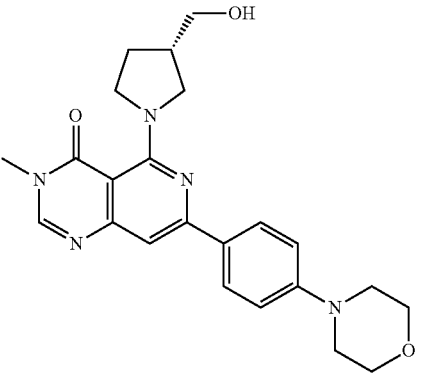 [SMILES: Cn1cnc2cc(-c3ccc(N4CCOCC4)cc3)nc(N3CC[C@H](CO)C3)c2c1=O] | $^1$H NMR (CDCl$_3$) δ (ppm) 8.06 (d, 2H), 8.01 (s, 1H), 7.19 (s, 1H), 6.96 (d, 2H), 3.91-3.81 (m, 5H), 3.78-3.65 (m, 4H), 3.65-3.58 (m, 1H), 3.50 (s, 3H), 3.27-3.24 (m, 4H), 2.57-2.47 (m, 1H), 2.15-2.07 (m, 1H), 1.90 (s, br, 1H), 1.82-1.72 (m, 1H); HPLC-MS calculated C$_{23}$H$_{27}$N$_5$O$_3$ (M + H$^+$): 422.22, found: 422.20. | 0.117 |

TABLE 1-continued
| Compound Number | Structure | Physical Data <br> ¹H NMR 400 MHz (CDCl₃), HPLC Retention Time, and/or MS (m/z) | Syk Enzyme IC₅₀ (uM) |
|---|---|---|---|
| 504 | 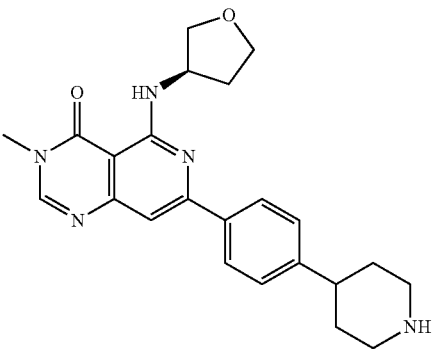 [SMILES: Cn1cnc2cc(-c3ccc(C4CCNCC4)cc3)nc(N[C@@H]3CCOC3)c2c1=O] | HPLC-MS calculated $C_{23}H_{27}N_5O_2$ (M + H⁺): 406.23, found: 406.20. | 0.025 |
| 505 | 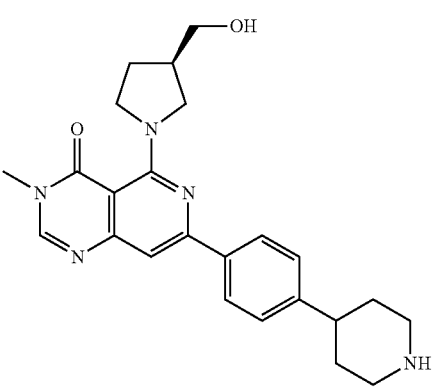 [SMILES: Cn1cnc2cc(-c3ccc(C4CCNCC4)cc3)nc(N3CC[C@@H](CO)C3)c2c1=O] | HPLC-MS calculated $C_{24}H_{29}N_5O_2$ (M + H⁺): 420.24, found: 420.20. | 0.094 |
| 506 | 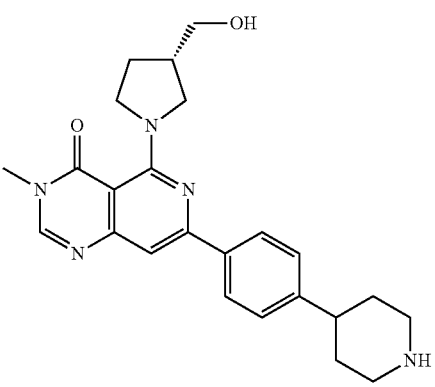 [SMILES: Cn1cnc2cc(-c3ccc(C4CCNCC4)cc3)nc(N3CC[C@H](CO)C3)c2c1=O] | HPLC-MS calculated $C_{24}H_{29}N_5O_2$ (M + H⁺): 420.24, found: 420.20. | 0.04 |
| 507 | 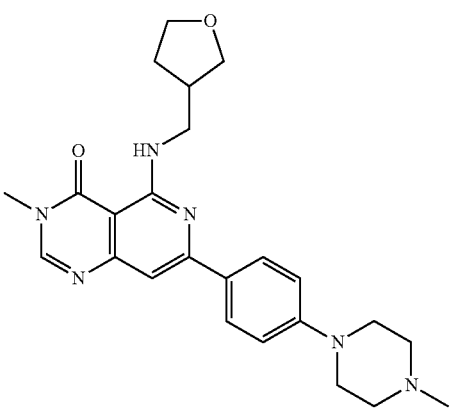 | HPLC-MS calculated $C_{24}H_{30}N_6O_2$ (M + H⁺): 435.25, found: 435.20. | 0.125 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 508 | 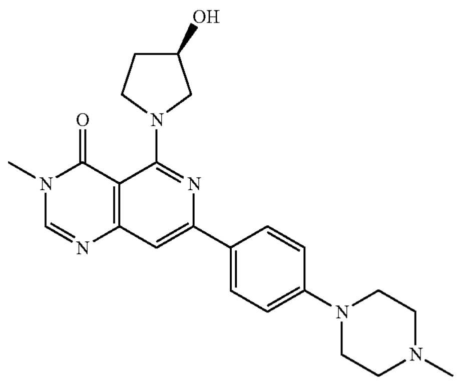 | HPLC-MS calculated $C_{23}H_{28}N_6O_2$ (M + H⁺): 421.24, found: 421.20. | 0.2 |
| 509 | 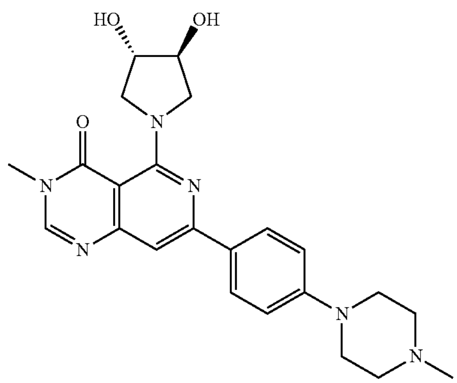 | HPLC-MS calculated $C_{23}H_{28}N_6O_3$ (M + H⁺): 437.23, found: 437.20. | 0.447 |
| 510 | 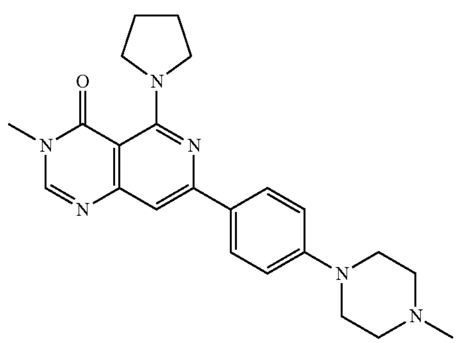 | HPLC-MS calculated $C_{23}H_{28}N_6O$ (M + H⁺): 405.24, found: 405.20. | 0.419 |
| 511 | 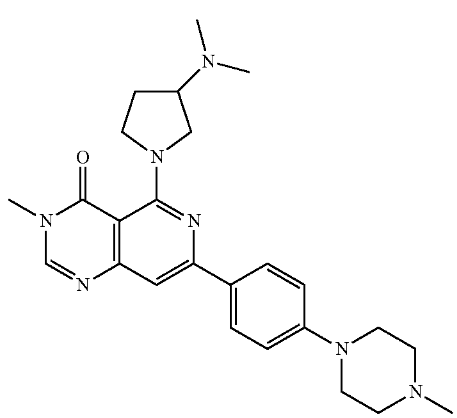 | HPLC-MS calculated $C_{25}H_{33}N_7O$ (M + H⁺): 448.28, found: 448.30. | 0.379 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 512 | 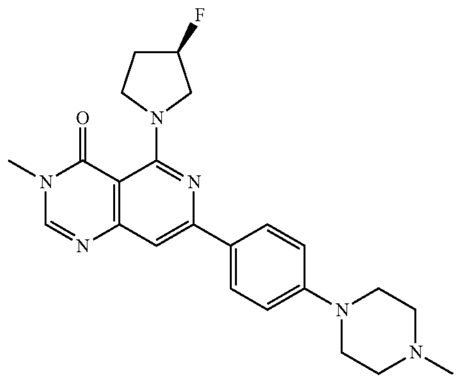 | HPLC-MS calculated C$_{23}$H$_{27}$FN$_6$O (M + H⁺): 423.23, found: 423.20. | 0.163 |
| 513 | 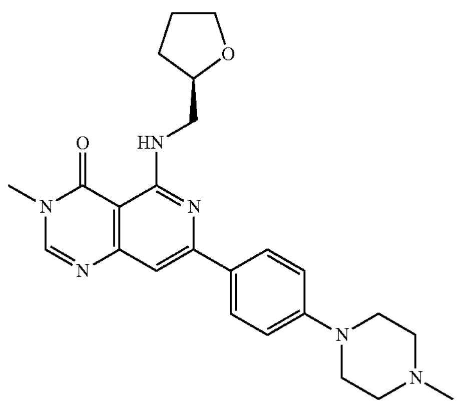 | HPLC-MS calculated C$_{24}$H$_{30}$N$_6$O$_2$ (M + H⁺): 435.25, found: 435.20. | 0.11 |
| 514 | 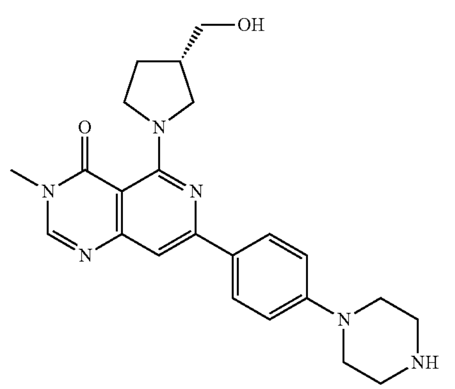 | HPLC-MS calculated C$_{23}$H$_{28}$N$_6$O$_2$ (M + H⁺): 421.24, found: 421.20. | 0.071 |
| 515 | 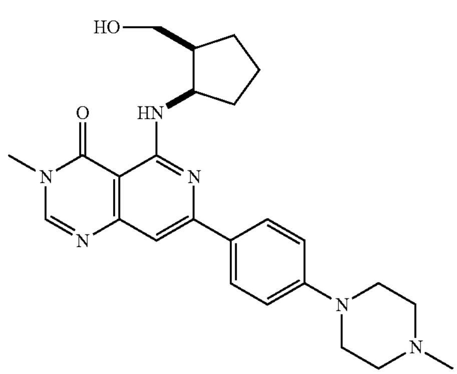 | HPLC-MS calculated C$_{25}$H$_{32}$N$_6$O$_2$ (M + H⁺): 449.27, found: 449.20. | 0.374 |

TABLE 1-continued
| Compound Number | Structure | Physical Data<br>$^1$H NMR 400 MHz (CDCl$_3$),<br>HPLC Retention Time, and/or<br>MS (m/z) | Syk Enzyme IC$_{50}$ (uM) |
|---|---|---|---|
| 516 | 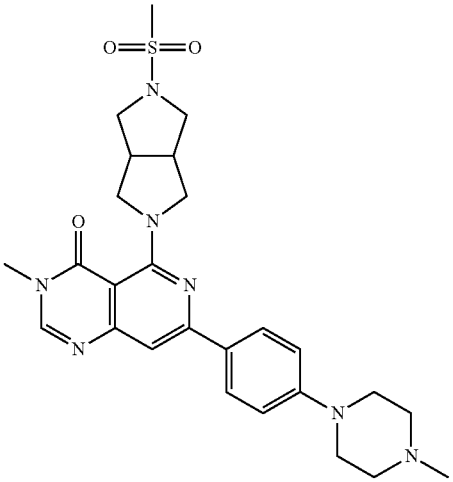 | HPLC-MS calculated<br>C$_{26}$H$_{33}$N$_7$O$_3$S (M + H$^+$): 524.25,<br>found: 524.20. | 0.761 |
| 517 | 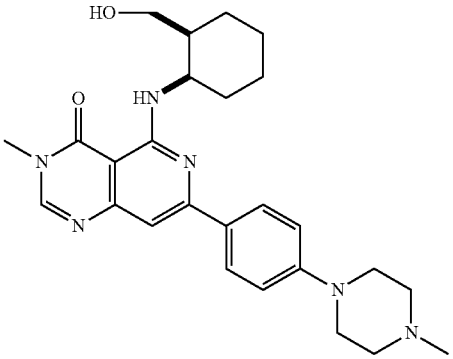 | HPLC-MS calculated C$_{26}$H$_{34}$N$_6$O$_2$<br>(M + H$^+$): 463.28, found: 463.20. | 0.958 |
| 518 | 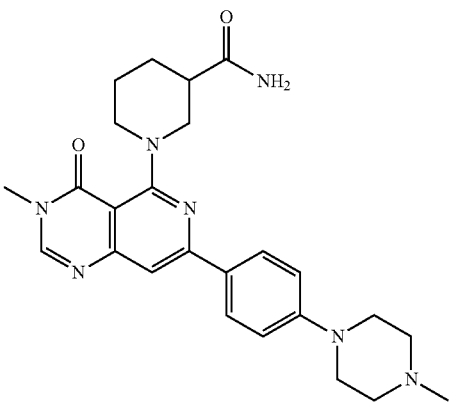 | HPLC-MS calculated C$_{25}$H$_{31}$N$_7$O$_2$<br>(M + H$^+$): 462.26, found: 462.20. | 0.436 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 519 | 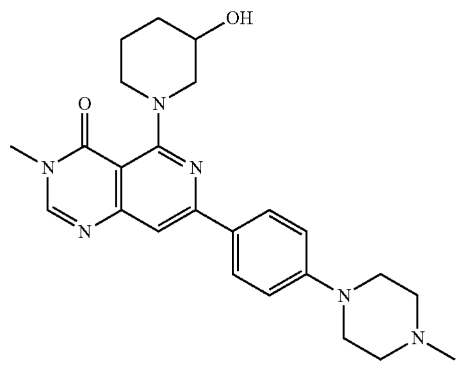 | HPLC-MS calculated C$_{24}$H$_{30}$N$_6$O$_2$ (M + H$^+$): 435.25, found: 435.20. | 0.671 |
| 520 | 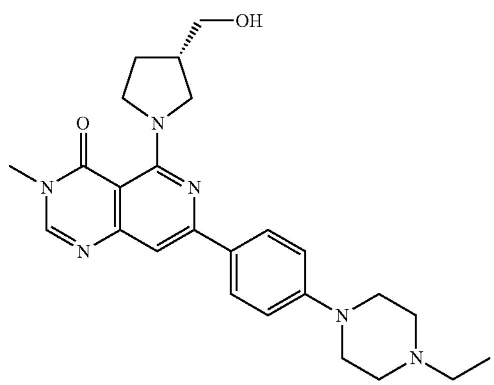 [SMILES: CCN1CCN(c2ccc(-c3cc4ncn(C)c(=O)c4c(N4CC[C@H](CO)C4)n3)cc2)CC1] | HPLC-MS calculated C$_{25}$H$_{32}$N$_6$O$_2$ (M + H$^+$): 449.27, found: 449.20. | 0.078 |
| 521 | 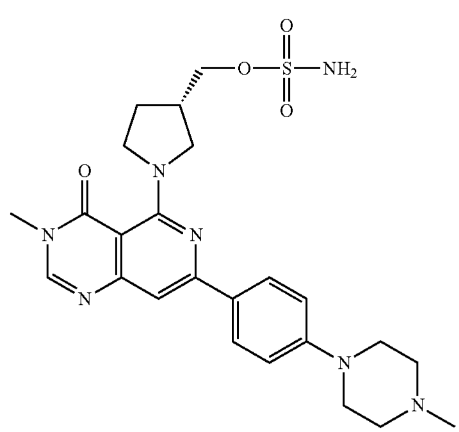 | HPLC-MS calculated C$_{24}$H$_{31}$N$_7$O$_4$S (M + H$^+$): 514.23, found: 514.20. | 0.257 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 522 | 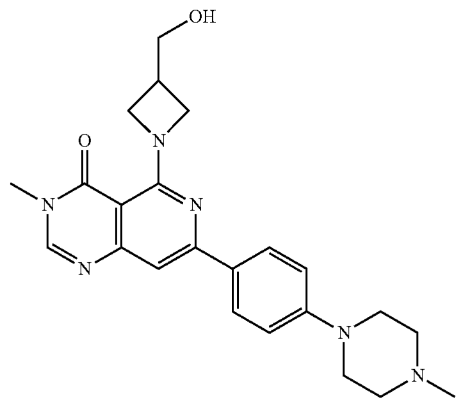 | ¹H NMR (CDCl₃) δ (ppm) 8.05 (d, 2H), 8.00 (s, 1H), 7.19 (s, 1H), 6.97 (d, 2H), 4.42 (dd, 2H), 4.12 (dd, 2H), 3.88 (d, 2H), 3.47 (s, 3H), 3.35-3.31 (m, 4H), 2.91-2.83 (m, 1H), 2.63-2.59 (m, 4H), 2.38 (s, 3H), 1.87 (s, br, 1H); HPLC-MS calculated C$_{23}$H$_{28}$N$_6$O$_2$ (M + H⁺): 421.24, found: 421.20. | 0.196 |
| 523 | 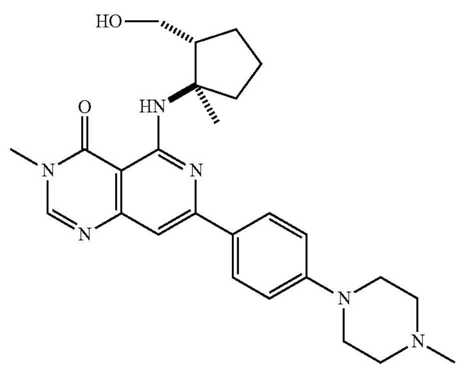 | HPLC-MS calculated C$_{26}$H$_{34}$N$_6$O$_2$ (M + H⁺): 463.28, found: 463.20. | 0.511 |
| 524 | 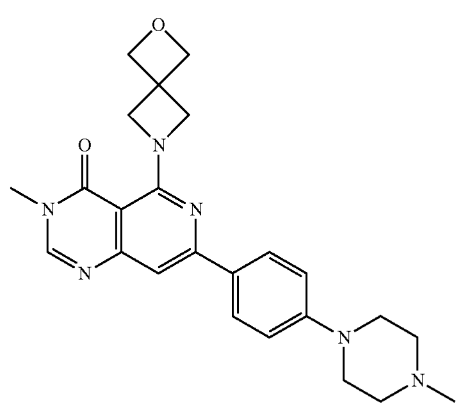 | HPLC-MS calculated C$_{24}$H$_{28}$N$_6$O$_2$ (M + H⁺): 433.24, found: 433.20. | 1.011 |
| 525 | 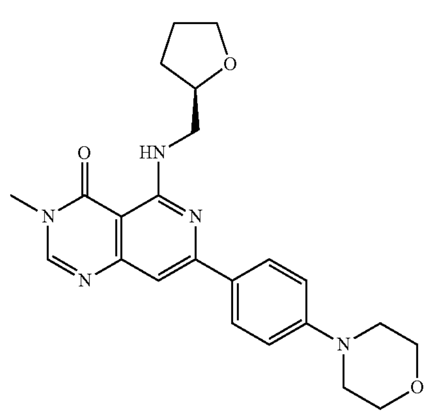 [SMILES: Cn1cnc2cc(-c3ccc(N4CCOCC4)cc3)nc(NC[C@H]3CCCO3)c2c1=O] | HPLC-MS calculated C$_{23}$H$_{27}$N$_5$O$_3$ (M + H⁺): 422.22, found: 422.20. | 0.264 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 526 | 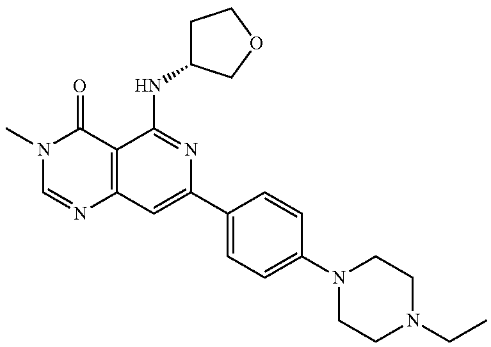 [SMILES: CCN1CCN(c2ccc(-c3cc4ncn(C)c(=O)c4c(N[C@@H]4CCOC4)n3)cc2)CC1] | HPLC-MS calculated $C_{24}H_{30}N_6O_2$ (M + H⁺): 435.25, found: 435.10. | 0.036 |
| 527 | 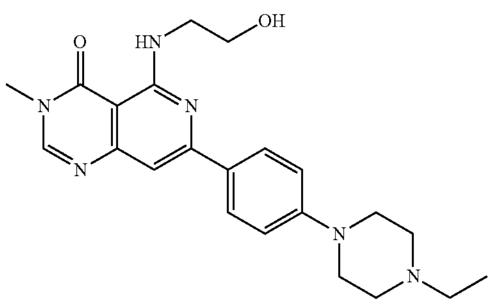 [SMILES: CCN1CCN(c2ccc(-c3cc4ncn(C)c(=O)c4c(NCCO)n3)cc2)CC1] | HPLC-MS calculated $C_{22}H_{28}N_6O_2$ (M + H⁺): 409.24, found: 409.20. | 0.131 |
| 528 | 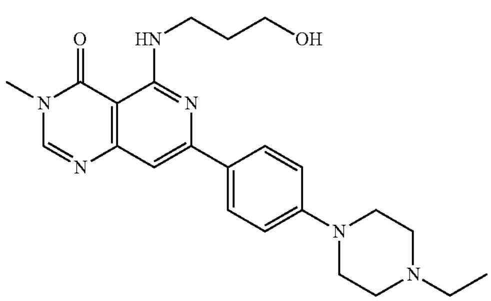 [SMILES: CCN1CCN(c2ccc(-c3cc4ncn(C)c(=O)c4c(NCCCO)n3)cc2)CC1] | HPLC-MS calculated $C_{23}H_{30}N_6O_2$ (M + H⁺): 423.25, found: 423.20. | 0.05 |
| 529 | 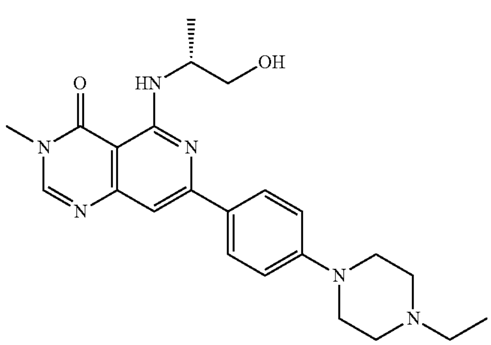 [SMILES: CCN1CCN(c2ccc(-c3cc4ncn(C)c(=O)c4c(N[C@H](C)CO)n3)cc2)CC1] | HPLC-MS calculated $C_{23}H_{30}N_6O_2$ (M + H⁺): 423.25, found: 423.20. | 0.031 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 530 | 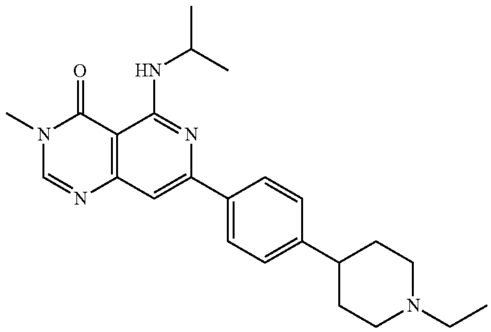 [SMILES: CCN1CCC(c2ccc(-c3cc4ncn(C)c(=O)c4c(NC(C)C)n3)cc2)CC1] | HPLC-MS calculated $C_{24}H_{31}N_5O$<br>(M + H⁺): 406.26, found: 406.20. | 0.097 |
| 531 | 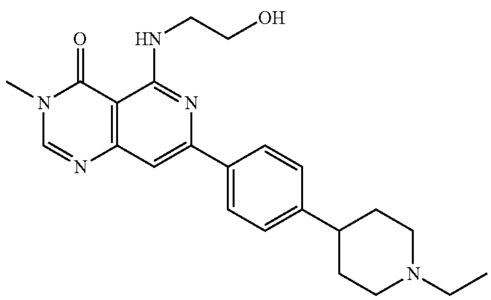 [SMILES: CCN1CCC(c2ccc(-c3cc4ncn(C)c(=O)c4c(NCCO)n3)cc2)CC1] | HPLC-MS calculated $C_{23}H_{29}N_5O_2$<br>(M + H⁺): 408.24, found: 408.20. | 0.114 |
| 532 | 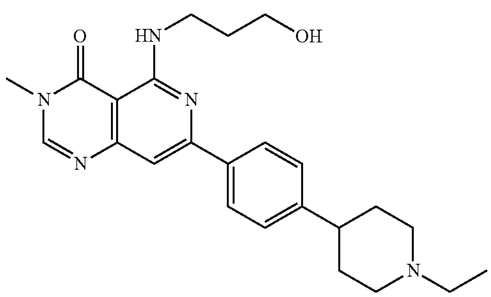 [SMILES: CCN1CCC(c2ccc(-c3cc4ncn(C)c(=O)c4c(NCCCO)n3)cc2)CC1] | HPLC-MS calculated $C_{24}H_{31}N_5O_2$<br>(M + H⁺): 422.26, found: 422.20. | 0.072 |
| 533 | 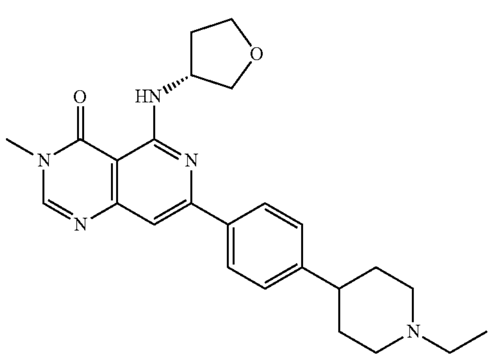 [SMILES: CCN1CCC(c2ccc(-c3cc4ncn(C)c(=O)c4c(N[C@@H]4CCOC4)n3)cc2)CC1] | HPLC-MS calculated $C_{25}H_{31}N_5O_2$<br>(M + H⁺): 434.26, found: 434.20. | 0.049 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 534 | 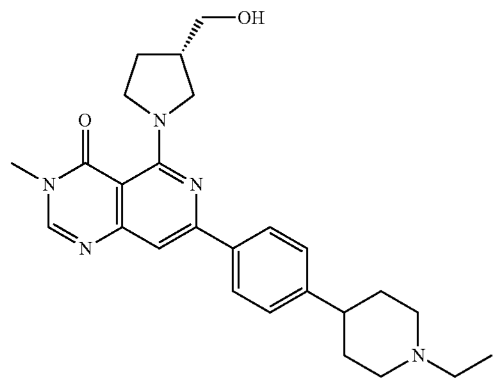 | HPLC-MS calculated $C_{26}H_{33}N_5O_2$ (M + H⁺): 448.27, found: 448.20. | 0.072 |
| 535 | 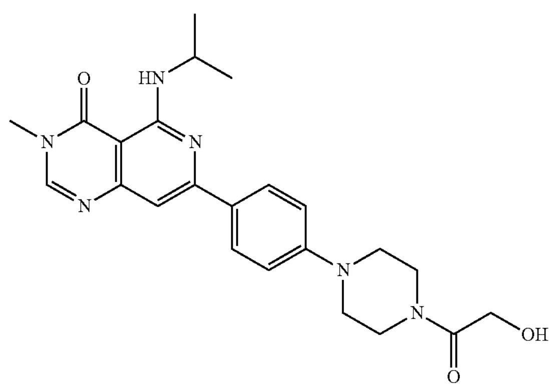 [SMILES: CC(C)Nc1nc(-c2ccc(N3CCN(C(=O)CO)CC3)cc2)cc2ncn(C)c(=O)c12] | HPLC-MS calculated $C_{23}H_{28}N_6O_3$ (M + H⁺): 437.23, found: 437.10. | 0.1 |
| 536 | 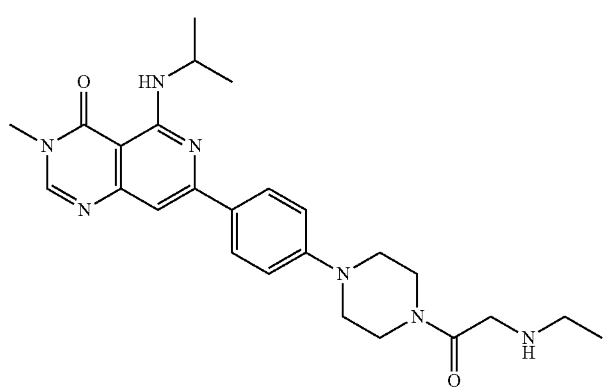 [SMILES: CCNCC(=O)N1CCN(c2ccc(-c3cc4ncn(C)c(=O)c4c(NC(C)C)n3)cc2)CC1] | HPLC-MS calculated $C_{25}H_{33}N_7O_2$ (M + H⁺): 464.28, found: 464.20. | 0.045 |
| 537 | 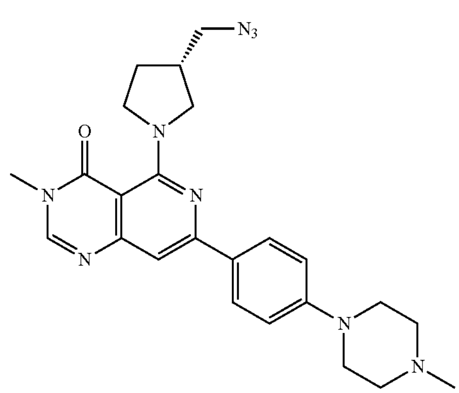 | HPLC-MS calculated $C_{24}H_{29}N_9O$ (M + H⁺): 460.26, found: 460.20. | 0.306 |

TABLE 1-continued

| Compound Number | Structure | Physical Data <sup>1</sup>H NMR 400 MHz (CDCl$_3$), HPLC Retention Time, and/or MS (m/z) | Syk Enzyme IC$_{50}$ (uM) |
|---|---|---|---|
| 538 | 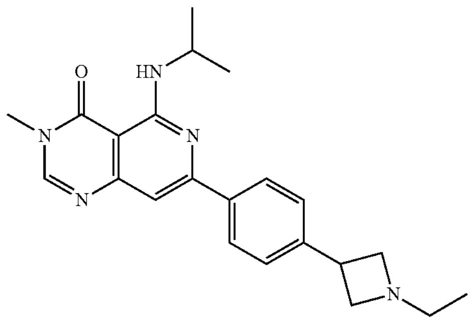 [SMILES: CCN1CC(c2ccc(-c3cc4ncn(C)c(=O)c4c(NC(C)C)n3)cc2)C1] | HPLC-MS calculated C$_{22}$H$_{28}$N$_5$O (M + H$^+$): 378.23, found: 378.20. | 0.13 |
| 539 | 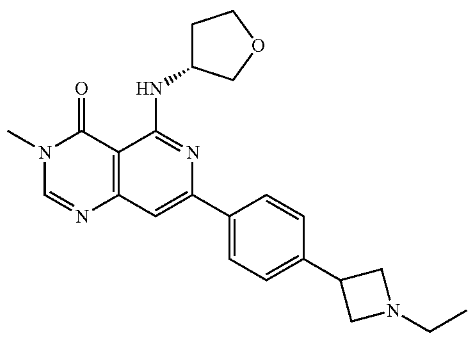 [SMILES: CCN1CC(c2ccc(-c3cc4ncn(C)c(=O)c4c(N[C@@H]4CCOC4)n3)cc2)C1] | HPLC-MS calculated C$_{23}$H$_{27}$N$_5$O$_2$ (M + H$^+$): 406.23, found: 406.20. | 0.105 |
| 540 | 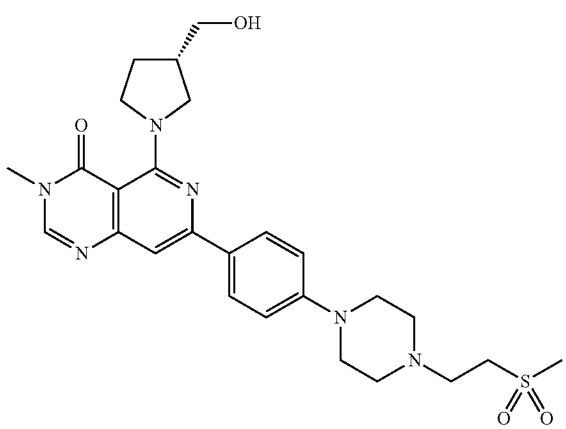 | HPLC-MS calculated C$_{26}$H$_{34}$N$_6$O$_4$S (M + H$^+$): 527.25, found: 527.20. | 0.084 |
| 541 | 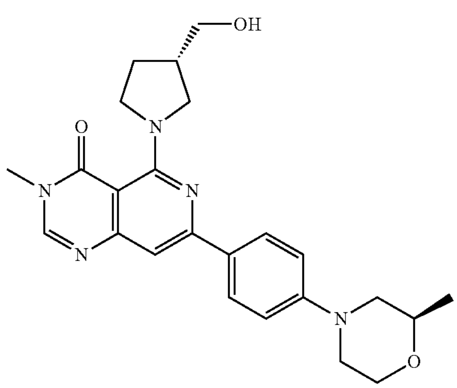 | HPLC-MS calculated C$_{24}$H$_{29}$N$_5$O$_3$ (M + H$^+$): 436.24, found: 436.20. | 0.147 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 542 | 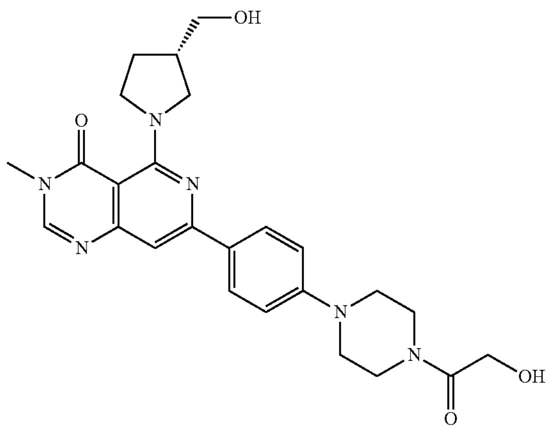 [SMILES: Cn1cnc2cc(-c3ccc(N4CCN(C(=O)CO)CC4)cc3)nc(N3CC[C@H](CO)C3)c2c1=O] | HPLC-MS calculated C$_{25}$H$_{30}$N$_6$O$_4$<br>(M + H⁺): 479.24, found: 479.30. | 0.086 |
| 543 | 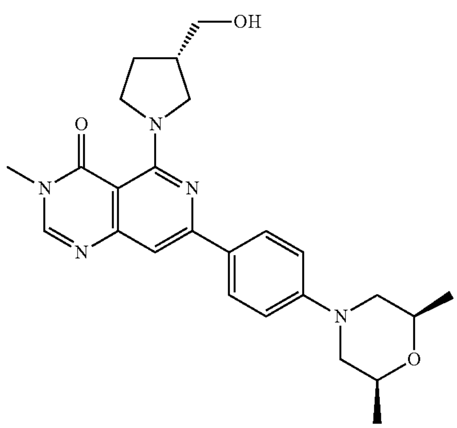 | HPLC-MS calculated C$_{26}$H$_{31}$N$_5$O$_3$<br>(M + H⁺): 450.25, found: 450.20. | 0.332 |
| 544 | 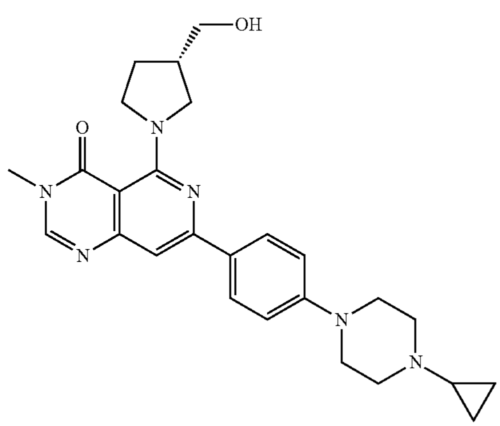 [SMILES: Cn1cnc2cc(-c3ccc(N4CCN(C5CC5)CC4)cc3)nc(N3CC[C@H](CO)C3)c2c1=O] | HPLC-MS calculated C$_{26}$H$_{32}$N$_6$O$_2$<br>(M + H⁺): 461.27, found: 461.20. | 0.081 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 545 | 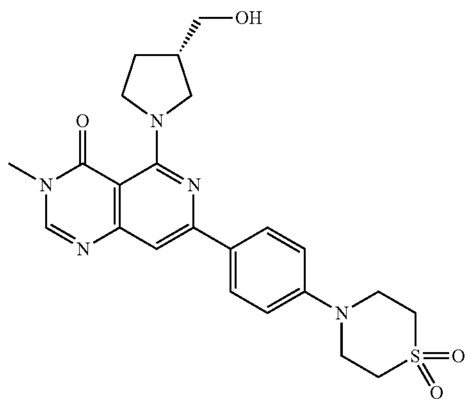 [SMILES: Cn1cnc2cc(-c3ccc(N4CCS(=O)(=O)CC4)cc3)nc(N3CC[C@H](CO)C3)c2c1=O] | $^1$H NMR (CDCl$_3$) δ (ppm) 8.08 (d, 2H), 8.02 (s, 1H), 7.18 (s, 1H), 6.97 (d, 2H), 3.98-3.92 (m, 4H), 3.90-3.80 (m, 1H), 3.78-3.58 (m, 5H), 3.51 (s, 5H), 3.14-3.08 (m, 4H), 2.55-2.46 (m, 1H), 2.15-2.07 (m, 1H), 1.91 (s, br, 1H), 1.82-1.72 (m, 1H); HPLC-MS calculated C$_{23}$H$_{27}$N$_5$O$_4$S (M + H$^+$): 470.19, found: 470.10. | 0.066 |
| 546 | 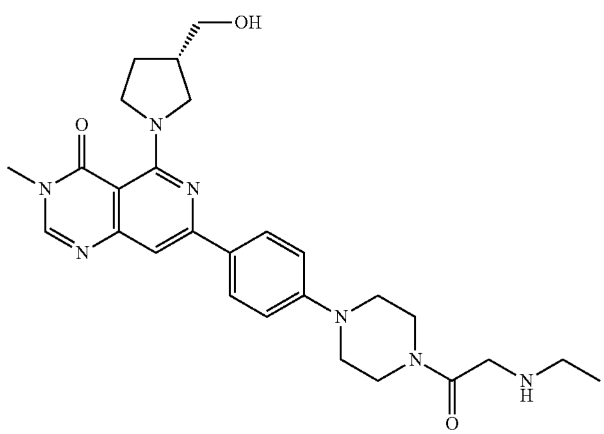 [SMILES: CCNCC(=O)N1CCN(c2ccc(-c3cc4ncn(C)c(=O)c4c(N4CC[C@H](CO)C4)n3)cc2)CC1] | HPLC-MS calculated C$_{27}$H$_{35}$N$_7$O$_3$ (M + H$^+$): 506.29, found: 506.20. | 0.038 |
| 547 | 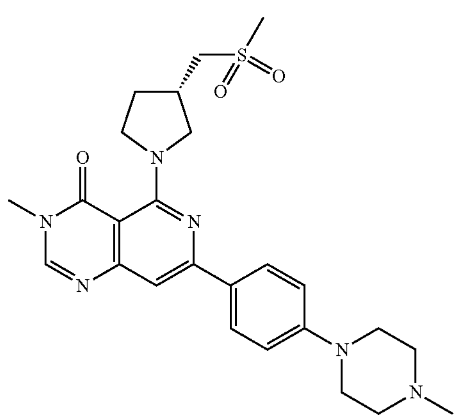 | HPLC-MS calculated C$_{25}$H$_{32}$N$_6$O$_3$S (M + H$^+$): 497.24, found: 497.20. | 0.223 |

TABLE 1-continued

| Compound Number | Structure | Physical Data<br>¹H NMR 400 MHz (CDCl₃),<br>HPLC Retention Time, and/or<br>MS (m/z) | Syk Enzyme IC₅₀ (uM) |
|---|---|---|---|
| 548 | 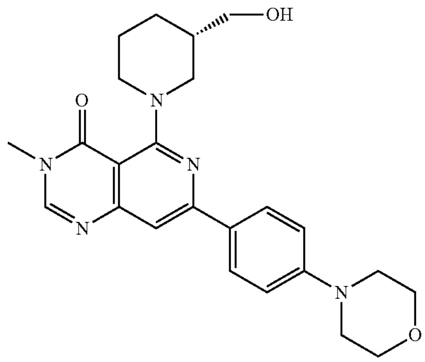 [SMILES: Cn1cnc2cc(-c3ccc(N4CCOCC4)cc3)nc(N3CCC[C@H](CO)C3)c2c1=O] | ¹H NMR (CDCl₃) δ (ppm) 8.04 (s, 1H), 8.00 (d, 2H), 7.26 (s, 1H), 6.97 (d, 2H), 3.89-3.86 (m, 4H), 3.78-3.64 (m, 3H), 3.62-3.52 (m, 2H), 3.51 (s, 3H), 3.34-3.24 (m, 5H), 3.01 (s, br, 1H), 2.16-2.04 (m, 1H), 1.88-1.66 (m, 3H), 1.48-1.38 (m, 1H); HPLC-MS calculated C₂₄H₂₉N₅O₃ (M + H⁺): 436.24, found: 436.20. | 0.925 |
| 549 | 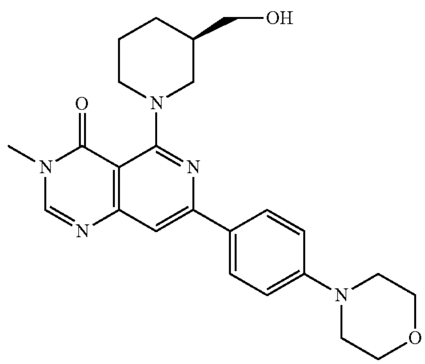 [SMILES: Cn1cnc2cc(-c3ccc(N4CCOCC4)cc3)nc(N3CCC[C@@H](CO)C3)c2c1=O] | ¹H NMR (CDCl₃) δ (ppm) 8.04 (s, 1H), 8.00 (d, 2H), 7.26 (s, 1H), 6.97 (d, 2H), 3.89-3.86 (m, 4H), 3.78-3.64 (m, 3H), 3.62-3.52 (m, 2H), 3.51 (s, 3H), 3.34-3.24 (m, 5H), 3.01 (s, br, 1H), 2.16-2.04 (m, 1H), 1.88-1.66 (m, 3H), 1.48-1.38 (m, 1H); HPLC-MS calculated C₂₄H₂₉N₅O₃ (M + H⁺): 436.24, found: 436.20. | 0.111 |
| 550 | 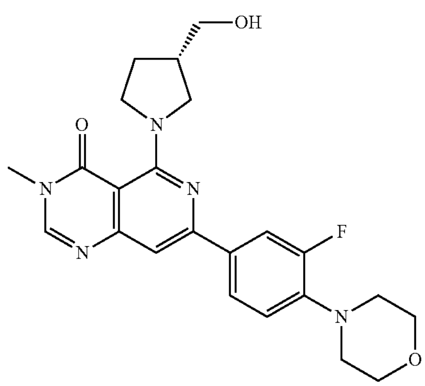 [SMILES: Cn1cnc2cc(-c3ccc(N4CCOCC4)c(F)c3)nc(N3CC[C@H](CO)C3)c2c1=O] | HPLC-MS calculated C₂₃H₂₆FN₅O₃ (M + H⁺): 440.21, found: 440.20. | 0.401 |
| 551 | 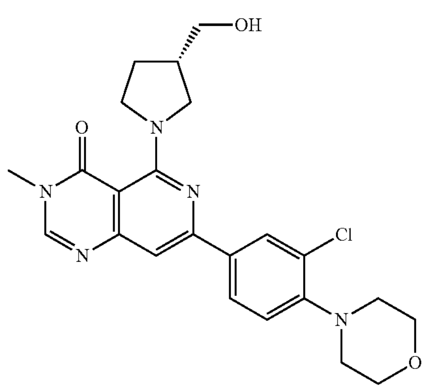 [SMILES: Cn1cnc2cc(-c3ccc(N4CCOCC4)c(Cl)c3)nc(N3CC[C@H](CO)C3)c2c1=O] | HPLC-MS calculated C₂₃H₂₆ClN₅O₃ (M + H⁺): 456.18, found: 456.20. | 0.29 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 552 | 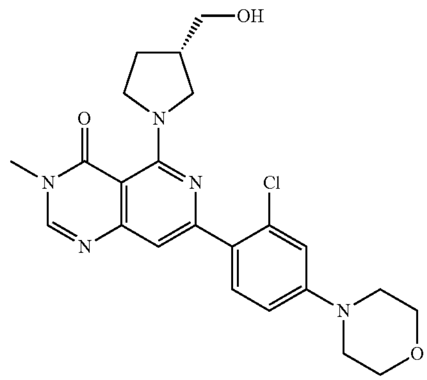 [SMILES: Cn1cnc2cc(-c3ccc(N4CCOCC4)cc3Cl)nc(N3CC[C@H](CO)C3)c2c1=O] | HPLC-MS calculated C$_{23}$H$_{26}$ClN$_5$O$_3$ (M + H$^+$): 456.18, found: 456.20. | 0.731 |
| 553 | 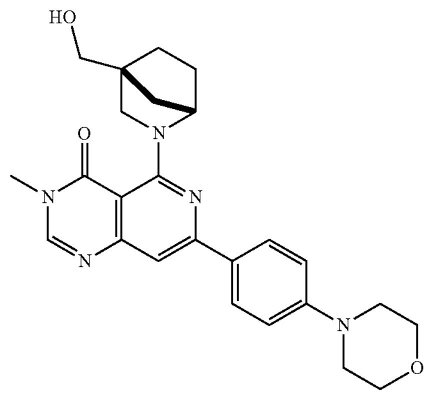 [SMILES: Cn1cnc2cc(-c3ccc(N4CCOCC4)cc3)nc(N3C[C@]4(CO)CC[C@H]3C4)c2c1=O] | HPLC-MS calculated C$_{25}$H$_{29}$N$_5$O$_3$ (M + H$^+$): 448.24, found: 448.20. | 0.168 |
| 554 | 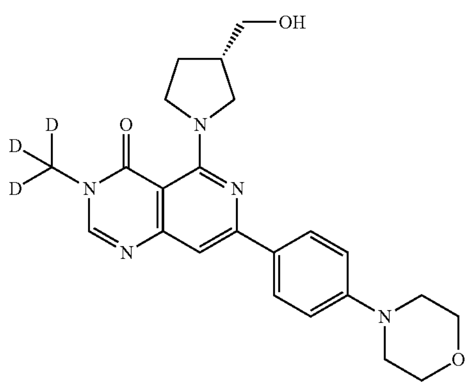 [SMILES: [2H]C([2H])([2H])n1cnc2cc(-c3ccc(N4CCOCC4)cc3)nc(N3CC[C@H](CO)C3)c2c1=O] | HPLC-MS calculated C$_{23}$H$_{24}$D$_3$N$_5$O$_3$ (M + H$^+$): 425.24, found: 425.20. | 0.104 |
| 555 | 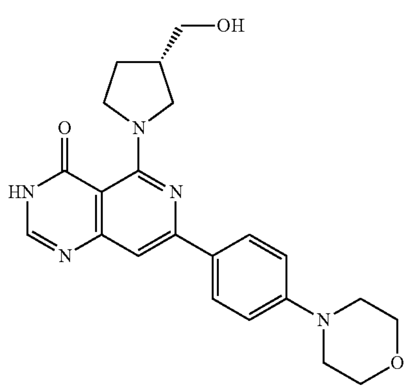 [SMILES: O=c1[nH]cnc2cc(-c3ccc(N4CCOCC4)cc3)nc(N3CC[C@H](CO)C3)c12] | HPLC-MS calculated C$_{22}$H$_{25}$N$_5$O$_3$ (M + H$^+$): 408.21, found: 408.20. | 0.182 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 556 | 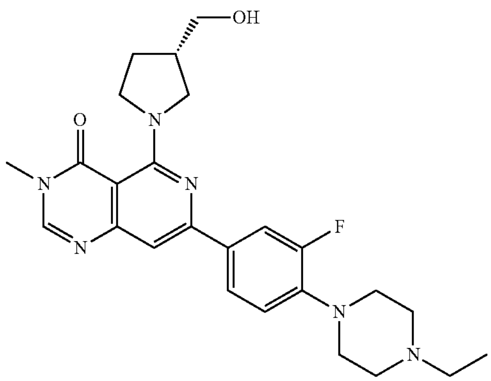 [SMILES: CCN1CCN(c2ccc(-c3cc4ncn(C)c(=O)c4c(N4CC[C@H](CO)C4)n3)cc2F)CC1] | HPLC-MS calculated C$_{25}$H$_{31}$FN$_6$O$_2$ (M + H⁺): 467.26, found: 467.20. | 0.179 |
| 557 | 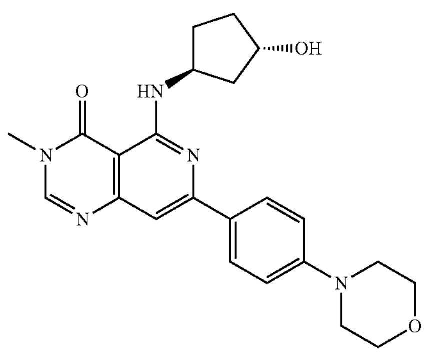 [SMILES: Cn1cnc2cc(-c3ccc(N4CCOCC4)cc3)nc(N[C@H]3CC[C@H](O)C3)c2c1=O] | HPLC-MS calculated C$_{23}$H$_{27}$N$_5$O$_3$ (M + H⁺): 422.22, found: 422.10. | 0.151 |
| 558 | 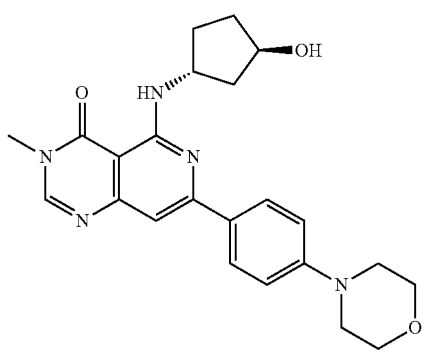 [SMILES: Cn1cnc2cc(-c3ccc(N4CCOCC4)cc3)nc(N[C@@H]3CC[C@@H](O)C3)c2c1=O] | HPLC-MS calculated C$_{23}$H$_{27}$N$_5$O$_3$ (M + H⁺): 422.22, found: 422.20. | 0.028 |
| 559 | 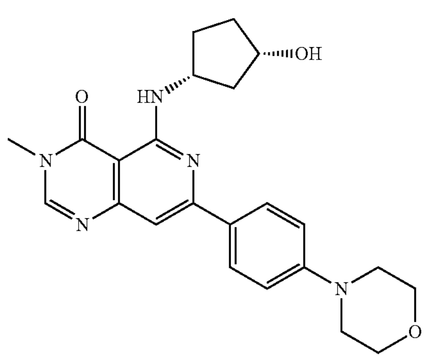 [SMILES: Cn1cnc2cc(-c3ccc(N4CCOCC4)cc3)nc(N[C@@H]3CC[C@H](O)C3)c2c1=O] | HPLC-MS calculated C$_{23}$H$_{27}$N$_5$O$_3$ (M + H⁺): 422.22, found: 422.20. | 0.064 |

TABLE 1-continued

| Compound Number | Structure | Physical Data<br>$^1$H NMR 400 MHz (CDCl$_3$),<br>HPLC Retention Time, and/or<br>MS (m/z) | Syk Enzyme IC$_{50}$ (uM) |
|---|---|---|---|
| 560 | 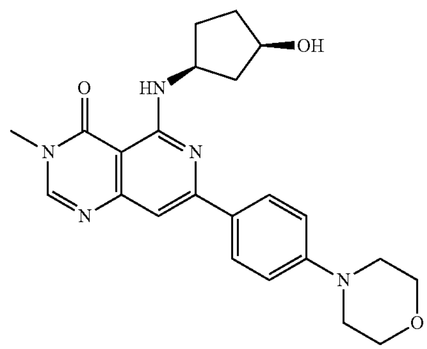 [SMILES: Cn1cnc2cc(-c3ccc(N4CCOCC4)cc3)nc(N[C@H]3CC[C@@H](O)C3)c2c1=O] | HPLC-MS calculated C$_{23}$H$_{27}$N$_5$O$_3$ (M + H$^+$): 422.22, found: 422.20. | 0.106 |
| 561 | 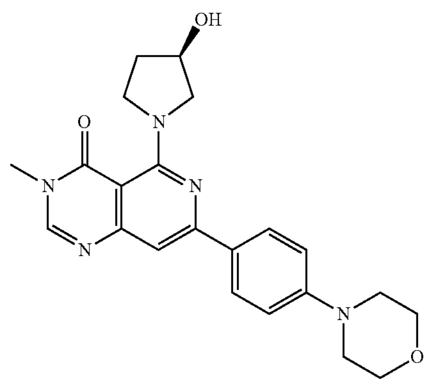 [SMILES: Cn1cnc2cc(-c3ccc(N4CCOCC4)cc3)nc(N3CC[C@@H](O)C3)c2c1=O] | HPLC-MS calculated C$_{22}$H$_{25}$N$_5$O$_3$ (M + H$^+$): 408.21, found: 408.20. | 0.296 |
| 562 | 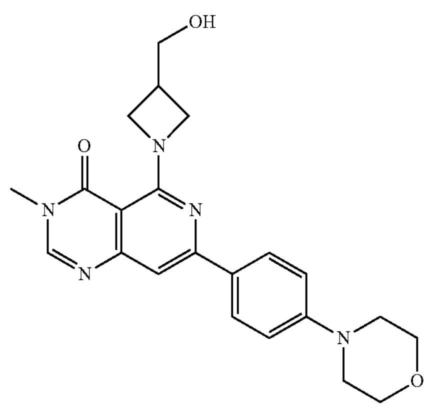 [SMILES: Cn1cnc2cc(-c3ccc(N4CCOCC4)cc3)nc(N3CC(CO)C3)c2c1=O] | HPLC-MS calculated C$_{22}$H$_{25}$N$_5$O$_3$ (M + H$^+$): 408.20, found: 408.10. | 0.257 |
| 563 | 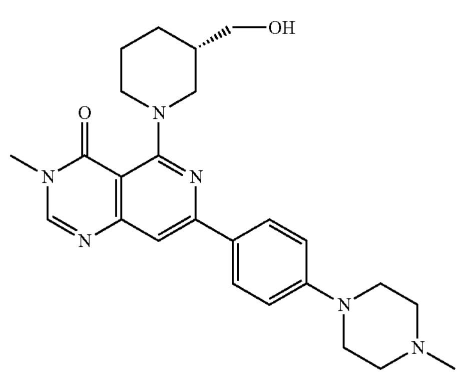 | HPLC-MS calculated C$_{25}$H$_{32}$N$_6$O$_2$ (M + H$^+$): 449.27, found: 449.20. | 0.177 |

TABLE 1-continued

| Compound Number | Structure | Physical Data<br>¹H NMR 400 MHz (CDCl₃),<br>HPLC Retention Time, and/or<br>MS (m/z) | Syk Enzyme IC₅₀ (uM) |
| --- | --- | --- | --- |
| 564 | 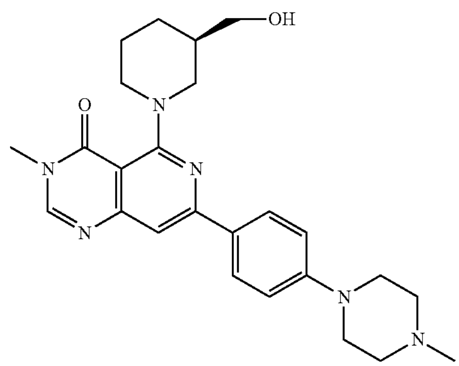 | HPLC-MS calculated $C_{25}H_{32}N_6O_2$ (M + H⁺): 449.27, found: 449.20. | 0.0911 |
| 565 | 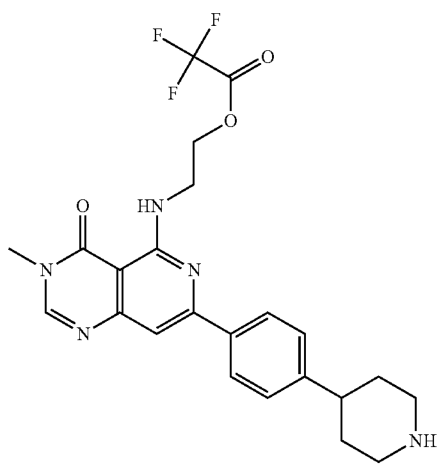 [SMILES: Cn1cnc2cc(-c3ccc(C4CCNCC4)cc3)nc(NCCOC(=O)C(F)(F)F)c2c1=O] | HPLC-MS calculated $C_{23}H_{24}F_3N_5O_3$ (M + H⁺): 476.19, found: 476.20. | 0.371 |
| 566 | 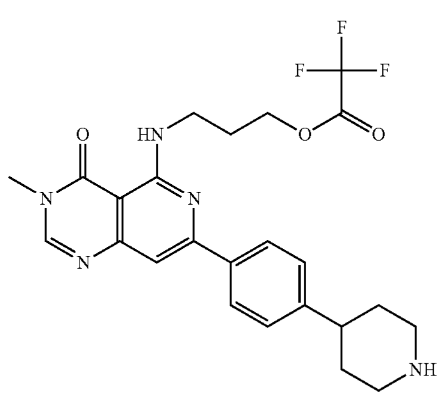 [SMILES: Cn1cnc2cc(-c3ccc(C4CCNCC4)cc3)nc(NCCCOC(=O)C(F)(F)F)c2c1=O] | HPLC-MS calculated $C_{24}H_{26}F_3N_5O_3$ (M + H⁺): 490.21, found: 490.20. | 0.384 |

TABLE 1-continued
| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 567 | 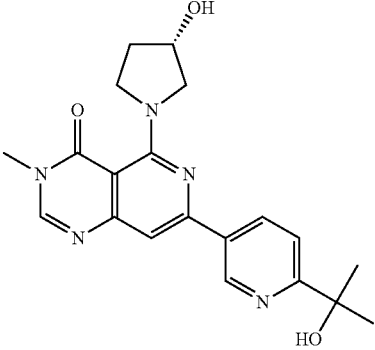 [SMILES: Cn1cnc2cc(-c3ccc(C(C)(C)O)nc3)nc(N3CC[C@H](O)C3)c2c1=O] | HPLC-MS calculated $C_{20}H_{23}N_5O_3$ (M + H⁺): 382.19, found: 382.20. | 2.182 |
| 568 | 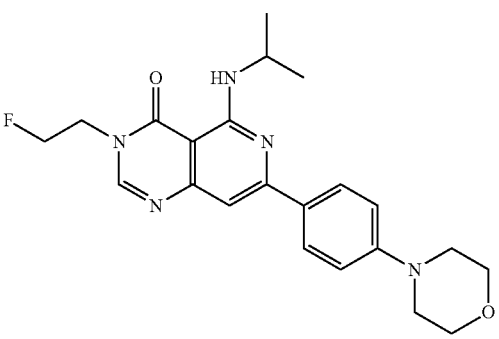 [SMILES: CC(C)Nc1nc(-c2ccc(N3CCOCC3)cc2)cc2ncn(CCF)c(=O)c12] | HPLC-MS calculated $C_{22}H_{26}FN_5O_2$ (M + H⁺): 412.22, found: 412.20. | 4.586 |
| 569 | 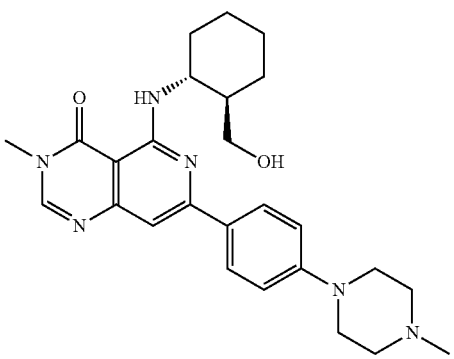 | HPLC-MS calculated $C_{26}H_{34}N_6O_2$ (M + H⁺): 463.28, found: 463.30. | 1.456 |
| 570 | 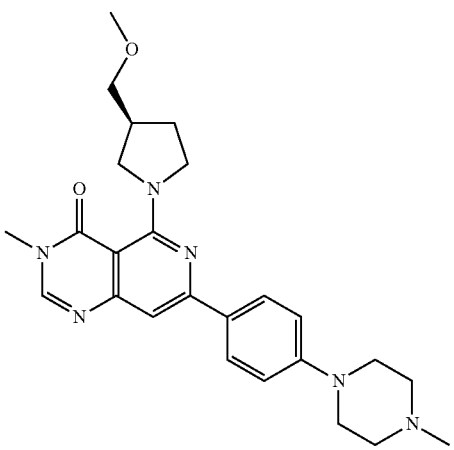 | HPLC-MS calculated $C_{25}H_{32}N_6O_2$ (M + H⁺): 449.27, found: 449.20. | 1.084 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 571 | 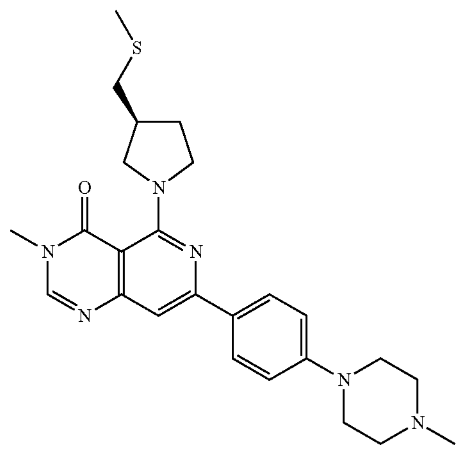 | HPLC-MS calculated C$_{25}$H$_{32}$N$_6$OS (M + H⁺): 465.25, found: 465.20. | 1.991 |
| 572 | 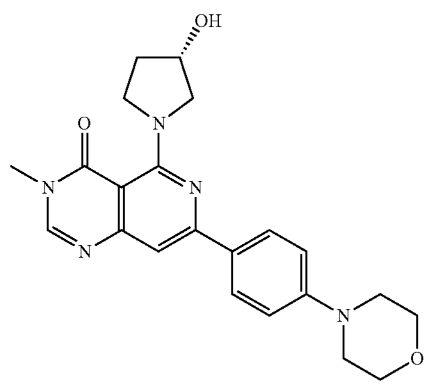 [SMILES: Cn1cnc2cc(-c3ccc(N4CCOCC4)cc3)nc(N3CC[C@H](O)C3)c2c1=O] | HPLC-MS calculated C$_{22}$H$_{25}$N$_5$O$_3$ (M + H⁺): 408.21, found: 408.20. | 0.76 |
| 573 | 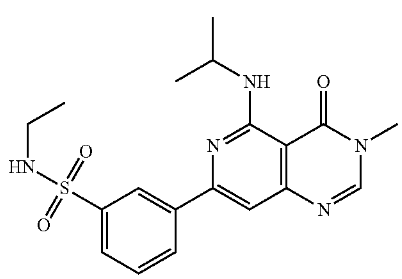 [SMILES: CCNS(=O)(=O)c1cccc(-c2cc3ncn(C)c(=O)c3c(NC(C)C)n2)c1] | ESI-MS m/z 402.2 (MH⁺) | 0.417 |
| 574 | 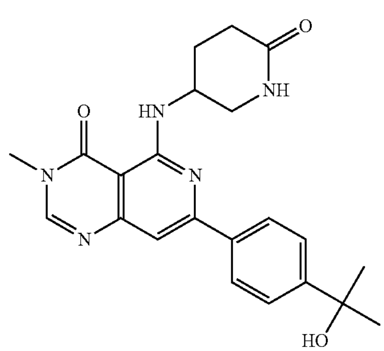 [SMILES: Cn1cnc2cc(-c3ccc(C(C)(C)O)cc3)nc(NC3CCC(=O)NC3)c2c1=O] | ESI-MS m/z 408.2 (MH⁺) | 0.169 |

TABLE 1-continued

| Compound Number | Structure | Physical Data<br>$^1$H NMR 400 MHz (CDCl$_3$),<br>HPLC Retention Time, and/or<br>MS (m/z) | Syk Enzyme IC$_{50}$ (uM) |
| --- | --- | --- | --- |
| 575 | 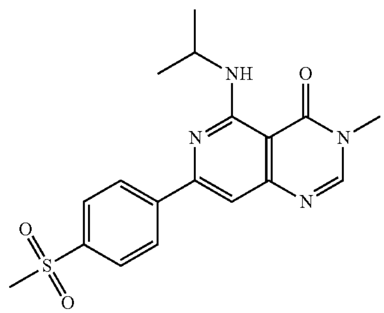 | ESI-MS m/z 373.1 (MH$^+$) | 0.216 |
| 576 | 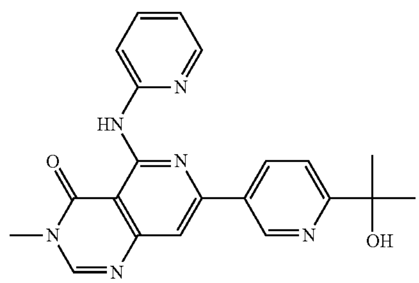 [SMILES: Cn1cnc2cc(-c3ccc(C(C)(C)O)nc3)nc(Nc3ccccn3)c2c1=O] | HPLC-MS calculated for C$_{21}$H$_{20}$N$_6$O$_2$ (M + H$^+$) 389.2, found 389.2 | 0.926 |
| 577 | 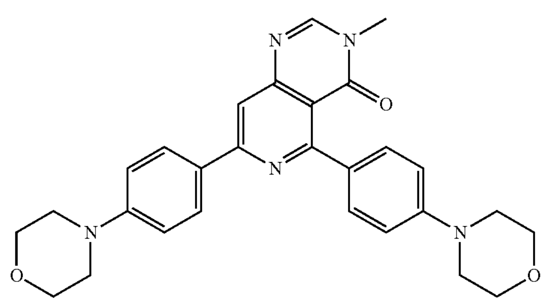 [SMILES: Cn1cnc2cc(-c3ccc(N4CCOCC4)cc3)nc(-c3ccc(N4CCOCC4)cc3)c2c1=O] | HPLC-MS calculated for C$_{28}$H$_{29}$N$_5$O$_3$ (M + H$^+$) 484.2, found 484.2 | 0.535 |
| 578 | 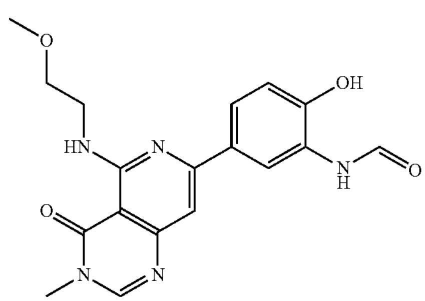 [SMILES: COCCNc1nc(-c2ccc(O)c(NC=O)c2)cc2ncn(C)c(=O)c12] | HPLC-MS calculated for C$_{18}$H$_{19}$N$_5$O$_4$ (M + H$^+$) 370.1, found 370.1 | 0.174 |
| 579 | 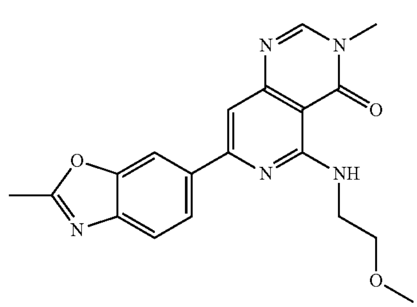 | $^1$H NMR (CD$_3$OD, 400 MHz) δ 8.29 (s, 1H), 8.26 (d, J = 1.6 Hz, 1H), 8.07 (dd, J = 8.4, 1.6 Hz, 1H), 7.62 (d, J = 8.4 Hz, 1H), 7.10 (s, 1H), 3.87 (t, J = 5.6 Hz, 2H), 3.71 (t, J = 5.6 Hz, 2H), 3.51 (s, 3H), 3.45 (s, 3H), 2.67 (s, 3H); HPLC-MS calculated for C$_{19}$H$_{19}$N$_5$O$_3$ (M + H$^+$) 366.1, found 366.1. | 0.633 |

TABLE 1-continued

| Compound Number | Structure | Physical Data <br> ¹H NMR 400 MHz (CDCl$_3$), HPLC Retention Time, and/or MS (m/z) | Syk Enzyme IC$_{50}$ (uM) |
|---|---|---|---|
| 580 | 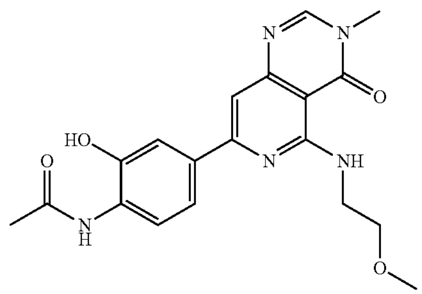 [SMILES: COCCNc1nc(-c2ccc(NC(C)=O)c(O)c2)cc2ncn(C)c(=O)c12] | ¹H NMR (CD$_3$OD with a drop of CDCl$_3$, 400 MHz) δ 8.25 (s, 1H), 7.84 (d, J = 8.4 Hz, 1H), 7.66 (d, J = 1.6 Hz, 1H), 7.55 (dd, J = 8.4, 1.6 Hz, 1H), 7.01 (s, 1H), 3.86 (t, J = 5.6 Hz, 2H), 3.69 (t, J = 5.6 Hz, 2H), 3.50 (s, 3H), 3.43 (s, 3H), 2.21 (s, 3H); HPLC-MS calculated for C$_{19}$H$_{21}$N$_5$O$_4$ (M + H⁺) 384.2, found 384.2. | 0.21 |
| 581 | 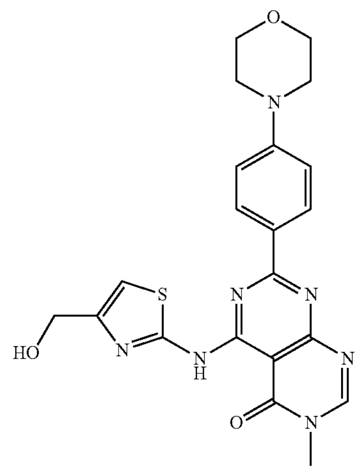 [SMILES: Cn1cnc2nc(-c3ccc(N4CCOCC4)cc3)nc(Nc3nc(CO)cs3)c2c1=O] | ¹H NMR (CD$_3$OD, 400 MHz) δ 8.58 (s, 1H), 8.27 (d, J = 8.8 Hz, 2H), 7.75 (s, 1H), 7.40 (d, J = 8.8 2H), 7.26 (s, 1H), 4.70 (s, 2H), 3.97 (t, J = 4.8 Hz, 4H), 3.67 (s, 3H), 3.49 (t, J = 4.8 Hz, 4H); HPLC-MS calculated for C22H22N6O3S (M + H+) 451.1, found 451.1. | 0.187 |
| 582 | 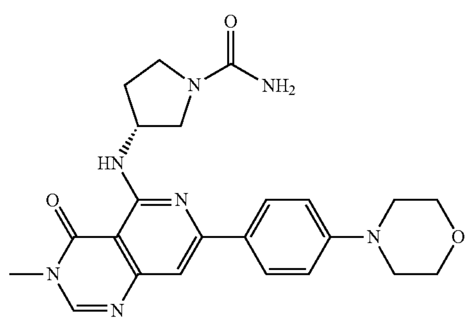 [SMILES: Cn1cnc2cc(-c3ccc(N4CCOCC4)cc3)nc(N[C@@H]3CCN(C(N)=O)C3)c2c1=O] | HPLC-MS calculated for C23H27N7O3 (M + H+) 450.2, found 450.2. | 0.547 |
| 583 | 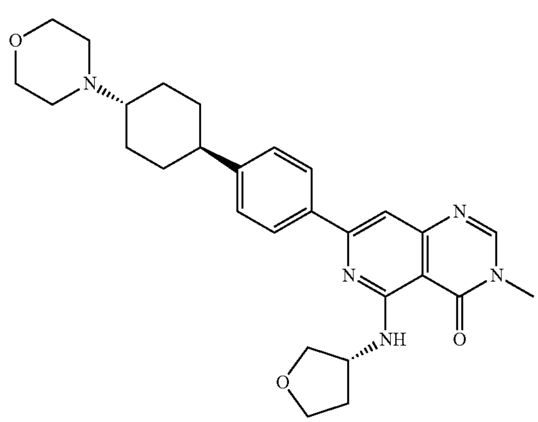 [SMILES: Cn1cnc2cc(-c3ccc([C@H]4CC[C@H](N5CCOCC5)CC4)cc3)nc(N[C@@H]3CCOC3)c2c1=O] | MS m/z 490.16 (M + 1). | 0.138 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 584 | 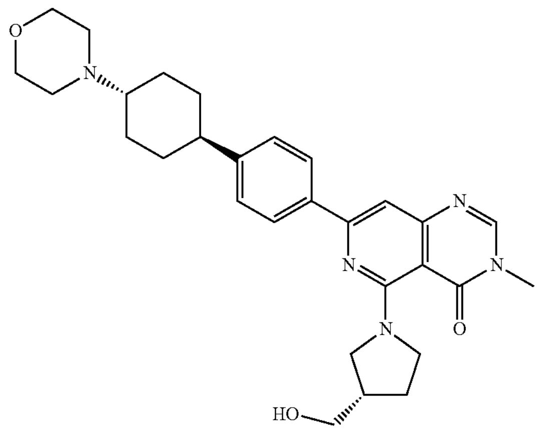 [SMILES: Cn1cnc2cc(-c3ccc([C@H]4CC[C@H](N5CCOCC5)CC4)cc3)nc(N3CC[C@H](CO)C3)c2c1=O] | MS m/z 504.19 (M + 1). | 0.368 |
| 585 | 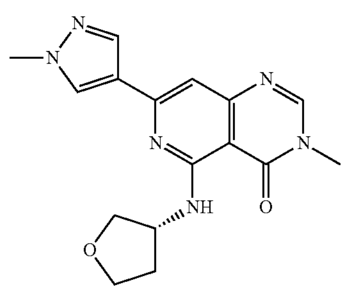 | 1H NMR (400 MHz, DMSOd6) δ 8.88 (brs, 1H), 8.37 (s, 1H), 8.32 (s, 1H), 8.04 (s, 1H), 6.92 (s, 1H), 4.73-4.71 (m, 1H), 4.03 (dd, 1H), 3.89-3.84 (m, 1H), 3.89 (s, 3H), 3.80-3.76 (m, 1H), 3.60-3.58 (m, 1H), 2.56 (s, 3H), 2.39-2.30 (m, 1H), 1.86-1.84 (m, 1H); m/z 327.35 (M + 1). | 0.109 |
| 586 | 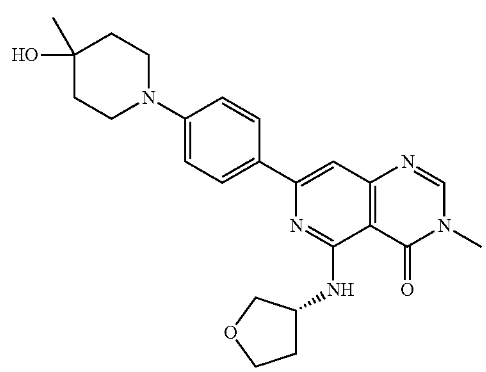 [SMILES: Cn1cnc2cc(-c3ccc(N4CCC(C)(O)CC4)cc3)nc(N[C@@H]3CCOC3)c2c1=O] | MS m/z 436.21 (M + 1). | 0.114 |
| 587 | 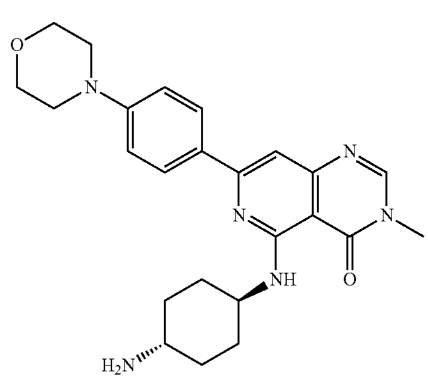 [SMILES: Cn1cnc2cc(-c3ccc(N4CCOCC4)cc3)nc(N[C@H]3CC[C@H](N)CC3)c2c1=O] | ESI-MS m/z 435.3 (MH⁺); ¹H NMR (DMSO-d6) δ 8.04 (s, 1H), 8.00 (d, J = 8.4 Hz, 2H), 7.26 (s, 1H), 6.97 (d, J = 8.4 Hz, 2H), 4.07 (brs, 2H), 3.18 (m, 4H), 3.67 (m, 4H), 3.76 (s, 3H), 2.54 (brs, 2H), 2.22 (m, 2H), 2.03 (m, 2H), 1.41 (m, 4H). | 0.912 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 588 | 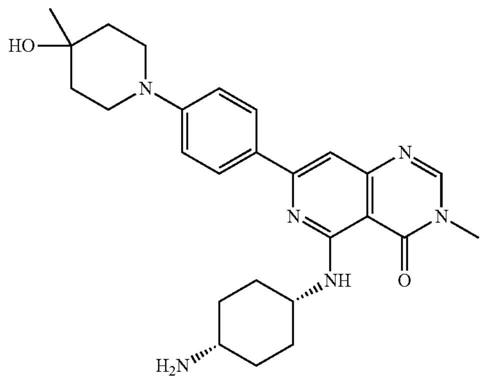 [SMILES: Cn1cnc2cc(-c3ccc(N4CCC(C)(O)CC4)cc3)nc(N[C@H]3CC[C@@H](N)CC3)c2c1=O] | ESI-MS m/z 463.2 (MH⁺). | 0.00561 |
| 589 | 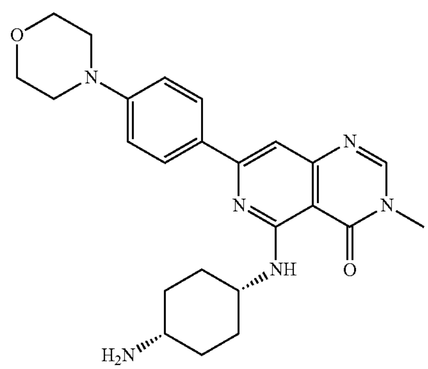 [SMILES: Cn1cnc2cc(-c3ccc(N4CCOCC4)cc3)nc(N[C@H]3CC[C@@H](N)CC3)c2c1=O] | ESI-MS m/z 435.3 (MH⁺). | 0.00389 |
| 590 | 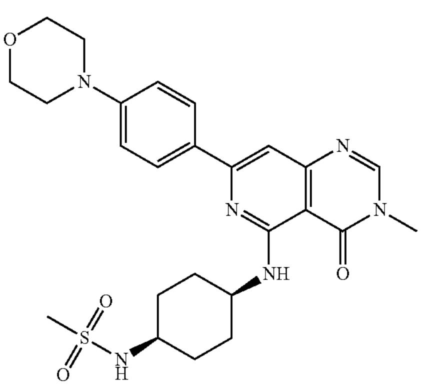 [SMILES: Cn1cnc2cc(-c3ccc(N4CCOCC4)cc3)nc(N[C@H]3CC[C@@H](NS(C)(=O)=O)CC3)c2c1=O] | ESI-MS m/z 513.3 (MH⁺). | 0.812 |
| 591 | 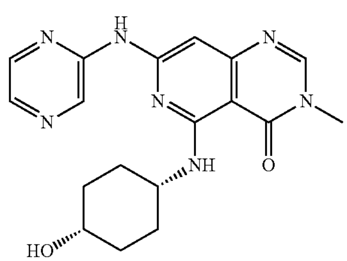 [SMILES: Cn1cnc2cc(Nc3cnccn3)nc(N[C@H]3CC[C@@H](O)CC3)c2c1=O] | ESI-MS m/z 367.4 (MH⁺). | 0.351 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 592 | 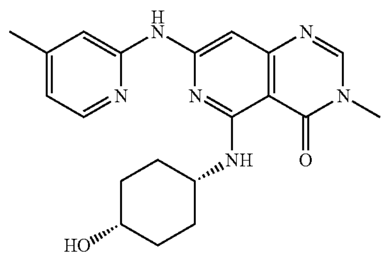 | ESI-MS m/z 381.2 (MH⁺). | 0.169 |
| 593 | 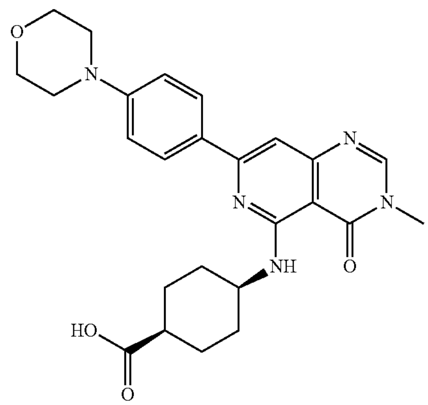 [SMILES: Cn1cnc2cc(-c3ccc(N4CCOCC4)cc3)nc(N[C@H]3CC[C@@H](C(=O)O)CC3)c2c1=O] | ESI-MS m/z 464.1 (MH⁺). | 0.445 |
| 594 | 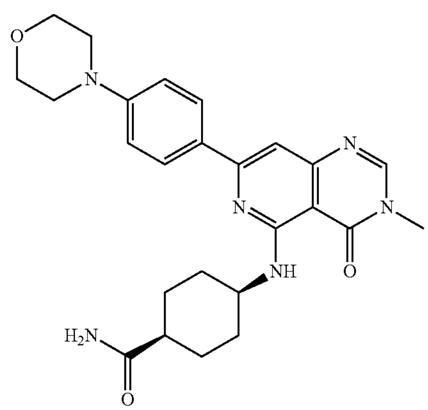 [SMILES: Cn1cnc2cc(-c3ccc(N4CCOCC4)cc3)nc(N[C@H]3CC[C@@H](C(N)=O)CC3)c2c1=O] | ESI-MS m/z 463.5 (MH⁺). | 0.0511 |
| 595 | 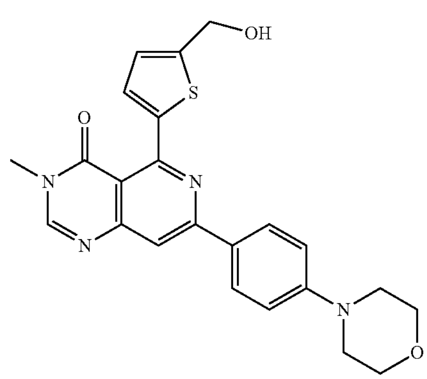 [SMILES: Cn1cnc2cc(-c3ccc(N4CCOCC4)cc3)nc(-c3ccc(CO)s3)c2c1=O] | ESI-MS m/z 435.1 (MH⁺). | 0.154 |

TABLE 1-continued

| Compound Number | Structure | Physical Data<br>¹H NMR 400 MHz (CDCl₃),<br>HPLC Retention Time, and/or<br>MS (m/z) | Syk Enzyme IC₅₀ (uM) |
|---|---|---|---|
| 596 | 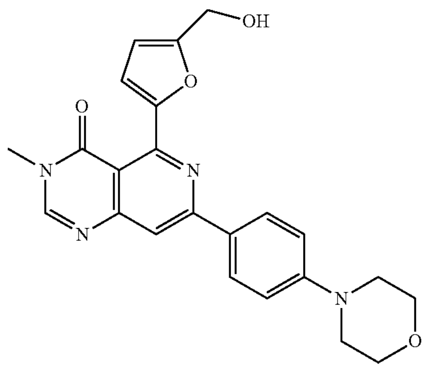 [SMILES: Cn1cnc2cc(-c3ccc(N4CCOCC4)cc3)nc(-c3ccc(CO)o3)c2c1=O] | ESI-MS m/z 419.2 (MH⁺). | 0.17 |
| 597 | 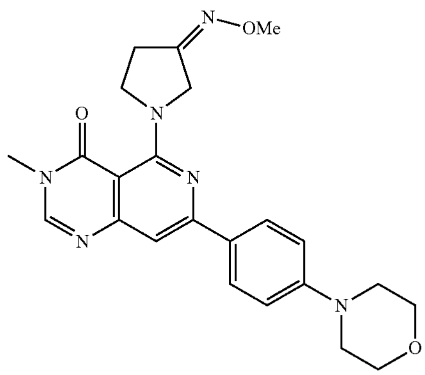 [SMILES: CO/N=C1/CCN(c2nc(-c3ccc(N4CCOCC4)cc3)cc3ncn(C)c(=O)c23)C1] | ESI-MS m/z 435.2 (MH⁺). | 0.475 |
| 598 | 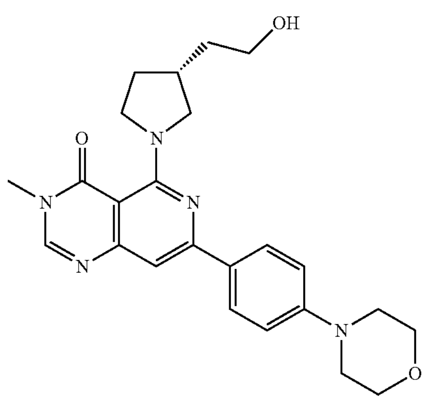 [SMILES: Cn1cnc2cc(-c3ccc(N4CCOCC4)cc3)nc(N3CC[C@H](CCO)C3)c2c1=O] | ¹H NMR (CD₃OD, 400 MHz) δ 8.27 (s, 1H), 8.06 (d, J = 9.2 Hz, 2H), 7.12 (s, 1H), 7.03 (d, J = 9.2 Hz, 2H), 3.91 (m, 1H), 3.85 (t, J = 4.8 Hz, 4H), 3.65 (t, J = 6.4 Hz, 2H), 3.55 (m, 3H), 3.51 (s, 3H), 3.25 (t, J = 4.8 Hz, 4H), 2.33 (m, 1H), 2.16 (m, 1H), 1.72 (m, 2H), 1.62 (m, 1H); ESI-MS m/z 436.2 (MH⁺). | 0.0761 |
| 599 | 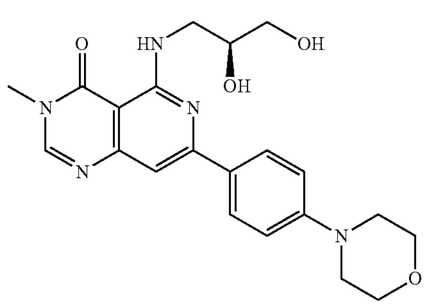 [SMILES: Cn1cnc2cc(-c3ccc(N4CCOCC4)cc3)nc(NC[C@H](O)CO)c2c1=O] | ESI-MS m/z 412.2 (MH⁺). | 0.0974 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 600 | 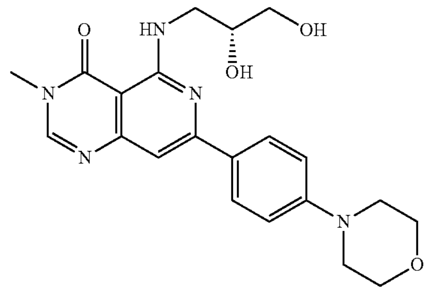 [SMILES: Cn1cnc2cc(-c3ccc(N4CCOCC4)cc3)nc(NC[C@@H](O)CO)c2c1=O] | ESI-MS m/z 412.2 (MH⁺). | 0.173 |
| 601 | 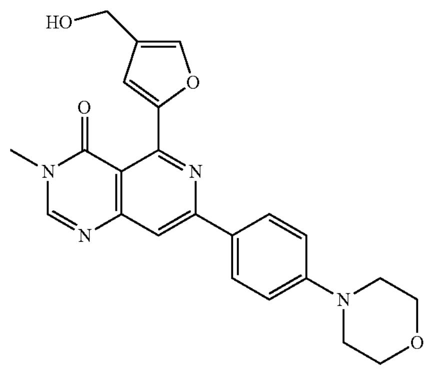 [SMILES: Cn1cnc2cc(-c3ccc(N4CCOCC4)cc3)nc(-c3cc(CO)co3)c2c1=O] | ESI-MS m/z 419.2 (MH⁺). | 0.572 |
| 602 | 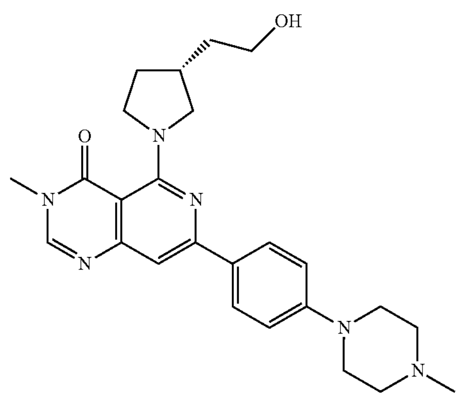 | ESI-MS m/z 449.3 (MH⁺). | 0.0509 |
| 603 | 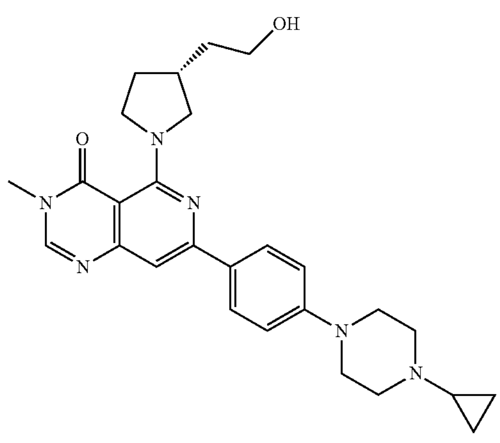 [SMILES: Cn1cnc2cc(-c3ccc(N4CCN(C5CC5)CC4)cc3)nc(N3CC[C@H](CCO)C3)c2c1=O] | ESI-MS m/z 475.3 (MH⁺). | 0.0962 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 604 | 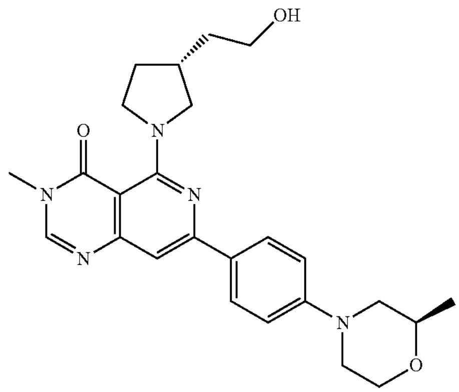 | ESI-MS m/z 450.2 (MH⁺). | 0.0893 |
| 605 | 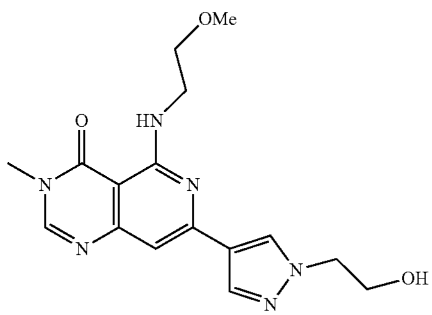 [SMILES: COCCNc1nc(-c2cnn(CCO)c2)cc2ncn(C)c(=O)c12] | ¹H NMR (CD₃OD, 400 MHz) δ 8.68 (s, 1H), 8.37 (s, 2H), 7.17 (s, 1H), 3.98 (t, J = 4.4 Hz, 2H), 3.83 (t, J = 4.4 Hz, 2H), 3.74 (m, 1H), 3.67 (m, 2H), 3.62 (s, 3H), 3.58 (m, 1H), 3.48 (s, 3H); ESI-MS m/z 345.2 (MH⁺). | 0.825 |
| 606 | 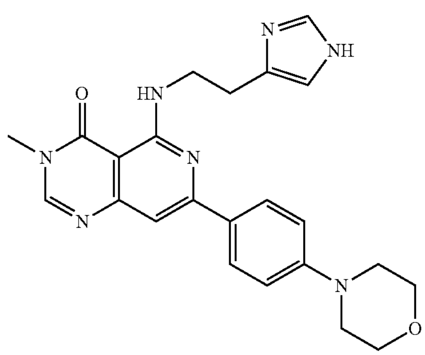 [SMILES: Cn1cnc2cc(-c3ccc(N4CCOCC4)cc3)nc(NCCc3c[nH]cn3)c2c1=O] | ESI-MS m/z 432.2 (MH⁺). | 0.0813 |
| 607 | 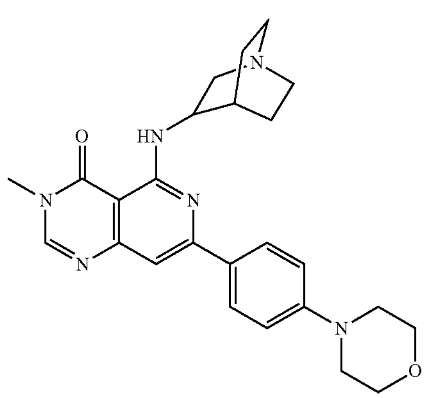 [SMILES: Cn1cnc2cc(-c3ccc(N4CCOCC4)cc3)nc(NC3CN4CCC3CC4)c2c1=O] | ESI-MS m/z 447.2 (MH⁺). | 0.81 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 608 | 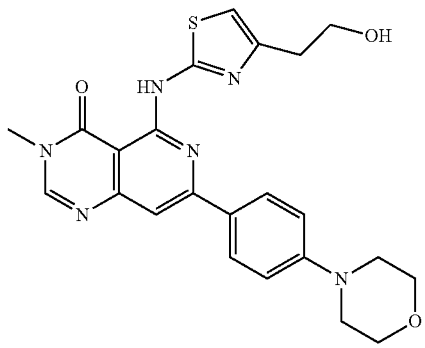 [SMILES: Cn1cnc2cc(-c3ccc(N4CCOCC4)cc3)nc(Nc3nc(CCO)cs3)c2c1=O] | ESI-MS m/z 465.2 (MH⁺). | 0.319 |
| 609 | 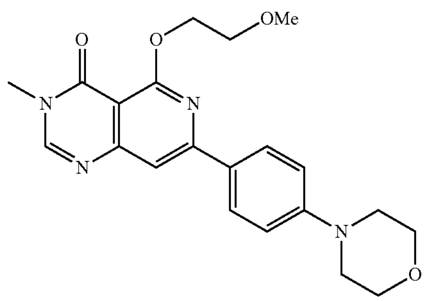 [SMILES: COCCOc1nc(-c2ccc(N3CCOCC3)cc2)cc2ncn(C)c(=O)c12] | ESI-MS m/z 397.2 (MH⁺). | 0.2212 |
| 610 | 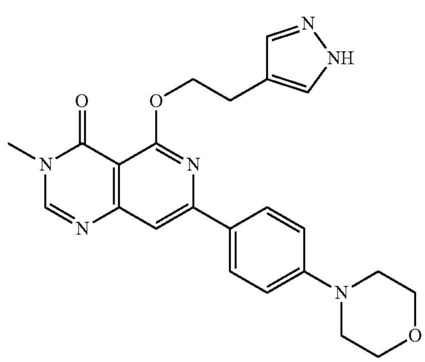 [SMILES: Cn1cnc2cc(-c3ccc(N4CCOCC4)cc3)nc(OCCc3cn[nH]c3)c2c1=O] | ¹H NMR (CD₃OD, 400 MHz) δ 8.37 (s, 1H), 8.06 (d, J = 9.2 Hz, 2H), 7.71 (s, 2H), 7.43 (s, 1H), 7.04 (d, J = 9.2 Hz, 2H), 4.71 (t, J = 6.4 Hz, 2H), 3.85 (t, J = 4.8 Hz, 4H), 3.55 (s, 3H), 3.27 (t, J = 4.8 Hz, 4H), 3.10 (t, J = 6.4 Hz, 2H); ESI-MS m/z 433.1 (MH⁺). | 0.0271 |
| 611 | 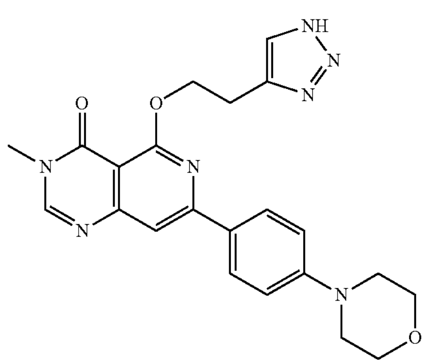 [SMILES: Cn1cnc2cc(-c3ccc(N4CCOCC4)cc3)nc(OCCc3c[nH]nn3)c2c1=O] | ESI-MS m/z 434.2 (MH⁺). | 0.0472 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 612 | 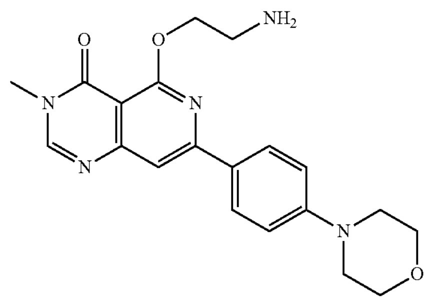 [SMILES: Cn1cnc2cc(-c3ccc(N4CCOCC4)cc3)nc(OCCN)c2c1=O] | ESI-MS m/z 382.2 (MH⁺). | 0.286 |
| 613 | 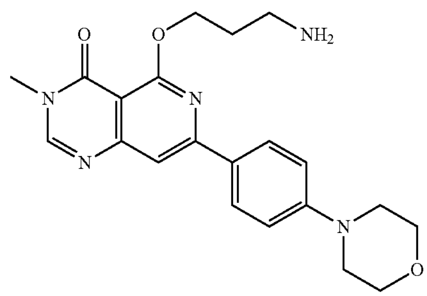 [SMILES: Cn1cnc2cc(-c3ccc(N4CCOCC4)cc3)nc(OCCCN)c2c1=O] | ESI-MS m/z 396.2 (MH⁺). | 0.0879 |
| 614 | 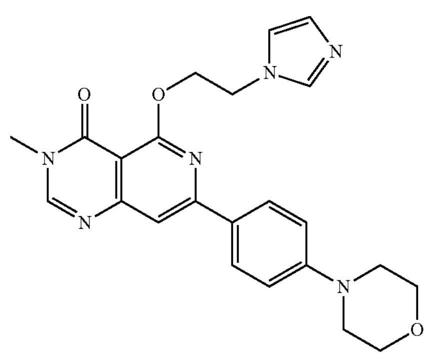 [SMILES: Cn1cnc2cc(-c3ccc(N4CCOCC4)cc3)nc(OCCn3ccnc3)c2c1=O] | ESI-MS m/z 433.2 (MH⁺). | 0.159 |
| 615 | 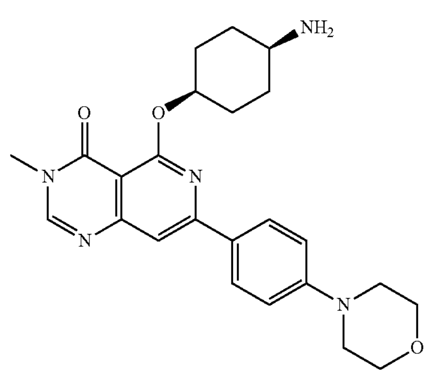 [SMILES: Cn1cnc2cc(-c3ccc(N4CCOCC4)cc3)nc(O[C@H]3CC[C@@H](N)CC3)c2c1=O] | ESI-MS m/z 436.2 (MH⁺). | 0.00531 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 616 | 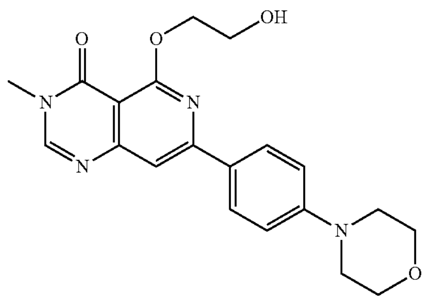 [SMILES: Cn1cnc2cc(-c3ccc(N4CCOCC4)cc3)nc(OCCO)c2c1=O] | ESI-MS m/z 383.2 (MH⁺). | 0.156 |
| 617 | 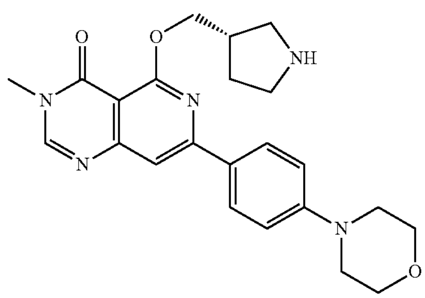 [SMILES: Cn1cnc2cc(-c3ccc(N4CCOCC4)cc3)nc(OC[C@H]3CCNC3)c2c1=O] | ESI-MS m/z 422.2 (MH⁺). | 0.0641 |
| 618 | 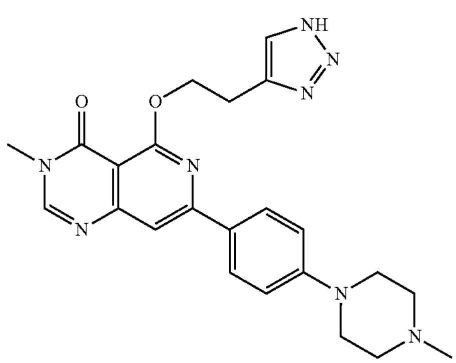 | ESI-MS m/z 447.2 (MH⁺). | 0.0243 |
| 619 | 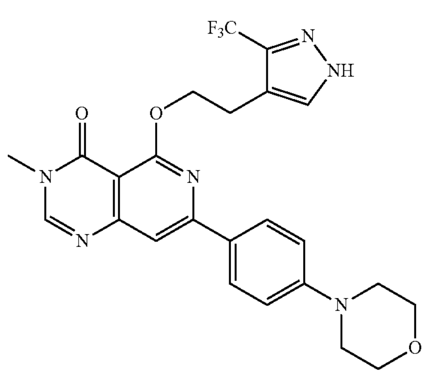 [SMILES: Cn1cnc2cc(-c3ccc(N4CCOCC4)cc3)nc(OCCc3c[nH]nc3C(F)(F)F)c2c1=O] | ¹H NMR (CD₃OD, 400 MHz) δ 8.38 (s, 1H), 8.13 (s, 1H), 8.06 (d, J = 9.2 Hz, 2H), 7.45 (s, 1H), 7.04 (d, J = 9.2 Hz, 2H), 4.75 (t, J = 6.4 Hz, 2H), 3.85 (t, J = 4.8 Hz, 4H), 3.55 (s, 3H), 3.27 (t, J = 4.8 Hz, 4H), 3.19 (t, J = 6.4 Hz, 2H); ESI-MS m/z 501.2 (MH⁺). | 0.358 |

TABLE 1-continued

| Compound Number | Structure | Physical Data <br> ¹H NMR 400 MHz (CDCl₃), HPLC Retention Time, and/or MS (m/z) | Syk Enzyme IC$_{50}$ (uM) |
|---|---|---|---|
| 620 | 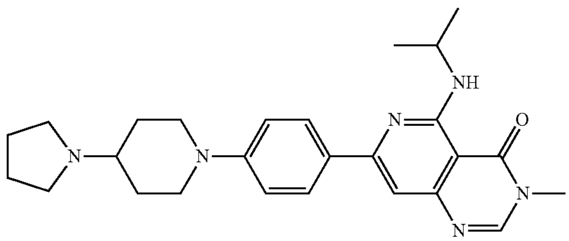 [SMILES: CC(C)Nc1nc(-c2ccc(N3CCC(N4CCCC4)CC3)cc2)cc2ncn(C)c(=O)c12] | ESI-MS m/z 447.20 (MH⁺). | 0.055 |
| 621 | 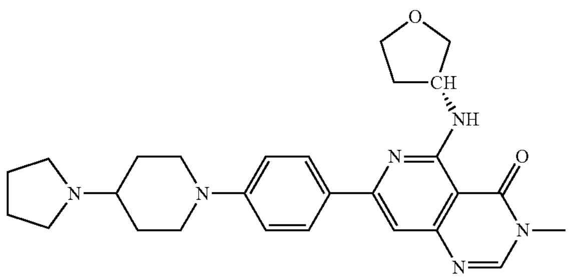 [SMILES: Cn1cnc2cc(-c3ccc(N4CCC(N5CCCC5)CC4)cc3)nc(N[C@@H]3CCOC3)c2c1=O] | ESI-MS m/z 475.2 (MH⁺). | 0.0242 |
| 622 | 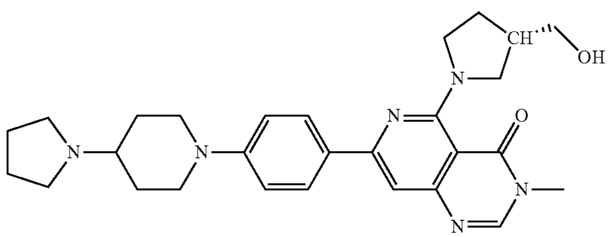 [SMILES: Cn1cnc2cc(-c3ccc(N4CCC(N5CCCC5)CC4)cc3)nc(N3CC[C@H](CO)C3)c2c1=O] | ESI-MS m/z 489.2 (MH⁺). | 0.0814 |
| 623 | 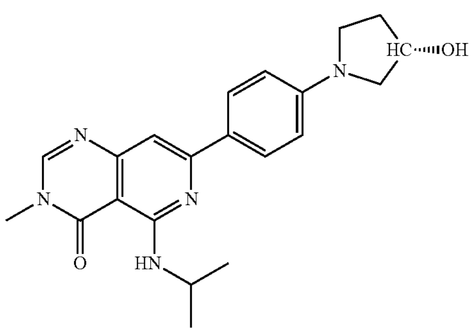 [SMILES: CC(C)Nc1nc(-c2ccc(N3CC[C@H](O)C3)cc2)cc2ncn(C)c(=O)c12] | ESI-MS m/z 380.20 (MH⁺). | 0.438 |
| 624 | 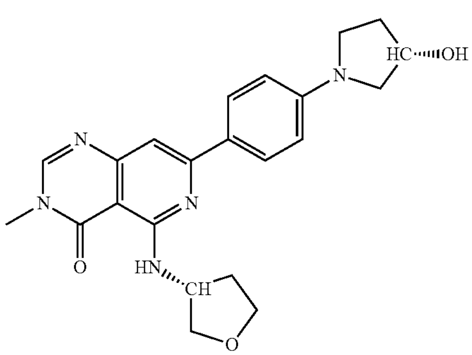 [SMILES: Cn1cnc2cc(-c3ccc(N4CC[C@H](O)C4)cc3)nc(N[C@@H]3CCOC3)c2c1=O] | ESI-MS m/z 408.2 (MH⁺). | 0.0663 |

TABLE 1-continued
| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 625 | 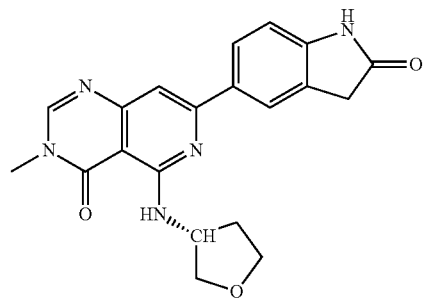 [SMILES: Cn1cnc2cc(-c3ccc4c(c3)CC(=O)N4)nc(N[C@@H]3CCOC3)c2c1=O] | ESI-MS m/z 378.2 (MH⁺). | 0.178 |
| 626 | 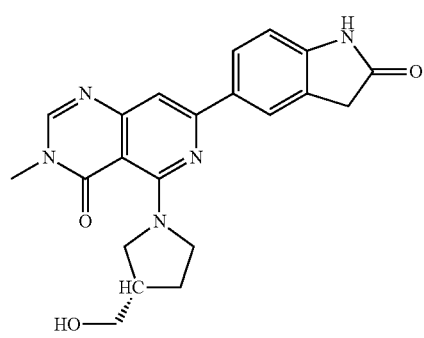 [SMILES: Cn1cnc2cc(-c3ccc4c(c3)CC(=O)N4)nc(N3CC[C@H](CO)C3)c2c1=O] | ESI-MS m/z 392.20 (MH⁺). | 0.359 |
| 627 | 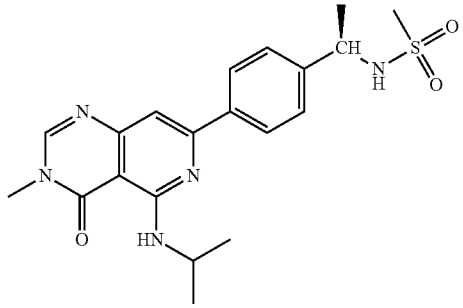 [SMILES: CC(C)Nc1nc(-c2ccc([C@@H](C)NS(C)(=O)=O)cc2)cc2ncn(C)c(=O)c12] | ESI-MS m/z 416.2 (MH⁺). | 0.697 |
| 628 | 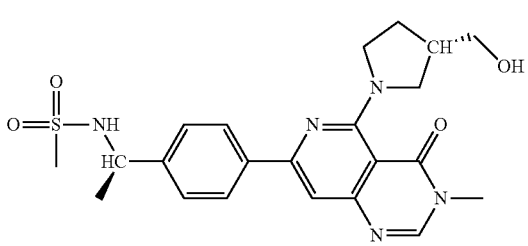 [SMILES: C[C@@H](NS(C)(=O)=O)c1ccc(-c2cc3ncn(C)c(=O)c3c(N3CC[C@H](CO)C3)n2)cc1] | ESI-MS m/z 458.2 (MH⁺). | 0.199 |
| 629 | 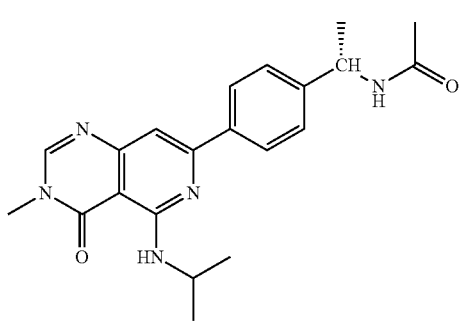 [SMILES: CC(=O)N[C@@H](C)c1ccc(-c2cc3ncn(C)c(=O)c3c(NC(C)C)n2)cc1] | ESI-MS m/z 380.20 (MH⁺). | 0.312 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 630 | 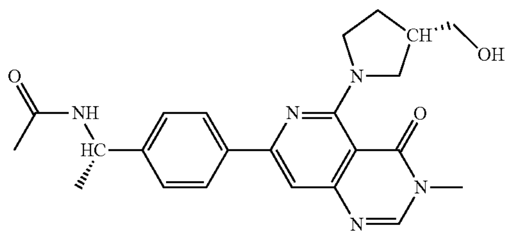 [SMILES: CC(=O)N[C@@H](C)c1ccc(-c2cc3ncn(C)c(=O)c3c(N3CC[C@H](CO)C3)n2)cc1] | ESI-MS m/z 422.2 (MH⁺). | 0.246 |
| 631 | 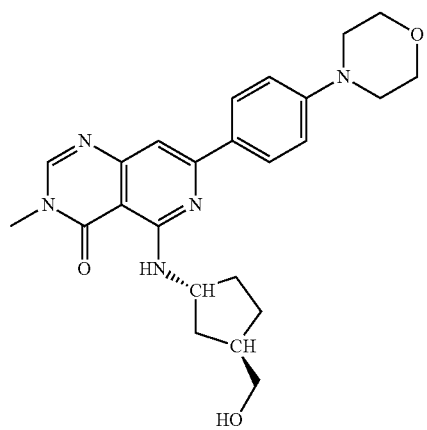 [SMILES: Cn1cnc2cc(-c3ccc(N4CCOCC4)cc3)nc(N[C@@H]3CC[C@@H](CO)C3)c2c1=O] | ESI-MS m/z 436.2 (MH⁺). | 0.0919 |
| 632 | 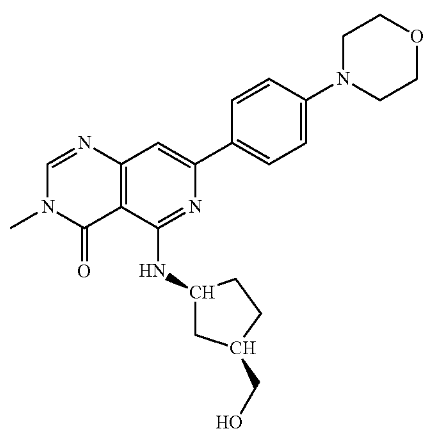 [SMILES: Cn1cnc2cc(-c3ccc(N4CCOCC4)cc3)nc(N[C@H]3CC[C@@H](CO)C3)c2c1=O] | ESI-MS m/z 436.2 (MH⁺). | 0.149 |
| 633 | 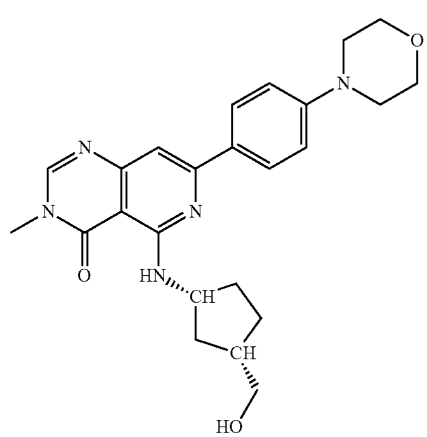 [SMILES: Cn1cnc2cc(-c3ccc(N4CCOCC4)cc3)nc(N[C@@H]3CC[C@H](CO)C3)c2c1=O] | ESI-MS m/z 436.20 (MH⁺). | 0.0763 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 634 | 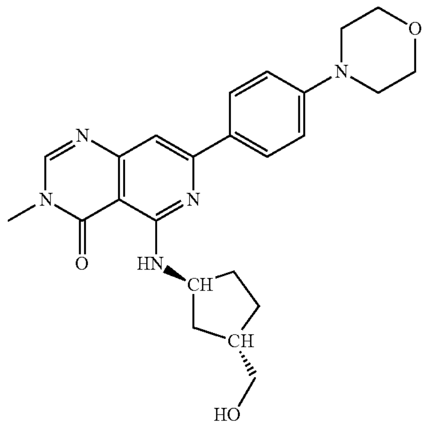 [SMILES: Cn1cnc2cc(-c3ccc(N4CCOCC4)cc3)nc(N[C@H]3CC[C@H](CO)C3)c2c1=O] | ESI-MS m/z 436.2 (MH⁺). | 0.262 |
| 635 | 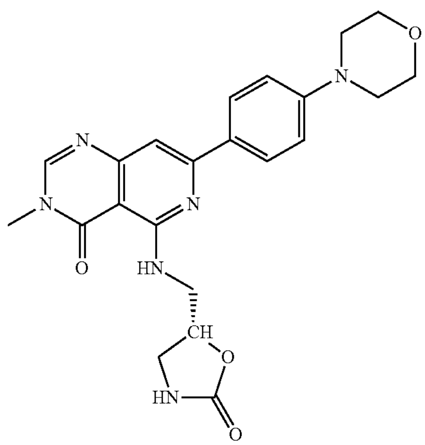 [SMILES: Cn1cnc2cc(-c3ccc(N4CCOCC4)cc3)nc(NC[C@H]3CNC(=O)O3)c2c1=O] | ESI-MS m/z 437.20 (MH⁺). | 0.244 |
| 636 | 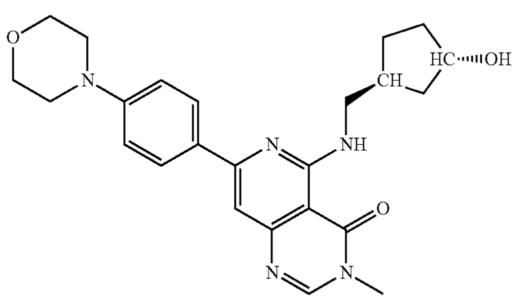 [SMILES: Cn1cnc2cc(-c3ccc(N4CCOCC4)cc3)nc(NC[C@H]3CC[C@H](O)C3)c2c1=O] | ESI-MS m/z 436.2 (MH⁺). | 0.162 |
| 637 | 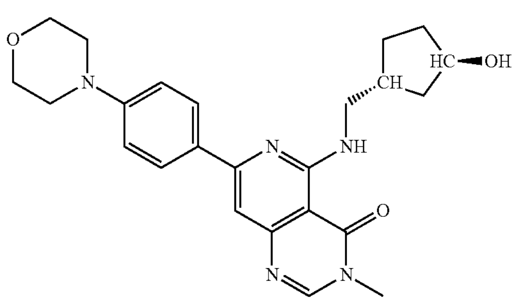 [SMILES: Cn1cnc2cc(-c3ccc(N4CCOCC4)cc3)nc(NC[C@@H]3CC[C@@H](O)C3)c2c1=O] | ESI-MS m/z 436.20 (MH⁺). | 0.158 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 638 | 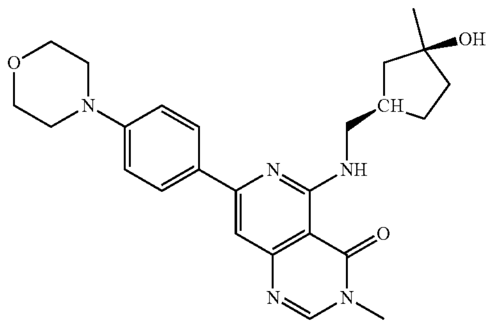 [SMILES: Cn1cnc2cc(-c3ccc(N4CCOCC4)cc3)nc(NC[C@@H]3CC[C@](C)(O)C3)c2c1=O] | ESI-MS m/z 450.2 (MH⁺). | 0.843 |
| 639 | 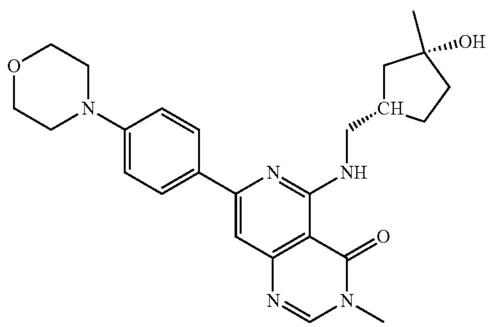 [SMILES: Cn1cnc2cc(-c3ccc(N4CCOCC4)cc3)nc(NC[C@H]3CC[C@@](C)(O)C3)c2c1=O] | ESI-MS m/z 450.20 (MH⁺). | 1.162 |
| 640 | 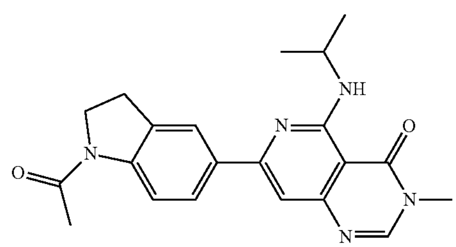 [SMILES: CC(=O)N1CCc2cc(-c3cc4ncn(C)c(=O)c4c(NC(C)C)n3)ccc21] | ESI-MS m/z 378.2 (MH⁺). | 1.064 |
| 641 | 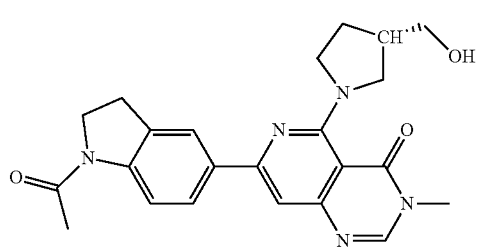 [SMILES: CC(=O)N1CCc2cc(-c3cc4ncn(C)c(=O)c4c(N4CC[C@H](CO)C4)n3)ccc21] | ESI-MS m/z 420.20 (MH⁺). | 0.434 |
| 642 | 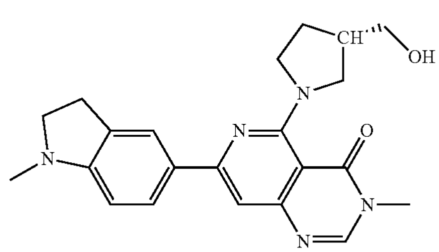 [SMILES: CN1CCc2cc(-c3cc4ncn(C)c(=O)c4c(N4CC[C@H](CO)C4)n3)ccc21] | ESI-MS m/z 392.2 (MH⁺). | 0.336 |

TABLE 1-continued

| Compound Number | Structure | Physical Data <br> ¹H NMR 400 MHz (CDCl₃), HPLC Retention Time, and/or MS (m/z) | Syk Enzyme IC$_{50}$ (uM) |
|---|---|---|---|
| 643 | 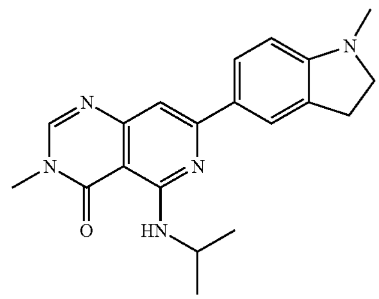 [SMILES: CC(C)Nc1nc(-c2ccc3c(c2)CCN3C)cc2ncn(C)c(=O)c12] | ESI-MS m/z 350.20 (MH⁺). | 1.451 |
| 644 | 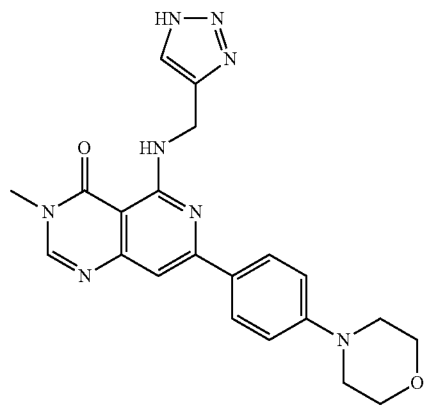 [SMILES: Cn1cnc2cc(-c3ccc(N4CCOCC4)cc3)nc(NCc3c[nH]nn3)c2c1=O] | ESI-MS m/z 419.2 (MH⁺). | 0.0372 |
| 645 | 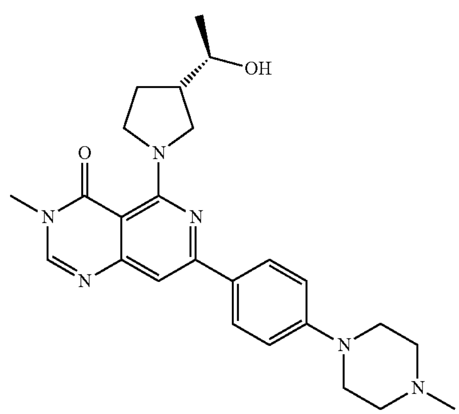 | ESI-MS m/z 449.3 (MH⁺). | 0.309 |
| 646 | 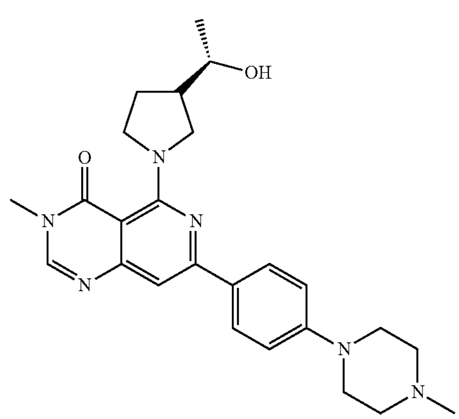 | ESI-MS m/z 449.3 (MH⁺). | 0.616 |

TABLE 1-continued

| Compound Number | Structure | Physical Data<br>¹H NMR 400 MHz (CDCl₃),<br>HPLC Retention Time, and/or<br>MS (m/z) | Syk Enzyme IC₅₀ (uM) |
| --- | --- | --- | --- |
| 647 | 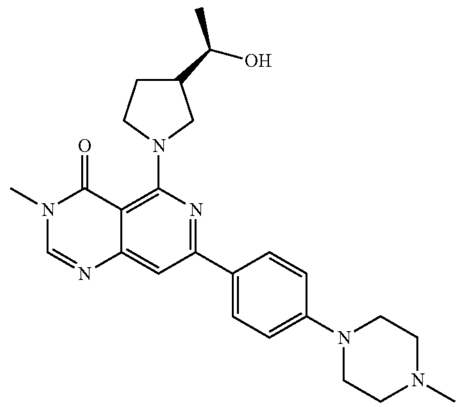 | ESI-MS m/z 449.3 (MH⁺). | 0.331 |
| 648 | 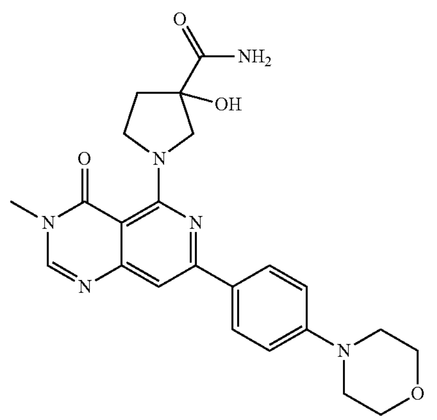 [SMILES: Cn1cnc2cc(-c3ccc(N4CCOCC4)cc3)nc(N3CCC(O)(C(N)=O)C3)c2c1=O] | ESI-MS m/z 451.2 (MH⁺). | 0.189 |
| 649 | 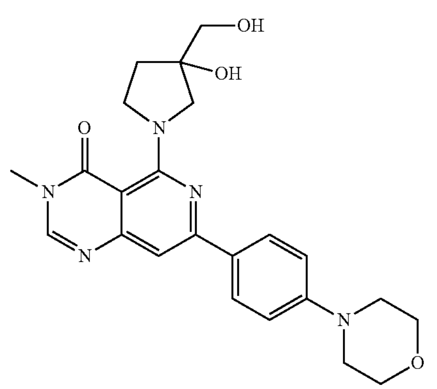 [SMILES: Cn1cnc2cc(-c3ccc(N4CCOCC4)cc3)nc(N3CCC(O)(CO)C3)c2c1=O] | ¹H NMR (DMSO-d₆, 400 MHz) δ 8.62 (s, 1H), 8.05 (d, 2H), 7.15 (s, 1H), 7.07 (d, 2H), 4.02 (m, 1H), 3.91 (m, 1H), 3.78 (s, 2H), 3.25 (s, 3H), 3.05 (m, 1H), 2.55 (m, 6H), 2.00 (m, 1H), 1.73 (m, 1H); ESI-MS m/z 438.2 (MH⁺). | 0.326 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 650 | 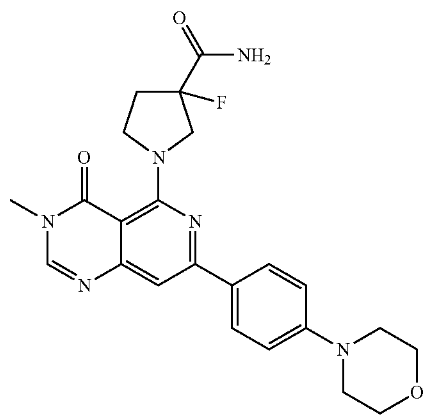 [SMILES: Cn1cnc2cc(-c3ccc(N4CCOCC4)cc3)nc(N3CCC(F)(C(N)=O)C3)c2c1=O] | ESI-MS m/z 453.2 (MH⁺). | 0.119 |
| 651 | 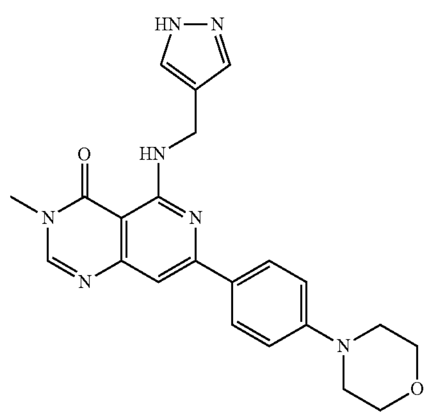 [SMILES: Cn1cnc2cc(-c3ccc(N4CCOCC4)cc3)nc(NCc3cn[nH]c3)c2c1=O] | ¹H NMR (DMSO-d₆, 400 MHz) δ 8.45 (s, 1H), 8.05 (d, 2H), 7.67 (s, 1H), 7.05-7.12 (m, 4H), 3.77 (s, 3H), 3.21 (b, 2H), 2.55 (m, 8H); ESI-MS m/z 418.2 (MH⁺). | 0.242 |
| 652 | 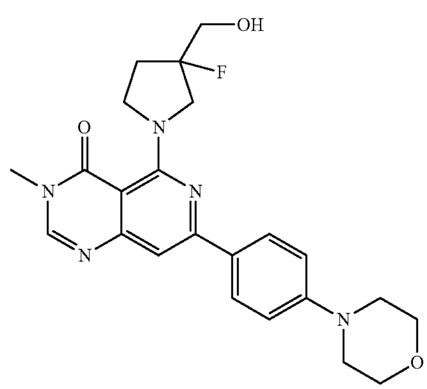 [SMILES: Cn1cnc2cc(-c3ccc(N4CCOCC4)cc3)nc(N3CCC(F)(CO)C3)c2c1=O] | ESI-MS m/z 440.2 (MH⁺). | 0.232 |
| 653 | 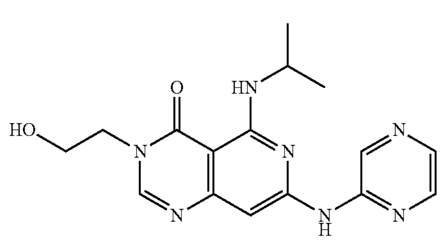 [SMILES: CC(C)Nc1nc(Nc2cnccn2)cc2ncn(CCO)c(=O)c12] | ESI-MS m/z 342.10 (MH⁺). ¹H NMR (DMSO-d₆) δ 10.03 (s, 1H), 9.25 (d, J = 1.2 Hz), 8.65 (d, J = 7.6 Hz, 1H), 8.29 (dd, J = 2.4, 1.6 Hz, 1H), 8.14 (d, J = 2.4 Hz, 1H), 8.13 (s, 1H), 6.76 (s, 1H), 4.95 (t, J = 5.6 Hz, 1H), 4.28 (m, 1H), 3.91 (m, 2H), 3.61 (m, 2H), 1.27 (d, J = 6.8 Hz, 6H). | 0.209 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 654 | 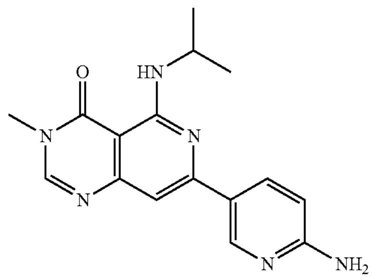 [SMILES: CC(C)Nc1nc(-c2ccc(N)nc2)cc2ncn(C)c(=O)c12] | ESI-MS m/z 311.10 (MH⁺). ¹H NMR (DMSO-d$_6$) δ 8.74 (d, J = 2.0 Hz, 1H), 8.68 (d, J = 7.2 Hz, 1H), 8.37 (s, 1H), 8.11 (dd, J = 8.8, 2.4 Hz, 1H), 6.99 (s, 1H), 6.51 (d, J = 8.8 Hz, 1H), 6.38 (s, 2H), 4.38 (m, 1H), 3.41 (s, 3H), 1.27 (d, J = 6.8 Hz, 6H). | 0.152 |
| 655 | 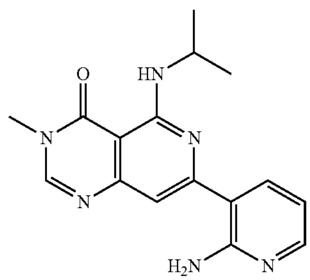 [SMILES: CC(C)Nc1nc(-c2cccnc2N)cc2ncn(C)c(=O)c12] | ESI-MS m/z 311.10 (MH⁺). ¹H NMR (DMSO-d$_6$) δ 8.87 (d, J = 8.0 Hz, 1H), 8.43 (s, 1H), 8.05-8.01 (m, 2H), 7.41 (s, 2H), 7.05 (s, 1H), 6.65 (dd, J = 7.6, 4.8 Hz, 1H), 4.17 (m, 1H), 3.44 (s, 3H), 1.28 (d, J = 6.8 Hz, 6H). | 0.126 |
| 656 | 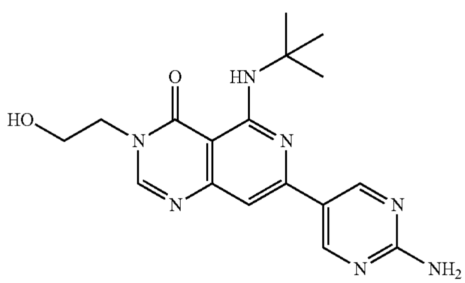 [SMILES: CC(C)(C)Nc1nc(-c2cnc(N)nc2)cc2ncn(CCO)c(=O)c12] | ESI-MS m/z 356.10 (MH⁺). ¹H NMR (DMSO-d$_6$) δ 9.06 (s, 1H), 8.97 (s, 2H), 8.27 (s, 1H), 7.1 (s, 1H), 7.09 (s, 2H), 4.97 (t, J = 5.6 Hz, 1H), 3.97 (m, 2H), 3.64 (m, 2H), 1.53 (s, 9H). | 0.525 |
| 657 | 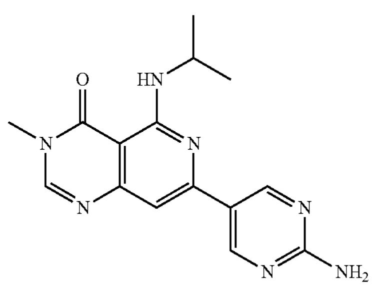 [SMILES: CC(C)Nc1nc(-c2cnc(N)nc2)cc2ncn(C)c(=O)c12] | ESI-MS m/z 312.2 (MH⁺). | 0.324 |
| 658 | 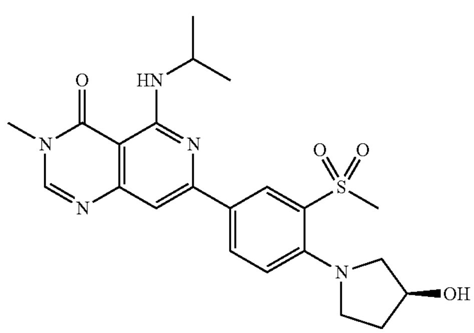 [SMILES: CC(C)Nc1nc(-c2ccc(N3CC[C@H](O)C3)c(S(C)(=O)=O)c2)cc2ncn(C)c(=O)c12] | ¹H NMR (400 MHz, DMSO-d$_6$) of the HCl salt of the compound: δ 1.30 (d, J = 6.4 Hz, 6H), 1.85 (m, 1H), 2.06 (m, 1H), 2.23 (m, 1H), 3.31 (m, 1H), 3.40 (s, 3H), 3.43 (s, 3H), 3.59-3.68 (2H), 4.38 (m, 1H), 4.39 (m, 1H), 7.13 (s, 1H), 7.35 (d, J = 8.8 Hz, 1H), 8.24 (dd, J = 8.4, 2.4 Hz, 1H), 8.64 (s, 1H), 8.65 (d, J = 2.4 Hz, 1H); ESI-MS m/z 458.2 (MH⁺). | 0.0769 |

TABLE 1-continued
| Compound Number | Structure | Physical Data<br>¹H NMR 400 MHz (CDCl₃),<br>HPLC Retention Time, and/or<br>MS (m/z) | Syk Enzyme IC₅₀ (uM) |
|---|---|---|---|
| 659 | 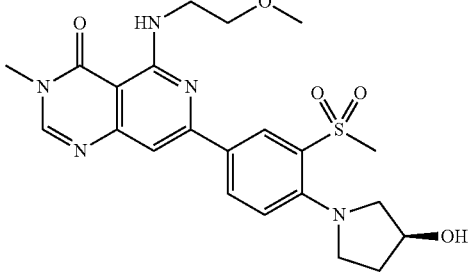 | ESI-MS m/z 474.2 (MH⁺). | 0.0605 |
| 660 | 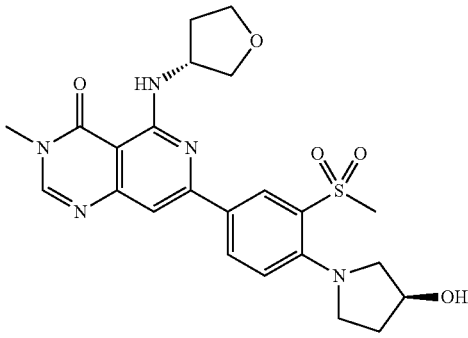 [SMILES: Cn1cnc2cc(-c3ccc(N4CC[C@H](O)C4)c(S(C)(=O)=O)c3)nc(N[C@@H]3CCOC3)c2c1=O] | ESI-MS m/z 486.2 (MH⁺). | 0.0537 |
| 661 | 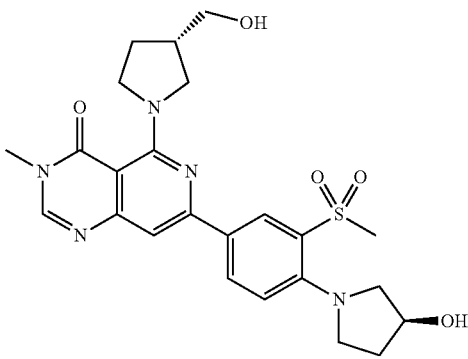 [SMILES: Cn1cnc2cc(-c3ccc(N4CC[C@H](O)C4)c(S(C)(=O)=O)c3)nc(N3CC[C@H](CO)C3)c2c1=O] | ¹H NMR (400 MHz, DMSO-d₆) of the TFA salt of the compound: δ 1.68 (m, 1H), 1.85 (m, 1H), 1.98 (m, 1H), 2.07 (m, 1H), 2.33 (m, 1H), 3.21 (m, 1H), 3.29 (m, 1H), 3.49-3.73 (8H), 3.40 (s, 3H), 3.43 (s, 3H), 4.38 (m, 1H), 7.20 (s, 1H), 7.36 (d, J = 8.8 Hz, 1H), 8.28 (dd, J = 8.4, 2.4 Hz, 1H), 8.63 (d, J = 2.4 Hz, 1H); ESI-MS m/z 500.2 (MH⁺). | 0.104 |
| 662 | 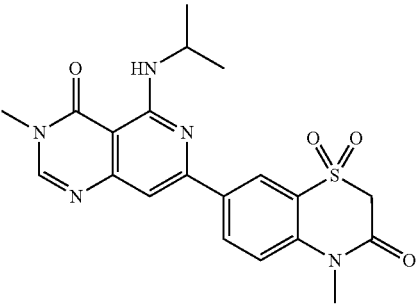 [SMILES: CC(C)Nc1nc(-c2ccc3c(c2)S(=O)(=O)CC(=O)N3C)cc2ncn(C)c(=O)c12] | ESI-MS m/z 428.1 (MH⁺). | 0.554 |

… TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 663 | 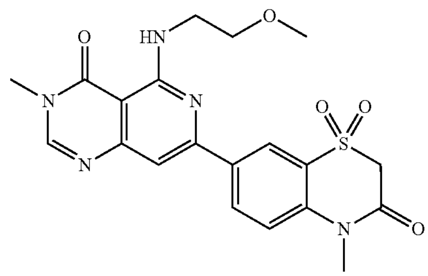 [SMILES: COCCNc1nc(-c2ccc3c(c2)S(=O)(=O)CC(=O)N3C)cc2ncn(C)c(=O)c12] | ESI-MS m/z 444.1 (MH⁺). | 0.236 |
| 664 | 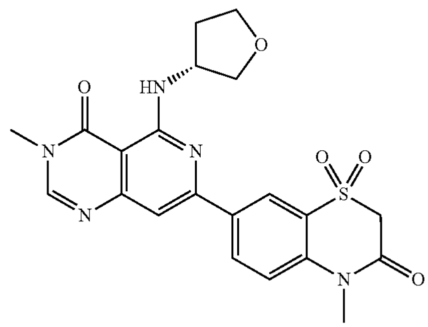 [SMILES: CN1C(=O)CS(=O)(=O)c2cc(-c3cc4ncn(C)c(=O)c4c(N[C@@H]4CCOC4)n3)ccc21] | ESI-MS m/z 456.1 (MH⁺). | 0.243 |
| 665 | 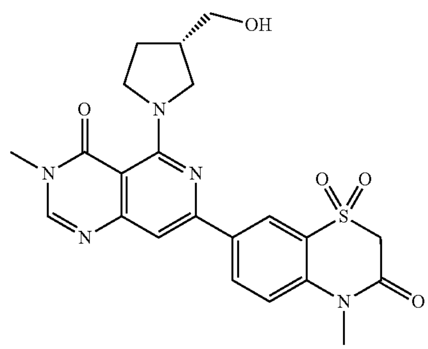 [SMILES: CN1C(=O)CS(=O)(=O)c2cc(-c3cc4ncn(C)c(=O)c4c(N4CC[C@H](CO)C4)n3)ccc21] | ESI-MS m/z 470.1 (MH⁺). | 0.204 |
| 666 | 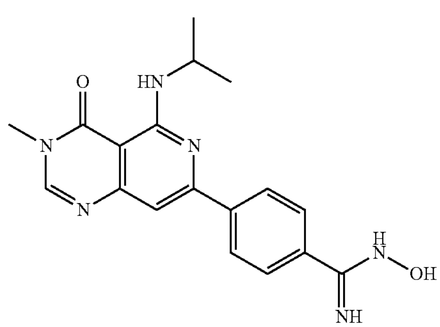 | ¹H NMR (400 MHz, DMSO-d₆) of the TFA salt of the compound: δ 1.30 (d, J = 6.4 Hz, 6H), 4.43 (m, 1H), 7.25 (s, 1H), 7.80 (d, J = 8.4 Hz, 2H), 8.23 (d, J = 8.4 Hz, 2H), 8.46 (s, 1H), 8.75 (br d, J = 7.2 Hz, 1H, NH); ESI-MS m/z 369.2 (MH⁺). | 0.616 |
| 667 | 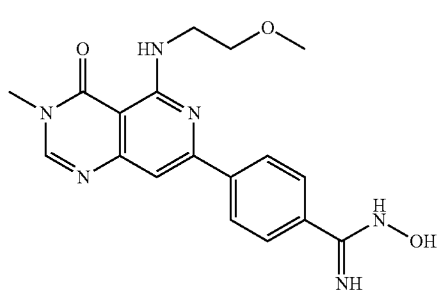 [SMILES: COCCNc1nc(-c2ccc(C(=N)NO)cc2)cc2ncn(C)c(=O)c12] | ESI-MS m/z 369.2 (MH⁺). | 0.548 |

433
434

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 668 | 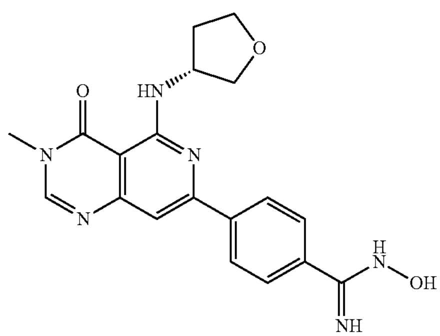 [SMILES: Cn1cnc2cc(-c3ccc(C(=N)NO)cc3)nc(N[C@@H]3CCOC3)c2c1=O] | ESI-MS m/z 381.2 (MH⁺). | 0.149 |
| 669 | 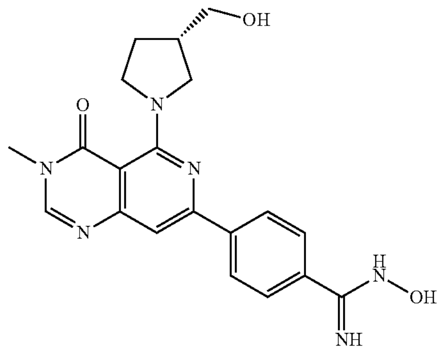 [SMILES: Cn1cnc2cc(-c3ccc(C(=N)NO)cc3)nc(N3CC[C@H](CO)C3)c2c1=O] | ESI-MS m/z 395.2 (MH⁺). | 0.262 |
| 670 | 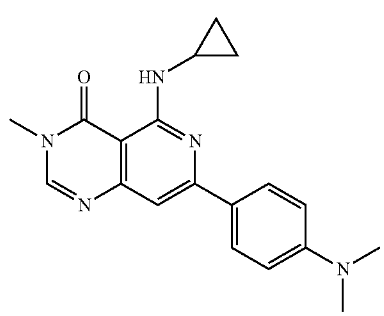 | ESI-MS m/z 336.2 (MH⁺). | 0.194 |
| 671 | 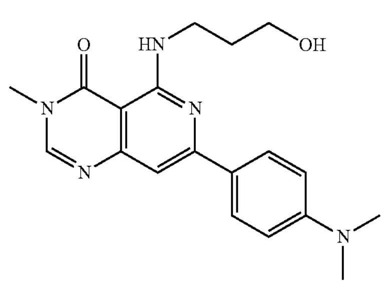 | ESI-MS m/z 354.2 (MH⁺). | 0.0821 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 672 | 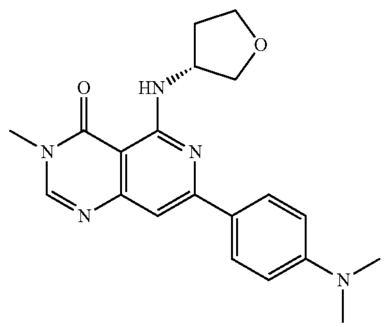 | ESI-MS m/z 366.2 (MH⁺). | 0.161 |
| 673 | 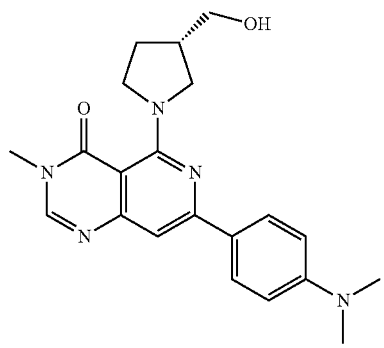 | ESI-MS m/z 380.2 (MH⁺). | 0.147 |
| 674 | 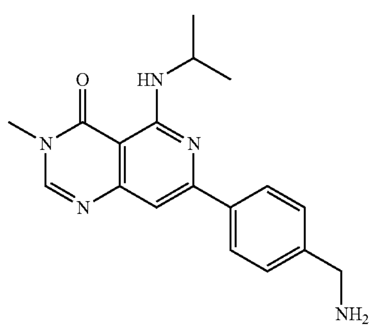 [SMILES: CC(C)Nc1nc(-c2ccc(CN)cc2)cc2ncn(C)c(=O)c12] | ESI-MS m/z 324.2 (MH⁺). | 0.587 |
| 675 | 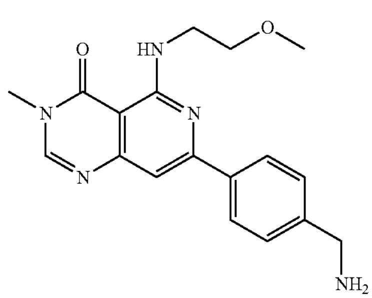 [SMILES: COCCNc1nc(-c2ccc(CN)cc2)cc2ncn(C)c(=O)c12] | ESI-MS m/z 340.2 (MH⁺). | 0.909 |

TABLE 1-continued

| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 676 | 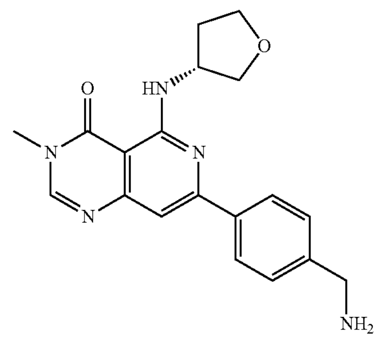 [SMILES: Cn1cnc2cc(-c3ccc(CN)cc3)nc(N[C@@H]3CCOC3)c2c1=O] | ESI-MS m/z 352.2 (MH$^+$). | 0.19 |
| 677 | 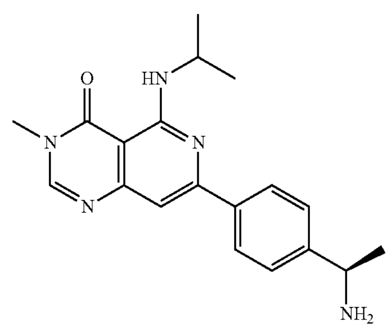 [SMILES: CC(C)Nc1nc(-c2ccc([C@@H](C)N)cc2)cc2ncn(C)c(=O)c12] | ESI-MS m/z 338.2 (MH$^+$). | 0.179 |
| 678 | 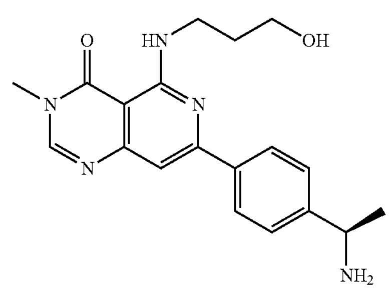 [SMILES: C[C@@H](N)c1ccc(-c2cc3ncn(C)c(=O)c3c(NCCCO)n2)cc1] | ESI-MS m/z 354.2 (MH$^+$). | 0.13 |
| 679 | 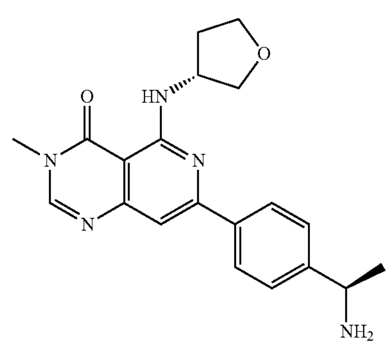 [SMILES: C[C@@H](N)c1ccc(-c2cc3ncn(C)c(=O)c3c(N[C@@H]3CCOC3)n2)cc1] | ESI-MS m/z 366.2 (MH$^+$). | 0.157 |

TABLE 1-continued
| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 680 | 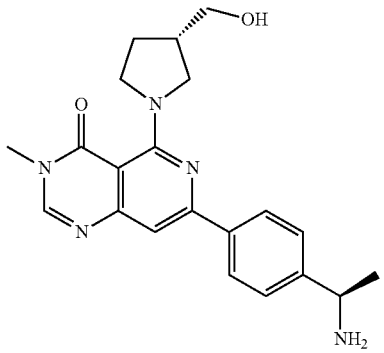 [SMILES: C[C@@H](N)c1ccc(-c2cc3ncn(C)c(=O)c3c(N3CC[C@H](CO)C3)n2)cc1] | ESI-MS m/z 380.2 (MH⁺). | 0.139 |
| 681 | 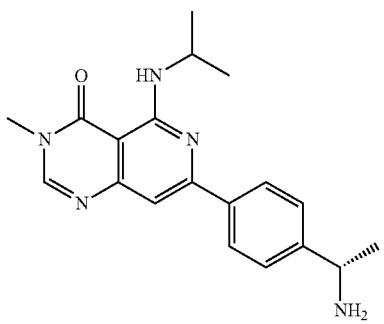 [SMILES: CC(C)Nc1nc(-c2ccc([C@H](C)N)cc2)cc2ncn(C)c(=O)c12] | ESI-MS m/z 338.2 (MH⁺). | 0.181 |
| 682 | 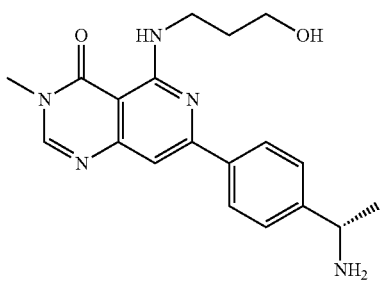 [SMILES: C[C@H](N)c1ccc(-c2cc3ncn(C)c(=O)c3c(NCCCO)n2)cc1] | ESI-MS m/z 354.2 (MH⁺). | 0.127 |
| 683 | 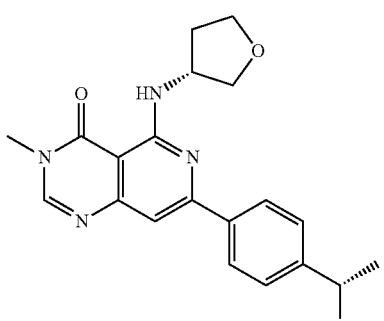 | ESI-MS m/z 366.2 (MH⁺). | 0.181 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 684 | 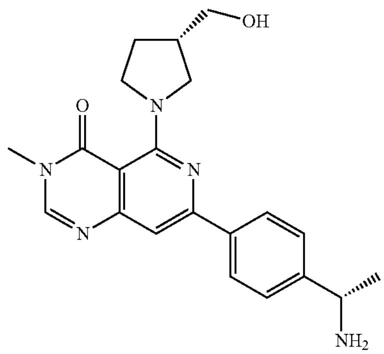 [SMILES: C[C@H](N)c1ccc(-c2cc3ncn(C)c(=O)c3c(N3CC[C@H](CO)C3)n2)cc1] | ESI-MS m/z 380.2 (MH⁺). | 0.258 |
| 685 | 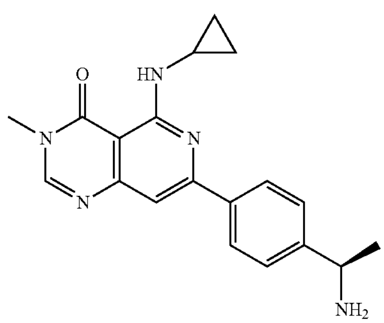 [SMILES: C[C@@H](N)c1ccc(-c2cc3ncn(C)c(=O)c3c(NC3CC3)n2)cc1] | ESI-MS m/z 336.2 (MH⁺). | 0.15 |
| 686 | 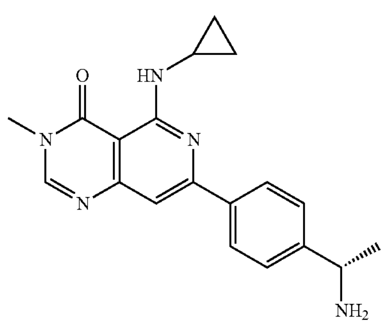 [SMILES: C[C@H](N)c1ccc(-c2cc3ncn(C)c(=O)c3c(NC3CC3)n2)cc1] | ESI-MS m/z 336.2 (MH⁺). | 0.46 |
| 687 | 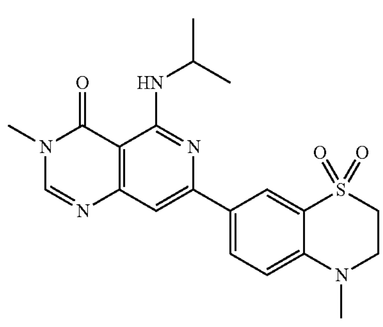 [SMILES: CC(C)Nc1nc(-c2ccc3c(c2)S(=O)(=O)CCN3C)cc2ncn(C)c(=O)c12] | ¹H NMR (400 MHz, DMSO-d₆) of the HCl salt of the compound: δ 1.30 (d, J = 6.4 Hz, 6H), 3.10 (s, 3H), 3.43 (s, 3H), 3.60 (m, 2H), 3.90 (m, 2H), 4.38 (m, 1H), 6.94 (d, J = 8.8 Hz, 2H), 7.07 (s, 1H), 8.18 (dd, J = 8.8, 2.0 Hz, 1H), 8.42 (d, J = 2.0 Hz, 1H), 8.45 (s, 1H); ESI-MS m/z 414.2 (MH⁺). | 0.14 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 688 | 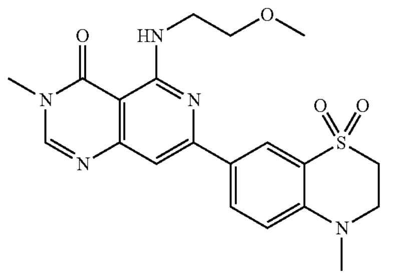 [SMILES: COCCNc1nc(-c2ccc3c(c2)S(=O)(=O)CCN3C)cc2ncn(C)c(=O)c12] | ESI-MS m/z 430.2 (MH⁺). | 0.053 |
| 689 | 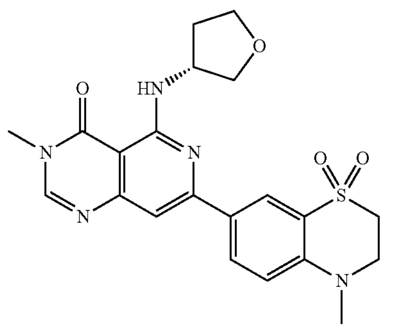 [SMILES: CN1CCS(=O)(=O)c2cc(-c3cc4ncn(C)c(=O)c4c(N[C@@H]4CCOC4)n3)ccc21] | ESI-MS m/z 442.2 (MH⁺). | 0.0464 |
| 690 | 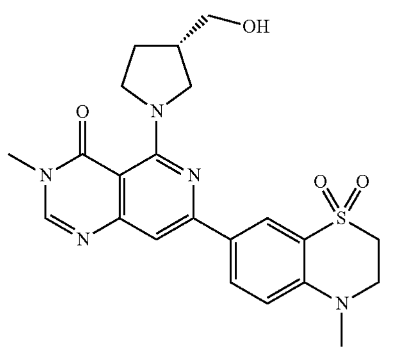 [SMILES: CN1CCS(=O)(=O)c2cc(-c3cc4ncn(C)c(=O)c4c(N4CC[C@H](CO)C4)n3)ccc21] | ESI-MS m/z 456.2 (MH⁺). | 0.102 |
| 691 | 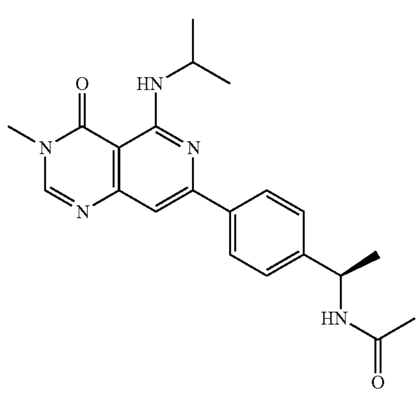 [SMILES: CC(=O)N[C@H](C)c1ccc(-c2cc3ncn(C)c(=O)c3c(NC(C)C)n2)cc1] | ESI-MS m/z 380.2 (MH⁺). | 0.264 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
| --- | --- | --- | --- |
| 692 | 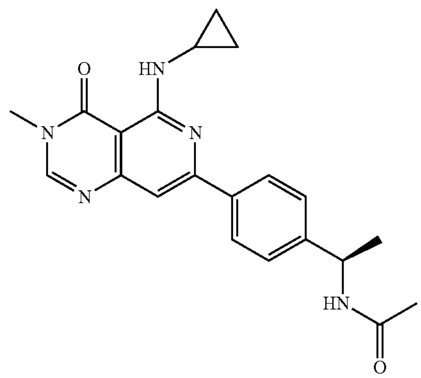 [SMILES: CC(=O)N[C@H](C)c1ccc(-c2cc3ncn(C)c(=O)c3c(NC3CC3)n2)cc1] | ESI-MS m/z 378.2 (MH⁺). | 0.167 |
| 693 | 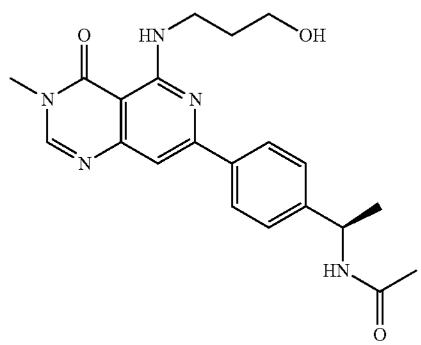 [SMILES: CC(=O)N[C@H](C)c1ccc(-c2cc3ncn(C)c(=O)c3c(NCCCO)n2)cc1] | ESI-MS m/z 396.2 (MH⁺). | 0.148 |
| 694 | 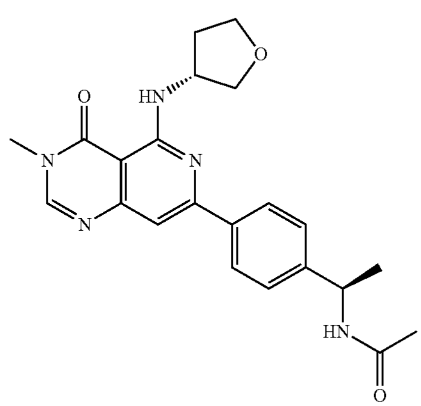 [SMILES: CC(=O)N[C@H](C)c1ccc(-c2cc3ncn(C)c(=O)c3c(N[C@@H]3CCOC3)n2)cc1] | ESI-MS m/z 408.2 (MH⁺). | 0.274 |
| 695 | 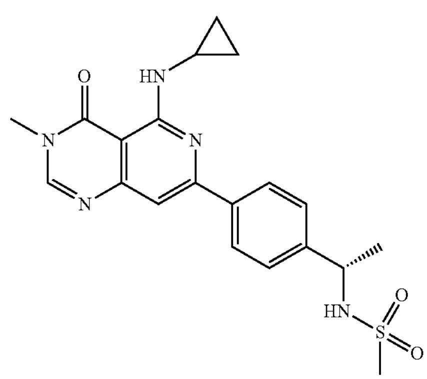 [SMILES: C[C@H](NS(C)(=O)=O)c1ccc(-c2cc3ncn(C)c(=O)c3c(NC3CC3)n2)cc1] | ESI-MS m/z 414.2 (MH⁺). | 0.302 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 696 | 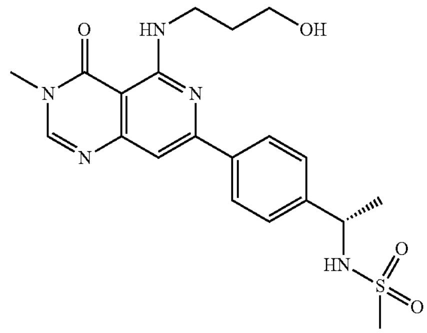 [SMILES: C[C@H](NS(C)(=O)=O)c1ccc(-c2cc3ncn(C)c(=O)c3c(NCCCO)n2)cc1] | ESI-MS m/z 432.2 (MH⁺). | 0.586 |
| 697 | 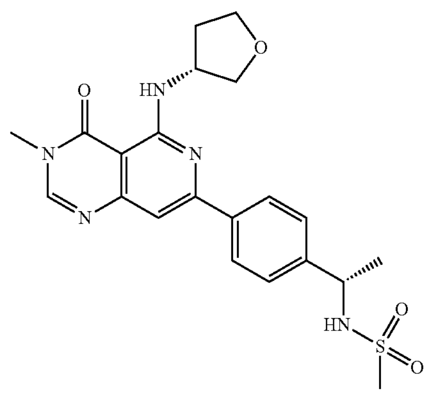 [SMILES: C[C@H](NS(C)(=O)=O)c1ccc(-c2cc3ncn(C)c(=O)c3c(N[C@@H]3CCOC3)n2)cc1] | ESI-MS m/z 444.2 (MH⁺). | 0.122 |
| 698 | 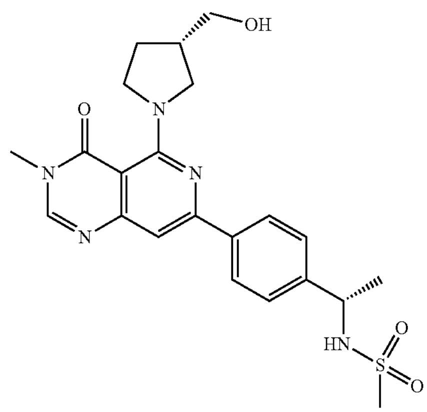 [SMILES: C[C@H](NS(C)(=O)=O)c1ccc(-c2cc3ncn(C)c(=O)c3c(N3CC[C@H](CO)C3)n2)cc1] | ESI-MS m/z 458.2 (MH⁺). | 0.221 |
| 699 | 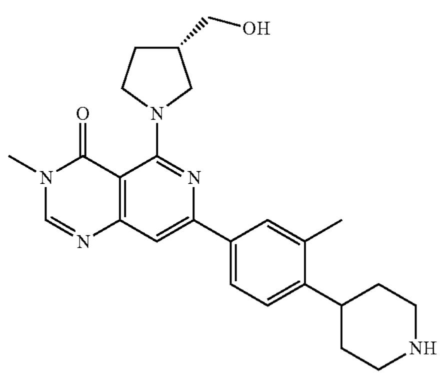 [SMILES: Cc1cc(-c2cc3ncn(C)c(=O)c3c(N3CC[C@H](CO)C3)n2)ccc1C1CCNCC1] | ESI-MS m/z 434.2 (MH⁺). | 0.0912 |

TABLE 1-continued
| Compound Number | Structure | Physical Data<br>¹H NMR 400 MHz (CDCl₃),<br>HPLC Retention Time, and/or<br>MS (m/z) | Syk Enzyme IC$_{50}$ (uM) |
| --- | --- | --- | --- |
| 700 | 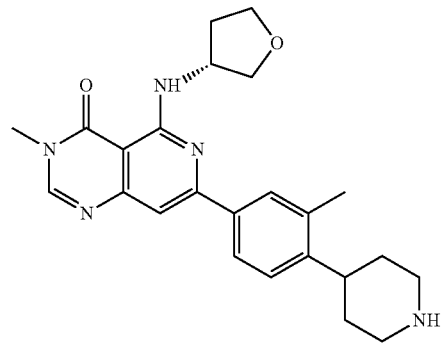 [SMILES: Cc1cc(-c2cc3ncn(C)c(=O)c3c(N[C@@H]3CCOC3)n2)ccc1C1CCNCC1] | ESI-MS m/z 420.2 (MH⁺). | 0.0514 |
| 701 | 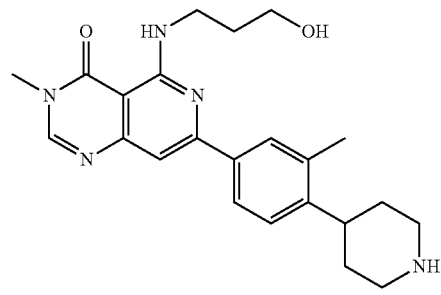 [SMILES: Cc1cc(-c2cc3ncn(C)c(=O)c3c(NCCCO)n2)ccc1C1CCNCC1] | ESI-MS m/z 408.2 (MH⁺). | 0.0775 |
| 702 | 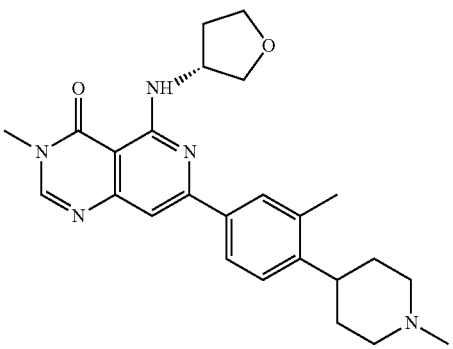 | ESI-MS m/z 434.2 (MH⁺). | 0.0608 |
| 703 | 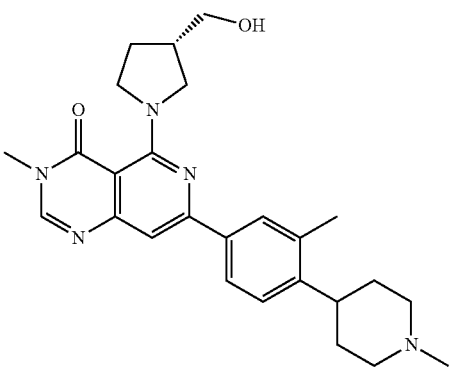 | ESI-MS m/z 448.3 (MH⁺). | 0.111 |

TABLE 1-continued

| Compound Number | Structure | Physical Data<br>¹H NMR 400 MHz (CDCl₃),<br>HPLC Retention Time, and/or<br>MS (m/z) | Syk Enzyme IC$_{50}$ (uM) |
|---|---|---|---|
| 704 | 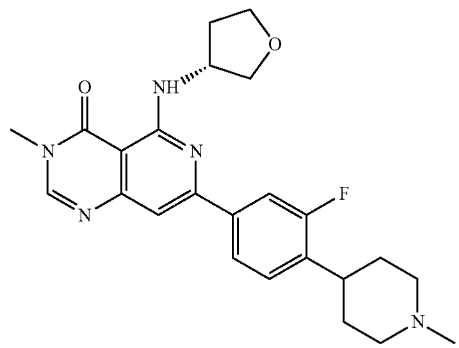 | ESI-MS m/z 438.2 (MH⁺). | 0.14 |
| 705 | 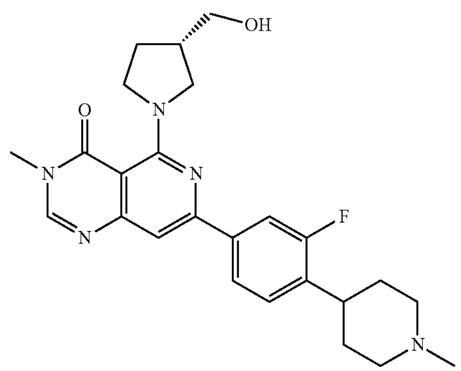 | ESI-MS m/z 452.2 (MH⁺). | 0.174 |
| 706 | 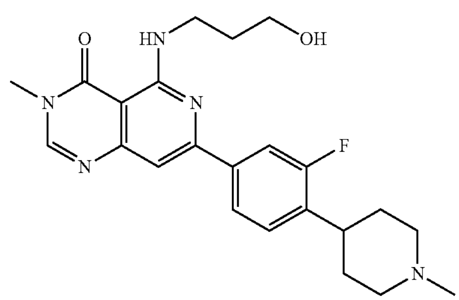 | ESI-MS m/z 426.2 (MH⁺). | 0.428 |
| 707 | 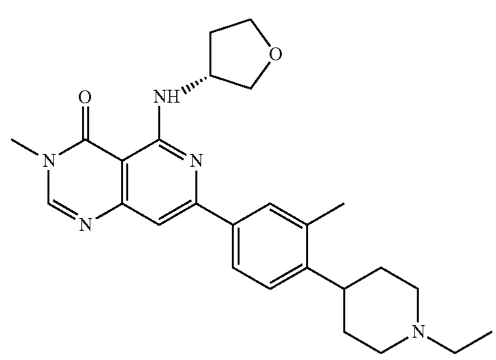 [SMILES: CCN1CCC(c2ccc(-c3cc4ncn(C)c(=O)c4c(N[C@@H]4CCOC4)n3)cc2C)CC1] | ESI-MS m/z 448.3 (MH⁺). | 0.0788 |

TABLE 1-continued
| Compound Number | Structure | Physical Data ¹H NMR 400 MHz (CDCl$_3$), HPLC Retention Time, and/or MS (m/z) | Syk Enzyme IC$_{50}$ (uM) |
|---|---|---|---|
| 708 | 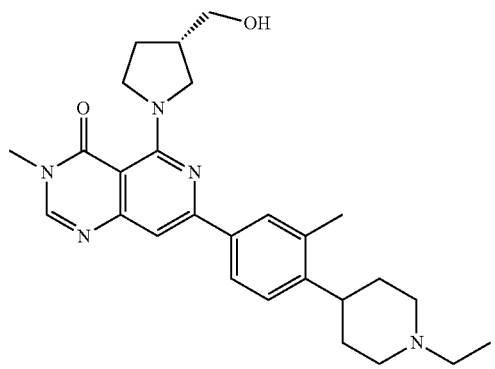 [SMILES: CCN1CCC(c2ccc(-c3cc4ncn(C)c(=O)c4c(N4CC[C@H](CO)C4)n3)cc2C)CC1] | ESI-MS m/z 462.3 (MH$^+$). | 0.155 |
| 709 | 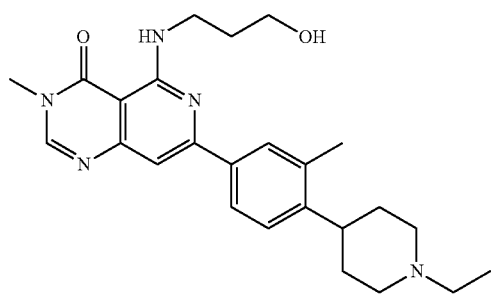 [SMILES: CCN1CCC(c2ccc(-c3cc4ncn(C)c(=O)c4c(NCCCO)n3)cc2C)CC1] | ESI-MS m/z 436.3 (MH$^+$). | 0.165 |
| 710 | 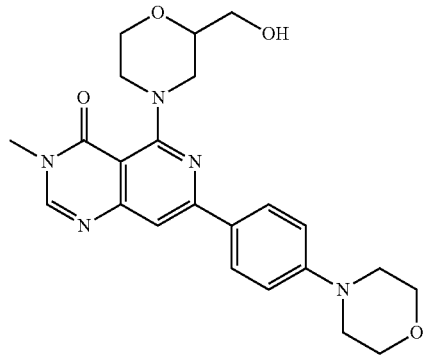 [SMILES: Cn1cnc2cc(-c3ccc(N4CCOCC4)cc3)nc(N3CCOC(CO)C3)c2c1=O] | ESI-MS m/z 438.2 (MH$^+$). | 0.682 |
| 711 | 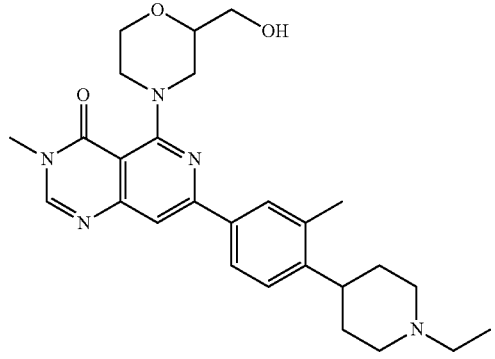 [SMILES: CCN1CCC(c2ccc(-c3cc4ncn(C)c(=O)c4c(N4CCOC(CO)C4)n3)cc2C)CC1] | ESI-MS m/z 478.3 (MH$^+$). | 0.23 |

TABLE 1-continued
| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 712 | 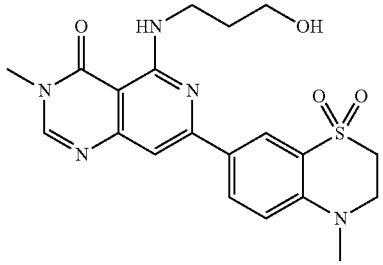 [SMILES: CN1CCS(=O)(=O)c2cc(-c3cc4ncn(C)c(=O)c4c(NCCCO)n3)ccc21] | ESI-MS m/z 430.2 (MH$^+$). | 0.039 |
| 713 | 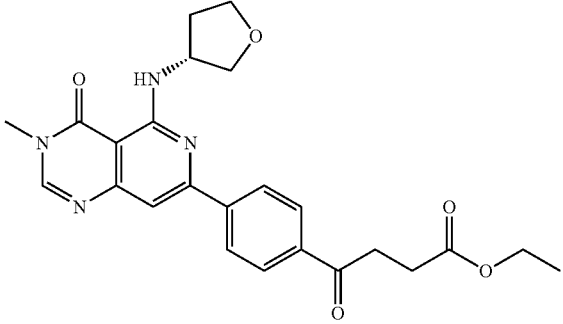 [SMILES: CCOC(=O)CCC(=O)c1ccc(-c2cc3ncn(C)c(=O)c3c(N[C@@H]3CCOC3)n2)cc1] | ESI-MS m/z 451.2 (MH$^+$). | 0.434 |
| 714 | 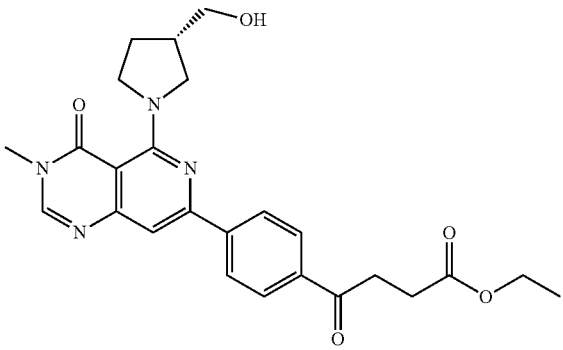 [SMILES: CCOC(=O)CCC(=O)c1ccc(-c2cc3ncn(C)c(=O)c3c(N3CC[C@H](CO)C3)n2)cc1] | ESI-MS m/z 465.2 (MH$^+$). | 0.381 |
| 715 | 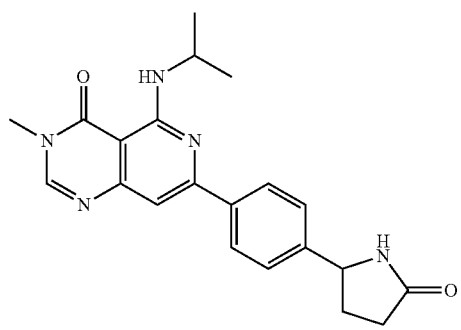 [SMILES: CC(C)Nc1nc(-c2ccc(C3CCC(=O)N3)cc2)cc2ncn(C)c(=O)c12] | ESI-MS m/z 378.2 (MH$^+$). | 0.276 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 716 | 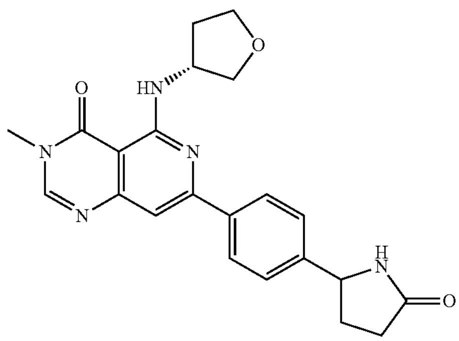 [SMILES: Cn1cnc2cc(-c3ccc(C4CCC(=O)N4)cc3)nc(N[C@@H]3CCOC3)c2c1=O] | ESI-MS m/z 406.2 (MH⁺). | 0.282 |
| 717 | 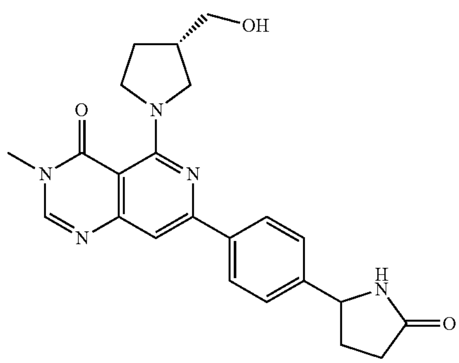 [SMILES: Cn1cnc2cc(-c3ccc(C4CCC(=O)N4)cc3)nc(N3CC[C@H](CO)C3)c2c1=O] | ESI-MS m/z 420.2 (MH⁺). | 0.167 |
| 718 | 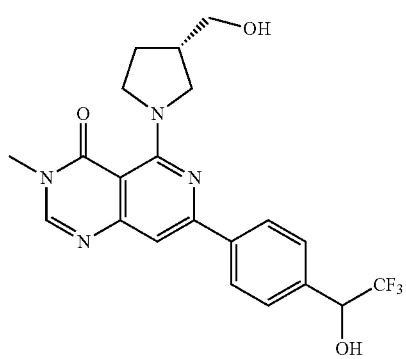 [SMILES: Cn1cnc2cc(-c3ccc(C(O)C(F)(F)F)cc3)nc(N3CC[C@H](CO)C3)c2c1=O] | ESI-MS m/z 435.2 (MH⁺). | 0.339 |
| 719 | 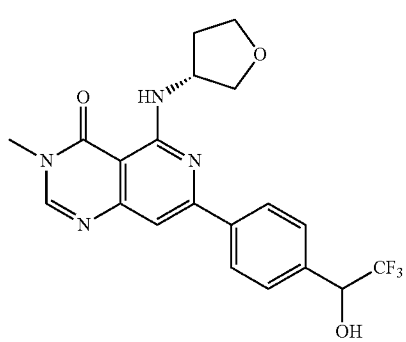 [SMILES: Cn1cnc2cc(-c3ccc(C(O)C(F)(F)F)cc3)nc(N[C@@H]3CCOC3)c2c1=O] | ESI-MS m/z 421.1 (MH⁺). | 0.964 |

| Compound Number | Structure | Physical Data <sup>1</sup>H NMR 400 MHz (CDCl$_3$), HPLC Retention Time, and/or MS (m/z) | Syk Enzyme IC$_{50}$ (uM) |
|---|---|---|---|
| 720 | 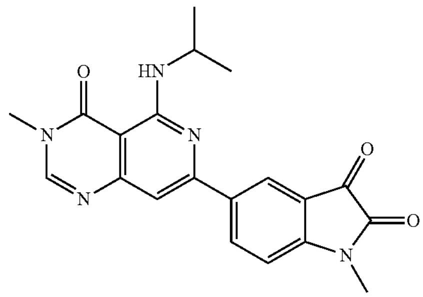 [SMILES: CC(C)Nc1nc(-c2ccc3c(c2)C(=O)C(=O)N3C)cc2ncn(C)c(=O)c12] | ESI-MS m/z 378.2 (MH$^+$). | 0.396 |
| 721 | 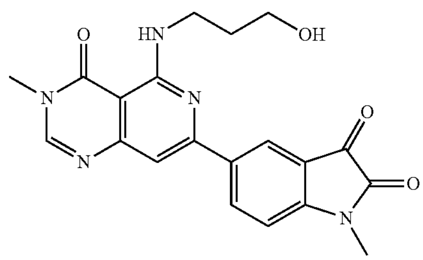 [SMILES: CN1C(=O)C(=O)c2cc(-c3cc4ncn(C)c(=O)c4c(NCCCO)n3)ccc21] | ESI-MS m/z 394.1 (MH$^+$). | 0.633 |
| 722 | 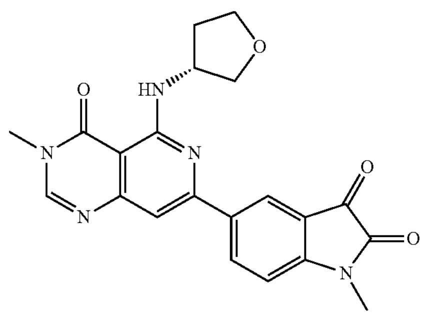 [SMILES: CN1C(=O)C(=O)c2cc(-c3cc4ncn(C)c(=O)c4c(N[C@@H]4CCOC4)n3)ccc21] | ESI-MS m/z 406.1 (MH$^+$). | 0.189 |
| 723 | 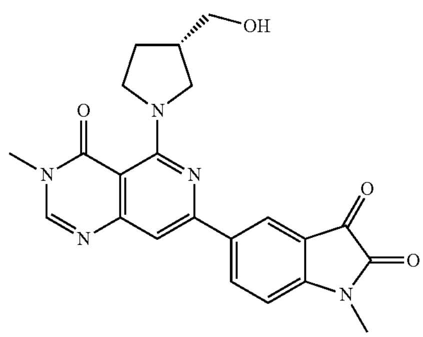 [SMILES: CN1C(=O)C(=O)c2cc(-c3cc4ncn(C)c(=O)c4c(N4CC[C@H](CO)C4)n3)ccc21] | ESI-MS m/z 420.2 (MH$^+$). | 0.497 |
| 724 | 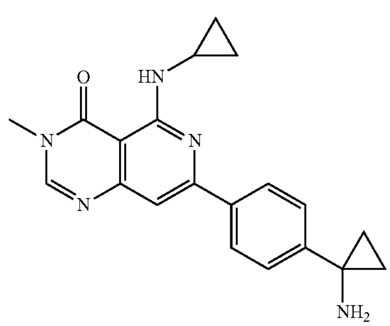 [SMILES: Cn1cnc2cc(-c3ccc(C4(N)CC4)cc3)nc(NC3CC3)c2c1=O] | ESI-MS m/z 348.2 (MH$^+$). | 1.152 |

TABLE 1-continued
| Compound Number | Structure | Physical Data $^1$H NMR 400 MHz (CDCl$_3$), HPLC Retention Time, and/or MS (m/z) | Syk Enzyme IC$_{50}$ (uM) |
|---|---|---|---|
| 725 | 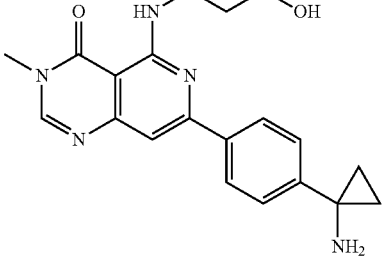 | ESI-MS m/z 366.2 (MH$^+$). | 0.884 |
| 726 | 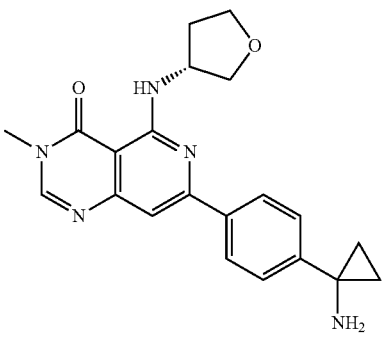 [SMILES: Cn1cnc2cc(-c3ccc(C4(N)CC4)cc3)nc(N[C@@H]3CCOC3)c2c1=O] | ESI-MS m/z 378.2 (MH$^+$). | 0.514 |
| 727 | 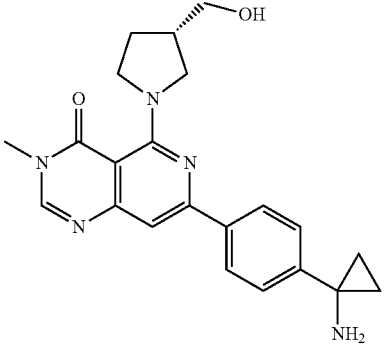 [SMILES: Cn1cnc2cc(-c3ccc(C4(N)CC4)cc3)nc(N3CC[C@H](CO)C3)c2c1=O] | ESI-MS m/z 392.2 (MH$^+$). | 0.326 |
| 728 | 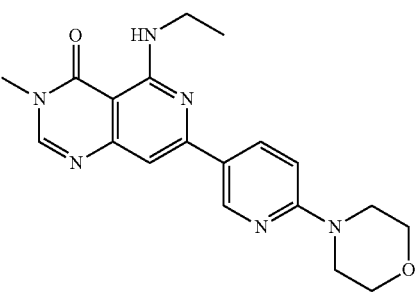 [SMILES: CCNc1nc(-c2ccc(N3CCOCC3)nc2)cc2ncn(C)c(=O)c12] | ESI-MS m/z 367.2 (MH$^+$). | 0.1 |
| 729 | 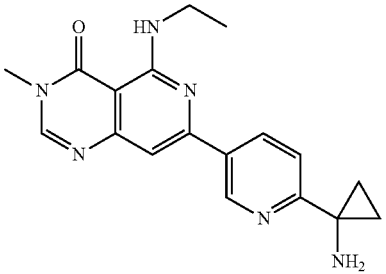 [SMILES: CCNc1nc(-c2ccc(C3(N)CC3)nc2)cc2ncn(C)c(=O)c12] | ESI-MS m/z 337.2 (MH$^+$). | 0.136 |

TABLE 1-continued

| Compound Number | Structure | Physical Data ¹H NMR 400 MHz (CDCl₃), HPLC Retention Time, and/or MS (m/z) | Syk Enzyme IC$_{50}$ (uM) |
|---|---|---|---|
| 730 | 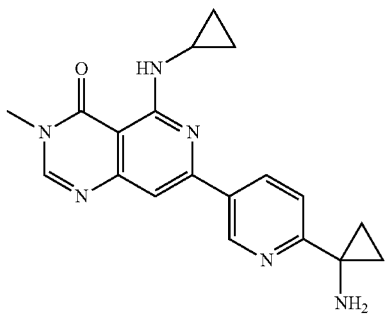 [SMILES: Cn1cnc2cc(-c3ccc(C4(N)CC4)nc3)nc(NC3CC3)c2c1=O] | ESI-MS m/z 349.2 (MH⁺). | 0.219 |
| 731 | 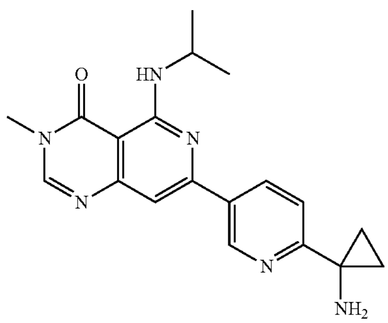 [SMILES: CC(C)Nc1nc(-c2ccc(C3(N)CC3)nc2)cc2ncn(C)c(=O)c12] | ESI-MS m/z 351.2 (MH⁺). | 0.158 |
| 732 | 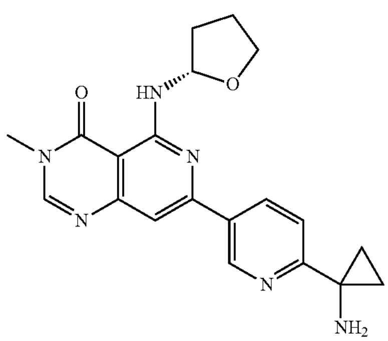 [SMILES: Cn1cnc2cc(-c3ccc(C4(N)CC4)nc3)nc(N[C@@H]3CCCO3)c2c1=O] | ESI-MS m/z 379.2 (MH⁺). | 0.338 |
| 733 | 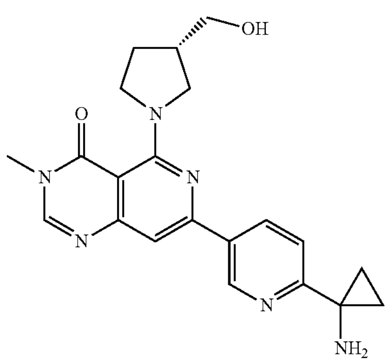 [SMILES: Cn1cnc2cc(-c3ccc(C4(N)CC4)nc3)nc(N3CC[C@H](CO)C3)c2c1=O] | ESI-MS m/z 393.2 (MH⁺). | 0.579 |

Assays

Compounds of the examples and Table 1 provided herein were assayed to measure their capacity to inhibit Syk kinase.

Compounds of the examples and Table 1 provided herein were assessed for their ability to inhibit Syk kinase by utilizing Caliper Life Sciences' proprietary LabChip™ technology. The off-chip incubation mobility-shift kinase assay uses a microfluidic chip to measure the conversion of a fluorescent peptide substrate to a phosphorylated product. The reaction mixture, from a microtiter plate well, is introduced through a capillary sipper onto the chip, where the nonphosphorylated substrate and phosphorylated product are separated by electrophoresis and detected via laser induced fluorescence. The signature of the fluorescence signal over time reveals the extent of the reaction. The phosphorylated product migrates through the chip faster than the non-phosphorylated substrate, and signals from the two forms of the peptide appear as distinct peaks. Caliper's data analysis software (HTSWA) determines peak heights, from which the ratio of product to the peak sum P/(P+S) and percent (%) conversion is calculated. This value is used to compare compound wells to control wells present on the plate, and thereby determine the % inhibition values for the compound. The formula used to calculate % inhibition is as follows, where $C_{100\%}$ is the average % conversion of the 100% activity wells and $C_{0\%}$ is the average % conversion of the 0% activity wells: $(1-(\%\ \text{conversionofsample}-C_{0\%})/(C_{100\%}-C_{0\%}))*100$.

Compounds (10 mM stocks in 100% DMSO) are diluted to a final concentration of 5 μM for single point inhibition experiments, and a series dilution of 10, 3, 1, 0.3, 0.1, 0.03, 0.01, 0.003, 0.001, 0.0003, 0.0001, and 0.00003 μM were made for $IC_{50}$ determination. Generally, 12 μL of enzyme buffer containing purified kinase (various amount; various suppliers), 100 mM HEPES, pH 7.5, 1 mM DTT (Calbiochem, 2333153), 10 mM $MgCl_2$ (Sigma, M-1028) or 10 mM $MnCl_2$ (Sigma, M-1787) (assay specific), and 0.002% Brij-35 (Sigma, B4184) are added to each well. Compound and enzyme are allowed to pre-incubate for 15 minutes. 12 μL of peptide/ATP buffer containing 100 mM HEPES, pH 7.5, 1.5 μM fluorescein-labeled peptide (specific to kinase of interest), ATP (at $K_M$ apparent, Sigma, A9187), and 0.002% Brij-35 is then added to each well to initiate the reaction. The final concentration of DMSO in the well is 4%. Generally, reactions are incubated for 1 to 1.5 hours at room temperature to obtain adequate conversion of peptide to phosphorylated product in the linear range of the reaction. Reactions are terminated with the addition of 45 μL of Stop Buffer (containing 20 mM EDTA). Plates are then read on the LabChip 3000 using a 12-sipper LabChip. % conversion values and % inhibition values are obtained as provided and $IC_{50}$ curves of compounds are generated using GraphPad Prism Version 4 or 5.01, or XLfit Version 4.3.2. When using GraphPad Prism, a nonlinear curve fit using the sigmoidal dose response—variable slope fit was used to graph $IC_{50}$ curves and determine $IC_{50}$ values and hillslopes. When using XLfit, Fit Model 205 (4-Parameter Logistic Model) is used to generate and fit the $IC_{50}$ curve.

In certain embodiments, compounds of Formula (I) given in the examples and in Table 1, in free form or in pharmaceutically acceptable salt form, exhibit valuable pharmacological properties, for example, as indicated by the in vitro tests provided in this application. In general, compounds provided herein have $IC_{50}$ values for Syk kinase inhibition from 1 nM to 10 μM. In other embodiments, compounds of Formula (I) provided herein have $IC_{50}$ values for Syk kinase inhibition from 1 nM to 5 μM. In other embodiments, compounds of Formula (I) provided herein have $IC_{50}$ values for Syk kinase inhibition from 1 nM to 1 μM. In other embodiments, compounds of Formula (I) provided herein have $IC_{50}$ values for Syk kinase inhibition from 1 nM to 800 nM. In other embodiments, compounds of Formula (I) provided herein have $IC_{50}$ values for Syk kinase inhibition from 1 nM to 600 nM. In other embodiments, compounds of Formula (I) provided herein have $IC_{50}$ values for Syk kinase inhibition from 1 nM to 500 nM. In other embodiments, compounds of Formula (I) provided herein have $IC_{50}$ values for Syk kinase inhibition from 1 nM to 400 nM. In certain embodiments, compounds of Formula (I) provided herein have $IC_{50}$ values for Syk kinase inhibition from 1 nM to 200 μM. In certain embodiments, compounds of Formula (I) exhibit a percentage inhibition of greater than 50%, or in other embodiments compounds of Formula (I) exhibit a percentage inhibition greater than about 70%, against Syk kinase.

In addition certain compounds of the examples and Table 1 provided herein were assayed to measure their capacity to inhibit ZAP70, KDR, FMS, FLT3, c-Kit, RET, TrkA, TrkB, TrkC, IGR-1R, Alk and c-FMS kinases.

Compounds of the examples and Table 1 provided herein were assessed for their ability to inhibit ZAP70, KDR, FMS, FLT3, c-Kit, RET, TrkA, TrkB, TrkC, IGR-1R, Alk and c-FMS kinases by utilizing Caliper Life Sciences' proprietary LabChip™ technology. The off-chip incubation mobility-shift kinase assay uses a microfluidic chip to measure the conversion of a fluorescent peptide substrate to a phosphorylated product. The reaction mixture, from a microtiter plate well, is introduced through a capillary sipper onto the chip, where the nonphosphorylated substrate and phosphorylated product are separated by electrophoresis and detected via laser induced fluorescence. The signature of the fluorescence signal over time reveals the extent of the reaction. The phosphorylated product migrates through the chip faster than the non-phosphorylated substrate, and signals from the two forms of the peptide appear as distinct peaks. Caliper's data analysis software (HTSWA) determines peak heights, from which the ratio of product to the peak sum P/(P+S) and percent (%) conversion is calculated. This value is used to compare compound wells to control wells present on the plate, and thereby determine the % inhibition values for the compound. The formula used to calculate % inhibition is as follows, where $C_{100\%}$ is the average % conversion of the 100% activity wells and $C_{0\%}$ is the average % conversion of the 0% activity wells: $(1-(\%\ \text{conversionofsample}-C_{0\%})/(C_{100\%}-C_{0\%}))*100$.

Compounds (10 mM stocks in 100% DMSO) are diluted to a final concentration of 5 μM for single point inhibition experiments, and a series dilution of 10, 3, 1, 0.3, 0.1, 0.03, 0.01, 0.003, 0.001, 0.0003, 0.0001, 0.00003 μM were made for $IC_{50}$ determination. Generally, 12 μL of enzyme buffer containing purified kinase (various amount; various suppliers), 100 mM HEPES, pH 7.5, 1 mM DTT (Calbiochem, 2333153), 10 mM $MgCl_2$ (Sigma, M-1028) or 10 mM $MnCl_2$ (Sigma, M-1787) (assay specific), and 0.002% Brij-35 (Sigma, B4184) are added to each well. Compound and enzyme are allowed to pre-incubate for 15 minutes. 12 μL of peptide/ATP buffer containing 100 mM HEPES, pH 7.5, 1.5 μM fluorescein-labeled peptide (specific to kinase of interest), ATP (at $K_M$ apparent, Sigma, A9187), and 0.002% Brij-35 is then added to each well to initiate the reaction. The final concentration of DMSO in the well is 4%. Generally, reactions are incubated for 1 to 1.5 hours at room temperature to obtain adequate conversion of peptide to phosphorylated product in the linear range of the reaction. Reactions are terminated with the addition of 45 μL of Stop Buffer (containing 20 mM EDTA). Plates are then read on the LabChip 3000 using a 12-sipper LabChip. % conversion values and % inhibition values are obtained as provided and $IC_{50}$ curves of compounds are generated using GraphPad Prism Version 4 or 5.01, or XLfit Version 4.3.2. When using GraphPad Prism, a nonlinear curve fit using the sigmoidal dose response—variable slope fit was used to graph $IC_{50}$ curves and determine $IC_{50}$ values and hillslopes. When using XLfit, Fit Model 205 (4-Parameter Logistic Model) is used to generate and fit the $IC_{50}$ curve.

Ceratin Assay Results

By way of example only, the $IC_{50}$ for Syk inhibition by certain other compounds of Formula (I) are also listed in Table 1.

It is understood that the examples and embodiments provided herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula (I), pharmaceutically acceptable salt, or pharmaceutically acceptable solvate thereof:

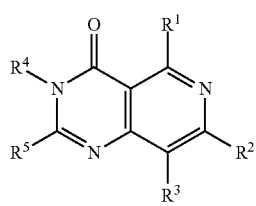

Formula (I)

wherein:

$R^1$ is —$NR^6R^7$, —$O(CR^9R^9)_nR^{11}$, —$O(CR^9R^9)_mR^{14}$, $R^{15}$, phenyl, a 5 or 6 membered heteroaryl containing 1 to 3 heteroatoms independently selected from N, O and S, or a 4-6 membered heterocycloalkyl containing 1 to 2 heteroatoms independently selected from N, O and S, or $R^1$ is selected from phenyl and a 5 or 6 membered heteroaryl containing 1 to 3 heteroatoms independently selected from N, O and S, each of which is substituted with 1 to 3 substituents independently selected from hydroxyl, hydroxyl-$C_1$-$C_6$alkyl and $R^{10}$;

or $R^1$ is a 4-6 membered heterocycloalkyl containing 1 to 2 heteroatoms independently selected from N, O and S, substituted with 1 to 3 substituents independently selected from halogen, hydroxyl, hydroxyl-$C_1$-$C_6$alkyl, —$(CR^9R^9)_nOR^9$, =N—OH, =N—$OR^9$, —$(CR^9R^9)_mSR^9$, —$(CR^9R^9)_mOS(O)_2N(R^9)_2$, —$(CR^9R^9)_nS(O)_2N(R^9)_2$, —$(CR^9R^9)_mN3$, —$(CR^9R^9)_nNR^9R^9$, —$(CR^9R^9)_nC(O)NR^9R^9$ and —$(CR^9R^9)_nC(O)OR^9$;

$R^2$ is selected from —$NR^9(CR^9R^9)_nR^{10}$, $R^{15}$, phenyl and a 5, 6 or 9 membered heteroaryl containing 1 to 3 heteroatoms independently selected from N, O and S;

or $R^2$ is selected from phenyl and a 5, 6, or 9 membered heteroaryl containing 1 to 3 heteroatoms independently selected from N, O and S, each of which is substituted with 1 to 3 substituents independently selected from halogen, $R^{10}$, $R^{15}$, hydroxyl-$C_1$-$C_6$alkyl —CN, —$OR^9$, —$C(O)OR^9$, —$N(R^9)_2$, —$NR^9(CR^9R^9)_nR^{10}$, —$NR^9(CR^9R^9)_mR^{14}$, —$N(R^9)C(O)R^9$, —$(CR^9R^9)_nR^{10}$, —$(CR^9R^9)_mC(O)R^{10}$, —$O(CR^9R^9)_nR^{10}$, —$C(O)(CR^9R^9)_mR^{14}$, —$(CR^9R^9)_nR^{14}$, $C(R^9R^{36}R^{36})$, —$C(R^9R^9R^{14})$, —$O(CR^9R^9)_mR^{14}$, —$NR^9S(O)_2R^9$, —$S(O)_2R^9$, —$S(O)_2R^{10}$, —$S(O)_2N(R^9R^{10})$, —$S(O)_2N(R^9)_2$, —$S(O)_2(CR^9R^9)_mR^1$, —$S(O)_2NR^9(CR^9R^9)_mR^{14}$, —$S(O)_2(CR^9R^9)_mR^{14}$, —$(CR^9R^9)_nR^{15}$, $C_1$-$C_6$alkyl and

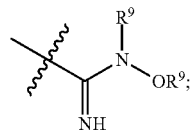

$R^4$ is H, $C_1$-$C_6$alkyl, hydroxyl-$C_1$-$C_6$alkyl, deuterated $C_1$-$C_6$alkyl or $C_1$-$C_6$haloalkyl;

$R^3$ and $R^5$ are independently selected from H or $C_1$-$C_6$alkyl;

$R^6$ is H, —$(CR^9R^9)_mR^{14}$, —$(CR^9R^9)_nR^{10}$, —$(CR^9R^9)_nR^{15}$, —$O(CR^9R^9)_nR^{10}$, —$(CR^9R^9)_n(CR^9R^{14})_nR^{10}$, $R^{15}$, $C_1$-$C_6$ alkyl, $C_1$-$C_6$alkyl substituted with 1-4 hydroxyl groups, $C_3$-$C_8$cycloalkyl, phenyl, a 5, 6 or 9 membered heteroaryl containing 1 to 3 heteroatoms independently selected from N, O and S, or a 4-6 membered heterocycloalkyl containing 1 to 2 heteroatoms independently selected from N, O and S;

or $R^6$ is selected from phenyl, a 5, 6, or 9 membered heteroaryl containing 1 to 3 heteroatoms independently selected from N, O and S, a 4-6 membered heterocycloalkyl containing 1 to 2 heteroatoms independently selected from N, O and S, and a $C_3$-$C_8$cycloalkyl, each of which is substituted with 1 to 3 substituents independently selected from $C_1$-$C_6$alkyl, hydroxyl, hydroxyl-$C_1$-$C_6$alkyl, —CN, —$OR^9$, —$C(O)OR^9$, tetrazole, —$C(O)N(R^9)_2$, —$S(O)_2R^9$, —$NR^9S(O)_2R^9$, —$N(R^9)_2$ and —$C(O)(CR^9R^9)_mR^{14}$;

$R^7$ is H or $C_1$-$C_6$ alkyl;

$R^8$ is H or $C_1$-$C_6$ alkyl;

each $R^9$ is independently selected from H and $C_1$-$C_6$alkyl;

$R^{10}$ is phenyl, a $C_3$-$C_8$cycloalkyl, a 5, 6 or 9 membered heteroaryl containing 1 to 3 heteroatoms independently selected from N, O and S, or a 4-6 membered heterocycloalkyl containing 1 to 2 heteroatoms independently selected from N, O and S;

or $R^{10}$ is selected from phenyl, a $C_3$-$C_8$cycloalkyl, 5, 6 or 9 membered heteroaryl containing 1 to 3 heteroatoms independently selected from N, O and S, and a 4-8 membered heterocycloalkyl containing 1 to 2 heteroatoms independently selected from N, O and S, each of which is substituted with 1 to 3 substituents independently selected from halogen, —$C_1$-$C_6$alkyl, hydroxyl, benzyl, hydroxyl-$C_1$-$C_6$alkyl, $C_3$-$C_8$cycloalkyl, —$OR^9$, —$C(O)OR^9$, —$N(R^9)_2$, —$C(O)(CR^9R^9)_nN(R^9)_2$, —$C(O)(CR^9R^9)_nOR^9$, —$(CR^9R^9)_nR^{14}$, —$S(O)_2R^9$, —$(CR^9R^9)_nS(O)_2R^9$ and $R^{13}$;

$R^{11}$ is $C_1$-$C_6$alkyl, $C_3$-$C_8$cycloalkyl, phenyl, a 5 or 6 membered heteroaryl containing 1 to 3 heteroatoms independently selected from N, O and S, or a 4-6 membered heterocycloalkyl containing 1 to 2 heteroatoms independently selected from N, O and S;

or $R^{11}$ is selected from $C_3$-$C_8$cycloalkyl, phenyl, a 5 or 6 membered heteroaryl containing 1 to 3 heteroatoms independently selected from N, O and S, and a 4-6 membered heterocycloalkyl containing 1 to 2 heteroatoms independently selected from N, O and S, each of which is substituted with 1 to 3 substituents independently selected from hydroxyl, —$C_1$-$C_6$alkyl, hydroxyl-$C_1$-$C_6$alkyl and —$(CR^9R^9)_nR^{14}$;

$R^{13}$ is halo-substituted $C_1$-$C_6$alkyl, $C_3$-$C_8$cycloalkyl, or a 4-6 membered heterocycloalkyl containing 1 to 2 heteroatoms independently selected from N, O and S;

$R^{14}$ is H, $C_1$-$C_6$alkyl, $C_1$-$C_6$haloalkyl, —$OR^9$, —$N(R^9)_2$, —$C(O)N(R^9)_2$, —$C(O)R^9$, —$C(O)OR^9$—$OC(O)R^{13}$, —CN, —$S(O)_2R^9$, —$N(R^9)S(O)_2R^9$, —$NR^9C(O)(R^9)$, —$N(R^9)C(O)(CR^9R^9)_nOR^9$, —$N(R^9)(CR^9R^9)_mOR^9$, and —$N(R^9)(CR^9R^9)_nR^{10}$;

$R^{15}$ is

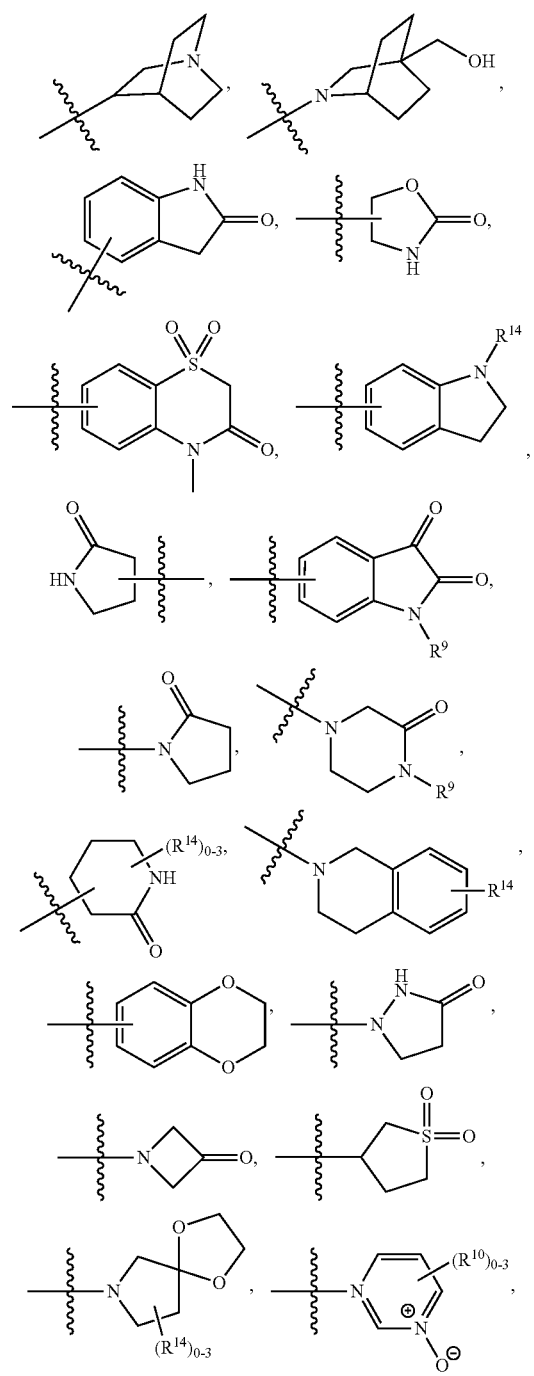

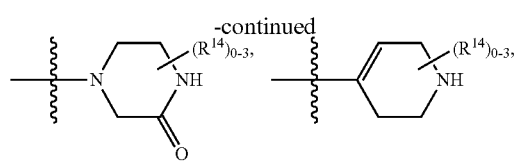

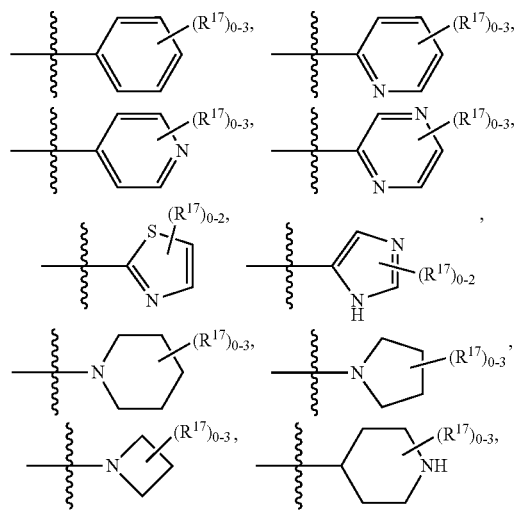

each $R^{36}$ is independently hydroxyl or $C_1$-$C_6$haloalkyl, each m is independently 1, 2, 3, 4, 5 or 6, and each n is independently 0, 1, 2, 3, 4, 5 or 6.

2. The compound of claim 1, wherein $R^1$ is —$NR^6R^7$.

3. The compound of claim 2, wherein:

$R^6$ is phenyl, a 5, 6 or 9 membered heteroaryl containing 1 to 3 heteroatoms independently selected from N, O and S, a 4-6 membered heterocycloalkyl containing 1 to 2 heteroatoms independently selected from N, O and S, $C_3$-$C_8$cycloalkyl or $R^{15}$;

or $R^6$ is selected from phenyl, a 5, 6, or 9 membered heteroaryl containing 1 to 3 heteroatoms independently selected from N, O and S, a 4-6 membered heterocycloalkyl containing 1 to 2 heteroatoms independently selected from N, O and S, and a $C_3$-$C_8$cycloalkyl, each of which is substituted with 1 to 3 substituents independently selected from $C_1$-$C_6$alkyl, hydroxyl, hydroxyl-$C_1$-$C_6$alkyl, —CN, —$OR^9$, —$C(O)OR^9$, tetrazole, —$C(O)N(R^9)_2$, —$S(O)_2R^9$, —$NR^9S(O)_2R^9$, —$N(R^9)_2$ and —$C(O)(CR^9R^9)_mR^{14}$;

each m is independently 0, 1, 2, 3 or 4, and each n is independently 0, 1, 2, 3 or 4.

4. The compound of claim 3, wherein $R^6$ is

-continued

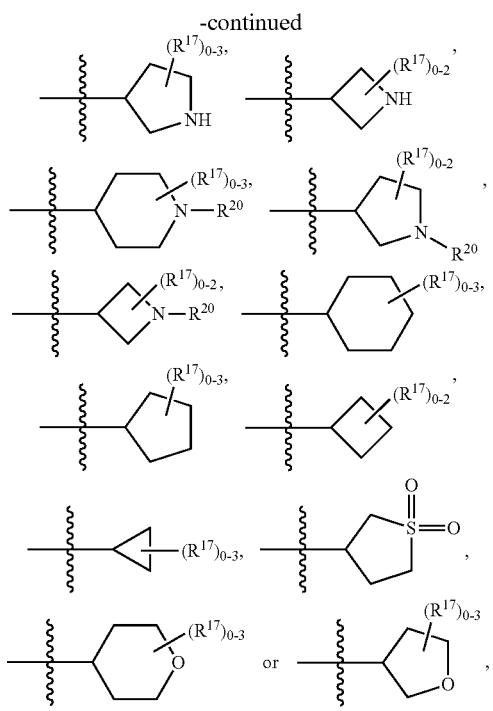

and
each $R^{17}$ is independently selected from $C_1$-$C_6$alkyl, hydroxyl, hydroxyl-$C_1$-$C_6$alkyl, —CN, —$OR^9$, —C(O)$OR^9$, tetrazole, —C(O)N($R^9$)$_2$, —S(O)$_2R^9$, —$NR^9$S(O)$_2$ $R^9$, —N($R^9$)$_2$ and —C(O)(C$R^9R^9$)$_m$$R^{14}$
$R^{20}$ is H, $C_1$-$C_6$alkyl, or hydroxyl-$C_1$-$C_6$alkyl;
each m is independently 0, 1, 2, 3 or 4, and
each n is independently 0, 1, 2, 3 or 4.

5. The compound of claim 2, wherein $R^6$ is $C_1$-$C_6$ alkyl, $C_1$-$C_6$alkyl substituted with 1-4 hydroxyl groups, —(C$R^9R^9$)$_n$ $R^{10}$, or —(C$R^9R^9$)$_m$$R^{14}$.

6. The compound of claim 5, wherein $R^6$ is —(C$R^{12}R^{12}$)$_m$$R^{14}$.

7. The compound of claim 1, wherein:
$R^1$ is a 4-6 membered heterocycloalkyl containing 1 to 2 heteroatoms independently selected from N, O and S,
or $R^1$ is a 4-6 membered heterocycloalkyl containing 1 to 2 heteroatoms independently selected from N, O and S, substituted with 1 to 3 substituents independently selected from halogen, hydroxyl, hydroxyl-$C_1$-$C_6$alkyl, —(C$R^9R^9$)$_n$$OR^9$, =N—OH, =N—$OR^9$, —(C$R^9R^9$)$_m$$SR^9$, —(C$R^9R^9$)$_m$$OS(O)_2N(R^9)_2$, —(C$R^9R^9$)$_n$S(O)$_2$N($R^9$)$_2$, —(C$R^9R^9$)$_m$$N_3$,—(C$R^9R^9$)$_n$$NR^9R^9$, —(C$R^9R^9$)$_n$C(O)N$R^9R^9$ and —(C$R^9R^9$)$_n$C(O)$OR^9$.

8. The compound of claim 1, wherein $R^1$ is selected from

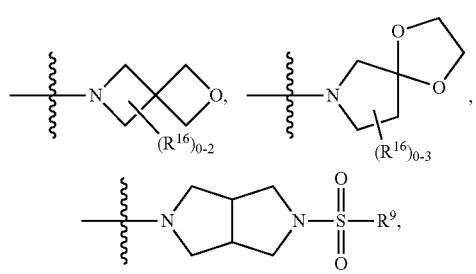

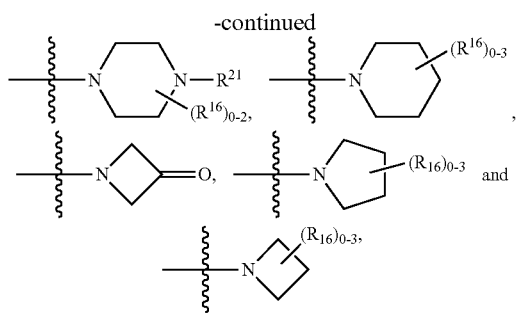

wherein
each $R^{16}$ is independently selected from halogen, hydroxyl, hydroxyl-$C_1$-$C_6$alkyl, —(C$R^9R^9$)$_n$$OR^9$, =N—OH, =N—$OR^9$, —(C$R^9R^9$)$_m$$SR^9$, —(C$R^9R^9$)$_m$$OS(O)_2N(R^9)_2$, —(C$R^9R^9$)$_n$S(O)$_2$N($R^9$)$_2$, —(C$R^9R^9$)$_m$$N_3$, —(C$R^9R^9$)$_n$$NR^9R^9$, —(C$R^9R^9$)$_n$C(O)N$R^9R^9$ and —(C$R^9R^9$)$_n$C(O)$OR^9$, and
$R^{21}$ is H, hydroxyl-$C_1$-$C_6$alkyl, —(C$R^9R^9$)$_m$$OR^9$, —(C$R^9R^9$)$_m$$SR^9$, —(C$R^9R^9$)$_m$$OS(O)_2N(R^9)_2$, —(C$R^9R^9$)$_m$$S(O)_2N(R^9)_2$, —(C$R^9R^9$)$_m$$N_3$, —(C$R^9R^9$)$_m$ $NR^9R^9$, —(C$R^9R^9$)$_n$C(O)N$R^9R^9$ and —(C$R^9R^9$)$_n$C(O)$OR^9$.

9. The compound of claim 8, wherein $R^1$ is selected from

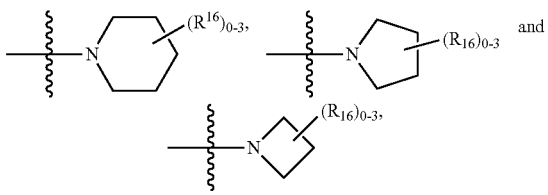

wherein each $R^{16}$ is independently selected from halogen, hydroxyl, hydroxyl-$C_1$-$C_6$alkyl, —(C$R^9R^9$)$_n$$OR^9$, =N—OH, =N—$OR^9$, —(C$R^9R^9$)$_m$$SR^9$, —(C$R^9R^9$)$_m$OS(O)$_2$N($R^9$)$_2$, —(C$R^9R^9$)$_n$S(O)$_2$N($R^9$)$_2$, —(C$R^9R^9$)$_m$$N_3$, —(C$R^9R^9$)$_n$$NR^9R^9$, —(C$R^9R^9$)$_n$C(O)N$R^9R^9$ and —(C$R^9R^9$)$_n$ C(O)$OR^9$.

10. The compound of claim 1, wherein:
$R^1$ is a phenyl or a 5 or 6 membered heteroaryl containing 1 to 3 heteroatoms independently selected from N, O and S,
or $R^1$ is a phenyl or a 5 or 6 membered heteroaryl containing 1 to 3 heteroatoms independently selected from N, O and S, each of which is substituted with 1 to 3 substituents independently selected from hydroxyl, hydroxyl-$C_1$-$C_6$alkyl and $R^{10}$.

11. The compound of claim 1, wherein $R^1$ is

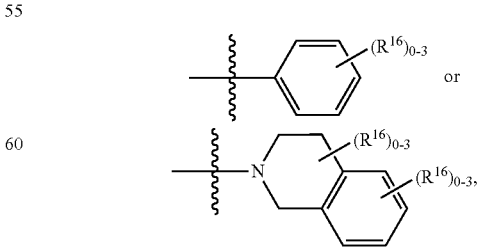

wherein each $R^{16}$ is independently selected from hydroxyl, hydroxyl-$C_1$-$C_6$alkyl and $R^{10}$.

12. The compound of claim 1, wherein:

$R^2$ is a phenyl or a 5, 6, or 9 membered heteroaryl containing 1 to 3 heteroatoms independently selected from N, O and S, or $R^2$ is selected from a phenyl and a 5, 6, or 9 membered heteroaryl containing 1 to 3 heteroatoms independently selected from N, O and S, each of which is substituted with 1 to 3 substituents independently selected from halogen, $R^{10}$, $R^5$, hydroxyl-$C_1$-$C_6$alkyl —CN, —$OR^9$, —C(O)$OR^9$, —N($R^9$)$_2$, —$NR^9$(C$R^9R^9$)$_n R^{10}$, —$NR^9$(C$R^9R^9$)$_m R^{14}$, —N($R^9$)C(O)$R^9$, —(C$R^9R^9$)$_m R^{10}$, —(C$R^9R^9$)$_m$C(O)$R^{10}$, —O(C$R^9R^9$)$_n R^{10}$, —C(O)(C$R^9R^9$)$_m R^{14}$, —(C$R^9R^9$)$_n R^{14}$, (C$R^9R^9$)$_m R^{14}$, —C($R^{9}R^{36}R^{36}$), —C($R^9R^9R^{14}$), —O(C$R^9R^9$)$_m R^{14}$, —$NR^9$S(O)$_2R^9$, —S(O)$_2R^9$, —S(O)$_2R^{10}$, —S(O)$_2$N($R^9R^{10}$), —S(O)$_2$N($R^9$)$_2$, —S(O)$_2$(C$R^9R^9$)$_m R^{10}$, —S(O)$_2NR^9$(C$R^9R^9$)$_m R^{14}$, S(O)$_2$(C$R^9R^9$)$_m R^{14}$, —(C$R^9R^9$)$_n R^{15}$, $C_1$-$C_6$alkyl and

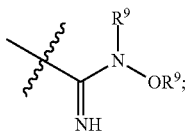

each m is independently 0, 1, 2, 3 or 4, and
each n is independently 0, 1, 2, 3 or 4.

13. The compound of claim 12, wherein $R^2$ is selected from

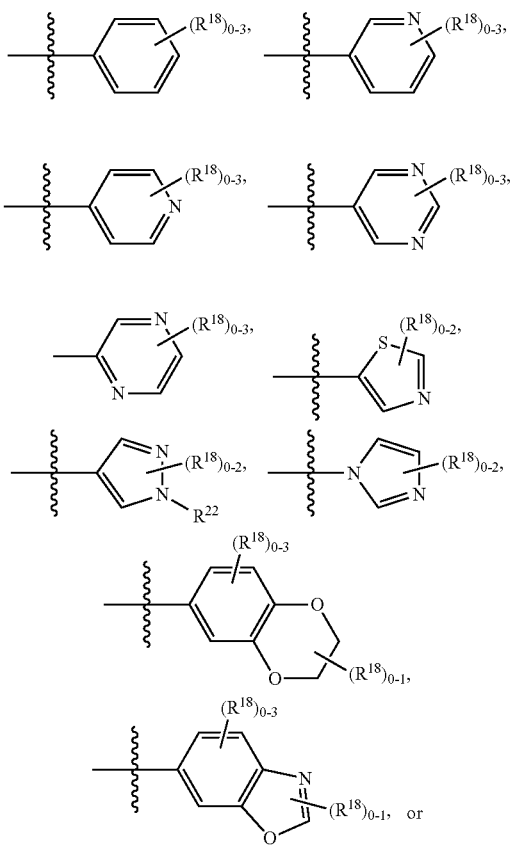

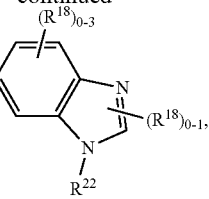

wherein each $R^{18}$ is independently selected from halogen, $R^{10}$, $R^{15}$, hydroxyl-$C_1$-$C_6$alkyl —CN, —$OR^9$, —C(O)$OR^9$, —N($R^9$)$_2$, —$NR^9$(C$R^9R^9$)$_n R^{10}$, —$NR^9$(C$R^9R^9$)$_m R^{14}$, —N($R^9$)C(O)$R^9$, —(C$R^9R^9$)$_m R^{10}$, (C$R^9R^9$)$_m$C(O)$R^{10}$, —O(C$R^9R^9$)$_n R^{10}$, —C(O)(C$R^9R^9$)$_m R^{14}$, —(C$R^9R^9$)$_n R^{14}$, —C($R^{9}R^{36}R^{36}$), —C($R^9R^9R^{14}$), —O(C$R^9R^9$)$_m R^{14}$, —$NR^9$S(O)$_2R^9$, —S(O)$_2R^9$, —S(O)$_2R^{10}$, —S(O)$_2$N($R^9R^{10}$), —S(O)$_2$N($R^9$)$_2$, —S(O)$_2$(C$R^9R^9$)$_m R^{10}$, —S(O)$_2NR^9$(C$R^9R^9$)$_m R^{14}$, —S(O)$_2$(C$R^9R^9$)$_m R^{14}$, —(C$R^9R^9$)$_n R^{15}$, $C_1$-$C_6$alkyl and

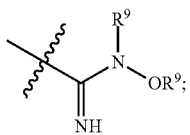

$R^{22}$ is H, $C_1$-$C_6$alkyl, —(C$R^9R^9$)$_m R^{14}$ or hydroxyl-$C_1$-$C_6$alkyl;

each m is independently 0, 1, 2, 3 or 4, and
each n is independently 0, 1, 2, 3 or 4.

14. The compound of claim 1, wherein $R^2$ is —$NR^8$(C$R^9R^9$)$_n R^{10}$ and n is 0, 1, 2, 3 or 4.

15. The compound of claim 1, wherein:

$R^{10}$ is phenyl, a $C_3$-$C_8$cycloalkyl, a 5, 6 or 9 membered heteroaryl containing 1 to 3 heteroatoms independently selected from N, O and S, or a 4-6 membered heterocycloalkyl containing 1 to 2 heteroatoms independently selected from N, O and S;

or $R^{10}$ is selected from phenyl, a $C_3$-$C_8$cycloalkyl, 5, 6 or 9 membered heteroaryl containing 1 to 3 heteroatoms independently selected from N, O and S, and a 4-8 membered heterocycloalkyl containing 1 to 2 heteroatoms independently selected from N, O and S, each of which is substituted with 1 to 3 substituents independently selected from halogen, —$C_1$-$C_6$alkyl, hydroxyl, benzyl, hydroxyl-$C_1$-$C_6$alkyl, $C_3$-$C_8$cycloalkyl, —$OR^9$, —C(O)$OR^9$, —N($R^9$)$_2$, —C(O)(C$R^9R^9$)$_n$N($R^9$)$_2$, —C(O)(C$R^9R^9$)$_n OR^9$, —(C$R^9R^9$)$_n R^{14}$, —S(O)$_2R^9$, —(C$R^9R^9$)$_n$S(O)$_2R^9$ and $R^{13}$.

16. The compound of claim 15, wherein $R^{10}$ is selected from

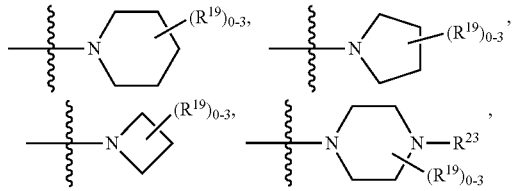

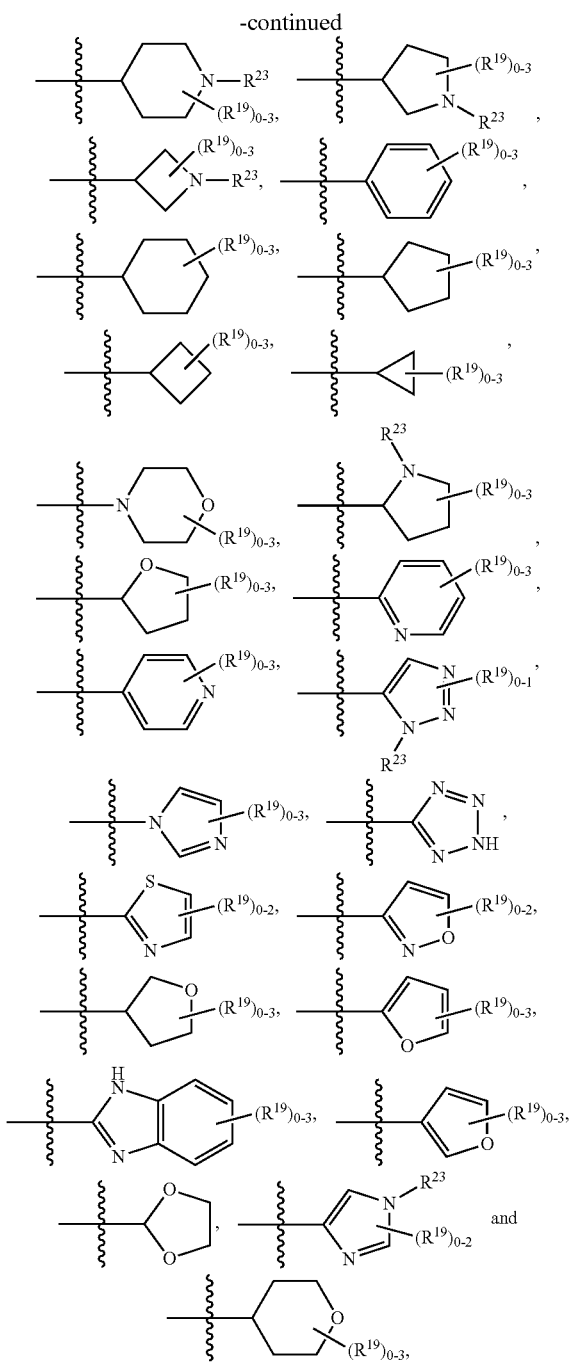

wherein;
each $R^{19}$ is independently selected from halogen, —$C_1$-$C_6$alkyl, hydroxyl, benzyl, hydroxyl-$C_1$-$C_6$alkyl, $C_3$-$C_8$cycloalkyl, —$OR^9$, —$C(O)OR^9$, —$N(R^9)_2$, —$C(O)(CR^9R^9)_nN(R^9)_2$, —$C(O)(CR^9R^9)_nOR^9$, —$(CR^9R^9)_nOR^{14}$, —$S(O)_2R^9$, —$(CR^9R^9)_n$—$S(O)_2R^9$ and $R^{13}$;

$R^{23}$ is H, $C_1$-$C_6$alkyl, —$(CR^9R^9)_mR^{14}$ or hydroxyl-$C_1$-$C_6$alkyl;

each m is independently 0, 1, 2, 3 or 4, and
each n is independently 0, 1, 2, 3 or 4.

17. The compound of claim 1, wherein:
$R^{11}$ is $C_1$-$C_6$alkyl, phenyl, a 5 or 6 membered heteroaryl containing 1 to 3 heteroatoms independently selected from N, O and S, or a 4-8 membered heterocycloalkyl containing 1 to 2 heteroatoms independently selected from N, O and S;
or $R^{11}$ is selected from $C_3$-$C_8$cycloalkyl, and a 4-8 membered heterocycloalkyl containing 1 to 2 heteroatoms independently selected from N, O and S, each of which is substituted with 1 to 3 substituents independently selected from hydroxyl, —$C_1$-$C_6$alkyl, hydroxyl-$C_1$-$C_6$alkyl and —$(CR^9R^9)_nR^{14}$.

18. The compound of claim 1, wherein $R^3$ and $R^5$ are H.
19. The compound of claim 1, wherein $R^4$ is $C_1$-$C_6$alkyl, —$CD_3$, deuterated $C_1$-$C_6$alkyl or $C_1$-$C_6$haloalkyl.
20. The compound of claim 1, wherein $R^4$ is hydroxyl-$C_1$-$C_6$alkyl.
21. The compound of claim 1, wherein $R^7$ is $C_1$-$C_6$alkyl.
22. The compound of claim 1 selected from:
5-[(3S)-3-(hydroxymethyl)pyrrolidin-1-yl]-3-methyl-7-[4-(methylamino)phenyl]-3H,4H-pyrido[4,3-d]pyrimidin-4-one;
5-(cyclopropylamino)-7-(3-methanesulfonyl-4-{[2-(pyrrolidin-1-yl)ethyl]amino}phenyl)-3-methyl-3H,4H-pyrido[4,3-d]pyrimidin-4-one;
7-(3-methanesulfonyl-4-{[2-(pyrrolidin-1-yl)ethyl]amino}phenyl)-3-methyl-5-(propan-2-ylamino)-3H,4H-pyrido[4,3-d]pyrimidin-4-one;
5-(cyclopropylamino)-7-[3-methanesulfonyl-4-(methylamino)phenyl]-3-methyl-3H,4H-pyrido[4,3-d]pyrimidin-4-one;
5-(cyclopropylamino)-7-{3-methanesulfonyl-4-[(2-methoxyethyl)amino]phenyl}-3-methyl-3H,4H-pyrido[4,3-d]pyrimidin-4-one;
7-{3-methanesulfonyl-4-[(2-methoxyethyl)amino]phenyl}-3-methyl-5-(propan-2-ylamino)-3H,4H-pyrido[4,3-d]pyrimidin-4-one;
5-(cyclopropylamino)-7-{4-[(2-hydroxyethyl)amino]-3-methanesulfonylphenyl}-3-methyl-3H,4H-pyrido[4,3-d]pyrimidin-4-one;
7-{4-[(2-hydroxyethyl)amino]-3-methanesulfonylphenyl}-3-methyl-5-(propan-2-ylamino)-3H,4H-pyrido[4,3-d]pyrimidin-4-one;
5-(cyclopropylamino)-7-[4-(dimethylamino)-3-methanesulfonylphenyl]-3-methyl-3H,4H-pyrido[4,3-d]pyrimidin-4-one;
7-[4-(dimethylamino)-3-methanesulfonylphenyl]-3-methyl-5-(propan-2-ylamino)-3H,4H-pyrido[4,3-d]pyrimidin-4-one;
5-(cyclopropylamino)-7-{4-[4-(2-hydroxyethyl)piperazin-1-yl]-3-methanesulfonylphenyl}-3-methyl-3H,4H-pyrido[4,3-d]pyrimidin-4-one;
7-{4-[4-(2-hydroxyethyl)piperazin-1-yl]-3-methanesulfonylphenyl}-3-methyl-5-(propan-2-ylamino)-3H,4H-pyrido[4,3-d]pyrimidin-4-one;
5-[(2-methoxyethyl)amino]-3-methyl-7-{4-[(2R)-2-methylmorpholin-4-yl]phenyl}-3H,4H-pyrido[4,3-d]pyrimidin-4-one;
3-methyl-7-{4-[(2R)-2-methylmorpholin-4-yl]phenyl}-5-(propan-2-ylamino)-3H,4H-pyrido[4,3-d]pyrimidin-4-one;
7-(4-fluoro-3-methanesulfonylphenyl)-3-methyl-5-(propan-2-ylamino)-3H,4H-pyrido[4,3-d]pyrimidin-4-one;
5-(cyclopropylamino)-7-(4-fluoro-3-methanesulfonylphenyl)-3-methyl-3H,4H-pyrido[4,3-d]pyrimidin-4-one;
3-methyl-7-{[3-(4-methylpiperazin-1-yl)propyl]amino}-5-(propan-2-ylamino)-3H,4H-pyrido[4,3-d]pyrimidin-4-one;

3-methyl-7-[4-(morpholin-4-yl)phenyl]-5-{[(2S)-oxolan-2-ylmethyl]amino}-3H,4H-pyrido[4,3-d]pyrimidin-4-one;

5-(cyclopropylamino)-3-methyl-7-{4-[2-(morpholin-4-yl)ethoxy]phenyl}-3H,4H-pyrido[4,3-d]pyrimidin-4-one;

3-methyl-7-{4-[2-(morpholin-4-yl)ethoxy]phenyl}-5-(propan-2-ylamino)-3H,4H-pyrido[4,3-d]pyrimidin-4-one;

5-(cyclopropylamino)-3-methyl-7-{4-[2-(pyrrolidin-1-yl)ethoxy]phenyl}-3H,4H-pyrido[4,3-d]pyrimidin-4-one;

3-methyl-5-(propan-2-ylamino)-7-{4-[2-(pyrrolidin-1-yl)ethoxy]phenyl}-3H,4H-pyrido[4,3-d]pyrimidin-4-one;

5-(cyclopropylamino)-7-{3-methanesulfonyl-4-[(1-methylpiperidin-4-yl)amino]phenyl}-3-methyl-3H,4H-pyrido[4,3-d]pyrimidin-4-one;

7-{3-methanesulfonyl-4-[(1-methylpiperidin-4-yl)amino]phenyl}-3-methyl-5-(propan-2-ylamino)-3H,4H-pyrido[4,3-d]pyrimidin-4-one;

7-[3-methanesulfonyl-4-(methylamino)phenyl]-5-[(2-methoxyethyl)amino]-3-methyl-3H,4H-pyrido[4,3-d]pyrimidin-4-one;

7-{3-methanesulfonyl-4-[methyl(1-methylpiperidin-4-yl)amino]phenyl}-3-methyl-5-(propan-2-ylamino)-3H,4H-pyrido[4,3-d]pyrimidin-4-one;

5-(cyclopropylamino)-7-(3-methanesulfonyl-4-{[2-(4-methylpiperazin-1-yl)ethyl]amino}phenyl)-3-methyl-3H,4H-pyrido[4,3-d]pyrimidin-4-one;

7-(3-methanesulfonyl-4-{[2-(4-methylpiperazin-1-yl)ethyl]amino}phenyl)-3-methyl-5-(propan-2-ylamino)-3H,4H-pyrido[4,3-d]pyrimidin-4-one;

5-(cyclopropylamino)-7-(3-methanesulfonyl-4-{[3-(4-methylpiperazin-1-yl)propyl]amino}phenyl)-3-methyl-3H,4H-pyrido[4,3-d]pyrimidin-4-one;

7-(3-methanesulfonyl-4-{[3-(4-methylpiperazin-1-yl)propyl]amino}phenyl)-3-methyl-5-(propan-2-ylamino)-3H,4H-pyrido[4,3-d]pyrimidin-4-one;

3-methyl-7-[1-(2-methylpropyl)-1H-pyrazol-4-yl]-5-(propan-2-ylamino)-3H,4H-pyrido[4,3-d]pyrimidin-4-one;

3-methyl-7-[1-(3-methylbutyl)-1H-pyrazol-4-yl]-5-(propan-2-ylamino)-3H,4H-pyrido[4,3-d]pyrimidin-4-one;

3-methyl-5-(propan-2-ylamino)-7-(1-propyl-1H-pyrazol-4-yl)-3H,4H-pyrido[4,3-d]pyrimidin-4-one;

2-{4-[3-methyl-4-oxo-5-(propan-2-ylamino)-3H,4H-pyrido[4,3-d]pyrimidin-7-yl]-1H-pyrazol-1-yl}acetic acid;

7-[1-(2-methoxyethyl)-1H-pyrazol-4-yl]-3-methyl-5-(propan-2-ylamino)-3H,4H-pyrido[4,3-d]pyrimidin-4-one;

2-{4-[3-methyl-4-oxo-5-(propan-2-ylamino)-3H,4H-pyrido[4,3-d]pyrimidin-7-yl]-1H-pyrazol-1-yl}propanamide;

3-methyl-7-{1-[2-(morpholin-4-yl)ethyl]-1H-pyrazol-4-yl}-5-(propan-2-ylamino)-3H,4H-pyrido[4,3-d]pyrimidin-4-one;

3-methyl-7-{1-[2-(morpholin-4-yl)-2-oxoethyl]-1H-pyrazol-4-yl}-5-(propan-2-ylamino)-3H,4H-pyrido[4,3-d]pyrimidin-4-one;

7-{1-[2-(4-ethylpiperazin-1-yl)-2-oxoethyl]-1H-pyrazol-4-yl}-3-methyl-5-(propan-2-ylamino)-3H,4H-pyrido[4,3-d]pyrimidin-4-one;

methyl 2-{4-[3-methyl-4-oxo-5-(propan-2-ylamino)-3H,4H-pyrido[4,3-d]pyrimidin-7-yl]-1H-pyrazol-1-yl}acetate;

3-methyl-7-(2-methyl-1,3-thiazol-5-yl)-5-(propan-2-ylamino)-3H,4H-pyrido[4,3-d]pyrimidin-4-one;

3-methyl-7-(4-methyl-1H-imidazol-1-yl)-5-(propan-2-ylamino)-3H,4H-pyrido[4,3-d]pyrimidin-4-one;

5-(cyclopropylamino)-3-methyl-7-[2-(morpholin-4-yl)pyrimidin-5-yl]-3H,4H-pyrido[4,3-d]pyrimidin-4-one;

3-methyl-7-[2-(morpholin-4-yl)pyrimidin-5-yl]-5-(propan-2-ylamino)-3H,4H-pyrido[4,3-d]pyrimidin-4-one;

2-{4-[5-(cyclopropylamino)-3-methyl-4-oxo-3H,4H-pyrido[4,3-d]pyrimidin-7-yl]phenyl}-2-methylpropanenitrile;

2-methyl-2-{4-[3-methyl-4-oxo-5-(propan-2-ylamino)-3H,4H-pyrido[4,3-d]pyrimidin-7-yl]phenyl}propanenitrile;

7-[4-(4-hydroxypiperidin-4-yl)phenyl]-3-methyl-5-(propan-2-ylamino)-3H,4H-pyrido[4,3-d]pyrimidin-4-one;

5-(cyclopropylamino)-7-(3-methanesulfonyl-4-{[2-(morpholin-4-yl)ethyl]amino}phenyl)-3-methyl-3H,4H-pyrido[4,3-d]pyrimidin-4-one;

7-(3-methanesulfonyl-4-{[2-(morpholin-4-yl)ethyl]amino}phenyl)-3-methyl-5-(propan-2-ylamino)-3H,4H-pyrido[4,3-d]pyrimidin-4-one;

5-(cyclopropylamino)-7-[3-methanesulfonyl-4-(morpholin-4-yl)phenyl]-3-methyl-3H,4H-pyrido[4,3-d]pyrimidin-4-one;

7-[3-methanesulfonyl-4-(morpholin-4-yl)phenyl]-3-methyl-5-(propan-2-ylamino)-3H,4H-pyrido[4,3-d]pyrimidin-4-one;

5-(cyclopropylamino)-7-[4-(4-ethylpiperazin-1-yl)-3-methanesulfonylphenyl]-3-methyl-3H,4H-pyrido[4,3-d]pyrimidin-4-one;

7-[4-(4-ethylpiperazin-1-yl)-3-methanesulfonylphenyl]-3-methyl-5-(propan-2-ylamino)-3H,4H-pyrido[4,3-d]pyrimidin-4-one;

methyl 1-[3-methyl-4-oxo-5-(propan-2-ylamino)-3H,4H-pyrido[4,3-d]pyrimidin-7-yl]-1H-imidazole-4-carboxylate;

5-(cyclopropylamino)-7-{3-methanesulfonyl-4-[2-(pyrrolidin-1-yl)ethoxy]phenyl}-3-methyl-3H,4H-pyrido[4,3-d]pyrimidin-4-one;

7-{3-methanesulfonyl-4-[2-(pyrrolidin-1-yl)ethoxy]phenyl}-3-methyl-5-(propan-2-ylamino)-3H,4H-pyrido[4,3-d]pyrimidin-4-one;

5-(cyclopropylamino)-3-methyl-7-[4-(propane-2-sulfonyl)phenyl]-3H,4H-pyrido[4,3-d]pyrimidin-4-one;

3-methyl-5-(propan-2-ylamino)-7-[4-(propane-2-sulfonyl)phenyl]-3H,4H-pyrido[4,3-d]pyrimidin-4-one;

7-[3-methanesulfonyl-4-(morpholin-4-yl)phenyl]-3-methyl-5-{[(2S)-oxolan-2-ylmethyl]amino}-3H,4H-pyrido[4,3-d]pyrimidin-4-one;

7-[3-methanesulfonyl-4-(morpholin-4-yl)phenyl]-3-methyl-5-{[(5-methylfuran-2-yl)methyl]amino}-3H,4H-pyrido[4,3-d]pyrimidin-4-one;

5-(cyclopropylamino)-7-[3-methanesulfonyl-4-(pyrrolidin-1-yl)phenyl]-3-methyl-3H,4H-pyrido[4,3-d]pyrimidin-4-one;

7-[3-methanesulfonyl-4-(pyrrolidin-1-yl)phenyl]-3-methyl-5-(propan-2-ylamino)-3H,4H-pyrido[4,3-d]pyrimidin-4-one;

5-(cyclopropylamino)-7-[4-methanesulfonyl-3-(morpholin-4-yl)phenyl]-3-methyl-3H,4H-pyrido[4,3-d]pyrimidin-4-one;

7-[4-methanesulfonyl-3-(morpholin-4-yl)phenyl]-3-methyl-5-(propan-2-ylamino)-3H,4H-pyrido[4,3-d]pyrimidin-4-one;

5-(cyclopropylamino)-7-[3-(4-ethylpiperazin-1-yl)-4-methanesulfonylphenyl]-3-methyl-3H,4H-pyrido[4,3-d]pyrimidin-4-one;

7-[3-(4-ethylpiperazin-1-yl)-4-methanesulfonylphenyl]-3-methyl-5-(propan-2-ylamino)-3H,4H-pyrido[4,3-d]pyrimidin-4-one;

5-(cyclopropylamino)-7-(4-methanesulfonyl-3-{[2-(morpholin-4-yl)ethyl]amino}phenyl)-3-methyl-3H,4H-pyrido[4,3-d]pyrimidin-4-one;

7-(4-methanesulfonyl-3-{[2-(morpholin-4-yl)ethyl]amino}phenyl)-3-methyl-5-(propan-2-ylamino)-3H,4H-pyrido[4,3-d]pyrimidin-4-one;

7-[3-methanesulfonyl-4-(morpholin-4-yl)phenyl]-5-[(2-methoxyethyl)amino]-3-methyl-3H,4H-pyrido[4,3-d]pyrimidin-4-one;

7-[4-methanesulfonyl-3-(morpholin-4-yl)phenyl]-5-[(2-methoxyethyl)amino]-3-methyl-3H,4H-pyrido[4,3-d]pyrimidin-4-one;

7-(3-methanesulfonyl-4-{[2-(morpholin-4-yl)ethyl]amino}phenyl)-5-[(2-methoxyethyl)amino]-3-methyl-3H,4H-pyrido[4,3-d]pyrimidin-4-one;

7-[4-(4-ethylpiperazin-1-yl)-3-methanesulfonylphenyl]-5-[(2-methoxyethyl)amino]-3-methyl-3H,4H-pyrido[4,3-d]pyrimidin-4-one;

5-(cyclopropylamino)-3-methyl-7-{4-[2-(morpholin-4-yl)-2-oxoethyl]phenyl}-3H,4H-pyrido[4,3-d]pyrimidin-4-one;

3-methyl-7-{4-[2-(morpholin-4-yl)-2-oxoethyl]phenyl}-5-(propan-2-ylamino)-3H,4H-pyrido[4,3-d]pyrimidin-4-one;

5-(cyclopropylamino)-7-{4-[2-(4-ethylpiperazin-1-yl)-2-oxoethyl]phenyl}-3-methyl-3H,4H-pyrido[4,3-d]pyrimidin-4-one;

7-{4-[2-(4-ethylpiperazin-1-yl)-2-oxoethyl]phenyl}-3-methyl-5-(propan-2-ylamino)-3H,4H-pyrido[4,3-d]pyrimidin-4-one;

7-[3-methanesulfonyl-4-(methylamino)phenyl]-3-methyl-5-(propan-2-ylamino)-3H,4H-pyrido[4,3-d]pyrimidin-4-one;

3-methyl-7-[3-(4-methylpiperazin-1-yl)propoxy]-5-(propan-2-ylamino)-3H,4H-pyrido[4,3-d]pyrimidin-4-one;

5-[(2-hydroxyethyl)amino]-7-[3-methanesulfonyl-4-(methylamino)phenyl]-3-methyl-3H,4H-pyrido[4,3-d]pyrimidin-4-one;

5-[(3-hydroxypropyl)amino]-7-[3-methanesulfonyl-4-(methylamino)phenyl]-3-methyl-3H,4H-pyrido[4,3-d]pyrimidin-4-one;

7-[3-methanesulfonyl-4-(methylamino)phenyl]-3-methyl-5-[(3R)-oxolan-3-ylamino]-3H,4H-pyrido[4,3-d]pyrimidin-4-one;

5-[(3S)-3-(hydroxymethyl)pyrrolidin-1-yl]-7-[3-methanesulfonyl-4-(methylamino)phenyl]-3-methyl-3H,4H-pyrido[4,3-d]pyrimidin-4-one;

7-(3-methanesulfonyl-4-methoxyphenyl)-5-[(2-methoxyethyl)amino]-3-methyl-3H,4H-pyrido[4,3-d]pyrimidin-4-one;

5-(cyclopropylamino)-7-(3-methanesulfonyl-4-methoxyphenyl)-3-methyl-3H,4H-pyrido[4,3-d]pyrimidin-4-one;

7-(3-methanesulfonyl-4-methoxyphenyl)-3-methyl-5-(propan-2-ylamino)-3H,4H-pyrido[4,3-d]pyrimidin-4-one;

5-[(3-hydroxypropyl)amino]-7-{3-methanesulfonyl-4-[(1-methylpiperidin-4-yl)amino]phenyl}-3-methyl-3H,4H-pyrido[4,3-d]pyrimidin-4-one;

7-{3-methanesulfonyl-4-[(1-methylpiperidin-4-yl)amino]phenyl}-5-[(2-methoxyethyl)amino]-3-methyl-3H,4H-pyrido[4,3-d]pyrimidin-4-one;

7-{3-methanesulfonyl-4-[(1-methylpiperidin-4-yl)amino]phenyl}-3-methyl-5-[(3R)-oxolan-3-ylamino]-3H,4H-pyrido[4,3-d]pyrimidin-4-one;

5-(cyclopropylamino)-7-{4-[(3R)-3-hydroxypyrrolidin-1-yl]-3-methanesulfonylphenyl}-3-methyl-3H,4H-pyrido[4,3-d]pyrimidin-4-one;

7-{4-[(3R)-3-hydroxypyrrolidin-1-yl]-3-methanesulfonylphenyl}-3-methyl-5-(propan-2-ylamino)-3H,4H-pyrido[4,3-d]pyrimidin-4-one;

5-(cyclopropylamino)-7-{3-methanesulfonyl-4-[(3S)-pyrrolidin-3-ylamino]phenyl}-3-methyl-3H,4H-pyrido[4,3-d]pyrimidin-4-one;

7-{3-methanesulfonyl-4-[(3S)-pyrrolidin-3-ylamino]phenyl}-3-methyl-5-(propan-2-ylamino)-3H,4H-pyrido[4,3-d]pyrimidin-4-one;

5-(cyclopropylamino)-7-[3-methanesulfonyl-4-(pyrrolidin-3-ylamino)phenyl]-3-methyl-3H,4H-pyrido[4,3-d]pyrimidin-4-one;

7-[3-methanesulfonyl-4-(pyrrolidin-3-ylamino)phenyl]-3-methyl-5-(propan-2-ylamino)-3H,4H-pyrido[4,3-d]pyrimidin-4-one;

5-(cyclopropylamino)-7-{4-[(3S)-3-(hydroxymethyl)pyrrolidin-1-yl]-3-methanesulfonylphenyl}-3-methyl-3H,4H-pyrido[4,3-d]pyrimidin-4-one;

7-{4-[(3S)-3-(hydroxymethyl)pyrrolidin-1-yl]-3-methanesulfonylphenyl}-3-methyl-5-(propan-2-ylamino)-3H,4H-pyrido[4,3-d]pyrimidin-4-one;

5-(cyclopropylamino)-7-{4-[(3R)-3-(hydroxymethyl)pyrrolidin-1-yl]-3-methanesulfonylphenyl}-3-methyl-3H,4H-pyrido[4,3-d]pyrimidin-4-one;

7-{4-[(3R)-3-(hydroxymethyl)pyrrolidin-1-yl]-3-methanesulfonylphenyl}-3-methyl-5-(propan-2-ylamino)-3H,4H-pyrido[4,3-d]pyrimidin-4-one;

1-{4-[5-(cyclopropylamino)-3-methyl-4-oxo-3H,4H-pyrido[4,3-d]pyrimidin-7-yl]phenyl}pyrrolidin-2-one;

1-(4-{5-[(2-methoxyethyl)amino]-3-methyl-4-oxo-3H,4H-pyrido[4,3-d]pyrimidin-7-yl}phenyl)pyrrolidin-2-one;

1-{4-[3-methyl-4-oxo-5-(propan-2-ylamino)-3H,4H-pyrido[4,3-d]pyrimidin-7-yl]phenyl}pyrrolidin-2-one;

7-{4-[(3S)-3-(hydroxymethyl)pyrrolidin-1-yl]-3-methanesulfonylphenyl}-5-[(2-methoxyethyl)amino]-3-methyl-3H,4H-pyrido[4,3-d]pyrimidin-4-one;

7-{4-[(3R)-3-(hydroxymethyl)pyrrolidin-1-yl]-3-methanesulfonylphenyl}-5-[(2-methoxyethyl)amino]-3-methyl-3H,4H-pyrido[4,3-d]pyrimidin-4-one;

5-[(3S)-3-(hydroxymethyl)pyrrolidin-1-yl]-7-{3-methanesulfonyl-4-[(1-methylpiperidin-4-yl)amino]phenyl}-3-methyl-3H,4H-pyrido[4,3-d]pyrimidin-4-one;

1-(4-{5-[(2-hydroxyethyl)amino]-3-methyl-4-oxo-3H,4H-pyrido[4,3-d]pyrimidin-7-yl}phenyl)pyrrolidin-2-one;

1-(4-{5-[(3-hydroxypropyl)amino]-3-methyl-4-oxo-3H,4H-pyrido[4,3-d]pyrimidin-7-yl}phenyl)pyrrolidin-2-one;

1-(4-{5-[(3S)-3-(hydroxymethyl)pyrrolidin-1-yl]-3-methyl-4-oxo-3H,4H-pyrido[4,3-d]pyrimidin-7-yl}phenyl)pyrrolidin-2-one;

7-[4-(2-aminopropan-2-yl)phenyl]-3-methyl-5-(propan-2-ylamino)-3H,4H-pyrido[4,3-d]pyrimidin-4-one;

7-[4-(2-aminopropan-2-yl)phenyl]-5-(ethylamino)-3-methyl-3H,4H-pyrido[4,3-d]pyrimidin-4-one;

5-(ethylamino)-7-[4-methoxy-3-(morpholine-4-sulfonyl)phenyl]-3-methyl-3H,4H-pyrido[4,3-d]pyrimidin-4-one;

5-(cyclopropylamino)-7-[4-methoxy-3-(morpholine-4-sulfonyl)phenyl]-3-methyl-3H,4H-pyrido[4,3-d]pyrimidin-4-one;

7-[4-methoxy-3-(morpholine-4-sulfonyl)phenyl]-3-methyl-5-(propan-2-ylamino)-3H,4H-pyrido[4,3-d]pyrimidin-4-one;

5-(cyclopropylamino)-7-[3-fluoro-4-(piperidin-4-yl)phenyl]-3-methyl-3H,4H-pyrido[4,3-d]pyrimidin-4-one;

5-(cyclopropylamino)-7-[3-fluoro-4-(1-methylpiperidin-4-yl)phenyl]-3-methyl-3H,4H-pyrido[4,3-d]pyrimidin-4-one;

5-(cyclopropylamino)-7-[4-(1-ethylpiperidin-4-yl)-3-fluorophenyl]-3-methyl-3H,4H-pyrido[4,3-d]pyrimidin-4-one;

5-(ethylamino)-7-[4-(1-hydroxycyclobutyl)phenyl]-3-methyl-3H,4H-pyrido[4,3-d]pyrimidin-4-one;

5-(ethylamino)-3-methyl-7-(4-{[2-(morpholin-4-yl)ethane]sulfonyl}phenyl)-3H,4H-pyrido[4,3-d]pyrimidin-4-one;

5-(cyclopropylamino)-3-methyl-7-(4-{[2-(morpholin-4-yl)ethane]sulfonyl}phenyl)-3H,4H-pyrido[4,3-d]pyrimidin-4-one;

3-methyl-7-(4-{[2-(morpholin-4-yl)ethane]sulfonyl}phenyl)-5-(propan-2-ylamino)-3H,4H-pyrido[4,3-d]pyrimidin-4-one;

5-[(2-methoxyethyl)amino]-3-methyl-7-(4-{[2-(morpholin-4-yl)ethane]sulfonyl}phenyl)-3H,4H-pyrido[4,3-d]pyrimidin-4-one;

5-(ethylamino)-3-methyl-7-(4-{[2-(pyrrolidin-1-yl)ethane]sulfonyl}phenyl)-3H,4H-pyrido[4,3-d]pyrimidin-4-one;

5-(cyclopropylamino)-7-[4-(1-hydroxycyclobutyl)phenyl]-3-methyl-3H,4H-pyrido[4,3-d]pyrimidin-4-one;

7-[4-(1-hydroxycyclobutyl)phenyl]-3-methyl-5-(propan-2-ylamino)-3H,4H-pyrido[4,3-d]pyrimidin-4-one;

7-[4-(1-hydroxycyclobutyl)phenyl]-5-[(2-methoxyethyl)amino]-3-methyl-3H,4H-pyrido[4,3-d]pyrimidin-4-one;

5-(ethylamino)-3-methyl-7-(4-{[2-(pyrrolidin-1-yl)ethane]sulfonyl}phenyl)-3H,4H-pyrido[4,3-d]pyrimidin-4-one;

5-(cyclopropylamino)-3-methyl-7-(4-{[2-(pyrrolidin-1-yl)ethane]sulfonyl}phenyl)-3H,4H-pyrido[4,3-d]pyrimidin-4-one;

3-methyl-5-(propan-2-ylamino)-7-(4-{[2-(pyrrolidin-1-yl)ethane]sulfonyl}phenyl)-3H,4H-pyrido[4,3-d]pyrimidin-4-one;

5-[(2-methoxyethyl)amino]-3-methyl-7-(4-{[2-(pyrrolidin-1-yl)ethane]sulfonyl}phenyl)-3H,4H-pyrido[4,3-d]pyrimidin-4-one;

7-[4-(2-aminopropan-2-yl)phenyl]-5-(cyclopropylamino)-3-methyl-3H,4H-pyrido[4,3-d]pyrimidin-4-one;

7-[3-fluoro-4-(1-methylpiperidin-4-yl)phenyl]-5-[(2-methoxyethyl)amino]-3-methyl-3H,4H-pyrido[4,3-d]pyrimidin-4-one;

7-[3-fluoro-4-(1-methylpiperidin-4-yl)phenyl]-3-methyl-5-(propan-2-ylamino)-3H,4H-pyrido[4,3-d]pyrimidin-4-one;

5-(ethylamino)-7-[3-fluoro-4-(piperidin-4-yl)phenyl]-3-methyl-3H,4H-pyrido[4,3-d]pyrimidin-4-one;

5-(ethylamino)-7-[4-(1-hydroxycyclopentyl)phenyl]-3-methyl-3H,4H-pyrido[4,3-d]pyrimidin-4-one;

7-[4-(1-hydroxycyclopentyl)phenyl]-3-methyl-5-(propan-2-ylamino)-3H,4H-pyrido[4,3-d]pyrimidin-4-one;

5-(ethylamino)-7-[3-fluoro-4-(1-methylpiperidin-4-yl)phenyl]-3-methyl-3H,4H-pyrido[4,3-d]pyrimidin-4-one;

5-(ethylamino)-7-[4-(1-ethylpiperidin-4-yl)-3-fluorophenyl]-3-methyl-3H,4H-pyrido[4,3-d]pyrimidin-4-one;

5-(cyclopropylamino)-7-[4-(1-hydroxycyclopentyl)phenyl]-3-methyl-3H,4H-pyrido[4,3-d]pyrimidin-4-one;

5-(ethylamino)-7-{3-fluoro-4-[1-(propan-2-yl)piperidin-4-yl]phenyl}-3-methyl-3H,4H-pyrido[4,3-d]pyrimidin-4-one;

3-[5-(cyclopropylamino)-3-methyl-4-oxo-3H,4H-pyrido[4,3-d]pyrimidin-7-yl]-N-methylbenzene-1-sulfonamide;

7-(3,4-diaminophenyl)-3-methyl-5-(propan-2-ylamino)-3H,4H-pyrido[4,3-d]pyrimidin-4-one;

7-(1H-1,3-benzodiazol-6-yl)-3-methyl-5-(propan-2-ylamino)-3H,4H-pyrido[4,3-d]pyrimidin-4-one;

7-[6-(2-hydroxypropan-2-yl)pyridin-3-yl]-3-methyl-5-(propan-2-yloxy)-3H,4H-pyrido[4,3-d]pyrimidin-4-one;

5-(benzyloxy)-7-[6-(2-hydroxypropan-2-yl)pyridin-3-yl]-3-methyl-3H,4H-pyrido[4,3-d]pyrimidin-4-one;

5-(cyclobutylamino)-7-(4-methanesulfonylphenyl)-3-methyl-3H,4H-pyrido[4,3-d]pyrimidin-4-one;

N-[2-({7-[4-(2-hydroxypropan-2-yl)phenyl]-3-methyl-4-oxo-3H,4H-pyrido[4,3-d]pyrimidin-5-yl}amino)ethyl]-2-methoxyacetamide;

N-[2-({7-[6-(2-hydroxypropan-2-yl)pyridin-3-yl]-3-methyl-4-oxo-3H,4H-pyrido[4,3-d]pyrimidin-5-yl}amino)ethyl]-2-methoxyacetamide;

N-(2-{[7-(3,4-dimethoxyphenyl)-3-methyl-4-oxo-3H,4H-pyrido[4,3-d]pyrimidin-5-yl]amino}ethyl)-2-methoxyacetamide;

methyl N-[2-({7-[4-(2-hydroxypropan-2-yl)phenyl]-3-methyl-4-oxo-3H,4H-pyrido[4,3-d]pyrimidin-5-yl}amino)ethyl]carbamate;

methyl N-[2-({7-[6-(2-hydroxypropan-2-yl)pyridin-3-yl]-3-methyl-4-oxo-3H,4H-pyrido[4,3-d]pyrimidin-5-yl}amino)ethyl]carbamate;

methyl N-(2-{[7-(3,4-dimethoxyphenyl)-3-methyl-4-oxo-3H,4H-pyrido[4,3-d]pyrimidin-5-yl]amino}ethyl)carbamate;

N-[(2S)-1-{[7-(3,4-dimethoxyphenyl)-3-methyl-4-oxo-3H,4H-pyrido[4,3-d]pyrimidin-5-yl]amino}propan-2-yl]-2-methoxyacetamide;

7-[6-(2-hydroxypropan-2-yl)pyridin-3-yl]-3-methyl-5-(pyridin-3-ylmethoxy)-3H,4H-pyrido[4,3-d]pyrimidin-4-one;

7-[6-(2-hydroxypropan-2-yl)pyridin-3-yl]-3-methyl-5-(pyridin-4-ylmethoxy)-3H,4H-pyrido[4,3-d]pyrimidin-4-one;

N-[(2S)-1-({7-[4-(2-hydroxypropan-2-yl)phenyl]-3-methyl-4-oxo-3H,4H-pyrido[4,3-d]pyrimidin-5-yl}amino)propan-2-yl]-2-methoxyacetamide;

N-[(2S)-1-({7-[6-(2-hydroxypropan-2-yl)pyridin-3-yl]-3-methyl-4-oxo-3H,4H-pyrido[4,3-d]pyrimidin-5-yl}amino)propan-2-yl]-2-methoxyacetamide;

N-methyl-5-[3-methyl-4-oxo-5-(propan-2-ylamino)-3H,4H-pyrido[4,3-d]pyrimidin-7-yl]pyridine-2-sulfonamide;

2,2-dimethyl-7-[3-methyl-4-oxo-5-(propan-2-ylamino)-3H,4H-pyrido[4,3-d]pyrimidin-7-yl]-3,4-dihydro-2H-1,4-benzoxazin-3-one;

2,2-dimethyl-6-[3-methyl-4-oxo-5-(propan-2-ylamino)-3H,4H-pyrido[4,3-d]pyrimidin-7-yl]-3,4-dihydro-2H-1,4-benzoxazin-3-one;

5-(cyclopropylamino)-7-[3-methanesulfonyl-4-(morpholin-4-ylmethyl)phenyl]-3-methyl-3H,4H-pyrido[4,3-d]pyrimidin-4-one;

3-methyl-7-(2-methyl-1H-1,3-benzodiazol-6-yl)-5-(propan-2-ylamino)-3H,4H-pyrido[4,3-d]pyrimidin-4-one;

3-methyl-7-(6-{[2-(morpholin-4-yl)ethyl]amino}pyridin-3-yl)-5-(propan-2-ylamino)-3H,4H-pyrido[4,3-d]pyrimidin-4-one;

5-(cyclopropylamino)-3-methyl-7-(6-{[2-(morpholin-4-yl)ethyl]amino}pyridin-3-yl)-3H,4H-pyrido[4,3-d]pyrimidin-4-one;

5-(ethylamino)-7-[4-(2-hydroxypropan-2-yl)phenyl]-3-methyl-3H,4H-pyrido[4,3-d]pyrimidin-4-one;

3-[3-methyl-4-oxo-5-(propan-2-ylamino)-3H,4H-pyrido[4,3-d]pyrimidin-7-yl]benzene-1-sulfonamide;

3-[5-(cyclopropylamino)-3-methyl-4-oxo-3H,4H-pyrido[4,3-d]pyrimidin-7-yl]benzene-1-sulfonamide;

4-[3-methyl-4-oxo-5-(propan-2-ylamino)-3H,4H-pyrido[4,3-d]pyrimidin-7-yl]benzene-1-sulfonamide;

4-[5-(cyclopropylamino)-3-methyl-4-oxo-3H,4H-pyrido[4,3-d]pyrimidin-7-yl]benzene-1-sulfonamide;

5-(cyclopropylamino)-7-(6-methoxypyridin-3-yl)-3-methyl-3H,4H-pyrido[4,3-d]pyrimidin-4-one;

5-(cyclopropylamino)-7-(6-fluoropyridin-3-yl)-3-methyl-3H,4H-pyrido[4,3-d]pyrimidin-4-one;

5-(cyclopropylamino)-7-[4-(hydroxymethyl)phenyl]-3-methyl-3H,4H-pyrido[4,3-d]pyrimidin-4-one;

5-(cyclopropylamino)-7-[4-(methoxymethyl)phenyl]-3-methyl-3H,4H-pyrido[4,3-d]pyrimidin-4-one;

5-(cyclopropylamino)-7-[6-(dimethylamino)pyridin-3-yl]-3-methyl-3H,4H-pyrido[4,3-d]pyrimidin-4-one;

N-{5-[5-(cyclopropylamino)-3-methyl-4-oxo-3H,4H-pyrido[4,3-d]pyrimidin-7-yl]pyridin-2-yl}acetamide;

7-[6-(dimethylamino)pyridin-3-yl]-3-methyl-5-(propan-2-ylamino)-3H,4H-pyrido[4,3-d]pyrimidin-4-one;

N-{5-[3-methyl-4-oxo-5-(propan-2-ylamino)-3H,4H-pyrido[4,3-d]pyrimidin-7-yl]pyridin-2-yl}acetamide;

3-methyl-5-(propan-2-ylamino)-7-[6-(pyrrolidin-1-yl)pyridin-3-yl]-3H,4H-pyrido[4,3-d]pyrimidin-4-one;

5-(cyclopropylamino)-3-methyl-7-[6-(pyrrolidin-1-yl)pyridin-3-yl]-3H,4H-pyrido[4,3-d]pyrimidin-4-one;

5-(cyclopropylamino)-7-[4-(2-methoxypropan-2-yl)phenyl]-3-methyl-3H,4H-pyrido[4,3-d]pyrimidin-4-one;

7-(2-methoxypyridin-4-yl)-3-methyl-5-(propan-2-ylamino)-3H,4H-pyrido[4,3-d]pyrimidin-4-one;

5-(cyclopropylamino)-7-(2-methoxypyridin-4-yl)-3-methyl-3H,4H-pyrido[4,3-d]pyrimidin-4-one;

7-(5-methoxypyridin-3-yl)-3-methyl-5-(propan-2-ylamino)-3H,4H-pyrido[4,3-d]pyrimidin-4-one;

5-(cyclopropylamino)-7-(5-methoxypyridin-3-yl)-3-methyl-3H,4H-pyrido[4,3-d]pyrimidin-4-one;

5-[3-methyl-4-oxo-5-(propan-2-ylamino)-3H,4H-pyrido[4,3-d]pyrimidin-7-yl]pyridine-2-carbonitrile;

7-[4-(2-methoxypropan-2-yl)phenyl]-3-methyl-5-(propan-2-ylamino)-3H,4H-pyrido[4,3-d]pyrimidin-4-one;

3-methyl-7-[4-(morpholin-4-yl)phenyl]-5-(propan-2-ylamino)-3H,4H-pyrido[4,3-d]pyrimidin-4-one;

5-[5-(cyclopropylamino)-3-methyl-4-oxo-3H,4H-pyrido[4,3-d]pyrimidin-7-yl]pyridine-2-carbonitrile;

7-[6-(1-hydroxyethyl)pyridin-3-yl]-3-methyl-5-(propan-2-ylamino)-3H,4H-pyrido[4,3-d]pyrimidin-4-one;

7-[6-(hydroxymethyl)pyridin-3-yl]-3-methyl-5-(propan-2-ylamino)-3H,4H-pyrido[4,3-d]pyrimidin-4-one;

3-methyl-7-(6-methylpyridin-3-yl)-5-(propan-2-ylamino)-3H,4H-pyrido[4,3-d]pyrimidin-4-one;

7-[4-(1-hydroxyethyl)phenyl]-3-methyl-5-(propan-2-ylamino)-3H,4H-pyrido[4,3-d]pyrimidin-4-one;

7-[4-(hydroxymethyl)phenyl]-3-methyl-5-(propan-2-ylamino)-3H,4H-pyrido[4,3-d]pyrimidin-4-one;

7-(6-methoxypyridin-3-yl)-3-methyl-5-(propan-2-ylamino)-3H,4H-pyrido[4,3-d]pyrimidin-4-one;

7-[4-(2-hydroxyethyl)phenyl]-3-methyl-5-(propan-2-ylamino)-3H,4H-pyrido[4,3-d]pyrimidin-4-one;

7-[4-(methoxymethyl)phenyl]-3-methyl-5-(propan-2-ylamino)-3H,4H-pyrido[4,3-d]pyrimidin-4-one;

S-{3-[5-(cyclopropylamino)-3-methyl-4-oxo-3H,4H-pyrido[4,3-d]pyrimidin-7-yl]phenyl}-2-hydroxyethane-1-sulfonamido;

N-methyl-3-[3-methyl-4-oxo-5-(propan-2-ylamino)-3H,4H-pyrido[4,3-d]pyrimidin-7-yl]benzene-1-sulfonamide;

N,N-dimethyl-3-[3-methyl-4-oxo-5-(propan-2-ylamino)-3H,4H-pyrido[4,3-d]pyrimidin-7-yl]benzene-1-sulfonamide;

2-hydroxy-S-{3-[3-methyl-4-oxo-5-(propan-2-ylamino)-3H,4H-pyrido[4,3-d]pyrimidin-7-yl]phenyl}ethane-1-sulfonamido;

N-cyclopropyl-3-[3-methyl-4-oxo-5-(propan-2-ylamino)-3H,4H-pyrido[4,3-d]pyrimidin-7-yl]benzene-1-sulfonamide;

3-methyl-7-[3-(morpholine-4-sulfonyl)phenyl]-5-(propan-2-ylamino)-3H,4H-pyrido[4,3-d]pyrimidin-4-one;

5-(cyclopropylamino)-3-methyl-7-[4-(morpholin-4-yl)phenyl]-3H,4H-pyrido[4,3-d]pyrimidin-4-one;

5-(cyclopropylamino)-3-methyl-7-[6-(morpholin-4-yl)pyridin-3-yl]-3H,4H-pyrido[4,3-d]pyrimidin-4-one;

3-methyl-7-[6-(morpholin-4-yl)pyridin-3-yl]-5-(propan-2-ylamino)-3H,4H-pyrido[4,3-d]pyrimidin-4-one;

5-(ethylamino)-7-[4-(2-methoxypropan-2-yl)phenyl]-3-methyl-3H,4H-pyrido[4,3-d]pyrimidin-4-one;

5-(cyclopropylamino)-3-methyl-7-[4-(morpholin-4-ylmethyl)phenyl]-3H,4H-pyrido[4,3-d]pyrimidin-4-one;

3-methyl-7-[4-(morpholin-4-ylmethyl)phenyl]-5-(propan-2-ylamino)-3H,4H-pyrido[4,3-d]pyrimidin-4-one;

5-(cyclopropylamino)-7-[4-(1-hydroxycyclopropyl)phenyl]-3-methyl-3H,4H-pyrido[4,3-d]pyrimidin-4-one;

4-[5-(cyclopropylamino)-3-methyl-4-oxo-3H,4H-pyrido[4,3-d]pyrimidin-7-yl]-N-methylbenzene-1-sulfonamide;

3-[5-(cyclopropylamino)-3-methyl-4-oxo-3H,4H-pyrido[4,3-d]pyrimidin-7-yl]-N,N-dimethylbenzene-1-sulfonamide;

3-[5-(cyclopropylamino)-3-methyl-4-oxo-3H,4H-pyrido[4,3-d]pyrimidin-7-yl]-N-ethylbenzene-1-sulfonamide;

N-methyl-4-[3-methyl-4-oxo-5-(propan-2-ylamino)-3H,4H-pyrido[4,3-d]pyrimidin-7-yl]benzene-1-sulfonamide;

2-hydroxy-S-{4-[3-methyl-4-oxo-5-(propan-2-ylamino)-3H,4H-pyrido[4,3-d]pyrimidin-7-yl]phenyl}ethane-1-sulfonamido;

S-{4-[5-(cyclopropylamino)-3-methyl-4-oxo-3H,4H-pyrido[4,3-d]pyrimidin-7-yl]phenyl}-2-hydroxyethane-1-sulfonamido;

5-(cyclopropylamino)-7-(6-methoxypyrazin-2-yl)-3-methyl-3H,4H-pyrido[4,3-d]pyrimidin-4-one;

5-(ethylamino)-7-(6-methoxypyrazin-2-yl)-3-methyl-3H,4H-pyrido[4,3-d]pyrimidin-4-one;

5-(cyclopropylamino)-7-[4-(ethanesulfonyl)phenyl]-3-methyl-3H,4H-pyrido[4,3-d]pyrimidin-4-one;

5-(cyclopropylamino)-7-[6-(4-ethylpiperazin-1-yl)pyridin-3-yl]-3-methyl-3H,4H-pyrido[4,3-d]pyrimidin-4-one;

5-(cyclopropylamino)-7-{6-[(3-methoxypropyl)amino]
pyridin-3-yl}-3-methyl-3H,4H-pyrido[4,3-d]pyrimidin-4-one;
5-(cyclopropylamino)-7-{4-[2-(4-ethylpiperazin-1-yl)
ethyl]phenyl}-3-methyl-3H,4H-pyrido[4,3-d]pyrimidin-4-one;
5-(cyclopropylamino)-3-methyl-7-[6-(4-methyl-H-imidazol-1-yl)pyridin-3-yl]-3H,4H-pyrido[4,3-d]pyrimidin-4-one;
5-(cyclopropylamino)-7-{6-[(2-hydroxyethyl)amino]pyridin-3-yl}-3-methyl-3H,4H-pyrido[4,3-d]pyrimidin-4-one;
5-(cyclopropylamino)-7-{6-[(2-methoxyethyl)amino]pyridin-3-yl}-3-methyl-3H,4H-pyrido[4,3-d]pyrimidin-4-one;
5-(cyclopropylamino)-3-methyl-7-[6-(piperidin-1-yl)pyridin-3-yl]-3H,4H-pyrido[4,3-d]pyrimidin-4-one;
5-(cyclopropylamino)-3-methyl-7-{6-[(1-methylpiperidin-4-yl)amino]pyridin-3-yl}-3H,4H-pyrido[4,3-d]pyrimidin-4-one;
N-cyclopropyl-3-[5-(cyclopropylamino)-3-methyl-4-oxo-3H,4H-pyrido[4,3-d]pyrimidin-7-yl]benzene-1-sulfonamide;
7-[4-(ethanesulfonyl)phenyl]-5-(ethylamino)-3-methyl-3H,4H-pyrido[4,3-d]pyrimidin-4-one;
7-[4-(ethanesulfonyl)phenyl]-3-methyl-5-(propan-2-ylamino)-3H,4H-pyrido[4,3-d]pyrimidin-4-one;
5-(cyclopropylamino)-3-methyl-7-{4-[2-(morpholin-4-yl)ethyl]phenyl}-3H,4H-pyrido[4,3-d]pyrimidin-4-one;
7-{4-[2-(4-ethylpiperazin-1-yl)ethyl]phenyl}-3-methyl-5-(propan-2-ylamino)-3H,4H-pyrido[4,3-d]pyrimidin-4-one;
3-methyl-7-{4-[2-(morpholin-4-yl)ethyl]phenyl}-5-(propan-2-ylamino)-3H,4H-pyrido[4,3-d]pyrimidin-4-one;
5-(cyclopropylamino)-3-methyl-7-{4-[2-(piperidin-1-yl)ethyl]phenyl}-3H,4H-pyrido[4,3-d]pyrimidin-4-one;
3-methyl-7-{4-[2-(piperidin-1-yl)ethyl]phenyl}-5-(propan-2-ylamino)-3H,4H-pyrido[4,3-d]pyrimidin-4-one;
5-(cyclopropylamino)-3-methyl-7-{4-[2-(pyrrolidin-1-yl)ethyl]phenyl}-3H,4H-pyrido[4,3-d]pyrimidin-4-one;
3-methyl-5-(propan-2-ylamino)-7-{4-[2-(pyrrolidin-1-yl)ethyl]phenyl}-3H,4H-pyrido[4,3-d]pyrimidin-4-one;
5-(cyclopropylamino)-7-(4-{2-[(2-methoxyethyl)amino]ethyl}phenyl)-3-methyl-3H,4H-pyrido[4,3-d]pyrimidin-4-one;
7-(4-{2-[(2-methoxyethyl)amino]ethyl}phenyl)-3-methyl-5-(propan-2-ylamino)-3H,4H-pyrido[4,3-d]pyrimidin-4-one;
5-(cyclopropylamino)-3-methyl-7-(4-{2-[(1-methylpiperidin-4-yl)amino]ethyl}phenyl)-3H,4H-pyrido[4,3-d]pyrimidin-4-one;
3-methyl-7-(4-{2-[(1-methylpiperidin-4-yl)amino]ethyl}phenyl)-5-(propan-2-ylamino)-3H,4H-pyrido[4,3-d]pyrimidin-4-one;
7-(6-ethoxypyridin-3-yl)-3-methyl-5-(propan-2-ylamino)-3H,4H-pyrido[4,3-d]pyrimidin-4-one;
5-(cyclopropylamino)-3-methyl-7-(4-{2-[(2R)-2-methylmorpholin-4-yl]ethyl}phenyl)-3H,4H-pyrido[4,3-d]pyrimidin-4-one;
3-methyl-7-(4-{2-[(2R)-2-methylmorpholin-4-yl]ethyl}phenyl)-5-(propan-2-ylamino)-3H,4H-pyrido[4,3-d]pyrimidin-4-one;
5-(cyclopropylamino)-3-methyl-7-{6-[(2R)-2-methylmorpholin-4-yl]pyridin-3-yl}-3H,4H-pyrido[4,3-d]pyrimidin-4-one;
5-(cyclopropylamino)-7-(6-ethoxypyridin-3-yl)-3-methyl-3H,4H-pyrido[4,3-d]pyrimidin-4-one;
N-{4-[5-(cyclopropylamino)-3-methyl-4-oxo-3H,4H-pyrido[4,3-d]pyrimidin-7-yl]phenyl}methanesulfonamide;
N-{4-[3-methyl-4-oxo-5-(propan-2-ylamino)-3H,4H-pyrido[4,3-d]pyrimidin-7-yl]phenyl}methanesulfonamide;
4-(2-{4-[5-(cyclopropylamino)-3-methyl-4-oxo-3H,4H-pyrido[4,3-d]pyrimidin-7-yl]phenyl}ethyl)piperazin-2-one;
4-(2-{4-[3-methyl-4-oxo-5-(propan-2-ylamino)-3H,4H-pyrido[4,3-d]pyrimidin-7-yl]phenyl}ethyl)piperazin-2-one;
7-(4-{[2-(dimethylamino)ethane]sulfonyl}phenyl)-5-(ethylamino)-3-methyl-3H,4H-pyrido[4,3-d]pyrimidin-4-one;
5-(cyclopropylamino)-7-(4-{[2-(dimethylamino)ethane]sulfonyl}phenyl)-3-methyl-3H,4H-pyrido[4,3-d]pyrimidin-4-one;
3-methyl-7-[3-methyl-4-(piperidin-4-yl)phenyl]-5-(propan-2-ylamino)-3H,4H-pyrido[4,3-d]pyrimidin-4-one;
7-[4-(2-aminopropan-2-yl)phenyl]-5-[(3-hydroxypropyl)amino]-3-methyl-3H,4H-pyrido[4,3-d]pyrimidin-4-one;
7-[4-(2-aminopropan-2-yl)phenyl]-5-[(2-hydroxyethyl)amino]-3-methyl-3H,4H-pyrido[4,3-d]pyrimidin-4-one;
7-[4-(2-aminopropan-2-yl)phenyl]-3-methyl-5-(oxolan-3-ylamino)-3H,4H-pyrido[4,3-d]pyrimidin-4-one;
7-(4-{[2-(dimethylamino)ethane]sulfonyl}phenyl)-5-[(2-methoxyethyl)amino]-3-methyl-3H,4H-pyrido[4,3-d]pyrimidin-4-one;
7-(4-{[2-(dimethylamino)ethane]sulfonyl}phenyl)-5-[(3-hydroxypropyl)amino]-3-methyl-3H,4H-pyrido[4,3-d]pyrimidin-4-one;
3-methyl-7-[3-methyl-4-(1-methylpiperidin-4-yl)phenyl]-5-(propan-2-ylamino)-3H,4H-pyrido[4,3-d]pyrimidin-4-one;
7-[4-(1-ethylpiperidin-4-yl)-3-methylphenyl]-3-methyl-5-(propan-2-ylamino)-3H,4H-pyrido[4,3-d]pyrimidin-4-one;
5-(ethylamino)-3-methyl-7-[6-(piperidin-4-yl)pyridin-3-yl]-3H,4H-pyrido[4,3-d]pyrimidin-4-one;
5-(ethylamino)-3-methyl-7-[6-(1-methylpiperidin-4-yl)pyridin-3-yl]-3H,4H-pyrido[4,3-d]pyrimidin-4-one;
5-(ethylamino)-7-[6-(1-ethylpiperidin-4-yl)pyridin-3-yl]-3-methyl-3H,4H-pyrido[4,3-d]pyrimidin-4-one;
3-methyl-7-(4-{[2-(morpholin-4-yl)ethane]sulfonyl}phenyl)-5-(oxolan-3-ylamino)-3H,4H-pyrido[4,3-d]pyrimidin-4-one;
5-[(2-hydroxyethyl)amino]-3-methyl-7-(4-{[2-(morpholin-4-yl)ethane]sulfonyl}phenyl)-3H,4H-pyrido[4,3-d]pyrimidin-4-one;
5-[(3-hydroxypropyl)amino]-3-methyl-7-(4-{[2-(morpholin-4-yl)ethane]sulfonyl}phenyl)-3H,4H-pyrido[4,3-d]pyrimidin-4-one;
5-[(3S)-3-(hydroxymethyl)pyrrolidin-1-yl]-3-methyl-7-(4-{[2-(morpholin-4-yl)ethane]sulfonyl}phenyl)-3H,4H-pyrido[4,3-d]pyrimidin-4-one;
5-(ethylamino)-7-(4-{[2-(4-ethylpiperazin-1-yl)ethane]sulfonyl}phenyl)-3-methyl-3H,4H-pyrido[4,3-d]pyrimidin-4-one;
7-[4-(2-aminopropan-2-yl)phenyl]-5-[(3S)-3-(hydroxymethyl)pyrrolidin-1-yl]-3-methyl-3H,4H-pyrido[4,3-d]pyrimidin-4-one;

7-(4-{[2-(4-ethylpiperazin-1-yl)ethane]sulfonyl}phenyl)-5-[(3-hydroxypropyl)amino]-3-methyl-3H,4H-pyrido[4,3-d]pyrimidin-4-one;

7-[6-(2-aminopropan-2-yl)pyridin-3-yl]-5-(ethylamino)-3-methyl-3H,4H-pyrido[4,3-d]pyrimidin-4-one;

7-[6-(2-aminopropan-2-yl)pyridin-3-yl]-5-(cyclopropylamino)-3-methyl-3H,4H-pyrido[4,3-d]pyrimidin-4-one;

7-[6-(2-aminopropan-2-yl)pyridin-3-yl]-3-methyl-5-(propan-2-ylamino)-3H,4H-pyrido[4,3-d]pyrimidin-4-one;

7-(4-amino-3-methanesulfonylphenyl)-5-(ethylamino)-3-methyl-3H,4H-pyrido[4,3-d]pyrimidin-4-one;

7-(4-amino-3-methanesulfonylphenyl)-5-(cyclopropylamino)-3-methyl-3H,4H-pyrido[4,3-d]pyrimidin-4-one;

7-(4-amino-3-methanesulfonylphenyl)-5-[(2-methoxyethyl)amino]-3-methyl-3H,4H-pyrido[4,3-d]pyrimidin-4-one;

7-(4-amino-3-methanesulfonylphenyl)-5-[(3-hydroxypropyl)amino]-3-methyl-3H,4H-pyrido[4,3-d]pyrimidin-4-one;

5-(ethylamino)-7-(4-{[(2S)-1-hydroxypropan-2-yl]amino}-3-methanesulfonylphenyl)-3-methyl-3H,4H-pyrido[4,3-d]pyrimidin-4-one;

7-(4-{[(2S)-1-hydroxypropan-2-yl]amino}-3-methanesulfonylphenyl)-3-methyl-5-(propan-2-ylamino)-3H,4H-pyrido[4,3-d]pyrimidin-4-one;

5-(ethylamino)-7-(4-{[(2S)-2-hydroxypropyl]amino}-3-methanesulfonylphenyl)-3-methyl-3H,4H-pyrido[4,3-d]pyrimidin-4-one;

7-(4-{[(2S)-2-hydroxypropyl]amino}-3-methanesulfonylphenyl)-3-methyl-5-(propan-2-ylamino)-3H,4H-pyrido[4,3-d]pyrimidin-4-one;

7-(4-{[(2S)-2-hydroxypropyl]amino}-3-methanesulfonylphenyl)-5-[(2-methoxyethyl)amino]-3-methyl-3H,4H-pyrido[4,3-d]pyrimidin-4-one;

5-(ethylamino)-7-(4-{[(2R)-1-hydroxypropan-2-yl]amino}-3-methanesulfonylphenyl)-3-methyl-3H,4H-pyrido[4,3-d]pyrimidin-4-one;

5-(cyclopropylamino)-7-(4-{[(2R)-1-hydroxypropan-2-yl]amino}-3-methanesulfonylphenyl)-3-methyl-3H,4H-pyrido[4,3-d]pyrimidin-4-one;

5-(ethylamino)-7-(4-{[(2R)-2-hydroxypropyl]amino}-3-methanesulfonylphenyl)-3-methyl-3H,4H-pyrido[4,3-d]pyrimidin-4-one;

5-(cyclopropylamino)-7-(4-{[(2R)-2-hydroxypropyl]amino}-3-methanesulfonylphenyl)-3-methyl-3H,4H-pyrido[4,3-d]pyrimidin-4-one;

7-(4-{[(2R)-2-hydroxypropyl]amino}-3-methanesulfonylphenyl)-3-methyl-5-(propan-2-ylamino)-3H,4H-pyrido[4,3-d]pyrimidin-4-one;

7-(4-{[(2R)-2-hydroxypropyl]amino}-3-methanesulfonylphenyl)-5-[(2-methoxyethyl)amino]-3-methyl-3H,4H-pyrido[4,3-d]pyrimidin-4-one;

5-(cyclopropylamino)-7-(4-{[(2S)-1-hydroxypropan-2-yl]amino}-3-methanesulfonylphenyl)-3-methyl-3H,4H-pyrido[4,3-d]pyrimidin-4-one;

5-(cyclopropylamino)-7-(4-{[(2S)-2-hydroxypropyl]amino}-3-methanesulfonylphenyl)-3-methyl-3H,4H-pyrido[4,3-d]pyrimidin-4-one;

7-(4-{[(2R)-1-hydroxypropan-2-yl]amino}-3-methanesulfonylphenyl)-3-methyl-5-(propan-2-ylamino)-3H,4H-pyrido[4,3-d]pyrimidin-4-one;

7-(4-{[(2R)-1-hydroxypropan-2-yl]amino}-3-methanesulfonylphenyl)-5-[(2-methoxyethyl)amino]-3-methyl-3H,4H-pyrido[4,3-d]pyrimidin-4-one;

7-(4-{[(2S)-1-hydroxypropan-2-yl]amino}-3-methanesulfonylphenyl)-5-[(3-hydroxypropyl)amino]-3-methyl-3H,4H-pyrido[4,3-d]pyrimidin-4-one;

5-[(3-hydroxypropyl)amino]-7-(4-{[(2S)-2-hydroxypropyl]amino}-3-methanesulfonylphenyl)-3-methyl-3H,4H-pyrido[4,3-d]pyrimidin-4-one;

7-(4-{[(2R)-1-hydroxypropan-2-yl]amino}-3-methanesulfonylphenyl)-5-[(3-hydroxypropyl)amino]-3-methyl-3H,4H-pyrido[4,3-d]pyrimidin-4-one;

5-[(3-hydroxypropyl)amino]-7-(4-{[(2R)-2-hydroxypropyl]amino}-3-methanesulfonylphenyl)-3-methyl-3H,4H-pyrido[4,3-d]pyrimidin-4-one;

7-(4-{[(2S)-1-hydroxypropan-2-yl]amino}-3-methanesulfonylphenyl)-3-methyl-5-[(3R)-oxolan-3-ylamino]-3H,4H-pyrido[4,3-d]pyrimidin-4-one;

7-(4-{[(2S)-2-hydroxypropyl]amino}-3-methanesulfonylphenyl)-3-methyl-5-[(3R)-oxolan-3-ylamino]-3H,4H-pyrido[4,3-d]pyrimidin-4-one;

7-(4-{[(2R)-2-hydroxypropyl]amino}-3-methanesulfonylphenyl)-3-methyl-5-[(3R)-oxolan-3-ylamino]-3H,4H-pyrido[4,3-d]pyrimidin-4-one;

3-methyl-7-[4-(methylamino)phenyl]-5-(propan-2-ylamino)-3H,4H-pyrido[4,3-d]pyrimidin-4-one;

5-[(2-methoxyethyl)amino]-3-methyl-7-[4-(methylamino)phenyl]-3H,4H-pyrido[4,3-d]pyrimidin-4-one;

3-methyl-7-[4-(methylamino)phenyl]-5-[(3R)-oxolan-3-ylamino]-3H,4H-pyrido[4,3-d]pyrimidin-4-one;

7-{4-[(2R)-2-(hydroxymethyl)pyrrolidin-1-yl]-3-methanesulfonylphenyl}-3-methyl-5-(propan-2-ylamino)-3H,4H-pyrido[4,3-d]pyrimidin-4-one;

7-{4-[(2R)-2-(hydroxymethyl)pyrrolidin-1-yl]-3-methanesulfonylphenyl}-5-[(2-methoxyethyl)amino]-3-methyl-3H,4H-pyrido[4,3-d]pyrimidin-4-one;

7-{4-[(2R)-2-(hydroxymethyl)pyrrolidin-1-yl]-3-methanesulfonylphenyl}-3-methyl-5-[(3R)-oxolan-3-ylamino]-3H,4H-pyrido[4,3-d]pyrimidin-4-one;

5-[(3S)-3-(hydroxymethyl)pyrrolidin-1-yl]-7-{4-[(2R)-2-(hydroxymethyl)pyrrolidin-1-yl]-3-methanesulfonylphenyl}-3-methyl-3H,4H-pyrido[4,3-d]pyrimidin-4-one;

7-{4-[(2S)-2-(hydroxymethyl)pyrrolidin-1-yl]-3-methanesulfonylphenyl}-3-methyl-5-(propan-2-ylamino)-3H,4H-pyrido[4,3-d]pyrimidin-4-one;

7-{4-[(2S)-2-(hydroxymethyl)pyrrolidin-1-yl]-3-methanesulfonylphenyl}-5-[(2-methoxyethyl)amino]-3-methyl-3H,4H-pyrido[4,3-d]pyrimidin-4-one;

7-{4-[(2S)-2-(hydroxymethyl)pyrrolidin-1-yl]-3-methanesulfonylphenyl}-3-methyl-5-[(3R)-oxolan-3-ylamino]-3H,4H-pyrido[4,3-d]pyrimidin-4-one;

5-[(3S)-3-(hydroxymethyl)pyrrolidin-1-yl]-7-{4-[(2S)-2-(hydroxymethyl)pyrrolidin-1-yl]-3-methanesulfonylphenyl}-3-methyl-3H,4H-pyrido[4,3-d]pyrimidin-4-one;

5-(cyclopropylamino)-7-[4-(2-hydroxyethyl)phenyl]-3-methyl-3H,4H-pyrido[4,3-d]pyrimidin-4-one;

7-(6-methoxypyrazin-2-yl)-3-methyl-5-(propan-2-ylamino)-3H,4H-pyrido[4,3-d]pyrimidin-4-one;

5-(cyclopropylamino)-3-methyl-7-[3-(morpholine-4-sulfonyl)phenyl]-3H,4H-pyrido[4,3-d]pyrimidin-4-one;

7-(4-{[2-(dimethylamino)ethane]sulfonyl}phenyl)-3-methyl-5-(propan-2-ylamino)-3H,4H-pyrido[4,3-d]pyrimidin-4-one;

7-(3,4-dimethoxyphenyl)-3-methyl-5-[(3-methyl-1H-indazol-6-yl)amino]-3H,4H-pyrido[4,3-d]pyrimidin-4-one;

3-methyl-7-[5-(morpholin-4-ylmethyl)pyridin-3-yl]-5-(propan-2-ylamino)-3H,4H-pyrido[4,3-d]pyrimidin-4-one;
7-[3-methanesulfonyl-4-(morpholin-4-ylmethyl)phenyl]-3-methyl-5-(propan-2-ylamino)-3H,4H-pyrido[4,3-d]pyrimidin-4-one;
3-methyl-5-(propan-2-ylamino)-7-[6-(pyrrolidin-1-ylmethyl)pyridin-3-yl]-3H,4H-pyrido[4,3-d]pyrimidin-4-one;
5-(cyclopropylamino)-7-(5,6-diaminopyridin-3-yl)-3-methyl-3H,4H-pyrido[4,3-d]pyrimidin-4-one;
7-(3,4-dimethoxyphenyl)-3-methyl-5-{[(2R)-3,3,3-trifluoro-2-hydroxypropyl]amino}-3H,4H-pyrido[4,3-d]pyrimidin-4-one;
3-methyl-7-[4-(propan-2-yl)phenyl]-5-(propan-2-ylamino)-3H,4H-pyrido[4,3-d]pyrimidin-4-one;
5-(cyclopropylamino)-3-methyl-7-[4-(propan-2-yl)phenyl]-3H,4H-pyrido[4,3-d]pyrimidin-4-one;
7-(4-tert-butylphenyl)-3-methyl-5-(propan-2-ylamino)-3H,4H-pyrido[4,3-d]pyrimidin-4-one;
7-(4-tert-butylphenyl)-5-(cyclopropylamino)-3-methyl-3H,4H-pyrido[4,3-d]pyrimidin-4-one;
7-(3,4-dimethoxyphenyl)-3-methyl-5-[(pyridin-2-ylmethoxy)amino]-3H,4H-pyrido[4,3-d]pyrimidin-4-one;
7-(4-ethylphenyl)-3-methyl-5-(propan-2-ylamino)-3H,4H-pyrido[4,3-d]pyrimidin-4-one;
5-(cyclopropylamino)-7-(4-ethylphenyl)-3-methyl-3H,4H-pyrido[4,3-d]pyrimidin-4-one;
5-({7-[4-(2-hydroxypropan-2-yl)phenyl]-3-methyl-4-oxo-3H,4H-pyrido[4,3-d]pyrimidin-5-yl}amino)piperidin-2-one;
5-({7-[6-(2-hydroxypropan-2-yl)pyridin-3-yl]-3-methyl-4-oxo-3H,4H-pyrido[4,3-d]pyrimidin-5-yl}amino)piperidin-2-one;
5-{[7-(3,4-dimethoxyphenyl)-3-methyl-4-oxo-3H,4H-pyrido[4,3-d]pyrimidin-5-yl]amino}piperidin-2-one;
N-[(2S)-1-({7-[4-(2-hydroxypropan-2-yl)phenyl]-3-methyl-4-oxo-3H,4H-pyrido[4,3-d]pyrimidin-5-yl}amino)propan-2-yl]methanesulfonamide;
N-[(2S)-1-({7-[6-(2-hydroxypropan-2-yl)pyridin-3-yl]-3-methyl-4-oxo-3H,4H-pyrido[4,3-d]pyrimidin-5-yl}amino)propan-2-yl]methanesulfonamide;
N-[(2S)-1-{[7-(3,4-dimethoxyphenyl)-3-methyl-4-oxo-3H,4H-pyrido[4,3-d]pyrimidin-5-yl]amino}propan-2-yl]methanesulfonamide;
5-(cyclopropylamino)-7-{1H-imidazo[4,5-b]pyridin-6-yl}-3-methyl-3H,4H-pyrido[4,3-d]pyrimidin-4-one;
5-(cyclopropylamino)-3-methyl-7-{2-methyl-1H-imidazo[4,5-b]pyridin-6-yl}-3H,4H-pyrido[4,3-d]pyrimidin-4-one;
5-amino-7-[4-(2-hydroxypropan-2-yl)phenyl]-3-methyl-3H,4H-pyrido[4,3-d]pyrimidin-4-one;
7-[6-(2-hydroxypropan-2-yl)pyridin-3-yl]-5-(2-methoxyethoxy)-3-methyl-3H,4H-pyrido[4,3-d]pyrimidin-4-one;
7-[6-(2-hydroxypropan-2-yl)pyridin-3-yl]-3-methyl-5-[(1-methylpiperidin-4-yl)oxy]-3H,4H-pyrido[4,3-d]pyrimidin-4-one;
5-[5-(cyclopropylamino)-3-methyl-4-oxo-3H,4H-pyrido[4,3-d]pyrimidin-7-yl]-N-methylpyridine-2-sulfonamide;
methyl N-[(2S)-1-({7-[4-(2-hydroxypropan-2-yl)phenyl]-3-methyl-4-oxo-3H,4H-pyrido[4,3-d]pyrimidin-5-yl}amino)propan-2-yl]carbamate;
methyl N-[(2S)-1-({7-[6-(2-hydroxypropan-2-yl)pyridin-3-yl]-3-methyl-4-oxo-3H,4H-pyrido[4,3-d]pyrimidin-5-yl}amino)propan-2-yl]carbamate;
methyl N-[(2S)-1-{[7-(3,4-dimethoxyphenyl)-3-methyl-4-oxo-3H,4H-pyrido[4,3-d]pyrimidin-5-yl]amino}propan-2-yl]carbamate;
5-{[(2R)-1-hydroxybutan-2-yl]amino}-7-[6-(2-hydroxypropan-2-yl)pyridin-3-yl]-3-methyl-3H,4H-pyrido[4,3-d]pyrimidin-4-one;
5-{[(2R)-1-hydroxy-3-methylbutan-2-yl]amino}-7-[6-(2-hydroxypropan-2-yl)pyridin-3-yl]-3-methyl-3H,4H-pyrido[4,3-d]pyrimidin-4-one;
3-({7-[6-(2-hydroxypropan-2-yl)pyridin-3-yl]-3-methyl-4-oxo-3H,4H-pyrido[4,3-d]pyrimidin-5-yl}amino)-1-thiolane-1,1-dione;
7-[6-(2-hydroxypropan-2-yl)pyridin-3-yl]-3-methyl-5-(phenylamino)-3H,4H-pyrido[4,3-d]pyrimidin-4-one;
5-{[1-(2-hydroxyethyl)piperidin-4-yl]amino}-7-[6-(2-hydroxypropan-2-yl)pyridin-3-yl]-3-methyl-3H,4H-pyrido[4,3-d]pyrimidin-4-one;
5-[4-(2-hydroxyethyl)piperazin-1-yl]-7-[6-(2-hydroxypropan-2-yl)pyridin-3-yl]-3-methyl-3H,4H-pyrido[4,3-d]pyrimidin-4-one;
7-[6-(2-hydroxypropan-2-yl)pyridin-3-yl]-3-methyl-5-(oxan-4-ylamino)-3H,4H-pyrido[4,3-d]pyrimidin-4-one;
5-{[1-(4-chlorophenyl)propan-2-yl]amino}-7-[6-(2-hydroxypropan-2-yl)pyridin-3-yl]-3-methyl-3H,4H-pyrido[4,3-d]pyrimidin-4-one;
7-[6-(2-hydroxypropan-2-yl)pyridin-3-yl]-3-methyl-5-[methyl(propan-2-yl)amino]-3H,4H-pyrido[4,3-d]pyrimidin-4-one;
7-[6-(2-hydroxypropan-2-yl)pyridin-3-yl]-3-methyl-5-{[(1S)-1-phenylethyl]amino}-3H,4H-pyrido[4,3-d]pyrimidin-4-one;
5-[(3-aminopropyl)amino]-3-methyl-7-[4-(pyridin-2-yl)piperazin-1-yl]-3H,4H-pyrido[4,3-d]pyrimidin-4-one;
5-[(3-aminopropyl)amino]-3-methyl-7-[6-(morpholin-4-yl)pyridin-3-yl]-3H,4H-pyrido[4,3-d]pyrimidin-4-one;
7-[6-(2-hydroxypropan-2-yl)pyridin-3-yl]-5-[(3-hydroxypropyl)amino]-3-methyl-3H,4H-pyrido[4,3-d]pyrimidin-4-one;
7-[6-(2-hydroxypropan-2-yl)pyridin-3-yl]-3-methyl-5-{[(2S)-pyrrolidin-2-ylmethyl]amino}-3H,4H-pyrido[4,3-d]pyrimidin-4-one;
7-[6-(2-hydroxypropan-2-yl)pyridin-3-yl]-3-methyl-5-[(2-phenylethyl)amino]-3H,4H-pyrido[4,3-d]pyrimidin-4-one;
7-[6-(2-hydroxypropan-2-yl)pyridin-3-yl]-3-methyl-5-[(3R)-pyrrolidin-3-ylamino]-3H,4H-pyrido[4,3-d]pyrimidin-4-one;
5-[(1H-1,3-benzodiazol-2-ylmethyl)amino]-7-[6-(2-hydroxypropan-2-yl)pyridin-3-yl]-3-methyl-3H,4H-pyrido[4,3-d]pyrimidin-4-one;
ethyl 2-({7-[6-(2-hydroxypropan-2-yl)pyridin-3-yl]-3-methyl-4-oxo-3H,4H-pyrido[4,3-d]pyrimidin-5-yl}amino)pyridine-4-carboxylate;
5-{[(1R,2S)-2-hydroxycyclopentyl]amino}-7-[6-(2-hydroxypropan-2-yl)pyridin-3-yl]-3-methyl-3H,4H-pyrido[4,3-d]pyrimidin-4-one;
5-{[(1R,2R)-2-hydroxycyclopentyl]amino}-7-[6-(2-hydroxypropan-2-yl)pyridin-3-yl]-3-methyl-3H,4H-pyrido[4,3-d]pyrimidin-4-one;
5-[(1-hydroxy-2-methylpropan-2-yl)amino]-7-[6-(2-hydroxypropan-2-yl)pyridin-3-yl]-3-methyl-3H,4H-pyrido[4,3-d]pyrimidin-4-one;

methyl 4-({7-[6-(2-hydroxypropan-2-yl)pyridin-3-yl]-3-methyl-4-oxo-3H,4H-pyrido[4,3-d]pyrimidin-5-yl}amino)butanoate;

2-({7-[6-(2-hydroxypropan-2-yl)pyridin-3-yl]-3-methyl-4-oxo-3H,4H-pyrido[4,3-d]pyrimidin-5-yl}amino)pyridine-4-carboxylic acid;

3-[({7-[6-(2-hydroxypropan-2-yl)pyridin-3-yl]-3-methyl-4-oxo-3H,4H-pyrido[4,3-d]pyrimidin-5-yl}amino)methyl]benzoic acid;

4-({7-[6-(2-hydroxypropan-2-yl)pyridin-3-yl]-3-methyl-4-oxo-3H,4H-pyrido[4,3-d]pyrimidin-5-yl}amino)butanoic acid;

7-[6-(2-hydroxypropan-2-yl)pyridin-3-yl]-5-[(3-methoxypropyl)amino]-3-methyl-3H,4H-pyrido[4,3-d]pyrimidin-4-one;

5-[(4-hydroxybutyl)amino]-7-[6-(2-hydroxypropan-2-yl)pyridin-3-yl]-3-methyl-3H,4H-pyrido[4,3-d]pyrimidin-4-one;

7-[6-(2-hydroxypropan-2-yl)pyridin-3-yl]-3-methyl-5-[(oxan-4-ylmethyl)amino]-3H,4H-pyrido[4,3-d]pyrimidin-4-one;

3-({7-[6-(2-hydroxypropan-2-yl)pyridin-3-yl]-3-methyl-4-oxo-3H,4H-pyrido[4,3-d]pyrimidin-5-yl}amino)propanenitrile;

7-[6-(2-hydroxypropan-2-yl)pyridin-3-yl]-3-methyl-5-[(3-methyl-1H-pyrazol-5-yl)amino]-3H,4H-pyrido[4,3-d]pyrimidin-4-one;

7-[6-(2-hydroxypropan-2-yl)pyridin-3-yl]-3-methyl-5-(pyrazin-2-ylamino)-3H,4H-pyrido[4,3-d]pyrimidin-4-one;

5-[4-(hydroxymethyl)piperidin-1-yl]-7-[6-(2-hydroxypropan-2-yl)pyridin-3-yl]-3-methyl-3H,4H-pyrido[4,3-d]pyrimidin-4-one;

5-[3-(hydroxymethyl)piperidin-1-yl]-7-[6-(2-hydroxypropan-2-yl)pyridin-3-yl]-3-methyl-3H,4H-pyrido[4,3-d]pyrimidin-4-one;

5-[4-(2-hydroxyethyl)piperidin-1-yl]-7-[6-(2-hydroxypropan-2-yl)pyridin-3-yl]-3-methyl-3H,4H-pyrido[4,3-d]pyrimidin-4-one;

5-[(furan-3-ylmethyl)amino]-7-[6-(2-hydroxypropan-2-yl)pyridin-3-yl]-3-methyl-3H,4H-pyrido[4,3-d]pyrimidin-4-one;

5-[(2,3-dihydroxypropyl)amino]-7-[6-(2-hydroxypropan-2-yl)pyridin-3-yl]-3-methyl-3H,4H-pyrido[4,3-d]pyrimidin-4-one;

7-[6-(2-hydroxypropan-2-yl)pyridin-3-yl]-5-[(3-methanesulfonylphenyl)amino]-3-methyl-3H,4H-pyrido[4,3-d]pyrimidin-4-one;

7-[6-(2-hydroxypropan-2-yl)pyridin-3-yl]-5-{[(3-methanesulfonylphenyl)methyl]amino}-3-methyl-3H,4H-pyrido[4,3-d]pyrimidin-4-one;

7-[6-(2-hydroxypropan-2-yl)pyridin-3-yl]-5-{[(4-methanesulfonylphenyl)methyl]amino}-3-methyl-3H,4H-pyrido[4,3-d]pyrimidin-4-one;

3-({7-[6-(2-hydroxypropan-2-yl)pyridin-3-yl]-3-methyl-4-oxo-3H,4H-pyrido[4,3-d]pyrimidin-5-yl}amino)benzonitrile;

7-[6-(2-hydroxypropan-2-yl)pyridin-3-yl]-3-methyl-5-{[3-(2H-1,2,3,4-tetrazol-5-yl)phenyl]amino}-3H,4H-pyrido[4,3-d]pyrimidin-4-one;

methyl 2-{7-[6-(2-hydroxypropan-2-yl)pyridin-3-yl]-3-methyl-4-oxo-3H,4H-pyrido[4,3-d]pyrimidin-5-yl}-1,2,3,4-tetrahydroisoquinoline-5-carboxylate;

methyl 2-{7-[6-(2-hydroxypropan-2-yl)pyridin-3-yl]-3-methyl-4-oxo-3H,4H-pyrido[4,3-d]pyrimidin-5-yl}-1,2,3,4-tetrahydroisoquinoline-8-carboxylate;

2-{7-[6-(2-hydroxypropan-2-yl)pyridin-3-yl]-3-methyl-4-oxo-3H,4H-pyrido[4,3-d]pyrimidin-5-yl}-1,2,3,4-tetrahydroisoquinoline-5-carboxylic acid;

2-{7-[6-(2-hydroxypropan-2-yl)pyridin-3-yl]-3-methyl-4-oxo-3H,4H-pyrido[4,3-d]pyrimidin-5-yl}-1,2,3,4-tetrahydroisoquinoline-8-carboxylic acid;

2-{7-[6-(2-hydroxypropan-2-yl)pyridin-3-yl]-3-methyl-4-oxo-3H,4H-pyrido[4,3-d]pyrimidin-5-yl}-1,2,3,4-tetrahydroisoquinoline-7-carboxylic acid;

5-[(3-hydroxy-2,2-dimethylpropyl)amino]-7-[6-(2-hydroxypropan-2-yl)pyridin-3-yl]-3-methyl-3H,4H-pyrido[4,3-d]pyrimidin-4-one;

7-[6-(2-hydroxypropan-2-yl)pyridin-3-yl]-5-[(1H-imidazol-4-ylmethyl)amino]-3-methyl-3H,4H-pyrido[4,3-d]pyrimidin-4-one;

5-[3-methyl-4-oxo-5-(propan-2-ylamino)-3H,4H-pyrido[4,3-d]pyrimidin-7-yl]-2-(morpholin-4-yl)-1-oxidopyridin-1-ium;

7-[6-(2-hydroxypropan-2-yl)pyridin-3-yl]-3-methyl-5-[(1H-1,2,3-triazol-4-ylmethyl)amino]-3H,4H-pyrido[4,3-d]pyrimidin-4-one;

3-methyl-7-[4-(4-methylpiperazin-1-yl)phenyl]-5-[(1H-1,2,3-triazol-4-ylmethyl)amino]-3H,4H-pyrido[4,3-d]pyrimidin-4-one;

5-[7-(hydroxymethyl)-1,2,3,4-tetrahydroisoquinolin-2-yl]-3-methyl-7-[4-(piperazin-1-yl)phenyl]-3H,4H-pyrido[4,3-d]pyrimidin-4-one;

5-[5-(hydroxymethyl)-1,2,3,4-tetrahydroisoquinolin-2-yl]-3-methyl-7-[4-(piperazin-1-yl)phenyl]-3H,4H-pyrido[4,3-d]pyrimidin-4-one;

5-[8-(hydroxymethyl)-1,2,3,4-tetrahydroisoquinolin-2-yl]-3-methyl-7-[4-(piperazin-1-yl)phenyl]-3H,4H-pyrido[4,3-d]pyrimidin-4-one;

5-[(3Z)-3-(hydroxyimino)pyrrolidin-1-yl]-3-methyl-7-[4-(piperazin-1-yl)phenyl]-3H,4H-pyrido[4,3-d]pyrimidin-4-one;

5-[(3S)-3-(hydroxymethyl)pyrrolidin-1-yl]-3-methyl-7-[4-(oxolan-2-ylmethoxy)phenyl]-3H,4H-pyrido[4,3-d]pyrimidin-4-one;

7-(4-{[(2R)-1-benzylpyrrolidin-2-yl]methoxy}phenyl)-5-[(3S)-3-(hydroxymethyl)pyrrolidin-1-yl]-3-methyl-3H,4H-pyrido[4,3-d]pyrimidin-4-one;

7-(4-{[(2S)-1-benzylpyrrolidin-2-yl]methoxy}phenyl)-5-[(3S)-3-(hydroxymethyl)pyrrolidin-1-yl]-3-methyl-3H,4H-pyrido[4,3-d]pyrimidin-4-one;

7-[4-(2-hydroxyethoxy)phenyl]-5-[(3S)-3-(hydroxymethyl)pyrrolidin-1-yl]-3-methyl-3H,4H-pyrido[4,3-d]pyrimidin-4-one;

5-[(3R)-3-aminopyrrolidin-1-yl]-3-methyl-7-[4-(4-methylpiperazin-1-yl)phenyl]-3H,4H-pyrido[4,3-d]pyrimidin-4-one;

5-[(3S)-3-aminopyrrolidin-1-yl]-3-methyl-7-[4-(4-methylpiperazin-1-yl)phenyl]-3H,4H-pyrido[4,3-d]pyrimidin-4-one;

5-[3-(1-hydroxyethyl)pyrrolidin-1-yl]-3-methyl-7-[4-(4-methylpiperazin-1-yl)phenyl]-3H,4H-pyrido[4,3-d]pyrimidin-4-one;

5-[3-(2-hydroxypropan-2-yl)pyrrolidin-1-yl]-3-methyl-7-[4-(4-methylpiperazin-1-yl)phenyl]-3H,4H-pyrido[4,3-d]pyrimidin-4-one;

5-[(3S)-3-(hydroxymethyl)pyrrolidin-1-yl]-3-methyl-7-{4-[(2R)-pyrrolidin-2-ylmethoxy]phenyl}-3H,4H-pyrido[4,3-d]pyrimidin-4-one;

5-[(3S)-3-(hydroxymethyl)pyrrolidin-1-yl]-3-methyl-7-{4-[(2S)-pyrrolidin-2-ylmethoxy]phenyl}-3H,4H-pyrido[4,3-d]pyrimidin-4-one;

4-hydroxy-1-{3-methyl-7-[4-(4-methylpiperazin-1-yl) phenyl]-4-oxo-3H,4H-pyrido[4,3-d]pyrimidin-5-yl}pyrrolidine-3-carboxylic acid;

5-[(3S,4R)-3-hydroxy-4-(hydroxymethyl)pyrrolidin-1-yl]-3-methyl-7-[4-(4-methylpiperazin-1-yl)phenyl]-3H,4H-pyrido[4,3-d]pyrimidin-4-one;

5-[(3S,4S)-3-hydroxy-4-(hydroxymethyl)pyrrolidin-1-yl]-3-methyl-7-[4-(4-methylpiperazin-1-yl)phenyl]-3H,4H-pyrido[4,3-d]pyrimidin-4-one;

5-[(3Z)-3-(hydroxyimino)pyrrolidin-1-yl]-3-methyl-7-[4-(4-methylpiperazin-1-yl)phenyl]-3H,4H-pyrido[4,3-d]pyrimidin-4-one;

5-[9-(hydroxymethyl)-1,4-dioxa-7-azaspiro[4.4]nonan-7-yl]-3-methyl-7-[4-(4-methylpiperazin-1-yl)phenyl]-3H,4H-pyrido[4,3-d]pyrimidin-4-one;

3-methyl-7-[4-(4-methylpiperazin-1-yl)phenyl]-5-(3-propanoylpyrrolidin-1-yl)-3H,4H-pyrido[4,3-d]pyrimidin-4-one;

7-(2,3-dihydro-1,4-benzodioxin-6-yl)-5-[(2-methoxyethyl)amino]-3-methyl-3H,4H-pyrido[4,3-d]pyrimidin-4-one;

7-(3-fluoro-4-methoxyphenyl)-5-[(2-methoxyethyl)amino]-3-methyl-3H,4H-pyrido[4,3-d]pyrimidin-4-one;

2-({3-methyl-7-[4-(morpholin-4-yl)phenyl]-4-oxo-3H, 4H-pyrido[4,3-d]pyrimidin-5-yl}amino)acetonitrile;

3-({3-methyl-7-[4-(morpholin-4-yl)phenyl]-4-oxo-3H, 4H-pyrido[4,3-d]pyrimidin-5-yl}amino)propanenitrile;

3-methyl-7-[4-(morpholin-4-yl)phenyl]-5-[(pyridin-4-ylmethyl)amino]-3H,4H-pyrido[4,3-d]pyrimidin-4-one;

5-[(2-methoxyethyl)amino]-3-methyl-7-[4-(morpholin-4-yl)phenyl]-3H,4H-pyrido[4,3-d]pyrimidin-4-one;

7-(3,4-dimethoxyphenyl)-5-[(2-methoxyethyl)amino]-3-methyl-3H,4H-pyrido[4,3-d]pyrimidin-4-one;

7-[6-(2-hydroxypropan-2-yl)pyridin-3-yl]-3-methyl-5-(1,3-thiazol-2-ylamino)-3H,4H-pyrido[4,3-d]pyrimidin-4-one;

3-methyl-7-[4-(morpholin-4-yl)phenyl]-5-(1,3-thiazol-2-ylamino)-3H,4H-pyrido[4,3-d]pyrimidin-4-one;

7-[6-(2-hydroxypropan-2-yl)pyridin-3-yl]-5-[(2-methanesulfonylethyl)amino]-3-methyl-3H,4H-pyrido[4,3-d]pyrimidin-4-one;

5-[(2-methanesulfonylethyl)amino]-3-methyl-7-[4-(morpholin-4-yl)phenyl]-3H,4H-pyrido[4,3-d]pyrimidin-4-one;

7-[6-(2-hydroxypropan-2-yl)pyridin-3-yl]-3-methyl-5-(pyridin-4-ylamino)-3H,4H-pyrido[4,3-d]pyrimidin-4-one;

3-methyl-7-[4-(morpholin-4-yl)phenyl]-5-{[(1S)-1-phenylethyl]amino}-3H,4H-pyrido[4,3-d]pyrimidin-4-one;

5-[(1-methoxypropan-2-yl)amino]-3-methyl-7-[4-(morpholin-4-yl)phenyl]-3H,4H-pyrido[4,3-d]pyrimidin-4-one;

5-(dimethylamino)-3-methyl-7-[4-(morpholin-4-yl)phenyl]-3H,4H-pyrido[4,3-d]pyrimidin-4-one;

3-methyl-7-[4-(morpholin-4-yl)phenyl]-5-{[(1S)-1-phenylethyl]amino}-1H,2H,3H,4H-pyrido[4,3-d]pyrimidin-4-one;

5-[(1-methoxypropan-2-yl)amino]-3-methyl-7-[4-(morpholin-4-yl)phenyl]-1H,2H,3H,4H-pyrido[4,3-d]pyrimidin-4-one;

3-methyl-7-[4-(morpholin-4-yl)phenyl]-5-(propan-2-ylamino)-3H,4H-pyrido[4,3-d]pyrimidin-4-one;

5-[(3-hydroxypropyl)amino]-3-methyl-7-[4-(morpholin-4-yl)phenyl]-3H,4H-pyrido[4,3-d]pyrimidin-4-one;

5-[(3-methoxypropyl)amino]-3-methyl-7-[4-(morpholin-4-yl)phenyl]-3H,4H-pyrido[4,3-d]pyrimidin-4-one;

5-{[3-(dimethylamino)propyl]amino}-3-methyl-7-[4-(morpholin-4-yl)phenyl]-3H,4H-pyrido[4,3-d]pyrimidin-4-one;

5-[(cyclopropylmethyl)amino]-3-methyl-7-[4-(morpholin-4-yl)phenyl]-3H,4H-pyrido[4,3-d]pyrimidin-4-one;

3-methyl-7-[4-(morpholin-4-yl)phenyl]-5-{[2-(pyridin-4-yl)ethyl]amino}-3H,4H-pyrido[4,3-d]pyrimidin-4-one;

3-methyl-7-[4-(morpholin-4-yl)phenyl]-5-(oxolan-3-ylamino)-3H,4H-pyrido[4,3-d]pyrimidin-4-one;

3-methyl-7-[4-(morpholin-4-yl)phenyl]-5-[(oxan-4-ylmethyl)amino]-3H,4H-pyrido[4,3-d]pyrimidin-4-one;

5-[(2-methoxyethyl)amino]-3-methyl-7-[2-(morpholin-4-yl)pyrimidin-5-yl]-3H,4H-pyrido[4,3-d]pyrimidin-4-one;

3-{5-[(2-methoxyethyl)amino]-3-methyl-4-oxo-3H,4H-pyrido[4,3-d]pyrimidin-7-yl}benzene-1-sulfonamide;

5-[(2-hydroxyethyl)amino]-3-methyl-7-[4-(morpholin-4-yl)phenyl]-3H,4H-pyrido[4,3-d]pyrimidin-4-one;

5-{[2-(dimethylamino)ethyl]amino}-3-methyl-7-[4-(morpholin-4-yl)phenyl]-3H,4H-pyrido[4,3-d]pyrimidin-4-one;

tert-butyl 4-(4-{5-[(2-methoxyethyl)amino]-3-methyl-4-oxo-3H,4H-pyrido[4,3-d]pyrimidin-7-yl}phenyl)piperidine-1-carboxylate;

5-[(2-methoxyethyl)amino]-3-methyl-7-[4-(piperidin-4-yl)phenyl]-3H,4H-pyrido[4,3-d]pyrimidin-4-one;

7-(6-fluoropyridin-3-yl)-5-[(2-methoxyethyl)amino]-3-methyl-3H,4H-pyrido[4,3-d]pyrimidin-4-one;

7-{6-[(2-hydroxyethyl)amino]pyridin-3-yl}-5-[(2-methoxyethyl)amino]-3-methyl-3H,4H-pyrido[4,3-d]pyrimidin-4-one;

7-[6-(4-ethylpiperazin-1-yl)pyridin-3-yl]-5-[(2-methoxyethyl)amino]-3-methyl-3H,4H-pyrido[4,3-d]pyrimidin-4-one;

5-[(2-methoxyethyl)amino]-3-methyl-7-(6-{[2-(morpholin-4-yl)ethyl]amino}pyridin-3-yl)-3H,4H-pyrido[4,3-d]pyrimidin-4-one;

3-methyl-7-[4-(morpholin-4-yl)phenyl]-5-[(3R)-oxolan-3-ylamino]-3H,4H-pyrido[4,3-d]pyrimidin-4-one;

3-methyl-7-[4-(morpholin-4-yl)phenyl]-5-[(3S)-oxolan-3-ylamino]-3H,4H-pyrido[4,3-d]pyrimidin-4-one;

5-{[(2S)-2-hydroxy-2-phenylethyl]amino}-3-methyl-7-[4-(morpholin-4-yl)phenyl]-3H,4H-pyrido[4,3-d]pyrimidin-4-one;

5-{[(3R)-1-methanesulfonylpyrrolidin-3-yl]amino}-3-methyl-7-[4-(morpholin-4-yl)phenyl]-3H,4H-pyrido[4,3-d]pyrimidin-4-one;

5-{[(3R)-1-[2-(dimethylamino)acetyl]pyrrolidin-3-yl]amino}-3-methyl-7-[4-(morpholin-4-yl)phenyl]-3H,4H-pyrido[4,3-d]pyrimidin-4-one;

5-{[(3R)-1-(2-hydroxyacetyl)pyrrolidin-3-yl]amino}-3-methyl-7-[4-(morpholin-4-yl)phenyl]-3H,4H-pyrido[4,3-d]pyrimidin-4-one;

3-methyl-7-[4-(morpholin-4-yl)phenyl]-5-[(3R)-pyrrolidin-3-ylamino]-3H,4H-pyrido[4,3-d]pyrimidin-4-one;

5-{[(1S,2R)-2-hydroxycyclopentyl]amino}-3-methyl-7-[4-(morpholin-4-yl)phenyl]-3H,4H-pyrido[4,3-d]pyrimidin-4-one;

5-{[(1S,2S)-2-hydroxycyclopentyl]amino}-3-methyl-7-[4-(morpholin-4-yl)phenyl]-3H,4H-pyrido[4,3-d]pyrimidin-4-one;

5-{[(1S,2R)-2-hydroxycyclopentyl]amino}-3-methyl-7-[4-(morpholin-4-yl)phenyl]-3H,4H-pyrido[4,3-d]pyrimidin-4-one;

5-{[(1S,2S)-2-hydroxycyclopentyl]amino}-3-methyl-7-[4-(morpholin-4-yl)phenyl]-3H,4H-pyrido[4,3-d]pyrimidin-4-one;

5-{[4-(hydroxymethyl)-1,3-thiazol-2-yl]amino}-3-methyl-7-[4-(4-methylpiperazin-1-yl)phenyl]-3H,4H-pyrido[4,3-d]pyrimidin-4-one;

1-{3-methyl-7-[4-(morpholin-4-yl)phenyl]-4-oxo-3H,4H-pyrido[4,3-d]pyrimidin-5-yl}piperidine-3-carboxamide;

3-methyl-5-[(4-methyl-1,3-thiazol-2-yl)amino]-7-[4-(morpholin-4-yl)phenyl]-3H,4H-pyrido[4,3-d]pyrimidin-4-one;

3-methyl-5-[(5-methyl-1,3-thiazol-2-yl)amino]-7-[4-(morpholin-4-yl)phenyl]-3H,4H-pyrido[4,3-d]pyrimidin-4-one;

3-methyl-7-[4-(morpholin-4-yl)phenyl]-5-[(1,3-thiazol-2-ylmethyl)amino]-3H,4H-pyrido[4,3-d]pyrimidin-4-one;

3-methyl-5-{[(5-methyl-1,2-oxazol-3-yl)methyl]amino}-7-[4-(morpholin-4-yl)phenyl]-3H,4H-pyrido[4,3-d]pyrimidin-4-one;

5-[(1,3-dioxolan-2-ylmethyl)amino]-3-methyl-7-[4-(morpholin-4-yl)phenyl]-3H,4H-pyrido[4,3-d]pyrimidin-4-one;

1-{3-methyl-7-[4-(morpholin-4-yl)phenyl]-4-oxo-3H,4H-pyrido[4,3-d]pyrimidin-5-yl}pyrazolidin-3-one;

7-[6-(2-hydroxypropan-2-yl)pyridin-3-yl]-3-methyl-5-[(3S)-oxolan-3-ylamino]-3H,4H-pyrido[4,3-d]pyrimidin-4-one;

5-(cyclopentylamino)-7-[6-(2-hydroxypropan-2-yl)pyridin-3-yl]-3-methyl-3H,4H-pyrido[4,3-d]pyrimidin-4-one;

7-[4-(morpholin-4-yl)phenyl]-5-(propan-2-ylamino)-3H,4H-pyrido[4,3-d]pyrimidin-4-one;

7-[6-(2-hydroxypropan-2-yl)pyridin-3-yl]-3-methyl-5-[(3R)-oxolan-3-ylamino]-3H,4H-pyrido[4,3-d]pyrimidin-4-one;

5-{[(1R,2S)-2-(hydroxymethyl)cyclopentyl]amino}-7-[6-(2-hydroxypropan-2-yl)pyridin-3-yl]-3-methyl-3H,4H-pyrido[4,3-d]pyrimidin-4-one;

3-methyl-7-[4-(piperazin-1-yl)phenyl]-5-(propan-2-ylamino)-3H,4H-pyrido[4,3-d]pyrimidin-4-one;

3-methyl-7-[4-(4-methylpiperazin-1-yl)phenyl]-5-[(3R)-oxolan-3-ylamino]-3H,4H-pyrido[4,3-d]pyrimidin-4-one;

3-methyl-7-{4-[4-(propan-2-yl)piperazin-1-yl]phenyl}-5-(propan-2-ylamino)-3H,4H-pyrido[4,3-d]pyrimidin-4-one;

3-methyl-7-[4-(4-methylpiperazin-1-yl)phenyl]-5-(propan-2-ylamino)-3H,4H-pyrido[4,3-d]pyrimidin-4-one;

5-[3-(hydroxymethyl)azetidin-1-yl]-7-[6-(2-hydroxypropan-2-yl)pyridin-3-yl]-3-methyl-3H,4H-pyrido[4,3-d]pyrimidin-4-one;

3-methyl-5-[(3R)-oxolan-3-ylamino]-7-[4-(piperazin-1-yl)phenyl]-3H,4H-pyrido[4,3-d]pyrimidin-4-one;

3-methyl-7-[4-(piperidin-4-yl)phenyl]-5-(propan-2-ylamino)-3H,4H-pyrido[4,3-d]pyrimidin-4-one;

5-[(2-hydroxyethyl)amino]-3-methyl-7-[4-(4-methylpiperazin-1-yl)phenyl]-3H,4H-pyrido[4,3-d]pyrimidin-4-one;

5-[(3-hydroxypropyl)amino]-3-methyl-7-[4-(4-methylpiperazin-1-yl)phenyl]-3H,4H-pyrido[4,3-d]pyrimidin-4-one;

7-[6-(2-hydroxypropan-2-yl)pyridin-3-yl]-5-{[(2R)-1-hydroxypropan-2-yl]amino}-3-methyl-3H,4H-pyrido[4,3-d]pyrimidin-4-one;

7-[6-(2-hydroxypropan-2-yl)pyridin-3-yl]-5-{[(2S)-1-hydroxypropan-2-yl]amino}-3-methyl-3H,4H-pyrido[4,3-d]pyrimidin-4-one;

5-[(2-hydroxyethyl)amino]-3-methyl-7-[4-(piperidin-4-yl)phenyl]-3H,4H-pyrido[4,3-d]pyrimidin-4-one;

5-[(3-hydroxypropyl)amino]-3-methyl-7-[4-(piperidin-4-yl)phenyl]-3H,4H-pyrido[4,3-d]pyrimidin-4-one;

5-{[(2R)-1-hydroxypropan-2-yl]amino}-3-methyl-7-[4-(4-methylpiperazin-1-yl)phenyl]-3H,4H-pyrido[4,3-d]pyrimidin-4-one;

5-{[(2S)-1-hydroxypropan-2-yl]amino}-3-methyl-7-[4-(4-methylpiperazin-1-yl)phenyl]-3H,4H-pyrido[4,3-d]pyrimidin-4-one;

5-[(2-hydroxyethyl)amino]-3-methyl-7-[4-(piperazin-1-yl)phenyl]-3H,4H-pyrido[4,3-d]pyrimidin-4-one;

5-[(3-hydroxypropyl)amino]-3-methyl-7-[4-(piperazin-1-yl)phenyl]-3H,4H-pyrido[4,3-d]pyrimidin-4-one;

5-{[(2R)-1-hydroxypropan-2-yl]amino}-3-methyl-7-[4-(piperazin-1-yl)phenyl]-3H,4H-pyrido[4,3-d]pyrimidin-4-one;

5-{[(2S)-1-hydroxypropan-2-yl]amino}-3-methyl-7-[4-(piperazin-1-yl)phenyl]-3H,4H-pyrido[4,3-d]pyrimidin-4-one;

5-(3-hydroxyazetidin-1-yl)-7-[6-(2-hydroxypropan-2-yl)pyridin-3-yl]-3-methyl-3H,4H-pyrido[4,3-d]pyrimidin-4-one;

1-{7-[6-(2-hydroxypropan-2-yl)pyridin-3-yl]-3-methyl-4-oxo-3H,4H-pyrido[4,3-d]pyrimidin-5-yl}azetidin-3-one;

7-[6-(2-hydroxypropan-2-yl)pyridin-3-yl]-3-methyl-5-{2-oxa-6-azaspiro[3.3]heptan-6-yl}-3H,4H-pyrido[4,3-d]pyrimidin-4-one;

7-[6-(2-hydroxypropan-2-yl)pyridin-3-yl]-5-[(3R)-3-hydroxypyrrolidin-1-yl]-3-methyl-3H,4H-pyrido[4,3-d]pyrimidin-4-one;

5-[(3R)-3-(hydroxymethyl)pyrrolidin-1-yl]-7-[6-(2-hydroxypropan-2-yl)pyridin-3-yl]-3-methyl-3H,4H-pyrido[4,3-d]pyrimidin-4-one;

5-[(3S)-3-(hydroxymethyl)pyrrolidin-1-yl]-7-[6-(2-hydroxypropan-2-yl)pyridin-3-yl]-3-methyl-3H,4H-pyrido[4,3-d]pyrimidin-4-one;

5-[(3R)-3-(hydroxymethyl)pyrrolidin-1-yl]-3-methyl-7-[4-(4-methylpiperazin-1-yl)phenyl]-3H,4H-pyrido[4,3-d]pyrimidin-4-one;

5-[(3S)-3-(hydroxymethyl)pyrrolidin-1-yl]-3-methyl-7-[4-(4-methylpiperazin-1-yl)phenyl]-3H,4H-pyrido[4,3-d]pyrimidin-4-one;

7-[4-(azetidin-3-yl)phenyl]-3-methyl-5-(propan-2-ylamino)-3H,4H-pyrido[4,3-d]pyrimidin-4-one;

7-[4-(azetidin-3-yl)phenyl]-3-methyl-5-[(3R)-oxolan-3-ylamino]-3H,4H-pyrido[4,3-d]pyrimidin-4-one;

5-[(3R)-3-(hydroxymethyl)pyrrolidin-1-yl]-3-methyl-7-{4-[4-(propan-2-yl)piperazin-1-yl]phenyl}-3H,4H-pyrido[4,3-d]pyrimidin-4-one;

5-[(3S)-3-(hydroxymethyl)pyrrolidin-1-yl]-3-methyl-7-{4-[4-(propan-2-yl)piperazin-1-yl]phenyl}-3H,4H-pyrido[4,3-d]pyrimidin-4-one;

3-methyl-5-[(3R)-oxolan-3-ylamino]-7-{4-[4-(propan-2-yl)piperazin-1-yl]phenyl}-3H,4H-pyrido[4,3-d]pyrimidin-4-one;

5-{[(2R)-1-hydroxypropan-2-yl]amino}-3-methyl-7-{4-[4-(propan-2-yl)piperazin-1-yl]phenyl}-3H,4H-pyrido[4,3-d]pyrimidin-4-one;

5-{[(2R)-1-hydroxypropan-2-yl]amino}-3-methyl-7-[4-(morpholin-4-yl)phenyl]-3H,4H-pyrido[4,3-d]pyrimidin-4-one;

5-[(3R)-3-(hydroxymethyl)pyrrolidin-1-yl]-3-methyl-7-[4-(morpholin-4-yl)phenyl]-3H,4H-pyrido[4,3-d]pyrimidin-4-one;
5-[(3S)-3-(hydroxymethyl)pyrrolidin-1-yl]-3-methyl-7-[4-(morpholin-4-yl)phenyl]-3H,4H-pyrido[4,3-d]pyrimidin-4-one;
3-methyl-5-[(3R)-oxolan-3-ylamino]-7-[4-(piperidin-4-yl)phenyl]-3H,4H-pyrido[4,3-d]pyrimidin-4-one;
5-[(3R)-3-(hydroxymethyl)pyrrolidin-1-yl]-3-methyl-7-[4-(piperidin-4-yl)phenyl]-3H,4H-pyrido[4,3-d]pyrimidin-4-one;
5-[(3S)-3-(hydroxymethyl)pyrrolidin-1-yl]-3-methyl-7-[4-(piperidin-4-yl)phenyl]-3H,4H-pyrido[4,3-d]pyrimidin-4-one;
3-methyl-7-[4-(4-methylpiperazin-1-yl)phenyl]-5-[(oxolan-3-ylmethyl)amino]-3H,4H-pyrido[4,3-d]pyrimidin-4-one;
5-[(3R)-3-hydroxypyrrolidin-1-yl]-3-methyl-7-[4-(4-methylpiperazin-1-yl)phenyl]-3H,4H-pyrido[4,3-d]pyrimidin-4-one;
5-[(3S,4S)-3,4-dihydroxypyrrolidin-1-yl]-3-methyl-7-[4-(4-methylpiperazin-1-yl)phenyl]-3H,4H-pyrido[4,3-d]pyrimidin-4-one;
3-methyl-7-[4-(4-methylpiperazin-1-yl)phenyl]-5-(pyrrolidin-1-yl)-3H,4H-pyrido[4,3-d]pyrimidin-4-one;
5-[3-(dimethylamino)pyrrolidin-1-yl]-3-methyl-7-[4-(4-methylpiperazin-1-yl)phenyl]-3H,4H-pyrido[4,3-d]pyrimidin-4-one;
5-[(3R)-3-fluoropyrrolidin-1-yl]-3-methyl-7-[4-(4-methylpiperazin-1-yl)phenyl]-3H,4H-pyrido[4,3-d]pyrimidin-4-one;
3-methyl-7-[4-(4-methylpiperazin-1-yl)phenyl]-5-{[(2R)-oxolan-2-ylmethyl]amino}-3H,4H-pyrido[4,3-d]pyrimidin-4-one;
5-[(3S)-3-(hydroxymethyl)pyrrolidin-1-yl]-3-methyl-7-[4-(piperazin-1-yl)phenyl]-3H,4H-pyrido[4,3-d]pyrimidin-4-one;
5-{[(1R,2S)-2-(hydroxymethyl)cyclopentyl]amino}-3-methyl-7-[4-(4-methylpiperazin-1-yl)phenyl]-3H,4H-pyrido[4,3-d]pyrimidin-4-one;
5-{5-methanesulfonyl-octahydropyrrolo[3,4-c]pyrrol-2-yl}-3-methyl-7-[4-(4-methylpiperazin-1-yl)phenyl]-3H,4H-pyrido[4,3-d]pyrimidin-4-one;
5-{[(1R,2S)-2-(hydroxymethyl)cyclohexyl]amino}-3-methyl-7-[4-(4-methylpiperazin-1-yl)phenyl]-3H,4H-pyrido[4,3-d]pyrimidin-4-one;
1-{3-methyl-7-[4-(4-methylpiperazin-1-yl)phenyl]-4-oxo-3H,4H-pyrido[4,3-d]pyrimidin-5-yl}piperidine-3-carboxamide;
5-(3-hydroxypiperidin-1-yl)-3-methyl-7-[4-(4-methylpiperazin-1-yl)phenyl]-3H,4H-pyrido[4,3-d]pyrimidin-4-one;
7-[4-(4-ethylpiperazin-1-yl)phenyl]-5-[(3S)-3-(hydroxymethyl)pyrrolidin-1-yl]-3-methyl-3H,4H-pyrido[4,3-d]pyrimidin-4-one;
[(3S)-1-{3-methyl-7-[4-(4-methylpiperazin-1-yl)phenyl]-4-oxo-3H,4H-pyrido[4,3-d]pyrimidin-5-yl}pyrrolidin-3-yl]methyl sulfamate;
5-[3-(hydroxymethyl)azetidin-1-yl]-3-methyl-7-[4-(4-methylpiperazin-1-yl)phenyl]-3H,4H-pyrido[4,3-d]pyrimidin-4-one;
5-{[(1R,2R)-2-(hydroxymethyl)-1-methylcyclopentyl]amino}-3-methyl-7-[4-(4-methylpiperazin-1-yl)phenyl]-3H,4H-pyrido[4,3-d]pyrimidin-4-one;
3-methyl-7-[4-(4-methylpiperazin-1-yl)phenyl]-5-{2-oxa-6-azaspiro[3.3]heptan-6-yl}-3H,4H-pyrido[4,3-d]pyrimidin-4-one;
3-methyl-7-[4-(morpholin-4-yl)phenyl]-5-{[(2R)-oxolan-2-ylmethyl]amino}-3H,4H-pyrido[4,3-d]pyrimidin-4-one;
7-[4-(4-ethylpiperazin-1-yl)phenyl]-3-methyl-5-[(3R)-oxolan-3-ylamino]-3H,4H-pyrido[4,3-d]pyrimidin-4-one;
7-[4-(4-ethylpiperazin-1-yl)phenyl]-5-[(2-hydroxyethyl)amino]-3-methyl-3H,4H-pyrido[4,3-d]pyrimidin-4-one;
7-[4-(4-ethylpiperazin-1-yl)phenyl]-5-[(3-hydroxypropyl)amino]-3-methyl-3H,4H-pyrido[4,3-d]pyrimidin-4-one;
7-[4-(4-ethylpiperazin-1-yl)phenyl]-5-{[(2R)-1-hydroxypropan-2-yl]amino}-3-methyl-3H,4H-pyrido[4,3-d]pyrimidin-4-one;
7-[4-(1-ethylpiperidin-4-yl)phenyl]-3-methyl-5-(propan-2-ylamino)-3H,4H-pyrido[4,3-d]pyrimidin-4-one;
7-[4-(1-ethylpiperidin-4-yl)phenyl]-5-[(2-hydroxyethyl)amino]-3-methyl-3H,4H-pyrido[4,3-d]pyrimidin-4-one;
7-[4-(1-ethylpiperidin-4-yl)phenyl]-5-[(3-hydroxypropyl)amino]-3-methyl-3H,4H-pyrido[4,3-d]pyrimidin-4-one;
7-[4-(1-ethylpiperidin-4-yl)phenyl]-3-methyl-5-[(3R)-oxolan-3-ylamino]-3H,4H-pyrido[4,3-d]pyrimidin-4-one;
7-[4-(1-ethylpiperidin-4-yl)phenyl]-5-[(3S)-3-(hydroxymethyl)pyrrolidin-1-yl]-3-methyl-3H,4H-pyrido[4,3-d]pyrimidin-4-one;
7-{4-[4-(2-hydroxyacetyl)piperazin-1-yl]phenyl}-3-methyl-5-(propan-2-ylamino)-3H,4H-pyrido[4,3-d]pyrimidin-4-one;
7-(4-{4-[2-(ethylamino)acetyl]piperazin-1-yl}phenyl)-3-methyl-5-(propan-2-ylamino)-3H,4H-pyrido[4,3-d]pyrimidin-4-one;
5-[(3S)-3-(azidomethyl)pyrrolidin-1-yl]-3-methyl-7-[4-(4-methylpiperazin-1-yl)phenyl]-3H,4H-pyrido[4,3-d]pyrimidin-4-one;
7-[4-(1-ethylazetidin-3-yl)phenyl]-3-methyl-5-(propan-2-ylamino)-3H,4H-pyrido[4,3-d]pyrimidin-4-one;
7-[4-(1-ethylazetidin-3-yl)phenyl]-3-methyl-5-[(3R)-oxolan-3-ylamino]-3H,4H-pyrido[4,3-d]pyrimidin-4-one;
5-[(3S)-3-(hydroxymethyl)pyrrolidin-1-yl]-7-{4-[4-(2-methanesulfonylethyl)piperazin-1-yl]phenyl}-3-methyl-3H,4H-pyrido[4,3-d]pyrimidin-4-one;
5-[(3S)-3-(hydroxymethyl)pyrrolidin-1-yl]-3-methyl-7-{4-[(2R)-2-methylmorpholin-4-yl]phenyl}-3H,4H-pyrido[4,3-d]pyrimidin-4-one;
7-{4-[4-(2-hydroxyacetyl)piperazin-1-yl]phenyl}-5-[(3S)-3-(hydroxymethyl)pyrrolidin-1-yl]-3-methyl-3H,4H-pyrido[4,3-d]pyrimidin-4-one;
7-{4-[(2R,6S)-2,6-dimethylmorpholin-4-yl]phenyl}-5-[(3S)-3-(hydroxymethyl)pyrrolidin-1-yl]-3-methyl-3H,4H-pyrido[4,3-d]pyrimidin-4-one;
7-[4-(4-cyclopropylpiperazin-1-yl)phenyl]-5-[(3S)-3-(hydroxymethyl)pyrrolidin-1-yl]-3-methyl-3H,4H-pyrido[4,3-d]pyrimidin-4-one;
4-(4-{5-[(3S)-3-(hydroxymethyl)pyrrolidin-1-yl]-3-methyl-4-oxo-3H,4H-pyrido[4,3-d]pyrimidin-7-yl}phenyl)-1,4-thiomorpholine-1,1-dione;
7-(4-{4-[2-(ethylamino)acetyl]piperazin-1-yl}phenyl)-5-[(3S)-3-(hydroxymethyl)pyrrolidin-1-yl]-3-methyl-3H,4H-pyrido[4,3-d]pyrimidin-4-one;
5-[(3S)-3-(methanesulfonylmethyl)pyrrolidin-1-yl]-3-methyl-7-[4-(4-methylpiperazin-1-yl)phenyl]-3H,4H-pyrido[4,3-d]pyrimidin-4-one;

5-[(3S)-3-(hydroxymethyl)piperidin-1-yl]-3-methyl-7-[4-(morpholin-4-yl)phenyl]-3H,4H-pyrido[4,3-d]pyrimidin-4-one;

5-[(3R)-3-(hydroxymethyl)piperidin-1-yl]-3-methyl-7-[4-(morpholin-4-yl)phenyl]-3H,4H-pyrido[4,3-d]pyrimidin-4-one;

7-[3-fluoro-4-(morpholin-4-yl)phenyl]-5-[(3S)-3-(hydroxymethyl)pyrrolidin-1-yl]-3-methyl-3H,4H-pyrido[4,3-d]pyrimidin-4-one;

7-[3-chloro-4-(morpholin-4-yl)phenyl]-5-[(3S)-3-(hydroxymethyl)pyrrolidin-1-yl]-3-methyl-3H,4H-pyrido[4,3-d]pyrimidin-4-one;

7-[2-chloro-4-(morpholin-4-yl)phenyl]-5-[(3S)-3-(hydroxymethyl)pyrrolidin-1-yl]-3-methyl-3H,4H-pyrido[4,3-d]pyrimidin-4-one;

5-[(1S,4S)-4-(hydroxymethyl)-2-azabicyclo[2.2.1]heptan-2-yl]-3-methyl-7-[4-(morpholin-4-yl)phenyl]-3H,4H-pyrido[4,3-d]pyrimidin-4-one;

5-[(3S)-3-(hydroxymethyl)pyrrolidin-1-yl]-3-methyl-7-[4-(morpholin-4-yl)phenyl]-3H,4H-pyrido[4,3-d]pyrimidin-4-one;

5-[(3S)-3-(hydroxymethyl)pyrrolidin-1-yl]-7-[4-(morpholin-4-yl)phenyl]-3H,4H-pyrido[4,3-d]pyrimidin-4-one;

7-[4-(4-ethylpiperazin-1-yl)-3-fluorophenyl]-5-[(3S)-3-(hydroxymethyl)pyrrolidin-1-yl]-3-methyl-3H,4H-pyrido[4,3-d]pyrimidin-4-one;

5-{[(1S,3S)-3-hydroxycyclopentyl]amino}-3-methyl-7-[4-(morpholin-4-yl)phenyl]-3H,4H-pyrido[4,3-d]pyrimidin-4-one;

5-{[(1R,3R)-3-hydroxycyclopentyl]amino}-3-methyl-7-[4-(morpholin-4-yl)phenyl]-3H,4H-pyrido[4,3-d]pyrimidin-4-one;

5-{[(1R,3S)-3-hydroxycyclopentyl]amino}-3-methyl-7-[4-(morpholin-4-yl)phenyl]-3H,4H-pyrido[4,3-d]pyrimidin-4-one;

5-{[(1S,3R)-3-hydroxycyclopentyl]amino}-3-methyl-7-[4-(morpholin-4-yl)phenyl]-3H,4H-pyrido[4,3-d]pyrimidin-4-one;

5-[(3R)-3-hydroxypyrrolidin-1-yl]-3-methyl-7-[4-(morpholin-4-yl)phenyl]-3H,4H-pyrido[4,3-d]pyrimidin-4-one;

5-[3-(hydroxymethyl)azetidin-1-yl]-3-methyl-7-[4-(morpholin-4-yl)phenyl]-3H,4H-pyrido[4,3-d]pyrimidin-4-one;

5-[3-(hydroxymethyl)piperidin-1-yl]-3-methyl-7-[4-(4-methylpiperazin-1-yl)phenyl]-3H,4H-pyrido[4,3-d]pyrimidin-4-one;

5-[(3R)-3-(hydroxymethyl)piperidin-1-yl]-3-methyl-7-[4-(4-methylpiperazin-1-yl)phenyl]-3H,4H-pyrido[4,3-d]pyrimidin-4-one;

2-({3-methyl-4-oxo-7-[4-(piperidin-4-yl)phenyl]-3H,4H-pyrido[4,3-d]pyrimidin-5-yl}amino)ethyl 2,2,2-trifluoroacetate;

3-({3-methyl-4-oxo-7-[4-(piperidin-4-yl)phenyl]-3H,4H-pyrido[4,3-d]pyrimidin-5-yl}amino)propyl 2,2,2-trifluoroacetate;

7-[6-(2-hydroxypropan-2-yl)pyridin-3-yl]-5-[(3S)-3-hydroxypyrrolidin-1-yl]-3-methyl-3H,4H-pyrido[4,3-d]pyrimidin-4-one;

3-(2-fluoroethyl)-7-[4-(morpholin-4-yl)phenyl]-5-(propan-2-ylamino)-3H,4H-pyrido[4,3-d]pyrimidin-4-one;

5-{[(1R,2R)-2-(hydroxymethyl)cyclohexyl]amino}-3-methyl-7-[4-(4-methylpiperazin-1-yl)phenyl]-3H,4H-pyrido[4,3-d]pyrimidin-4-one;

5-[(3S)-3-(methoxymethyl)pyrrolidin-1-yl]-3-methyl-7-[4-(4-methylpiperazin-1-yl)phenyl]-3H,4H-pyrido[4,3-d]pyrimidin-4-one;

3-methyl-7-[4-(4-methylpiperazin-1-yl)phenyl]-5-[(3S)-3-[(methylsulfanyl)methyl]pyrrolidin-1-yl]-3H,4H-pyrido[4,3-d]pyrimidin-4-one;

5-[(3S)-3-hydroxypyrrolidin-1-yl]-3-methyl-7-[4-(morpholin-4-yl)phenyl]-3H,4H-pyrido[4,3-d]pyrimidin-4-one;

N-ethyl-3-[3-methyl-4-oxo-5-(propan-2-ylamino)-3H,4H-pyrido[4,3-d]pyrimidin-7-yl]benzene-1-sulfonamide;

5-({7-[4-(2-hydroxypropan-2-yl)phenyl]-3-methyl-4-oxo-3H,4H-pyrido[4,3-d]pyrimidin-5-yl}amino)piperidin-2-one;

5-({7-[4-(2-hydroxypropan-2-yl)phenyl]-3-methyl-4-oxo-3H,4H-pyrido[4,3-d]pyrimidin-5-yl}amino)piperidin-2-one;

7-[6-(2-hydroxypropan-2-yl)pyridin-3-yl]-3-methyl-5-(pyridin-2-ylamino)-3H,4H-pyrido[4,3-d]pyrimidin-4-one;

3-methyl-5,7-bis[4-(morpholin-4-yl)phenyl]-3H,4H-pyrido[4,3-d]pyrimidin-4-one;

N-(2-hydroxy-5-{5-[(2-methoxyethyl)amino]-3-methyl-4-oxo-3H,4H-pyrido[4,3-d]pyrimidin-7-yl}phenyl)formamide;

5-[(2-methoxyethyl)amino]-3-methyl-7-(2-methyl-1,3-benzoxazol-6-yl)-3H,4H-pyrido[4,3-d]pyrimidin-4-one;

N-(2-hydroxy-4-{5-[(2-methoxyethyl)amino]-3-methyl-4-oxo-3H,4H-pyrido[4,3-d]pyrimidin-7-yl}phenyl)acetamide;

5-{[4-(hydroxymethyl)-1,3-thiazol-2-yl]amino}-3-methyl-7-[4-(morpholin-4-yl)phenyl]-3H,4H-pyrido[4,3-d]pyrimidin-4-one;

(3R)-3-({3-methyl-7-[4-(morpholin-4-yl)phenyl]-4-oxo-3H,4H-pyrido[4,3-d]pyrimidin-5-yl}amino)pyrrolidine-1-carboxamide;

3-methyl-7-{4-[4-(morpholin-4-yl)cyclohexyl]phenyl}-5-[(3R)-oxolan-3-ylamino]-3H,4H-pyrido[4,3-d]pyrimidin-4-one;

5-[(3S)-3-(hydroxymethyl)pyrrolidin-1-yl]-3-methyl-7-{4-[4-(morpholin-4-yl)cyclohexyl]phenyl}-3H,4H-pyrido[4,3-d]pyrimidin-4-one;

3-methyl-7-(1-methyl-1H-pyrazol-4-yl)-5-[(3R)-oxolan-3-ylamino]-3H,4H-pyrido[4,3-d]pyrimidin-4-one;

7-[4-(4-hydroxy-4-methylpiperidin-1-yl)phenyl]-3-methyl-5-[(3R)-oxolan-3-ylamino]-3H,4H-pyrido[4,3-d]pyrimidin-4-one;

5-[(4-aminocyclohexyl)amino]-3-methyl-7-[4-(morpholin-4-yl)phenyl]-3H,4H-pyrido[4,3-d]pyrimidin-4-one;

5-[(4-aminocyclohexyl)amino]-7-[4-(4-hydroxy-4-methylpiperidin-1-yl)phenyl]-3-methyl-3H,4H-pyrido[4,3-d]pyrimidin-4-one;

5-[(4-aminocyclohexyl)amino]-3-methyl-7-[4-(morpholin-4-yl)phenyl]-3H,4H-pyrido[4,3-d]pyrimidin-4-one;

N-[4-({3-methyl-7-[4-(morpholin-4-yl)phenyl]-4-oxo-3H,4H-pyrido[4,3-d]pyrimidin-5-yl}amino)cyclohexyl]methanesulfonamide;

5-[(4-hydroxycyclohexyl)amino]-3-methyl-7-(pyrazin-2-ylamino)-3H,4H-pyrido[4,3-d]pyrimidin-4-one;

5-[(4-hydroxycyclohexyl)amino]-3-methyl-7-[(4-methylpyridin-2-yl)amino]-3H,4H-pyrido[4,3-d]pyrimidin-4-one;

4-({3-methyl-7-[4-(morpholin-4-yl)phenyl]-4-oxo-3H,4H-pyrido[4,3-d]pyrimidin-5-yl}amino)cyclohexane-1-carboxylic acid;

4-({3-methyl-7-[4-(morpholin-4-yl)phenyl]-4-oxo-3H,4H-pyrido[4,3-d]pyrimidin-5-yl}amino)cyclohexane-1-carboxamide;

5-[5-(hydroxymethyl)thiophen-2-yl]-3-methyl-7-[4-(morpholin-4-yl)phenyl]-3H,4H-pyrido[4,3-d]pyrimidin-4-one;

5-[5-(hydroxymethyl)furan-2-yl]-3-methyl-7-[4-(morpholin-4-yl)phenyl]-3H,4H-pyrido[4,3-d]pyrimidin-4-one;

5-[(3Z)-3-(methoxyimino)pyrrolidin-1-yl]-3-methyl-7-[4-(morpholin-4-yl)phenyl]-3H,4H-pyrido[4,3-d]pyrimidin-4-one;

5-[(3R)-3-(2-hydroxyethyl)pyrrolidin-1-yl]-3-methyl-7-[4-(morpholin-4-yl)phenyl]-3H,4H-pyrido[4,3-d]pyrimidin-4-one;

5-{[(2S)-2,3-dihydroxypropyl]amino}-3-methyl-7-[4-(morpholin-4-yl)phenyl]-3H,4H-pyrido[4,3-d]pyrimidin-4-one;

5-{[(2R)-2,3-dihydroxypropyl]amino}-3-methyl-7-[4-(morpholin-4-yl)phenyl]-3H,4H-pyrido[4,3-d]pyrimidin-4-one;

5-[4-(hydroxymethyl)furan-2-yl]-3-methyl-7-[4-(morpholin-4-yl)phenyl]-3H,4H-pyrido[4,3-d]pyrimidin-4-one;

5-[(3R)-3-(2-hydroxyethyl)pyrrolidin-1-yl]-3-methyl-7-[4-(4-methylpiperazin-1-yl)phenyl]-3H,4H-pyrido[4,3-d]pyrimidin-4-one;

7-[4-(4-cyclopropylpiperazin-1-yl)phenyl]-5-[(3R)-3-(2-hydroxyethyl)pyrrolidin-1-yl]-3-methyl-3H,4H-pyrido[4,3-d]pyrimidin-4-one;

5-[(3R)-3-(2-hydroxyethyl)pyrrolidin-1-yl]-3-methyl-7-{4-[(2R)-2-methylmorpholin-4-yl]phenyl}-3H,4H-pyrido[4,3-d]pyrimidin-4-one;

7-[1-(2-hydroxyethyl)-1H-pyrazol-4-yl]-5-[(2-methoxyethyl)amino]-3-methyl-3H,4H-pyrido[4,3-d]pyrimidin-4-one;

5-{[2-(1H-imidazol-4-yl)ethyl]amino}-3-methyl-7-[4-(morpholin-4-yl)phenyl]-3H,4H-pyrido[4,3-d]pyrimidin-4-one;

5-{1-azabicyclo[2.2.2]octan-3-ylamino}-3-methyl-7-[4-(morpholin-4-yl)phenyl]-3H,4H-pyrido[4,3-d]pyrimidin-4-one;

5-{[4-(2-hydroxyethyl)-1,3-thiazol-2-yl]amino}-3-methyl-7-[4-(morpholin-4-yl)phenyl]-3H,4H-pyrido[4,3-d]pyrimidin-4-one;

5-(2-methoxyethoxy)-3-methyl-7-[4-(morpholin-4-yl)phenyl]-3H,4H-pyrido[4,3-d]pyrimidin-4-one;

3-methyl-7-[4-(morpholin-4-yl)phenyl]-5-[2-(1H-pyrazol-4-yl)ethoxy]-3H,4H-pyrido[4,3-d]pyrimidin-4-one;

3-methyl-7-[4-(morpholin-4-yl)phenyl]-5-[2-(1H-1,2,3-triazol-4-yl)ethoxy]-3H,4H-pyrido[4,3-d]pyrimidin-4-one;

5-(2-aminoethoxy)-3-methyl-7-[4-(morpholin-4-yl)phenyl]-3H,4H-pyrido[4,3-d]pyrimidin-4-one;

5-(3-aminopropoxy)-3-methyl-7-[4-(morpholin-4-yl)phenyl]-3H,4H-pyrido[4,3-d]pyrimidin-4-one;

5-[2-(1H-imidazol-1-yl)ethoxy]-3-methyl-7-[4-(morpholin-4-yl)phenyl]-3H,4H-pyrido[4,3-d]pyrimidin-4-one;

5-[(4-aminocyclohexyl)oxy]-3-methyl-7-[4-(morpholin-4-yl)phenyl]-3H,4H-pyrido[4,3-d]pyrimidin-4-one;

5-(2-hydroxyethoxy)-3-methyl-7-[4-(morpholin-4-yl)phenyl]-3H,4H-pyrido[4,3-d]pyrimidin-4-one;

3-methyl-7-[4-(morpholin-4-yl)phenyl]-5-[(3S)-pyrrolidin-3-ylmethoxy]-3H,4H-pyrido[4,3-d]pyrimidin-4-one;

3-methyl-7-[4-(4-methylpiperazin-1-yl)phenyl]-5-[2-(1H,1,2,3-triazol-4-yl)ethoxy]-3H,4H-pyrido[4,3-d]pyrimidin-4-one;

3-methyl-7-[4-(morpholin-4-yl)phenyl]-5-{2-[3-(trifluoromethyl)-1H-pyrazol-4-yl]ethoxy}-3H,4H-pyrido[4,3-d]pyrimidin-4-one;

3-methyl-5-(propan-2-ylamino)-7-{4-[4-(pyrrolidin-1-yl)piperidin-1-yl]phenyl}-3H,4H-pyrido[4,3-d]pyrimidin-4-one;

3-methyl-5-[(3R)-oxolan-3-ylamino]-7-{4-[4-(pyrrolidin-1-yl)piperidin-1-yl]phenyl}-3H,4H-pyrido[4,3-d]pyrimidin-4-one;

5-[(3S)-3-(hydroxymethyl)pyrrolidin-1-yl]-3-methyl-7-{4-[4-(pyrrolidin-1-yl)piperidin-1-yl]phenyl}-3H,4H-pyrido[4,3-d]pyrimidin-4-one;

7-{4-[(3S)-3-hydroxypyrrolidin-1-yl]phenyl}-3-methyl-5-(propan-2-ylamino)-3H,4H-pyrido[4,3-d]pyrimidin-4-one;

7-{4-[(3S)-3-hydroxypyrrolidin-1-yl]phenyl}-3-methyl-5-[(3R)-oxolan-3-ylamino]-3H,4H-pyrido[4,3-d]pyrimidin-4-one;

5-{3-methyl-4-oxo-5-[(3R)-oxolan-3-ylamino]-3H,4H-pyrido[4,3-d]pyrimidin-7-yl}-2,3-dihydro-1H-indol-2-one;

5-{5-[(3S)-3-(hydroxymethyl)pyrrolidin-1-yl]-3-methyl-4-oxo-3H,4H-pyrido[4,3-d]pyrimidin-7-yl}-2,3-dihydro-1H-indol-2-one;

N-[(1R)-1-{4-[3-methyl-4-oxo-5-(propan-2-ylamino)-3H,4H-pyrido[4,3-d]pyrimidin-7-yl]phenyl}ethyl]methanesulfonamide;

N-[(1R)-1-(4-{5-[(3S)-3-(hydroxymethyl)pyrrolidin-1-yl]-3-methyl-4-oxo-3H,4H-pyrido[4,3-d]pyrimidin-7-yl}phenyl)ethyl]methanesulfonamide;

N-[(1S)-1-{4-[3-methyl-4-oxo-5-(propan-2-ylamino)-3H,4H-pyrido[4,3-d]pyrimidin-7-yl]phenyl}ethyl]acetamide;

N-[(1S)-1-(4-{5-[(3S)-3-(hydroxymethyl)pyrrolidin-1-yl]-3-methyl-4-oxo-3H,4H-pyrido[4,3-d]pyrimidin-7-yl}phenyl)ethyl]acetamide;

5-{[(1R,3R)-3-(hydroxymethyl)cyclopentyl]amino}-3-methyl-7-[4-(morpholin-4-yl)phenyl]-3H,4H-pyrido[4,3-d]pyrimidin-4-one;

5-{[(1S,3R)-3-(hydroxymethyl)cyclopentyl]amino}-3-methyl-7-[4-(morpholin-4-yl)phenyl]-3H,4H-pyrido[4,3-d]pyrimidin-4-one;

5-{[(1R,3S)-3-(hydroxymethyl)cyclopentyl]amino}-3-methyl-7-[4-(morpholin-4-yl)phenyl]-3H,4H-pyrido[4,3-d]pyrimidin-4-one;

5-{[(1S,3S)-3-(hydroxymethyl)cyclopentyl]amino}-3-methyl-7-[4-(morpholin-4-yl)phenyl]-3H,4H-pyrido[4,3-d]pyrimidin-4-one;

(5S)-5-[({3-methyl-7-[4-(morpholin-4-yl)phenyl]-4-oxo-3H,4H-pyrido[4,3-d]pyrimidin-5-yl}amino)methyl]-1,3-oxazolidin-2-one;

5-({[(1S,3S)-3-hydroxycyclopentyl]methyl}amino)-3-methyl-7-[4-(morpholin-4-yl)phenyl]-3H,4H-pyrido[4,3-d]pyrimidin-4-one;

5-({[(1R,3R)-3-hydroxycyclopentyl]methyl}amino)-3-methyl-7-[4-(morpholin-4-yl)phenyl]-3H,4H-pyrido[4,3-d]pyrimidin-4-one;

5-({[(1R,3S)-3-hydroxy-3-methylcyclopentyl]methyl}amino)-3-methyl-7-[4-(morpholin-4-yl)phenyl]-3H,4H-pyrido[4,3-d]pyrimidin-4-one;

5-({[(1S,3R)-3-hydroxy-3-methylcyclopentyl]methyl}amino)-3-methyl-7-[4-(morpholin-4-yl)phenyl]-3H,4H-pyrido[4,3-d]pyrimidin-4-one;

7-(1-acetyl-2,3-dihydro-1H-indol-5-yl)-3-methyl-5-(propan-2-ylamino)-3H,4H-pyrido[4,3-d]pyrimidin-4-one;

7-(1-acetyl-2,3-dihydro-1H-indol-5-yl)-5-[(3S)-3-(hydroxymethyl)pyrrolidin-1-yl]-3-methyl-3H,4H-pyrido[4,3-d]pyrimidin-4-one;

5-[(3S)-3-(hydroxymethyl)pyrrolidin-1-yl]-3-methyl-7-(1-methyl-2,3-dihydro-H-indol-5-yl)-3H,4H-pyrido[4,3-d]pyrimidin-4-one;

3-methyl-7-(1-methyl-2,3-dihydro-H-indol-5-yl)-5-(propan-2-ylamino)-3H,4H-pyrido[4,3-d]pyrimidin-4-one;

3-methyl-7-[4-(morpholin-4-yl)phenyl]-5-[(1H-1,2,3-triazol-4-ylmethyl)amino]-3H,4H-pyrido[4,3-d]pyrimidin-4-one;

5-[(3S)-3-[(1R)-1-hydroxyethyl]pyrrolidin-1-yl]-3-methyl-7-[4-(4-methylpiperazin-1-yl)phenyl]-3H,4H-pyrido[4,3-d]pyrimidin-4-one;

5-[(3R)-3-[(1S)-1-hydroxyethyl]pyrrolidin-1-yl]-3-methyl-7-[4-(4-methylpiperazin-1-yl)phenyl]-3H,4H-pyrido[4,3-d]pyrimidin-4-one;

5-[(3R)-3-[(1R)-1-hydroxyethyl]pyrrolidin-1-yl]-3-methyl-7-[4-(4-methylpiperazin-1-yl)phenyl]-3H,4H-pyrido[4,3-d]pyrimidin-4-one;

3-hydroxy-1-{3-methyl-7-[4-(morpholin-4-yl)phenyl]-4-oxo-3H,4H-pyrido[4,3-d]pyrimidin-5-yl}pyrrolidine-3-carboxamide;

5-[3-hydroxy-3-(hydroxymethyl)pyrrolidin-1-yl]-3-methyl-7-[4-(morpholin-4-yl)phenyl]-3H,4H-pyrido[4,3-d]pyrimidin-4-one;

3-fluoro-1-{3-methyl-7-[4-(morpholin-4-yl)phenyl]-4-oxo-3H,4H-pyrido[4,3-d]pyrimidin-5-yl}pyrrolidine-3-carboxamide;

3-methyl-7-[4-(morpholin-4-yl)phenyl]-5-[(1H-pyrazol-4-ylmethyl)amino]-3H,4H-pyrido[4,3-d]pyrimidin-4-one;

5-[3-fluoro-3-(hydroxymethyl)pyrrolidin-1-yl]-3-methyl-7-[4-(morpholin-4-yl)phenyl]-3H,4H-pyrido[4,3-d]pyrimidin-4-one;

3-(2-hydroxyethyl)-5-(propan-2-ylamino)-7-(pyrazin-2-ylamino)-3H,4H-pyrido[4,3-d]pyrimidin-4-one;

7-(6-aminopyridin-3-yl)-3-methyl-5-(propan-2-ylamino)-3H,4H-pyrido[4,3-d]pyrimidin-4-one;

7-(2-aminopyridin-3-yl)-3-methyl-5-(propan-2-ylamino)-3H,4H-pyrido[4,3-d]pyrimidin-4-one;

7-(2-aminopyrimidin-5-yl)-5-(tert-butylamino)-3-(2-hydroxyethyl)-3H,4H-pyrido[4,3-d]pyrimidin-4-one;

7-(2-aminopyrimidin-5-yl)-3-methyl-5-(propan-2-ylamino)-3H,4H-pyrido[4,3-d]pyrimidin-4-one;

7-{4-[(3S)-3-hydroxypyrrolidin-1-yl]-3-methanesulfonylphenyl}-3-methyl-5-(propan-2-ylamino)-3H,4H-pyrido[4,3-d]pyrimidin-4-one;

7-{4-[(3S)-3-hydroxypyrrolidin-1-yl]-3-methanesulfonylphenyl}-5-[(2-methoxyethyl)amino]-3-methyl-3H,4H-pyrido[4,3-d]pyrimidin-4-one;

7-{4-[(3S)-3-hydroxypyrrolidin-1-yl]-3-methanesulfonylphenyl}-3-methyl-5-[(3R)-oxolan-3-ylamino]-3H,4H-pyrido[4,3-d]pyrimidin-4-one;

5-[(3S)-3-(hydroxymethyl)pyrrolidin-1-yl]-7-{4-[(3S)-3-hydroxypyrrolidin-1-yl]-3-methanesulfonylphenyl}-3-methyl-3H,4H-pyrido[4,3-d]pyrimidin-4-one;

4-methyl-7-[3-methyl-4-oxo-5-(propan-2-ylamino)-3H,4H-pyrido[4,3-d]pyrimidin-7-yl]-3,4-dihydro-2H-1,1-dioxo-2H-benzo[b][1,4]thiazin-3(4H)-one;

7-{5-[(2-methoxyethyl)amino]-3-methyl-4-oxo-3H,4H-pyrido[4,3-d]pyrimidin-7-yl}-4-methyl-3,4-dihydro-2H-1,1-dioxo-2H-benzo[b][1,4]thiazin-3(4H)-one;

4-methyl-7-{3-methyl-4-oxo-5-[(3R)-oxolan-3-ylamino]-3H,4H-pyrido[4,3-d]pyrimidin-7-yl}-3,4-dihydro-2H-1,1-dioxo-2H-benzo[b][1,4]thiazin-3(4H)-one;

7-{5-[(3S)-3-(hydroxymethyl)pyrrolidin-1-yl]-3-methyl-4-oxo-3H,4H-pyrido[4,3-d]pyrimidin-7-yl}-4-methyl-3,4-dihydro-2H-1,1-dioxo-2H-benzo[b][1,4]thiazin-3(4H)-one;

N-hydroxy-4-[3-methyl-4-oxo-5-(propan-2-ylamino)-3H,4H-pyrido[4,3-d]pyrimidin-7-yl]benzene-1-carboximidamide;

N-hydroxy-4-{5-[(2-methoxyethyl)amino]-3-methyl-4-oxo-3H,4H-pyrido[4,3-d]pyrimidin-7-yl}benzene-1-carboximidamide;

N-hydroxy-4-{3-methyl-4-oxo-5-[(3R)-oxolan-3-ylamino]-3H,4H-pyrido[4,3-d]pyrimidin-7-yl}benzene-1-carboximidamide;

N-hydroxy-4-{5-[(3S)-3-(hydroxymethyl)pyrrolidin-1-yl]-3-methyl-4-oxo-3H,4H-pyrido[4,3-d]pyrimidin-7-yl}benzene-1-carboximidamide;

5-(cyclopropylamino)-7-[4-(dimethylamino)phenyl]-3-methyl-3H,4H-pyrido[4,3-d]pyrimidin-4-one;

7-[4-(dimethylamino)phenyl]-5-[(3-hydroxypropyl)amino]-3-methyl-3H,4H-pyrido[4,3-d]pyrimidin-4-one;

7-[4-(dimethylamino)phenyl]-3-methyl-5-[(3R)-oxolan-3-ylamino]-3H,4H-pyrido[4,3-d]pyrimidin-4-one;

7-[4-(dimethylamino)phenyl]-5-[(3S)-3-(hydroxymethyl)pyrrolidin-1-yl]-3-methyl-3H,4H-pyrido[4,3-d]pyrimidin-4-one;

7-[4-(aminomethyl)phenyl]-3-methyl-5-(propan-2-ylamino)-3H,4H-pyrido[4,3-d]pyrimidin-4-one;

7-[4-(aminomethyl)phenyl]-5-[(2-methoxyethyl)amino]-3-methyl-3H,4H-pyrido[4,3-d]pyrimidin-4-one;

7-[4-(aminomethyl)phenyl]-3-methyl-5-[(3R)-oxolan-3-ylamino]-3H,4H-pyrido[4,3-d]pyrimidin-4-one;

7-{4-[(1R)-1-aminoethyl]phenyl}-3-methyl-5-(propan-2-ylamino)-3H,4H-pyrido[4,3-d]pyrimidin-4-one;

7-{4-[(1R)-1-aminoethyl]phenyl}-5-[(3-hydroxypropyl)amino]-3-methyl-3H,4H-pyrido[4,3-d]pyrimidin-4-one;

7-{4-[(1R)-1-aminoethyl]phenyl}-3-methyl-5-[(3R)-oxolan-3-ylamino]-3H,4H-pyrido[4,3-d]pyrimidin-4-one;

7-{4-[(1R)-1-aminoethyl]phenyl}-5-[(3S)-3-(hydroxymethyl)pyrrolidin-1-yl]-3-methyl-3H,4H-pyrido[4,3-d]pyrimidin-4-one;

7-{4-[(1S)-1-aminoethyl]phenyl}-3-methyl-5-(propan-2-ylamino)-3H,4H-pyrido[4,3-d]pyrimidin-4-one;

7-{4-[(1S)-1-aminoethyl]phenyl}-5-[(3-hydroxypropyl)amino]-3-methyl-3H,4H-pyrido[4,3-d]pyrimidin-4-one;

7-{4-[(1S)-1-aminoethyl]phenyl}-3-methyl-5-[(3R)-oxolan-3-ylamino]-3H,4H-pyrido[4,3-d]pyrimidin-4-one;

7-{4-[(1S)-1-aminoethyl]phenyl}-5-[(3S)-3-(hydroxymethyl)pyrrolidin-1-yl]-3-methyl-3H,4H-pyrido[4,3-d]pyrimidin-4-one;

7-{4-[(1R)-1-aminoethyl]phenyl}-5-(cyclopropylamino)-3-methyl-3H,4H-pyrido[4,3-d]pyrimidin-4-one;

7-{4-[(1S)-1-aminoethyl]phenyl}-5-(cyclopropylamino)-3-methyl-3H,4H-pyrido[4,3-d]pyrimidin-4-one;

4-methyl-7-[3-methyl-4-oxo-5-(propan-2-ylamino)-3H,4H-pyrido[4,3-d]pyrimidin-7-yl]-3,4-dihydro-2H-1,1-dioxo-2H-benzo[b][1,4]thiazine;

7-{5-[(2-methoxyethyl)amino]-3-methyl-4-oxo-3H,4H-pyrido[4,3-d]pyrimidin-7-yl}-4-methyl-3,4-dihydro-2H-1,1-dioxo-2H-benzo[b][1,4]thiazine;

4-methyl-7-{3-methyl-4-oxo-5-[(3R)-oxolan-3-ylamino]-3H,4H-pyrido[4,3-d]pyrimidin-7-yl}-3,4-dihydro-2H-1,1-dioxo-2H-benzo[b][1,4]thiazine;

7-{5-[(3S)-3-(hydroxymethyl)pyrrolidin-1-yl]-3-methyl-4-oxo-3H,4H-pyrido[4,3-d]pyrimidin-7-yl}-4-methyl-3,4-dihydro-2H-1,1-dioxo-2H-benzo[b][1,4]thiazine;

N-[(1R)-1-{4-[3-methyl-4-oxo-5-(propan-2-ylamino)-3H,4H-pyrido[4,3-d]pyrimidin-7-yl]phenyl}ethyl]acetamide;

N-[(1R)-1-{4-[5-(cyclopropylamino)-3-methyl-4-oxo-3H,4H-pyrido[4,3-d]pyrimidin-7-yl]phenyl}ethyl]acetamide;

N-[(1R)-1-(4-{5-[(3-hydroxypropyl)amino]-3-methyl-4-oxo-3H,4H-pyrido[4,3-d]pyrimidin-7-yl}phenyl)ethyl]acetamide;

N-[(1R)-1-(4-{3-methyl-4-oxo-5-[(3R)-oxolan-3-ylamino]-3H,4H-pyrido[4,3-d]pyrimidin-7-yl}phenyl)ethyl]acetamide;

N-[(1S)-1-{4-[5-(cyclopropylamino)-3-methyl-4-oxo-3H,4H-pyrido[4,3-d]pyrimidin-7-yl]phenyl}ethyl]methanesulfonamide;

N-[(1S)-1-(4-{5-[(3-hydroxypropyl)amino]-3-methyl-4-oxo-3H,4H-pyrido[4,3-d]pyrimidin-7-yl}phenyl)ethyl]methanesulfonamide;

N-[(1S)-1-(4-{3-methyl-4-oxo-5-[(3R)-oxolan-3-ylamino]-3H,4H-pyrido[4,3-d]pyrimidin-7-yl}phenyl)ethyl]methanesulfonamide;

N-[(1S)-1-(4-{5-[(3S)-3-(hydroxymethyl)pyrrolidin-1-yl]-3-methyl-4-oxo-3H,4H-pyrido[4,3-d]pyrimidin-7-yl}phenyl)ethyl]methanesulfonamide;

5-[(3S)-3-(hydroxymethyl)pyrrolidin-1-yl]-3-methyl-7-[3-methyl-4-(piperidin-4-yl)phenyl]-3H,4H-pyrido[4,3-d]pyrimidin-4-one;

3-methyl-7-[3-methyl-4-(piperidin-4-yl)phenyl]-5-[(3R)-oxolan-3-ylamino]-3H,4H-pyrido[4,3-d]pyrimidin-4-one;

5-[(3-hydroxypropyl)amino]-3-methyl-7-[3-methyl-4-(piperidin-4-yl)phenyl]-3H,4H-pyrido[4,3-d]pyrimidin-4-one;

3-methyl-7-[3-methyl-4-(1-methylpiperidin-4-yl)phenyl]-5-[(3R)-oxolan-3-ylamino]-3H,4H-pyrido[4,3-d]pyrimidin-4-one;

5-[(3S)-3-(hydroxymethyl)pyrrolidin-1-yl]-3-methyl-7-[3-methyl-4-(1-methylpiperidin-4-yl)phenyl]-3H,4H-pyrido[4,3-d]pyrimidin-4-one;

7-[3-fluoro-4-(1-methylpiperidin-4-yl)phenyl]-3-methyl-5-[(3R)-oxolan-3-ylamino]-3H,4H-pyrido[4,3-d]pyrimidin-4-one;

7-[3-fluoro-4-(1-methylpiperidin-4-yl)phenyl]-5-[(3S)-3-(hydroxymethyl)pyrrolidin-1-yl]-3-methyl-3H,4H-pyrido[4,3-d]pyrimidin-4-one;

7-[3-fluoro-4-(1-methylpiperidin-4-yl)phenyl]-5-[(3-hydroxypropyl)amino]-3-methyl-3H,4H-pyrido[4,3-d]pyrimidin-4-one;

7-[4-(1-ethylpiperidin-4-yl)-3-methylphenyl]-3-methyl-5-[(3R)-oxolan-3-ylamino]-3H,4H-pyrido[4,3-d]pyrimidin-4-one;

7-[4-(1-ethylpiperidin-4-yl)-3-methylphenyl]-5-[(3S)-3-(hydroxymethyl)pyrrolidin-1-yl]-3-methyl-3H,4H-pyrido[4,3-d]pyrimidin-4-one;

7-[4-(1-ethylpiperidin-4-yl)-3-methylphenyl]-5-[(3-hydroxypropyl)amino]-3-methyl-3H,4H-pyrido[4,3-d]pyrimidin-4-one;

5-[2-(hydroxymethyl)morpholin-4-yl]-3-methyl-7-[4-(morpholin-4-yl)phenyl]-3H,4H-pyrido[4,3-d]pyrimidin-4-one;

7-[4-(1-ethylpiperidin-4-yl)-3-methylphenyl]-5-[2-(hydroxymethyl)morpholin-4-yl]-3-methyl-3H,4H-pyrido[4,3-d]pyrimidin-4-one;

ethyl 4-(4-{3-methyl-4-oxo-5-[(3R)-oxolan-3-ylamino]-3H,4H-pyrido[4,3-d]pyrimidin-7-yl}phenyl)-4-oxobutanoate;

ethyl 4-(4-{5-[(3S)-3-(hydroxymethyl)pyrrolidin-1-yl]-3-methyl-4-oxo-3H,4H-pyrido[4,3-d]pyrimidin-7-yl}phenyl)-4-oxobutanoate;

5-{4-[3-methyl-4-oxo-5-(propan-2-ylamino)-3H,4H-pyrido[4,3-d]pyrimidin-7-yl]phenyl}pyrrolidin-2-one;

5-(4-{3-methyl-4-oxo-5-[(3R)-oxolan-3-ylamino]-3H,4H-pyrido[4,3-d]pyrimidin-7-yl}phenyl)pyrrolidin-2-one;

5-(4-{5-[(3S)-3-(hydroxymethyl)pyrrolidin-1-yl]-3-methyl-4-oxo-3H,4H-pyrido[4,3-d]pyrimidin-7-yl}phenyl)pyrrolidin-2-one;

5-[(3S)-3-(hydroxymethyl)pyrrolidin-1-yl]-3-methyl-7-[4-(2,2,2-trifluoro-1-hydroxyethyl)phenyl]-3H,4H-pyrido[4,3-d]pyrimidin-4-one;

3-methyl-5-[(3R)-oxolan-3-ylamino]-7-[4-(2,2,2-trifluoro-1-hydroxyethyl)phenyl]-3H,4H-pyrido[4,3-d]pyrimidin-4-one;

1-methyl-5-[3-methyl-4-oxo-5-(propan-2-ylamino)-3H,4H-pyrido[4,3-d]pyrimidin-7-yl]-2,3-dihydro-1H-indole-2,3-dione;

5-{5-[(3-hydroxypropyl)amino]-3-methyl-4-oxo-3H,4H-pyrido[4,3-d]pyrimidin-7-yl}-1-methyl-2,3-dihydro-1H-indole-2,3-dione;

1-methyl-5-{3-methyl-4-oxo-5-[(3R)-oxolan-3-ylamino]-3H,4H-pyrido[4,3-d]pyrimidin-7-yl}-2,3-dihydro-1H-indole-2,3-dione;

5-{5-[(3S)-3-(hydroxymethyl)pyrrolidin-1-yl]-3-methyl-4-oxo-3H,4H-pyrido[4,3-d]pyrimidin-7-yl}-1-methyl-2,3-dihydro-1H-indole-2,3-dione;

7-[4-(1-aminocyclopropyl)phenyl]-5-(cyclopropylamino)-3-methyl-3H,4H-pyrido[4,3-d]pyrimidin-4-one;

7-[4-(1-aminocyclopropyl)phenyl]-5-[(3-hydroxypropyl)amino]-3-methyl-3H,4H-pyrido[4,3-d]pyrimidin-4-one;

7-[4-(1-aminocyclopropyl)phenyl]-3-methyl-5-[(3R)-oxolan-3-ylamino]-3H,4H-pyrido[4,3-d]pyrimidin-4-one;

7-[4-(1-aminocyclopropyl)phenyl]-5-[(3S)-3-(hydroxymethyl)pyrrolidin-1-yl]-3-methyl-3H,4H-pyrido[4,3-d]pyrimidin-4-one;

5-(ethylamino)-3-methyl-7-[6-(morpholin-4-yl)pyridin-3-yl]-3H,4H-pyrido[4,3-d]pyrimidin-4-one;

7-[6-(1-aminocyclopropyl)pyridin-3-yl]-5-(ethylamino)-3-methyl-3H,4H-pyrido[4,3-d]pyrimidin-4-one;

7-[6-(1-aminocyclopropyl)pyridin-3-yl]-5-(cyclopropylamino)-3-methyl-3H,4H-pyrido[4,3-d]pyrimidin-4-one;

7-[6-(1-aminocyclopropyl)pyridin-3-yl]-3-methyl-5-(propan-2-ylamino)-3H,4H-pyrido[4,3-d]pyrimidin-4-one;

7-[6-(1-aminocyclopropyl)pyridin-3-yl]-3-methyl-5-[(2S)-oxolan-2-ylamino]-3H,4H-pyrido[4,3-d]pyrimidin-4-one, and 7-[6-(1-aminocyclopropyl)pyridin-3-yl]-5-[(3S)-3-(hydroxymethyl)pyrrolidin-1-yl]-3-methyl-3H,4H-pyrido[4,3-d]pyrimidin-4-one.

23. A pharmaceutical composition for treating a Syk kinase mediated disease comprising a therapeutically effective amount of a compound of Formula (I) of claim 1 and a pharmaceutically acceptable excipient.

* * * * *